(12) United States Patent
Fiske et al.

(10) Patent No.: US 12,331,125 B2
(45) Date of Patent: *Jun. 17, 2025

(54) ANTI-cMet ANTIBODY-DRUG CONJUGATES AND USES THEREOF

(71) Applicant: Mythic Therapeutics, Inc., Waltham, MA (US)

(72) Inventors: Brian P. Fiske, Waltham, MA (US); Nimish Gera, Waltham, MA (US); Alexander J. Nichols, Lincoln, MA (US)

(73) Assignee: Mythic Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/510,256

(22) Filed: Nov. 15, 2023

(65) Prior Publication Data

US 2024/0101688 A1 Mar. 28, 2024

Related U.S. Application Data

(63) Continuation of application No. 18/273,078, filed as application No. PCT/US2022/015116 on Feb. 3, 2022.
(Continued)

(51) Int. Cl.
| | | |
|---|---|---|
| C07K 16/28 | (2006.01) | |
| A61K 38/00 | (2006.01) | |
| A61K 39/00 | (2006.01) | |
| A61K 47/68 | (2017.01) | |
| A61P 35/00 | (2006.01) | |
| C07K 16/32 | (2006.01) | |

(52) U.S. Cl.
CPC .... *C07K 16/2863* (2013.01); *A61K 47/68031* (2023.08); *A61K 47/68035* (2023.08); *A61K 47/6849* (2017.08); *A61P 35/00* (2018.01); *C07K 16/32* (2013.01); *A61K 38/00* (2013.01); *A61K 2039/505* (2013.01); *C07K 2317/52* (2013.01); *C07K 2317/73* (2013.01); *C07K 2317/77* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,652,138 A | 7/1997 | Burton et al. |
| 7,612,181 B2 | 11/2009 | Wu et al. |

(Continued)

FOREIGN PATENT DOCUMENTS

| | | |
|---|---|---|
| CN | 102174106 | 9/2011 |
| CN | 102918057 | 2/2013 |

(Continued)

OTHER PUBLICATIONS

Zhou. Site-specific antibody conjugation for ADC and Beyond. Biomedicines 2017, 5, 64; doi:10.3390/biomedicines5040064 (Year: 2017).*

(Continued)

*Primary Examiner* — Amy E Juedes
*Assistant Examiner* — Hilary Ann Petrash
(74) *Attorney, Agent, or Firm* — Fish & Richardson P.C.

(57) ABSTRACT

Provided herein are antibodies and uses of the same.

10 Claims, 18 Drawing Sheets

Specification includes a Sequence Listing.

Related U.S. Application Data

(60) Provisional application No. 63/145,348, filed on Feb. 3, 2021.

(56) References Cited

U.S. PATENT DOCUMENTS

| | | | |
|---|---|---|---|
| 8,088,376 | B2 | 1/2012 | Chamberlain et al. |
| 8,217,148 | B2* | 7/2012 | Davies ............... A61P 35/02 |
| | | | 530/388.8 |
| 8,258,268 | B2 | 9/2012 | Wu et al. |
| 8,394,925 | B2 | 3/2013 | Chamberlain et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,822,645 | B2 | 9/2014 | Ghayur et al. |
| 10,336,818 | B2 | 7/2019 | Chamberlain et al. |
| 10,383,948 | B2* | 8/2019 | Allan ............ A61K 47/6811 |
| 10,799,597 | B2 | 10/2020 | Goldenberg |
| 2011/0111406 | A1* | 5/2011 | Igawa ............. A61K 39/145 |
| | | | 435/69.6 |
| 2013/0243775 | A1 | 9/2013 | Papadopoulos et al. |
| 2016/0161500 | A1 | 6/2016 | Lee et al. |
| 2017/0007715 | A1 | 7/2017 | Andreev et al. |
| 2017/0191055 | A1 | 7/2017 | Short et al. |
| 2017/0348429 | A1 | 12/2017 | Reilly et al. |
| 2018/0208658 | A1 | 7/2018 | Liu et al. |
| 2018/0230218 | A1 | 8/2018 | Chittenden et al. |
| 2019/0024078 | A1 | 1/2019 | Short et al. |
| 2020/0061204 | A1 | 2/2020 | Feng et al. |
| 2022/0281984 | A1 | 9/2022 | Nichols et al. |
| 2024/0197906 | A1 | 6/2024 | Fiske et al. |

FOREIGN PATENT DOCUMENTS

| | | |
|---|---|---|
| CN | 103002916 | 3/2013 |
| EP | 2552955 | 2/2013 |
| JP | 2015-502397 A | 1/2015 |
| KR | 20180025865 | 3/2018 |
| WO | WO 2009/125825 | 10/2009 |
| WO | WO 2011/111007 | 9/2011 |
| WO | WO 2011/122011 | 10/2011 |
| WO | WO 2011/151412 | 12/2011 |
| WO | WO 2013/093809 A1 | 6/2013 |
| WO | WO 2013/138400 | 9/2013 |
| WO | WO 2017/134197 | 8/2017 |
| WO | WO 2017/201204 | 11/2017 |
| WO | WO 2018/044619 | 3/2018 |
| WO | WO 2018/062402 | 4/2018 |
| WO | WO 2018/093669 | 5/2018 |
| WO | WO 2018/129029 | 7/2018 |
| WO | WO 2018/136455 | 7/2018 |
| WO | WO 2019/189453 | 10/2019 |
| WO | WO 2020/014306 | 1/2020 |
| WO | WO 2020/092385 A1 | 5/2020 |
| WO | WO 2021/022039 | 2/2021 |
| WO | WO 2022/169975 | 8/2022 |

OTHER PUBLICATIONS

Dimasi et al. Efficient preparation of site specifici antibody drug conjugates using cysteine insertion. Mol/ Pharmaceutics 2017, 14, 1501-1516; DOI: 10.1021/acs.molpharmaceut.6b00995 (Year: 2017).*
Li et al. 2019. Evaluation and use of an anti-cynomolgus monkey CD79b surrogate antibody-drug conjugate to enable clinical development of polatuzumab vedotin. Br J Pharmacol. 2019; 176: 3805-3818. https://doi.org/10.1111/bph.14784 (Year: 2019).*
Abdiche et al., "Exploring blocking assays using Octet, ProteOn, and Biacore biosensors", Anal Biochem., Mar. 2009, 386(2):172-180.
Amini, "Hospital Adminstration Routine," Sanqin Publishing House, 2013, pp. 397-398.
Bonvin et al., "De novo isolation of antibodies with pH-dependent binding properties," MABS, Mar. 11, 2015, 7(2):294-302.
Borrok et al., "pH-dependent Binding Engineering Reveals an FcRn Affinity Threshold That Governs IgG Recycling," The Journal of Biological Chemistry, Feb. 13, 2015, 290(7):4282-4290.
BroadInstitute.Org [online], "Cancer Cell Line Encyclopedia", available on or before Jul. 2016, retrieved on Mar. 29, 2022, retrieved from URL <https://portals.broadinstitute.org/ccle>, 6 pages.
Carter et al., "Antibody-Drug Conjugates for Cancer Therapy", Cancer J., May 2008, 14(3):154-169.
Catcott et al., "Microscale screening of antibody libraries as maytansinoid antibody-drug conjugates", mAbs, 2016 8(3):513-523.
Chandna, "Single-Cell Gel Electrophoresis Assay Monitors Precise Kinetics of DNA Fragmentation Induced During Programmed Cell Death", Cytometry, 2004, 61A:127-133.
Chari, "Targeted Cancer Therapy: Conferring Specificity to Cytotoxic Drugs", Acc. Chem. Res., Jan. 2008, 41(1):98-107.
Cromie et al., "Nanobodies and their use in GPCR drug discovery", Curr. Top. Med. Chem., 2015, 15(24):2543-2557.
Dall et al., "Increasing the Affinity of a Human IgG1 for the Neonatal Fc Receptor: Biological Consequences", J Immunol., 2002, 169:5171-5180.
De Genst et al., "Antibody repertoire development in camelids", Dev. Comp.Immunol., 2006, 30(1-2):187-198.
De Meyer et al., "Nanobody-based products as research and diagnostic tools", Trends Biotechnol., May 2014, 32(5):263-270.
DiGiammarino et al., "Design and generation of DVD-Ig™ molecules for dual-specific targeting", Methods Mol. Biol., 2012, 899:145-156.
Fischer et al., "The assay design used for measurement of therapeutic antibody concentrations can affect pharmacokinetic parameters", mAbs, 2012, 4(5):623-631.
Fujita et al., "A Novel Non-Agonist c-Met Antibody Drug Conjugate with Superior Potency Over a c-Met Tyrosine Kinase Inhibitor in c-Met Amplified and Non-Amplified Cancers", Cancer Biol. Ther., 2002, 21(6):549-559.
Garber, "Bispecific antibodies rise again", Nat. Rev. Drug Discov., Nov. 2014, 13:799-801.
Gera et al., "Design of pH Sensitive Binding Proteins from the Hyperthermophilic Sso7d Scaffold", PLoS One, Nov. 2012, 7(11):e48928.
Gupta et al., "Preclinical pharmacokinetics of MHAA4549A, a human monoclonal antibody to influenza A virus, and the prediction of its efficacious clinical dose for the treatment of patients hospitalized with influenza A", mAbs, 2016, 8(5):991-997.
Huang et al., "Assessment of Histone H2AX Phosphorylation Induced by DNA Topoisomerase I and II Inhibitors Topotecan and Mitoxantrone and by the DNA Cross-Linking Agent Cisplatin", Cytometry Part A., 2004, 58A:99-110.
Igawa et al., "pH-dependent antigen-binding antibodies as a novel therapeutic modality," Proteomics, , 2014, 1844(11):1943-1950.
International Preliminary Report on Patentability in International Appln. No. PCT/US2020/044263, dated Feb. 10, 2022, 15 pages.
International Search Report and Written Opinion in International Application No. PCT/US2022/015116, dated Jun. 30, 2022, 21 pages.
International Search Report and Written Opinion in International Appln. No. PCT/US2020/044263, dated Dec. 23, 2020, 25 pages.
Invitation to Pay Additional Fees in International Appln. No. PCT/US2020/044263, dated Oct. 30, 2020, 19 pages.
Invitation to Pay Additional Fees in International Appln. No. PCT/US2022/015116, May 9, 2022, 22 pages.
Jakob et al., "Structure reveals function of the dual variable domain immunoglobulin (DVD-Ig™) molecule", mAbs, 2013, 5(3):358-363.
Jamur et al., "Permeabilization of cell membranes", Methods Mol Biol., 2010, 588:63-66.
Kijanka et al., "Nanobody-based cancer therapy of solid tumors", Nanomedicine, 2015, 10:161-174.
Kovaleva et al., "Shark variable new antigen receptor biologics—a novel technology platform for therapeutic drug development", Expert. Opin. Biol. Ther., 2014, 14(10):1527-1539.

(56) References Cited

OTHER PUBLICATIONS

Krah et al., "Single-domain antibodies for biomedical applications", Immunopharmacol. Immunotoxicol., 2016, 38:21-28.
Labrijn et al., "Controlled Fab-arm exchange for the generation of stable bispecific IgG1", Nature Protcols, 2014, 9(10):2450-2463.
Lefranc, "The IMGT unique numbering for Immunoglobulins, T cell receptors and Ig-like domains", Immunologist, Jul. 1999, 7(4):132-136.
Li et al., "A Biparatopic HER2-Targeting Antibody-Drug Conjugate Induces Tumor Regression in Primary Models Refractory to or Ineligible for HER2-Targeted Therapy", Jan. 2016, Cancer Cell 29:117-29.
Lu et al., "Linkers Having a Crucial Role in Antibody-Drug Conjugates", Int. J. Mol. Sci., Apr. 2016, 17(4):561, 22 pages.
Mahmutefendic et al., "Segregation of open Major Histocompatibility Class I conformers at the plasma membrane and during endosomal trafficking reveals conformation-based sorting in the endosomal system", Int. J. Biochem. Cell Bio., Apr. 2011, 43(4):504-515.
McCombs et al., "Antibody drug conjugates: design and selection of linker, payload and conjugation chemistry", Aaps J., Mar. 2015, 17(2):339-351.
Mendoza et al., "Inhibition of Ligand-mediated HER2 Activation in Androgen-independent Prostate Cancer", Cancer Res., Oct. 2002, 62:5485-5488.
Mujic-Delic et al., "GPCR-targeting nanobodies: attractive research tools, diagnostics, and therapeutics", Trends Pharmacol. Sci., May 2014, 35(5):247-255.
Muyldermans et al., "Recognition of antigens by single-domain antibody fragments: the superfluous luxury of paired domains", Trends Biochem. Sci., Apr. 2001, 26(4):230-235.
Muyldermans, "Nanobodies: Natural Single-Domain Antibodies", Annu. Rev. Biochem., Jun. 2013, 82:775-797.
Muyldermans, "Single domain camel antibodies: current status", Rev. Mol. Biotechnol., 2001, 74:277-302.
Office Action in Chinese Appln. No. 114746123, mailed on Oct. 31, 2023, 85 pages (with Machine translation).
Oflazoglu et al., "Potent Anticarcinoma Activity of the Humanized Anti-CD70 Antibody h1F6 Conjugated to the Tubulin Inhibitor Auristatin via an Uncleavable Linker", Clin. Cancer Res., 2008, 14(19): 6171-6180.
Promega Corporation, "CellTiter-Glo™ Luminescent Cell Viability Assay," Technical Bulletin #TB288, revised Mar. 2015, 15 pages.
Rahbarizadeh et al., "Nanobody; an Old Concept and New Vehicle for Immunotargeting", Immunol. Invest., 2011, 40:299-338.
Sanderson et al., "In vivo Drug-Linker Stability of an Anti-CD30 Dipeptide-Linked Auristatin Immunoconjugate", Clin. Cancer Res., Jan. 2005, 11(2 Pt1):843-852.
Schneider et al., "Quantification of human Alu sequences by real-time PCR—an improved method to measure therapeutic efficacy of anti-metastatic drugs in human xenotransplants", Clin. Exp. Metas., 2002, 19:571-582.
Singh et al., "Measurement and Mathematical Characterization of Cell-Level Pharmacokinetics of Antibody-Drug Conjugates: A Case Study with Trastuzumab-vc-MMAE", Drug Metabolism and Disposition, 2017, 45(11):1120-1132.
Sorkin et al., "Quantitative analysis of endocytosis and turnover of epidermal growth factor (EGF) and EGF receptor", Curr. Protoc. Cell Biol., Mar. 2010, Chapter 15, Unit-15.14.
Spiess et al., "Alternative molecular formats and therapeutic applications of bispecific antibodies", Mol. Immunol., 2015, 67(2 Pt A):95-106.
Tiberghien et al., "Design and Synthesis of Tesirine, a Clinical Antibody-Drug Conjugate Pyrrolobenzodiazepine Dimer Payload", ACS Med Chem Lett, Nov. 2016, 7(11):983-987.
Tillotson et al., "Engineering an Anti-Transferrin Receptor ScFv for pH-Sensitive Binding Leads to Increased Intracellular Accumulation," Plos One, Dec. 29, 2015, 10(12): e0145820.

Vainshtein et al., "Quantitative Measurement of the Target-Mediated Internalization Kinetics of Biopharmaceuticals", Pharm Res., 2015, 32:286-299.
Van Audenhove et al., "Nanobodies as Versatile Tools to Understand, Diagnose, Visualize and Treat Cancer", EBioMedicine, Jun. 2016, 8:40-48.
Van Bockstaele et al., "The development of nanobodies for therapeutic applications", Curr. Opin. Investig. Drugs, 2009, 10(11):1212-1224.
Vincke et al., "Introduction to heavy chain antibodies and derived Nanobodies", Methods Mol. Biol., 2012, 911:15-26.
Wang et al., "ABBV-399, a c-Met Antibody—Drug Conjugate that Targets Both MET-Amplified and c-Met-Overexpressing Tumors, Irrespective of MET Pathway Dependence", Clin Cancer Res, Feb. 2017, 23(4):992-1000.
Wesolowski et al., "Single domain antibodies: promising experimental and therapeutic tools in infection and immunity", Med. Microbiol. Immunol., Aug. 2009, 198(3):157-174.
Wiley et al., "The Role of Tyrosine Kinase Activity in Endocytosis, Compartmentation, and Down-regulation of the Epidermal Growth Factor Receptor", J. Biol. Chem., 1991, 266(17):11083-11094.
Wustner, "Steady State Analysis and Experimental Validation of a Model for Hepatic High-Density Lipoprotein Transport", Traffic, 2006, 7(6):699-715.
Awad, "Impaired c-Met Receptor Degradation Mediated by MET Exon 14 Mutations in Non-Small-Cell Lung Cancer," Journal of Clinical Oncology, Mar. 10, 2016, 34(8):879-881.
Cappuzzo et al., "Epidermal growth factor receptor gene and protein and gefitinib sensitivity in non-small-cell lung cancer," Journal of the National Cancer Institute, May 4, 2005, 97(9):643-655.
Castañeda-González et al., "Multiple mutations in the EGFR gene in lung cancer: a systematic review," Translational Lung Cancer Research, Oct. 2022, 11(10):2148-2163.
Chang et al., "Whole-Body Pharmacokinetics and Physiologically Based Pharmacokinetic Model for Monomethyl Auristatin E (MMAE)," Journal of Clinical Medicine, Mar. 23, 2021, 10(6):1332, 18 pages.
Chon et al., "FDA Approval Summary: Amivantamab for the Treatment of Patients with Non-Small Cell Lung Cancer with EGFR Exon 20 Insertion Mutations, " Clinical Cancer Research, Sep. 1, 2003, 29(17):3262-3266.
Coleman et al., "Antibody-drug conjugates in lung cancer: dawn of a new era?, " NPJ Precision Oncology, Jan. 2023, 7(5):1-12.
De George et al., "Guidance for Industry: S9 Nonclinical Evaluation for Anticancer Pharmaceuticals," U.S. Department of Health and Human Services, Mar. 2010, 12 pages.
Dong et al., "MET-Targeted Therapies and Clinical Outcomes: A Systematic Literature Review," Molecular Diagnosis & Therapy, Mar. 10, 2022, 26(2):203-227.
Doronina et al., "Novel peptide linkers for highly potent antibody-auristatin conjugate," Bioconjugate chemistry, Oct. 15, 2008, 19(10):1960-3.
Dubowchik et al., "Cathepsin B-sensitive dipeptide prodrugs. 1. A model study of structural requirements for efficient release of doxorubicin, " Bioorganic & Medicinal Chemistry Letters, Dec. 1, 1998, 8(23):3341-3346.
Fernandes et al., "When the MET receptor kicks in to resist targeted therapies," Oncogene, Jun. 2021, 40(24):4061-4078.
Fisher Jr., "Considerations for the Nonclinical Safety Evaluation of Antibody-Drug Conjugates," Antibodies, Apr. 19, 2021, 10(2):15.
Francisco et al., "cAC10-vcMMAE, an anti-CD30-monomethyl auristatin E conjugate with potent and selective antitumor activity," Aug. 15, 2003, Blood, 102(4):1458-1465.
Fujino et al., "Lung Cancer with MET exon 14 Skipping Mutation: Genetic Feature, Current Treatments, and Future Challenges," Lung Cancer: Targets and Therapy, May 20, 2021, 35-50.
Gera et al., "Abstract 5000: MYTX:011: A novel cMET_targeting antibody drug conjugate (ADC) engineered to increase on-target uptake in and efficacy against cMET expressing tumors," Poster, Presented for the American Association for Cancer Research, Apr. 14-19, 2023, 83(7 Supplement):1 page.

(56) References Cited

OTHER PUBLICATIONS

Gymnopoulos et al., "TR1801-ADC: a highly potent cMet antibody-drug conjugate with high activity in patient-derived xenograft models of solid tumors," Molecular Oncology, Dec. 3, 2019, 14(1):54-68.

Han et al., "CYP3A-mediated drug-drug interaction potential and excretion of brentuximab vedotin, an antibody-drug conjugate, in patients with CD30-positive hematologic malignancies," Journal of Clinical Pharmacology, Aug. 2013, 53(8):866-877.

International Search Report and Written Opinion in International Appln. No. PCT/US2023/083354, mailed on Mar. 20, 2024, 16 pages.

Jackman et al., "Exon 19 Deletion Mutations of Epidermal Growth Factor Receptor Are Associated with Prolonged Survival in Non-Small Cell Lung Cancer Patients Treated with Gefitinib or Erlotinib," Clinical Cancer Research, Jul. 2006, 12(13):3908-3914.

Junutula et al., "Site-specific conjugation of a cytotoxic drug to an antibody improves the therapeutic index," Nature biotechnology, Aug. 2008, 26(8):925-932.

Kinoshita et al., "Safety and pharmacokinetics of polatuzumab vedotin in Japanese patients with relapsed/refractory B-cell non-Hodgkin lymphoma: a phase 1 dose-escalation study," Japanese Journal of Clinical Oncology, Jan. 2021, 51(1):70-77.

Koeppen et al., "Biomarker Analyses from a Placebo-Controlled Phase II Study Evaluating Erlotinib + Onartuzumab in Advanced Non-Small Cell Lung Cancer: MET Expression Levels Are Predictive of Patient Benefit," Clinical Cancer Research, Sep. 2014, 20(19):4488-4498.

Kontermann et al., "Bispecific antibodies," Drug Discovery Today, Jul. 2015, 20(7):838-847.

Lai et al., "Preclinical Evaluation of a New, Non-Agonist ADC Targeting MET-Amplified Tumors with a Peptide-linked Maytansinoid," Poster, AACR Annual Meeting, Mar. 29-Apr. 3, 2019, 1 page.

Lee et al., "MET in gastric carcinomas: comparison between protein express and gene copy number and impact on outcome," British Journal of Cancer, Jul. 2012, 107(2):325-333.

Lv et al., "Soluble c-Met is a Reliable and Sensitive Marker to Detect c-Met Expression Level in Lung Cancer," BioMed Research International, Jan. 1, 2015, 2015(626578):1-9.

Okamoto et al., "Pharmacokinetics of trastuzumab deruxtecan (T-DXd), a novel anti-HER2 Adc, in HER2-positive tumor-bearing mice," Xenobiotica, Oct. 2, 2020, 50(10):1242-1250.

Park et al., "MET amplification, protein expression, and mutations in pulmonary adenocarcinoma," Lung Cancer, Dec. 2015, 90(3):381-387.

Pastuskovas et al., "Tissue distribution, metabolism, and excretion of the antibody-drug conjugate Herceptin-monomethyl auristatin E in rats," Cancer Res, May 1, 2005, 65(9 Supplement):1195-6, 1 page (abstract only).

Resnick et al., "Epidermal growth factor receptor, cMET, B-catenin, and p53 expression as prognostic indicators in stage II colon cancer: a tissue microarray study," Clinical Cancer Research, May 2004, 10(9):3069-3075.

Saber et al., "An FDA oncology analysis of antibody-drug conjugates," Regulatory Toxicology and Pharmacology, Apr. 2015, 71(3):444-52.

Salgia, "MET in Lung Cancer: Biomarker Selection Based on Scientific Rationale," Molecular Cancer Therapeutics, Apr. 2017, 16(4):555-565.

Scagliotti et al., "A Randomized-Controlled Phase 2 Study of the MET Antibody Emibetuzumab in Combination with Erlotinib as First-Line Treatment for EGFR Mutation-Positive NSCLC Patients," Journal of Thoracic Oncology, Jan. 2020, 15(1):80-90.

Shen et al., "Conjugation site modulates the in vivo stability and therapeutic activity of antibody-drug conjugates," Nature Biotechnology, Feb. 2012, 30(2):184-189.

Sierra Jr. et al., "c-MET as a potential therapeutic target and biomarker in cancer," Therapeutic advances in medical oncology, Nov. 2011, 3(1 Suppl):S21-35.

Spigel et al., "Randomized Phase II trial of onartuzumab in combination with erlotinib in patients with advanced non-small-cell lung cancer," Journal of Clinical Oncology, Nov. 2013, 31(32):4105-4114.

Strickler et al., "Phase 1 dose-escalation and -expansion study of telisotuzumab (ABT-700), an Anti-c-met antibody, in patients with advanced solid tumors," Molecular cancer therapeutics, May 2020, 19(5):1210-1217.

Takahashi et al., "A phase I study of enfortumab vedotin in Japanese patients with locally advanced or metastatic urothelial carcinoma," Investigational new drugs, Aug. 2020, 38:1056-1066.

Toki et al., "Protease-mediated fragmentation of p-amidobenzyl ethers: a new strategy for the activation of anticancer prodrugs," The Journal of organic chemistry, Mar. 22, 2002, 67(6):1866-72.

Walker et al., "Monoclonal antibody mediated intracellular targeting of tallysomycin S10b," Bioorganic & medicinal chemistry letters, Aug. 16, 2004, 14(16):4323-7.

Walker et al., "Synthesis of an immunoconjugate of camptothecin," Bioorganic & medicinal chemistry letters, Jan. 2002, 12(2):217-219.

Wolf et al., "Capmatinib in MET Exon 14-Mutated or MET-Amplified Non-Small- Cell Lung Cancer," New England Journal of Medicine, Sep. 2020, 383(10):944-957.

Yang et al., "SHR-A1403, a novel c-Met antibody-drug conjugate, exerts encouraging anti-tumor activity in c-Met-overexpressing models," Acta Pharmacologica Sinica, Jan. 14, 2019, 40(7):971-979.

Yang et al., "EGFR-tyrosine kinase inhibitor treatment in a patient with advanced non-small cell lung cancer and concurrent exon 19 and 21 EGFR mutations: A case report and review of the literature," Oncol Lett. May 2016, 11(5):3546-3550.

Yuan et al., "Bayesian Optimal Interval Design: A Simple and Well-Performing Design for Phase I Oncology Trials," Clinical Cancer Research, Jul. 2016, 22(17):4291-4301.

Zalevsky et al., "Enhanced antibody half-life improves in vivo activity," Nature biotechnology, Feb. 2010, 28(2):157-9.

Lee et al., "An engineered human Fc domain that behaves like a pH-toggle switch for ultra-long circulation persistence," Nature Communications, Nov. 6, 2019, 10(1):5031, 11 pages.

Majumdar et al., "Correlations between changes in conformational dynamics and physical stability in a mutant IgG1 mAb engineered for extended serum half-life," Mabs, Jan. 2, 2015, 7(1);84-95, 13 pages.

* cited by examiner

| MYT # | Variable Heavy | Variable Light |
|---|---|---|
| MYT5351 | SEQ ID NO: 5 | SEQ ID NO: 6 |
| MYT4313 | SEQ ID NO: 7 | SEQ ID NO: 8 |
| MYT4325 | SEQ ID NO: 9 | SEQ ID NO: 10 |
| MYT4826 | SEQ ID NO: 11 | SEQ ID NO: 12 |
| MYT4837 | SEQ ID NO: 13 | SEQ ID NO: 14 |
| MYT4849 | SEQ ID NO: 15 | SEQ ID NO: 16 |
| MYT4942 | SEQ ID NO: 17 | SEQ ID NO: 18 |
| MYT5309 | SEQ ID NO: 19 | SEQ ID NO: 20 |
| MYT5344 | SEQ ID NO: 21 | SEQ ID NO: 22 |
| MYT5367 | SEQ ID NO: 23 | SEQ ID NO: 24 |
| MYT4827 | SEQ ID NO: 25 | SEQ ID NO: 26 |
| MYT4312 | SEQ ID NO: 27 | SEQ ID NO: 28 |
| MYT4953 | SEQ ID NO: 29 | SEQ ID NO: 30 |
| MYT4940 | SEQ ID NO: 31 | SEQ ID NO: 32 |
| MYT4888 | SEQ ID NO: 33 | SEQ ID NO: 34 |
| MYT2040 | SEQ ID NO: 159 | SEQ ID NO: 18 |
| MYT3463 | SEQ ID NO: 17 | SEQ ID NO: 190 |
| MYT3477 | SEQ ID NO: 17 | SEQ ID NO: 191 |
| MYT3491 | SEQ ID NO: 17 | SEQ ID NO: 192 |
| MYT3603 | SEQ ID NO: 17 | SEQ ID NO: 193 |
| MYT3604 | SEQ ID NO: 194 | SEQ ID NO: 193 |
| MYT3605 | SEQ ID NO: 195 | SEQ ID NO: 193 |
| MYT3606 | SEQ ID NO: 196 | SEQ ID NO: 193 |
| MYT3607 | SEQ ID NO: 197 | SEQ ID NO: 193 |
| MYT3608 | SEQ ID NO: 198 | SEQ ID NO: 193 |
| MYT3609 | SEQ ID NO: 199 | SEQ ID NO: 193 |
| MYT3610 | SEQ ID NO: 200 | SEQ ID NO: 193 |
| MYT3611 | SEQ ID NO: 31 | SEQ ID NO: 193 |
| MYT3612 | SEQ ID NO: 201 | SEQ ID NO: 193 |
| MYT3613 | SEQ ID NO: 202 | SEQ ID NO: 193 |
| MYT3614 | SEQ ID NO: 203 | SEQ ID NO: 193 |
| MYT3615 | SEQ ID NO: 17 | SEQ ID NO: 193 |
| MYT3616 | SEQ ID NO: 204 | SEQ ID NO: 193 |
| MYT4211 | SEQ ID NO: 17 | SEQ ID NO: 205 |
| MYT4212 | SEQ ID NO: 17 | SEQ ID NO: 206 |
| MYT4213 | SEQ ID NO: 17 | SEQ ID NO: 207 |
| MYT4214 | SEQ ID NO: 17 | SEQ ID NO: 208 |
| MYT4215 | SEQ ID NO: 17 | SEQ ID NO: 209 |
| MYT4216 | SEQ ID NO: 17 | SEQ ID NO: 210 |
| MYT4217 | SEQ ID NO: 17 | SEQ ID NO: 211 |
| MYT4218 | SEQ ID NO: 17 | SEQ ID NO: 212 |
| MYT4219 | SEQ ID NO: 17 | SEQ ID NO: 213 |
| MYT4220 | SEQ ID NO: 17 | SEQ ID NO: 214 |
| MYT2319 | SEQ ID NO: 19 | SEQ ID NO: 12 |
| MYT3978 | SEQ ID NO: 15 | SEQ ID NO: 20 |

FIG. 5

| | | |
|---|---|---|
| MYT2850 | SEQ ID NO: 11 | SEQ ID NO: 12 |
| MYT2861 | SEQ ID NO: 13 | SEQ ID NO: 12 |
| MYT4326 | SEQ ID NO: 15 | SEQ ID NO: 16 |
| MYT3999 | SEQ ID NO: 19 | SEQ ID NO: 215 |
| MYT4001 | SEQ NO: 11 | SEQ ID NO: 215 |
| MYT4007 | SEQ ID NO: 13 | SEQ ID NO: 215 |
| MYT4010 | SEQ ID NO: 19 | SEQ ID NO: 20 |
| MYT4011 | SEQ ID NO: 216 | SEQ ID NO: 20 |
| MYT4012 | SEQ ID NO: 11 | SEQ ID NO: 20 |
| MYT4013 | SEQ ID NO: 25 | SEQ ID NO: 20 |
| MYT4014 | SEQ ID NO: 217 | SEQ ID NO: 20 |
| MYT4015 | SEQ ID NO: 218 | SEQ ID NO: 20 |
| MYT4016 | SEQ ID NO: 219 | SEQ ID NO: 20 |
| MYT4017 | SEQ ID NO: 220 | SEQ ID NO: 20 |
| MYT4018 | SEQ ID NO: 13 | SEQ ID NO: 20 |
| MYT4019 | SEQ ID NO: 221 | SEQ ID NO: 20 |
| MYT4020 | SEQ ID NO: 222 | SEQ ID NO: 20 |
| MYT4021 | SEQ ID NO: 19 | SEQ ID NO: 223 |
| MYT4023 | SEQ ID NO: 11 | SEQ ID: NO: 223 |
| MYT4029 | SEQ ID NO: 13 | SEQ ID NO: 223 |
| MYT4032 | SEQ ID NO: 19 | SEQ ID NO: 224 |
| MYT4034 | SEQ ID NO: 11 | SEQ ID NO: 224 |
| MYT4040 | SEQ ID NO: 13 | SEQ ID NO: 224 |
| MYT4230 | SEQ ID NO: 225 | SEQ ID NO: 226 |
| MYT3698 | SEQ ID NO: 5 | SEQ ID NO: 8 |
| MYT3701 | SEQ ID NO: 21 | SEQ ID NO: 8 |
| MYT3735 | SEQ ID NO: 163 | SEQ ID NO: 22 |
| MYT3740 | SEQ ID NO: 163 | SEQ ID NO: 6 |
| MYT4313 | SEQ ID NO: 7 | SEQ ID NO: 8 |
| MYT4325 | SEQ ID NO: 9 | SEQ ID NO: 10 |
| MYT4247 | SEQ ID NO: 163 | SEQ ID NO: 24 |
| MYT5342 | SEQ ID NO: 227 | SEQ ID NO: 22 |
| MYT5343 | SEQ ID NO: 5 | SEQ ID NO: 22 |
| MYT5344 | SEQ ID NO: 21 | SEQ ID NO: 22 |
| MYT5345 | SEQ ID NO: 228 | SEQ ID NO: 22 |
| MYT5346 | SEQ ID NO: 229 | SEQ ID NO: 22 |
| MYT5347 | SEQ ID NO: 230 | SEQ ID NO: 22 |
| MYT5348 | SEQ ID NO: 231 | SEQ ID NO: 22 |
| MYT5349 | SEQ ID NO: 9 | SEQ ID NO: 22 |
| MYT5350 | SEQ ID NO: 227 | SEQ ID NO: 6 |
| MYT5351 | SEQ ID NO: 5 | SEQ ID NO: 6 |
| MYT5352 | SEQ ID NO: 21 | SEQ ID NO: 6 |
| MYT5353 | SEQ ID NO: 228 | SEQ ID NO: 6 |
| MYT5354 | SEQ ID NO: 229 | SEQ ID NO: 6 |
| MYT5355 | SEQ ID NO: 230 | SEQ ID NO: 6 |
| MYT5356 | SEQ ID NO: 231 | SEQ ID NO: 6 |

FIG. 5 (CONT)

| | | |
|---|---|---|
| MYT5357 | SEQ ID NO: 9 | SEQ ID NO: 6 |
| MYT5359 | SEQ ID NO: 5 | SEQ ID NO: 232 |
| MYT5360 | SEQ ID NO: 21 | SEQ ID NO: 232 |
| MYT5365 | SEQ ID NO: 9 | SEQ ID NO: 232 |
| MYT5366 | SEQ ID NO: 227 | SEQ ID NO: 24 |
| MYT5367 | SEQ ID NO: 5 | SEQ ID NO: 24 |
| MYT5368 | SEQ ID NO: 21 | SEQ ID NO: 24 |
| MYT5369 | SEQ ID NO: 228 | SEQ ID NO: 24 |
| MYT5370 | SEQ ID NO: 229 | SEQ ID NO: 24 |
| MYT5371 | SEQ ID NO: 230 | SEQ ID NO: 24 |
| MYT5372 | SEQ ID NO: 231 | SEQ ID NO: 24 |
| MYT5373 | SEQ ID NO: 9 | SEQ ID NO: 24 |
| MYT5375 | SEQ ID NO: 5 | SEQ ID NO: 233 |
| MYT5376 | SEQ ID NO: 21 | SEQ ID NO: 233 |
| MYT5381 | SEQ ID NO: 9 | SEQ ID NO: 233 |
| MYT4894 | SEQ ID NO: 159 | SEQ ID NO: 160 |
| MYT4970 | SEQ ID NO: 234 | SEQ ID NO: 160 |
| MYT3617 | SEQ ID NO: 225 | SEQ ID NO: 235 |

FIG. 5 (CONT)

| Candidate Name | Protein yield after purification from 50mL culture (mg) | Fold-change from corresponding control antibody in Internalization Assay (24h, 10nM antibody, Detroit 562 Cells) |
|---|---|---|
| MYT4826 | 0.52 | 5.00 |
| MYT4827 | 0.53 | 4.49 |
| MYT4837 | 0.54 | 4.22 |
| MYT4325 | 0.75 | 4.19 |
| MYT5351 | 0.33 | 3.82 |
| MYT4312 | 0.29 | 3.81 |
| MYT5309 | 0.42 | 3.52 |
| MYT4849 | 1.68 | 3.06 |
| MYT4888 | 0.40 | 3.01 |
| MYT5344 | 1.21 | 2.96 |
| MYT4313 | 0.58 | 2.94 |
| MYT5367 | 0.22 | 2.86 |
| MYT4942 | 0.73 | 2.03 |
| MYT4953 | 1.26 | 1.95 |
| MYT4940 | 0.57 | 1.79 |

FIG. 6

ANTI-cMet ANTIBODY-DRUG CONJUGATES AND USES THEREOF

CROSS-REFERENCE TO RELATED APPLICATIONS

This application is a continuation of U.S. patent application Ser. No. 18/273,078, filed Jul. 19, 2023, which is a National Phase application under 35 U.S.C. § 371 of International Patent Application No. PCT/US2022/015116, filed Feb. 3, 2022, which claims priority to U.S. Provisional Patent Application Ser. No. 63/145,348, filed Feb. 3, 2021; the entire contents each of which are herein incorporated by reference.

SEQUENCE LISTING

This application contains a Sequence Listing that has been submitted electronically as an XML file named "45395-0044002_SL_ST26.XML". The XML text file, created on Nov. 15, 2023, 371,236 bytes in size. The material in the XML file is hereby incorporated by reference in its entirety.

TECHNICAL FIELD

The present disclosure relates to the field of biotechnology, and more specifically, to antigen-binding molecules, such as antibodies.

BACKGROUND

Antibody-drug conjugates have been designed to combat a variety of diseases. One particular advantage of this approach is the ability for antibody-drug conjugates to have cytostatic or cytotoxic effects. Despite years of development, improved antibody-drug conjugates are desired.

SUMMARY

The present invention is based on the concept that antibodies can be generated that display enhanced efficacy (e.g., one or more of an increase (e.g., a detectable increase) in toxin liberation in a target mammalian cell, an increase (e.g., a detectable increase) in target mammalian cell killing, and an increase (e.g., a detectable increase) in endolysosomal delivery).

Provided herein are antibodies that include: (a) a heavy chain variable domain and a light chain variable domain selected from the group of: (i) SEQ ID NO: 5 and SEQ ID NO: 6, respectively; (ii) SEQ ID NO: 7 and SEQ ID NO: 8, respectively; (iii) SEQ ID NO: 9 and SEQ ID NO: 10, respectively; (iv) SEQ ID NO: 11 and SEQ ID NO: 12, respectively; (v) SEQ ID NO: 13 and SEQ ID NO: 14, respectively; (vi) SEQ ID NO: 15 and SEQ ID NO: 16, respectively; (vii) SEQ ID NO: 17 and SEQ ID NO: 18, respectively; (viii) SEQ ID NO: 19 and SEQ ID NO: 20, respectively; (ix) SEQ ID NO: 21 and SEQ ID NO: 22, respectively; (x) SEQ ID NO: 23 and SEQ ID NO: 24, respectively; (xi) SEQ ID NO: 25 and SEQ ID NO: 26, respectively; (xii) SEQ ID NO: 27 and SEQ ID NO: 28, respectively; (xiii) SEQ ID NO: 29 and SEQ ID NO: 30, respectively; (xiv) SEQ ID NO: 31 and SEQ ID NO: 32, respectively; (xv) SEQ ID NO: 33 and SEQ ID NO: 34, respectively; and (b) a heavy chain CH1-CH2-CH3 sequence of SEQ ID NO: 155 or SEQ ID NO: 189 comprising one or more of the following: (i) a lysine to cysteine substitution at amino acid position 105 and deletion of a threonine at amino acid positions 106 and 108; (ii) a methionine to tyrosine substitution at amino acid position 135, a serine to threonine substitution at amino acid position 137, and a threonine to glutamic acid substitution at amino acid position 139, (iii) a methionine to leucine substitution at amino acid position 311 and an asparagine to serine substitution at amino acid position 317; (iv) an alanine to a cysteine substitution at amino acid position 1; and/or a light chain $C_L$ sequence of SEQ ID NO: 157 comprising a valine to cysteine substitution at amino acid position 98.

In some embodiments of any of the antibodies described herein, the heavy chain CH1-CH2-CH3 sequence of SEQ ID NO: 155 or SEQ ID NO: 189 includes a lysine to cysteine substitution at amino acid position 105 and deletion of a threonine at amino acid positions 106 and 108. In some embodiments of any of the antibodies described herein, the antibody comprises heavy chain and light chain sequences selected from the group of: (i) SEQ ID NO: 35 and SEQ ID NO: 41, respectively; (ii) SEQ ID NO: 43 and SEQ ID NO: 49, respectively; (iii) SEQ ID NO: 51 and SEQ ID NO: 57, respectively; (iv) SEQ ID NO: 59 and SEQ ID NO: 65, respectively; (v) SEQ ID NO: 67 and SEQ ID NO: 73, respectively; (vi) SEQ ID NO: 75 and SEQ ID NO: 81, respectively; (vii) SEQ ID NO: 83 and SEQ ID NO: 89, respectively; (viii) SEQ ID NO: 91 and SEQ ID NO: 97, respectively; (ix) SEQ ID NO: 99 and SEQ ID NO: 105, respectively; (x) SEQ ID NO: 107 and SEQ ID NO: 113, respectively; (xi) SEQ ID NO: 115 and SEQ ID NO: 121, respectively; (xii) SEQ ID NO: 123 and SEQ ID NO: 129, respectively; (xiii) SEQ ID NO: 131 and SEQ ID NO: 137, respectively; (xiv) SEQ ID NO: 139 and SEQ ID NO: 145, respectively; or (xv) SEQ ID NO: 147 and SEQ ID NO: 153, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; and a methionine to leucine substitution at amino acid position 311 and an asparagine to serine substitution at amino acid position 317. In some embodiments of any of the antibodies described herein, the antibody comprises heavy chain and light chain sequences selected from the group of: (i) SEQ ID NO: 36 and SEQ ID NO: 41, respectively; (ii) SEQ ID NO: 44 and SEQ ID NO: 49, respectively; (iii) SEQ ID NO: 52 and SEQ ID NO: 57, respectively; (iv) SEQ ID NO: 60 and SEQ ID NO: 65, respectively; (v) SEQ ID NO: 68 and SEQ ID NO: 73, respectively; (vi) SEQ ID NO: 76 and SEQ ID NO: 81, respectively; (vii) SEQ ID NO: 84 and SEQ ID NO: 89, respectively; (viii) SEQ ID NO: 92 and SEQ ID NO: 97, respectively; (ix) SEQ ID NO: 100 and SEQ ID NO: 105, respectively; (x) SEQ ID NO: 108 and SEQ ID NO: 113, respectively; (xi) SEQ ID NO: 116 and SEQ ID NO: 121, respectively; (xii) SEQ ID NO: 124 and SEQ ID NO: 129, respectively; (xiii) SEQ ID NO: 132 and SEQ ID NO: 137, respectively; (xiv) SEQ ID NO: 140 and SEQ ID NO: 145, respectively; or (xv) SEQ ID NO: 148 and SEQ ID NO: 153, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; and a methionine to tyrosine substitution at amino acid position 135, a serine to threonine substitution at amino acid position 137, and a threonine to glutamic acid substitution at amino acid position 139. In some embodiments of any of the antibodies described herein, the antibody comprises heavy chain and light chain sequences selected from the group of: (i) SEQ ID NO: 37 and SEQ ID NO: 41, respectively; (ii) SEQ ID NO: 45 and SEQ ID NO: 49, respectively; (iii) SEQ ID NO: 53 and SEQ ID NO: 57, respectively; (iv) SEQ ID NO: 61 and SEQ ID NO: 65, respectively; (v) SEQ ID NO: 69 and SEQ ID NO: 73, respectively; (vi) SEQ ID NO: 77 and SEQ ID NO: 81, respectively; (vii) SEQ ID NO: 85 and SEQ ID NO: 89, respectively; (viii) SEQ ID NO: 93 and SEQ ID NO: 97, respectively; (ix) SEQ ID NO: 101 and SEQ ID NO: 105, respectively; (x) SEQ ID NO: 109 and SEQ ID NO: 113, respectively; (xi) SEQ ID NO: 117 and SEQ ID NO: 121, respectively; (xii) SEQ ID NO: 125 and SEQ ID NO: 129, respectively; (xiii) SEQ ID NO: 133 and SEQ ID NO: 137, respectively; (xiv) SEQ ID NO: 141 and SEQ ID NO: 145, respectively; or (xv) SEQ ID NO: 149 and SEQ ID NO: 153, respectively.

In some embodiments of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and the light chain $C_L$ sequence of SEQ ID NO: 157 comprises a valine to cysteine substitution at amino acid position 98. In some embodiments of any of the antibodies described herein, the antibody comprises heavy chain and light chain sequences selected from the group of: (i) SEQ ID NO: 35 and SEQ ID NO: 42, respectively; (ii) SEQ ID NO: 43 and SEQ ID NO: 50, respectively; (iii) SEQ ID NO: 51 and SEQ ID NO: 58, respectively; (iv) SEQ ID NO: 59 and SEQ ID NO: 66, respectively; (v) SEQ ID NO: 67 and SEQ ID NO: 74, respectively; (vi) SEQ ID NO: 75 and SEQ ID NO: 82, respectively; (vii) SEQ ID NO: 83 and SEQ ID NO: 90, respectively; (viii) SEQ ID NO: 91 and SEQ ID NO: 98, respectively; (ix) SEQ ID NO: 99 and SEQ ID NO: 106, respectively; (x) SEQ ID NO: 107 and SEQ ID NO: 114, respectively; (xi) SEQ ID NO: 115 and SEQ ID NO: 122, respectively; (xii) SEQ ID NO: 123 and SEQ ID NO: 130, respectively; (xiii) SEQ ID NO: 131 and SEQ ID NO: 138, respectively; (xiv) SEQ ID NO: 139 and SEQ ID NO: 146, respectively; or (xv) SEQ ID NO: 147 and SEQ ID NO: 154, respectively.

In some embodiments of any of the antibodies described herein, the heavy chain CH1-CH2-CH3 sequence of SEQ ID NO: 155 or SEQ ID NO: 189 comprises: a lysine to cysteine substitution at amino acid position 105 and deletion of a threonine at amino acid positions 106 and 108; and a methionine to leucine substitution at amino acid position 311 and an asparagine to serine substitution at amino acid position 317; and the light chain $C_L$ sequence of SEQ ID NO: 157 comprises a valine to cysteine substitution at amino acid position 98. In some embodiments of any of the antibodies described herein, the antibody comprises heavy chain and light chain sequences selected from the group of: (i) SEQ ID NO: 36 and SEQ ID NO: 42, respectively; (ii) SEQ ID NO: 44 and SEQ ID NO: 50, respectively; (iii) SEQ ID NO: 52 and SEQ ID NO: 58, respectively; (iv) SEQ ID NO: 60 and SEQ ID NO: 66, respectively; (v) SEQ ID NO: 68 and SEQ ID NO: 74, respectively; (vi) SEQ ID NO: 76 and SEQ ID NO: 82, respectively; (vii) SEQ ID NO: 84 and SEQ ID NO: 90, respectively; (viii) SEQ ID NO: 92 and SEQ ID NO: 98, respectively; (ix) SEQ ID NO: 100 and SEQ ID NO: 106, respectively; (x) SEQ ID NO: 108 and SEQ ID NO: 114, respectively; (xi) SEQ ID NO: 116 and SEQ ID NO: 122, respectively; (xii) SEQ ID NO: 124 and SEQ ID NO: 130, respectively; (xiii) SEQ ID NO: 132 and SEQ ID NO: 138, respectively; (xiv) SEQ ID NO: 140 and SEQ ID NO: 146, respectively; or (xv) SEQ ID NO: 148 and SEQ ID NO: 154, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; and a methionine to tyrosine substitution at amino acid position 135, a serine to threonine substitution at amino acid position 137, and a threonine to glutamic acid substitution at amino acid position 139; and the light chain $C_L$ sequence of SEQ ID NO: 157 comprises a valine to cysteine substitution at amino acid position 98. In some embodiments of any of the antibodies described herein, the antibody comprises heavy chain and light chain sequences selected from the group of: (i) SEQ ID NO: 37 and SEQ ID NO: 42, respectively; (ii) SEQ ID NO: 45 and SEQ ID NO: 50, respectively; (iii) SEQ ID NO: 53 and SEQ ID NO: 58, respectively; (iv) SEQ ID NO: 61 and SEQ ID NO: 66, respectively; (v) SEQ ID NO: 69 and SEQ ID NO: 74, respectively; (vi) SEQ ID NO: 77 and SEQ ID NO: 82, respectively; (vii) SEQ ID NO: 85 and SEQ ID NO: 90, respectively; (viii) SEQ ID NO: 93 and SEQ ID NO: 98, respectively; (ix) SEQ ID NO: 101 and SEQ ID NO: 106, respectively; (x) SEQ ID NO: 109 and SEQ ID NO: 114, respectively; (xi) SEQ ID NO: 117 and SEQ ID NO: 122, respectively; (xii) SEQ ID NO: 125 and SEQ ID NO: 130, respectively; (xiii) SEQ ID NO: 133 and SEQ ID NO: 138, respectively; (xiv) SEQ ID NO: 141 and SEQ ID NO: 146, respectively; or (xv) SEQ ID NO: 149 and SEQ ID NO: 154, respectively.

In some embodiments of any of the antibodies described herein, the heavy chain CH1-CH2-CH3 sequence of SEQ ID NO: 155 or SEQ ID NO: 189 includes: amino acid a lysine to cysteine substitution at amino acid position 105 and deletion of a threonine at positions 106 and 108; and an alanine to a cysteine substitution at amino acid position 1. In some embodiments of any of the antibodies described herein, the antibody comprises heavy chain and light chain sequences selected from the group of: (i) SEQ ID NO: 38 and SEQ ID NO: 41, respectively; (ii) SEQ ID NO: 46 and SEQ ID NO: 49, respectively; (iii) SEQ ID NO: 54 and SEQ ID NO: 57, respectively; (iv) SEQ ID NO: 62 and SEQ ID NO: 65, respectively; (v) SEQ ID NO: 70 and SEQ ID NO: 73, respectively; (vi) SEQ ID NO: 78 and SEQ ID NO: 81, respectively; (vii) SEQ ID NO: 86 and SEQ ID NO: 89, respectively; (viii) SEQ ID NO: 94 and SEQ ID NO: 97, respectively; (ix) SEQ ID NO: 102 and SEQ ID NO: 105, respectively; (x) SEQ ID NO: 110 and SEQ ID NO: 113, respectively; (xi) SEQ ID NO: 118 and SEQ ID NO: 121, respectively; (xii) SEQ ID NO: 126 and SEQ ID NO: 129, respectively; (xiii) SEQ ID NO: 134 and SEQ ID NO: 137, respectively; (xiv) SEQ ID NO: 142 and SEQ ID NO: 145, respectively; or (xv) SEQ ID NO: 150 and SEQ ID NO: 153, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; a methionine to leucine substitution at amino acid position 311 and an asparagine to serine substitution at amino acid position 317; and an alanine to a cysteine substitution at amino acid position 1. In some embodiments of any of the antibodies described herein, the antibody comprises a heavy chain and a light chain sequence selected from the group of: (i) SEQ ID NO: 39 and SEQ ID NO: 41, respectively; (ii) SEQ ID NO: 47 and SEQ ID NO: 49, respectively; (iii) SEQ ID NO:

55 and SEQ ID NO: 57, respectively; (iv) SEQ ID NO: 63 and SEQ ID NO: 65, respectively; (v) SEQ ID NO: 71 and SEQ ID NO: 73, respectively; (vi) SEQ ID NO: 79 and SEQ ID NO: 81, respectively; (vii) SEQ ID NO: 87 and SEQ ID NO: 89, respectively; (viii) SEQ ID NO: 95 and SEQ ID NO: 97, respectively; (ix) SEQ ID NO: 103 and SEQ ID NO: 105, respectively; (x) SEQ ID NO: 111 and SEQ ID NO: 113, respectively; (xi) SEQ ID NO: 119 and SEQ ID NO: 121, respectively; (xii) SEQ ID NO: 127 and SEQ ID NO: 129, respectively; (xiii) SEQ ID NO: 135 and SEQ ID NO: 137, respectively; (xiv) SEQ ID NO: 143 and SEQ ID NO: 145, respectively; or (xv) SEQ ID NO: 151 and SEQ ID NO: 153, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; a methionine to tyrosine substitution at amino acid position 135, a serine to threonine substitution at amino acid position 137, and a threonine to glutamic acid substitution at amino acid position 139; and an alanine to cysteine substitution at amino acid position 1. In some embodiments of any of the antibodies described herein, the antibody comprises a heavy chain and a light chain sequence selected from the group of: (i) SEQ ID NO: 40 and SEQ ID NO: 41, respectively; (ii) SEQ ID NO: 48 and SEQ ID NO: 49, respectively; (iii) SEQ ID NO: 56 and SEQ ID NO: 57, respectively; (iv) SEQ ID NO: 64 and SEQ ID NO: 65, respectively; (v) SEQ ID NO: 72 and SEQ ID NO: 73, respectively; (vi) SEQ ID NO: 80 and SEQ ID NO: 81, respectively; (vii) SEQ ID NO: 88 and SEQ ID NO: 89, respectively; (viii) SEQ ID NO: 96 and SEQ ID NO: 97, respectively; (ix) SEQ ID NO: 104 and SEQ ID NO: 105, respectively; (x) SEQ ID NO: 112 and SEQ ID NO: 113, respectively; (xi) SEQ ID NO: 120 and SEQ ID NO: 121, respectively; (xii) SEQ ID NO: 128 and SEQ ID NO: 129, respectively; (xiii) SEQ ID NO: 136 and SEQ ID NO: 137, respectively; (xiv) SEQ ID NO: 144 and SEQ ID NO: 145, respectively; or (xv) SEQ ID NO: 152 and SEQ ID NO: 153, respectively.

In some embodiments of any of the antibodies described herein, the antibody further comprises a cytotoxic drug conjugated to one or more of the following: (a) a heavy chain CH1-CH2-CH3 of SEQ ID NO: 155 or SEQ ID NO: 189 comprising one or more of the following: (i) the cysteine at amino acid position 103; (ii) the cysteine of a lysine to cysteine substitution at amino acid position 105; (iii) the cysteine at amino acid position 109; and (iv) the cysteine at amino acid position 112; and/or (b) the cysteine at amino acid position 107 of SEQ ID NO: 157.

In some embodiments of any of the antibodies described herein, the antibody further comprises a cytotoxic or cytostatic agent is conjugated to the cysteine at position 98 of SEQ ID NO: 157.

In some embodiments of any of the antibodies described herein, the antibody further comprises a cytotoxic or cytostatic agent is conjugated to the cysteine at position 1 of SEQ ID NO: 155 or SEQ ID NO: 189.

In some embodiments of any of the antibodies described herein, the cytotoxic or cytostatic agent is a conjugated toxin, a radioisotope, drug, or a small molecule.

In some embodiments of any of the antibodies described herein, (a) the dissociation rate of the antibody at a pH of about 4.0 to about 6.5 is faster than the dissociation rate at a pH of about 7.0 to about 8.0; or (b) the dissociation constant ($K_D$) of the antibody at a pH of about 4.0 to about 6.5 is greater than the $K_D$ at a pH of about 7.0 to about 8.0.

In some embodiments of any of the antibodies described herein, a composition comprising the antibody: provides for one or more of: an increase in toxin liberation in a target mammalian cell as compared to a composition comprising the same amount of a control antibody; an increase in target mammalian cell killing as compared to a composition comprising the same amount of a control antibody; and an increase in endolysosomal delivery in the target mammalian cell as compared to a composition comprising the same amount of a control antibody.

In some embodiments of any of the antibodies described herein, a composition comprising the antibody: results in a less of a reduction in the level of MET presented on the surface of a target mammalian cell as compared to a composition comprising the same amount of a control antibody; or does not result in a detectable reduction in the level of MET presented on the surface of the target mammalian cell.

In some embodiments of any of the antibodies described herein, the antibody is degraded in a target mammalian cell following internalization of the antibody by a target mammalian cell. In some embodiments of any of the antibodies described herein, the target mammalian cell is a cancer cell. In some embodiments of any of the antibodies described herein, the antibody is cytotoxic or cytostatic to the target mammalian cell. In some embodiments of any of the antibodies described herein, the antibody has an avidity that results in increased selectivity for cancer cells over non-cancerous cells.

In some embodiments of any of the antibodies described herein, the antibody is: cross-reactive with a non-human primate MET and human MET; or cross-reactive with a non-human primate MET, a human MET, and one or both of rat MET and a mouse MET. In some embodiments of any of the antibodies described herein, the half-life of the antibody in vivo is increased as compared to the half-life of a control antibody in vivo.

Also provided herein are pharmaceutical compositions comprising an effective amount of any of the antibodies described herein. Also provided herein are kits that include at least one dose of any of the antibodies described herein or any of the pharmaceutical compositions described herein.

Also provided herein are methods of treating a cancer characterized by having a population of cancer cells that have MET or an epitope of MET presented on their surface that include administering a therapeutically effective amount of any of the antibodies described herein or any of the pharmaceutical compositions described herein to a subject identified as having a cancer characterized by having the population of cancer cells.

Also provided herein are methods of reducing the volume of a tumor in a subject, where the tumor is characterized by having a population of cancer cells that have MET or an epitope of MET presented on their surface, that include: administering a therapeutically effective amount of any of the antibodies described herein or any of the pharmaceutical compositions described herein to a subject identified as having a cancer characterized by having the population of cancer cells.

Also provided herein are methods of inducing cell death in a cancer cell in a subject, wherein the cancer cell has MET or an epitope of MET presented on its surface, that include: administering a therapeutically effective amount of any of the antibodies described herein or any of the pharmaceutical compositions described herein to a subject identified as having a cancer characterized by having a population of the cancer cells.

Also provided herein are methods of decreasing the risk of developing a metastasis or decreasing the risk of developing an additional metastasis in a subject having a cancer, where the cancer is characterized by having a population of cancer cells that have MET or an epitope of MET presented on their surface, that include: administering a therapeutically effective amount of any of the antibodies described herein or any of the pharmaceutical compositions described herein to a subject identified as having a cancer characterized by having the population of cancer cells.

Also provided herein are antibodies that include: (a) heavy chain variable domain and a light chain variable domain selected from the group consisting of: (i) SEQ ID NO: 159 and SEQ ID NO: 160, respectively; (ii) SEQ ID NO: 161 and SEQ ID NO: 162, respectively; and (iii) SEQ ID NO: 163 and SEQ ID NO: 164; respectively; and (b) a heavy chain CH1-CH2-CH3 sequence of SEQ ID NO: 155 or SEQ ID NO: 189 comprising one or more of the following substitution(s): (i) a lysine to cysteine substitution at amino acid position 105 and deletion of a threonine amino acid at positions 106 and 108; (ii) a methionine to tyrosine substitution at amino acid position 135, a serine to threonine substitution at amino acid position 137, and a threonine to glutamic acid substitution at amino acid position 139, (iii) a methionine to leucine substitution at amino acid position 311 and an asparagine to serine substitution at amino acid position 317; (iv) an alanine to cysteine substitution at amino acid position 1; and/or a light chain $C_L$ sequence of SEQ ID NO: 157 comprising a valine to cysteine substitution at position 98.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108. In some embodiments of any of the antibodies described herein, the antibody comprises heavy chain and light chain sequences selected from the group of: (i) SEQ ID NO: 165 and SEQ ID NO: 171, respectively; (ii) SEQ ID NO: 173 and SEQ ID NO: 179, respectively; or (iii) SEQ ID NO: 181 and SEQ ID NO: 187, respectively.

In some embodiments of any of the antibodies described herein, the heavy CH1-CH2-CH3 sequence of SEQ ID NO: 155 or SEQ ID NO: 189 includes: a lysine to cysteine substitution at amino acid position 105 and deletion of a threonine at amino acid positions 106 and 108; a methionine to leucine substitution at amino acid position 311 and an asparagine to serine substitution at amino acid position 317. In some embodiments of any of the antibodies described herein, the antibody comprises heavy chain and light chain sequences selected from the group of: (i) SEQ ID NO: 166 and SEQ ID NO: 171, respectively; (ii) SEQ ID NO: 174 and SEQ ID NO: 179, respectively; or (iii) SEQ ID NO: 182 and SEQ ID NO: 187, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; and a methionine to tyrosine substitution at amino acid position 135, a serine to threonine substitution at amino acid position 137, and a threonine to glutamic acid substitution at amino acid position 139. In some embodiments of any of the antibodies described herein, the antibody comprises a heavy chain and a light chain sequence selected from the group of: (i) SEQ ID NO: 167 and SEQ ID NO: 171, respectively; (ii) SEQ ID NO: 175 and SEQ ID NO: 179, respectively; or (iii) SEQ ID NO: 183 and SEQ ID NO: 187, respectively.

In some embodiments of any of the antibodies described herein, the heavy chain CH1-CH2-CH3 sequence of SEQ ID NO: 155 or SEQ ID NO: 189 includes a lysine to cysteine substitution at amino acid position 105 and deletion of a threonine at amino acid positions 106 and 108; and the light chain $C_L$ sequence of SEQ ID NO: 157 includes a valine to cysteine substitution at amino acid position 98. In some embodiments of any of the antibodies described herein, the antibody comprises heavy chain and light chain sequences selected from the group of: (i) SEQ ID NO: 165 and SEQ ID NO: 172, respectively; (ii) SEQ ID NO: 173 and SEQ ID NO: 180, respectively; or (iii) SEQ ID NO: 181 and SEQ ID NO: 188, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; and a methionine to leucine substitution at amino acid position 311 and an asparagine to serine substitution at amino acid position 317; and the light chain $C_L$ sequence of SEQ ID NO: 157 includes a valine to cysteine substitution at amino acid position 98. In some embodiments of any of the antibodies described herein, the antibody comprises heavy chain and light chain sequences selected from the group of: (i) SEQ ID NO: 166 and SEQ ID NO: 172, respectively; (ii) SEQ ID NO: 174 and SEQ ID NO: 180, respectively; or (iii) SEQ ID NO: 182 and SEQ ID NO: 188, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; and a methionine to tyrosine substitution at amino acid position 135, a serine to threonine substitution at amino acid position 137, and a threonine to glutamic acid substitution at amino acid position 139; and the light chain $C_L$ sequence of SEQ ID NO: 157 includes a valine to cysteine substitution at amino acid position 98. In some embodiments of any of the antibodies described herein, the antibody comprises heavy chain and light chain sequences selected from the group of: (i) SEQ ID NO: 167 and SEQ ID NO: 172, respectively; (ii) SEQ ID NO: 175 and SEQ ID NO: 180, respectively; or (iii) SEQ ID NO: 183 and SEQ ID NO: 188, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; and an alanine to a cysteine substitution at amino acid position 1. In some embodiments of any of the antibodies described herein, the antibody comprises heavy chain and light chain sequences selected from the group of: (i) SEQ ID NO: 168 and SEQ ID NO: 171, respectively; (ii) SEQ ID NO: 176 and SEQ ID NO: 179, respectively; or (iii) SEQ ID NO: 184 and SEQ ID NO: 187, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; a methionine to leucine substitution at amino acid position 311 and an asparagine to serine substitution at amino acid position 317; and an alanine to a cysteine substitution at amino acid position 1. In some embodiments of any of the antibodies described herein, the antibody comprises a heavy chain and a light chain sequence selected from the group of: (i) SEQ ID NO: 169 and SEQ ID NO: 171, respectively; (ii) SEQ ID NO: 177 and SEQ ID NO: 179, respectively; or (iii) SEQ ID NO: 185 and SEQ ID NO: 187, respectively.

In some embodiments of any of the antibodies described herein, the heavy chain CH1-CH2-CH3 sequence of SEQ ID NO: 155 or SEQ ID NO: 189 includes: a lysine to cysteine substitution at amino acid position 105 and deletion of a threonine at amino acid positions 106 and 108; a methionine to tyrosine substitution at amino acid position 135, a serine to threonine substitution at amino acid position 137, and a threonine to glutamic acid substitution at amino acid position 139; and an alanine to a cysteine substitution at amino acid position 1. In some embodiments of any of the antibodies described herein, the antibody comprises heavy chain and light chain sequences selected from the group of: (i) SEQ ID NO: 170 and SEQ ID NO: 171, respectively; (ii) SEQ ID NO: 178 and SEQ ID NO: 179, respectively; or (iii) SEQ ID NO: 186 and SEQ ID NO: 187, respectively.

In some embodiments of any of the antibodies described herein, the antibody further comprises a cytotoxic drug conjugated to one or more of the following: (a) a heavy chain CH1-CH2-CH3 of SEQ ID NO: 155 or SEQ ID NO: 189 comprising one or more of the following: (i) the cysteine at amino acid position 103; (ii) the cysteine of a lysine to cysteine substitution at amino acid position 105; (iii) the cysteine at amino acid position 109; (iv) the cysteine at amino acid position 112; and/or (b) the cysteine at amino acid position 107 of SEQ ID NO: 157.

In some embodiments of any of the antibodies described herein, the antibody further comprises a cytotoxic or cytostatic agent is conjugated to the cysteine at position 98 of SEQ ID NO: 157. In some embodiments of any of the antibodies described herein, the antibody further comprises a cytotoxic or cytostatic agent is conjugated to the cysteine at position 1 of SEQ ID NO: 155 or SEQ ID NO: 189.

In some embodiments of any of the antibodies described herein, the cytotoxic or cytostatic agent is a conjugated toxin, a radioisotope, drug, or a small molecule. In some embodiments of any of the antibodies described herein, the antibody is cytotoxic or cytostatic to a target mammalian cell. In some embodiments of any of the antibodies described herein, the antibody is degraded in the target mammalian cell following internalization of the antibody by the target mammalian cell. In some embodiments of any of the antibodies described herein, the target mammalian cell is a cancer cell. In some embodiments of any of the antibodies described herein, the antibody has an avidity that results in increased selectivity for cancer cells over non-cancerous cells.

In some embodiments of any of the antibodies described herein, the antibody is: cross-reactive with a non-human primate MET and human MET; or cross-reactive with a non-human primate MET, a human MET, and one or both of rat MET and a mouse MET.

In some embodiments of any of the antibodies described herein, the half-life of the antibody in vivo is increased as compared to the half-life of a control antibody in vivo.

In some embodiments of any of the antibodies described herein, the target mammalian cell is a cancer cell.

Also provided herein are pharmaceutical compositions comprising an effective amount of any of the antibodies described herein. Also provided herein are kits that include at least one dose of any of the antibodies described herein or any of the pharmaceutical compositions described herein.

Also provided herein are methods of treating a cancer characterized by having a population of cancer cells that have MET or an epitope of MET presented on their surface that include administering a therapeutically effective amount of any of the antibodies described herein or any of the pharmaceutical compositions described herein to a subject identified as having a cancer characterized by having the population of cancer cells.

Also provided herein are methods of reducing the volume of a tumor in a subject, where the tumor is characterized by having a population of cancer cells that have MET or an epitope of MET presented on their surface, that include: administering a therapeutically effective amount of any of the antibodies described herein or any of the pharmaceutical compositions described herein to a subject identified as having a cancer characterized by having the population of cancer cells.

Also provided herein are methods of inducing cell death in a cancer cell in a subject, wherein the cancer cell has MET or an epitope of MET presented on its surface, that include: administering a therapeutically effective amount of any of the antibodies described herein or any of the pharmaceutical compositions described herein to a subject identified as having a cancer characterized by having a population of the cancer cells.

Also provided herein are methods of decreasing the risk of developing a metastasis or decreasing the risk of developing an additional metastasis in a subject having a cancer, where the cancer is characterized by having a population of cancer cells that have MET or an epitope of MET presented on their surface, that include: administering a therapeutically effective amount of any of the antibodies described herein or any of the pharmaceutical compositions described herein to a subject identified as having a cancer characterized by having the population of cancer cells.

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art. In some examples, an antigen-binding domain can bind to a single antigen.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins, e.g., human IgG (e.g., human IgG1, human IgG2, human IgG3, human IgG4)), antibody fragments, and multi-specific antibodies. One example of an antigen-binding domain is an antigen-binding domain formed by a VH-VL dimer. Additional examples of an antibody are described herein. Additional examples of an antibody are known in the art.

The phrase "endosomal/lysosomal pathway" refers to a network of endosomes (early endosomes, multi-vesicular bodies, late endosomes, and lysosomes) in the cytoplasm of a mammalian cell, wherein molecules internalized through cell-mediated internalization processes, e.g., pinocytosis, micropinocytosis, receptor-mediated endocytosis, and/or phagocytosis, are sorted.

Once the endosomes in the endosomal/lysosomal pathway are purified or isolated, assays for a target protein (e.g., an antibody described herein) can be performed using methods known in the art (ELISA, Western blot, immunofluorescence, and immunoprecipitation followed by an assay for protein concentration), and can be used to determine the concentration or relative level of the target protein in the endosomes. Alternatively, endosomes in the endosomal/lysosomal pathway can be imaged using immunofluorescence microscopy using an detectably-labelled antibody (e.g., a fluorophore-labelled, a dye-labelled, or a GFP-labelled antibody, e.g., CellLight™ Early Endosome-GFP) that specifically binds to a characteristic protein present in the endosomes (e.g., EEA1 for early endosomes) and a fluorophore-labelled antibody that specifically binds to the protein of interest (e.g., an antibody), and the level of the target protein in the endosomes can be determined by quantitation of the overlap in the fluorescence emissions of the two different antibodies.

The phrase "endolysosomal delivery" refers to rate of accumulation over time or the total accumulation at a specific timepoint of an antibody (e.g., any of the antibodies described herein) in the endosomal/lysosomal pathway in a mammalian cell (e.g., any of the exemplary target mammalian cells described herein).

An exemplary assay for measuring endolysosomal delivery of any of the antibodies described herein include those which involve labeling of an antibody with a fluorescent dye, followed by incubation of the labeled antibody with cells and measurement of cellular fluorescence as an indicator of endolysosomal delivery of the antibody (e.g., as described generally in Wustner, *Traffic* 7(6):699-715, 2006). Alternatively, pH-sensitive dyes which preferentially fluoresce at acidic pH but not neutral pH can be used to label any of the antibodies described herein, which can then be incubated with cells and the cellular fluorescence measured as an indicator of delivery of the antibody into acidic endolysosomal compartments.

The term "population" when used before a noun means two or more of the specific noun. For example, the phrase "a population of cancer cells" means "two or more cancer cells." Non-limiting examples of cancer cells are described herein.

The phrase "cytostatic to a cell" refers to a direct or indirect decrease in the proliferation (cell division) of the cell (e.g., a cancer cell) in vivo or in vitro. When an agent is cytostatic to a cell, the agent can, e.g., directly or indirectly result in cell cycle arrest of the cell (e.g., a cancer cell). In some examples, an agent that is cytostatic to a cell can reduce the number of cells in a population of the cells that are in S phase (as compared to the number of cells in a population of the cells that are in S phase prior to contact with the agent). In some examples, an agent that is cytostatic to a cell can reduce the percentage of the cells in S phase by at least 20%, at least 40%, at least 60%, or at least 80% (e.g., as compared to the percentage of cells in a population of the cells that are in S phase prior to contact with the agent).

The phrase "cytotoxic to a cell" refers to the inducement, directly or indirectly, in the death (e.g., necrosis or apoptosis) of the cell (e.g., a mammalian cell, e.g., a cancer cell).

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

The term "epitope" means a portion of an antigen that is specifically bound by an antigen-binding domain through a set of physical interactions between: (i) all monomers (e.g. individual amino acid residues, sugar side chains, and post-translationally modified amino acid residues) on the portion of the antigen-binding domain that specifically binds the antigen and (ii) all monomers (e.g. individual amino acid residues, sugar side chains, post-translationally modified amino acid residues) on the portion of the antigen that is specifically bound by the antigen-binding domain. Epitopes can, e.g., consist of surface-accessible amino acid residues, sugar side chains, phosphorylated amino acid residues, methylated amino acid residues, and/or acetylated amino acid residues and may have specific three-dimensional structural characteristics, as well as specific charge characteristics. Conformational and non-conformational epitopes are distinguished in that binding to the former, but not the latter, may be lost in the presence of denaturing solvents. In some embodiments, an epitope is defined by a linear amino acid sequence of at least about 3 to 6 amino acids, or about 10 to 15 amino acids. In some embodiments, an epitope refers to a portion of a full-length protein or a portion thereof that is defined by a three-dimensional structure (e.g., protein folding). In some embodiments, an epitope is defined by a discontinuous amino acid sequence that is brought together via protein folding. In some embodiments, an epitope is defined by a discontinuous amino acid sequence that is brought together by quaternary structure (e.g., a cleft formed by the interaction of two different polypeptide chains). The amino acid sequences between the residues that define the epitope may not be critical to three-dimensional structure of the epitope. A conformational epitope may be determined and screened using assays that compare binding of an antibody to a denatured version of the antigen, such that a linear epitope is generated. An epitope may include amino acid residues that are directly involved in the binding, and other amino acid residues, which are not directly involved in the binding.

Methods for identifying an epitope to which an antigen-binding domain specifically binds are known in the art, e.g., structure-based analysis (e.g. X-ray crystallography, NMR, and/or electron microscopy) (e.g. on the antigen and/or the antigen-antigen binding domain complex) and/or mutagenesis-based analysis (e.g. alanine scanning mutagenesis, glycine scanning mutagenesis, and homology scanning mutagenesis) wherein mutants are measured in a binding assay with a binding partner, many of which are known in the art.

The term "paratope" means a portion of an antigen-binding domain that specifically binds to an antigen through a set of physical interactions between: (i) all monomers (e.g. individual amino acid residues, sugar side chains, posttranslationally modified amino acid residues) on the portion of the antigen-binding domain that specifically binds the antigen and (ii) all monomers (e.g. individual amino acid residues, sugar side chains, posttranslationally modified amino acid residues) on the portion of the antigen that is specifically bound by the antigen-binding domain. Paratopes can, e.g. consist of surface-accessible amino acid residues and may have specific three-dimensional structural characteristics, as well as specific charge characteristics. In some embodiments, a paratope refers to a portion of a full-length antigen-binding domain or a portion thereof that is defined by a three-dimensional structure (e.g., protein folding). In some embodiments, a paratope is defined by a discontinuous amino acid sequence that is brought together via protein folding. In some embodiments, an epitope is defined by a discontinuous amino acid sequence that is brought together by quaternary structure (e.g., a cleft formed by the interaction of two different polypeptide chains). The amino acid sequences between the residues that define the paratope may not be critical to three-dimensional structure of the paratope. A paratope may comprise amino acid residues that are directly involved in the binding, and other amino acid residues, which are not directly involved in the binding.

Methods for identifying a paratope to which an antigen-binding domain specifically binds are known in the art, e.g., structure-based analysis (e.g., X-ray crystallography, NMR, and/or electron microscopy) (e.g. on the antigen-binding domain, and/or the antigen binding domain-antigen complex), and/or mutagenesis-based analysis (e.g., alanine scanning mutagenesis, glycine scanning mutagenesis, and homology scanning mutagenesis) wherein mutants are measured in a binding assay with a binding partner, many of which are known in the art.

The phrase "present on the surface of a mammalian cell" means (1) an antigen that physically attached to or at least partially embedded in the plasma membrane of a mammalian cell (e.g., a transmembrane protein, a peripheral membrane protein, a lipid-anchored protein (e.g., a GPI-anchor), an N-myristolyated protein, or a S-palmitoylated protein) or (2) an antigen that is stably bound to its cognate receptor, where the cognate receptor is physically attached to the plasma membrane of a mammalian cell (e.g., a ligand bound to its cognate receptor, where the cognate receptor is physically attached to the plasma membrane). Non-limiting methods for determining the presence of antigen on the surface of a mammalian cell include fluorescence-activated cell sorting (FACS), immunohistochemistry, cell-fractionation assays and Western blotting.

The phrase "control antibody" means (i) an antibody that is capable of specifically binding to MET or an epitope of MET presented on the surface of a mammalian cell (e.g., a target mammalian cell), where one or both of the following is true: (a) the dissociation rate of the first antigen-binding domain at a pH of about 4.0 to about 6.5 (e.g., any of the subranges of this range described herein) is no more than 3-fold (e.g., no more than 2.8-fold, no more than 2.6-fold, no more than 2.5-fold, no more than 2.4-fold, no more than 2.2-fold, no more than 2.0-fold, no more than 1.8-fold, no more than 1.6-fold, no more than 1.5-fold, no more than 1.4-fold, no more than 1.2-fold, no more than 1.0-fold, no more than 0.8-fold, no more than 0.6-fold, no more than 0.5-fold, no more than 0.4-fold, no more than 0.3-fold no more than 0.2-fold, or no more than 0.1-fold) faster than the dissociation rate at a pH of about 7.0 to about 8.0 (e.g., any of the subranges of this range described herein); or (b) the dissociation constant ($K_D$) of the first antigen-binding domain at a pH of about 4.0 to about 6.5 (e.g., any of the subranges of this range described herein) is no more than 3-fold (e.g., no more than 2.8-fold, no more than 2.6-fold, no more than 2.5-fold, no more than 2.4-fold, no more than 2.2-fold, no more than 2.0-fold, no more than 1.8-fold, no more than 1.6-fold, no more than 1.5-fold, no more than 1.4-fold, no more than 1.2-fold, no more than 1.0-fold, no more than 0.8-fold, no more than 0.6-fold, no more than 0.5-fold, no more than 0.4-fold, no more than 0.3-fold no more than 0.2-fold, or no more than 0.1-fold) greater than the $K_D$ at a pH of about 7.0 to about 8.0 (e.g., any of the subranges of this range described herein); and/or (ii) Telisotuzumab; (iii) Emibetuzumab; and/or (iv) P3D12.

The term "extracellular space" means the liquid exterior to the plasma membrane of a mammalian cell. When a mammalian cell is in vitro, the extracellular space can be a liquid culture medium. When a mammalian cell is in vivo, the extracellular space can be, e.g., plasma, serum, blood, interstitial fluid, or lymph.

The term "endolysosomal space" means the fluid encapsulated by the vesicles and organelles that make-up the endosomal/lysosomal pathway in a mammalian cell.

The phrase "a reduced level" or "a decreased level" can be a reduction or decrease of at least a 1% (e.g., at least 2%, at least 4%, at least 6%, at least 8%, at least 10%, at least 12%, at least 14%, at least 16%, at least 18%, at least 20%, at least 22%, at least 24%, at least 26%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) reduction as compared to a reference level or value.

The term "cell killing potency" refers to the ability of an agent (e.g., any of the antibodies described herein) to induce, directly or indirectly, the apoptosis and/or necrosis of a mammalian cell (e.g., a cancer cell), measured as a rate over time or at a relevant timepoint. Methods for determining the cell killing potency of a cell are known in the art (e.g., trypan blue staining, microscopy, fluorescence-assisted cell sorting, and assays to detect markers of apoptosis (e.g., Annexin V)). In non-limiting examples, cell killing potency can be measured, e.g., by cell killing at a single concentration of an agent, by the IC50 of the agent (i.e. the concentration of the agent whereby half the maximal cell killing potency is achieved), or by the ratio of an agent's dissociation constant KD on mammalian cells divided by its IC50. In some non-limiting examples, the IC50s and/or the KD ratios described herein are compared to those of a control antibody (as defined herein), and, optionally, demonstrate that the antibodies described herein have a higher cell killing potency as compared to the control antibody.

The term "toxin liberation" refers to the ability of a mammalian cell (e.g., a non-cancerous mammalian cell or a cancer cell) to internalize (e.g., via pinocytosis and/or receptor-mediated endocytosis) any of the antibodies described herein (e.g., any of antibodies or control antibodies described herein) that are conjugated to a toxin, and subsequently release the toxin conjugated to the antibody, measured as a rate over time or at a specific timepoint. Toxin liberation can be assessed using a variety of different exemplary assays, e.g., ELISA, immunofluorescence, cell killing assays, cell cycle arrest assays, DNA damage assays, mass spectrometry, HPLC, and/or an isotope-labeled toxin.

The phrase "target cell" or "target mammalian cell" or "mammalian target cell" means a mammalian cell that has at least one MET present on its surface. In some examples, a mammalian target cell can be a cancer cell. In some embodiments of a target mammalian cell can have a total of about 1 to about 10,000,000, about 1 to about 9,000,000, about 1 to about 8,000,000, about 1 to about 7,000,000, about 1 to about 6,000,000, about 1 to about 5,000,000, about 1 to about 4,000,000, about 1 to about 3,000,000, about 1 to about 2,000,000, about 1 to about 1,000,000, about 1 to about 800,000, about 1 to about 600,000, about 1 to about 400,000, about 1 to about 200,000, about 1 to about 100,000, about 1 to about 80,000, about 1 to about 80,000, about 1 to about 75,000, about 1 to about 70,000, about 1 to about 65,000, about 1 to about 60,000, about 1 to about 55,000, about 1 to about 50,000, about 1 to about 45,000, about 1 to about 40,000, about 1 to about 35,000, about 1 to about 30,000, about 1 to about 25,000, about 1 to about 20,000, about 1 to about 15,000, about 1 to about 10,000, about 1 to about 7,500, about 1 to about 5,000, about 1 to about 4,000, about 1 to about 3,000, about 1 to about 2,000, about 1 to about 1,000, about 1 to about 500, about 1 to about 100, about 1 to about 50, about 1 to about 10, about 10 to about 10,000,000, about 10 to about 9,000,000, about 10 to about 8,000,000, about 10 to about 7,000,000, about 10 to about 6,000,000, about 10 to about 5,000,000, about 10 to about 4,000,000, about 10 to about 3,000,000, about 10 to about 2,000,000, about 10 to about 1,000,000, about 10 to about 800,000, about 10 to about 600,000, about 10 to about 400,000, about 10 to about 200,000, about 10 to about 100,000, about 10 to about 80,000, about 10 to about 80,000, about 10 to about 75,000, about 10 to about 70,000, about 10 to about 65,000, about 10 to about 60,000, about 10 to about 55,000, about 10 to about 50,000, about 10 to about 45,000, about 10 to about 40,000, about 10 to about 35,000, about 10 to about 30,000, about 10 to about 25,000, about 10 to about 20,000, about 10 to about 15,000, about 10 to about 10,000, about 10 to about 7,500, about 10 to about 5,000, about 10 to about 4,000, about 10 to about 3,000, about 10 to about 2,000, about 10 to about 1,000, about 10 to about 500, about 10 to about 100, about 10 to about 50, about 50 to about 10,000,000, about 50 to about 9,000,000, about 50 to about 8,000,000, about 50 to about 7,000,000, about 50 to about 6,000,000, about 50 to about 5,000,000, about 50 to about 4,000,000, about 50 to about 3,000,000, about 50 to about 2,000,000, about 50 to about 1,000,000, about 50 to about 800,000, about 50 to about 600,000, about 50 to about 400,000, about 50 to about 200,000, about 50 to about 100,000, about 50 to about 80,000, about 50 to about 80,000, about 50 to about 75,000, about 50 to about 70,000, about 50 to about 65,000, about 50 to about 60,000, about 50 to about 55,000, about 50 to about 50,000, about 50 to about 45,000, about 50 to about 40,000, about 50 to about 35,000, about 50 to about 30,000, about 50 to about 25,000, about 50 to about 20,000, about 50 to about 15,000, about 50 to about 10,000, about 50 to about 7,500, about 50 to about 5,000, about 50 to about 4,000, about 50 to about 3,000, about 50 to about 2,000, about 50 to about 1,000, about 50 to about 500, about 50 to about 100, about 100 to about 10,000,000, about 100 to about 9,000,000, about 100 to about 8,000,000, about 100 to about 7,000,000, about 100 to about 6,000,000, about 100 to about 5,000,000, about 100 to about 4,000,000, about 100 to about 3,000,000, about 100 to about 2,000,000, about 100 to about 1,000,000, about 100 to about 800,000, about 100 to about 600,000, about 100 to about 400,000, about 100 to about 200,000, about 100 to about 100,000, about 100 to about 80,000, about 100 to about 75,000, about 100 to about 70,000, about 100 to about 65,000, about 100 to about 60,000, about 100 to about 55,000, about 100 to about 50,000, about 100 to about 45,000, about 100 to about 40,000, about 100 to about 35,000, about 100 to about 30,000, about 100 to about 25,000, about 100 to about 20,000, about 100 to about 15,000, about 100 to about 10,000, about 100 to about 7,500, about 100 to about 5,000, about 100 to about 4,000, about 100 to about 3,000, about 100 to about 2,000, about 100 to about 1,000, about 100 to about 500, about 500 to about 10,000,000, about 500 to about 9,000,000, about 500 to about 8,000,000, about 500 to about 7,000,000, about 500 to about 6,000,000, about 500 to about 5,000,000, about 500 to about 4,000,000, about 500 to about 3,000,000, about 500 to about 2,000,000, about 500 to about 1,000,000, about 500 to about 800,000, about 500 to about 600,000, about 500 to about 400,000, about 500 to about 200,000, about 500 to about 100,000, about 500 to about 80,000, about 500 to about 75,000, about 500 to about 70,000, about 500 to about 65,000, about 500 to about 60,000, about 500 to about 55,000, about 500 to about 50,000, about 500 to about 45,000, about 500 to about 40,000, about 500 to about 35,000, about 500 to about 30,000, about 500 to about 25,000, about 500 to about 20,000, about 500 to about 15,000, about 500 to about 10,000, about 500 to about 7,500, about 500 to about 5,000, about 500 to about 4,000, about 500 to about 3,000, about 500 to about 2,000, about 500 to about 1,000, about 1,000 to about 10,000,000, about 1,000 to about 9,000,000, about 1,000 to about 8,000,000, about 1,000 to about 7,000,000, about 1,000 to about 6,000,000, about 1,000 to about 5,000,000, about 1,000 to about 4,000,000, about 1,000 to about 3,000,000, about 1,000 to about 2,000,000, about 1,000 to about 1,000,000, about 1,000 to about 800,000, about 1,000 to about 600,000, about 1,000 to about 400,000, about 1,000 to about 200,000, about 1,000 to about 100,000, about 1,000 to about 80,000, about 1,000 to about 75,000, about 1,000 to about 70,000, about 1,000 to about 65,000, about 1,000 to about 60,000, about 1,000 to about 55,000, about 1,000 to about 50,000, about 1,000 to about 45,000, about 1,000 to about 40,000, about 1,000 to about 35,000, about 1,000 to about 30,000, about 1,000 to about 25,000, about 1,000 to about 20,000, about 1,000 to about 15,000, about 1,000 to about 10,000, about 1,000 to about 7,500, about 1,000 to about 5,000, about 1,000 to about 4,000, about 1,000 to about 3,000, about 1,000 to about 2,000, about 2,000 to about 10,000,000, about 2,000 to about 9,000,000, about 2,000 to about 8,000,000, about 2,000 to about 7,000,000, about 2,000 to about 6,000,000, about 2,000 to about 5,000,000, about 2,000 to about 4,000,000, about 2,000 to about 3,000,000, about 2,000 to about 2,000,000, about 2,000 to about 1,000,000, about 2,000 to about 800,000, about 2,000 to about 600,000, about 2,000 to about 400,000, about 2,000 to about 200,000, about 2,000 to about 100,000, about 2,000 to about 80,000, about 2,000 to about 75,000, about 2,000 to about 70,000, about 2,000 to about 65,000, about 2,000 to about 60,000, about 2,000 to about 55,000, about 2,000 to about 50,000, about 2,000 to about 45,000, about 2,000 to about 40,000, about 2,000 to about 35,000, about 2,000 to about 30,000, about 2,000 to about 25,000, about 2,000 to about 20,000, about 2,000 to about 15,000, about 2,000 to about 10,000, about 2,000 to about 7,500, about 2,000 to about 5,000, about 2,000 to about 4,000, about 2,000 to about 3,000, about 3,000 to about 10,000,000, about 3,000 to about 9,000,000, about 3,000 to about 8,000,000, about 3,000 to about 7,000,000, about 3,000 to about 6,000,000, about 3,000 to about 5,000,000, about 3,000 to about 4,000,000, about 3,000 to about 3,000,000, about 3,000 to about 2,000,000, about 3,000 to about 1,000,000, about 3,000 to about 800,000, about 3,000 to about 600,000, about 3,000 to about 400,000, about 3,000 to about 200,000, about 3,000 to about 100,000, about 3,000 to about 80,000, about 3,000 to about 75,000, about 3,000 to about 70,000, about 3,000 to about 65,000, about 3,000 to about 60,000, about 3,000 to about 55,000, about 3,000 to about 50,000, about 3,000 to about 45,000, about 3,000 to about 40,000, about 3,000 to about 35,000, about 3,000 to about 30,000, about 3,000 to about 25,000, about 3,000 to about 20,000, about 3,000 to about 15,000, about 3,000 to about 10,000, about 3,000 to about 7,500, about 3,000 to about 5,000, about 3,000 to about 4,000, about 4,000 to about 10,000,000, about 4,000 to about 9,000,000, about 4,000 to about 8,000,000, about 4,000 to about 7,000,000, about 4,000 to about 6,000,000, about 4,000 to about 5,000,000, about 4,000 to about 4,000,000, about 4,000 to about 3,000,000, about 4,000 to about 2,000,000, about 4,000 to about 1,000,000, about 4,000 to about 800,000, about 4,000 to about 600,000, about 4,000 to about 400,000, about 4,000 to about 200,000, about 4,000 to about 100,000, about 4,000 to about 80,000, about 4,000 to about 75,000, about 4,000 to about 70,000, about 4,000 to about 65,000, about 4,000 to about 60,000, about 4,000 to about 55,000, about 4,000 to about 50,000, about 4,000 to about 45,000, about 4,000 to about 40,000, about 4,000 to about 35,000, about 4,000 to about 30,000, about 4,000 to about 25,000, about 4,000 to about 20,000, about 4,000 to about 15,000, about 4,000 to about 10,000, about 4,000 to about 7,500, about 4,000 to about 5,000, about 5,000 to about 10,000,000, about 5,000 to about 9,000,000, about 5,000 to about 8,000,000, about 5,000 to about 7,000,000, about 5,000 to about 6,000,000, about 5,000 to about 5,000,000, about 5,000 to about 4,000,000, about 5,000 to about 3,000,000, about 5,000 to about 2,000,000, about 5,000 to about 1,000,000, about 5,000 to about 800,000, about 5,000 to about 600,000, about 5,000 to about 400,000, about 5,000 to about 200,000, about 5,000 to about 100,000, about 5,000 to about 80,000, about 5,000 to about 75,000, about 5,000 to about 70,000, about 5,000 to about 65,000, about 5,000 to about 60,000, about 5,000 to about 55,000, about 5,000 to about 50,000, about 5,000 to about 45,000, about 5,000 to about 40,000, about 5,000 to about 35,000, about 5,000 to about 30,000, about 5,000 to about 25,000, about 5,000 to about 20,000, about 5,000 to about 15,000, about 5,000 to about 10,000, about 5,000 to about 7,500, about 7,500 to about 10,000,000, about 7,500 to about 9,000,000, about 7,500 to about 8,000,000, about 7,500 to about 7,000,000, about 7,500 to about 6,000,000, about 7,500 to about 5,000,000, about 7,500 to about 4,000,000, about 7,500 to about 3,000,000, about 7,500 to about 2,000,000, about 7,500 to about 1,000,000, about 7,500 to about 800,000, about 7,500 to about 600,000, about 7,500 to about 400,000, about 7,500 to about 200,000, about 7,500 to about 100,000, about 7,500 to about 80,000, about 7,500 to about 75,000, about 7,500 to about 70,000, about 7,500 to about 65,000, about 7,500 to about 60,000, about 7,500 to about 55,000, about 7,500 to about 50,000, about 7,500 to about 45,000, about 7,500 to about 40,000, about 7,500 to about 35,000, about 7,500 to about 30,000, about 7,500 to about 25,000, about 7,500 to about 20,000, about 7,500 to about 15,000, about 7,500 to about 10,000, about 10,000 to about 10,000,000, about 10,000 to about 9,000,000, about 10,000 to about 8,000,000, about 10,000 to about 7,000,000, about 10,000 to about 6,000,000, about 10,000 to about 5,000,000, about 10,000 to about 4,000,000, about 10,000 to about 3,000,000, about 10,000 to about 2,000,000, about 10,000 to about 1,000,000, about 10,000 to about 800,000, about 10,000 to about 600,000, about 10,000 to about 400,000, about 10,000 to about 200,000, about 10,000 to about 100,000, about 10,000 to about 80,000, about 10,000 to about 75,000, about 10,000 to about 70,000, about 10,000 to about 65,000, about 10,000 to about 60,000, about 10,000 to about 55,000, about 10,000 to about 50,000, about 10,000 to about 45,000, about 10,000 to about 40,000, about 10,000 to about 35,000, about 10,000 to about 30,000, about 10,000 to about 25,000, about 10,000 to about 20,000, about 10,000 to about 15,000, about 15,000 to about 10,000,000, about 15,000 to about 9,000,000, about 15,000 to about 8,000,000, about 15,000 to about 7,000,000, about 15,000 to about 6,000,000, about 15,000 to about 5,000,000, about 15,000 to about 4,000,000, about 15,000 to about 3,000,000, about 15,000 to about 2,000,000, about 15,000 to about 1,000,000, about 15,000 to about 800,000, about 15,000 to about 600,000, about 15,000 to about 400,000, about 15,000 to about 200,000, about 15,000 to about 100,000, about 15,000 to about 80,000, about 15,000 to about 75,000, about 15,000 to about 70,000, about 15,000 to about 65,000, about 15,000 to about 60,000, about 15,000 to about 55,000, about 15,000 to about 50,000, about 15,000 to about 45,000, about 15,000 to about 40,000, about 15,000 to about 35,000, about 15,000 to about 30,000, about 15,000 to about 25,000, about 15,000 to about 20,000, about 20,000 to about 10,000,000, about 20,000 to about 9,000,000, about 20,000 to about 8,000,000, about 20,000 to about 7,000,000, about 20,000 to about 6,000,000, about 20,000 to about 5,000,000, about 20,000 to about 4,000,000, about 20,000 to about 3,000,000, about 20,000 to about 2,000,000, about 20,000 to about 1,000,000, about 20,000 to about 800,000, about 20,000 to about 600,000, about 20,000 to about 400,000, about 20,000 to about 200,000, about 20,000 to about 100,000, about 20,000 to about 80,000, about 20,000 to about 75,000, about 20,000 to about 70,000, about 20,000 to about 65,000, about 210,000 to about 60,000, about 20,000 to about 55,000, about 20,000 to about 50,000, about 20,000 to about 45,000, about 20,000 to about 40,000, about 20,000 to about 35,000, about 20,000 to about 30,000, about 20,000 to about 25,000, about 25,000 to about 10,000,000, about 25,000 to about 9,000,000, about 25,000 to about 8,000,000, about 25,000 to about 7,000,000, about 25,000 to about 6,000,000, about 25,000 to about 5,000,000, about 25,000 to about 4,000,000, about 25,000 to about 3,000,000, about 25,000 to about 2,000,000, about 25,000 to about 1,000,000, about 25,000 to about 800,000, about 25,000 to about 600,000, about 25,000 to about 400,000, about 25,000 to about 200,000, about 25,000 to about 100,000, about 25,000 to about 80,000, about 25,000 to about 75,000, about 25,000 to about 70,000, about 25,000 to about 65,000, about 25,000 to about 60,000, about 25,000 to about 55,000, about 25,000 to about 50,000, about 25,000 to about 45,000, about 25,000 to about 40,000, about 25,000 to about 35,000, about 25,000 to about 30,000, about 30,000 to about 10,000,000, about 30,000 to about 9,000,000, about 30,000 to about 8,000,000, about 30,000 to about 7,000,000, about 30,000 to about 6,000,000, about 30,000 to about 5,000,000, about 30,000 to about 4,000,000, about 30,000 to about 3,000,000, about 30,000 to about 2,000,000, about 30,000 to about 1,000,000, about 30,000 to about 800,000, about 30,000 to about 600,000, about 30,000 to about 400,000, about 30,000 to about 200,000, about 30,000 to about 100,000, about 30,000 to about 80,000, about 30,000 to about 75,000, about 30,000 to about 70,000, about 30,000 to about 65,000, about 30,000 to about 60,000, about 30,000 to about 55,000, about 30,000 to about 50,000, about 30,000 to about 45,000, about 30,000 to about 40,000, about 30,000 to about 35,000, about 35,000 to about 10,000,000, about 35,000 to about 9,000,000, about 35,000 to about 8,000,000, about 35,000 to about 7,000,000, about 35,000 to about 6,000,000, about 35,000 to about 5,000,000, about 35,000 to about 4,000,000, about 35,000 to about 3,000,000, about 35,000 to about 2,000,000, about 35,000 to about 1,000,000, about 35,000 to about 800,000, about 35,000 to about 600,000, about 35,000 to about 400,000, about 35,000 to about 200,000, about 35,000 to about 100,000, about 35,000 to about 80,000, about 35,000 to about 75,000, about 35,000 to about 70,000, about 35,000 to about 65,000, about 35,000 to about 60,000, about 35,000 to about 55,000, about 35,000 to about 50,000, about 35,000 to about 45,000, about 35,000 to about 40,000, about 40,000 to about 10,000,000, about 40,000 to about 9,000,000, about 40,000 to about 8,000,000, about 40,000 to about 7,000,000, about 40,000 to about 6,000,000, about 40,000 to about 5,000,000, about 40,000 to about 4,000,000, about 40,000 to about 3,000,000, about 40,000 to about 2,000,000, about 40,000 to about 1,000,000, about 40,000 to about 800,000, about 40,000 to about 600,000, about 40,000 to about 400,000, about 40,000 to about 200,000, about 40,000 to about 100,000, about 40,000 to about 80,000, about 40,000 to about 75,000, about 40,000 to about 70,000, about 40,000 to about 65,000, about 40,000 to about 60,000, about 40,000 to about 55,000, about 40,000 to about 50,000, about 40,000 to about 45,000, about 45,000 to about 10,000,000, about 45,000 to about 9,000,000, about 45,000 to about 8,000,000, about 45,000 to about 7,000,000, about 45,000 to about 6,000,000, about 45,000 to about 5,000,000, about 45,000 to about 4,000,000, about 45,000 to about 3,000,000, about 45,000 to about 2,000,000, about 45,000 to about 1,000,000, about 45,000 to about 800,000, about 45,000 to about 600,000, about 45,000 to about 400,000, about 45,000 to about 200,000, about 45,000 to about 100,000, about 45,000 to about 80,000, about 45,000 to about 75,000, about 45,000 to about 70,000, about 45,000 to about 65,000, about 45,000 to about 60,000, about 45,000 to about 55,000, about 45,000 to about 50,000, about 50,000 to about 10,000,000, about 50,000 to about 9,000,000, about 50,000 to about 8,000,000, about 50,000 to about 7,000,000, about 50,000 to about 6,000,000, about 50,000 to about 5,000,000, about 50,000 to about 4,000,000, about 50,000 to about 3,000,000, about 50,000 to about 2,000,000, about 50,000 to about 1,000,000, about 50,000 to about 800,000, about 50,000 to about 600,000, about 50,000 to about 400,000, about 50,000 to about 200,000, about 50,000 to about 100,000, about 50,000 to about 80,000, about 50,000 to about 75,000, about 50,000 to about 70,000, about 50,000 to about 65,000, about 50,000 to about 60,000, about 50,000 to about 55,000, about 55,000 to about 10,000,000, about 55,000 to about 9,000,000, about 55,000 to about 8,000,000, about 55,000 to about 7,000,000, about 55,000 to about 6,000,000, about 55,000 to about 5,000,000, about 55,000 to about 4,000,000, about 55,000 to about 3,000,000, about 55,000 to about 2,000,000, about 55,000 to about 1,000,000, about 55,000 to about 800,000, about 55,000 to about 600,000, about 55,000 to about 400,000, about 55,000 to about 200,000, about 55,000 to about 100,000, about 55,000 to about 80,000, about 55,000 to about 75,000, about 55,000 to about 70,000, about 55,000 to about 65,000, about 55,000 to about 60,000, about 60,000 to about 10,000,000, about 60,000 to about 9,000,000, about 60,000 to about 8,000,000, about 60,000 to about 7,000,000, about 60,000 to about 6,000,000, about 60,000 to about 5,000,000, about 60,000 to about 4,000,000, about 60,000 to about 3,000,000, about 60,000 to about 2,000,000, about 60,000 to about 1,000,000, about 60,000 to about 800,000, about 60,000 to about 600,000, about 60,000 to about 400,000, about 60,000 to about 200,000, about 60,000 to about 100,000, about 60,000 to about 80,000, about 60,000 to about 75,000, about 60,000 to about 70,000, about 60,000 to about 65,000, about 65,000 to about 10,000,000, about 65,000 to about 9,000,000, about 65,000 to about 8,000,000, about 65,000 to about 7,000,000, about 65,000 to about 6,000,000, about 65,000 to about 5,000,000, about 65,000 to about 4,000,000, about 65,000 to about 3,000,000, about 65,000 to about 2,000,000, about 65,000 to about 1,000,000, about 65,000 to about 800,000, about 65,000 to about 600,000, about 65,000 to about 400,000, about 65,000 to about 200,000, about 65,000 to about 100,000, about 65,000 to about 80,000, about 65,000 to about 75,000, about 65,000 to about 70,000, about 70,000 to about 10,000,000, about 70,000 to about 9,000,000, about 70,000 to about 8,000,000, about 70,000 to about 7,000,000, about 70,000 to about 6,000,000, about 70,000 to about 5,000,000, about 70,000 to about 4,000,000, about 70,000 to about 3,000,000, about 70,000 to about 2,000,000, about 70,000 to about 1,000,000, about 70,000 to about 800,000, about 70,000 to about 600,000, about 70,000 to about 400,000, about 70,000 to about 200,000, about 70,000 to about 100,000, about 70,000 to about 90,000, about 70,000 to about 80,000, about 80,000 to about 10,000,000, about 80,000 to about 9,000,000, about 80,000 to about 8,000,000, about 80,000 to about 7,000,000, about 80,000 to about 6,000,000, about 80,000 to about 5,000,000, about 80,000 to about 4,000,000, about 80,000 to about 3,000,000, about 80,000 to about 2,000,000, about 80,000 to about 1,000,000, about 80,000 to about 800,000, about 80,000 to about 600,000, about 80,000 to about 400,000, about 80,000 to about 200,000, about 80,000 to about 100,000, about 80,000 to about 90,000, about 90,000 to about 10,000,000, about 90,000 to about 9,000,000, about 90,000 to about 8,000,000, about 90,000 to about 7,000,000, about 90,000 to about 6,000,000, about 90,000 to about 5,000,000, about 90,000 to about 4,000,000, about 90,000 to about 3,000,000, about 90,000 to about 2,000,000, about 90,000 to about 1,000,000, about 90,000 to about 800,000, about 90,000 to about 600,000, about 90,000 to about 400,000, about 90,000 to about 200,000, about 90,000 to about 100,000, about 100,000 to about 10,000,000, about 100,000 to about 9,000,000, about 100,000 to about 8,000,000, about 100,000 to about 7,000,000, about 100,000 to about 6,000,000, about 100,000 to about 5,000,000, about 100,000 to about 4,000,000, about 100,000 to about 3,000,000, about 100,000 to about 2,000,000, about 100,000 to about 1,000,000, about 100,000 to about 800,000, about 100,000 to about 600,000, about 100,000 to about 400,000, about 100,000 to about 200,000, about 200,000 to about 10,000,000, about 200,000 to about 9,000,000, about 200,000 to about 8,000,000, about 200,000 to about 7,000,000, about 200,000 to about 6,000,000, about 200,000 to about 5,000,000, about 200,000 to about 4,000,000, about 200,000 to about 3,000,000, about 200,000 to about 2,000,000, about 200,000 to about 1,000,000, about 200,000 to about 800,000, about 200,000 to about 600,000, about 200,000 to about 400,000, about 400,000 to about 10,000,000, about 400,000 to about 9,000,000, about 400,000 to about 8,000,000, about 400,000 to about 7,000,000, about 400,000 to about 6,000,000, about 400,000 to about 5,000,000, about 400,000 to about 4,000,000, about 400,000 to about 3,000,000, about 400,000 to about 2,000,000, about 400,000 to about 1,000,000, about 400,000 to about 800,000, about 400,000 to about 600,000, about 600,000 to about 10,000,000, about 600,000 to about 9,000,000, about 600,000 to about 8,000,000, about 600,000 to about 7,000,000, about 600,000 to about 6,000,000, about 600,000 to about 5,000,000, about 600,000 to about 4,000,000, about 600,000 to about 3,000,000, about 600,000 to about 2,000,000, about 600,000 to about 1,000,000, about 600,000 to about 800,000, about 800,000 to about 10,000,000, about 800,000 to about 9,000,000, about 800,000 to about 8,000,000, about 800,000 to about 7,000,000, about 800,000 to about 6,000,000, about 800,000 to about 5,000,000, about 800,000 to about 4,000,000, about 800,000 to about 3,000,000, about 800,000 to about 2,000,000, about 800,000 to about 1,000,000, about 1,000,000 to about 10,000,000, about 1,000,000 to about 9,000,000, about 1,000,000 to about 8,000,000, about 1,000,000 to about 7,000,000, about 1,000,000 to about 6,000,000, about 1,000,000 to about 5,000,000, about 1,000,000 to about 4,000,000, about 1,000,000 to about 3,000,000, about 1,000,000 to about 2,000,000, about 2,000,000 to about 10,000,000, about 2,000,000 to about 9,000,000, about 2,000,000 to about 8,000,000, about 2,000,000 to about 7,000,000, about 2,000,000 to about 6,000,000, about 2,000,000 to about 5,000,000, about 2,000,000 to about 4,000,000, about 2,000,000 to about 3,000,000, about 3,000,000 to about 10,000,000, about 3,000,000 to about 9,000,000, about 3,000,000 to about 8,000,000, about 3,000,000 to about 7,000,000, about 3,000,000 to about 6,000,000, about 3,000,000 to about 5,000,000, about 3,000,000 to about 4,000,000, about 4,000,000 to about 10,000,000, about 4,000,000 to about 9,000,000, about 4,000,000 to about 8,000,000, about 4,000,000 to about 7,000,000, about 4,000,000 to about 6,000,000, about 4,000,000 to about 5,000,000, about 5,000,000 to about 10,000,000, about 5,000,000 to about 9,000,000, about 5,000,000 to about 8,000,000, about 5,000,000 to about 7,000,000, about 5,000,000 to about 6,000,000, about 6,000,000 to about 10,000,000, about 6,000,000 to about 9,000,000, about 6,000,000 to about 8,000,000, about 6,000,000 to about 7,000,000, about 7,000,000 to about 10,000,000, about 7,000,000 to about 9,000,000, about 7,000,000 to about 8,000,000, about 8,000,000 to about 10,000,000, about 8,000,000 to about 9,000,000, or about 9,000,000 to about 10,000,000 of the MET on present on the plasma membrane of the target mammalian cell.

The phrase "antigen density" means the number of MET present on the surface of a target mammalian cell or the average number of MET on the surface of a population of particular type of target mammalian cells. It can be measured, e.g., using the Quantibright bead kit or radiolabel (e.g., BD Biosciences PE Phycoerythrin Fluorescence Quantitation Kit, catalog #340495).

The phrase "amino acid substituted with a histidine" means the substitution of an amino acid residue that is not histidine in a reference polypeptide sequence with a histidine. Non-limiting methods for substituting an amino acid residue in a reference polypeptide with a histidine are described herein. Additional methods for substituting an amino acid residue in a reference polypeptide with a histidine are known in the art.

The phrase "amino acid substituted with an alanine" means the substitution of an amino acid residue that is a histidine in a reference polypeptide sequence with an alanine. Non-limiting methods for substituting a histidine in a reference polypeptide with an alanine are described herein. Additional methods for substituting a histidine in a reference polypeptide with an alanine are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 5: Table of different tested antibodies with the variable heavy and variable light chain sequences listed.

FIG. 6: Internalization and endolysosomal delivery of histidine scanning and alanine scanning variants of MYT variants in Detroit 562 cells MYT4826, MYT4827, MYT4837, MYT4325, MYT5351, MYT4312, MYT5309, MYT4849, MYTH4888, MYT5344, MYT4313, MYT5367, MYT4942, MYT4953, and MYT4940, heavy chain combination histidine scanning and alanine scanning variants, were assayed for internalization on Detroit 562 cells using Incucyte Human FabFluor-pH red antibody labeling reagent at the indicated timepoint and final concentration of antibody. Fold-increases in internalization and endolysosomal delivery are indicated by the numbers next to each variant. All variants include the TH and YTE substitution format.

DETAILED DESCRIPTION

Figure 1A:
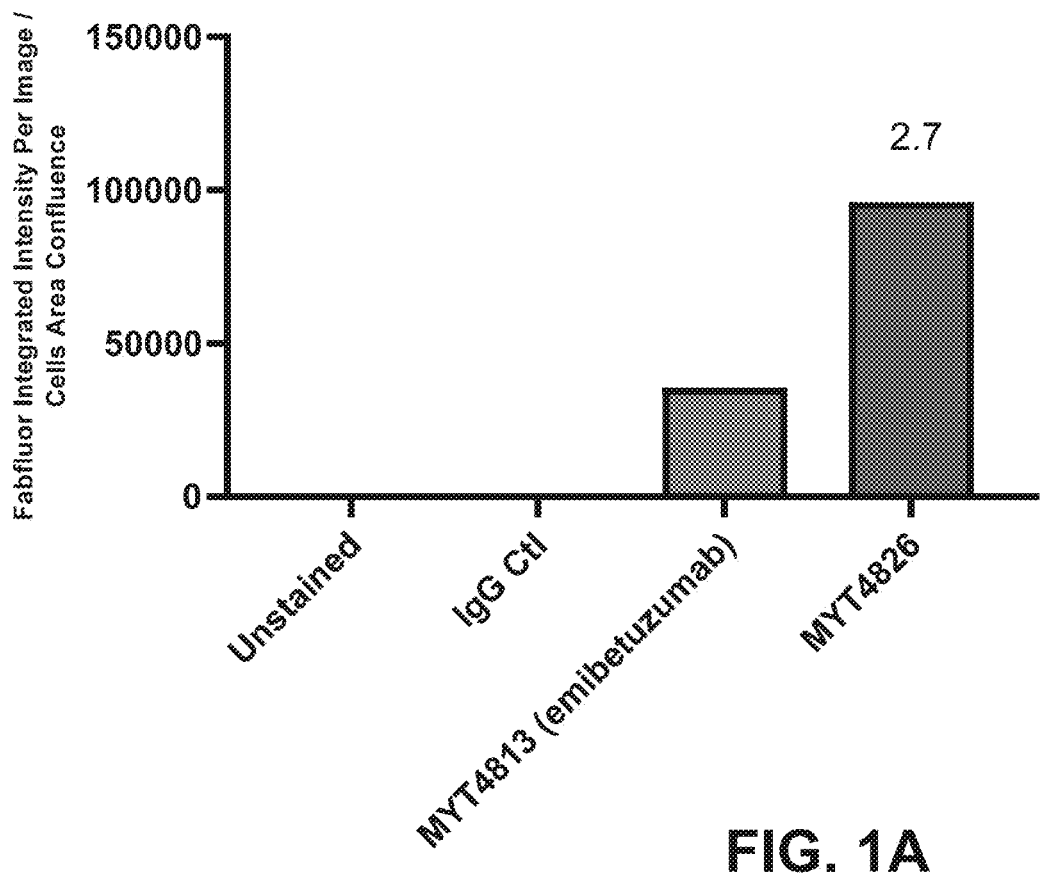
FIGS. 1A-C: Internalization and endolysosomal delivery of histidine scanning and alanine scanning variants of EMIBETUZUMAB and P3D12 in Detroit 562 cells. MYT4826 (EMIBETUZUMAB) and MYT4325 (P3D12), heavy chain combination histidine scanning and alanine scanning variants, were assayed for internalization on Detroit 562 cells using Incucyte Human FabFluor-pH red antibody labeling reagent at the indicated timepoint and final concentration of ABPC. Fold-increases in internalization and endolysosomal delivery are indicated by the numbers above each variant. All variants include the TH and YTE substitution format.

Provided herein are antibodies that are capable of specifically binding MET or an epitope of MET presented on the surface of a target mammalian cell, where: (a) the dissociation rate at a pH of about 4.0 to about 6.5 is faster than the dissociation rate at a pH of about 7.0 to about 8.0; and/or (b) the dissociation constant ($K_D$) at a pH of about 4.0 to about 6.5 is greater than the $K_D$ at a pH of about 7.0 to about 8.0. In some examples of these antibodies, the antibody is degraded in the target mammalian cell following internalization of the antibody by the target mammalian cell. Some examples of any of the antibodies described herein can further include a conjugated toxin, radioisotope, drug, or small molecule (e.g., a fluorophore or dye).

Also provided are antibodies that are capable of specifically binding MET or an epitope of MET presented on the surface of a target mammalian cell; and a conjugated toxin, radioisotope, drug, or small molecule, where: (a) the dissociation rate at a pH of about 4.0 to about 6.5 is faster the dissociation rate at a pH of about 7.0 to about 8.0; and/or the dissociation constant ($K_D$) at a pH of about 4.0 to about 6.5 is greater than the $K_D$ at a pH of about 7.0 to about 8.0; and (b) a composition including the antibody provides for one or more (e.g., two or three) of: an increase (e.g., a detectable increase) in toxin liberation in the target mammalian cell as compared to a composition comprising the same amount of a control antibody; an increase (e.g., a detectable increase) in target mammalian cell killing as compared to a composition comprising the same amount of a control antibody; and an increase (e.g., a detectable increase) in endolysosomal delivery in the target mammalian cell as compared to a composition comprising the same amount of a control antibody.

In some examples of any of the antibodies described herein, the antibody comprises a heavy chain variable domain and a light chain variable domain of Telisotuzumab and or more substitutions in the heavy chain CH1-CH2-CH3 domain and/or the $C_L$ domain of Telisotuzumab. In some examples of any of the antibodies described herein, the antibody includes a heavy chain variable domain and a light chain variable domain of Emibetuzumab and one or more amino acid substitutions in the heavy CH1-CH2-CH3 domain and/or the $C_L$ domain of Emibetuzumab. In some example of any of the antibodies described herein, the antibody includes a heavy chain variable domain and a light chain variable domain of P3D12 anti-cMET and one or more amino acid substitutions in the heavy CH1-CH2-CH3 domain and/or the $C_L$ domain of P3D12-cMet.

In some examples of any of the antibodies described herein, the antibody comprises (a) a heavy chain variable domain and a light chain variable domain selected from the group of: (i) SEQ ID NO: 5 and SEQ ID NO: 6, respectively; (ii) SEQ ID NO: 7 and SEQ ID NO: 8, respectively; (iii) SEQ ID NO: 9 and SEQ ID NO: 10, respectively; (iv) SEQ ID NO: 11 and SEQ ID NO: 12, respectively; (v) SEQ ID NO: 13 and SEQ ID NO: 14, respectively; (vi) SEQ ID NO: 15 and SEQ ID NO: 16, respectively; (vii) SEQ ID NO: 17 and SEQ ID NO: 18, respectively; (viii) SEQ ID NO: 19 and SEQ ID NO: 20, respectively; (ix) SEQ ID NO: 21 and SEQ ID NO: 22, respectively; (x) SEQ ID NO: 23 and SEQ ID NO: 24, respectively; (xi) SEQ ID NO: 25 and SEQ ID NO: 26, respectively; (xii) SEQ ID NO: 27 and SEQ ID NO: 28, respectively; (xiii) SEQ ID NO: 29 and SEQ ID NO: 30, respectively; (xiv) SEQ ID NO: 31 and SEQ ID NO: 32, respectively; (xv) SEQ ID NO: 33 and SEQ ID NO: 34, respectively; and (b) a heavy chain CH1-CH2-CH3 sequence of SEQ ID NO: 155 or SEQ ID NO: 189 comprising one or more of the following: (i) a lysine to cysteine substitution at amino acid position 105 and deletion of a threonine at amino acid positions 106 and 108; (ii) a methionine to tyrosine substitution at amino acid position 135, a serine to threonine substitution at amino acid position 137, and a threonine to glutamic acid substitution at amino acid position 139, (iii) a methionine to leucine substitution at amino acid position 311 and an asparagine to serine substitution at amino acid position 317; (iv) an alanine to a cysteine substitution at amino acid position 1; and/or a light chain $C_L$ sequence of SEQ ID NO: 157 comprising a valine to cysteine substitution at amino acid position 98.

In some examples of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108. In some examples of any of the antibodies described herein, the heavy chain and light chain sequences are: (i) SEQ ID NO: 35 and SEQ ID NO: 41, respectively; (ii) SEQ ID NO: 43 and SEQ ID NO: 49, respectively; (iii) SEQ ID NO: 51 and SEQ ID NO: 57, respectively (iv) SEQ ID NO: 59 and SEQ ID NO: 65, respectively; (v) SEQ ID NO: 67 and SEQ ID NO: 73, respectively; (vi) SEQ ID NO: 75 and SEQ ID NO: 81, respectively; (vii) SEQ ID NO: 83 and SEQ ID NO: 89, respectively; (viii) SEQ ID NO: 91 and SEQ ID NO: 97, respectively; (ix) SEQ ID NO: 99 and SEQ ID NO: 105, respectively; (x) SEQ ID NO: 107 and SEQ ID NO: 113, respectively; (xi) SEQ ID NO: 115 and SEQ ID NO: 121, respectively; (xii) SEQ ID NO: 123 and SEQ ID NO: 129, respectively; (xiii) SEQ ID NO: 131 and SEQ ID NO: 137, respectively; (xiv) SEQ ID NO: 139 and SEQ ID NO: 145, respectively; or (xv) SEQ ID NO: 147 and SEQ ID NO: 153, respectively.

In some examples of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and a methionine to leucine substitution at amino acid position 311 and an asparagine to serine substitution at amino acid position 317. In some examples of any of the antibodies described herein, the heavy chain and light chain sequences are: (i) SEQ ID NO: 36 and SEQ ID NO: 41, respectively; (ii) SEQ ID NO: 44 and SEQ ID NO: 49, respectively; (iii) SEQ ID NO: 52 and SEQ ID NO: 57, respectively; (iv) SEQ ID NO: 60 and SEQ ID NO: 65, respectively; (v) SEQ ID NO: 68 and SEQ ID NO: 73, respectively; (vi) SEQ ID NO: 76 and SEQ ID NO: 81, respectively; (vii) SEQ ID NO: 84 and SEQ ID NO: 89, respectively; (viii) SEQ ID NO: 92 and SEQ ID NO: 97, respectively; (ix) SEQ ID NO: 100 and SEQ ID NO: 105, respectively; (x) SEQ ID NO: 108 and SEQ ID NO: 113, respectively; (xi) SEQ ID NO: 116 and SEQ ID NO: 121, respectively; (xii) SEQ ID NO: 124 and SEQ ID NO: 129, respectively; (xiii) SEQ ID NO: 132 and SEQ ID NO: 137, respectively; (xiv) SEQ ID NO: 140 and SEQ ID NO: 145, respectively; or (xv) SEQ ID NO: 148 and SEQ ID NO: 153, respectively.

In some examples of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and a methionine to tyrosine substitution at amino acid position 135, a serine to threonine substitution at amino acid position 137, and a threonine to glutamic acid substitution at amino acid position 139. In some examples of any of the antibodies described herein, the heavy chain and a light chain sequences are: (i) SEQ ID NO: 37 and SEQ ID NO: 41, respectively; (ii) SEQ ID NO: 45 and SEQ ID NO: 49, respectively; (iii) SEQ ID NO: 53 and SEQ ID NO: 57, respectively (iv) SEQ ID NO: 61 and SEQ ID NO: 65, respectively; (v) SEQ ID NO: 69 and SEQ ID NO: 73, respectively; (vi) SEQ ID NO: 77 and SEQ ID NO: 81, respectively; (vii) SEQ ID NO: 85 and SEQ ID NO: 89, respectively; (viii) SEQ ID NO: 93 and SEQ ID NO: 97, respectively; (ix) SEQ ID NO: 101 and SEQ ID NO: 105, respectively; (x) SEQ ID NO: 109 and SEQ ID NO: 113, respectively; (xi) SEQ ID NO: 117 and SEQ ID NO: 121, respectively; (xii) SEQ ID NO: 125 and SEQ ID NO: 129, respectively; (xiii) SEQ ID NO: 133 and SEQ ID NO: 137, respectively; (xiv) SEQ ID NO: 141 and SEQ ID NO: 145, respectively; or (xv). SEQ ID NO: 149 and SEQ ID NO: 153, respectively.

In some examples of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and the light chain $C_L$ sequence of SEQ ID NO: 157 comprises a valine to cysteine substitution at amino acid position 98. In some examples of any of the antibodies described herein, heavy chain and light chain sequences are: (i) SEQ ID NO: 35 and SEQ ID NO: 42, respectively; (ii) SEQ ID NO: 43 and SEQ ID NO: 50, respectively; (iii) SEQ ID NO: 51 and SEQ ID NO: 58, respectively (iv) SEQ ID NO: 59 and SEQ ID NO: 66, respectively; (v) SEQ ID NO: 67 and SEQ ID NO: 74, respectively; (vi) SEQ ID NO: 75 and SEQ ID NO: 82, respectively; (vii) SEQ ID NO: 83 and SEQ ID NO: 90, respectively; (viii) SEQ ID NO: 91 and SEQ ID NO: 98, respectively; (ix) SEQ ID NO: 99 and SEQ ID NO: 106, respectively; (x) SEQ ID NO: 107 and SEQ ID NO: 114, respectively; (xi) SEQ ID NO: 115 and SEQ ID NO: 122, respectively; (xii) SEQ ID NO: 123 and SEQ ID NO: 130, respectively; (xiii) SEQ ID NO: 131 and SEQ ID NO: 138, respectively; (xiv) SEQ ID NO: 139 and SEQ ID NO: 146, respectively; or (xv) SEQ ID NO: 147 and SEQ ID NO: 154, respectively.

In some examples of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and a methionine to leucine substitution at amino acid position 311 and an asparagine to serine substitution at amino acid position 317; and the light chain $C_L$ sequence of SEQ ID NO: 157 comprises a valine to cysteine substitution at amino acid position 98. In some examples of any of the antibodies described herein, the heavy chain and light chain sequences are: (i) SEQ ID NO: 36 and SEQ ID NO: 42, respectively; (ii) SEQ ID NO: 44 and SEQ ID NO: 50, respectively; (iii) SEQ ID NO: 52 and SEQ ID NO: 58, respectively; (iv) SEQ ID NO: 60 and SEQ ID NO: 66, respectively; (v) SEQ ID NO: 68 and SEQ ID NO: 74, respectively; (vi) SEQ ID NO: 76 and SEQ ID NO: 82, respectively; (vii) SEQ ID NO: 84 and SEQ ID NO: 90, respectively; (viii) SEQ ID NO: 92 and SEQ ID NO: 98, respectively; (ix) SEQ ID NO: 100 and SEQ ID NO: 106, respectively; (x) SEQ ID NO: 108 and SEQ ID NO: 114, respectively; (xi) SEQ ID NO: 116 and SEQ ID NO: 122, respectively; (xii) SEQ ID NO: 124 and SEQ ID NO: 130, respectively; (xiii) SEQ ID NO: 132 and SEQ ID NO: 138, respectively; (xiv) SEQ ID NO: 140 and SEQ ID NO: 146, respectively; or (xv) SEQ ID NO: 148 and SEQ ID NO: 154, respectively.

In some examples of any of the antibodies described herein, the heavy chain CH1-CH2-CH3 sequence of SEQ ID NO: 155 or SEQ ID NO: 189 comprises: a lysine to cysteine substitution at amino acid position 105 and deletion of a threonine at amino acid positions 106 and 108; and a methionine to tyrosine substitution at amino acid position 135, a serine to threonine substitution at amino acid position 137, and a threonine to glutamic acid substitution at amino acid position 139; and the light chain $C_L$ sequence of SEQ ID NO: 157 comprises a valine to cysteine substitution at amino acid position 98. In some examples of any of the antibodies described herein, the heavy chain and light chain sequences are: (i) SEQ ID NO: 37 and SEQ ID NO: 42, respectively; (ii) SEQ ID NO: 45 and SEQ ID NO: 50, respectively; (iii) SEQ ID NO: 53 and SEQ ID NO: 58, respectively; (iv) SEQ ID NO: 61 and SEQ ID NO: 66, respectively; (v) SEQ ID NO: 69 and SEQ ID NO: 74, respectively; (vi) SEQ ID NO: 77 and SEQ ID NO: 82, respectively; (vii) SEQ ID NO: 85 and SEQ ID NO: 90, respectively; (viii) SEQ ID NO: 93 and SEQ ID NO: 98, respectively; (ix) SEQ ID NO: 101 and SEQ ID NO: 106, respectively; (x) SEQ ID NO: 109 and SEQ ID NO: 114, respectively; (xi) SEQ ID NO: 117 and SEQ ID NO: 122, respectively; (xii) SEQ ID NO: 125 and SEQ ID NO: 130, respectively; (xiii) SEQ ID NO: 133 and SEQ ID NO: 138, respectively; (xiv) SEQ ID NO: 141 and SEQ ID NO: 146, respectively; or (xv) SEQ ID NO: 149 and SEQ ID NO: 154, respectively.

In some examples of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and an alanine to a cysteine substitution at amino acid position 1. In some examples of any of the antibodies described herein, heavy chain and light chain sequences are: (i) SEQ ID NO: 38 and SEQ ID NO: 41, respectively; (ii) SEQ ID NO: 46 and SEQ ID NO: 49, respectively; (iii) SEQ ID NO: 54 and SEQ ID NO: 57, respectively; (iv) SEQ ID NO: 62 and SEQ ID NO: 65, respectively; (v) SEQ ID NO: 70 and SEQ ID NO: 73, respectively; (vi) SEQ ID NO: 78 and SEQ ID NO: 81, respectively; (vii) SEQ ID NO: 86 and SEQ ID NO: 89, respectively; (viii) SEQ ID NO: 94 and SEQ ID NO: 97, respectively; (ix) SEQ ID NO: 102 and SEQ ID NO: 105, respectively; (x) SEQ ID NO: 110 and SEQ ID NO: 113, respectively; (xi) SEQ ID NO: 118 and SEQ ID NO: 121, respectively; (xii) SEQ ID NO: 126 and SEQ ID NO: 129, respectively; (xiii) SEQ ID NO: 134 and SEQ ID NO: 137, respectively; (xiv) SEQ ID NO: 142 and SEQ ID NO: 145, respectively; or (xv) SEQ ID NO: 150 and SEQ ID NO: 153, respectively.

In some examples of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; a methionine to leucine substitution at amino acid position 311 and an asparagine to serine substitution at amino acid position 317; and an alanine to a cysteine substitution at amino acid position 1. In some examples of any of the antibodies described herein, heavy chain and light chain sequences are: (i) SEQ ID NO: 39 and SEQ ID NO: 41, respectively; (ii)

SEQ ID NO: 47 and SEQ ID NO: 49, respectively; (iii) SEQ ID NO: 55 and SEQ ID NO: 57, respectively; (iv) SEQ ID NO: 63 and SEQ ID NO: 65, respectively; (v) SEQ ID NO: 71 and SEQ ID NO: 73, respectively; (vi) SEQ ID NO: 79 and SEQ ID NO: 81, respectively; (vii) SEQ ID NO: 87 and SEQ ID NO: 89, respectively; (viii) SEQ ID NO: 95 and SEQ ID NO: 97, respectively; (ix) SEQ ID NO: 103 and SEQ ID NO: 105, respectively; (x) SEQ ID NO: 111 and SEQ ID NO: 113, respectively; (xi) SEQ ID NO: 119 and SEQ ID NO: 121, respectively; (xii) SEQ ID NO: 127 and SEQ ID NO: 129, respectively; (xiii) SEQ ID NO: 135 and SEQ ID NO: 137, respectively; (xiv) SEQ ID NO: 143 and SEQ ID NO: 145, respectively; or (xv) SEQ ID NO: 151 and SEQ ID NO: 153, respectively.

In some examples of any of any of the antibodies described herein, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; a methionine to tyrosine substitution at amino acid position 135, a serine to threonine substitution at amino acid position 137, and a threonine to glutamic acid substitution at amino acid position 139; and an alanine to a cysteine substitution at amino acid position 1. In some examples of any of the antibodies described herein, the heavy chain and a light chain sequences are: (i) SEQ ID NO: 40 and SEQ ID NO: 41, respectively; (ii) SEQ ID NO: 48 and SEQ ID NO: 49, respectively; (iii) SEQ ID NO: 56 and SEQ ID NO: 57, respectively; (iv) SEQ ID NO: 64 and SEQ ID NO: 65, respectively; (v) SEQ ID NO: 72 and SEQ ID NO: 73, respectively; (vi) SEQ ID NO: 80 and SEQ ID NO: 81, respectively; (vii) SEQ ID NO: 88 and SEQ ID NO: 89, respectively; (viii) SEQ ID NO: 96 and SEQ ID NO: 97, respectively; (ix) SEQ ID NO: 104 and SEQ ID NO: 105, respectively; (x) SEQ ID NO: 112 and SEQ ID NO: 113, respectively; (xi) SEQ ID NO: 120 and SEQ ID NO: 121, respectively; (xii) SEQ ID NO: 128 and SEQ ID NO: 129, respectively; (xiii) SEQ ID NO: 136 and SEQ ID NO: 137, respectively; (xiv) SEQ ID NO: 144 and SEQ ID NO: 145, respectively; or (xv) SEQ ID NO: 152 and SEQ ID NO: 153, respectively.

In some embodiments, (a) the dissociation rate of the antibody at a pH of about 4.0 to about 6.5 is not faster than the dissociation rate at a pH of about 7.0 to about 8.0; or (b) the dissociation constant ($K_D$) of the antibody at a pH of about 4.0 to about 6.5 is greater than the $K_D$ at a pH of about 7.0 to about 8.0.

In such examples, the antibody comprises (a) heavy chain variable domain and a light chain variable domain selected from the group consisting of: (i) SEQ ID NO: 159 and SEQ ID NO: 160, respectively; (ii) SEQ ID NO: 161 and SEQ ID NO: 162, respectively; (iii) SEQ ID NO: 163 and SEQ ID NO: 164; respectively; (b) a heavy chain CH1-CH2-CH3 sequence of SEQ ID NO: 155 or SEQ ID NO: 189 comprising one or more of the following substitution(s): (i) a lysine to cysteine substitution at amino acid position 105 and deletion of a threonine amino acid at positions 106 and 108; (ii) a methionine to tyrosine substitution at amino acid position 135, a serine to threonine substitution at amino acid position 137, and a threonine to glutamic acid substitution at amino acid position 139, (iii) a methionine to leucine substitution at amino acid position 311 and an asparagine to serine substitution at amino acid position 317; and (iv) an alanine to cysteine substitution at amino acid position 1; and/or a light chain $C_L$ sequence of SEQ ID NO: 157 comprising a valine to cysteine substitution at position 98.

In such examples, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108 of SEQ ID NO: 155 or SEQ ID NO: 189. In some examples, the heavy chain and light chain sequences are: (i) SEQ ID NO: 165 and SEQ ID NO: 171, respectively; (ii) SEQ ID NO: 173 and SEQ ID NO: 179, respectively; or (iii) SEQ ID NO: 181 and SEQ ID NO: 187, respectively.

In some examples, the heavy CH1-CH2-CH3 sequence of SEQ ID NO: 155 or SEQ ID NO: 189 comprises: a lysine to cysteine substitution at amino acid position 105 and deletion of a threonine at amino acid positions 106 and 108; and a methionine to leucine substitution at amino acid position 311 and an asparagine to serine substitution at amino acid position 317. In some examples, the heavy chain and light chain sequences are: (i) SEQ ID NO: 166 and SEQ ID NO: 171, respectively; (ii) SEQ ID NO: 174 and SEQ ID NO: 179, respectively; or (iii) SEQ ID NO: 182 and SEQ ID NO: 187, respectively.

In some examples, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and the light chain $C_L$ sequence of SEQ ID NO: 157 comprises a valine to cysteine substitution at amino acid position 98. In some examples, heavy chain and light chain sequences are: (i) SEQ ID NO: 165 and SEQ ID NO: 172, respectively; (ii) SEQ ID NO: 173 and SEQ ID NO: 180, respectively; or (iii) SEQ ID NO: 181 and SEQ ID NO: 188, respectively.

In some examples, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and a methionine to leucine substitution at amino acid position 311 and an asparagine to serine substitution at amino acid position 317; and the light chain $C_L$ sequence of SEQ ID NO: 157 comprises a valine to cysteine substitution at amino acid position 98. In some examples, heavy chain and light chain sequences are: (i) SEQ ID NO: 166 and SEQ ID NO: 172, respectively; (ii) SEQ ID NO: 174 and SEQ ID NO: 180, respectively; or (iii) SEQ ID NO: 182 and SEQ ID NO: 188, respectively.

In some examples, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and a methionine to tyrosine substitution at amino acid position 135, a serine to threonine substitution at amino acid position 137, and a threonine to glutamic acid substitution at amino acid position 139; and the light chain $C_L$ sequence of SEQ ID NO: 157 comprises a valine to cysteine substitution at amino acid position 98. In some examples, the heavy chain and light chain sequences are: (i) SEQ ID NO: 167 and SEQ ID NO: 172, respectively; (ii) SEQ ID NO: 175 and SEQ ID NO: 180, respectively; or (iii) SEQ ID NO: 183 and SEQ ID NO: 188, respectively.

In such examples, the heavy chain CH1-CH2-CH3 sequence of SEQ ID NO: 155 or SEQ ID NO: 189 comprises a lysine to cysteine substitution at amino acid position 105 and deletion of a threonine at amino acid positions 106 and 108; and an alanine to a cysteine substitution at amino acid position 1. In such examples, the heavy chain and light chain sequences are: (i) SEQ ID NO: 168 and SEQ ID NO: 171, respectively; (ii) SEQ ID NO: 176 and SEQ ID NO: 179, respectively; or (iii) SEQ ID NO: 184 and SEQ ID NO: 187, respectively.

In some examples, heavy chain CH1-CH2-CH3 sequence of SEQ ID NO: 155 or SEQ ID NO: 189 comprises: a lysine to cysteine substitution at amino acid position 105 and deletion of a threonine at amino acid positions 106 and 108; a methionine to leucine substitution at amino acid position 311 and an asparagine to serine substitution at amino acid position 317; and an alanine to a cysteine substitution at amino acid position 1. In some examples, the heavy chain and light chain sequences are: (i) SEQ ID NO: 169 and SEQ ID NO: 171, respectively; (ii) SEQ ID NO: 177 and SEQ ID NO: 179, respectively; or (iii) SEQ ID NO: 185 and SEQ ID NO: 187, respectively.

In some examples, the heavy chain CH1-CH2-CH3 sequence of SEQ ID NO: 155 or SEQ ID NO: 189 comprises: a lysine to cysteine substitution at amino acid position 105 and deletion of a threonine at amino acid positions 106 and 108; a methionine to tyrosine substitution at amino acid position 135, a serine to threonine substitution at amino acid position 137, and a threonine to glutamic acid substitution at amino acid position 139; and an alanine to a cysteine substitution at amino acid position 1. In some examples, the heavy chain and light chain sequences are: (i) SEQ ID NO: 170 and SEQ ID NO: 171, respectively; (ii) SEQ ID NO: 178 and SEQ ID NO: 179, respectively; or (iii) SEQ ID NO: 186 and SEQ ID NO: 187, respectively.

Also provided herein are pharmaceutical compositions including any of the antibodies described herein. Also provided herein are methods of treating a subject in need thereof that include administering a therapeutically effective amount of any of the antibodies described herein to the subject.

In some examples of any of the antibodies described herein, a composition including the antibody (e.g., any of the antibodies described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at a least a 9,000% increase, or at least a 10,000% increase, or about a 1% increase to about 10,000% increase, about a 1% increase to about a 9,000% increase, about a 1% increase to about a 8,000% increase, about a 1% increase to about a 7,000% increase, about a 1% increase to about a 6,000% increase, about a 1% increase to about a 5,000% increase, about a 1% increase to about a 4,000% increase, about a 1% increase to about a 3,000% increase, about a 1% increase to about a 2,000% increase, about a 1% increase to about a 1,000% increase, about a 1% increase to about a 500% increase, about a 1% increase to about a 450% increase, about a 1% increase to about a 400% increase, about a 1% increase to about a 350% increase, about a 1% increase to about a 300% increase, about a 1% increase to about a 250% increase, about a 1% increase to about a 200% increase, about a 1% increase to about a 180% increase, about a 1% increase to about a 160% increase, about a 1% increase to about a 140% increase, about a 1% increase to about a 120% increase, about a 1% increase to about a 100% increase, about a 1% increase to about a 95% increase, about a 1% increase to about a 90% increase, about a 1% increase to about a 85% increase, about a 1% increase to about a 80% increase, about a 1% increase to about a 75% increase, about a 1% increase to about a 70% increase, about a 1% increase to about a 65% increase, about a 1% increase to about a 60% increase, about a 1% increase to about a 55% increase, about a 1% increase to about a 50% increase, about a 1% increase to about a 45% increase, about a 1% increase to about a 40% increase, about a 1% increase to about a 35% increase, about a 1% increase to about a 25% increase, about a 1% increase to about a 20% increase, about a 1% increase to about a 15% increase, about a 1% increase to about a 10% increase, about a 1% increase to about a 5% increase, about a 2% increase to about 10,000% increase, about a 2% increase to about a 9,000% increase, about a 2% increase to about a 8,000% increase, about a 2% increase to about a 7,000% increase, about a 2% increase to about a 6,000% increase, about a 2% increase to about a 5,000% increase, about a 2% increase to about a 4,000% increase, about a 2% increase to about a 3,000% increase, about a 2% increase to about a 2,000% increase, about a 2% increase to about a 1,000% increase, about a 2% increase to about a 500% increase, about a 2% increase to about a 450% increase, about a 2% increase to about a 400% increase, about a 2% increase to about a 350% increase, about a 2% increase to about a 300% increase, about a 2% increase to about a 250% increase, about a 2% increase to about a 200% increase, about a 2% increase to about a 180% increase, about a 2% increase to about a 160% increase, about a 2% increase to about a 140% increase, about a 2% increase to about a 120% increase, about a 2% increase to about a 100% increase, about a 2% increase to about a 95% increase, about a 2% increase to about a 90% increase, about a 2% increase to about a 85% increase, about a 2% increase to about a 80% increase, about a 2% increase to about a 75% increase, about a 2% increase to about a 70% increase, about a 2% increase to about a 65% increase, about a 2% increase to about a 60% increase, about a 2% increase to about a 55% increase, about a 2% increase to about a 50% increase, about a 2% increase to about a 45% increase, about a 2% increase to about a 40% increase, about a 2% increase to about a 35% increase, about a 2% increase to about a 25% increase, about a 2% increase to about a 20% increase, about a 2% increase to about a 15% increase, about a 2% increase to about a 10% increase, about a 2% increase to about a 5% increase, about a 5% increase to about 10,000% increase, about a 5% increase to about a 9,000% increase, about a 5% increase to about a 8,000% increase, about a 5% increase to about a 7,000% increase, about a 5% increase to about a 6,000% increase, about a 5% increase to about a 5,000% increase, about a 5% increase to about a 4,000% increase, about a 5% increase to about a 3,000% increase, about a 5% increase to about a 2,000% increase, about a 5% increase to about a 1,000% increase, about a 5% increase to about a 500% increase, about a 5% increase to about a 450% increase, about a 5% increase to about a 400% increase, about a 5% increase to about a 350% increase, about a 5% increase to about a 300% increase, about a 5% increase to about a 250% increase, about a 5% increase to about a 200% increase, about a 5% increase to about a 180% increase, about a 5% increase to about a 160% increase, about a 5% increase to about a 140% increase, about a 5% increase to about a 120% increase, about a 5% increase to about a 100% increase, about a 5% increase to about a 95% increase, about a 5% increase to about a 90% increase, about a 5% increase to about a 85% increase, about a 5% increase to about a 80% increase, about a 5% increase to about a 75% increase, about a 5% increase to about a 70% increase, about a 5% increase to about a 65% increase, about a 5% increase to about a 60% increase, about a 5% increase to about a 55% increase, about a 5% increase to about a 50% increase, about a 5% increase to about a 45% increase, about a 5% increase to about a 40% increase, about a 5% increase to about a 35% increase, about a 5% increase to about a 25% increase, about a 5% increase to about a 20% increase, about a 5% increase to about a 15% increase, about a 5% increase to about a 10% increase, about a 10% increase to about 10,000% increase, about a 10% increase to about a 9,000% increase, about a 10% increase to about a 8,000% increase, about a 10% increase to about a 7,000% increase, about a 10% increase to about a 6,000% increase, about a 10% increase to about a 5,000% increase, about a 10% increase to about a 4,000% increase, about a 10% increase to about a 3,000% increase, about a 10% increase to about a 2,000% increase, about a 10% increase to about a 1,000% increase, about a 10% increase to about a 500% increase, about a 10% increase to about a 450% increase, about a 10% increase to about a 400% increase, about a 10% increase to about a 350% increase, about a 10% increase to about a 300% increase, about a 10% increase to about a 250% increase, about a 10% increase to about a 200% increase, about a 10% increase to about a 180% increase, about a 10% increase to about a 160% increase, about a 10% increase to about a 140% increase, about a 10% increase to about a 120% increase, about a 10% increase to about a 100% increase, about a 10% increase to about a 95% increase, about a 10% increase to about a 90% increase, about a 10% increase to about a 85% increase, about a 10% increase to about a 80% increase, about a 10% increase to about a 75% increase, about a 10% increase to about a 70% increase, about a 10% increase to about a 65% increase, about a 10% increase to about a 60% increase, about a 10% increase to about a 55% increase, about a 10% increase to about a 50% increase, about a 10% increase to about a 45% increase, about a 10% increase to about a 40% increase, about a 10% increase to about a 35% increase, about a 10% increase to about a 30% increase, about a 10% increase to about a 25% increase, about a 10% increase to about a 20% increase, about a 10% increase to about a 15% increase, about a 15% increase to about 10,000% increase, about a 15% increase to about a 9,000% increase, about a 15% increase to about a 8,000% increase, about a 15% increase to about a 7,000% increase, about a 15% increase to about a 6,000% increase, about a 15% increase to about a 5,000% increase, about a 15% increase to about a 4,000% increase, about a 15% increase to about a 3,000% increase, about a 15% increase to about a 2,000% increase, about a 15% increase to about a 1,000% increase, about a 15% increase to about a 500% increase, about a 15% increase to about a 450% increase, about a 15% increase to about a 400% increase, about a 15% increase to about a 350% increase, about a 15% increase to about a 300% increase, about a 15% increase to about a 250% increase, about a 15% increase to about a 200% increase, about a 15% increase to about a 180% increase, about a 15% increase to about a 160% increase, about a 15% increase to about a 140% increase, about a 15% increase to about a 120% increase, about a 15% increase to about a 100% increase, about a 15% increase to about a 95% increase, about a 15% increase to about a 90% increase, about a 15% increase to about a 85% increase, about a 15% increase to about a 80% increase, about a 15% increase to about a 75% increase, about a 15% increase to about a 70% increase, about a 15% increase to about a 65% increase, about a 15% increase to about a 60% increase, about a 15% increase to about a 55% increase, about a 15% increase to about a 50% increase, about a 15% increase to about a 45% increase, about a 15% increase to about a 40% increase, about a 15% increase to about a 35% increase, about a 15% increase to about a 30% increase, about a 15% increase to about a 25% increase, about a 15% increase to about a 20% increase, about a 20% increase to about 10,000% increase, about a 20% increase to about a 9,000% increase, about a 20% increase to about a 8,000% increase, about a 20% increase to about a 7,000% increase, about a 20% increase to about a 6,000% increase, about a 20% increase to about a 5,000% increase, about a 20% increase to about a 4,000% increase, about a 20% increase to about a 3,000% increase, about a 20% increase to about a 2,000% increase, about a 20% increase to about a 1,000% increase, about a 20% increase to about a 500% increase, about a 20% increase to about a 450% increase, about a 20% increase to about a 400% increase, about a 20% increase to about a 350% increase, about a 20% increase to about a 300% increase, about a 20% increase to about a 250% increase, about a 20% increase to about a 200% increase, about a 20% increase to about a 180% increase, about a 20% increase to about a 160% increase, about a 20% increase to about a 140% increase, about a 20% increase to about a 120% increase, about a 20% increase to about a 100% increase, about a 20% increase to about a 95% increase, about a 20% increase to about a 90% increase, about a 20% increase to about a 85% increase, about a 20% increase to about a 80% increase, about a 20% increase to about a 75% increase, about a 20% increase to about a 70% increase, about a 20% increase to about a 65% increase, about a 20% increase to about a 60% increase, about a 20% increase to about a 55% increase, about a 20% increase to about a 50% increase, about a 20% increase to about a 45% increase, about a 20% increase to about a 40% increase, about a 20% increase to about a 35% increase, about a 20% increase to about a 30% increase, about a 20% increase to about a 25% increase, about a 25% increase to about 10,000% increase, about a 25% increase to about a 9,000% increase, about a 25% increase to about a 8,000% increase, about a 25% increase to about a 7,000% increase, about a 25% increase to about a 6,000% increase, about a 25% increase to about a 5,000% increase, about a 25% increase to about a 4,000% increase, about a 25% increase to about a 3,000% increase, about a 25% increase to about a 2,000% increase, about a 25% increase to about a 1,000% increase, about a 25% increase to about a 500% increase, about a 25% increase to about a 450% increase, about a 25% increase to about a 400% increase, about a 25% increase to about a 350% increase, about a 25% increase to about a 300% increase, about a 25% increase to about a 250% increase, about a 25% increase to about a 200% increase, about a 25% increase to about a 180% increase, about a 25% increase to about a 160% increase, about a 25% increase to about a 140% increase, about a 25% increase to about a 120% increase, about a 25% increase to about a 100% increase, about a 25% increase to about a 95% increase, about a 25% increase to about a 90% increase, about a 25% increase to about a 85% increase, about a 25% increase to about a 80% increase, about a 25% increase to about a 75% increase, about a 25% increase to about a 70% increase, about a 25% increase to about a 65% increase, about a 25% increase to about a 60% increase, about a 25% increase to about a 55% increase, about a 25% increase to about a 50% increase, about a 25% increase to about a 45% increase, about a 25% increase to about a 40% increase, about a 25% increase to about a 35% increase, about a 25% increase to about a 30% increase, about a 30% increase to about 10,000% increase, about a 30% increase to about a 9,000% increase, about a 30% increase to about a 8,000% increase, about a 30% increase to about a 7,000% increase, about a 30% increase to about a 6,000% increase, about a 30% increase to about a 5,000% increase, about a 30% increase to about a 4,000% increase, about a 30% increase to about a 3,000% increase, about a 30% increase to about a 2,000% increase, about a 30% increase to about a 1,000% increase, about a 30% increase to about a 500% increase, about a 30% increase to about a 450% increase, about a 30% increase to about a 400% increase, about a 30% increase to about a 350% increase, about a 30% increase to about a 300% increase, about a 30% increase to about a 250% increase, about a 30% increase to about a 200% increase, about a 30% increase to about a 180% increase, about a 30% increase to about a 160% increase, about a 30% increase to about a 140% increase, about a 30% increase to about a 120% increase, about a 30% increase to about a 100% increase, about a 30% increase to about a 95% increase, about a 30% increase to about a 90% increase, about a 30% increase to about a 85% increase, about a 30% increase to about a 80% increase, about a 30% increase to about a 75% increase, about a 30% increase to about a 70% increase, about a 30% increase to about a 65% increase, about a 30% increase to about a 60% increase, about a 30% increase to about a 55% increase, about a 30% increase to about a 50% increase, about a 30% increase to about a 45% increase, about a 30% increase to about a 40% increase, about a 30% increase to about a 35% increase, about a 35% increase to about 10,000% increase, about a 35% increase to about a 9,000% increase, about a 35% increase to about a 8,000% increase, about a 35% increase to about a 7,000% increase, about a 35% increase to about a 6,000% increase, about a 35% increase to about a 5,000% increase, about a 35% increase to about a 4,000% increase, about a 35% increase to about a 3,000% increase, about a 35% increase to about a 2,000% increase, about a 35% increase to about a 1,000% increase, about a 35% increase to about a 500% increase, about a 35% increase to about a 450% increase, about a 35% increase to about a 400% increase, about a 35% increase to about a 350% increase, about a 35% increase to about a 300% increase, about a 35% increase to about a 250% increase, about a 35% increase to about a 200% increase, about a 35% increase to about a 180% increase, about a 35% increase to about a 160% increase, about a 35% increase to about a 140% increase, about a 35% increase to about a 120% increase, about a 35% increase to about a 100% increase, about a 35% increase to about a 95% increase, about a 35% increase to about a 90% increase, about a 35% increase to about a 85% increase, about a 35% increase to about a 80% increase, about a 35% increase to about a 75% increase, about a 35% increase to about a 70% increase, about a 35% increase to about a 65% increase, about a 35% increase to about a 60% increase, about a 35% increase to about a 55% increase, about a 35% increase to about a 50% increase, about a 35% increase to about a 45% increase, about a 35% increase to about a 40% increase, about a 40% increase to about 10,000% increase, about a 40% increase to about a 9,000% increase, about a 40% increase to about a 8,000% increase, about a 40% increase to about a 7,000% increase, about a 40% increase to about a 6,000% increase, about a 40% increase to about a 5,000% increase, about a 40% increase to about a 4,000% increase, about a 40% increase to about a 3,000% increase, about a 40% increase to about a 2,000% increase, about a 40% increase to about a 1,000% increase, about a 40% increase to about a 500% increase, about a 40% increase to about a 450% increase, about a 40% increase to about a 400% increase, about a 40% increase to about a 350% increase, about a 40% increase to about a 300% increase, about a 40% increase to about a 250% increase, about a 40% increase to about a 200% increase, about a 40% increase to about a 180% increase, about a 40% increase to about a 160% increase, about a 40% increase to about a 140% increase, about a 40% increase to about a 120% increase, about a 40% increase to about a 100% increase, about a 40% increase to about a 95% increase, about a 40% increase to about a 90% increase, about a 40% increase to about a 85% increase, about a 40% increase to about a 80% increase, about a 40% increase to about a 75% increase, about a 40% increase to about a 70% increase, about a 40% increase to about a 65% increase, about a 40% increase to about a 60% increase, about a 40% increase to about a 55% increase, about a 40% increase to about a 50% increase, about a 40% increase to about a 45% increase, about a 45% increase to about 10,000% increase, about a 45% increase to about a 9,000% increase, about a 45% increase to about a 8,000% increase, about a 45% increase to about a 7,000% increase, about a 45% increase to about a 6,000% increase, about a 45% increase to about a 5,000% increase, about a 45% increase to about a 4,000% increase, about a 45% increase to about a 3,000% increase, about a 45% increase to about a 2,000% increase, about a 45% increase to about a 1,000% increase, about a 45% increase to about a 500% increase, about a 45% increase to about a 450% increase, about a 45% increase to about a 400% increase, about a 45% increase to about a 350% increase, about a 45% increase to about a 300% increase, about a 45% increase to about a 250% increase, about a 45% increase to about a 200% increase, about a 45% increase to about a 180% increase, about a 45% increase to about a 160% increase, about a 45% increase to about a 140% increase, about a 45% increase to about a 120% increase, about a 45% increase to about a 100% increase, about a 45% increase to about a 95% increase, about a 45% increase to about a 90% increase, about a 45% increase to about a 85% increase, about a 45% increase to about a 80% increase, about a 45% increase to about a 75% increase, about a 45% increase to about a 70% increase, about a 45% increase to about a 65% increase, about a 45% increase to about a 60% increase, about a 45% increase to about a 55% increase, about a 45% increase to about a 50% increase, about a 50% increase to about 10,000% increase, about a 50% increase to about a 9,000% increase, about a 50% increase to about a 8,000% increase, about a 50% increase to about a 7,000% increase, about a 50% increase to about a 6,000% increase, about a 50% increase to about a 5,000% increase, about a 50% increase to about a 4,000% increase, about a 50% increase to about a 3,000% increase, about a 50% increase to about a 2,000% increase, about a 50% increase to about a 1,000% increase, about a 50% increase to about a 500% increase, about a 50% increase to about a 450% increase, about a 50% increase to about a 400% increase, about a 50% increase to about a 350% increase, about a 50% increase to about a 300% increase, about a 50% increase to about a 250% increase, about a 50% increase to about a 200% increase, about a 50% increase to about a 180% increase, about a 50% increase to about a 160% increase, about a 50% increase to about a 140% increase, about a 50% increase to about a 120% increase, about a 50% increase to about a 100% increase, about a 50% increase to about a 95% increase, about a 50% increase to about a 90% increase, about a 50% increase to about a 85% increase, about a 50% increase to about a 80% increase, about a 50% increase to about a 75% increase, about a 50% increase to about a 70% increase, about a 50% increase to about a 65% increase, about a 50% increase to about a 60% increase, about a 50% increase to about a 55% increase, about a 55% increase to about 10,000% increase, about a 55% increase to about a 9,000% increase, about a 55% increase to about a 8,000% increase, about a 55% increase to about a 7,000% increase, about a 55% increase to about a 6,000% increase, about a 55% increase to about a 5,000% increase, about a 55% increase to about a 4,000% increase, about a 55% increase to about a 3,000% increase, about a 55% increase to about a 2,000% increase, about a 55% increase to about a 1,000% increase, about a 55% increase to about a 500% increase, about a 55% increase to about a 450% increase, about a 55% increase to about a 400% increase, about a 55% increase to about a 350% increase, about a 55% increase to about a 300% increase, about a 55% increase to about a 250% increase, about a 55% increase to about a 200% increase, about a 55% increase to about a 180% increase, about a 55% increase to about a 160% increase, about a 55% increase to about a 140% increase, about a 55% increase to about a 120% increase, about a 55% increase to about a 100% increase, about a 55% increase to about a 95% increase, about a 55% increase to about a 90% increase, about a 55% increase to about a 85% increase, about a 55% increase to about a 80% increase, about a 55% increase to about a 75% increase, about a 55% increase to about a 70% increase, about a 55% increase to about a 65% increase, about a 55% increase to about a 60% increase, about a 60% increase to about 10,000% increase, about a 60% increase to about a 9,000% increase, about a 60% increase to about a 8,000% increase, about a 60% increase to about a 7,000% increase, about a 60% increase to about a 6,000% increase, about a 60% increase to about a 5,000% increase, about a 60% increase to about a 4,000% increase, about a 60% increase to about a 3,000% increase, about a 60% increase to about a 2,000% increase, about a 60% increase to about a 1,000% increase, about a 60% increase to about a 500% increase, about a 60% increase to about a 450% increase, about a 60% increase to about a 400% increase, about a 60% increase to about a 350% increase, about a 60% increase to about a 300% increase, about a 60% increase to about a 250% increase, about a 60% increase to about a 200% increase, about a 60% increase to about a 180% increase, about a 60% increase to about a 160% increase, about a 60% increase to about a 140% increase, about a 60% increase to about a 120% increase, about a 60% increase to about a 100% increase, about a 60% increase to about a 95% increase, about a 60% increase to about a 90% increase, about a 60% increase to about a 85% increase, about a 60% increase to about a 80% increase, about a 60% increase to about a 75% increase, about a 60% increase to about a 70% increase, about a 60% increase to about a 65% increase, about a 65% increase to about 10,000% increase, about a 65% increase to about a 9,000% increase, about a 65% increase to about a 8,000% increase, about a 65% increase to about a 7,000% increase, about a 65% increase to about a 6,000% increase, about a 65% increase to about a 5,000% increase, about a 65% increase to about a 4,000% increase, about a 65% increase to about a 3,000% increase, about a 65% increase to about a 2,000% increase, about a 65% increase to about a 1,000% increase, about a 65% increase to about a 500% increase, about a 65% increase to about a 450% increase, about a 65% increase to about a 400% increase, about a 65% increase to about a 350% increase, about a 65% increase to about a 300% increase, about a 65% increase to about a 250% increase, about a 65% increase to about a 200% increase, about a 65% increase to about a 180% increase, about a 65% increase to about a 160% increase, about a 65% increase to about a 140% increase, about a 65% increase to about a 120% increase, about a 65% increase to about a 100% increase, about a 65% increase to about a 95% increase, about a 65% increase to about a 90% increase, about a 65% increase to about a 85% increase, about a 65% increase to about a 80% increase, about a 65% increase to about a 75% increase, about a 65% increase to about a 70% increase, about a 70% increase to about 10,000% increase, about a 70% increase to about a 9,000% increase, about a 70% increase to about a 8,000% increase, about a 70% increase to about a 7,000% increase, about a 70% increase to about a 6,000% increase, about a 70% increase to about a 5,000% increase, about a 70% increase to about a 4,000% increase, about a 70% increase to about a 3,000% increase, about a 70% increase to about a 2,000% increase, about a 70% increase to about a 1,000% increase, about a 70% increase to about a 500% increase, about a 70% increase to about a 450% increase, about a 70% increase to about a 400% increase, about a 70% increase to about a 350% increase, about a 70% increase to about a 300% increase, about a 70% increase to about a 250% increase, about a 70% increase to about a 200% increase, about a 70% increase to about a 180% increase, about a 70% increase to about a 160% increase, about a 70% increase to about a 140% increase, about a 70% increase to about a 120% increase, about a 70% increase to about a 100% increase, about a 70% increase to about a 95% increase, about a 70% increase to about a 90% increase, about a 70% increase to about a 85% increase, about a 70% increase to about a 80% increase, about a 70% increase to about a 75% increase, about a 75% increase to about 10,000% increase, about a 75% increase to about a 9,000% increase, about a 75% increase to about a 8,000% increase, about a 75% increase to about a 7,000% increase, about a 75% increase to about a 6,000% increase, about a 75% increase to about a 5,000% increase, about a 75% increase to about a 4,000% increase, about a 75% increase to about a 3,000% increase, about a 75% increase to about a 2,000% increase, about a 75% increase to about a 1,000% increase, about a 75% increase to about a 500% increase, about a 75% increase to about a 450% increase, about a 75% increase to about a 400% increase, about a 75% increase to about a 350% increase, about a 75% increase to about a 300% increase, about a 75% increase to about a 250% increase, about a 75% increase to about a 200% increase, about a 75% increase to about a 180% increase, about a 75% increase to about a 160% increase, about a 75% increase to about a 140% increase, about a 75% increase to about a 120% increase, about a 75% increase to about a 100% increase, about a 75% increase to about a 95% increase, about a 75% increase to about a 90% increase, about a 75% increase to about a 85% increase, about a 75% increase to about a 80%, about a 80% increase to about 10,000% increase, about a 80% increase to about a 9,000% increase, about a 80% increase to about a 8,000% increase, about a 80% increase to about a 7,000% increase, about a 80% increase to about a 6,000% increase, about a 80% increase to about a 5,000% increase, about a 80% increase to about a 4,000% increase, about a 80% increase to about a 3,000% increase, about a 80% increase to about a 2,000% increase, about a 80% increase to about a 1,000% increase, increase, about a 80% increase to about a 500% increase, about a 80% increase to about a 450% increase, about a 80% increase to about a 400% increase, about a 80% increase to about a 350% increase, about a 80% increase to about a 300% increase, about a 80% increase to about a 250% increase, about a 80% increase to about a 200% increase, about a 80% increase to about a 180% increase, about a 80% increase to about a 160% increase, about a 80% increase to about a 140% increase, about a 80% increase to about a 120% increase, about a 80% increase to about a 100% increase, about a 80% increase to about a 95% increase, about a 80% increase to about a 90% increase, about a 80% increase to about a 85% increase, about a 85% increase to about 10,000% increase, about a 85% increase to about a 9,000% increase, about a 85% increase to about a 8,000% increase, about a 85% increase to about a 7,000% increase, about a 85% increase to about a 6,000% increase, about a 85% increase to about a 5,000% increase, about a 85% increase to about a 4,000% increase, about a 85% increase to about a 3,000% increase, about a 85% increase to about a 2,000% increase, about a 85% increase to about a 1,000% increase, about a 85% increase to about a 500% increase, about a 85% increase to about a 450% increase, about a 85% increase to about a 400% increase, about a 85% increase to about a 350% increase, about a 85% increase to about a 300% increase, about a 85% increase to about a 250% increase, about a 85% increase to about a 200% increase, about a 85% increase to about a 180% increase, about a 85% increase to about a 160% increase, about a 85% increase to about a 140% increase, about a 85% increase to about a 120% increase, about a 85% increase to about a 100% increase, about a 85% increase to about a 95% increase, about a 85% increase to about a 90% increase, about a 90% increase to about 10,000% increase, about a 90% increase to about a 9,000% increase, about a 90% increase to about a 8,000% increase, about a 90% increase to about a 7,000% increase, about a 90% increase to about a 6,000% increase, about a 90% increase to about a 5,000% increase, about a 90% increase to about a 4,000% increase, about a 90% increase to about a 3,000% increase, about a 90% increase to about a 2,000% increase, about a 90% increase to about a 1,000% increase, about a 90% increase to about a 500% increase, about a 90% increase to about a 450% increase, about a 90% increase to about a 400% increase, about a 90% increase to about a 350% increase, about a 90% increase to about a 300% increase, about a 90% increase to about a 250% increase, about a 90% increase to about a 200% increase, about a 90% increase to about a 180% increase, about a 90% increase to about a 160% increase, about a 90% increase to about a 140% increase, about a 90% increase to about a 120% increase, about a 90% increase to about a 100% increase, about a 90% increase to about a 95% increase, about a 95% increase to about 10,000% increase, about a 95% increase to about a 9,000% increase, about a 95% increase to about a 8,000% increase, about a 95% increase to about a 7,000% increase, about a 95% increase to about a 6,000% increase, about a 95% increase to about a 5,000% increase, about a 95% increase to about a 4,000% increase, about a 95% increase to about a 3,000% increase, about a 95% increase to about a 2,000% increase, about a 95% increase to about a 1,000% increase, about a 95% increase to about a 500% increase, about a 95% increase to about a 450% increase, about a 95% increase to about a 400% increase, about a 95% increase to about a 350% increase, about a 95% increase to about a 300% increase, about a 95% increase to about a 250% increase, about a 95% increase to about a 200% increase, about a 95% increase to about a 180% increase, about a 95% increase to about a 160% increase, about a 95% increase to about a 140% increase, about a 95% increase to about a 120% increase, about a 95% increase to about a 100% increase, about a 100% increase to about 10,000% increase, about a 100% increase to about a 9,000% increase, about a 100% increase to about a 8,000% increase, about a 100% increase to about a 7,000% increase, about a 100% increase to about a 6,000% increase, about a 100% increase to about a 5,000% increase, about a 100% increase to about a 4,000% increase, about a 100% increase to about a 3,000% increase, about a 100% increase to about a 2,000% increase, about a 100% increase to about a 1,000% increase, about a 100% increase to about a 500% increase, about a 100% increase to about a 450% increase, about a 100% increase to about a 400% increase, about a 100% increase to about a 350% increase, about a 100% increase to about a 300% increase, about a 100% increase to about a 250% increase, about a 100% increase to about a 200% increase, about a 100% increase to about a 180% increase, about a 100% increase to about a 160% increase, about a 100% increase to about a 140% increase, about a 100% increase to about a 120% increase, about a 120% increase to about 10,000% increase, about a 120% increase to about a 9,000% increase, about a 120% increase to about a 8,000% increase, about a 120% increase to about a 7,000% increase, about a 120% increase to about a 6,000% increase, about a 120% increase to about a 5,000% increase, about a 120% increase to about a 4,000% increase, about a 120% increase to about a 3,000% increase, about a 120% increase to about a 2,000% increase, about a 120% increase to about a 1,000% increase, about a 120% increase to about a 500% increase, about a 120% increase to about a 450% increase, about a 120% increase to about a 400% increase, about a 120% increase to about a 350% increase, about a 120% increase to about a 300% increase, about a 120% increase to about a 250% increase, about a 120% increase to about a 200% increase, about a 120% increase to about a 180% increase, about a 120% increase to about a 160% increase, about a 120% increase to about a 140% increase, about a 140% increase to about 10,000% increase, about a 140% increase to about a 9,000% increase, about a 140% increase to about a 8,000% increase, about a 140% increase to about a 7,000% increase, about a 140% increase to about a 6,000% increase, about a 140% increase to about a 5,000% increase, about a 140% increase to about a 4,000% increase, about a 140% increase to about a 3,000% increase, about a 140% increase to about a 2,000% increase, about a 140% increase to about a 1,000% increase, about a 140% increase to about a 500% increase, about a 140% increase to about a 450% increase, about a 140% increase to about a 400% increase, about a 140% increase to about a 350% increase, about a 140% increase to about a 300% increase, about a 140% increase to about a 250% increase, about a 140% increase to about a 200% increase, about a 140% increase to about a 180% increase, about a 140% increase to about a 160% increase, about a 160% increase to about 10,000% increase, about a 160% increase to about a 9,000% increase, about a 160% increase to about a 8,000% increase, about a 160% increase to about a 7,000% increase, about a 160% increase to about a 6,000% increase, about a 160% increase to about a 5,000% increase, about a 160% increase to about a 4,000% increase, about a 160% increase to about a 3,000% increase, about a 160% increase to about a 2,000% increase, about a 160% increase to about a 1,000% increase, about a 160% increase to about a 500% increase, about a 160% increase to about a 450% increase, about a 160% increase to about a 400% increase, about a 160% increase to about a 350% increase, about a 160% increase to about a 300% increase, about a 160% increase to about a 250% increase, about a 160% increase to about a 200% increase, about a 160% increase to about a 180% increase, about a 180% increase to about 10,000% increase, about a 180% increase to about a 9,000% increase, about a 180% increase to about a 8,000% increase, about a 180% increase to about a 7,000% increase, about a 180% increase to about a 6,000% increase, about a 180% increase to about a 5,000% increase, about a 180% increase to about a 4,000% increase, about a 180% increase to about a 3,000% increase, about a 180% increase to about a 2,000% increase, about a 180% increase to about a 1,000% increase, about a 180% increase to about a 500% increase, about a 180% increase to about a 450% increase, about a 180% increase to about a 400% increase, about a 180% increase to about a 350% increase, about a 180% increase to about a 300% increase, about a 180% increase to about a 250% increase, about a 180% increase to about a 200% increase, about a 200% increase to about 10,000% increase, about a 200% increase to about a 9,000% increase, about a 200% increase to about a 8,000% increase, about a 200% increase to about a 7,000% increase, about a 200% increase to about a 6,000% increase, about a 200% increase to about a 5,000% increase, about a 200% increase to about a 4,000% increase, about a 200% increase to about a 3,000% increase, about a 200% increase to about a 2,000% increase, about a 200% increase to about a 1,000% increase, about a 200% increase to about a 500% increase, about a 200% increase to about a 450% increase, about a 200% increase to about a 400% increase, about a 200% increase to about a 350% increase, about a 200% increase to about a 300% increase, about a 200% increase to about a 250% increase, about a 250% increase to about 10,000% increase, about a 250% increase to about a 9,000% increase, about a 250% increase to about a 8,000% increase, about a 250% increase to about a 7,000% increase, about a 250% increase to about a 6,000% increase, about a 250% increase to about a 5,000% increase, about a 250% increase to about a 4,000% increase, about a 250% increase to about a 3,000% increase, about a 250% increase to about a 2,000% increase, about a 250% increase to about a 1,000% increase, about a 250% increase to about a 500% increase, about a 250% increase to about a 450% increase, about a 250% increase to about a 400% increase, about a 250% increase to about a 350% increase, about a 250% increase to about a 300% increase, about a 300% increase to about 10,000% increase, about a 300% increase to about a 9,000% increase, about a 300% increase to about a 8,000% increase, about a 300% increase to about a 7,000% increase, about a 300% increase to about a 6,000% increase, about a 300% increase to about a 5,000% increase, about a 300% increase to about a 4,000% increase, about a 300% increase to about a 3,000% increase, about a 300% increase to about a 2,000% increase, about a 300% increase to about a 1,000% increase, about a 300% increase to about a 500% increase, about a 300% increase to about a 450% increase, about a 300% increase to about a 400% increase, about a 300% increase to about a 350% increase, about a 350% increase to about 10,000% increase, about a 350% increase to about a 9,000% increase, about a 350% increase to about a 8,000% increase, about a 350% increase to about a 7,000% increase, about a 350% increase to about a 6,000% increase, about a 350% increase to about a 5,000% increase, about a 350% increase to about a 4,000% increase, about a 350% increase to about a 3,000% increase, about a 350% increase to about a 2,000% increase, about a 350% increase to about a 1,000% increase, about a 350% increase to about a 500% increase, about a 350% increase to about a 450% increase, about a 350% increase to about a 400% increase, about a 400% increase to about 10,000% increase, about a 400% increase to about a 9,000% increase, about a 400% increase to about a 8,000% increase, about a 400% increase to about a 7,000% increase, about a 400% increase to about a 6,000% increase, about a 400% increase to about a 5,000% increase, about a 400% increase to about a 4,000% increase, about a 400% increase to about a 3,000% increase, about a 400% increase to about a 2,000% increase, about a 400% increase to about a 1,000% increase, about a 400% increase to about a 500% increase, about a 400% increase to about a 450% increase, about a 450% increase to about 10,000% increase, about a 450% increase to about a 9,000% increase, about a 450% increase to about a 8,000% increase, about a 450% increase to about a 7,000% increase, about a 450% increase to about a 6,000% increase, about a 450% increase to about a 5,000% increase, about a 450% increase to about a 4,000% increase, about a 450% increase to about a 3,000% increase, about a 450% increase to about a 2,000% increase, about a 450% increase to about a 1,000% increase, about a 450% increase to about a 500% increase, about a 500% increase to about 10,000% increase, about a 500% increase to about a 9,000% increase, about a 500% increase to about a 8,000% increase, about a 500% increase to about a 7,000% increase, about a 500% increase to about a 6,000% increase, about a 500% increase to about a 5,000% increase, about a 500% increase to about a 4,000% increase, about a 500% increase to about a 3,000% increase, about a 500% increase to about a 2,000% increase, about a 500% increase to about a 1,000% increase, about a 1,000% increase to about 10,000% increase, about a 1,000% increase to about a 9,000% increase, about a 1,000% increase to about a 8,000% increase, about a 1,000% increase to about a 7,000% increase, about a 1,000% increase to about a 6,000% increase, about a 1,000% increase to about a 5,000% increase, about a 1,000% increase to about a 4,000% increase, about a 1,000% increase to about a 3,000% increase, about a 1,000% increase to about a 2,000% increase, about a 2,000% increase to about 10,000% increase, about a 2,000% increase to about a 9,000% increase, about a 2,000% increase to about a 8,000% increase, about a 2,000% increase to about a 7,000% increase, about a 2,000% increase to about a 6,000% increase, about a 2,000% increase to about a 5,000% increase, about a 2,000% increase to about a 4,000% increase, about a 2,000% increase to about a 3,000% increase, about a 3,000% increase to about 10,000% increase, about a 3,000% increase to about a 9,000% increase, about a 3,000% increase to about a 8,000% increase, about a 3,000% increase to about a 7,000% increase, about a 3,000% increase to about a 6,000% increase, about a 3,000% increase to about a 5,000% increase, about a 3,000% increase to about a 4,000% increase, about a 4,000% increase to about 10,000% increase, about a 4,000% increase to about a 9,000% increase, about a 4,000% increase to about a 8,000% increase, about a 4,000% increase to about a 7,000% increase, about a 4,000% increase to about a 6,000% increase, about a 4,000% increase to about a 5,000% increase, about a 5,000% increase to about 10,000% increase, about a 5,000% increase to about a 9,000% increase, about a 5,000% increase to about a 8,000% increase, about a 5,000% increase to about a 7,000% increase, about a 5,000% increase to about a 6,000% increase, about a 6,000% increase to about 10,000% increase, about a 6,000% increase to about a 9,000% increase, about a 6,000% increase to about a 8,000% increase, about a 6,000% increase to about a 7,000% increase, about a 7,000% increase to about 10,000% increase, about a 7,000% increase to about a 9,000% increase, about a 7,000% increase to about a 8,000% increase, about a 8,000% increase to about 10,000% increase, about a 8,000% increase to about a 9,000% increase, or about a 9,000% increase to about 10,000%) in toxin liberation in the target mammalian cell (e.g., any of the target mammalian cells described herein) as compared to a composition including the same amount of a control antibody (e.g., any of the exemplary control antibodies described herein).

In some examples of any of the antibodies described herein, a composition including the antibody (e.g., any of the antibodies described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about a 100-fold increase, about 0.1-fold increase to about a 90-fold increase, about 0.1-fold increase to about a 80-fold increase, about a 0.1-fold increase to about a 70-fold increase, about a 0.1-fold increase to about a 60-fold increase, about a 0.1-fold increase to about a 50-fold increase, about a 0.1-fold increase to about a 40-fold increase, about a 0.1-fold increase to about a 30-fold increase, about 0.1-fold increase to about 20-fold increase, about a 0.1-fold increase to about a 10-fold increase, about a 0.1-fold increase to about a 9.5-fold increase, about a 0.1-fold increase to about a 9.0-fold increase, about a 0.1-fold increase to about a 8.5-fold increase, about a 0.1-fold increase to about a 8.0-fold increase, about a 0.1-fold increase to about a 7.5-fold increase, about a 0.1-fold increase to about a 7.0-fold increase, about a 0.1-fold increase to about a 6.5-fold increase, about a 0.1-fold increase to about a 6.0-fold increase, about a 0.1-fold increase to about a 5.5-fold increase, about a 0.1-fold increase to about a 5.0-fold increase, about a 0.1-fold increase to about a 4.5-fold increase, about a 0.1-fold increase to about a 4.0-fold increase, about a 0.1-fold increase to about a 3.5-fold increase, about 0.1-fold increase to about a 3.0-fold increase, about a 0.1-fold increase to about a 2.8-fold increase, about a 0.1-fold increase to about a 2.6-fold increase, about a 0.1-fold increase to about a 2.5-fold increase, about a 0.1-fold increase to about a 2.4-fold increase, about a 0.1-fold increase to about a 2.2-fold increase, about a 0.1-fold increase to about a 2.0-fold increase, about a 0.1-fold increase to about a 1.8-fold increase, about a 0.1-fold increase to about a 1.6-fold increase, about a 0.1-fold increase to about a 1.5-fold increase, about a 0.1-fold increase to about a 1.4-fold increase, about a 0.1-fold increase to about a 1.2-fold increase, about a 0.1-fold increase to about a 1.0-fold increase, about a 0.1-fold increase to about a 0.9-fold increase, about a 0.1-fold increase to about a 0.8-fold increase, about a 0.1-fold increase to about a 0.7-fold increase, about a 0.1-fold increase to about a 0.6-fold increase, about a 0.1-fold increase to about a 0.5-fold increase, about a 0.1-fold increase to about a 0.4-fold increase, about a 0.1-fold increase to about a 0.3-fold increase, about a 0.2-fold increase to about a 100-fold increase, about 0.2-fold increase to about a 90-fold increase, about 0.2-fold increase to about a 80-fold increase, about a 0.2-fold increase to about a 70-fold increase, about a 0.2-fold increase to about a 60-fold increase, about a 0.2-fold increase to about a 50-fold increase, about a 0.2-fold increase to about a 40-fold increase, about a 0.2-fold increase to about a 30-fold increase, about 0.2-fold increase to about 20-fold increase, about a 0.2-fold increase to about a 10-fold increase, about a 0.2-fold increase to about a 9.5-fold increase, about a 0.2-fold increase to about a 9.0-fold increase, about a 0.2-fold increase to about a 8.5-fold increase, about a 0.2-fold increase to about a 8.0-fold increase, about a 0.2-fold increase to about a 7.5-fold increase, about a 0.2-fold increase to about a 7.0-fold increase, about a 0.2-fold increase to about a 6.5-fold increase, about a 0.2-fold increase to about a 6.0-fold increase, about a 0.2-fold increase to about a 5.5-fold increase, about a 0.2-fold increase to about a 5.0-fold increase, about a 0.2-fold increase to about a 4.5-fold increase, about a 0.2-fold increase to about a 4.0-fold increase, about a 0.2-fold increase to about a 3.5-fold increase, about 0.2-fold increase to about a 3.0-fold increase, about a 0.2-fold increase to about a 2.8-fold increase, about a 0.2-fold increase to about a 2.6-fold increase, about a 0.2-fold increase to about a 2.5-fold increase, about a 0.2-fold increase to about a 2.4-fold increase, about a 0.2-fold increase to about a 2.2-fold increase, about a 0.2-fold increase to about a 2.0-fold increase, about a 0.2-fold increase to about a 1.8-fold increase, about a 0.2-fold increase to about a 1.6-fold increase, about a 0.2-fold increase to about a 1.5-fold increase, about a 0.2-fold increase to about a 1.4-fold increase, about a 0.2-fold increase to about a 1.2-fold increase, about a 0.2-fold increase to about a 1.0-fold increase, about a 0.2-fold increase to about a 0.9-fold increase, about a 0.2-fold increase to about a 0.8-fold increase, about a 0.2-fold increase to about a 0.7-fold increase, about a 0.2-fold increase to about a 0.6-fold increase, about a 0.2-fold increase to about a 0.5-fold increase, about a 0.2-fold increase to about a 0.4-fold increase, about a 0.3-fold increase to about a 100-fold increase, about 0.3-fold increase to about a 90-fold increase, about 0.3-fold increase to about a 80-fold increase, about a 0.3-fold increase to about a 70-fold increase, about a 0.3-fold increase to about a 60-fold increase, about a 0.3-fold increase to about a 50-fold increase, about a 0.3-fold increase to about a 40-fold increase, about a 0.3-fold increase to about a 30-fold increase, about 0.3-fold increase to about 20-fold increase, about a 0.3-fold increase to about a 10-fold increase, about a 0.3-fold increase to about a 9.5-fold increase, about a 0.3-fold increase to about a 9.0-fold increase, about a 0.3-fold increase to about a 8.5-fold increase, about a 0.3-fold increase to about a 8.0-fold increase, about a 0.3-fold increase to about a 7.5-fold increase, about a 0.3-fold increase to about a 7.0-fold increase, about a 0.3-fold increase to about a 6.5-fold increase, about a 0.3-fold increase to about a 6.0-fold increase, about a 0.3-fold increase to about a 5.5-fold increase, about a 0.3-fold increase to about a 5.0-fold increase, about a 0.3-fold increase to about a 4.5-fold increase, about a 0.3-fold increase to about a 4.0-fold increase, about a 0.3-fold increase to about a 3.5-fold increase, about 0.3-fold increase to about a 3.0-fold increase, about a 0.3-fold increase to about a 2.8-fold increase, about a 0.3-fold increase to about a 2.6-fold increase, about a 0.3-fold increase to about a 2.5-fold increase, about a 0.3-fold increase to about a 2.4-fold increase, about a 0.3-fold increase to about a 2.2-fold increase, about a 0.3-fold increase to about a 2.0-fold increase, about a 0.3-fold increase to about a 1.8-fold increase, about a 0.3-fold increase to about a 1.6-fold increase, about a 0.3-fold increase to about a 1.5-fold increase, about a 0.3-fold increase to about a 1.4-fold increase, about a 0.3-fold increase to about a 1.2-fold increase, about a 0.3-fold increase to about a 1.0-fold increase, about a 0.3-fold increase to about a 0.9-fold increase, about a 0.3-fold increase to about a 0.8-fold increase, about a 0.3-fold increase to about a 0.7-fold increase, about a 0.3-fold increase to about a 0.6-fold increase, about a 0.3-fold increase to about a 0.5-fold increase, about a 0.4-fold increase to about a 100-fold increase, about 0.4-fold increase to about a 90-fold increase, about 0.4-fold increase to about a 80-fold increase, about a 0.4-fold increase to about a 70-fold increase, about a 0.4-fold increase to about a 60-fold increase, about a 0.4-fold increase to about a 50-fold increase, about a 0.4-fold increase to about a 40-fold increase, about a 0.4-fold increase to about a 30-fold increase, about 0.4-fold increase to about 20-fold increase, about a 0.4-fold increase to about a 10-fold increase, about a 0.4-fold increase to about a 9.5-fold increase, about a 0.4-fold increase to about a 9.0-fold increase, about a 0.4-fold increase to about a 8.5-fold increase, about a 0.4-fold increase to about a 8.0-fold increase, about a 0.4-fold increase to about a 7.5-fold increase, about a 0.4-fold increase to about a 7.0-fold increase, about a 0.4-fold increase to about a 6.5-fold increase, about a 0.4-fold increase to about a 6.0-fold increase, about a 0.4-fold increase to about a 5.5-fold increase, about a 0.4-fold increase to about a 5.0-fold increase, about a 0.4-fold increase to about a 4.5-fold increase, about a 0.4-fold increase to about a 4.0-fold increase, about a 0.4-fold increase to about a 3.5-fold increase, about 0.4-fold increase to about a 3.0-fold increase, about a 0.4-fold increase to about a 2.8-fold increase, about a 0.4-fold increase to about a 2.6-fold increase, about a 0.4-fold increase to about a 2.5-fold increase, about a 0.4-fold increase to about a 2.4-fold increase, about a 0.4-fold increase to about a 2.2-fold increase, about a 0.4-fold increase to about a 2.0-fold increase, about a 0.4-fold increase to about a 1.8-fold increase, about a 0.4-fold increase to about a 1.6-fold increase, about a 0.4-fold increase to about a 1.5-fold increase, about a 0.4-fold increase to about a 1.4-fold increase, about a 0.4-fold increase to about a 1.2-fold increase, about a 0.4-fold increase to about a 1.0-fold increase, about a 0.4-fold increase to about a 0.9-fold increase, about a 0.4-fold increase to about a 0.8-fold increase, about a 0.4-fold increase to about a 0.7-fold increase, about a 0.4-fold increase to about a 0.6-fold increase, about a 0.5-fold increase to about a 100-fold increase, about 0.5-fold increase to about a 90-fold increase, about 0.5-fold increase to about a 80-fold increase, about a 0.5-fold increase to about a 70-fold increase, about a 0.5-fold increase to about a 60-fold increase, about a 0.5-fold increase to about a 50-fold increase, about a 0.5-fold increase to about a 40-fold increase, about a 0.5-fold increase to about a 30-fold increase, about 0.5-fold increase to about 20-fold increase, about a 0.5-fold increase to about a 10-fold increase, about a 0.5-fold increase to about a 9.5-fold increase, about a 0.5-fold increase to about a 9.0-fold increase, about a 0.5-fold increase to about a 8.5-fold increase, about a 0.5-fold increase to about a 8.0-fold increase, about a 0.5-fold increase to about a 7.5-fold increase, about a 0.5-fold increase to about a 7.0-fold increase, about a 0.5-fold increase to about a 6.5-fold increase, about a 0.5-fold increase to about a 6.0-fold increase, about a 0.5-fold increase to about a 5.5-fold increase, about a 0.5-fold increase to about a 5.0-fold increase, about a 0.5-fold increase to about a 4.5-fold increase, about a 0.5-fold increase to about a 4.0-fold increase, about a 0.5-fold increase to about a 3.5-fold increase, about 0.5-fold increase to about a 3.0-fold increase, about a 0.5-fold increase to about a 2.8-fold increase, about a 0.5-fold increase to about a 2.6-fold increase, about a 0.5-fold increase to about a 2.5-fold increase, about a 0.5-fold increase to about a 2.4-fold increase, about a 0.5-fold increase to about a 2.2-fold increase, about a 0.5-fold increase to about a 2.0-fold increase, about a 0.5-fold increase to about a 1.8-fold increase, about a 0.5-fold increase to about a 1.6-fold increase, about a 0.5-fold increase to about a 1.5-fold increase, about a 0.5-fold increase to about a 1.4-fold increase, about a 0.5-fold increase to about a 1.2-fold increase, about a 0.5-fold increase to about a 1.0-fold increase, about a 0.5-fold increase to about a 0.9-fold increase, about a 0.5-fold increase to about a 0.8-fold increase, about a 0.5-fold increase to about a 0.7-fold increase, about a 0.6-fold increase to about a 100-fold increase, about 0.6-fold increase to about a 90-fold increase, about 0.6-fold increase to about a 80-fold increase, about a 0.6-fold increase to about a 70-fold increase, about a 0.6-fold increase to about a 60-fold increase, about a 0.6-fold increase to about a 50-fold increase, about a 0.6-fold increase to about a 40-fold increase, about a 0.6-fold increase to about a 30-fold increase, about 0.6-fold increase to about 20-fold increase, about a 0.6-fold increase to about a 10-fold increase, about a 0.6-fold increase to about a 9.5-fold increase, about a 0.6-fold increase to about a 9.0-fold increase, about a 0.6-fold increase to about a 8.5-fold increase, about a 0.6-fold increase to about a 8.0-fold increase, about a 0.6-fold increase to about a 7.5-fold increase, about a 0.6-fold increase to about a 7.0-fold increase, about a 0.6-fold increase to about a 6.5-fold increase, about a 0.6-fold increase to about a 6.0-fold increase, about a 0.6-fold increase to about a 5.5-fold increase, about a 0.6-fold increase to about a 5.0-fold increase, about a 0.6-fold increase to about a 4.5-fold increase, about a 0.6-fold increase to about a 4.0-fold increase, about a 0.6-fold increase to about a 3.5-fold increase, about 0.6-fold increase to about a 3.0-fold increase, about a 0.6-fold increase to about a 2.8-fold increase, about a 0.6-fold increase to about a 2.6-fold increase, about a 0.6-fold increase to about a 2.5-fold increase, about a 0.6-fold increase to about a 2.4-fold increase, about a 0.6-fold increase to about a 2.2-fold increase, about a 0.6-fold increase to about a 2.0-fold increase, about a 0.6-fold increase to about a 1.8-fold increase, about a 0.6-fold increase to about a 1.6-fold increase, about a 0.6-fold increase to about a 1.5-fold increase, about a 0.6-fold increase to about a 1.4-fold increase, about a 0.6-fold increase to about a 1.2-fold increase, about a 0.6-fold increase to about a 1.0-fold increase, about a 0.6-fold increase to about a 0.9-fold increase, about a 0.6-fold increase to about a 0.8-fold increase, about a 0.7-fold increase to about a 100-fold increase, about 0.7-fold increase to about a 90-fold increase, about 0.7-fold increase to about a 80-fold increase, about a 0.7-fold increase to about a 70-fold increase, about a 0.7-fold increase to about a 60-fold increase, about a 0.7-fold increase to about a 50-fold increase, about a 0.7-fold increase to about a 40-fold increase, about a 0.7-fold increase to about a 30-fold increase, about 0.7-fold increase to about 20-fold increase, about a 0.7-fold increase to about a 10-fold increase, about a 0.7-fold increase to about a 9.5-fold increase, about a 0.7-fold increase to about a 9.0-fold increase, about a 0.7-fold increase to about a 8.5-fold increase, about a 0.7-fold increase to about a 8.0-fold increase, about a 0.7-fold increase to about a 7.5-fold increase, about a 0.7-fold increase to about a 7.0-fold increase, about a 0.7-fold increase to about a 6.5-fold increase, about a 0.7-fold increase to about a 6.0-fold increase, about a 0.7-fold increase to about a 5.5-fold increase, about a 0.7-fold increase to about a 5.0-fold increase, about a 0.7-fold increase to about a 4.5-fold increase, about a 0.7-fold increase to about a 4.0-fold increase, about a 0.7-fold increase to about a 3.5-fold increase, about 0.7-fold increase to about a 3.0-fold increase, about a 0.7-fold increase to about a 2.8-fold increase, about a 0.7-fold increase to about a 2.6-fold increase, about a 0.7-fold increase to about a 2.5-fold increase, about a 0.7-fold increase to about a 2.4-fold increase, about a 0.7-fold increase to about a 2.2-fold increase, about a 0.7-fold increase to about a 2.0-fold increase, about a 0.7-fold increase to about a 1.8-fold increase, about a 0.7-fold increase to about a 1.6-fold increase, about a 0.7-fold increase to about a 1.5-fold increase, about a 0.7-fold increase to about a 1.4-fold increase, about a 0.7-fold increase to about a 1.2-fold increase, about a 0.7-fold increase to about a 1.0-fold increase, about a 0.7-fold increase to about a 0.9-fold increase, about a 0.8-fold increase to about a 100-fold increase, about 0.8-fold increase to about a 90-fold increase, about 0.8-fold increase to about a 80-fold increase, about a 0.8-fold increase to about a 70-fold increase, about a 0.8-fold increase to about a 60-fold increase, about a 0.8-fold increase to about a 50-fold increase, about a 0.8-fold increase to about a 40-fold increase, about a 0.8-fold increase to about a 30-fold increase, about 0.8-fold increase to about 20-fold increase, about a 0.8-fold increase to about a 10-fold increase, about a 0.8-fold increase to about a 9.5-fold increase, about a 0.8-fold increase to about a 9.0-fold increase, about a 0.8-fold increase to about a 8.5-fold increase, about a 0.8-fold increase to about a 8.0-fold increase, about a 0.8-fold increase to about a 7.5-fold increase, about a 0.8-fold increase to about a 7.0-fold increase, about a 0.8-fold increase to about a 6.5-fold increase, about a 0.8-fold increase to about a 6.0-fold increase, about a 0.8-fold increase to about a 5.5-fold increase, about a 0.8-fold increase to about a 5.0-fold increase, about a 0.8-fold increase to about a 4.5-fold increase, about a 0.8-fold increase to about a 4.0-fold increase, about a 0.8-fold increase to about a 3.5-fold increase, about 0.8-fold increase to about a 3.0-fold increase, about a 0.8-fold increase to about a 2.8-fold increase, about a 0.8-fold increase to about a 2.6-fold increase, about a 0.8-fold increase to about a 2.5-fold increase, about a 0.8-fold increase to about a 2.4-fold increase, about a 0.8-fold increase to about a 2.2-fold increase, about a 0.8-fold increase to about a 2.0-fold increase, about a 0.8-fold increase to about a 1.8-fold increase, about a 0.8-fold increase to about a 1.6-fold increase, about a 0.8-fold increase to about a 1.5-fold increase, about a 0.8-fold increase to about a 1.4-fold increase, about a 0.8-fold increase to about a 1.2-fold increase, about a 0.8-fold increase to about a 1.0-fold increase, about a 1.0-fold increase to about a 100-fold increase, about 1.0-fold increase to about a 90-fold increase, about 1.0-fold increase to about a 80-fold increase, about a 1.0-fold increase to about a 70-fold increase, about a 1.0-fold increase to about a 60-fold increase, about a 1.0-fold increase to about a 50-fold increase, about a 1.0-fold increase to about a 40-fold increase, about a 1.0-fold increase to about a 30-fold increase, about 1.0-fold increase to about 20-fold increase, about a 1.0-fold increase to about a 10-fold increase, about a 1.0-fold increase to about a 9.5-fold increase, about a 1.0-fold increase to about a 9.0-fold increase, about a 1.0-fold increase to about a 8.5-fold increase, about a 1.0-fold increase to about a 8.0-fold increase, about a 1.0-fold increase to about a 7.5-fold increase, about a 1.0-fold increase to about a 7.0-fold increase, about a 1.0-fold increase to about a 6.5-fold increase, about a 1.0-fold increase to about a 6.0-fold increase, about a 1.0-fold increase to about a 5.5-fold increase, about a 1.0-fold increase to about a 5.0-fold increase, about a 1.0-fold increase to about a 4.5-fold increase, about a 1.0-fold increase to about a 4.0-fold increase, about a 1.0-fold increase to about a 3.5-fold increase, about 1.0-fold increase to about a 3.0-fold increase, about a 1.0-fold increase to about a 2.8-fold increase, about a 1.0-fold increase to about a 2.6-fold increase, about a 1.0-fold increase to about a 2.5-fold increase, about a 1.0-fold increase to about a 2.4-fold increase, about a 1.0-fold increase to about a 2.2-fold increase, about a 1.0-fold increase to about a 2.0-fold increase, about a 1.0-fold increase to about a 1.8-fold increase, about a 1.0-fold increase to about a 1.6-fold increase, about a 1.0-fold increase to about a 1.5-fold increase, about a 1.0-fold increase to about a 1.4-fold increase, about a 1.0-fold increase to about a 1.2-fold increase, about a 1.2-fold increase to about a 100-fold increase, about 1.2-fold increase to about a 90-fold increase, about 1.2-fold increase to about a 80-fold increase, about a 1.2-fold increase to about a 70-fold increase, about a 1.2-fold increase to about a 60-fold increase, about a 1.2-fold increase to about a 50-fold increase, about a 1.2-fold increase to about a 40-fold increase, about a 1.2-fold increase to about a 30-fold increase, about 1.2-fold increase to about 20-fold increase, about a 1.2-fold increase to about a 10-fold increase, about a 1.2-fold increase to about a 9.5-fold increase, about a 1.2-fold increase to about a 9.0-fold increase, about a 1.2-fold increase to about a 8.5-fold increase, about a 1.2-fold increase to about a 8.0-fold increase, about a 1.2-fold increase to about a 7.5-fold increase, about a 1.2-fold increase to about a 7.0-fold increase, about a 1.2-fold increase to about a 6.5-fold increase, about a 1.2-fold increase to about a 6.0-fold increase, about a 1.2-fold increase to about a 5.5-fold increase, about a 1.2-fold increase to about a 5.0-fold increase, about a 1.2-fold increase to about a 4.5-fold increase, about a 1.2-fold increase to about a 4.0-fold increase, about a 1.2-fold increase to about a 3.5-fold increase, about 1.2-fold increase to about a 3.0-fold increase, about a 1.2-fold increase to about a 2.8-fold increase, about a 1.2-fold increase to about a 2.6-fold increase, about a 1.2-fold increase to about a 2.5-fold increase, about a 1.2-fold increase to about a 2.4-fold increase, about a 1.2-fold increase to about a 2.2-fold increase, about a 1.2-fold increase to about a 2.0-fold increase, about a 1.2-fold increase to about a 1.8-fold increase, about a 1.2-fold increase to about a 1.6-fold increase, about a 1.2-fold increase to about a 1.5-fold increase, about a 1.2-fold increase to about a 1.4-fold increase, about a 1.4-fold increase to about a 100-fold increase, about 1.4-fold increase to about a 90-fold increase, about 1.4-fold increase to about a 80-fold increase, about a 1.4-fold increase to about a 70-fold increase, about a 1.4-fold increase to about a 60-fold increase, about a 1.4-fold increase to about a 50-fold increase, about a 1.4-fold increase to about a 40-fold increase, about a 1.4-fold increase to about a 30-fold increase, about 1.4-fold increase to about 20-fold increase, about a 1.4-fold increase to about a 10-fold increase, about a 1.4-fold increase to about a 9.5-fold increase, about a 1.4-fold increase to about a 9.0-fold increase, about a 1.4-fold increase to about a 8.5-fold increase, about a 1.4-fold increase to about a 8.0-fold increase, about a 1.4-fold increase to about a 7.5-fold increase, about a 1.4-fold increase to about a 7.0-fold increase, about a 1.4-fold increase to about a 6.5-fold increase, about a 1.4-fold increase to about a 6.0-fold increase, about a 1.4-fold increase to about a 5.5-fold increase, about a 1.4-fold increase to about a 5.0-fold increase, about a 1.4-fold increase to about a 4.5-fold increase, about a 1.4-fold increase to about a 4.0-fold increase, about a 1.4-fold increase to about a 3.5-fold increase, about 1.4-fold increase to about a 3.0-fold increase, about a 1.4-fold increase to about a 2.8-fold increase, about a 1.4-fold increase to about a 2.6-fold increase, about a 1.4-fold increase to about a 2.5-fold increase, about a 1.4-fold increase to about a 2.4-fold increase, about a 1.4-fold increase to about a 2.2-fold increase, about a 1.4-fold increase to about a 2.0-fold increase, about a 1.4-fold increase to about a 1.8-fold increase, about a 1.4-fold increase to about a 1.6-fold increase, about a 1.6-fold increase to about a 10-fold increase, about a 1.6-fold increase to about a 100-fold increase, about 1.6-fold increase to about a 90-fold increase, about 1.6-fold increase to about a 80-fold increase, about a 1.6-fold increase to about a 70-fold increase, about a 1.6-fold increase to about a 60-fold increase, about a 1.6-fold increase to about a 50-fold increase, about a 1.6-fold increase to about a 40-fold increase, about 1.6-fold increase to about a 30-fold increase, about 1.6-fold increase to about 20-fold increase, about a 1.6-fold increase to about a 9.5-fold increase, about a 1.6-fold increase to about a 9.0-fold increase, about a 1.6-fold increase to about a 8.5-fold increase, about a 1.6-fold increase to about a 8.0-fold increase, about a 1.6-fold increase to about a 7.5-fold increase, about a 1.6-fold increase to about a 7.0-fold increase, about a 1.6-fold increase to about a 6.5-fold increase, about a 1.6-fold increase to about a 6.0-fold increase, about a 1.6-fold increase to about a 5.5-fold increase, about a 1.6-fold increase to about a 5.0-fold increase, about a 1.6-fold increase to about a 4.5-fold increase, about a 1.6-fold increase to about a 4.0-fold increase, about a 1.6-fold increase to about a 3.5-fold increase, about 1.6-fold increase to about a 3.0-fold increase, about a 1.6-fold increase to about a 2.8-fold increase, about a 1.6-fold increase to about a 2.6-fold increase, about a 1.6-fold increase to about a 2.5-fold increase, about a 1.6-fold increase to about a 2.4-fold increase, about a 1.6-fold increase to about a 2.2-fold increase, about a 1.6-fold increase to about a 2.0-fold increase, about a 1.6-fold increase to about a 1.8-fold increase, about a 1.8-fold increase to about a 100-fold increase, about 1.8-fold increase to about a 90-fold increase, about 1.8-fold increase to about a 80-fold increase, about a 1.8-fold increase to about a 70-fold increase, about a 1.8-fold increase to about a 60-fold increase, about a 1.8-fold increase to about a 50-fold increase, about a 1.8-fold increase to about a 40-fold increase, about a 1.8-fold increase to about a 30-fold increase, about 1.8-fold increase to about 20-fold increase, about a 1.8-fold increase to about a 10-fold increase, about a 1.8-fold increase to about a 9.5-fold increase, about a 1.8-fold increase to about a 9.0-fold increase, about a 1.8-fold increase to about a 8.5-fold increase, about a 1.8-fold increase to about a 8.0-fold increase, about a 1.8-fold increase to about a 7.5-fold increase, about a 1.8-fold increase to about a 7.0-fold increase, about a 1.8-fold increase to about a 6.5-fold increase, about a 1.8-fold increase to about a 6.0-fold increase, about a 1.8-fold increase to about a 5.5-fold increase, about a 1.8-fold increase to about a 5.0-fold increase, about a 1.8-fold increase to about a 4.5-fold increase, about a 1.8-fold increase to about a 4.0-fold increase, about a 1.8-fold increase to about a 3.5-fold increase, about 1.8-fold increase to about a 3.0-fold increase, about a 1.8-fold increase to about a 2.8-fold increase, about a 1.8-fold increase to about a 2.6-fold increase, about a 1.8-fold increase to about a 2.5-fold increase, about a 1.8-fold increase to about a 2.4-fold increase, about a 1.8-fold increase to about a 2.2-fold increase, about a 1.8-fold increase to about a 2.0-fold increase, about a 2.0-fold increase to about a 100-fold increase, about 2.0-fold increase to about a 90-fold increase, about 2.0-fold increase to about a 80-fold increase, about a 2.0-fold increase to about a 70-fold increase, about a 2.0-fold increase to about a 60-fold increase, about a 2.0-fold increase to about a 50-fold increase, about a 2.0-fold increase to about a 40-fold increase, about a 2.0-fold increase to about a 30-fold increase, about 2.0-fold increase to about 20-fold increase, about a 2.0-fold increase to about a 10-fold increase, about a 2.0-fold increase to about a 9.5-fold increase, about a 2.0-fold increase to about a 9.0-fold increase, about a 2.0-fold increase to about a 8.5-fold increase, about a 2.0-fold increase to about a 8.0-fold increase, about a 2.0-fold increase to about a 7.5-fold increase, about a 2.0-fold increase to about a 7.0-fold increase, about a 2.0-fold increase to about a 6.5-fold increase, about a 2.0-fold increase to about a 6.0-fold increase, about a 2.0-fold increase to about a 5.5-fold increase, about a 2.0-fold increase to about a 5.0-fold increase, about a 2.0-fold increase to about a 4.5-fold increase, about a 2.0-fold increase to about a 4.0-fold increase, about a 2.0-fold increase to about a 3.5-fold increase, about 2.0-fold increase to about a 3.0-fold increase, about a 2.0-fold increase to about a 2.8-fold increase, about a 2.0-fold increase to about a 2.6-fold increase, about a 2.0-fold increase to about a 2.5-fold increase, about a 2.0-fold increase to about a 2.4-fold increase, about a 2.0-fold increase to about a 2.2-fold increase, about a 2.2-fold increase to about a 100-fold increase, about 2.2-fold increase to about a 90-fold increase, about 2.2-fold increase to about a 80-fold increase, about a 2.2-fold increase to about a 70-fold increase, about a 2.2-fold increase to about a 60-fold increase, about a 2.2-fold increase to about a 50-fold increase, about a 2.2-fold increase to about a 40-fold increase, about a 2.2-fold increase to about a 30-fold increase, about 2.2-fold increase to about 20-fold increase, about a 2.2-fold increase to about a 10-fold increase, about a 2.2-fold increase to about a 9.5-fold increase, about a 2.2-fold increase to about a 9.0-fold increase, about a 2.2-fold increase to about a 8.5-fold increase, about a 2.2-fold increase to about a 8.0-fold increase, about a 2.2-fold increase to about a 7.5-fold increase, about a 2.2-fold increase to about a 7.0-fold increase, about a 2.2-fold increase to about a 6.5-fold increase, about a 2.2-fold increase to about a 6.0-fold increase, about a 2.2-fold increase to about a 5.5-fold increase, about a 2.2-fold increase to about a 5.0-fold increase, about a 2.2-fold increase to about a 4.5-fold increase, about a 2.2-fold increase to about a 4.0-fold increase, about a 2.2-fold increase to about a 3.5-fold increase, about 2.2-fold increase to about a 3.0-fold increase, about a 2.2-fold increase to about a 2.8-fold increase, about a 2.2-fold increase to about a 2.6-fold increase, about a 2.2-fold increase to about a 2.5-fold increase, about a 2.2-fold increase to about a 2.4-fold increase, about a 2.4-fold increase to about a 100-fold increase, about 2.4-fold increase to about a 90-fold increase, about 2.4-fold increase to about a 80-fold increase, about a 2.4-fold increase to about a 70-fold increase, about a 2.4-fold increase to about a 60-fold increase, about a 2.4-fold increase to about a 50-fold increase, about a 2.4-fold increase to about a 40-fold increase, about a 2.4-fold increase to about a 30-fold increase, about 2.4-fold increase to about 20-fold increase, about a 2.4-fold increase to about a 10-fold increase, about a 2.4-fold increase to about a 9.5-fold increase, about a 2.4-fold increase to about a 9.0-fold increase, about a 2.4-fold increase to about a 8.5-fold increase, about a 2.4-fold increase to about a 8.0-fold increase, about a 2.4-fold increase to about a 7.5-fold increase, about a 2.4-fold increase to about a 7.0-fold increase, about a 2.4-fold increase to about a 6.5-fold increase, about a 2.4-fold increase to about a 6.0-fold increase, about a 2.4-fold increase to about a 5.5-fold increase, about a 2.4-fold increase to about a 5.0-fold increase, about a 2.4-fold increase to about a 4.5-fold increase, about a 2.4-fold increase to about a 4.0-fold increase, about a 2.4-fold increase to about a 3.5-fold increase, about 2.4-fold increase to about a 3.0-fold increase, about a 2.4-fold increase to about a 2.8-fold increase, about a 2.4-fold increase to about a 2.6-fold increase, about a 2.6-fold increase to about a 100-fold increase, about 2.6-fold increase to about a 90-fold increase, about 2.6-fold increase to about a 80-fold increase, about a 2.6-fold increase to about a 70-fold increase, about a 2.6-fold increase to about a 60-fold increase, about a 2.6-fold increase to about a 50-fold increase, about a 2.6-fold increase to about a 40-fold increase, about a 2.6-fold increase to about a 30-fold increase, about 2.6-fold increase to about 20-fold increase, about a 2.6-fold increase to about a 10-fold increase, about a 2.6-fold increase to about a 9.5-fold increase, about a 2.6-fold increase to about a 9.0-fold increase, about a 2.6-fold increase to about a 8.5-fold increase, about a 2.6-fold increase to about a 8.0-fold increase, about a 2.6-fold increase to about a 7.5-fold increase, about a 2.6-fold increase to about a 7.0-fold increase, about a 2.6-fold increase to about a 6.5-fold increase, about a 2.6-fold increase to about a 6.0-fold increase, about a 2.6-fold increase to about a 5.5-fold increase, about a 2.6-fold increase to about a 5.0-fold increase, about a 2.6-fold increase to about a 4.5-fold increase, about a 2.6-fold increase to about a 4.0-fold increase, about a 2.6-fold increase to about a 3.5-fold increase, about 2.6-fold increase to about a 3.0-fold increase, about a 2.6-fold increase to about a 2.8-fold increase, about a 2.8-fold increase to about a 100-fold increase, about 2.8-fold increase to about a 90-fold increase, about 2.8-fold increase to about a 80-fold increase, about a 2.8-fold increase to about a 70-fold increase, about a 2.8-fold increase to about a 60-fold increase, about a 2.8-fold increase to about a 50-fold increase, about a 2.8-fold increase to about a 40-fold increase, about a 2.8-fold increase to about a 30-fold increase, about 2.8-fold increase to about 20-fold increase, about a 2.8-fold increase to about a 10-fold increase, about a 2.8-fold increase to about a 9.5-fold increase, about a 2.8-fold increase to about a 9.0-fold increase, about a 2.8-fold increase to about a 8.5-fold increase, about a 2.8-fold increase to about a 8.0-fold increase, about a 2.8-fold increase to about a 7.5-fold increase, about a 2.8-fold increase to about a 7.0-fold increase, about a 2.8-fold increase to about a 6.5-fold increase, about a 2.8-fold increase to about a 6.0-fold increase, about a 2.8-fold increase to about a 5.5-fold increase, about a 2.8-fold increase to about a 5.0-fold increase, about a 2.8-fold increase to about a 4.5-fold increase, about a 2.8-fold increase to about a 4.0-fold increase, about a 2.8-fold increase to about a 3.5-fold increase, about 2.8-fold increase to about a 3.0-fold increase, about a 3.0-fold increase to about a 100-fold increase, about 3.0-fold increase to about a 90-fold increase, about 3.0-fold increase to about a 80-fold increase, about a 3.0-fold increase to about a 70-fold increase, about a 3.0-fold increase to about a 60-fold increase, about a 3.0-fold increase to about a 50-fold increase, about a 3.0-fold increase to about a 40-fold increase, about a 3.0-fold increase to about a 30-fold increase, about 3.0-fold increase to about 20-fold increase, about a 3.0-fold increase to about a 10-fold increase, about a 3.0-fold increase to about a 9.5-fold increase, about a 3.0-fold increase to about a 9.0-fold increase, about a 3.0-fold increase to about a 8.5-fold increase, about a 3.0-fold increase to about a 8.0-fold increase, about a 3.0-fold increase to about a 7.5-fold increase, about a 3.0-fold increase to about a 7.0-fold increase, about a 3.0-fold increase to about a 6.5-fold increase, about a 3.0-fold increase to about a 6.0-fold increase, about a 3.0-fold increase to about a 5.5-fold increase, about a 3.0-fold increase to about a 5.0-fold increase, about a 3.0-fold increase to about a 4.5-fold increase, about a 3.0-fold increase to about a 4.0-fold increase, about a 3.0-fold increase to about a 3.5-fold increase, about a 3.5-fold increase to about a 100-fold increase, about 3.5-fold increase to about a 90-fold increase, about 3.5-fold increase to about a 80-fold increase, about a 3.5-fold increase to about a 70-fold increase, about a 3.5-fold increase to about a 60-fold increase, about a 3.5-fold increase to about a 50-fold increase, about a 3.5-fold increase to about a 40-fold increase, about a 3.5-fold increase to about a 30-fold increase, about 3.5-fold increase to about 20-fold increase, about a 3.5-fold increase to about a 10-fold increase, about a 3.5-fold increase to about a 9.5-fold increase, about a 3.5-fold increase to about a 9.0-fold increase, about a 3.5-fold increase to about a 8.5-fold increase, about a 3.5-fold increase to about a 8.0-fold increase, about a 3.5-fold increase to about a 7.5-fold increase, about a 3.5-fold increase to about a 7.0-fold increase, about a 3.5-fold increase to about a 6.5-fold increase, about a 3.5-fold increase to about a 6.0-fold increase, about a 3.5-fold increase to about a 5.5-fold increase, about a 3.5-fold increase to about a 5.0-fold increase, about a 3.5-fold increase to about a 4.5-fold increase, about a 3.5-fold increase to about a 4.0-fold increase, about a 4.0-fold increase to about a 100-fold increase, about 4.0-fold increase to about a 90-fold increase, about 4.0-fold increase to about a 80-fold increase, about a 4.0-fold increase to about a 70-fold increase, about a 4.0-fold increase to about a 60-fold increase, about a 4.0-fold increase to about a 50-fold increase, about a 4.0-fold increase to about a 40-fold increase, about a 4.0-fold increase to about a 30-fold increase, about 4.0-fold increase to about 20-fold increase, about a 4.0-fold increase to about a 10-fold increase, about a 4.0-fold increase to about a 9.5-fold increase, about a 4.0-fold increase to about a 9.0-fold increase, about a 4.0-fold increase to about a 8.5-fold increase, about a 4.0-fold increase to about a 8.0-fold increase, about a 4.0-fold increase to about a 7.5-fold increase, about a 4.0-fold increase to about a 7.0-fold increase, about a 4.0-fold increase to about a 6.5-fold increase, about a 4.0-fold increase to about a 6.0-fold increase, about a 4.0-fold increase to about a 5.5-fold increase, about a 4.0-fold increase to about a 5.0-fold increase, about a 4.0-fold increase to about a 4.5-fold increase, about a 4.5-fold increase to about a 100-fold increase, about 4.5-fold increase to about a 90-fold increase, about 4.5-fold increase to about a 80-fold increase, about a 4.5-fold increase to about a 70-fold increase, about a 4.5-fold increase to about a 60-fold increase, about a 4.5-fold increase to about a 50-fold increase, about a 4.5-fold increase to about a 40-fold increase, about a 4.5-fold increase to about a 30-fold increase, about 4.5-fold increase to about 20-fold increase, about a 4.5-fold increase to about a 10-fold increase, about a 4.5-fold increase to about a 9.5-fold increase, about a 4.5-fold increase to about a 9.0-fold increase, about a 4.5-fold increase to about a 8.5-fold increase, about a 4.5-fold increase to about a 8.0-fold increase, about a 4.5-fold increase to about a 7.5-fold increase, about a 4.5-fold increase to about a 7.0-fold increase, about a 4.5-fold increase to about a 6.5-fold increase, about a 4.5-fold increase to about a 6.0-fold increase, about a 4.5-fold increase to about a 5.5-fold increase, about a 4.5-fold increase to about a 5.0-fold increase, about a 5.0-fold increase to about a 100-fold increase, about 5.0-fold increase to about a 90-fold increase, about 5.0-fold increase to about a 80-fold increase, about a 5.0-fold increase to about a 70-fold increase, about a 5.0-fold increase to about a 60-fold increase, about a 5.0-fold increase to about a 50-fold increase, about a 5.0-fold increase to about a 40-fold increase, about a 5.0-fold increase to about a 30-fold increase, about 5.0-fold increase to about 20-fold increase, about a 5.0-fold increase to about a 10-fold increase, about a 5.0-fold increase to about a 9.5-fold increase, about a 5.0-fold increase to about a 9.0-fold increase, about a 5.0-fold increase to about a 8.5-fold increase, about a 5.0-fold increase to about a 8.0-fold increase, about a 5.0-fold increase to about a 7.5-fold increase, about a 5.0-fold increase to about a 7.0-fold increase, about a 5.0-fold increase to about a 6.5-fold increase, about a 5.0-fold increase to about a 6.0-fold increase, about a 5.0-fold increase to about a 5.5-fold increase, about a 5.5-fold increase to about a 100-fold increase, about 5.5-fold increase to about a 90-fold increase, about 5.5-fold increase to about a 80-fold increase, about a 5.5-fold increase to about a 70-fold increase, about a 5.5-fold increase to about a 60-fold increase, about a 5.5-fold increase to about a 50-fold increase, about a 5.5-fold increase to about a 40-fold increase, about a 5.5-fold increase to about a 30-fold increase, about 5.5-fold increase to about 20-fold increase, about a 5.5-fold increase to about a 10-fold increase, about a 5.5-fold increase to about a 9.5-fold increase, about a 5.5-fold increase to about a 9.0-fold increase, about a 5.5-fold increase to about a 8.5-fold increase, about a 5.5-fold increase to about a 8.0-fold increase, about a 5.5-fold increase to about a 7.5-fold increase, about a 5.5-fold increase to about a 7.0-fold increase, about a 5.5-fold increase to about a 6.5-fold increase, about a 5.5-fold increase to about a 6.0-fold increase, about a 6.0-fold increase to about a 100-fold increase, about 6.0-fold increase to about a 90-fold increase, about 6.0-fold increase to about a 80-fold increase, about a 6.0-fold increase to about a 70-fold increase, about a 6.0-fold increase to about a 60-fold increase, about a 6.0-fold increase to about a 50-fold increase, about a 6.0-fold increase to about a 40-fold increase, about a 6.0-fold increase to about a 30-fold increase, about 6.0-fold increase to about 20-fold increase, about a 6.0-fold increase to about a 10-fold increase, about a 6.0-fold increase to about a 9.5-fold increase, about a 6.0-fold increase to about a 9.0-fold increase, about a 6.0-fold increase to about a 8.5-fold increase, about a 6.0-fold increase to about a 8.0-fold increase, about a 6.0-fold increase to about a 7.5-fold increase, about a 6.0-fold increase to about a 7.0-fold increase, about a 6.0-fold increase to about a 6.5-fold increase, about a 6.5-fold increase to about a 100-fold increase, about 6.5-fold increase to about a 90-fold increase, about 6.5-fold increase to about a 80-fold increase, about a 6.5-fold increase to about a 70-fold increase, about a 6.5-fold increase to about a 60-fold increase, about a 6.5-fold increase to about a 50-fold increase, about a 6.5-fold increase to about a 40-fold increase, about a 6.5-fold increase to about a 30-fold increase, about 6.5-fold increase to about 20-fold increase, about a 6.5-fold increase to about a 10-fold increase, about a 6.5-fold increase to about a 9.5-fold increase, about a 6.5-fold increase to about a 9.0-fold increase, about a 6.5-fold increase to about a 8.5-fold increase, about a 6.5-fold increase to about a 8.0-fold increase, about a 6.5-fold increase to about a 7.5-fold increase, about a 6.5-fold increase to about a 7.0-fold increase, about a 7.0-fold increase to about a 100-fold increase, about 7.0-fold increase to about a 90-fold increase, about 7.0-fold increase to about a 80-fold increase, about a 7.0-fold increase to about a 70-fold increase, about a 7.0-fold increase to about a 60-fold increase, about a 7.0-fold increase to about a 50-fold increase, about a 7.0-fold increase to about a 40-fold increase, about a 7.0-fold increase to about a 30-fold increase, about 7.0-fold increase to about 20-fold increase, about a 7.0-fold increase to about a 10-fold increase, about a 7.0-fold increase to about a 9.5-fold increase, about a 7.0-fold increase to about a 9.0-fold increase, about a 7.0-fold increase to about a 8.5-fold increase, about a 7.0-fold increase to about a 8.0-fold increase, about a 7.0-fold increase to about a 7.5-fold increase, about a 7.5-fold increase to about a 100-fold increase, about 7.5-fold increase to about a 90-fold increase, about 7.5-fold increase to about a 80-fold increase, about a 7.5-fold increase to about a 70-fold increase, about a 7.5-fold increase to about a 60-fold increase, about a 7.5-fold increase to about a 50-fold increase, about a 7.5-fold increase to about a 40-fold increase, about a 7.5-fold increase to about a 30-fold increase, about 7.5-fold increase to about 20-fold increase, about a 7.5-fold increase to about a 10-fold increase, about a 7.5-fold increase to about a 9.5-fold increase, about a 7.5-fold increase to about a 9.0-fold increase, about a 7.5-fold increase to about a 8.5-fold increase, about a 7.5-fold increase to about a 8.0-fold increase, about a 8.0-fold increase to about a 100-fold increase, about 8.0-fold increase to about a 90-fold increase, about 8.0-fold increase to about a 80-fold increase, about a 8.0-fold increase to about a 70-fold increase, about a 8.0-fold increase to about a 60-fold increase, about a 8.0-fold increase to about a 50-fold increase, about a 8.0-fold increase to about a 40-fold increase, about a 8.0-fold increase to about a 30-fold increase, about 8.0-fold increase to about 20-fold increase, about a 8.0-fold increase to about a 10-fold increase, about a 8.0-fold increase to about a 9.5-fold increase, about a 8.0-fold increase to about a 9.0-fold increase, about a 8.0-fold increase to about a 8.5-fold increase, about a 8.5-fold increase to about a 100-fold increase, about 8.5-fold increase to about a 90-fold increase, about 8.5-fold increase to about a 80-fold increase, about a 8.5-fold increase to about a 70-fold increase, about a 8.5-fold increase to about a 60-fold increase, about a 8.5-fold increase to about a 50-fold increase, about a 8.5-fold increase to about a 40-fold increase, about a 8.5-fold increase to about a 30-fold increase, about 8.5-fold increase to about 20-fold increase, about a 8.5-fold increase to about a 10-fold increase, about a 8.5-fold increase to about a 9.5-fold increase, about a 8.5-fold increase to about a 9.0-fold increase, about a 9.0-fold increase to about a 100-fold increase, about 9.0-fold increase to about a 90-fold increase, about 9.0-fold increase to about a 80-fold increase, about a 9.0-fold increase to about a 70-fold increase, about a 9.0-fold increase to about a 60-fold increase, about a 9.0-fold increase to about a 50-fold increase, about a 9.0-fold increase to about a 40-fold increase, about a 9.0-fold increase to about a 30-fold increase, about 9.0-fold increase to about 20-fold increase, about a 9.0-fold increase to about a 10-fold increase, about a 9.0-fold increase to about a 9.5-fold increase, about a 9.5-fold increase to about a 100-fold increase, about 9.5-fold increase to about a 90-fold increase, about 9.5-fold increase to about a 80-fold increase, about a 9.5-fold increase to about a 70-fold increase, about a 9.5-fold increase to about a 60-fold increase, about a 9.5-fold increase to about a 50-fold increase, about a 9.5-fold increase to about a 40-fold increase, about a 9.5-fold increase to about a 30-fold increase, about 9.5-fold increase to about 20-fold increase, about a 9.5-fold increase to about a 10-fold increase, about a 10-fold increase to about a 100-fold increase, about 10-fold increase to about a 90-fold increase, about 10-fold increase to about a 80-fold increase, about a 10-fold increase to about a 70-fold increase, about a 10-fold increase to about a 60-fold increase, about a 10-fold increase to about a 50-fold increase, about a 10-fold increase to about a 40-fold increase, about a 10-fold increase to about a 30-fold increase, about 10-fold increase to about 20-fold increase, about a 20-fold increase to about a 100-fold increase, about 20-fold increase to about a 90-fold increase, about 20-fold increase to about a 80-fold increase, about a 20-fold increase to about a 70-fold increase, about a 20-fold increase to about a 60-fold increase, about a 20-fold increase to about a 50-fold increase, about a 20-fold increase to about a 40-fold increase, about a 20-fold increase to about a 30-fold increase, about a 30-fold increase to about a 100-fold increase, about 30-fold increase to about a 90-fold increase, about 30-fold increase to about a 80-fold increase, about a 30-fold increase to about a 70-fold increase, about a 30-fold increase to about a 60-fold increase, about a 30-fold increase to about a 50-fold increase, about a 30-fold increase to about a 40-fold increase, about a 40-fold increase to about a 100-fold increase, about 40-fold increase to about a 90-fold increase, about 40-fold increase to about a 80-fold increase, about a 40-fold increase to about a 70-fold increase, about a 40-fold increase to about a 60-fold increase, about a 40-fold increase to about a 50-fold increase, about a 50-fold increase to about a 100-fold increase, about 50-fold increase to about a 90-fold increase, about 50-fold increase to about a 80-fold increase, about a 50-fold increase to about a 70-fold increase, about a 50-fold increase to about a 60-fold increase, about a 60-fold increase to about a 100-fold increase, about 60-fold increase to about a 90-fold increase, about 60-fold increase to about a 80-fold increase, about a 60-fold increase to about a 70-fold increase, about a 70-fold increase to about a 100-fold increase, about 70-fold increase to about a 90-fold increase, about 70-fold increase to about a 80-fold increase, about a 80-fold increase to about a 100-fold increase, about 80-fold increase to about a 90-fold increase, or about a 90-fold increase to about a 100-fold increase) in toxin liberation in the target mammalian cell (e.g., any of the target mammalian cells described herein) as compared to a composition including the same amount of a control antibody (e.g., any of the exemplary control antibodies described herein).

In some examples of any of the antibodies described herein, a composition including the antibody (e.g., any of the antibodies described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at a least a 9,000% increase, or at least a 10,000% increase, or about a 1% increase to about a 10,000% increase (e.g., or any of the subranges of this range described herein)) in target mammalian cell killing (e.g., any of the exemplary target mammalian cells described herein) as compared to a composition including the same amount of a control antibody (e.g., any of the exemplary control antibodies described herein).

In some examples of any of the antibodies described herein, a composition including the antibody (e.g., any of the antibodies described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 40-fold increase, at least a 45-fold increase, at least a 50-fold increase, at least a 55-fold increase, at least a 60-fold increase, at least a 65-fold increase, at least a 70-fold increase, at least a 80-fold increase, at least a 85-fold increase, at least a 90-fold increase, at least a 95-fold increase, or at least a 100-fold increase, or about a 0.1-fold increase to about a 100-fold increase (or any of the subranges of this range described herein)) in target mammalian cell killing (e.g., any of the exemplary target mammalian cells described herein) as compared to a composition including the same amount of a control antibody (e.g., any of the exemplary control antibodies described herein).

In some examples of any of the antibodies described herein, a composition including any of the antibodies described herein (e.g., upon contacting target mammalian cells presenting MET on their surface) results in decreased (e.g., at least a 1% decrease, at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease, about a 1% decrease to about a 99% decrease, or any of the subranges of this range described herein) $IC_{50}$ (for target mammalian cell killing) as compared to the $IC_{50}$ for a composition including the same amount of a control antibody (e.g., any of the control antibodies described herein) (e.g., upon contacting the same target mammalian cells).

In some examples of any of the antibodies described herein, a composition including any of the antibodies described herein (e.g., upon contacting target mammalian cells presenting MET on their surface) can provide for an increase (e.g., at least a 0.1-fold increase, at least a 0.2-fold increase, at least a 0.4-fold increase, at least a 0.6-fold increase, at least a 0.8-fold increase, at least a 1-fold increase, at least a 2-fold increase, at least a 5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about 500-fold increase (or any of the subranges of this range described herein) in the ratio of Ku on target mammalian cells presenting MET on their surface at a neutral pH (a pH of about 7.0 to about 8.0) to $IC_{50}$ at the neutral pH on the same target cells, e.g., as compared to a control antibody (e.g., any of the exemplary control antibodies described herein).

In some examples of any of the antibodies described herein, a composition including the antibody (e.g., any of the antibodies described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at least a 9,000% increase, or at least a 10,000% increase, or about a 1% increase to about a 10,000% increase (e.g., or any of the subranges of this range described herein)) in endolysosomal delivery in the target mammalian cell (e.g., any of the exemplary target mammalian cells described herein) as compared to a composition including the same amount of a control antibody (e.g., any of the exemplary control antibodies described herein).

In some examples of any of the antibodies described herein, a composition including the antibody (e.g., any of the antibodies described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about a 100-fold increase (or any of the subranges of this range described herein)) in endolysosomal delivery in the target mammalian cell (e.g., any of the exemplary target mammalian cells described herein) as compared to a composition including the same amount of a control antibody (e.g., any of the exemplary control antibodies described herein).

In examples of any of the antibodies described herein, the target mammalian cell does not express an FcRn receptor, or expresses a lower (e.g., a detectably lower) level (e.g., at least a 1% decreased, at least a 2% decreased, at least a 5% decreased, at least a 10% decrease, at least a 15% decreased, at least a 20% decreased, at least a 25% decreased, at least a 30% decreased, at least a 35% decreased, at least a 40% decreased, at least a 45% decreased, at least a 50% decreased, at least a 55% decreased, at least a 60% decreased, at least a 65% decreased, at least a 70% decreased, at least a 75% decreased, at least a 80% decreased, at least a 85% decreased, at least a 90% decreased, at least a 95% decreased, or at least a 99% decreased level) of FcRn receptor as compared to a FcRn expressing control cell (e.g., HUVEC—ThermoFisher #C0035C). In some examples of any of the antibodies described herein, the target mammalian cell is a cancer cell. In some examples of any of the antibodies described herein, the antibody is cytotoxic or cytostatic to the target mammalian cell.

In some examples of any of the antibodies described herein, a composition including any of the antibodies described herein (e.g., upon administration to a subject) results in less (e.g., a 1% decrease to about a 99% decrease, or any of the subranges of this range described herein) of a reduction in the level of MET presented on the surface of the target cell as compared to a composition including the same amount of a control antibody (e.g., any of the control antibodies described herein). In some examples of any of the antibodies described herein, the composition does not result in a detectable reduction in the level of the MET presented on the surface of the target mammalian cell.

In some examples of any of the antibodies described herein, the antibody is cross-reactive with a non-human primate MET and a human MET. In some examples of any of the antibodies described herein, the antibody is cross-reactive with a non-human primate MET, a human MET, and one or both of rat MET and a mouse MET. In some examples of any of the antibodies described herein, the antibody is cross-reactive with a non-human primate MET, a human MET, a rat MET, and a mouse MET. In some examples of any of the antibodies described herein, the antibody is cross-reactive with mouse MET and rat MET. In some examples of any of the antibodies described herein, the antigen-binding domain binds to an epitope of MET that is present on the surface of cells from an Old World Monkey.

Some examples of any of the antibodies described herein can further include a second antigen-binding domain (e.g., any of the exemplary antigen-binding domains described herein). Non-limiting aspects of these methods are described below, and can be used in any combination without limitation. Additional aspects of these methods are known in the art.

MET or Epitope of MET

MET Proto-Oncogene, Receptor Tyrosine Kinase (MET) is a tumor antigen that is known in the art, and is the target of therapeutic antibodies in oncology (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000). The sequence of the mature Human MET can be found in SEQ ID NO: 1. The sequence of the cDNA encoding the mature Human MET can be found in SEQ ID NO: 2. The sequence of the extracellular domain of MET can be found in SEQ ID NO: 3. The sequence of the cDNA encoding the extracellular domain of MET can be found in SEQ ID NO: 4.

Exemplary Properties of Antibodies

In some embodiments of any of the antibodies described herein, the dissociation rate at a pH of about 4.0 to about 6.5 (e.g., about 4.0 to about 6.4, about 4.0 to about 6.3, about 4.0 to about 6.2, about 4.0 to about 6.1, about 4.0 to about 6.0, about 4.0 to about 5.9, about 4.0 to about 5.8, about 4.0 to about 5.7, about 4.0 to about 5.6, about 4.0 to about 5.5, about 4.0 to about 5.4, about 4.0 to about 5.3, about 4.0 to about 5.2, about 4.0 to about 5.1, about 4.0 to about 5.0, about 4.0 to about 4.9, about 4.0 to about 4.8, about 4.0 to about 4.7, about 4.0 to about 4.6, about 4.0 to about 4.5, about 4.0 to about 4.4, about 4.0 to about 4.3, about 4.0 to about 4.2, about 4.0 to about 4.1, about 4.1 to about 6.5, about 4.1 to about 6.4, about 4.1 to about 6.3, about 4.1 to about 6.2, about 4.1 to about 6.1, about 4.1 to about 6.0, about 4.1 to about 5.9, about 4.1 to about 5.8, about 4.1 to about 5.7, about 4.1 to about 5.6, about 4.1 to about 5.5, about 4.1 to about 5.4, about 4.1 to about 5.3, about 4.1 to about 5.2, about 4.1 to about 5.1, about 4.1 to about 5.0, about 4.1 to about 4.9, about 4.1 to about 4.8, about 4.1 to about 4.7, about 4.1 to about 4.6, about 4.1 to about 4.5, about 4.1 to about 4.4, about 4.1 to about 4.3, about 4.1 to about 4.2, about 4.2 to about 6.5, about 4.2 to about 6.4, about 4.2 to about 6.3, about 4.2 to about 6.2, about 4.2 to about 6.1, about 4.2 to about 6.0, about 4.2 to about 5.9, about 4.2 to about 5.8, about 4.2 to about 5.7, about 4.2 to about 5.6, about 4.2 to about 5.5, about 4.2 to about 5.4, about 4.2 to about 5.3, about 4.2 to about 5.2, about 4.2 to about 5.1, about 4.2 to about 5.0, about 4.2 to about 4.9, about 4.2 to about 4.8, about 4.2 to about 4.7, about 4.2 to about 4.6, about 4.2 to about 4.5, about 4.2 to about 4.4, about 4.2 to about 4.3, about 4.3 to about 6.5, about 4.3 to about 6.4, about 4.3 to about 6.3, about 4.3 to about 6.2, about 4.3 to about 6.1, about 4.3 to about 6.0, about 4.3 to about 5.9, about 4.3 to about 5.8, about 4.3 to about 5.7, about 4.3 to about 5.6, about 4.3 to about 5.5, about 4.3 to about 5.4, about 4.3 to about 5.3, about 4.3 to about 5.2, about 4.3 to about 5.1, about 4.3 to about 5.0, about 4.3 to about 4.9, about 4.3 to about 4.8, about 4.3 to about 4.7, about 4.3 to about 4.6, about 4.3 to about 4.5, about 4.3 to about 4.4, about 4.4 to about 6.5, about 4.4 to about 6.4, about 4.4 to about 6.3, about 4.4 to about 6.2, about 4.4 to about 6.1, about 4.4 to about 6.0, about 4.4 to about 5.9, about 4.4 to about 5.8, about 4.4 to about 5.7, about 4.4 to about 5.6, about 4.4 to about 5.5, about 4.4 to about 5.4, about 4.4 to about 5.3, about 4.4 to about 5.2, about 4.4 to about 5.1, about 4.4 to about 5.0, about 4.4 to about 4.9, about 4.4 to about 4.8, about 4.4 to about 4.7, about 4.4 to about 4.6, about 4.4 to about 4.5, about 4.5 to about 6.5, about 4.5 to about 6.4, about 4.5 to about 6.3, about 4.5 to about 6.2, about 4.5 to about 6.1, about 4.5 to about 6.0, about 4.5 to about 5.9, about 4.5 to about 5.8, about 4.5 to about 5.7, about 4.5 to about 5.6, about 4.5 to about 5.5, about 4.5 to about 5.4, about 4.5 to about 5.3, about 4.5 to about 5.2, about 4.5 to about 5.1, about 4.5 to about 5.0, about 4.5 to about 4.9, about 4.5 to about 4.8, about 4.5 to about 4.7, about 4.5 to about 4.6, about 4.6 to about 6.5, about 4.6 to about 6.4, about 4.6 to about 6.3, about 4.6 to about 6.2, about 4.6 to about 6.1, about 4.6 to about 6.0, about 4.6 to about 5.9, about 4.6 to about 5.8, about 4.6 to about 5.7, about 4.6 to about 5.6, about 4.6 to about 5.5, about 4.6 to about 5.4, about 4.6 to about 5.3, about 4.6 to about 5.2, about 4.6 to about 5.1, about 4.6 to about 5.0, about 4.6 to about 4.9, about 4.6 to about 4.8, about 4.6 to about 4.7, about 4.7 to about 6.5, about 4.7 to about 6.4, about 4.7 to about 6.3, about 4.7 to about 6.2, about 4.7 to about 6.1, about 4.7 to about 6.0, about 4.7 to about 5.9, about 4.7 to about 5.8, about 4.7 to about 5.7, about 4.7 to about 5.6, about 4.7 to about 5.5, about 4.7 to about 5.4, about 4.7 to about 5.3, about 4.7 to about 5.2, about 4.7 to about 5.1, about 4.7 to about 5.0, about 4.7 to about 4.9, about 4.7 to about 4.8, about 4.8 to about 6.5, about 4.8 to about 6.4, about 4.8 to about 6.3, about 4.8 to about 6.2, about 4.8 to about 6.1, about 4.8 to about 6.0, about 4.8 to about 5.9, about 4.8 to about 5.8, about 4.8 to about 5.7, about 4.8 to about 5.6, about 4.8 to about 5.5, about 4.8 to about 5.4, about 4.8 to about 5.3, about 4.8 to about 5.2, about 4.8 to about 5.1, about 4.8 to about 5.0, about 4.8 to about 4.9, about 4.9 to about 6.5, about 4.9 to about 6.4, about 4.9 to about 6.3, about 4.9 to about 6.2, about 4.9 to about 6.1, about 4.9 to about 6.0, about 4.9 to about 5.9, about 4.9 to about 5.8, about 4.9 to about 5.7, about 4.9 to about 5.6, about 4.9 to about 5.5, about 4.9 to about 5.4, about 4.9 to about 5.3, about 4.9 to about 5.2, about 4.9 to about 5.1, about 4.9 to about 5.0, about 5.0 to about 6.5, about 5.0 to about 6.4, about 5.0 to about 6.3, about 5.0 to about 6.2, about 5.0 to about 6.1, about 5.0 to about 6.0, about 5.0 to about 5.9, about 5.0 to about 5.8, about 5.0 to about 5.7, about 5.0 to about 5.6, about 5.0 to about 5.5, about 5.0 to about 5.4, about 5.0 to about 5.3, about 5.0 to about 5.2, about 5.0 to about 5.1, about 5.1 to about 6.5, about 5.1 to about 6.4, about 5.1 to about 6.3, about 5.1 to about 6.2, about 5.1 to about 6.1, about 5.1 to about 6.0, about 5.1 to about 5.9, about 5.1 to about 5.8, about 5.1 to about 5.7, about 5.1 to about 5.6, about 5.1 to about 5.5, about 5.1 to about 5.4, about 5.1 to about 5.3, about 5.1 to about 5.2, about 5.2 to about 6.5, about 5.2 to about 6.4, about 5.2 to about 6.3, about 5.2 to about 6.2, about 5.2 to about 6.1, about 5.2 to about 6.0, about 5.2 to about 5.9, about 5.2 to about 5.8, about 5.2 to about 5.7, about 5.2 to about 5.6, about 5.2 to about 5.5, about 5.2 to about 5.4, about 5.2 to about 5.3, about 5.3 to about 6.5, about 5.3 to about 6.4, about 5.3 to about 6.3, about 5.3 to about 6.2, about 5.3 to about 6.1, about 5.3 to about 6.0, about 5.3 to about 5.9, about 5.3 to about 5.8, about 5.3 to about 5.7, about 5.3 to about 5.6, about 5.3 to about 5.5, about 5.3 to about 5.4, about 5.4 to about 6.5, about 5.4 to about 6.4, about 5.4 to about 6.3, about 5.4 to about 6.2, about 5.4 to about 6.1, about 5.4 to about 6.0, about 5.4 to about 5.9, about 5.4 to about 5.8, about 5.4 to about 5.7, about 5.4 to about 5.6, about 5.4 to about 5.5, about 5.5 to about 6.5, about 5.5 to about 6.4, about 5.5 to about 6.3, about 5.5 to about 6.2, about 5.5 to about 6.1, about 5.5 to about 6.0, about 5.5 to about 5.9, about 5.5 to about 5.8, about 5.5 to about 5.7, about 5.5 to about 5.6, about 5.6 to about 6.5, about 5.6 to about 6.4, about 5.6 to about 6.3, about 5.6 to about 6.2, about 5.6 to about 6.1, about 5.6 to about 6.0, about 5.6 to about 5.9, about 5.6 to about 5.8, about 5.6 to about 5.7, about 5.7 to about 6.5, about 5.7 to about 6.4, about 5.7 to about 6.3, about 5.7 to about 6.2, about 5.7 to about 6.1, about 5.7 to about 6.0, about 5.7 to about 5.9, about 5.7 to about 5.8, about 5.8 to about 6.5, about 5.8 to about 6.4, about 5.8 to about 6.3, about 5.8 to about 6.2, about 5.8 to about 6.1, about 5.8 to about 6.0, about 5.8 to about 5.9, about 5.9 to about 6.5, about 5.9 to about 6.4, about 5.9 to about 6.3, about 5.9 to about 6.2, about 5.9 to about 6.1, about 5.9 to about 6.0, about 6.0 to about 6.5, about 6.0 to about 6.4, about 6.0 to about 6.3, about 6.0 to about 6.2, about 6.0 to about 6.1, about 6.1 to about 6.5, about 6.1 to about 6.4, about 6.1 to about 6.3, about 6.1 to about 6.2, about 6.2 to about 6.5, about 6.2 to about 6.4, about 6.2 to about 6.3, about 6.3 to about 6.5, about 6.3 to about 6.4, or about 6.4 to about 6.5) is faster (e.g., (e.g., at least 5% faster, at least 10% faster, at least 15% faster, at least 20%, at least 25% faster, at least 30% faster, at least 35% faster, at least 40% faster, at least 45% faster, at least 50% faster, at least 55% faster, at least 60% faster, at least 65% faster, at least 70% faster, at least 75% faster, at least 80% faster, at least 85% faster, at least 90% faster, at least 95% faster, at least 100% faster, at least 120% faster, at least 140% faster, at least 160% faster, at least 180% faster, at least 200% faster, at least 220% faster at least 240% faster at least 260% faster at least 280% faster at least 300% faster at least 320% faster at least 340% faster at least 360% faster at least 380% faster at least 400% faster at least 420% faster at least 440% faster at least 460% faster at least 480% faster, at least 500% faster, at least 1,000% faster, at least 2,000% faster, at least 3,000% faster, at least 4,000% faster, at least 5,000%, at least 6,000% faster, at least 7,000% faster, at least 8,000% faster, at least 9,000% faster, or at least 10,000% faster, or about 5% faster to about 10,000% faster, about 5% faster to about 9,000% faster, about 5% faster to about 8,000% faster, about 5% faster to about 7,000% faster, about 5% faster to about 6,000% faster, about 5% faster to about 5,000% faster, about 5% faster to about 4,000% faster, about 5% faster to about 3,000% faster, about 5% faster to about 2,000% faster, about 5% faster to about 1,000% faster, about 5% faster to about 500% faster, about 5% faster to about 480% faster, about 5% faster to about 460% faster, about 5% faster to about 440% faster, about 5% faster to about 420% faster, about 5% faster to about 400% faster, about 5% faster to about 380% faster, about 5% faster to about 360% faster, about 5% faster to about 340% faster, about 5% faster to about 320% faster, about 5% faster to about 300% faster, about 5% faster to about 280% faster, about 5% faster to about 260% faster, about 5% faster to about 240% faster, about 5% faster to about 220% faster, about 5% faster to about 200% faster, about 5% faster to about 180% faster, about 5% faster to about 160% faster, about 5% faster to about 140% faster, about 5% faster to about 120% faster, about 5% faster to about 100% faster, about 5% faster to about 95% faster, about 5% faster to about 90% faster, about 5% faster to about 85% faster, about 5% faster to about 80% faster, about 5% faster to about 75% faster, about 5% faster to about 70% faster, about 5% faster to about 65% faster, about 5% faster to about 60% faster, about 5% faster to about 55% faster, about 5% faster to about 50% faster, about 5% faster to about 45% faster, about 5% faster to about 40% faster, about 5% faster to about 35% faster, about 5% faster to about 30% faster, about 5% faster to about 25% faster, about 5% faster to about 20% faster, about 5% faster to about 15% faster, about 5% faster to about 10% faster, about 10% faster to about 10,000% faster, about 10% faster to about 9,000% faster, about 10% faster to about 8,000% faster, about 10% faster to about 7,000% faster, about 10% faster to about 6,000% faster, about 10% faster to about 5,000% faster, about 10% faster to about 4,000% faster, about 10% faster to about 3,000% faster, about 10% faster to about 2,000% faster, about 10% faster to about 1,000% faster, about 10% faster to about 500% faster, about 10% faster to about 480% faster, about 10% faster to about 460% faster, about 10% faster to about 440% faster, about 10% faster to about 420% faster, about 10% faster to about 400% faster, about 10% faster to about 380% faster, about 10% faster to about 360% faster, about 10% faster to about 340% faster, about 10% faster to about 320% faster, about 10% faster to about 300% faster, about 10% faster to about 280% faster, about 10% faster to about 260% faster, about 10% faster to about 240% faster, about 10% faster to about 220% faster, about 10% faster to about 200% faster, about 10% faster to about 180% faster, about 10% faster to about 160% faster, about 10% faster to about 140% faster, about 10% faster to about 120% faster, about 10% faster to about 100% faster, about 10% faster to about 95% faster, about 10% faster to about 90% faster, about 10% faster to about 85% faster, about 10% faster to about 80% faster, about 10% faster to about 75% faster, about 10% faster to about 70% faster, about 10% faster to about 65% faster, about 10% faster to about 60% faster, about 10% faster to about 55% faster, about 10% faster to about 50% faster, about 10% faster to about 45% faster, about 10% faster to about 40% faster, about 10% faster to about 35% faster, about 10% faster to about 30% faster, about 10% faster to about 25% faster, about 10% faster to about 20% faster, about 10% faster to about 15% faster, about 15% faster to about 10,000% faster, about 15% faster to about 9,000% faster, about 15% faster to about 8,000% faster, about 15% faster to about 7,000% faster, about 15% faster to about 6,000% faster, about 15% faster to about 5,000% faster, about 15% faster to about 4,000% faster, about 15% faster to about 3,000% faster, about 15% faster to about 2,000% faster, about 15% faster to about 1,000% faster, about 15% faster to about 500% faster, about 15% faster to about 480% faster, about 15% faster to about 460% faster, about 15% faster to about 440% faster, about 15% faster to about 420% faster, about 15% faster to about 400% faster, about 15% faster to about 380% faster, about 15% faster to about 360% faster, about 15% faster to about 340% faster, about 15% faster to about 320% faster, about 15% faster to about 300% faster, about 15% faster to about 280% faster, about 15% faster to about 260% faster, about 15% faster to about 240% faster, about 15% faster to about 220% faster, about 15% faster to about 200% faster, about 15% faster to about 180% faster, about 15% faster to about 160% faster, about 15% faster to about 140% faster, about 15% faster to about 120% faster, about 15% faster to about 100% faster, about 15% faster to about 95% faster, about 15% faster to about 90% faster, about 15% faster to about 85% faster, about 15% faster to about 80% faster, about 15% faster to about 75% faster, about 15% faster to about 70% faster, about 15% faster to about 65% faster, about 15% faster to about 60% faster, about 15% faster to about 55% faster, about 15% faster to about 50% faster, about 15% faster to about 45% faster, about 15% faster to about 40% faster, about 15% faster to about 35% faster, about 15% faster to about 30% faster, about 15% faster to about 25% faster, about 15% faster to about 20% faster, about 20% faster to about 10,000% faster, about 20% faster to about 9,000% faster, about 20% faster to about 8,000% faster, about 20% faster to about 7,000% faster, about 20% faster to about 6,000% faster, about 20% faster to about 5,000% faster, about 20% faster to about 4,000% faster, about 20% faster to about 3,000% faster, about 20% faster to about 2,000% faster, about 20% faster to about 1,000% faster, about 20% faster to about 500% faster, about 20% faster to about 480% faster, about 20% faster to about 460% faster, about 20% faster to about 440% faster, about 20% faster to about 420% faster, about 20% faster to about 400% faster, about 20% faster to about 380% faster, about 20% faster to about 360% faster, about 20% faster to about 340% faster, about 20% faster to about 320% faster, about 20% faster to about 300% faster, about 20% faster to about 280% faster, about 20% faster to about 260% faster, about 20% faster to about 240% faster, about 20% faster to about 220% faster, about 20% faster to about 200% faster, about 20% faster to about 180% faster, about 20% faster to about 160% faster, about 20% faster to about 140% faster, about 20% faster to about 120% faster, about 20% faster to about 100% faster, about 20% faster to about 95% faster, about 20% faster to about 90% faster, about 20% faster to about 85% faster, about 20% faster to about 80% faster, about 20% faster to about 75% faster, about 20% faster to about 70% faster, about 20% faster to about 65% faster, about 20% faster to about 60% faster, about 20% faster to about 55% faster, about 20% faster to about 50% faster, about 20% faster to about 45% faster, about 20% faster to about 40% faster, about 20% faster to about 35% faster, about 20% faster to about 30% faster, about 20% faster to about 25% faster, about 25% faster to about 10,000% faster, about 25% faster to about 9,000% faster, about 25% faster to about 8,000% faster, about 25% faster to about 7,000% faster, about 25% faster to about 6,000% faster, about 25% faster to about 5,000% faster, about 25% faster to about 4,000% faster, about 25% faster to about 3,000% faster, about 25% faster to about 2,000% faster, about 25% faster to about 1,000% faster, about 25% faster to about 500% faster, about 25% faster to about 480% faster, about 25% faster to about 460% faster, about 25% faster to about 440% faster, about 25% faster to about 420% faster, about 25% faster to about 400% faster, about 25% faster to about 380% faster, about 25% faster to about 360% faster, about 25% faster to about 340% faster, about 25% faster to about 320% faster, about 25% faster to about 300% faster, about 25% faster to about 280% faster, about 25% faster to about 260% faster, about 25% faster to about 240% faster, about 25% faster to about 220% faster, about 25% faster to about 200% faster, about 25% faster to about 180% faster, about 25% faster to about 160% faster, about 25% faster to about 140% faster, about 25% faster to about 120% faster, about 25% faster to about 100% faster, about 25% faster to about 95% faster, about 25% faster to about 90% faster, about 25% faster to about 85% faster, about 25% faster to about 80% faster, about 25% faster to about 75% faster, about 25% faster to about 70% faster, about 25% faster to about 65% faster, about 25% faster to about 60% faster, about 25% faster to about 55% faster, about 25% faster to about 50% faster, about 25% faster to about 45% faster, about 25% faster to about 40% faster, about 25% faster to about 35% faster, about 25% faster to about 30% faster, about 30% faster to about 10,000% faster, about 30% faster to about 9,000% faster, about 30% faster to about 8,000% faster, about 30% faster to about 7,000% faster, about 30% faster to about 6,000% faster, about 30% faster to about 5,000% faster, about 30% faster to about 4,000% faster, about 30% faster to about 3,000% faster, about 30% faster to about 2,000% faster, about 30% faster to about 1,000% faster, about 30% faster to about 500% faster, about 30% faster to about 480% faster, about 30% faster to about 460% faster, about 30% faster to about 440% faster, about 30% faster to about 420% faster, about 30% faster to about 400% faster, about 30% faster to about 380% faster, about 30% faster to about 360% faster, about 30% faster to about 340% faster, about 30% faster to about 320% faster, about 30% faster to about 300% faster, about 30% faster to about 280% faster, about 30% faster to about 260% faster, about 30% faster to about 240% faster, about 30% faster to about 220% faster, about 30% faster to about 200% faster, about 30% faster to about 180% faster, about 30% faster to about 160% faster, about 30% faster to about 140% faster, about 30% faster to about 120% faster, about 30% faster to about 100% faster, about 30% faster to about 95% faster, about 30% faster to about 90% faster, about 30% faster to about 85% faster, about 30% faster to about 80% faster, about 30% faster to about 75% faster, about 30% faster to about 70% faster, about 30% faster to about 65% faster, about 30% faster to about 60% faster, about 30% faster to about 55% faster, about 30% faster to about 50% faster, about 30% faster to about 45% faster, about 30% faster to about 40% faster, about 30% faster to about 35% faster, about 35% faster to about 10,000% faster, about 35% faster to about 9,000% faster, about 35% faster to about 8,000% faster, about 35% faster to about 7,000% faster, about 35% faster to about 6,000% faster, about 35% faster to about 5,000% faster, about 35% faster to about 4,000% faster, about 35% faster to about 3,000% faster, about 35% faster to about 2,000% faster, about 35% faster to about 1,000% faster, about 35% faster to about 500% faster, about 35% faster to about 480% faster, about 35% faster to about 460% faster, about 35% faster to about 440% faster, about 35% faster to about 420% faster, about 35% faster to about 400% faster, about 35% faster to about 380% faster, about 35% faster to about 360% faster, about 35% faster to about 340% faster, about 35% faster to about 320% faster, about 35% faster to about 300% faster, about 35% faster to about 280% faster, about 35% faster to about 260% faster, about 35% faster to about 240% faster, about 35% faster to about 220% faster, about 35% faster to about 200% faster, about 35% faster to about 180% faster, about 35% faster to about 160% faster, about 35% faster to about 140% faster, about 35% faster to about 120% faster, about 35% faster to about 100% faster, about 35% faster to about 95% faster, about 35% faster to about 90% faster, about 35% faster to about 85% faster, about 35% faster to about 80% faster, about 35% faster to about 75% faster, about 35% faster to about 70% faster, about 35% faster to about 65% faster, about 35% faster to about 60% faster, about 35% faster to about 55% faster, about 35% faster to about 50% faster, about 35% faster to about 45% faster, about 35% faster to about 40% faster, about 40% faster to about 10,000% faster, about 40% faster to about 9,000% faster, about 40% faster to about 8,000% faster, about 40% faster to about 7,000% faster, about 40% faster to about 6,000% faster, about 40% faster to about 5,000% faster, about 40% faster to about 4,000% faster, about 40% faster to about 3,000% faster, about 40% faster to about 2,000% faster, about 40% faster to about 1,000% faster, about 40% faster to about 500% faster, about 40% faster to about 480% faster, about 40% faster to about 460% faster, about 40% faster to about 440% faster, about 40% faster to about 420% faster, about 40% faster to about 400% faster, about 40% faster to about 380% faster, about 40% faster to about 360% faster, about 40% faster to about 340% faster, about 40% faster to about 320% faster, about 40% faster to about 300% faster, about 40% faster to about 280% faster, about 40% faster to about 260% faster, about 40% faster to about 240% faster, about 40% faster to about 220% faster, about 40% faster to about 200% faster, about 40% faster to about 180% faster, about 40% faster to about 160% faster, about 40% faster to about 140% faster, about 40% faster to about 120% faster, about 40% faster to about 100% faster, about 40% faster to about 95% faster, about 40% faster to about 90% faster, about 40% faster to about 85% faster, about 40% faster to about 80% faster, about 40% faster to about 75% faster, about 40% faster to about 70% faster, about 40% faster to about 65% faster, about 40% faster to about 60% faster, about 40% faster to about 55% faster, about 40% faster to about 50% faster, about 40% faster to about 45% faster, about 45% faster to about 10,000% faster, about 45% faster to about 9,000% faster, about 45% faster to about 8,000% faster, about 45% faster to about 7,000% faster, about 45% faster to about 6,000% faster, about 45% faster to about 5,000% faster, about 45% faster to about 4,000% faster, about 45% faster to about 3,000% faster, about 45% faster to about 2,000% faster, about 45% faster to about 1,000% faster, about 45% faster to about 500% faster, about 45% faster to about 480% faster, about 45% faster to about 460% faster, about 45% faster to about 440% faster, about 45% faster to about 420% faster, about 45% faster to about 400% faster, about 45% faster to about 380% faster, about 45% faster to about 360% faster, about 45% faster to about 340% faster, about 45% faster to about 320% faster, about 45% faster to about 300% faster, about 45% faster to about 280% faster, about 45% faster to about 260% faster, about 45% faster to about 240% faster, about 45% faster to about 220% faster, about 45% faster to about 200% faster, about 45% faster to about 180% faster, about 45% faster to about 160% faster, about 45% faster to about 140% faster, about 45% faster to about 120% faster, about 45% faster to about 100% faster, about 45% faster to about 95% faster, about 45% faster to about 90% faster, about 45% faster to about 85% faster, about 45% faster to about 80% faster, about 45% faster to about 75% faster, about 45% faster to about 70% faster, about 45% faster to about 65% faster, about 45% faster to about 60% faster, about 45% faster to about 55% faster, about 45% faster to about 50% faster, about 50% faster to about 10,000% faster, about 50% faster to about 9,000% faster, about 50% faster to about 8,000% faster, about 50% faster to about 7,000% faster, about 50% faster to about 6,000% faster, about 50% faster to about 5,000% faster, about 50% faster to about 4,000% faster, about 50% faster to about 3,000% faster, about 50% faster to about 2,000% faster, about 50% faster to about 1,000% faster, about 50% faster to about 500% faster, about 50% faster to about 480% faster, about 50% faster to about 460% faster, about 50% faster to about 440% faster, about 50% faster to about 420% faster, about 50% faster to about 400% faster, about 50% faster to about 380% faster, about 50% faster to about 360% faster, about 50% faster to about 340% faster, about 50% faster to about 320% faster, about 50% faster to about 300% faster, about 50% faster to about 280% faster, about 50% faster to about 260% faster, about 50% faster to about 240% faster, about 50% faster to about 220% faster, about 50% faster to about 200% faster, about 50% faster to about 180% faster, about 50% faster to about 160% faster, about 50% faster to about 140% faster, about 50% faster to about 120% faster, about 50% faster to about 100% faster, about 50% faster to about 95% faster, about 50% faster to about 90% faster, about 50% faster to about 85% faster, about 50% faster to about 80% faster, about 50% faster to about 75% faster, about 50% faster to about 70% faster, about 50% faster to about 65% faster, about 50% faster to about 60% faster, about 50% faster to about 55% faster, about 55% faster to about 10,000% faster, about 55% faster to about 9,000% faster, about 55% faster to about 8,000% faster, about 55% faster to about 7,000% faster, about 55% faster to about 6,000% faster, about 55% faster to about 5,000% faster, about 55% faster to about 4,000% faster, about 55% faster to about 3,000% faster, about 55% faster to about 2,000% faster, about 55% faster to about 1,000% faster, about 55% faster to about 500% faster, about 55% faster to about 480% faster, about 55% faster to about 460% faster, about 55% faster to about 440% faster, about 55% faster to about 420% faster, about 55% faster to about 400% faster, about 55% faster to about 380% faster, about 55% faster to about 360% faster, about 55% faster to about 340% faster, about 55% faster to about 320% faster, about 55% faster to about 300% faster, about 55% faster to about 280% faster, about 55% faster to about 260% faster, about 55% faster to about 240% faster, about 55% faster to about 220% faster, about 55% faster to about 200% faster, about 55% faster to about 180% faster, about 55% faster to about 160% faster, about 55% faster to about 140% faster, about 55% faster to about 120% faster, about 55% faster to about 100% faster, about 55% faster to about 95% faster, about 55% faster to about 90% faster, about 55% faster to about 85% faster, about 55% faster to about 80% faster, about 55% faster to about 75% faster, about 55% faster to about 70% faster, about 55% faster to about 65% faster, about 55% faster to about 60% faster, about 60% faster to about 10,000% faster, about 60% faster to about 9,000% faster, about 60% faster to about 8,000% faster, about 60% faster to about 7,000% faster, about 60% faster to about 6,000% faster, about 60% faster to about 5,000% faster, about 60% faster to about 4,000% faster, about 60% faster to about 3,000% faster, about 60% faster to about 2,000% faster, about 60% faster to about 1,000% faster, about 60% faster to about 500% faster, about 60% faster to about 480% faster, about 60% faster to about 460% faster, about 60% faster to about 440% faster, about 60% faster to about 420% faster, about 60% faster to about 400% faster, about 60% faster to about 380% faster, about 60% faster to about 360% faster, about 60% faster to about 340% faster, about 60% faster to about 320% faster, about 60% faster to about 300% faster, about 60% faster to about 280% faster, about 60% faster to about 260% faster, about 60% faster to about 240% faster, about 60% faster to about 220% faster, about 60% faster to about 200% faster, about 60% faster to about 180% faster, about 60% faster to about 160% faster, about 60% faster to about 140% faster, about 60% faster to about 120% faster, about 60% faster to about 100% faster, about 60% faster to about 95% faster, about 60% faster to about 90% faster, about 60% faster to about 85% faster, about 60% faster to about 80% faster, about 60% faster to about 75% faster, about 60% faster to about 70% faster, about 60% faster to about 65% faster, about 65% faster to about 10,000% faster, about 65% faster to about 9,000% faster, about 65% faster to about 8,000% faster, about 65% faster to about 7,000% faster, about 65% faster to about 6,000% faster, about 65% faster to about 5,000% faster, about 65% faster to about 4,000% faster, about 65% faster to about 3,000% faster, about 65% faster to about 2,000% faster, about 65% faster to about 1,000% faster, about 65% faster to about 500% faster, about 65% faster to about 480% faster, about 65% faster to about 460% faster, about 65% faster to about 440% faster, about 65% faster to about 420% faster, about 65% faster to about 400% faster, about 65% faster to about 380% faster, about 65% faster to about 360% faster, about 65% faster to about 340% faster, about 65% faster to about 320% faster, about 65% faster to about 300% faster, about 65% faster to about 280% faster, about 65% faster to about 260% faster, about 65% faster to about 240% faster, about 65% faster to about 220% faster, about 65% faster to about 200% faster, about 65% faster to about 180% faster, about 65% faster to about 160% faster, about 65% faster to about 140% faster, about 65% faster to about 120% faster, about 65% faster to about 100% faster, about 65% faster to about 95% faster, about 65% faster to about 90% faster, about 65% faster to about 85% faster, about 65% faster to about 80% faster, about 65% faster to about 75% faster, about 65% faster to about 70% faster, about 70% faster to about 10,000% faster, about 70% faster to about 9,000% faster, about 70% faster to about 8,000% faster, about 70% faster to about 7,000% faster, about 70% faster to about 6,000% faster, about 70% faster to about 5,000% faster, about 70% faster to about 4,000% faster, about 70% faster to about 3,000% faster, about 70% faster to about 2,000% faster, about 70% faster to about 1,000% faster, about 70% faster to about 500% faster, about 70% faster to about 480% faster, about 70% faster to about 460% faster, about 70% faster to about 440% faster, about 70% faster to about 420% faster, about 70% faster to about 400% faster, about 70% faster to about 380% faster, about 70% faster to about 360% faster, about 70% faster to about 340% faster, about 70% faster to about 320% faster, about 70% faster to about 300% faster, about 70% faster to about 280% faster, about 70% faster to about 260% faster, about 70% faster to about 240% faster, about 70% faster to about 220% faster, about 70% faster to about 200% faster, about 70% faster to about 180% faster, about 70% faster to about 160% faster, about 70% faster to about 140% faster, about 70% faster to about 120% faster, about 70% faster to about 100% faster, about 70% faster to about 95% faster, about 70% faster to about 90% faster, about 70% faster to about 85% faster, about 70% faster to about 80% faster, about 70% faster to about 75% faster, about 75% faster to about 10,000% faster, about 75% faster to about 9,000% faster, about 75% faster to about 8,000% faster, about 75% faster to about 7,000% faster, about 75% faster to about 6,000% faster, about 75% faster to about 5,000% faster, about 75% faster to about 4,000% faster, about 75% faster to about 3,000% faster, about 75% faster to about 2,000% faster, about 75% faster to about 1,000% faster, about 75% faster to about 500% faster, about 75% faster to about 480% faster, about 75% faster to about 460% faster, about 75% faster to about 440% faster, about 75% faster to about 420% faster, about 75% faster to about 400% faster, about 75% faster to about 380% faster, about 75% faster to about 360% faster, about 75% faster to about 340% faster, about 75% faster to about 320% faster, about 75% faster to about 300% faster, about 75% faster to about 280% faster, about 75% faster to about 260% faster, about 75% faster to about 240% faster, about 75% faster to about 220% faster, about 75% faster to about 200% faster, about 75% faster to about 180% faster, about 75% faster to about 160% faster, about 75% faster to about 140% faster, about 75% faster to about 120% faster, about 75% faster to about 100% faster, about 75% faster to about 95% faster, about 75% faster to about 90% faster, about 75% faster to about 85% faster, about 75% faster to about 80% faster, about 80% faster to about 10,000% faster, about 80% faster to about 9,000% faster, about 80% faster to about 8,000% faster, about 80% faster to about 7,000% faster, about 80% faster to about 6,000% faster, about 80% faster to about 5,000% faster, about 80% faster to about 4,000% faster, about 80% faster to about 3,000% faster, about 80% faster to about 2,000% faster, about 80% faster to about 1,000% faster, about 80% faster to about 500% faster, about 80% faster to about 480% faster, about 80% faster to about 460% faster, about 80% faster to about 440% faster, about 80% faster to about 420% faster, about 80% faster to about 400% faster, about 80% faster to about 380% faster, about 80% faster to about 360% faster, about 80% faster to about 340% faster, about 80% faster to about 320% faster, about 80% faster to about 300% faster, about 80% faster to about 280% faster, about 80% faster to about 260% faster, about 80% faster to about 240% faster, about 80% faster to about 220% faster, about 80% faster to about 200% faster, about 80% faster to about 180% faster, about 80% faster to about 160% faster, about 80% faster to about 140% faster, about 80% faster to about 120% faster, about 80% faster to about 100% faster, about 80% faster to about 95% faster, about 80% faster to about 90% faster, about 80% faster to about 85% faster, about 85% faster to about 10,000% faster, about 85% faster to about 9,000% faster, about 85% faster to about 8,000% faster, about 85% faster to about 7,000% faster, about 85% faster to about 6,000% faster, about 85% faster to about 5,000% faster, about 85% faster to about 4,000% faster, about 85% faster to about 3,000% faster, about 85% faster to about 2,000% faster, about 85% faster to about 1,000% faster, about 85% faster to about 500% faster, about 85% faster to about 480% faster, about 85% faster to about 460% faster, about 85% faster to about 440% faster, about 85% faster to about 420% faster, about 85% faster to about 400% faster, about 85% faster to about 380% faster, about 85% faster to about 360% faster, about 85% faster to about 340% faster, about 85% faster to about 320% faster, about 85% faster to about 300% faster, about 85% faster to about 280% faster, about 85% faster to about 260% faster, about 85% faster to about 240% faster, about 85% faster to about 220% faster, about 85% faster to about 200% faster, about 85% faster to about 180% faster, about 85% faster to about 160% faster, about 85% faster to about 140% faster, about 85% faster to about 120% faster, about 85% faster to about 100% faster, about 85% faster to about 95% faster, about 85% faster to about 90% faster, about 90% faster to about 10,000% faster, about 90% faster to about 9,000% faster, about 90% faster to about 8,000% faster, about 90% faster to about 7,000% faster, about 90% faster to about 6,000% faster, about 90% faster to about 5,000% faster, about 90% faster to about 4,000% faster, about 90% faster to about 3,000% faster, about 90% faster to about 2,000% faster, about 90% faster to about 1,000% faster, about 90% faster to about 500% faster, about 90% faster to about 480% faster, about 90% faster to about 460% faster, about 90% faster to about 440% faster, about 90% faster to about 420% faster, about 90% faster to about 400% faster, about 90% faster to about 380% faster, about 90% faster to about 360% faster, about 90% faster to about 340% faster, about 90% faster to about 320% faster, about 90% faster to about 300% faster, about 90% faster to about 280% faster, about 90% faster to about 260% faster, about 90% faster to about 240% faster, about 90% faster to about 220% faster, about 90% faster to about 200% faster, about 90% faster to about 180% faster, about 90% faster to about 160% faster, about 90% faster to about 140% faster, about 90% faster to about 120% faster, about 90% faster to about 100% faster, about 90% faster to about 95% faster, about 95% faster to about 10,000% faster, about 95% faster to about 9,000% faster, about 95% faster to about 8,000% faster, about 95% faster to about 7,000% faster, about 95% faster to about 6,000% faster, about 95% faster to about 5,000% faster, about 95% faster to about 4,000% faster, about 95% faster to about 3,000% faster, about 95% faster to about 2,000% faster, about 95% faster to about 1,000% faster, about 95% faster to about 500% faster, about 95% faster to about 480% faster, about 95% faster to about 460% faster, about 95% faster to about 440% faster, about 95% faster to about 420% faster, about 95% faster to about 400% faster, about 95% faster to about 380% faster, about 95% faster to about 360% faster, about 95% faster to about 340% faster, about 95% faster to about 320% faster, about 95% faster to about 300% faster, about 95% faster to about 280% faster, about 95% faster to about 260% faster, about 95% faster to about 240% faster, about 95% faster to about 220% faster, about 95% faster to about 200% faster, about 95% faster to about 180% faster, about 95% faster to about 160% faster, about 95% faster to about 140% faster, about 95% faster to about 120% faster, about 95% faster to about 100% faster, about 100% faster to about 10,000% faster, about 100% faster to about 9,000% faster, about 100% faster to about 8,000% faster, about 100% faster to about 7,000% faster, about 100% faster to about 6,000% faster, about 100% faster to about 5,000% faster, about 100% faster to about 4,000% faster, about 100% faster to about 3,000% faster, about 100% faster to about 2,000% faster, about 100% faster to about 1,000% faster, about 100% faster to about 500% faster, about 100% faster to about 480% faster, about 100% faster to about 460% faster, about 100% faster to about 440% faster, about 100% faster to about 420% faster, about 100% faster to about 400% faster, about 100% faster to about 380% faster, about 100% faster to about 360% faster, about 100% faster to about 340% faster, about 100% faster to about 320% faster, about 100% faster to about 300% faster, about 100% faster to about 280% faster, about 100% faster to about 260% faster, about 100% faster to about 240% faster, about 100% faster to about 220% faster, about 100% faster to about 200% faster, about 100% faster to about 180% faster, about 100% faster to about 160% faster, about 100% faster to about 140% faster, about 100% faster to about 120% faster, about 120% faster to about 10,000% faster, about 120% faster to about 9,000% faster, about 120% faster to about 8,000% faster, about 120% faster to about 7,000% faster, about 120% faster to about 6,000% faster, about 120% faster to about 5,000% faster, about 120% faster to about 4,000% faster, about 120% faster to about 3,000% faster, about 120% faster to about 2,000% faster, about 120% faster to about 1,000% faster, about 120% faster to about 500% faster, about 120% faster to about 480% faster, about 120% faster to about 460% faster, about 120% faster to about 440% faster, about 120% faster to about 420% faster, about 120% faster to about 400% faster, about 120% faster to about 380% faster, about 120% faster to about 360% faster, about 120% faster to about 340% faster, about 120% faster to about 320% faster, about 120% faster to about 300% faster, about 120% faster to about 280% faster, about 120% faster to about 260% faster, about 120% faster to about 240% faster, about 120% faster to about 220% faster, about 120% faster to about 200% faster, about 120% faster to about 180% faster, about 120% faster to about 160% faster, about 120% faster to about 140% faster, about 140% faster to about 10,000% faster, about 140% faster to about 9,000% faster, about 140% faster to about 8,000% faster, about 140% faster to about 7,000% faster, about 140% faster to about 6,000% faster, about 140% faster to about 5,000% faster, about 140% faster to about 4,000% faster, about 140% faster to about 3,000% faster, about 140% faster to about 2,000% faster, about 140% faster to about 1,000% faster, about 140% faster to about 500% faster, about 140% faster to about 480% faster, about 140% faster to about 460% faster, about 140% faster to about 440% faster, about 140% faster to about 420% faster, about 140% faster to about 400% faster, about 140% faster to about 380% faster, about 140% faster to about 360% faster, about 140% faster to about 340% faster, about 140% faster to about 320% faster, about 140% faster to about 300% faster, about 140% faster to about 280% faster, about 140% faster to about 260% faster, about 140% faster to about 240% faster, about 140% faster to about 220% faster, about 140% faster to about 200% faster, about 140% faster to about 180% faster, about 140% faster to about 160% faster, about 160% faster to about 10,000% faster, about 160% faster to about 9,000% faster, about 160% faster to about 8,000% faster, about 160% faster to about 7,000% faster, about 160% faster to about 6,000% faster, about 160% faster to about 5,000% faster, about 160% faster to about 4,000% faster, about 160% faster to about 3,000% faster, about 160% faster to about 2,000% faster, about 160% faster to about 1,000% faster, about 160% faster to about 500% faster, about 160% faster to about 480% faster, about 160% faster to about 460% faster, about 160% faster to about 440% faster, about 160% faster to about 420% faster, about 160% faster to about 400% faster, about 160% faster to about 380% faster, about 160% faster to about 360% faster, about 160% faster to about 340% faster, about 160% faster to about 320% faster, about 160% faster to about 300% faster, about 160% faster to about 280% faster, about 160% faster to about 260% faster, about 160% faster to about 240% faster, about 160% faster to about 220% faster, about 160% faster to about 200% faster, about 160% faster to about 180% faster, about 180% faster to about 10,000% faster, about 180% faster to about 9,000% faster, about 180% faster to about 8,000% faster, about 180% faster to about 7,000% faster, about 180% faster to about 6,000% faster, about 180% faster to about 5,000% faster, about 180% faster to about 4,000% faster, about 180% faster to about 3,000% faster, about 180% faster to about 2,000% faster, about 180% faster to about 1,000% faster, about 180% faster to about 500% faster, about 180% faster to about 480% faster, about 180% faster to about 460% faster, about 180% faster to about 440% faster, about 180% faster to about 420% faster, about 180% faster to about 400% faster, about 180% faster to about 380% faster, about 180% faster to about 360% faster, about 180% faster to about 340% faster, about 180% faster to about 320% faster, about 180% faster to about 300% faster, about 180% faster to about 280% faster, about 180% faster to about 260% faster, about 180% faster to about 240% faster, about 180% faster to about 220% faster, about 180% faster to about 200% faster, about 200% faster to about 10,000% faster, about 200% faster to about 9,000% faster, about 200% faster to about 8,000% faster, about 200% faster to about 7,000% faster, about 200% faster to about 6,000% faster, about 200% faster to about 5,000% faster, about 200% faster to about 4,000% faster, about 200% faster to about 3,000% faster, about 200% faster to about 2,000% faster, about 200% faster to about 1,000% faster, about 200% faster to about 500% faster, about 200% faster to about 480% faster, about 200% faster to about 460% faster, about 200% faster to about 440% faster, about 200% faster to about 420% faster, about 200% faster to about 400% faster, about 200% faster to about 380% faster, about 200% faster to about 360% faster, about 200% faster to about 340% faster, about 200% faster to about 320% faster, about 200% faster to about 300% faster, about 200% faster to about 280% faster, about 200% faster to about 260% faster, about 200% faster to about 240% faster, about 200% faster to about 220% faster, about 220% faster to about 10,000% faster, about 220% faster to about 9,000% faster, about 220% faster to about 8,000% faster, about 220% faster to about 7,000% faster, about 220% faster to about 6,000% faster, about 220% faster to about 5,000% faster, about 220% faster to about 4,000% faster, about 220% faster to about 3,000% faster, about 220% faster to about 2,000% faster, about 220% faster to about 1,000% faster, about 220% faster to about 500% faster, about 220% faster to about 480% faster, about 220% faster to about 460% faster, about 220% faster to about 440% faster, about 220% faster to about 420% faster, about 220% faster to about 400% faster, about 220% faster to about 380% faster, about 220% faster to about 360% faster, about 220% faster to about 340% faster, about 220% faster to about 320% faster, about 220% faster to about 300% faster, about 220% faster to about 280% faster, about 220% faster to about 260% faster, about 220% faster to about 240% faster, about 240% faster to about 10,000% faster, about 240% faster to about 9,000% faster, about 240% faster to about 8,000% faster, about 240% faster to about 7,000% faster, about 240% faster to about 6,000% faster, about 240% faster to about 5,000% faster, about 240% faster to about 4,000% faster, about 240% faster to about 3,000% faster, about 240% faster to about 2,000% faster, about 240% faster to about 1,000% faster, about 240% faster to about 500% faster, about 240% faster to about 480% faster, about 240% faster to about 460% faster, about 240% faster to about 440% faster, about 240% faster to about 420% faster, about 240% faster to about 400% faster, about 240% faster to about 380% faster, about 240% faster to about 360% faster, about 240% faster to about 340% faster, about 240% faster to about 320% faster, about 240% faster to about 300% faster, about 240% faster to about 280% faster, about 240% faster to about 260% faster, about 260% faster to about 10,000% faster, about 260% faster to about 9,000% faster, about 260% faster to about 8,000% faster, about 260% faster to about 7,000% faster, about 260% faster to about 6,000% faster, about 260% faster to about 5,000% faster, about 260% faster to about 4,000% faster, about 260% faster to about 3,000% faster, about 260% faster to about 2,000% faster, about 260% faster to about 1,000% faster, about 260% faster to about 500% faster, about 260% faster to about 480% faster, about 260% faster to about 460% faster, about 260% faster to about 440% faster, about 260% faster to about 420% faster, about 260% faster to about 400% faster, about 260% faster to about 380% faster, about 260% faster to about 360% faster, about 260% faster to about 340% faster, about 260% faster to about 320% faster, about 260% faster to about 300% faster, about 260% faster to about 280% faster, about 280% faster to about 10,000% faster, about 280% faster to about 9,000% faster, about 280% faster to about 8,000% faster, about 280% faster to about 7,000% faster, about 280% faster to about 6,000% faster, about 280% faster to about 5,000% faster, about 280% faster to about 4,000% faster, about 280% faster to about 3,000% faster, about 280% faster to about 2,000% faster, about 280% faster to about 1,000% faster, about 280% faster to about 500% faster, about 280% faster to about 480% faster, about 280% faster to about 460% faster, about 280% faster to about 440% faster, about 280% faster to about 420% faster, about 280% faster to about 400% faster, about 280% faster to about 380% faster, about 280% faster to about 360% faster, about 280% faster to about 340% faster, about 280% faster to about 320% faster, about 280% faster to about 300% faster, about 300% faster to about 10,000% faster, about 300% faster to about 9,000% faster, about 300% faster to about 8,000% faster, about 300% faster to about 7,000% faster, about 300% faster to about 6,000% faster, about 300% faster to about 5,000% faster, about 300% faster to about 4,000% faster, about 300% faster to about 3,000% faster, about 300% faster to about 2,000% faster, about 300% faster to about 1,000% faster, about 300% faster to about 500% faster, about 300% faster to about 480% faster, about 300% faster to about 460% faster, about 300% faster to about 440% faster, about 300% faster to about 420% faster, about 300% faster to about 400% faster, about 300% faster to about 380% faster, about 300% faster to about 360% faster, about 300% faster to about 340% faster, about 300% faster to about 320% faster, about 320% faster to about 10,000% faster, about 320% faster to about 9,000% faster, about 320% faster to about 8,000% faster, about 320% faster to about 7,000% faster, about 320% faster to about 6,000% faster, about 320% faster to about 5,000% faster, about 320% faster to about 4,000% faster, about 320% faster to about 3,000% faster, about 320% faster to about 2,000% faster, about 320% faster to about 1,000% faster, about 320% faster to about 500% faster, about 320% faster to about 480% faster, about 320% faster to about 460% faster, about 320% faster to about 440% faster, about 320% faster to about 420% faster, about 320% faster to about 400% faster, about 320% faster to about 380% faster, about 320% faster to about 360% faster, about 320% faster to about 340% faster, about 340% faster to about 10,000% faster, about 340% faster to about 9,000% faster, about 340% faster to about 8,000% faster, about 340% faster to about 7,000% faster, about 340% faster to about 6,000% faster, about 340% faster to about 5,000% faster, about 340% faster to about 4,000% faster, about 340% faster to about 3,000% faster, about 340% faster to about 2,000% faster, about 340% faster to about 1,000% faster, about 340% faster to about 500% faster, about 340% faster to about 480% faster, about 340% faster to about 460% faster, about 340% faster to about 440% faster, about 340% faster to about 420% faster, about 340% faster to about 400% faster, about 340% faster to about 380% faster, about 340% faster to about 360% faster, about 360% faster to about 10,000% faster, about 360% faster to about 9,000% faster, about 360% faster to about 8,000% faster, about 360% faster to about 7,000% faster, about 360% faster to about 6,000% faster, about 360% faster to about 5,000% faster, about 360% faster to about 4,000% faster, about 360% faster to about 3,000% faster, about 360% faster to about 2,000% faster, about 360% faster to about 1,000% faster, about 360% faster to about 500% faster, about 360% faster to about 480% faster, about 360% faster to about 460% faster, about 360% faster to about 440% faster, about 360% faster to about 420% faster, about 360% faster to about 400% faster, about 360% faster to about 380% faster, about 380% faster to about 10,000% faster, about 380% faster to about 9,000% faster, about 380% faster to about 8,000% faster, about 380% faster to about 7,000% faster, about 380% faster to about 6,000% faster, about 380% faster to about 5,000% faster, about 380% faster to about 4,000% faster, about 380% faster to about 3,000% faster, about 380% faster to about 2,000% faster, about 380% faster to about 1,000% faster, about 380% faster to about 500% faster, about 380% faster to about 480% faster, about 380% faster to about 460% faster, about 380% faster to about 440% faster, about 380% faster to about 420% faster, about 380% faster to about 400% faster, about 400% faster to about 10,000% faster, about 400% faster to about 9,000% faster, about 400% faster to about 8,000% faster, about 400% faster to about 7,000% faster, about 400% faster to about 6,000% faster, about 400% faster to about 5,000% faster, about 400% faster to about 4,000% faster, about 400% faster to about 3,000% faster, about 400% faster to about 2,000% faster, about 400% faster to about 1,000% faster, about 400% faster to about 500% faster, about 400% faster to about 480% faster, about 400% faster to about 460% faster, about 400% faster to about 440% faster, about 400% faster to about 420% faster, about 420% faster to about 10,000% faster, about 420% faster to about 9,000% faster, about 420% faster to about 8,000% faster, about 420% faster to about 7,000% faster, about 420% faster to about 6,000% faster, about 420% faster to about 5,000% faster, about 420% faster to about 4,000% faster, about 420% faster to about 3,000% faster, about 420% faster to about 2,000% faster, about 420% faster to about 1,000% faster, about 420% faster to about 500% faster, about 420% faster to about 480% faster, about 420% faster to about 460% faster, about 420% faster to about 440% faster, about 440% faster to about 10,000% faster, about 440% faster to about 9,000% faster, about 440% faster to about 8,000% faster, about 440% faster to about 7,000% faster, about 440% faster to about 6,000% faster, about 440% faster to about 5,000% faster, about 440% faster to about 4,000% faster, about 440% faster to about 3,000% faster, about 440% faster to about 2,000% faster, about 440% faster to about 1,000% faster, about 440% faster to about 500% faster, about 440% faster to about 480% faster, about 440% faster to about 460% faster, about 460% faster to about 10,000% faster, about 460% faster to about 9,000% faster, about 460% faster to about 8,000% faster, about 460% faster to about 7,000% faster, about 460% faster to about 6,000% faster, about 460% faster to about 5,000% faster, about 460% faster to about 4,000% faster, about 460% faster to about 3,000% faster, about 460% faster to about 2,000% faster, about 460% faster to about 1,000% faster, about 460% faster to about 500% faster, about 460% faster to about 480% faster, about 480% faster to about 10,000% faster, about 480% faster to about 9,000% faster, about 480% faster to about 8,000% faster, about 480% faster to about 7,000% faster, about 480% faster to about 6,000% faster, about 480% faster to about 5,000% faster, about 480% faster to about 4,000% faster, about 480% faster to about 3,000% faster, about 480% faster to about 2,000% faster, about 480% faster to about 1,000% faster, about 480% faster to about 500% faster, about 500% faster to about 10,000% faster, about 500% faster to about 9,000% faster, about 500% faster to about 8,000% faster, about 500% faster to about 7,000% faster, about 500% faster to about 6,000% faster, about 500% faster to about 5,000% faster, about 500% faster to about 4,000% faster, about 500% faster to about 3,000% faster, about 500% faster to about 2,000% faster, about 500% faster to about 1,000% faster, about 1,000% faster to about 10,000% faster, about 1,000% faster to about 9,000% faster, about 1,000% faster to about 8,000% faster, about 1,000% faster to about 7,000% faster, about 1,000% faster to about 6,000% faster, about 1,000% faster to about 5,000% faster, about 1,000% faster to about 4,000% faster, about 1,000% faster to about 3,000% faster, about 1,000% faster to about 2,000% faster, about 2,000% faster to about 10,000% faster, about 2,000% faster to about 9,000% faster, about 2,000% faster to about 8,000% faster, about 2,000% faster to about 7,000% faster, about 2,000% faster to about 6,000% faster, about 2,000% faster to about 5,000% faster, about 2,000% faster to about 4,000% faster, about 2,000% faster to about 3,000% faster, about 3,000% faster to about 10,000% faster, about 3,000% faster to about 9,000% faster, about 3,000% faster to about 8,000% faster, about 3,000% faster to about 7,000% faster, about 3,000% faster to about 6,000% faster, about 3,000% faster to about 5,000% faster, about 3,000% faster to about 4,000% faster, about 4,000% faster to about 10,000% faster, about 4,000% faster to about 9,000% faster, about 4,000% faster to about 8,000% faster, about 4,000% faster to about 7,000% faster, about 4,000% faster to about 6,000% faster, about 4,000% faster to about 5,000% faster, about 5,000% faster to about 10,000% faster, about 5,000% faster to about 9,000% faster, about 5,000% faster to about 8,000% faster, about 5,000% faster to about 7,000% faster, about 5,000% faster to about 6,000% faster, about 6,000% faster to about 10,000% faster, about 6,000% faster to about 9,000% faster, about 6,000% faster to about 8,000% faster, about 6,000% faster to about 7,000% faster, about 7,000% faster to about 10,000% faster, about 7,000% faster to about 9,000% faster, about 7,000% faster to about 8,000% faster, about 8,000% faster to about 10,000% faster, about 8,000% faster to about 9,000% faster, or about 9,000% faster to about 10,000% faster) than the dissociation rate at a pH of about 7.0 to about 8.0 (e.g., about 7.0 to about 7.9, about 7.0 to about 7.8, about 7.0 to about 7.7, about 7.0 to about 7.6, about 7.0 to about 7.5, about 7.0 to about 7.4, about 7.0 to about 7.3, about 7.0 to about 7.2, about 7.0 to about 7.1, about 7.1 to about 8.0, about 7.1 to about 7.9, about 7.1 to about 7.8, about 7.1 to about 7.7, about 7.1 to about 7.6, about 7.1 to about 7.5, about 7.1 to about 7.4, about 7.1 to about 7.3, about 7.1 to about 7.2, about 7.2 to about 8.0, about 7.2 to about 7.9, about 7.2 to about 7.8, about 7.2 to about 7.7, about 7.2 to about 7.6, about 7.2 to about 7.5, about 7.2 to about 7.4, about 7.2 to about 7.3, about 7.3 to about 8.0, about 7.3 to about 7.9, about 7.3 to about 7.8, about 7.3 to about 7.7, about 7.3 to about 7.6, about 7.3 to about 7.5, about 7.3 to about 7.4, about 7.4 to about 8.0, about 7.4 to about 7.9, about 7.4 to about 7.8, about 7.4 to about 7.7, about 7.4 to about 7.6, about 7.4 to about 7.5, about 7.5 to about 8.0, about 7.5 to about 7.9, about 7.5 to about 7.8, about 7.5 to about 7.7, about 7.5 to about 7.6, about 7.6 to about 8.0, about 7.6 to about 7.9, about 7.6 to about 7.8, about 7.6 to about 7.7, about 7.7 to about 8.0, about 7.7 to about 7.9, about 7.7 to about 7.8, about 7.8 to about 8.0, about 7.8 to about 7.9, or about 7.9 to about 8.0).

In some embodiments of any of the antibodies described herein, the dissociation constant ($K_D$) at a pH of about 4.0 to about 6.5 (e.g., any of the subranges of this range described herein) is greater (e.g., detectably greater) (e.g., at least 5% greater, at least 10% greater, at least 15% greater, at least 20% greater, at least 25% greater, at least 30% greater, at least 35% greater, at least 40% greater, at least 45% greater, at least 50% greater, at least 55% greater, at least 60% greater, at least 65% greater, at least 70% greater, at least 80% greater, at least 85% greater, at least 90% greater, at least 95% greater, at least 100% greater, at least 120% greater, at least 140% greater, at least 160% greater, at least 180% greater, at least 200% greater, at least 220% greater, at least 240% greater, at least 260% greater, at least 280% greater, at least 300% greater, at least 320% greater, at least 340% greater, at least 360% greater, at least 380% greater, at least 400% greater, at least 420% greater, at least 440% greater, at least 460% greater, at least 480% greater, at least 500% greater, at least 1,000% greater, at least 2,000% greater, at least 3,000% greater, at least 4,000% greater, at least 5,000% greater, at least 6,000% greater, at least 7,000% greater, at least 8,000% greater, at least 9,000% greater, or at least 10,000% greater, or about 5% greater to about 10,000% greater, about 5% greater to about 9,000% greater, about 5% greater to about 8,000% greater, about 5% greater to about 7,000% greater, about 5% greater to about 6,000% greater, about 5% greater to about 5,000% greater, about 5% greater to about 4,000% greater, about 5% greater to about 3,000% greater, about 5% greater to about 2,000% greater, about 5% greater to about 1,000% greater, about 5% greater to about 500% greater, about 5% greater to about 480% greater, about 5% greater to about 460% greater, about 5% greater to about 440% greater, about 5% greater to about 420% greater, about 5% greater to about 400% greater, about 5% greater to about 380% greater, about 5% greater to about 360% greater, about 5% greater to about 340% greater, about 5% greater to about 320% greater, about 5% greater to about 300% greater, about 5% greater to about 280% greater, about 5% greater to about 260% greater, about 5% greater to about 240% greater, about 5% greater to about 220% greater, about 5% greater to about 200% greater, about 5% greater to about 180% greater, about 5% greater to about 160% greater, about 5% greater to about 140% greater, about 5% greater to about 120% greater, about 5% greater to about 100% greater, about 5% greater to about 95% greater, about 5% greater to about 90% greater, about 5% greater to about 85% greater, about 5% greater to about 80% greater, about 5% greater to about 75% greater, about 5% greater to about 70% greater, about 5% greater to about 65% greater, about 5% greater to about 60% greater, about 5% greater to about 55% greater, about 5% greater to about 50% greater, about 5% greater to about 45% greater, about 5% greater to about 40% greater, about 5% greater to about 35% greater, about 5% greater to about 30% greater, about 5% greater to about 25% greater, about 5% greater to about 20% greater, about 5% greater to about 15% greater, about 5% greater to about 10% greater, about 10% greater to about 10,000% greater, about 10% greater to about 9,000% greater, about 10% greater to about 8,000% greater, about 10% greater to about 7,000% greater, about 10% greater to about 6,000% greater, about 10% greater to about 5,000% greater, about 10% greater to about 4,000% greater, about 10% greater to about 3,000% greater, about 10% greater to about 2,000% greater, about 10% greater to about 1,000% greater, about 10% greater to about 500% greater, about 10% greater to about 480% greater, about 10% greater to about 460% greater, about 10% greater to about 440% greater, about 10% greater to about 420% greater, about 10% greater to about 400% greater, about 10% greater to about 380% greater, about 10% greater to about 360% greater, about 10% greater to about 340% greater, about 10% greater to about 320% greater, about 10% greater to about 300% greater, about 10% greater to about 280% greater, about 10% greater to about 260% greater, about 10% greater to about 240% greater, about 10% greater to about 220% greater, about 10% greater to about 200% greater, about 10% greater to about 180% greater, about 10% greater to about 160% greater, about 10% greater to about 140% greater, about 10% greater to about 120% greater, about 10% greater to about 100% greater, about 10% greater to about 95% greater, about 10% greater to about 90% greater, about 10% greater to about 85% greater, about 10% greater to about 80% greater, about 10% greater to about 75% greater, about 10% greater to about 70% greater, about 10% greater to about 65% greater, about 10% greater to about 60% greater, about 10% greater to about 55% greater, about 10% greater to about 50% greater, about 10% greater to about 45% greater, about 10% greater to about 40% greater, about 10% greater to about 35% greater, about 10% greater to about 30% greater, about 10% greater to about 25% greater, about 10% greater to about 20% greater, about 10% greater to about 15% greater, about 15% greater to about 10,000% greater, about 15% greater to about 9,000% greater, about 15% greater to about 8,000% greater, about 15% greater to about 7,000% greater, about 15% greater to about 6,000% greater, about 15% greater to about 5,000% greater, about 15% greater to about 4,000% greater, about 15% greater to about 3,000% greater, about 15% greater to about 2,000% greater, about 15% greater to about 1,000% greater, about 15% greater to about 500% greater, about 15% greater to about 480% greater, about 15% greater to about 460% greater, about 15% greater to about 440% greater, about 15% greater to about 420% greater, about 15% greater to about 400% greater, about 15% greater to about 380% greater, about 15% greater to about 360% greater, about 15% greater to about 340% greater, about 15% greater to about 320% greater, about 15% greater to about 300% greater, about 15% greater to about 280% greater, about 15% greater to about 260% greater, about 15% greater to about 240% greater, about 15% greater to about 220% greater, about 15% greater to about 200% greater, about 15% greater to about 180% greater, about 15% greater to about 160% greater, about 15% greater to about 140% greater, about 15% greater to about 120% greater, about 15% greater to about 100% greater, about 15% greater to about 95% greater, about 15% greater to about 90% greater, about 15% greater to about 85% greater, about 15% greater to about 80% greater, about 15% greater to about 75% greater, about 15% greater to about 70% greater, about 15% greater to about 65% greater, about 15% greater to about 60% greater, about 15% greater to about 55% greater, about 15% greater to about 50% greater, about 15% greater to about 45% greater, about 15% greater to about 40% greater, about 15% greater to about 35% greater, about 15% greater to about 30% greater, about 15% greater to about 25% greater, about 15% greater to about 20% greater, about 20% greater to about 10,000% greater, about 20% greater to about 9,000% greater, about 20% greater to about 8,000% greater, about 20% greater to about 7,000% greater, about 20% greater to about 6,000% greater, about 20% greater to about 5,000% greater, about 20% greater to about 4,000% greater, about 20% greater to about 3,000% greater, about 20% greater to about 2,000% greater, about 20% greater to about 1,000% greater, about 20% greater to about 500% greater, about 20% greater to about 480% greater, about 20% greater to about 460% greater, about 20% greater to about 440% greater, about 20% greater to about 420% greater, about 20% greater to about 400% greater, about 20% greater to about 380% greater, about 20% greater to about 360% greater, about 20% greater to about 340% greater, about 20% greater to about 320% greater, about 20% greater to about 300% greater, about 20% greater to about 280% greater, about 20% greater to about 260% greater, about 20% greater to about 240% greater, about 20% greater to about 220% greater, about 20% greater to about 200% greater, about 20% greater to about 180% greater, about 20% greater to about 160% greater, about 20% greater to about 140% greater, about 20% greater to about 120% greater, about 20% greater to about 100% greater, about 20% greater to about 95% greater, about 20% greater to about 90% greater, about 20% greater to about 85% greater, about 20% greater to about 80% greater, about 20% greater to about 75% greater, about 20% greater to about 70% greater, about 20% greater to about 65% greater, about 20% greater to about 60% greater, about 20% greater to about 55% greater, about 20% greater to about 50% greater, about 20% greater to about 45% greater, about 20% greater to about 40% greater, about 20% greater to about 35% greater, about 20% greater to about 30% greater, about 20% greater to about 25% greater, about 25% greater to about 10,000% greater, about 25% greater to about 9,000% greater, about 25% greater to about 8,000% greater, about 25% greater to about 7,000% greater, about 25% greater to about 6,000% greater, about 25% greater to about 5,000% greater, about 25% greater to about 4,000% greater, about 25% greater to about 3,000% greater, about 25% greater to about 2,000% greater, about 25% greater to about 1,000% greater, about 25% greater to about 500% greater, about 25% greater to about 480% greater, about 25% greater to about 460% greater, about 25% greater to about 440% greater, about 25% greater to about 420% greater, about 25% greater to about 400% greater, about 25% greater to about 380% greater, about 25% greater to about 360% greater, about 25% greater to about 340% greater, about 25% greater to about 320% greater, about 25% greater to about 300% greater, about 25% greater to about 280% greater, about 25% greater to about 260% greater, about 25% greater to about 240% greater, about 25% greater to about 220% greater, about 25% greater to about 200% greater, about 25% greater to about 180% greater, about 25% greater to about 160% greater, about 25% greater to about 140% greater, about 25% greater to about 120% greater, about 25% greater to about 100% greater, about 25% greater to about 95% greater, about 25% greater to about 90% greater, about 25% greater to about 85% greater, about 25% greater to about 80% greater, about 25% greater to about 75% greater, about 25% greater to about 70% greater, about 25% greater to about 65% greater, about 25% greater to about 60% greater, about 25% greater to about 55% greater, about 25% greater to about 50% greater, about 25% greater to about 45% greater, about 25% greater to about 40% greater, about 25% greater to about 35% greater, about 25% greater to about 30% greater, about 30% greater to about 10,000% greater, about 30% greater to about 9,000% greater, about 30% greater to about 8,000% greater, about 30% greater to about 7,000% greater, about 30% greater to about 6,000% greater, about 30% greater to about 5,000% greater, about 30% greater to about 4,000% greater, about 30% greater to about 3,000% greater, about 30% greater to about 2,000% greater, about 30% greater to about 1,000% greater, about 30% greater to about 500% greater, about 30% greater to about 480% greater, about 30% greater to about 460% greater, about 30% greater to about 440% greater, about 30% greater to about 420% greater, about 30% greater to about 400% greater, about 30% greater to about 380% greater, about 30% greater to about 360% greater, about 30% greater to about 340% greater, about 30% greater to about 320% greater, about 30% greater to about 300% greater, about 30% greater to about 280% greater, about 30% greater to about 260% greater, about 30% greater to about 240% greater, about 30% greater to about 220% greater, about 30% greater to about 200% greater, about 30% greater to about 180% greater, about 30% greater to about 160% greater, about 30% greater to about 140% greater, about 30% greater to about 120% greater, about 30% greater to about 100% greater, about 30% greater to about 95% greater, about 30% greater to about 90% greater, about 30% greater to about 85% greater, about 30% greater to about 80% greater, about 30% greater to about 75% greater, about 30% greater to about 70% greater, about 30% greater to about 65% greater, about 30% greater to about 60% greater, about 30% greater to about 55% greater, about 30% greater to about 50% greater, about 30% greater to about 45% greater, about 30% greater to about 40% greater, about 30% greater to about 35% greater, about 35% greater to about 10,000% greater, about 35% greater to about 9,000% greater, about 35% greater to about 8,000% greater, about 35% greater to about 7,000% greater, about 35% greater to about 6,000% greater, about 35% greater to about 5,000% greater, about 35% greater to about 4,000% greater, about 35% greater to about 3,000% greater, about 35% greater to about 2,000% greater, about 35% greater to about 1,000% greater, about 35% greater to about 500% greater, about 35% greater to about 480% greater, about 35% greater to about 460% greater, about 35% greater to about 440% greater, about 35% greater to about 420% greater, about 35% greater to about 400% greater, about 35% greater to about 380% greater, about 35% greater to about 360% greater, about 35% greater to about 340% greater, about 35% greater to about 320% greater, about 35% greater to about 300% greater, about 35% greater to about 280% greater, about 35% greater to about 260% greater, about 35% greater to about 240% greater, about 35% greater to about 220% greater, about 35% greater to about 200% greater, about 35% greater to about 180% greater, about 35% greater to about 160% greater, about 35% greater to about 140% greater, about 35% greater to about 120% greater, about 35% greater to about 100% greater, about 35% greater to about 95% greater, about 35% greater to about 90% greater, about 35% greater to about 85% greater, about 35% greater to about 80% greater, about 35% greater to about 75% greater, about 35% greater to about 70% greater, about 35% greater to about 65% greater, about 35% greater to about 60% greater, about 35% greater to about 55% greater, about 35% greater to about 50% greater, about 35% greater to about 45% greater, about 35% greater to about 40% greater, about 40% greater to about 10,000% greater, about 40% greater to about 9,000% greater, about 40% greater to about 8,000% greater, about 40% greater to about 7,000% greater, about 40% greater to about 6,000% greater, about 40% greater to about 5,000% greater, about 40% greater to about 4,000% greater, about 40% greater to about 3,000% greater, about 40% greater to about 2,000% greater, about 40% greater to about 1,000% greater, about 40% greater to about 500% greater, about 40% greater to about 480% greater, about 40% greater to about 460% greater, about 40% greater to about 440% greater, about 40% greater to about 420% greater, about 40% greater to about 400% greater, about 40% greater to about 380% greater, about 40% greater to about 360% greater, about 40% greater to about 340% greater, about 40% greater to about 320% greater, about 40% greater to about 300% greater, about 40% greater to about 280% greater, about 40% greater to about 260% greater, about 40% greater to about 240% greater, about 40% greater to about 220% greater, about 40% greater to about 200% greater, about 40% greater to about 180% greater, about 40% greater to about 160% greater, about 40% greater to about 140% greater, about 40% greater to about 120% greater, about 40% greater to about 100% greater, about 40% greater to about 95% greater, about 40% greater to about 90% greater, about 40% greater to about 85% greater, about 40% greater to about 80% greater, about 40% greater to about 75% greater, about 40% greater to about 70% greater, about 40% greater to about 65% greater, about 40% greater to about 60% greater, about 40% greater to about 55% greater, about 40% greater to about 50% greater, about 40% greater to about 45% greater, about 45% greater to about 10,000% greater, about 45% greater to about 9,000% greater, about 45% greater to about 8,000% greater, about 45% greater to about 7,000% greater, about 45% greater to about 6,000% greater, about 45% greater to about 5,000% greater, about 45% greater to about 4,000% greater, about 45% greater to about 3,000% greater, about 45% greater to about 2,000% greater, about 45% greater to about 1,000% greater, about 45% greater to about 500% greater, about 45% greater to about 480% greater, about 45% greater to about 460% greater, about 45% greater to about 440% greater, about 45% greater to about 420% greater, about 45% greater to about 400% greater, about 45% greater to about 380% greater, about 45% greater to about 360% greater, about 45% greater to about 340% greater, about 45% greater to about 320% greater, about 45% greater to about 300% greater, about 45% greater to about 280% greater, about 45% greater to about 260% greater, about 45% greater to about 240% greater, about 45% greater to about 220% greater, about 45% greater to about 200% greater, about 45% greater to about 180% greater, about 45% greater to about 160% greater, about 45% greater to about 140% greater, about 45% greater to about 120% greater, about 45% greater to about 100% greater, about 45% greater to about 95% greater, about 45% greater to about 90% greater, about 45% greater to about 85% greater, about 45% greater to about 80% greater, about 45% greater to about 75% greater, about 45% greater to about 70% greater, about 45% greater to about 65% greater, about 45% greater to about 60% greater, about 45% greater to about 55% greater, about 45% greater to about 50% greater, about 50% greater to about 10,000% greater, about 50% greater to about 9,000% greater, about 50% greater to about 8,000% greater, about 50% greater to about 7,000% greater, about 50% greater to about 6,000% greater, about 50% greater to about 5,000% greater, about 50% greater to about 4,000% greater, about 50% greater to about 3,000% greater, about 50% greater to about 2,000% greater, about 50% greater to about 1,000% greater, about 50% greater to about 500% greater, about 50% greater to about 480% greater, about 50% greater to about 460% greater, about 50% greater to about 440% greater, about 50% greater to about 420% greater, about 50% greater to about 400% greater, about 50% greater to about 380% greater, about 50% greater to about 360% greater, about 50% greater to about 340% greater, about 50% greater to about 320% greater, about 50% greater to about 300% greater, about 50% greater to about 280% greater, about 50% greater to about 260% greater, about 50% greater to about 240% greater, about 50% greater to about 220% greater, about 50% greater to about 200% greater, about 50% greater to about 180% greater, about 50% greater to about 160% greater, about 50% greater to about 140% greater, about 50% greater to about 120% greater, about 50% greater to about 100% greater, about 50% greater to about 95% greater, about 50% greater to about 90% greater, about 50% greater to about 85% greater, about 50% greater to about 80% greater, about 50% greater to about 75% greater, about 50% greater to about 70% greater, about 50% greater to about 65% greater, about 50% greater to about 60% greater, about 50% greater to about 55% greater, about 55% greater to about 10,000% greater, about 55% greater to about 9,000% greater, about 55% greater to about 8,000% greater, about 55% greater to about 7,000% greater, about 55% greater to about 6,000% greater, about 55% greater to about 5,000% greater, about 55% greater to about 4,000% greater, about 55% greater to about 3,000% greater, about 55% greater to about 2,000% greater, about 55% greater to about 1,000% greater, about 55% greater to about 500% greater, about 55% greater to about 480% greater, about 55% greater to about 460% greater, about 55% greater to about 440% greater, about 55% greater to about 420% greater, about 55% greater to about 400% greater, about 55% greater to about 380% greater, about 55% greater to about 360% greater, about 55% greater to about 340% greater, about 55% greater to about 320% greater, about 55% greater to about 300% greater, about 55% greater to about 280% greater, about 55% greater to about 260% greater, about 55% greater to about 240% greater, about 55% greater to about 220% greater, about 55% greater to about 200% greater, about 55% greater to about 180% greater, about 55% greater to about 160% greater, about 55% greater to about 140% greater, about 55% greater to about 120% greater, about 55% greater to about 100% greater, about 55% greater to about 95% greater, about 55% greater to about 90% greater, about 55% greater to about 85% greater, about 55% greater to about 80% greater, about 55% greater to about 75% greater, about 55% greater to about 70% greater, about 55% greater to about 65% greater, about 55% greater to about 60% greater, about 60% greater to about 10,000% greater, about 60% greater to about 9,000% greater, about 60% greater to about 8,000% greater, about 60% greater to about 7,000% greater, about 60% greater to about 6,000% greater, about 60% greater to about 5,000% greater, about 60% greater to about 4,000% greater, about 60% greater to about 3,000% greater, about 60% greater to about 2,000% greater, about 60% greater to about 1,000% greater, about 60% greater to about 500% greater, about 60% greater to about 480% greater, about 60% greater to about 460% greater, about 60% greater to about 440% greater, about 60% greater to about 420% greater, about 60% greater to about 400% greater, about 60% greater to about 380% greater, about 60% greater to about 360% greater, about 60% greater to about 340% greater, about 60% greater to about 320% greater, about 60% greater to about 300% greater, about 60% greater to about 280% greater, about 60% greater to about 260% greater, about 60% greater to about 240% greater, about 60% greater to about 220% greater, about 60% greater to about 200% greater, about 60% greater to about 180% greater, about 60% greater to about 160% greater, about 60% greater to about 140% greater, about 60% greater to about 120% greater, about 60% greater to about 100% greater, about 60% greater to about 95% greater, about 60% greater to about 90% greater, about 60% greater to about 85% greater, about 60% greater to about 80% greater, about 60% greater to about 75% greater, about 60% greater to about 70% greater, about 60% greater to about 65% greater, about 65% greater to about 10,000% greater, about 65% greater to about 9,000% greater, about 65% greater to about 8,000% greater, about 65% greater to about 7,000% greater, about 65% greater to about 6,000% greater, about 65% greater to about 5,000% greater, about 65% greater to about 4,000% greater, about 65% greater to about 3,000% greater, about 65% greater to about 2,000% greater, about 65% greater to about 1,000% greater, about 65% greater to about 500% greater, about 65% greater to about 480% greater, about 65% greater to about 460% greater, about 65% greater to about 440% greater, about 65% greater to about 420% greater, about 65% greater to about 400% greater, about 65% greater to about 380% greater, about 65% greater to about 360% greater, about 65% greater to about 340% greater, about 65% greater to about 320% greater, about 65% greater to about 300% greater, about 65% greater to about 280% greater, about 65% greater to about 260% greater, about 65% greater to about 240% greater, about 65% greater to about 220% greater, about 65% greater to about 200% greater, about 65% greater to about 180% greater, about 65% greater to about 160% greater, about 65% greater to about 140% greater, about 65% greater to about 120% greater, about 65% greater to about 100% greater, about 65% greater to about 95% greater, about 65% greater to about 90% greater, about 65% greater to about 85% greater, about 65% greater to about 80% greater, about 65% greater to about 75% greater, about 65% greater to about 70% greater, about 70% greater to about 10,000% greater, about 70% greater to about 9,000% greater, about 70% greater to about 8,000% greater, about 70% greater to about 7,000% greater, about 70% greater to about 6,000% greater, about 70% greater to about 5,000% greater, about 70% greater to about 4,000% greater, about 70% greater to about 3,000% greater, about 70% greater to about 2,000% greater, about 70% greater to about 1,000% greater, about 70% greater to about 500% greater, about 70% greater to about 480% greater, about 70% greater to about 460% greater, about 70% greater to about 440% greater, about 70% greater to about 420% greater, about 70% greater to about 400% greater, about 70% greater to about 380% greater, about 70% greater to about 360% greater, about 70% greater to about 340% greater, about 70% greater to about 320% greater, about 70% greater to about 300% greater, about 70% greater to about 280% greater, about 70% greater to about 260% greater, about 70% greater to about 240% greater, about 70% greater to about 220% greater, about 70% greater to about 200% greater, about 70% greater to about 180% greater, about 70% greater to about 160% greater, about 70% greater to about 140% greater, about 70% greater to about 120% greater, about 70% greater to about 100% greater, about 70% greater to about 95% greater, about 70% greater to about 90% greater, about 70% greater to about 85% greater, about 70% greater to about 80% greater, about 70% greater to about 75% greater, about 75% greater to about 10,000% greater, about 75% greater to about 9,000% greater, about 75% greater to about 8,000% greater, about 75% greater to about 7,000% greater, about 75% greater to about 6,000% greater, about 75% greater to about 5,000% greater, about 75% greater to about 4,000% greater, about 75% greater to about 3,000% greater, about 75% greater to about 2,000% greater, about 75% greater to about 1,000% greater, about 75% greater to about 500% greater, about 75% greater to about 480% greater, about 75% greater to about 460% greater, about 75% greater to about 440% greater, about 75% greater to about 420% greater, about 75% greater to about 400% greater, about 75% greater to about 380% greater, about 75% greater to about 360% greater, about 75% greater to about 340% greater, about 75% greater to about 320% greater, about 75% greater to about 300% greater, about 75% greater to about 280% greater, about 75% greater to about 260% greater, about 75% greater to about 240% greater, about 75% greater to about 220% greater, about 75% greater to about 200% greater, about 75% greater to about 180% greater, about 75% greater to about 160% greater, about 75% greater to about 140% greater, about 75% greater to about 120% greater, about 75% greater to about 100% greater, about 75% greater to about 95% greater, about 75% greater to about 90% greater, about 75% greater to about 85% greater, about 75% greater to about 80% greater, about 80% greater to about 10,000% greater, about 80% greater to about 9,000% greater, about 80% greater to about 8,000% greater, about 80% greater to about 7,000% greater, about 80% greater to about 6,000% greater, about 80% greater to about 5,000% greater, about 80% greater to about 4,000% greater, about 80% greater to about 3,000% greater, about 80% greater to about 2,000% greater, about 80% greater to about 1,000% greater, about 80% greater to about 500% greater, about 80% greater to about 480% greater, about 80% greater to about 460% greater, about 80% greater to about 440% greater, about 80% greater to about 420% greater, about 80% greater to about 400% greater, about 80% greater to about 380% greater, about 80% greater to about 360% greater, about 80% greater to about 340% greater, about 80% greater to about 320% greater, about 80% greater to about 300% greater, about 80% greater to about 280% greater, about 80% greater to about 260% greater, about 80% greater to about 240% greater, about 80% greater to about 220% greater, about 80% greater to about 200% greater, about 80% greater to about 180% greater, about 80% greater to about 160% greater, about 80% greater to about 140% greater, about 80% greater to about 120% greater, about 80% greater to about 100% greater, about 80% greater to about 95% greater, about 80% greater to about 90% greater, about 80% greater to about 85% greater, about 85% greater to about 10,000% greater, about 85% greater to about 9,000% greater, about 85% greater to about 8,000% greater, about 85% greater to about 7,000% greater, about 85% greater to about 6,000% greater, about 85% greater to about 5,000% greater, about 85% greater to about 4,000% greater, about 85% greater to about 3,000% greater, about 85% greater to about 2,000% greater, about 85% greater to about 1,000% greater, about 85% greater to about 500% greater, about 85% greater to about 480% greater, about 85% greater to about 460% greater, about 85% greater to about 440% greater, about 85% greater to about 420% greater, about 85% greater to about 400% greater, about 85% greater to about 380% greater, about 85% greater to about 360% greater, about 85% greater to about 340% greater, about 85% greater to about 320% greater, about 85% greater to about 300% greater, about 85% greater to about 280% greater, about 85% greater to about 260% greater, about 85% greater to about 240% greater, about 85% greater to about 220% greater, about 85% greater to about 200% greater, about 85% greater to about 180% greater, about 85% greater to about 160% greater, about 85% greater to about 140% greater, about 85% greater to about 120% greater, about 85% greater to about 100% greater, about 85% greater to about 95% greater, about 85% greater to about 90% greater, about 90% greater to about 10,000% greater, about 90% greater to about 9,000% greater, about 90% greater to about 8,000% greater, about 90% greater to about 7,000% greater, about 90% greater to about 6,000% greater, about 90% greater to about 5,000% greater, about 90% greater to about 4,000% greater, about 90% greater to about 3,000% greater, about 90% greater to about 2,000% greater, about 90% greater to about 1,000% greater, about 90% greater to about 500% greater, about 90% greater to about 480% greater, about 90% greater to about 460% greater, about 90% greater to about 440% greater, about 90% greater to about 420% greater, about 90% greater to about 400% greater, about 90% greater to about 380% greater, about 90% greater to about 360% greater, about 90% greater to about 340% greater, about 90% greater to about 320% greater, about 90% greater to about 300% greater, about 90% greater to about 280% greater, about 90% greater to about 260% greater, about 90% greater to about 240% greater, about 90% greater to about 220% greater, about 90% greater to about 200% greater, about 90% greater to about 180% greater, about 90% greater to about 160% greater, about 90% greater to about 140% greater, about 90% greater to about 120% greater, about 90% greater to about 100% greater, about 90% greater to about 95% greater, about 95% greater to about 10,000% greater, about 95% greater to about 9,000% greater, about 95% greater to about 8,000% greater, about 95% greater to about 7,000% greater, about 95% greater to about 6,000% greater, about 95% greater to about 5,000% greater, about 95% greater to about 4,000% greater, about 95% greater to about 3,000% greater, about 95% greater to about 2,000% greater, about 95% greater to about 1,000% greater, about 95% greater to about 500% greater, about 95% greater to about 480% greater, about 95% greater to about 460% greater, about 95% greater to about 440% greater, about 95% greater to about 420% greater, about 95% greater to about 400% greater, about 95% greater to about 380% greater, about 95% greater to about 360% greater, about 95% greater to about 340% greater, about 95% greater to about 320% greater, about 95% greater to about 300% greater, about 95% greater to about 280% greater, about 95% greater to about 260% greater, about 95% greater to about 240% greater, about 95% greater to about 220% greater, about 95% greater to about 200% greater, about 95% greater to about 180% greater, about 95% greater to about 160% greater, about 95% greater to about 140% greater, about 95% greater to about 120% greater, about 95% greater to about 100% greater, about 100% greater to about 10,000% greater, about 100% greater to about 9,000% greater, about 100% greater to about 8,000% greater, about 100% greater to about 7,000% greater, about 100% greater to about 6,000% greater, about 100% greater to about 5,000% greater, about 100% greater to about 4,000% greater, about 100% greater to about 3,000% greater, about 100% greater to about 2,000% greater, about 100% greater to about 1,000% greater, about 100% greater to about 500% greater, about 100% greater to about 480% greater, about 100% greater to about 460% greater, about 100% greater to about 440% greater, about 100% greater to about 420% greater, about 100% greater to about 400% greater, about 100% greater to about 380% greater, about 100% greater to about 360% greater, about 100% greater to about 340% greater, about 100% greater to about 320% greater, about 100% greater to about 300% greater, about 100% greater to about 280% greater, about 100% greater to about 260% greater, about 100% greater to about 240% greater, about 100% greater to about 220% greater, about 100% greater to about 200% greater, about 100% greater to about 180% greater, about 100% greater to about 160% greater, about 100% greater to about 140% greater, about 100% greater to about 120% greater, about 120% greater to about 10,000% greater, about 120% greater to about 9,000% greater, about 120% greater to about 8,000% greater, about 120% greater to about 7,000% greater, about 120% greater to about 6,000% greater, about 120% greater to about 5,000% greater, about 120% greater to about 4,000% greater, about 120% greater to about 3,000% greater, about 120% greater to about 2,000% greater, about 120% greater to about 1,000% greater, about 120% greater to about 500% greater, about 120% greater to about 480% greater, about 120% greater to about 460% greater, about 120% greater to about 440% greater, about 120% greater to about 420% greater, about 120% greater to about 400% greater, about 120% greater to about 380% greater, about 120% greater to about 360% greater, about 120% greater to about 340% greater, about 120% greater to about 320% greater, about 120% greater to about 300% greater, about 120% greater to about 280% greater, about 120% greater to about 260% greater, about 120% greater to about 240% greater, about 120% greater to about 220% greater, about 120% greater to about 200% greater, about 120% greater to about 180% greater, about 120% greater to about 160% greater, about 120% greater to about 140% greater, about 140% greater to about 10,000% greater, about 140% greater to about 9,000% greater, about 140% greater to about 8,000% greater, about 140% greater to about 7,000% greater, about 140% greater to about 6,000% greater, about 140% greater to about 5,000% greater, about 140% greater to about 4,000% greater, about 140% greater to about 3,000% greater, about 140% greater to about 2,000% greater, about 140% greater to about 1,000% greater, about 140% greater to about 500% greater, about 140% greater to about 480% greater, about 140% greater to about 460% greater, about 140% greater to about 440% greater, about 140% greater to about 420% greater, about 140% greater to about 400% greater, about 140% greater to about 380% greater, about 140% greater to about 360% greater, about 140% greater to about 340% greater, about 140% greater to about 320% greater, about 140% greater to about 300% greater, about 140% greater to about 280% greater, about 140% greater to about 260% greater, about 140% greater to about 240% greater, about 140% greater to about 220% greater, about 140% greater to about 200% greater, about 140% greater to about 180% greater, about 140% greater to about 160% greater, about 160% greater to about 10,000% greater, about 160% greater to about 9,000% greater, about 160% greater to about 8,000% greater, about 160% greater to about 7,000% greater, about 160% greater to about 6,000% greater, about 160% greater to about 5,000% greater, about 160% greater to about 4,000% greater, about 160% greater to about 3,000% greater, about 160% greater to about 2,000% greater, about 160% greater to about 1,000% greater, about 160% greater to about 500% greater, about 160% greater to about 480% greater, about 160% greater to about 460% greater, about 160% greater to about 440% greater, about 160% greater to about 420% greater, about 160% greater to about 400% greater, about 160% greater to about 380% greater, about 160% greater to about 360% greater, about 160% greater to about 340% greater, about 160% greater to about 320% greater, about 160% greater to about 300% greater, about 160% greater to about 280% greater, about 160% greater to about 260% greater, about 160% greater to about 240% greater, about 160% greater to about 220% greater, about 160% greater to about 200% greater, about 160% greater to about 180% greater, about 180% greater to about 10,000% greater, about 180% greater to about 9,000% greater, about 180% greater to about 8,000% greater, about 180% greater to about 7,000% greater, about 180% greater to about 6,000% greater, about 180% greater to about 5,000% greater, about 180% greater to about 4,000% greater, about 180% greater to about 3,000% greater, about 180% greater to about 2,000% greater, about 180% greater to about 1,000% greater, about 180% greater to about 500% greater, about 180% greater to about 480% greater, about 180% greater to about 460% greater, about 180% greater to about 440% greater, about 180% greater to about 420% greater, about 180% greater to about 400% greater, about 180% greater to about 380% greater, about 180% greater to about 360% greater, about 180% greater to about 340% greater, about 180% greater to about 320% greater, about 180% greater to about 300% greater, about 180% greater to about 280% greater, about 180% greater to about 260% greater, about 180% greater to about 240% greater, about 180% greater to about 220% greater, about 180% greater to about 200% greater, about 200% greater to about 10,000% greater, about 200% greater to about 9,000% greater, about 200% greater to about 8,000% greater, about 200% greater to about 7,000% greater, about 200% greater to about 6,000% greater, about 200% greater to about 5,000% greater, about 200% greater to about 4,000% greater, about 200% greater to about 3,000% greater, about 200% greater to about 2,000% greater, about 200% greater to about 1,000% greater, about 200% greater to about 500% greater, about 200% greater to about 480% greater, about 200% greater to about 460% greater, about 200% greater to about 440% greater, about 200% greater to about 420% greater, about 200% greater to about 400% greater, about 200% greater to about 380% greater, about 200% greater to about 360% greater, about 200% greater to about 340% greater, about 200% greater to about 320% greater, about 200% greater to about 300% greater, about 200% greater to about 280% greater, about 200% greater to about 260% greater, about 200% greater to about 240% greater, about 200% greater to about 220% greater, about 220% greater to about 10,000% greater, about 220% greater to about 9,000% greater, about 220% greater to about 8,000% greater, about 220% greater to about 7,000% greater, about 220% greater to about 6,000% greater, about 220% greater to about 5,000% greater, about 220% greater to about 4,000% greater, about 220% greater to about 3,000% greater, about 220% greater to about 2,000% greater, about 220% greater to about 1,000% greater, about 220% greater to about 500% greater, about 220% greater to about 480% greater, about 220% greater to about 460% greater, about 220% greater to about 440% greater, about 220% greater to about 420% greater, about 220% greater to about 400% greater, about 220% greater to about 380% greater, about 220% greater to about 360% greater, about 220% greater to about 340% greater, about 220% greater to about 320% greater, about 220% greater to about 300% greater, about 220% greater to about 280% greater, about 220% greater to about 260% greater, about 220% greater to about 240% greater, about 240% greater to about 10,000% greater, about 240% greater to about 9,000% greater, about 240% greater to about 8,000% greater, about 240% greater to about 7,000% greater, about 240% greater to about 6,000% greater, about 240% greater to about 5,000% greater, about 240% greater to about 4,000% greater, about 240% greater to about 3,000% greater, about 240% greater to about 2,000% greater, about 240% greater to about 1,000% greater, about 240% greater to about 500% greater, about 240% greater to about 480% greater, about 240% greater to about 460% greater, about 240% greater to about 440% greater, about 240% greater to about 420% greater, about 240% greater to about 400% greater, about 240% greater to about 380% greater, about 240% greater to about 360% greater, about 240% greater to about 340% greater, about 240% greater to about 320% greater, about 240% greater to about 300% greater, about 240% greater to about 280% greater, about 240% greater to about 260% greater, about 260% greater to about 10,000% greater, about 260% greater to about 9,000% greater, about 260% greater to about 8,000% greater, about 260% greater to about 7,000% greater, about 260% greater to about 6,000% greater, about 260% greater to about 5,000% greater, about 260% greater to about 4,000% greater, about 260% greater to about 3,000% greater, about 260% greater to about 2,000% greater, about 260% greater to about 1,000% greater, about 260% greater to about 500% greater, about 260% greater to about 480% greater, about 260% greater to about 460% greater, about 260% greater to about 440% greater, about 260% greater to about 420% greater, about 260% greater to about 400% greater, about 260% greater to about 380% greater, about 260% greater to about 360% greater, about 260% greater to about 340% greater, about 260% greater to about 320% greater, about 260% greater to about 300% greater, about 260% greater to about 280% greater, about 280% greater to about 10,000% greater, about 280% greater to about 9,000% greater, about 280% greater to about 8,000% greater, about 280% greater to about 7,000% greater, about 280% greater to about 6,000% greater, about 280% greater to about 5,000% greater, about 280% greater to about 4,000% greater, about 280% greater to about 3,000% greater, about 280% greater to about 2,000% greater, about 280% greater to about 1,000% greater, about 280% greater to about 500% greater, about 280% greater to about 480% greater, about 280% greater to about 460% greater, about 280% greater to about 440% greater, about 280% greater to about 420% greater, about 280% greater to about 400% greater, about 280% greater to about 380% greater, about 280% greater to about 360% greater, about 280% greater to about 340% greater, about 280% greater to about 320% greater, about 280% greater to about 300% greater, about 300% greater to about 10,000% greater, about 300% greater to about 9,000% greater, about 300% greater to about 8,000% greater, about 300% greater to about 7,000% greater, about 300% greater to about 6,000% greater, about 300% greater to about 5,000% greater, about 300% greater to about 4,000% greater, about 300% greater to about 3,000% greater, about 300% greater to about 2,000% greater, about 300% greater to about 1,000% greater, about 300% greater to about 500% greater, about 300% greater to about 480% greater, about 300% greater to about 460% greater, about 300% greater to about 440% greater, about 300% greater to about 420% greater, about 300% greater to about 400% greater, about 300% greater to about 380% greater, about 300% greater to about 360% greater, about 300% greater to about 340% greater, about 300% greater to about 320% greater, about 320% greater to about 10,000% greater, about 320% greater to about 9,000% greater, about 320% greater to about 8,000% greater, about 320% greater to about 7,000% greater, about 320% greater to about 6,000% greater, about 320% greater to about 5,000% greater, about 320% greater to about 4,000% greater, about 320% greater to about 3,000% greater, about 320% greater to about 2,000% greater, about 320% greater to about 1,000% greater, about 320% greater to about 500% greater, about 320% greater to about 480% greater, about 320% greater to about 460% greater, about 320% greater to about 440% greater, about 320% greater to about 420% greater, about 320% greater to about 400% greater, about 320% greater to about 380% greater, about 320% greater to about 360% greater, about 320% greater to about 340% greater, about 340% greater to about 10,000% greater, about 340% greater to about 9,000% greater, about 340% greater to about 8,000% greater, about 340% greater to about 7,000% greater, about 340% greater to about 6,000% greater, about 340% greater to about 5,000% greater, about 340% greater to about 4,000% greater, about 340% greater to about 3,000% greater, about 340% greater to about 2,000% greater, about 340% greater to about 1,000% greater, about 340% greater to about 500% greater, about 340% greater to about 480% greater, about 340% greater to about 460% greater, about 340% greater to about 440% greater, about 340% greater to about 420% greater, about 340% greater to about 400% greater, about 340% greater to about 380% greater, about 340% greater to about 360% greater, about 360% greater to about 10,000% greater, about 360% greater to about 9,000% greater, about 360% greater to about 8,000% greater, about 360% greater to about 7,000% greater, about 360% greater to about 6,000% greater, about 360% greater to about 5,000% greater, about 360% greater to about 4,000% greater, about 360% greater to about 3,000% greater, about 360% greater to about 2,000% greater, about 360% greater to about 1,000% greater, about 360% greater to about 500% greater, about 360% greater to about 480% greater, about 360% greater to about 460% greater, about 360% greater to about 440% greater, about 360% greater to about 420% greater, about 360% greater to about 400% greater, about 360% greater to about 380% greater, about 380% greater to about 10,000% greater, about 380% greater to about 9,000% greater, about 380% greater to about 8,000% greater, about 380% greater to about 7,000% greater, about 380% greater to about 6,000% greater, about 380% greater to about 5,000% greater, about 380% greater to about 4,000% greater, about 380% greater to about 3,000% greater, about 380% greater to about 2,000% greater, about 380% greater to about 1,000% greater, about 380% greater to about 500% greater, about 380% greater to about 480% greater, about 380% greater to about 460% greater, about 380% greater to about 440% greater, about 380% greater to about 420% greater, about 380% greater to about 400% greater, about 400% greater to about 10,000% greater, about 400% greater to about 9,000% greater, about 400% greater to about 8,000% greater, about 400% greater to about 7,000% greater, about 400% greater to about 6,000% greater, about 400% greater to about 5,000% greater, about 400% greater to about 4,000% greater, about 400% greater to about 3,000% greater, about 400% greater to about 2,000% greater, about 400% greater to about 1,000% greater, about 400% greater to about 500% greater, about 400% greater to about 480% greater, about 400% greater to about 460% greater, about 400% greater to about 440% greater, about 400% greater to about 420% greater, about 420% greater to about 10,000% greater, about 420% greater to about 9,000% greater, about 420% greater to about 8,000% greater, about 420% greater to about 7,000% greater, about 420% greater to about 6,000% greater, about 420% greater to about 5,000% greater, about 420% greater to about 4,000% greater, about 420% greater to about 3,000% greater, about 420% greater to about 2,000% greater, about 420% greater to about 1,000% greater, about 420% greater to about 500% greater, about 420% greater to about 480% greater, about 420% greater to about 460% greater, about 420% greater to about 440% greater, about 440% greater to about 10,000% greater, about 440% greater to about 9,000% greater, about 440% greater to about 8,000% greater, about 440% greater to about 7,000% greater, about 440% greater to about 6,000% greater, about 440% greater to about 5,000% greater, about 440% greater to about 4,000% greater, about 440% greater to about 3,000% greater, about 440% greater to about 2,000% greater, about 440% greater to about 1,000% greater, about 440% greater to about 500% greater, about 440% greater to about 480% greater, about 440% greater to about 460% greater, about 460% greater to about 10,000% greater, about 460% greater to about 9,000% greater, about 460% greater to about 8,000% greater, about 460% greater to about 7,000% greater, about 460% greater to about 6,000% greater, about 460% greater to about 5,000% greater, about 460% greater to about 4,000% greater, about 460% greater to about 3,000% greater, about 460% greater to about 2,000% greater, about 460% greater to about 1,000% greater, about 460% greater to about 500% greater, about 460% greater to about 480% greater, about 480% greater to about 10,000% greater, about 480% greater to about 9,000% greater, about 480% greater to about 8,000% greater, about 480% greater to about 7,000% greater, about 480% greater to about 6,000% greater, about 480% greater to about 5,000% greater, about 480% greater to about 4,000% greater, about 480% greater to about 3,000% greater, about 480% greater to about 2,000% greater, about 480% greater to about 1,000% greater, about 480% greater to about 500% greater. about 500% greater to about 10,000% greater, about 500% greater to about 9,000% greater, about 500% greater to about 8,000% greater, about 500% greater to about 7,000% greater, about 500% greater to about 6,000% greater, about 500% greater to about 5,000% greater, about 500% greater to about 4,000% greater, about 500% greater to about 3,000% greater, about 500% greater to about 2,000% greater, about 500% greater to about 1,000% greater, about 1,000% greater to about 10,000% greater, about 1,000% greater to about 9,000% greater, about 1,000% greater to about 8,000% greater, about 1,000% greater to about 7,000% greater, about 1,000% greater to about 6,000% greater, about 1,000% greater to about 5,000% greater, about 1,000% greater to about 4,000% greater, about 1,000% greater to about 3,000% greater, about 1,000% greater to about 2,000% greater, about 2,000% greater to about 10,000% greater, about 2,000% greater to about 9,000% greater, about 2,000% greater to about 8,000% greater, about 2,000% greater to about 7,000% greater, about 2,000% greater to about 6,000% greater, about 2,000% greater to about 5,000% greater, about 2,000% greater to about 4,000% greater, about 2,000% greater to about 3,000% greater, about 3,000% greater to about 10,000% greater, about 3,000% greater to about 9,000% greater, about 3,000% greater to about 8,000% greater, about 3,000% greater to about 7,000% greater, about 3,000% greater to about 6,000% greater, about 3,000% greater to about 5,000% greater, about 3,000% greater to about 4,000% greater, about 4,000% greater to about 10,000% greater, about 4,000% greater to about 9,000% greater, about 4,000% greater to about 8,000% greater, about 4,000% greater to about 7,000% greater, about 4,000% greater to about 6,000% greater, about 4,000% greater to about 5,000% greater, about 5,000% greater to about 10,000% greater, about 5,000% greater to about 9,000% greater, about 5,000% greater to about 8,000% greater, about 5,000% greater to about 7,000% greater, about 5,000% greater to about 6,000% greater, about 6,000% greater to about 10,000% greater, about 6,000% greater to about 9,000% greater, about 6,000% greater to about 8,000% greater, about 6,000% greater to about 7,000% greater, about 7,000% greater to about 10,000% greater, about 7,000% greater to about 9,000% greater, about 7,000% greater to about 8,000% greater, about 8,000% greater to about 10,000% greater, about 8,000% greater to about 9,000% greater, or about 9,000% greater to about 10,000% greater) than the $K_D$ at a pH of about 7.0 to about 8.0 (e.g., any of the subranges of this range described herein).

In some embodiments of any of the antibodies described herein, the dissociation rate at a pH of about 4.0 to about 6.5 (e.g., any of the subranges of this range described herein) is faster (e.g., at least 0.2-fold faster, at least 0.3-fold, at least 0.4-fold, at least 0.5-fold, at least 0.6-fold, at least 0.7-fold, at least 0.8-fold, at least 0.9-fold, at least 1.0-fold, at least 1.5-fold, at least 2.0-fold, at least 2.5-fold, at least 3.0 fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, at least 10.0-fold, at least 10.5-fold, at least 11.0-fold, at least 11.5-fold, at least 12.0-fold, at least 12.5-fold, at least 13.0-fold, at least 13.5-fold, at least 14.0-fold, at least 14.5-fold, at least 15.0-fold, at least 15.5-fold, at least 16.0-fold, at least 16.5-fold, at least 17.0-fold, at least 17.5-fold, at least 18.0-fold, at least 18.5-fold, at least 19.0-fold, at least 19.5-fold, at least 20-fold, at least 25-fold, at least 30-fold, at least 35-fold, at least 40-fold, at least 45-fold, at least 50-fold, at least 55-fold, at least 60-fold, at least 65-fold, at least 70-fold, at least 75-fold, at least 80-fold, at least 85-fold, at least 90-fold, at least 95-fold, or at least 100-fold faster or about 0.2-fold to about 100-fold faster, about 0.2-fold to about 90-fold faster, about 0.2-fold to about 80-fold faster, about 0.2-fold to about 70-fold faster, about 0.2-fold to about 60-fold faster, about 0.2-fold to about 50-fold faster, about 0.2-fold to about 40-fold faster, about 0.2-fold to about 30-fold faster, about 0.2-fold to about 20-fold faster, about 0.2-fold to about 15-fold faster, about 0.2-fold to about 10-fold faster, about 0.2-fold to about 5-fold, about 0.2-fold to about 2-fold faster, about 0.2-fold to about 1-fold faster, about 0.2-fold to about 0.5-fold faster, about 0.5-fold to about 100-fold faster, about 0.5-fold to about 90-fold faster, about 0.5-fold to about 80-fold faster, about 0.5-fold to about 70-fold faster, about 0.5-fold to about 60-fold faster, about 0.5-fold to about 50-fold faster, about 0.5-fold to about 40-fold faster, about 0.5-fold to about 30-fold faster, about 0.5-fold to about 20-fold faster, about 0.5-fold to about 15-fold faster, about 0.5-fold to about 10-fold faster, about 0.5-fold to about 5-fold, about 0.5-fold to about 2-fold faster, about 0.5-fold to about 1-fold faster, about 1-fold to about 100-fold faster, about 1-fold to about 90-fold faster, about 1-fold to about 80-fold faster, about 1-fold to about 70-fold faster, about 1-fold to about 60-fold faster, about 1-fold to about 50-fold faster, about 1-fold to about 40-fold faster, about 1-fold to about 30-fold faster, about 1-fold to about 20-fold faster, about 1-fold to about 15-fold faster, about 1-fold to about 10-fold faster, about 1-fold to about 5-fold, about 1-fold to about 2-fold faster, about 2-fold to about 100-fold faster, about 2-fold to about 90-fold faster, about 2-fold to about 80-fold faster, about 2-fold to about 70-fold faster, about 2-fold to about 60-fold faster, about 2-fold to about 50-fold faster, about 2-fold to about 40-fold faster, about 2-fold to about 30-fold faster, about 2-fold to about 20-fold faster, about 2-fold to about 15-fold faster, about 2-fold to about 10-fold faster, about 2-fold to about 5-fold, about 5-fold to about 100-fold faster, about 5-fold to about 90-fold faster, about 5-fold to about 80-fold faster, about 5-fold to about 70-fold faster, about 5-fold to about 60-fold faster, about 5-fold to about 50-fold faster, about 5-fold to about 40-fold faster, about 5-fold to about 30-fold faster, about 5-fold to about 20-fold faster, about 5-fold to about 15-fold faster, about 5-fold to about 10-fold faster, about 10-fold to about 100-fold faster, about 10-fold to about 90-fold faster, about 10-fold to about 80-fold faster, about 10-fold to about 70-fold faster, about 10-fold to about 60-fold faster, about 10-fold to about 50-fold faster, about 10-fold to about 40-fold faster, about 10-fold to about 30-fold faster, about 10-fold to about 20-fold faster, about 10-fold to about 15-fold faster, about 15-fold to about 100-fold faster, about 15-fold to about 90-fold faster, about 15-fold to about 80-fold faster, about 15-fold to about 70-fold faster, about 15-fold to about 60-fold faster, about 15-fold to about 50-fold faster, about 15-fold to about 40-fold faster, about 15-fold to about 30-fold faster, about 15-fold to about 20-fold faster, about 20-fold to about 100-fold faster, about 20-fold to about 90-fold faster, about 20-fold to about 80-fold faster, about 20-fold to about 70-fold faster, about 20-fold to about 60-fold faster, about 20-fold to about 50-fold faster, about 20-fold to about 40-fold faster, about 20-fold to about 30-fold faster, about 30-fold to about 100-fold faster, about 30-fold to about 90-fold faster, about 30-fold to about 80-fold faster, about 30-fold to about 70-fold faster, about 30-fold to about 60-fold faster, about 30-fold to about 50-fold faster, about 30-fold to about 40-fold faster, about 40-fold to about 100-fold faster, about 40-fold to about 90-fold faster, about 40-fold to about 80-fold faster, about 40-fold to about 70-fold faster, about 40-fold to about 60-fold faster, about 40-fold to about 50-fold faster, about 50-fold to about 100-fold faster, about 50-fold to about 90-fold faster, about 50-fold to about 80-fold faster, about 50-fold to about 70-fold faster, about 50-fold to about 60-fold faster, about 60-fold to about 100-fold faster, about 60-fold to about 90-fold faster, about 60-fold to about 80-fold faster, about 60-fold to about 70-fold faster, about 70-fold to about 100-fold faster, about 70-fold to about 90-fold faster, about 70-fold to about 80-fold faster, about 80-fold to about 100-fold faster, about 80-fold to about 90-fold faster, or about 90-fold to about 100-fold faster) than the dissociation rate at a pH of about 7.0 to about 8.0 (e.g., or any of the subranges of this range described herein).

In some embodiments of any of the antibodies described herein, the dissociation constant ($K_D$) at a pH of about 4.0 to about 6.5 (e.g., any of the subranges of this range described herein) is greater (e.g., detectably greater) (e.g., at least 0.2-fold greater, at least 0.3-fold, at least 0.4-fold, at least 0.5-fold, at least 0.6-fold, at least 0.7-fold, at least 0.8-fold, at least 0.9-fold, at least 1.0-fold, at least 1.5-fold, at least 2.0-fold, at least 2.5-fold, at least 3.0 fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, at least 10.0-fold, at least 10.5-fold, at least 11.0-fold, at least 11.5-fold, at least 12.0-fold, at least 12.5-fold, at least 13.0-fold, at least 13.5-fold, at least 14.0-fold, at least 14.5-fold, at least 15.0-fold, at least 15.5-fold, at least 16.0-fold, at least 16.5-fold, at least 17.0-fold, at least 17.5-fold, at least 18.0-fold, at least 18.5-fold, at least 19.0-fold, at least 19.5-fold, at least 20-fold greater, at least 25-fold greater, at least 30-fold greater, at least 35-fold greater, at least 40-fold greater, at least 45-fold greater, at least 50-fold greater, at least 55-fold greater, at least 60-fold greater, at least 65-fold greater, at least 70-fold greater, at least 75-fold greater, at least 80-fold greater, at least 85-fold greater, at least 90-fold greater, at least 95-fold greater, or at least 100-fold greater, or about 0.2-fold to about 100-fold greater, about 0.2-fold to about 90-fold greater, about 0.2-fold to about 80-fold greater, about 0.2-fold to about 70-fold greater, about 0.2-fold to about 60-fold greater, about 0.2-fold to about 50-fold greater, about 0.2-fold to about 40-fold greater, about 0.2-fold to about 30-fold greater, about 0.2-fold to about 25-fold greater, about 0.2-fold to about 20-fold greater, about 0.2-fold to about 15-fold greater, about 0.2-fold to about 10-fold greater, about 0.2-fold to about 8-fold greater, about 0.2-fold to about 5-fold greater, about 0.2-fold to about 2-fold greater, about 0.2-fold to about 1-fold greater, about 0.2-fold to about 0.5-fold greater, about 0.5-fold to about 100-fold greater, about 0.5-fold to about 90-fold greater, about 0.5-fold to about 80-fold greater, about 0.5-fold to about 70-fold greater, about 0.5-fold to about 60-fold greater, about 0.5-fold to about 50-fold greater, about 0.5-fold to about 40-fold greater, about 0.5-fold to about 30-fold greater, about 0.5-fold to about 25-fold greater, about 0.5-fold to about 20-fold greater, about 0.5-fold to about 15-fold greater, about 0.5-fold to about 10-fold greater, about 0.5-fold to about 8-fold greater, about 0.5-fold to about 5-fold greater, about 0.5-fold to about 2-fold greater, about 0.5-fold to about 1-fold greater, about 1-fold to about 100-fold greater, about 1-fold to about 90-fold greater, about 1-fold to about 80-fold greater, about 1-fold to about 70-fold greater, about 1-fold to about 60-fold greater, about 1-fold to about 50-fold greater, about 1-fold to about 40-fold greater, about 1-fold to about 30-fold greater, about 1-fold to about 25-fold greater, about 1-fold to about 20-fold greater, about 1-fold to about 15-fold greater, about 1-fold to about 10-fold greater, about 1-fold to about 8-fold greater, about 1-fold to about 5-fold greater, about 1-fold to about 2-fold greater, about 2-fold to about 100-fold greater, about 2-fold to about 90-fold greater, about 2-fold to about 80-fold greater, about 2-fold to about 70-fold greater, about 2-fold to about 60-fold greater, about 2-fold to about 50-fold greater, about 2-fold to about 40-fold greater, about 2-fold to about 30-fold greater, about 2-fold to about 25-fold greater, about 2-fold to about 20-fold greater, about 2-fold to about 15-fold greater, about 2-fold to about 10-fold greater, about 2-fold to about 8-fold greater, about 2-fold to about 5-fold greater, about 5-fold to about 100-fold greater, about 5-fold to about 90-fold greater, about 5-fold to about 80-fold greater, about 5-fold to about 70-fold greater, about 5-fold to about 60-fold greater, about 5-fold to about 50-fold greater, about 5-fold to about 40-fold greater, about 5-fold to about 30-fold greater, about 5-fold to about 25-fold greater, about 5-fold to about 20-fold greater, about 5-fold to about 15-fold greater, about 5-fold to about 10-fold greater, about 5-fold to about 8-fold greater, about 8-fold to about 100-fold greater, about 8-fold to about 90-fold greater, about 8-fold to about 80-fold greater, about 8-fold to about 70-fold greater, about 8-fold to about 60-fold greater, about 8-fold to about 50-fold greater, about 8-fold to about 40-fold greater, about 8-fold to about 30-fold greater, about 8-fold to about 25-fold greater, about 8-fold to about 20-fold greater, about 8-fold to about 15-fold greater, about 8-fold to about 10-fold greater, about 10-fold to about 100-fold greater, about 10-fold to about 90-fold greater, about 10-fold to about 80-fold greater, about 10-fold to about 70-fold greater, about 10-fold to about 60-fold greater, about 10-fold to about 50-fold greater, about 10-fold to about 40-fold greater, about 10-fold to about 30-fold greater, about 10-fold to about 25-fold greater, about 10-fold to about 20-fold greater, about 10-fold to about 15-fold greater, about 15-fold to about 100-fold greater, about 15-fold to about 90-fold greater, about 15-fold to about 80-fold greater, about 15-fold to about 70-fold greater, about 15-fold to about 60-fold greater, about 15-fold to about 50-fold greater, about 15-fold to about 40-fold greater, about 15-fold to about 30-fold greater, about 15-fold to about 25-fold greater, about 15-fold to about 20-fold greater, about 20-fold to about 100-fold greater, about 20-fold to about 90-fold greater, about 20-fold to about 80-fold greater, about 20-fold to about 70-fold greater, about 20-fold to about 60-fold greater, about 20-fold to about 50-fold greater, about 20-fold to about 40-fold greater, about 20-fold to about 30-fold greater, about 20-fold to about 25-fold greater, about 25-fold to about 100-fold greater, about 25-fold to about 90-fold greater, about 25-fold to about 80-fold greater, about 25-fold to about 70-fold greater, about 25-fold to about 60-fold greater, about 25-fold to about 50-fold greater, about 25-fold to about 40-fold greater, about 25-fold to about 30-fold greater, about 30-fold to about 100-fold greater, about 30-fold to about 90-fold greater, about 30-fold to about 80-fold greater, about 30-fold to about 70-fold greater, about 30-fold to about 60-fold greater, about 30-fold to about 50-fold greater, about 30-fold to about 40-fold greater, about 40-fold to about 100-fold greater, about 40-fold to about 90-fold greater, about 40-fold to about 80-fold greater, about 40-fold to about 70-fold greater, about 40-fold to about 60-fold greater, about 40-fold to about 50-fold greater, about 50-fold to about 100-fold greater, about 50-fold to about 90-fold greater, about 50-fold to about 80-fold greater, about 50-fold to about 70-fold greater, about 50-fold to about 60-fold greater, about 60-fold to about 100-fold greater, about 60-fold to about 90-fold greater, about 60-fold to about 80-fold greater, about 60-fold to about 70-fold greater, about 70-fold to about 100-fold greater, about 70-fold to about 90-fold greater, about 70-fold to about 80-fold greater, about 80-fold to about 100-fold greater, about 80-fold to about 90-fold greater, or about 90-fold to about 100-fold greater), than the $K_D$ at a pH of about 7.0 to about 8.0 (e.g., any of the subranges of this range described herein).

In some embodiments of any of the antibodies described herein, the $K_D$ at a pH of about 7.0 to about 8.0 (e.g., any of the subranges of this range described herein) is between about 1 pM to about 5 μM (e.g., about 1 pM to about 2 μM, about 1 pM to about 1 μM, about 1 pM to about 500 nM, about 1 pM to about 250 nM, about 1 pM to about 240 nM, about 1 pM to about 230 nM, about 1 pM to about 220 nM, about 1 pM to about 210 nM, about 1 pM to about 200 nM, about 1 pM to about 190 nM, about 1 pM to about 180 nM, about 1 pM to about 170 nM, about 1 pM to about 160 nM, about 1 pM to about 150 nM, about 1 pM to about 140 nM, about 1 pM to about 130 nM, about 1 pM to about 120 nM, about 1 pM to about 110 nM, about 1 pM to about 100 nM, about 1 pM to about 95 nM, about 1 pM to about 90 nM, about 1 pM to about 85 nM, about 1 pM to about 80 nM, about 1 pM to about 75 nM, about 1 pM to about 70 nM, about 1 pM to about 65 nM, about 1 pM to about 60 nM, about 1 pM to about 55 nM, about 1 pM to about 50 nM, about 1 pM to about 45 nM, about 1 pM to about 40 nM, about 1 pM to about 35 nM, about 1 pM to about 30 nM, about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 5 µM, about 2 pM to about 2 µM, about 2 pM to about 1 µM, about 2 pM to about 500 nM, about 2 pM to about 250 nM, about 2 pM to about 240 nM, about 2 pM to about 230 nM, about 2 pM to about 220 nM, about 2 pM to about 210 nM, about 2 pM to about 200 nM, about 2 pM to about 190 nM, about 2 pM to about 180 nM, about 2 pM to about 170 nM, about 2 pM to about 160 nM, about 2 pM to about 150 nM, about 2 pM to about 140 nM, about 2 pM to about 130 nM, about 2 pM to about 120 nM, about 2 pM to about 110 nM, about 2 pM to about 100 nM, about 2 pM to about 95 nM, about 2 pM to about 90 nM, about 2 pM to about 85 nM, about 2 pM to about 80 nM, about 2 pM to about 75 nM, about 2 pM to about 70 nM, about 2 pM to about 65 nM, about 2 pM to about 60 nM, about 2 pM to about 55 nM, about 2 pM to about 50 nM, about 2 pM to about 45 nM, about 2 pM to about 40 nM, about 2 pM to about 35 nM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 5 µM, about 5 pM to about 2 µM, about 5 pM to about 1 µM, about 5 pM to about 500 nM, about 5 pM to about 250 nM, about 5 pM to about 240 nM, about 5 pM to about 230 nM, about 5 pM to about 220 nM, about 5 pM to about 210 nM, about 5 pM to about 200 nM, about 5 pM to about 190 nM, about 5 pM to about 180 nM, about 5 pM to about 170 nM, about 5 pM to about 160 nM, about 5 pM to about 150 nM, about 5 pM to about 140 nM, about 5 pM to about 130 nM, about 5 pM to about 120 nM, about 5 pM to about 110 nM, about 5 pM to about 100 nM, about 5 pM to about 95 nM, about 5 pM to about 90 nM, about 5 pM to about 85 nM, about 5 pM to about 80 nM, about 5 pM to about 75 nM, about 5 pM to about 70 nM, about 5 pM to about 65 nM, about 5 pM to about 60 nM, about 5 pM to about 55 nM, about 5 pM to about 50 nM, about 5 pM to about 45 nM, about 5 pM to about 40 nM, about 5 pM to about 35 nM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 5 µM, about 10 pM to about 2 µM, about 10 pM to about 1 µM, about 10 pM to about 500 nM, about 10 pM to about 250 nM, about 10 pM to about 240 nM, about 10 pM to about 230 nM, about 10 pM to about 220 nM, about 10 pM to about 210 nM, about 10 pM to about 200 nM, about 10 pM to about 190 nM, about 10 pM to about 180 nM, about 10 pM to about 170 nM, about 10 pM to about 160 nM, about 10 pM to about 150 nM, about 10 pM to about 140 nM, about 10 pM to about 130 nM, about 10 pM to about 120 nM, about 10 pM to about 110 nM, about 10 pM to about 100 nM, about 10 pM to about 95 nM, about 10 pM to about 90 nM, about 10 pM to about 85 nM, about 10 pM to about 80 nM, about 10 pM to about 75 nM, about 10 pM to about 70 nM, about 10 pM to about 65 nM, about 10 pM to about 60 nM, about 10 pM to about 55 nM, about 10 pM to about 50 nM, about 10 pM to about 45 nM, about 10 pM to about 40 nM, about 10 pM to about 35 nM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 5 µM, about 15 pM to about 2 µM, about 15 pM to about 1 µM, about 15 pM to about 500 nM, about 15 pM to about 250 nM, about 15 pM to about 240 nM, about 15 pM to about 230 nM, about 15 pM to about 220 nM, about 15 pM to about 210 nM, about 15 pM to about 200 nM, about 15 pM to about 190 nM, about 15 pM to about 180 nM, about 15 pM to about 170 nM, about 15 pM to about 160 nM, about 15 pM to about 150 nM, about 15 pM to about 140 nM, about 15 pM to about 130 nM, about 15 pM to about 120 nM, about 15 pM to about 110 nM, about 15 pM to about 100 nM, about 15 pM to about 95 nM, about 15 pM to about 90 nM, about 15 pM to about 85 nM, about 15 pM to about 80 nM, about 15 pM to about 75 nM, about 15 pM to about 70 nM, about 15 pM to about 65 nM, about 15 pM to about 60 nM, about 15 pM to about 55 nM, about 15 pM to about 50 nM, about 15 pM to about 45 nM, about 15 pM to about 40 nM, about 15 pM to about 35 nM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 5 µM, about 20 pM to about 2 µM, about 20 pM to about 1 µM, about 20 pM to about 500 nM, about 20 pM to about 250 nM, about 20 pM to about 240 nM, about 20 pM to about 230 nM, about 20 pM to about 220 nM, about 20 pM to about 210 nM, about 20 pM to about 200 nM, about 20 pM to about 190 nM, about 20 pM to about 180 nM, about 20 pM to about 170 nM, about 20 pM to about 160 nM, about 20 pM to about 150 nM, about 20 pM to about 140 nM, about 20 pM to about 130 nM, about 20 pM to about 120 nM, about 20 pM to about 110 nM, about 20 pM to about 100 nM, about 20 pM to about 95 nM, about 20 pM to about 90 nM, about 20 pM to about 85 nM, about 20 pM to about 80 nM, about 20 pM to about 75 nM, about 20 pM to about 70 nM, about 20 pM to about 65 nM, about 20 pM to about 60 nM, about 20 pM to about 55 nM, about 20 pM to about 50 nM, about 20 pM to about 45 nM, about 20 pM to about 40 nM, about 20 pM to about 35 nM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 5 µM, about 30 pM to about 2 µM, about 30 pM to about 1 µM, about 30 pM to about 500 nM, about 30 pM to about 250 nM, about 30 pM to about 240 nM, about 30 pM to about 230 nM, about 30 pM to about 220 nM, about 30 pM to about 210 nM, about 30 pM to about 200 nM, about 30 pM to about 190 nM, about 30 pM to about 180 nM, about 30 pM to about 170 nM, about 30 pM to about 160 nM, about 30 pM to about 150 nM, about 30 pM to about 140 nM, about 30 pM to about 130 nM, about 30 pM to about 120 nM, about 30 pM to about 110 nM, about 30 pM to about 100 nM, about 30 pM to about 95 nM, about 30 pM to about 90 nM, about 30 pM to about 85 nM, about 30 pM to about 80 nM, about 30 pM to about 75 nM, about 30 pM to about 70 nM, about 30 pM to about 65 nM, about 30 pM to about 60 nM, about 30 pM to about 55 nM, about 30 pM to about 50 nM, about 30 pM to about 45 nM, about 30 pM to about 40 nM, about 30 pM to about 35 nM, about 30 pM to about 30 nM, about 30 pM to about 25 nM, about 30 pM to about 20 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 5 µM, about 40 pM to about 2 µM, about 40 pM to about 1 µM, about 40 pM to about 500 nM, about 40 pM to about 250 nM, about 40 pM to about 240 nM, about 40 pM to about 230 nM, about 40 pM to about 220 nM, about 40 pM to about 210 nM, about 40 pM to about 200 nM, about 40 pM to about 190 nM, about 40 pM to about 180 nM, about 40 pM to about 170 nM, about 40 pM to about 160 nM, about 40 pM to about 150 nM, about 40 pM to about 140 nM, about 40 pM to about 130 nM, about 40 pM to about 120 nM, about 40 pM to about 110 nM, about 40 pM to about 100 nM, about 40 pM to about 95 nM, about 40 pM to about 90 nM, about 40 pM to about 85 nM, about 40 pM to about 80 nM, about 40 pM to about 75 nM, about 40 pM to about 70 nM, about 40 pM to about 65 nM, about 40 pM to about 60 nM, about 40 pM to about 55 nM, about 40 pM to about 50 nM, about 40 pM to about 45 nM, about 40 pM to about 40 nM, about 40 pM to about 35 nM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 5 µM, about 50 pM to about 2 µM, about 50 pM to about 1 µM, about 50 pM to about 500 nM, about 50 pM to about 250 nM, about 50 pM to about 240 nM, about 50 pM to about 230 nM, about 50 pM to about 220 nM, about 50 pM to about 210 nM, about 50 pM to about 200 nM, about 50 pM to about 190 nM, about 50 pM to about 180 nM, about 50 pM to about 170 nM, about 50 pM to about 160 nM, about 50 pM to about 150 nM, about 50 pM to about 140 nM, about 50 pM to about 130 nM, about 50 pM to about 120 nM, about 50 pM to about 110 nM, about 50 pM to about 100 nM, about 50 pM to about 95 nM, about 50 pM to about 90 nM, about 50 pM to about 85 nM, about 50 pM to about 80 nM, about 50 pM to about 75 nM, about 50 pM to about 70 nM, about 50 pM to about 65 nM, about 50 pM to about 60 nM, about 50 pM to about 55 nM, about 50 pM to about 50 nM, about 50 pM to about 45 nM, about 50 pM to about 40 nM, about 50 pM to about 35 nM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 5 μM, about 60 pM to about 2 μM, about 60 pM to about 1 μM, about 60 pM to about 500 nM, about 60 pM to about 250 nM, about 60 pM to about 240 nM, about 60 pM to about 230 nM, about 60 pM to about 220 nM, about 60 pM to about 210 nM, about 60 pM to about 200 nM, about 60 pM to about 190 nM, about 60 pM to about 180 nM, about 60 pM to about 170 nM, about 60 pM to about 160 nM, about 60 pM to about 150 nM, about 60 pM to about 140 nM, about 60 pM to about 130 nM, about 60 pM to about 120 nM, about 60 pM to about 110 nM, about 60 pM to about 100 nM, about 60 pM to about 95 nM, about 60 pM to about 90 nM, about 60 pM to about 85 nM, about 60 pM to about 80 nM, about 60 pM to about 75 nM, about 60 pM to about 70 nM, about 60 pM to about 65 nM, about 60 pM to about 60 nM, about 60 pM to about 55 nM, about 60 pM to about 50 nM, about 60 pM to about 45 nM, about 60 pM to about 40 nM, about 60 pM to about 35 nM, about 60 pM to about 30 nM, about 60 pM to about 25 nM, about 60 pM to about 20 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 5 μM, about 70 pM to about 2 μM, about 70 pM to about 1 μM, about 70 pM to about 500 nM, about 70 pM to about 250 nM, about 70 pM to about 240 nM, about 70 pM to about 230 nM, about 70 pM to about 220 nM, about 70 pM to about 210 nM, about 70 pM to about 200 nM, about 70 pM to about 190 nM, about 70 pM to about 180 nM, about 70 pM to about 170 nM, about 70 pM to about 160 nM, about 70 pM to about 150 nM, about 70 pM to about 140 nM, about 70 pM to about 130 nM, about 70 pM to about 120 nM, about 70 pM to about 110 nM, about 70 pM to about 100 nM, about 70 pM to about 95 nM, about 70 pM to about 90 nM, about 70 pM to about 85 nM, about 70 pM to about 80 nM, about 70 pM to about 75 nM, about 70 pM to about 70 nM, about 70 pM to about 65 nM, about 70 pM to about 60 nM, about 70 pM to about 55 nM, about 70 pM to about 50 nM, about 70 pM to about 45 nM, about 70 pM to about 40 nM, about 70 pM to about 35 nM, about 70 pM to about 30 nM, about 70 pM to about 25 nM, about 70 pM to about 20 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 5 μM, about 80 pM to about 2 μM, about 80 pM to about 1 μM, about 80 pM to about 500 nM, about 80 pM to about 250 nM, about 80 pM to about 240 nM, about 80 pM to about 230 nM, about 80 pM to about 220 nM, about 80 pM to about 210 nM, about 80 pM to about 200 nM, about 80 pM to about 190 nM, about 80 pM to about 180 nM, about 80 pM to about 170 nM, about 80 pM to about 160 nM, about 80 pM to about 150 nM, about 80 pM to about 140 nM, about 80 pM to about 130 nM, about 80 pM to about 120 nM, about 80 pM to about 110 nM, about 80 pM to about 100 nM, about 80 pM to about 95 nM, about 80 pM to about 90 nM, about 80 pM to about 85 nM, about 80 pM to about 80 nM, about 80 pM to about 75 nM, about 80 pM to about 70 nM, about 80 pM to about 65 nM, about 80 pM to about 60 nM, about 80 pM to about 55 nM, about 80 pM to about 50 nM, about 80 pM to about 45 nM, about 80 pM to about 40 nM, about 80 pM to about 35 nM, about 80 pM to about 30 nM, about 80 pM to about 25 nM, about 80 pM to about 20 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 5 μM, about 90 pM to about 2 μM, about 90 pM to about 1 μM, about 90 pM to about 500 nM, about 90 pM to about 250 nM, about 90 pM to about 240 nM, about 90 pM to about 230 nM, about 90 pM to about 220 nM, about 90 pM to about 210 nM, about 90 pM to about 200 nM, about 90 pM to about 190 nM, about 90 pM to about 180 nM, about 90 pM to about 170 nM, about 90 pM to about 160 nM, about 90 pM to about 150 nM, about 90 pM to about 140 nM, about 90 pM to about 130 nM, about 90 pM to about 120 nM, about 90 pM to about 110 nM, about 90 pM to about 100 nM, about 90 pM to about 95 nM, about 90 pM to about 90 nM, about 90 pM to about 85 nM, about 90 pM to about 80 nM, about 90 pM to about 75 nM, about 90 pM to about 70 nM, about 90 pM to about 65 nM, about 90 pM to about 60 nM, about 90 pM to about 55 nM, about 90 pM to about 50 nM, about 90 pM to about 45 nM, about 90 pM to about 40 nM, about 90 pM to about 35 nM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 5 µM, about 100 pM to about 2 µM, about 100 pM to about 1 µM, about 100 pM to about 500 nM, about 100 pM to about 250 nM, about 100 pM to about 240 nM, about 100 pM to about 230 nM, about 100 pM to about 220 nM, about 100 pM to about 210 nM, about 100 pM to about 200 nM, about 100 pM to about 190 nM, about 100 pM to about 180 nM, about 100 pM to about 170 nM, about 100 pM to about 160 nM, about 100 pM to about 150 nM, about 100 pM to about 140 nM, about 100 pM to about 130 nM, about 100 pM to about 120 nM, about 100 pM to about 110 nM, about 100 pM to about 100 nM, about 100 pM to about 95 nM, about 100 pM to about 90 nM, about 100 pM to about 85 nM, about 100 pM to about 80 nM, about 100 pM to about 75 nM, about 100 pM to about 70 nM, about 100 pM to about 65 nM, about 100 pM to about 60 nM, about 100 pM to about 55 nM, about 100 pM to about 50 nM, about 100 pM to about 45 nM, about 100 pM to about 40 nM, about 100 pM to about 35 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 5 µM, about 150 pM to about 2 µM, about 150 pM to about 1 µM, about 150 pM to about 500 nM, about 150 pM to about 250 nM, about 150 pM to about 240 nM, about 150 pM to about 230 nM, about 150 pM to about 220 nM, about 150 pM to about 210 nM, about 150 pM to about 200 nM, about 150 pM to about 190 nM, about 150 pM to about 180 nM, about 150 pM to about 170 nM, about 150 pM to about 160 nM, about 150 pM to about 150 nM, about 150 pM to about 140 nM, about 150 pM to about 130 nM, about 150 pM to about 120 nM, about 150 pM to about 110 nM, about 150 pM to about 100 nM, about 150 pM to about 95 nM, about 150 pM to about 90 nM, about 150 pM to about 85 nM, about 150 pM to about 80 nM, about 150 pM to about 75 nM, about 150 pM to about 70 nM, about 150 pM to about 65 nM, about 150 pM to about 60 nM, about 150 pM to about 55 nM, about 150 pM to about 50 nM, about 150 pM to about 45 nM, about 150 pM to about 40 nM, about 150 pM to about 35 nM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 5 µM, about 200 pM to about 2 µM, about 200 pM to about 1 µM, about 200 pM to about 500 nM, about 200 pM to about 250 nM, about 200 pM to about 240 nM, about 200 pM to about 230 nM, about 200 pM to about 220 nM, about 200 pM to about 210 nM, about 200 pM to about 200 nM, about 200 pM to about 190 nM, about 200 pM to about 180 nM, about 200 pM to about 170 nM, about 200 pM to about 160 nM, about 200 pM to about 150 nM, about 200 pM to about 140 nM, about 200 pM to about 130 nM, about 200 pM to about 120 nM, about 200 pM to about 110 nM, about 200 pM to about 100 nM, about 200 pM to about 95 nM, about 200 pM to about 90 nM, about 200 pM to about 85 nM, about 200 pM to about 80 nM, about 200 pM to about 75 nM, about 200 pM to about 70 nM, about 200 pM to about 65 nM, about 200 pM to about 60 nM, about 200 pM to about 55 nM, about 200 pM to about 50 nM, about 200 pM to about 45 nM, about 200 pM to about 40 nM, about 200 pM to about 35 nM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 5 µM, about 300 pM to about 2 µM, about 300 pM to about 1 µM, about 300 pM to about 500 nM, about 300 pM to about 250 nM, about 300 pM to about 240 nM, about 300 pM to about 230 nM, about 300 pM to about 220 nM, about 300 pM to about 210 nM, about 300 pM to about 200 nM, about 300 pM to about 190 nM, about 300 pM to about 180 nM, about 300 pM to about 170 nM, about 300 pM to about 160 nM, about 300 pM to about 150 nM, about 300 pM to about 140 nM, about 300 pM to about 130 nM, about 300 pM to about 120 nM, about 300 pM to about 110 nM, about 300 pM to about 100 nM, about 300 pM to about 95 nM, about 300 pM to about 90 nM, about 300 pM to about 85 nM, about 300 pM to about 80 nM, about 300 pM to about 75 nM, about 300 pM to about 70 nM, about 300 pM to about 65 nM, about 300 pM to about 60 nM, about 300 pM to about 55 nM, about 300 pM to about 50 nM, about 300 pM to about 45 nM, about 300 pM to about 40 nM, about 300 pM to about 35 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 5 µM, about 400 pM to about 2 µM, about 400 pM to about 1 µM, about 400 pM to about 500 nM, about 400 pM to about 250 nM, about 400 pM to about 240 nM, about 400 pM to about 230 nM, about 400 pM to about 220 nM, about 400 pM to about 210 nM, about 400 pM to about 200 nM, about 400 pM to about 190 nM, about 400 pM to about 180 nM, about 400 pM to about 170 nM, about 400 pM to about 160 nM, about 400 pM to about 150 nM, about 400 pM to about 140 nM, about 400 pM to about 130 nM, about 400 pM to about 120 nM, about 400 pM to about 110 nM, about 400 pM to about 100 nM, about 400 pM to about 95 nM, about 400 pM to about 90 nM, about 400 pM to about 85 nM, about 400 pM to about 80 nM, about 400 pM to about 75 nM, about 400 pM to about 70 nM, about 400 pM to about 65 nM, about 400 pM to about 60 nM, about 400 pM to about 55 nM, about 400 pM to about 50 nM, about 400 pM to about 45 nM, about 400 pM to about 40 nM, about 400 pM to about 35 nM, about 400 pM to about 30 nM, about 400 pM to about 25 nM, about 400 pM to about 20 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 5 µM, about 500 pM to about 2 µM, about 500 pM to about 1 µM, about 500 pM to about 500 nM, about 500 pM to about 250 nM, about 500 pM to about 240 nM, about 500 pM to about 230 nM, about 500 pM to about 220 nM, about 500 pM to about 210 nM, about 500 pM to about 200 nM, about 500 pM to about 190 nM, about 500 pM to about 180 nM, about 500 pM to about 170 nM, about 500 pM to about 160 nM, about 500 pM to about 150 nM, about 500 pM to about 140 nM, about 500 pM to about 130 nM, about 500 pM to about 120 nM, about 500 pM to about 110 nM, about 500 pM to about 100 nM, about 500 pM to about 95 nM, about 500 pM to about 90 nM, about 500 pM to about 85 nM, about 500 pM to about 80 nM, about 500 pM to about 75 nM, about 500 pM to about 70 nM, about 500 pM to about 65 nM, about 500 pM to about 60 nM, about 500 pM to about 55 nM, about 500 pM to about 50 nM, about 500 pM to about 45 nM, about 500 pM to about 40 nM, about 500 pM to about 35 nM, about 500 pM to about 30 nM, about 500 pM to about 25 nM, about 500 pM to about 20 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 5 µM, about 600 pM to about 2 µM, about 600 pM to about 1 µM, about 600 pM to about 500 nM, about 600 pM to about 250 nM, about 600 pM to about 240 nM, about 600 pM to about 230 nM, about 600 pM to about 220 nM, about 600 pM to about 210 nM, about 600 pM to about 200 nM, about 600 pM to about 190 nM, about 600 pM to about 180 nM, about 600 pM to about 170 nM, about 600 pM to about 160 nM, about 600 pM to about 150 nM, about 600 pM to about 140 nM, about 600 pM to about 130 nM, about 600 pM to about 120 nM, about 600 pM to about 110 nM, about 600 pM to about 100 nM, about 600 pM to about 95 nM, about 600 pM to about 90 nM, about 600 pM to about 85 nM, about 600 pM to about 80 nM, about 600 pM to about 75 nM, about 600 pM to about 70 nM, about 600 pM to about 65 nM, about 600 pM to about 60 nM, about 600 pM to about 55 nM, about 600 pM to about 50 nM, about 600 pM to about 45 nM, about 600 pM to about 40 nM, about 600 pM to about 35 nM, about 600 pM to about 30 nM, about 600 pM to about 25 nM, about 600 pM to about 20 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 5 µM, about 700 pM to about 2 µM, about 700 pM to about 1 µM, about 700 pM to about 500 nM, about 700 pM to about 250 nM, about 700 pM to about 240 nM, about 700 pM to about 230 nM, about 700 pM to about 220 nM, about 700 pM to about 210 nM, about 700 pM to about 200 nM, about 700 pM to about 190 nM, about 700 pM to about 180 nM, about 700 pM to about 170 nM, about 700 pM to about 160 nM, about 700 pM to about 150 nM, about 700 pM to about 140 nM, about 700 pM to about 130 nM, about 700 pM to about 120 nM, about 700 pM to about 110 nM, about 700 pM to about 100 nM, about 700 pM to about 95 nM, about 700 pM to about 90 nM, about 700 pM to about 85 nM, about 700 pM to about 80 nM, about 700 pM to about 75 nM, about 700 pM to about 70 nM, about 700 pM to about 65 nM, about 700 pM to about 60 nM, about 700 pM to about 55 nM, about 700 pM to about 50 nM, about 700 pM to about 45 nM, about 700 pM to about 40 nM, about 700 pM to about 35 nM, about 700 pM to about 30 nM, about 700 pM to about 25 nM, about 700 pM to about 20 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 5 µM, about 800 pM to about 2 µM, about 800 pM to about 1 µM, about 800 pM to about 500 nM, about 800 pM to about 250 nM, about 800 pM to about 240 nM, about 800 pM to about 230 nM, about 800 pM to about 220 nM, about 800 pM to about 210 nM, about 800 pM to about 200 nM, about 800 pM to about 190 nM, about 800 pM to about 180 nM, about 800 pM to about 170 nM, about 800 pM to about 160 nM, about 800 pM to about 150 nM, about 800 pM to about 140 nM, about 800 pM to about 130 nM, about 800 pM to about 120 nM, about 800 pM to about 110 nM, about 800 pM to about 100 nM, about 800 pM to about 95 nM, about 800 pM to about 90 nM, about 800 pM to about 85 nM, about 800 pM to about 80 nM, about 800 pM to about 75 nM, about 800 pM to about 70 nM, about 800 pM to about 65 nM, about 800 pM to about 60 nM, about 800 pM to about 55 nM, about 800 pM to about 50 nM, about 800 pM to about 45 nM, about 800 pM to about 40 nM, about 800 pM to about 35 nM, about 800 pM to about 30 nM, about 800 pM to about 25 nM, about 800 pM to about 20 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 5 µM, about 900 pM to about 2 µM, about 900 pM to about 1 µM, about 900 pM to about 500 nM, about 900 pM to about 250 nM, about 900 pM to about 240 nM, about 900 pM to about 230 nM, about 900 pM to about 220 nM, about 900 pM to about 210 nM, about 900 pM to about 200 nM, about 900 pM to about 190 nM, about 900 pM to about 180 nM, about 900 pM to about 170 nM, about 900 pM to about 160 nM, about 900 pM to about 150 nM, about 900 pM to about 140 nM, about 900 pM to about 130 nM, about 900 pM to about 120 nM, about 900 pM to about 110 nM, about 900 pM to about 100 nM, about 900 pM to about 95 nM, about 900 pM to about 90 nM, about 900 pM to about 85 nM, about 900 pM to about 80 nM, about 900 pM to about 75 nM, about 900 pM to about 70 nM, about 900 pM to about 65 nM, about 900 pM to about 60 nM, about 900 pM to about 55 nM, about 900 pM to about 50 nM, about 900 pM to about 45 nM, about 900 pM to about 40 nM, about 900 pM to about 35 nM, about 900 pM to about 30 nM, about 900 pM to about 25 nM, about 900 pM to about 20 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 5 µM, about 1 nM to about 2 µM, about 1 nM to about 1 µM, about 1 nM to about 500 nM, about 1 nM to about 250 nM, about 1 nM to about 240 nM, about 1 nM to about 230 nM, about 1 nM to about 220 nM, about 1 nM to about 210 nM, about 1 nM to about 200 nM, about 1 nM to about 190 nM, about 1 nM to about 180 nM, about 1 nM to about 170 nM, about 1 nM to about 160 nM, about 1 nM to about 150 nM, about 1 nM to about 140 nM, about 1 nM to about 130 nM, about 1 nM to about 120 nM, about 1 nM to about 110 nM, about 1 nM to about 100 nM, about 1 nM to about 95 nM, about 1 nM to about 90 nM, about 1 nM to about 85 nM, about 1 nM to about 80 nM, about 1 nM to about 75 nM, about 1 nM to about 70 nM, about 1 nM to about 65 nM, about 1 nM to about 60 nM, about 1 nM to about 55 nM, about 1 nM to about 50 nM, about 1 nM to about 45 nM, about 1 nM to about 40 nM, about 1 nM to about 35 nM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 5 µM, about 2 nM to about 2 µM, about 2 nM to about 1 µM, about 2 nM to about 500 nM, about 2 nM to about 250 nM, about 2 nM to about 240 nM, about 2 nM to about 230 nM, about 2 nM to about 220 nM, about 2 nM to about 210 nM, about 2 nM to about 200 nM, about 2 nM to about 190 nM, about 2 nM to about 180 nM, about 2 nM to about 170 nM, about 2 nM to about 160 nM, about 2 nM to about 150 nM, about 2 nM to about 140 nM, about 2 nM to about 130 nM, about 2 nM to about 120 nM, about 2 nM to about 110 nM, about 2 nM to about 100 nM, about 2 nM to about 95 nM, about 2 nM to about 90 nM, about 2 nM to about 85 nM, about 2 nM to about 80 nM, about 2 nM to about 75 nM, about 2 nM to about 70 nM, about 2 nM to about 65 nM, about 2 nM to about 60 nM, about 2 nM to about 55 nM, about 2 nM to about 50 nM, about 2 nM to about 45 nM, about 2 nM to about 40 nM, about 2 nM to about 35 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 5 µM, about 4 nM to about 2 µM, about 4 nM to about 1 µM, about 4 nM to about 500 nM, about 4 nM to about 250 nM, about 4 nM to about 240 nM, about 4 nM to about 230 nM, about 4 nM to about 220 nM, about 4 nM to about 210 nM, about 4 nM to about 200 nM, about 4 nM to about 190 nM, about 4 nM to about 180 nM, about 4 nM to about 170 nM, about 4 nM to about 160 nM, about 4 nM to about 150 nM, about 4 nM to about 140 nM, about 4 nM to about 130 nM, about 4 nM to about 120 nM, about 4 nM to about 110 nM, about 4 nM to about 100 nM, about 4 nM to about 95 nM, about 4 nM to about 90 nM, about 4 nM to about 85 nM, about 4 nM to about 80 nM, about 4 nM to about 75 nM, about 4 nM to about 70 nM, about 4 nM to about 65 nM, about 4 nM to about 60 nM, about 4 nM to about 55 nM, about 4 nM to about 50 nM, about 4 nM to about 45 nM, about 4 nM to about 40 nM, about 4 nM to about 35 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 5 µM, about 5 nM to about 2 µM, about 5 nM to about 1 µM, about 5 nM to about 500 nM, about 5 nM to about 250 nM, about 5 nM to about 240 nM, about 5 nM to about 230 nM, about 5 nM to about 220 nM, about 5 nM to about 210 nM, about 5 nM to about 200 nM, about 5 nM to about 190 nM, about 5 nM to about 180 nM, about 5 nM to about 170 nM, about 5 nM to about 160 nM, about 5 nM to about 150 nM, about 5 nM to about 140 nM, about 5 nM to about 130 nM, about 5 nM to about 120 nM, about 5 nM to about 110 nM, about 5 nM to about 100 nM, about 5 nM to about 95 nM, about 5 nM to about 90 nM, about 5 nM to about 85 nM, about 5 nM to about 80 nM, about 5 nM to about 75 nM, about 5 nM to about 70 nM, about 5 nM to about 65 nM, about 5 nM to about 60 nM, about 5 nM to about 55 nM, about 5 nM to about 50 nM, about 5 nM to about 45 nM, about 5 nM to about 40 nM, about 5 nM to about 35 nM, about 5 nM to about 30 nM, about 5 nM to about 25 nM, about 5 nM to about 20 nM, about 5 nM to about 15 nM, about 5 nM to about 10 nM, about 10 nM to about 5 µM, about 10 nM to about 2 µM, about 10 nM to about 1 µM, about 10 nM to about 500 nM, about 10 nM to about 250 nM, about 10 nM to about 240 nM, about 10 nM to about 230 nM, about 10 nM to about 220 nM, about 10 nM to about 210 nM, about 10 nM to about 200 nM, about 10 nM to about 190 nM, about 10 nM to about 180 nM, about 10 nM to about 170 nM, about 10 nM to about 160 nM, about 10 nM to about 150 nM, about 10 nM to about 140 nM, about 10 nM to about 130 nM, about 10 nM to about 120 nM, about 10 nM to about 110 nM, about 10 nM to about 100 nM, about 10 nM to about 95 nM, about 10 nM to about 90 nM, about 10 nM to about 85 nM, about 10 nM to about 80 nM, about 10 nM to about 75 nM, about 10 nM to about 70 nM, about 10 nM to about 65 nM, about 10 nM to about 60 nM, about 10 nM to about 55 nM, about 10 nM to about 50 nM, about 10 nM to about 45 nM, about 10 nM to about 40 nM, about 10 nM to about 35 nM, about 10 nM to about 30 nM, about 10 nM to about 25 nM, about 10 nM to about 20 nM, about 10 nM to about 15 nM, about 15 nM to about 5 µM, about 15 nM to about 2 µM, about 15 nM to about 1 µM, about 15 nM to about 500 nM, about 15 nM to about 250 nM, about 15 nM to about 240 nM, about 15 nM to about 230 nM, about 15 nM to about 220 nM, about 15 nM to about 210 nM, about 15 nM to about 200 nM, about 15 nM to about 190 nM, about 15 nM to about 180 nM, about 15 nM to about 170 nM, about 15 nM to about 160 nM, about 15 nM to about 150 nM, about 15 nM to about 140 nM, about 15 nM to about 130 nM, about 15 nM to about 120 nM, about 15 nM to about 110 nM, about 15 nM to about 100 nM, about 15 nM to about 95 nM, about 15 nM to about 90 nM, about 15 nM to about 85 nM, about 15 nM to about 80 nM, about 15 nM to about 75 nM, about 15 nM to about 70 nM, about 15 nM to about 65 nM, about 15 nM to about 60 nM, about 15 nM to about 55 nM, about 15 nM to about 50 nM, about 15 nM to about 45 nM, about 15 nM to about 40 nM, about 15 nM to about 35 nM, about 15 nM to about 30 nM, about 15 nM to about 25 nM, about 15 nM to about 20 nM, about 20 nM to about 5 µM, about 20 nM to about 2 µM, about 20 nM to about 1 µM, about 20 nM to about 500 nM, about 20 nM to about 250 nM, about 20 nM to about 240 nM, about 20 nM to about 230 nM, about 20 nM to about 220 nM, about 20 nM to about 210 nM, about 20 nM to about 200 nM, about 20 nM to about 190 nM, about 20 nM to about 180 nM, about 20 nM to about 170 nM, about 20 nM to about 160 nM, about 20 nM to about 150 nM, about 20 nM to about 140 nM, about 20 nM to about 130 nM, about 20 nM to about 120 nM, about 20 nM to about 110 nM, about 20 nM to about 100 nM, about 20 nM to about 95 nM, about 20 nM to about 90 nM, about 20 nM to about 85 nM, about 20 nM to about 80 nM, about 20 nM to about 75 nM, about 20 nM to about 70 nM, about 20 nM to about 65 nM, about 20 nM to about 60 nM, about 20 nM to about 55 nM, about 20 nM to about 50 nM, about 20 nM to about 45 nM, about 20 nM to about 40 nM, about 20 nM to about 35 nM, about 20 nM to about 30 nM, about 20 nM to about 25 nM, about 25 nM to about 5 µM, about 25 nM to about 2 µM, about 25 nM to about 1 µM, about 25 nM to about 500 nM, about 25 nM to about 250 nM, about 25 nM to about 240 nM, about 25 nM to about 230 nM, about 25 nM to about 220 nM, about 25 nM to about 210 nM, about 25 nM to about 200 nM, about 25 nM to about 190 nM, about 25 nM to about 180 nM, about 25 nM to about 170 nM, about 25 nM to about 160 nM, about 25 nM to about 150 nM, about 25 nM to about 140 nM, about 25 nM to about 130 nM, about 25 nM to about 120 nM, about 25 nM to about 110 nM, about 25 nM to about 100 nM, about 25 nM to about 95 nM, about 25 nM to about 90 nM, about 25 nM to about 85 nM, about 25 nM to about 80 nM, about 25 nM to about 75 nM, about 25 nM to about 70 nM, about 25 nM to about 65 nM, about 25 nM to about 60 nM, about 25 nM to about 55 nM, about 25 nM to about 50 nM, about 25 nM to about 45 nM, about 25 nM to about 40 nM, about 25 nM to about 35 nM, about 25 nM to about 30 nM, about 30 nM to about 5 µM, about 30 nM to about 2 µM, about 30 nM to about 1 µM, about 30 nM to about 500 nM, about 30 nM to about 250 nM, about 30 nM to about 240 nM, about 30 nM to about 230 nM, about 30 nM to about 220 nM, about 30 nM to about 210 nM, about 30 nM to about 200 nM, about 30 nM to about 190 nM, about 30 nM to about 180 nM, about 30 nM to about 170 nM, about 30 nM to about 160 nM, about 30 nM to about 150 nM, about 30 nM to about 140 nM, about 30 nM to about 130 nM, about 30 nM to about 120 nM, about 30 nM to about 110 nM, about 30 nM to about 100 nM, about 30 nM to about 95 nM, about 30 nM to about 90 nM, about 30 nM to about 85 nM, about 30 nM to about 80 nM, about 30 nM to about 75 nM, about 30 nM to about 70 nM, about 30 nM to about 65 nM, about 30 nM to about 60 nM, about 30 nM to about 55 nM, about 30 nM to about 50 nM, about 30 nM to about 45 nM, about 30 nM to about 40 nM, about 30 nM to about 35 nM, about 40 nM to about 5 µM, about 40 nM to about 2 µM, about 40 nM to about 1 µM, about 40 nM to about 500 nM, about 40 nM to about 250 nM, about 40 nM to about 240 nM, about 40 nM to about 230 nM, about 40 nM to about 220 nM, about 40 nM to about 210 nM, about 40 nM to about 200 nM, about 40 nM to about 190 nM, about 40 nM to about 180 nM, about 40 nM to about 170 nM, about 40 nM to about 160 nM, about 40 nM to about 150 nM, about 40 nM to about 140 nM, about 40 nM to about 130 nM, about 40 nM to about 120 nM, about 40 nM to about 110 nM, about 40 nM to about 100 nM, about 40 nM to about 95 nM, about 40 nM to about 90 nM, about 40 nM to about 85 nM, about 40 nM to about 80 nM, about 40 nM to about 75 nM, about 40 nM to about 70 nM, about 40 nM to about 65 nM, about 40 nM to about 60 nM, about 40 nM to about 55 nM, about 40 nM to about 50 nM, about 40 nM to about 45 nM, about 50 nM to about 5 µM, about 50 nM to about 2 µM, about 50 nM to about 1 µM, about 50 nM to about 500 nM, about 50 nM to about 250 nM, about 50 nM to about 240 nM, about 50 nM to about 230 nM, about 50 nM to about 220 nM, about 50 nM to about 210 nM, about 50 nM to about 200 nM, about 50 nM to about 190 nM, about 50 nM to about 180 nM, about 50 nM to about 170 nM, about 50 nM to about 160 nM, about 50 nM to about 150 nM, about 50 nM to about 140 nM, about 50 nM to about 130 nM, about 50 nM to about 120 nM, about 50 nM to about 110 nM, about 50 nM to about 100 nM, about 50 nM to about 95 nM, about 50 nM to about 90 nM, about 50 nM to about 85 nM, about 50 nM to about 80 nM, about 50 nM to about 75 nM, about 50 nM to about 70 nM, about 50 nM to about 65 nM, about 50 nM to about 60 nM, about 50 nM to about 55 nM, about 60 nM to about 5 µM, about 60 nM to about 2 µM, about 60 nM to about 1 µM, about 60 nM to about 500 nM, about 60 nM to about 250 nM, about 60 nM to about 240 nM, about 60 nM to about 230 nM, about 60 nM to about 220 nM, about 60 nM to about 210 nM, about 60 nM to about 200 nM, about 60 nM to about 190 nM, about 60 nM to about 180 nM, about 60 nM to about 170 nM, about 60 nM to about 160 nM, about 60 nM to about 150 nM, about 60 nM to about 140 nM, about 60 nM to about 130 nM, about 60 nM to about 120 nM, about 60 nM to about 110 nM, about 60 nM to about 100 nM, about 60 nM to about 95 nM, about 60 nM to about 90 nM, about 60 nM to about 85 nM, about 60 nM to about 80 nM, about 60 nM to about 75 nM, about 60 nM to about 70 nM, about 60 nM to about 65 nM, about 70 nM to about 5 µM, about 70 nM to about 2 µM, about 70 nM to about 1 µM, about 70 nM to about 500 nM, about 70 nM to about 250 nM, about 70 nM to about 240 nM, about 70 nM to about 230 nM, about 70 nM to about 220 nM, about 70 nM to about 210 nM, about 70 nM to about 200 nM, about 70 nM to about 190 nM, about 70 nM to about 180 nM, about 70 nM to about 170 nM, about 70 nM to about 160 nM, about 70 nM to about 150 nM, about 70 nM to about 140 nM, about 70 nM to about 130 nM, about 70 nM to about 120 nM, about 70 nM to about 110 nM, about 70 nM to about 100 nM, about 70 nM to about 95 nM, about 70 nM to about 90 nM, about 70 nM to about 85 nM, about 70 nM to about 80 nM, about 70 nM to about 75 nM, about 80 nM to about 5 µM, about 80 nM to about 2 µM, about 80 nM to about 1 µM, about 80 nM to about 500 nM, about 80 nM to about 250 nM, about 80 nM to about 240 nM, about 80 nM to about 230 nM, about 80 nM to about 220 nM, about 80 nM to about 210 nM, about 80 nM to about 200 nM, about 80 nM to about 190 nM, about 80 nM to about 180 nM, about 80 nM to about 170 nM, about 80 nM to about 160 nM, about 80 nM to about 150 nM, about 80 nM to about 140 nM, about 80 nM to about 130 nM, about 80 nM to about 120 nM, about 80 nM to about 110 nM, about 80 nM to about 100 nM, about 80 nM to about 95 nM, about 80 nM to about 90 nM, about 80 nM to about 85 nM, about 90 nM to about 5 µM, about 90 nM to about 2 µM, about 90 mM to about 1 µM, about 90 nM to about 500 nM, about 90 nM to about 250 nM, about 90 nM to about 240 nM, about 90 nM to about 230 nM, about 90 nM to about 220 nM, about 90 nM to about 210 nM, about 90 nM to about 200 nM, about 90 nM to about 190 nM, about 90 nM to about 180 nM, about 90 nM to about 170 nM, about 90 nM to about 160 nM, about 90 nM to about 150 nM, about 90 nM to about 140 nM, about 90 nM to about 130 nM, about 90 nM to about 120 nM, about 90 nM to about 110 nM, about 90 nM to about 100 nM, about 90 nM to about 95 nM, about 100 nM to about 5 µM, about 100 nM to about 2 µM, about 100 nM to about 1 µM, about 100 nM to about 500 nM, about 100 nM to about 250 nM, about 100 nM to about 240 nM, about 100 nM to about 230 nM, about 100 nM to about 220 nM, about 100 nM to about 210 nM, about 100 nM to about 200 nM, about 100 nM to about 190 nM, about 100 nM to about 180 nM, about 100 nM to about 170 nM, about 100 nM to about 160 nM, about 100 nM to about 150 nM, about 100 nM to about 140 nM, about 100 nM to about 130 nM, about 100 nM to about 120 nM, about 100 nM to about 110 nM, about 110 nM to about 5 μM, about 110 nM to about 2 μM, about 110 nM to about 1 μM, about 110 nM to about 500 nM, about 110 nM to about 250 nM, about 110 nM to about 240 nM, about 110 nM to about 230 nM, about 110 nM to about 220 nM, about 110 nM to about 210 nM, about 110 nM to about 200 nM, about 110 nM to about 190 nM, about 110 nM to about 180 nM, about 110 nM to about 170 nM, about 110 nM to about 160 nM, about 110 nM to about 150 nM, about 110 nM to about 140 nM, about 110 nM to about 130 nM, about 110 nM to about 120 nM, about 120 nM to about 5 μM, about 120 nM to about 2 μM, about 120 nM to about 1 μM, about 120 nM to about 500 nM, about 120 nM to about 250 nM, about 120 nM to about 240 nM, about 120 nM to about 230 nM, about 120 nM to about 220 nM, about 120 nM to about 210 nM, about 120 nM to about 200 nM, about 120 nM to about 190 nM, about 120 nM to about 180 nM, about 120 nM to about 170 nM, about 120 nM to about 160 nM, about 120 nM to about 150 nM, about 120 nM to about 140 nM, about 120 nM to about 130 nM, about 130 nM to about 5 μM, about 130 nM to about 2 μM, about 130 nM to about 1 μM, about 130 nM to about 500 nM, about 130 nM to about 250 nM, about 130 nM to about 240 nM, about 130 nM to about 230 nM, about 130 nM to about 220 nM, about 130 nM to about 210 nM, about 130 nM to about 200 nM, about 130 nM to about 190 nM, about 130 nM to about 180 nM, about 130 nM to about 170 nM, about 130 nM to about 160 nM, about 130 nM to about 150 nM, about 130 nM to about 140 nM, about 140 nM to about 5 μM, about 140 nM to about 2 μM, about 140 nM to about 1 μM, about 140 nM to about 500 nM, about 140 nM to about 250 nM, about 140 nM to about 240 nM, about 140 nM to about 230 nM, about 140 nM to about 220 nM, about 140 nM to about 210 nM, about 140 nM to about 200 nM, about 140 nM to about 190 nM, about 140 nM to about 180 nM, about 140 nM to about 170 nM, about 140 nM to about 160 nM, about 140 nM to about 150 nM, about 150 nM to about 5 μM, about 150 nM to about 2 μM, about 150 nM to about 1 μM, about 150 nM to about 500 nM, about 150 nM to about 250 nM, about 150 nM to about 240 nM, about 150 nM to about 230 nM, about 150 nM to about 220 nM, about 150 nM to about 210 nM, about 150 nM to about 200 nM, about 150 nM to about 190 nM, about 150 nM to about 180 nM, about 150 nM to about 170 nM, about 150 nM to about 160 nM, about 160 nM to about 5 μM, about 160 nM to about 2 μM, about 160 nM to about 1 μM, about 160 nM to about 500 nM, about 160 nM to about 250 nM, about 160 nM to about 240 nM, about 160 nM to about 230 nM, about 160 nM to about 220 nM, about 160 nM to about 210 nM, about 160 nM to about 200 nM, about 160 nM to about 190 nM, about 160 nM to about 180 nM, about 160 nM to about 170 nM, about 170 nM to about 5 μM, about 170 nM to about 2 μM, about 170 nM to about 1 μM, about 170 nM to about 500 nM, about 170 nM to about 250 nM, about 170 nM to about 240 nM, about 170 nM to about 230 nM, about 170 nM to about 220 nM, about 170 nM to about 210 nM, about 170 nM to about 200 nM, about 170 nM to about 190 nM, about 170 nM to about 180 nM, about 180 nM to about 5 μM, about 180 nM to about 2 μM, about 180 nM to about 1 μM, about 180 nM to about 500 nM, about 180 nM to about 250 nM, about 180 nM to about 240 nM, about 180 nM to about 230 nM, about 180 nM to about 220 nM, about 180 nM to about 210 nM, about 180 nM to about 200 nM, about 180 nM to about 190 nM, about 190 nM to about 5 μM, about 190 nM to about 2 μM, about 190 nM to about 1 μM, about 190 nM to about 500 nM, about 190 nM to about 250 nM, about 190 nM to about 240 nM, about 190 nM to about 230 nM, about 190 nM to about 220 nM, about 190 nM to about 210 nM, about 190 nM to about 200 nM, about 200 nM to about 5 μM, about 200 nM to about 2 μM, about 200 nM to about 1 μM, about 200 nM to about 500 nM, about 200 nM to about 250 nM, about 200 nM to about 240 nM, about 200 nM to about 230 nM, about 200 nM to about 220 nM, about 200 nM to about 210 nM, about 210 nM to about 5 μM, about 210 nM to about 2 μM, about 210 nM to about 1 μM, about 210 nM to about 500 nM, about 210 nM to about 250 nM, about 210 nM to about 240 nM, about 210 nM to about 230 nM, about 210 nM to about 220 nM, about 220 nM to about 5 μM, about 220 nM to about 2 μM, about 220 nM to about 1 μM, about 220 nM to about 500 nM, about 220 nM to about 250 nM, about 220 nM to about 240 nM, about 220 nM to about 230 nM, about 230 nM to about 5 μM, about 230 nM to about 2 μM, about 230 nM to about 1 μM, about 230 nM to about 500 nM, about 230 nM to about 250 nM, about 230 nM to about 240 nM, about 240 nM to about 5 μM, about 240 nM to about 2 μM, about 240 nM to about 1 μM, about 240 nM to about 500 nM, about 240 nM to about 250 nM, about 250 nM to about 5 μM, about 250 nM to about 2 μM, about 250 nM to about 1 μM, about 250 nM to about 500 nM, about 500 nM to about 5 μM, about 500 nM to about 2 μM, about 500 nM to about 1 μM, about 1 μM to about 5 μM, about 1 μM, to about 2 μM, or about 2 μM to about 5 μM).

In some embodiments of any of the antibodies described herein, the $K_D$ at a pH of about 4.0 to about 6.5 (e.g., any of the subranges of this range described herein) can be greater than 1 nM (e.g., between about 1 nM to about 1 mM, about 1 nM to about 900 μM, about 1 nM to about 800 μM, about 1 nM to about 700 μM, about 1 nM to about 600 μM, about 1 nM to about 500 μM, about 1 nM to about 400 μM, about 1 nM to about 300 μM, about 1 nM to about 200 μM, about 1 nM to about 100 μM, about 1 nM to about 90 μM, about 1 nM to about 80 μM, about 1 nM to about 70 μM, about 1 nM to about 60 μM, about 1 nM to about 50 μM, about 1 nM to about 40 μM, about 1 nM to about 30 μM, about 1 nM to about 20 μM, about 1 nM to about 10 μM, about 1 nM to about 5 μM, about 1 nM to about 4 μM, about 1 nM to about 2 μM, about 1 nM to about 1 μM, about 1 nM to about 900 nM, about 1 nM to about 800 nM, about 1 nM to about 700 nM, about 1 nM to about 600 nM, about 1 nM to about 500 nM, about 1 nM to about 400 nM, about 1 nM to about 300 nM, about 1 nM to about 200 nM, about 1 nM to about 100 nM, about 1 nM to about 90 nM, about 1 nM to about 80 nM, about 1 nM to about 70 nM, about 1 nM to about 60 nM, about 1 nM to about 50 nM, about 1 nM to about 40 nM, about 1 nM to about 30 nM, about 2 nM to about 1 mM, about 2 nM to about 900 μM, about 2 nM to about 800 μM, about 2 nM to about 700 μM, about 2 nM to about 600 μM, about 2 nM to about 500 μM, about 2 nM to about 400 μM, about 2 nM to about 300 μM, about 2 nM to about 200 μM, about 2 nM to about 100 μM, about 2 nM to about 90 μM, about 2 nM to about 80 μM, about 2 nM to about 70 μM, about 2 nM to about 60 μM, about 2 nM to about 50 μM, about 2 nM to about 40 μM, about 2 nM to about 30 μM, about 2 nM to about 20 μM, about 2 nM to about 10 μM, about 2 nM to about 5 μM, about 2 nM to about 4 μM, about 2 nM to about 2 μM, about 2 nM to about 1 μM, about 2 nM to about 900 nM, about 2 nM to about 800 nM, about 2 nM to about 700 nM, about 2 nM to about 600 nM, about 2 nM to about 500 nM, about 2 nM to about 400 nM, about 2 nM to about 300 nM, about 2 nM to about 200 nM, about 2 nM to about 100 nM, about 2 nM to about 90 nM, about 2 nM to about 80 nM, about 2 nM to about 70 nM, about 2 nM to about 60 nM, about 2 nM to about 50 nM, about 2 nM to about 40 nM, about 2 nM to about 30 nM, about 5 nM to about 1 mM, about 5 nM to about 900 μM, about 5 nM to about 800 μM, about 5 nM to about 700 μM, about 5 nM to about 600 μM, about 5 nM to about 500 μM, about 5 nM to about 400 μM, about 5 nM to about 300 μM, about 5 nM to about 200 μM, about 5 nM to about 100 μM, about 5 nM to about 90 μM, about 5 nM to about 80 μM, about 5 nM to about 70 μM, about 5 nM to about 60 μM, about 5 nM to about 50 μM, about 5 nM to about 40 μM, about 5 nM to about 30 μM, about 5 nM to about 20 μM, about 5 nM to about 10 μM, about 5 nM to about 5 μM, about 5 nM to about 4 μM, about 5 nM to about 2 μM, about 5 nM to about 1 μM, about 5 nM to about 900 nM, about 5 nM to about 800 nM, about 5 nM to about 700 nM, about 5 nM to about 600 nM, about 5 nM to about 500 nM, about 5 nM to about 400 nM, about 5 nM to about 300 nM, about 5 nM to about 200 nM, about 5 nM to about 100 nM, about 5 nM to about 90 nM, about 5 nM to about 80 nM, about 5 nM to about 70 nM, about 5 nM to about 60 nM, about 5 nM to about 50 nM, about 5 nM to about 40 nM, about 5 nM to about 30 nM, about 10 nM to about 1 mM, about 10 nM to about 900 μM, about 10 nM to about 800 μM, about 10 nM to about 700 μM, about 10 nM to about 600 μM, about 10 nM to about 500 μM, about 10 nM to about 400 μM, about 10 nM to about 300 μM, about 10 nM to about 200 μM, about 10 nM to about 100 μM, about 10 nM to about 90 μM, about 10 nM to about 80 μM, about 10 nM to about 70 μM, about 10 nM to about 60 μM, about 10 nM to about 50 μM, about 10 nM to about 40 μM, about 10 nM to about 30 μM, about 10 nM to about 20 μM, about 10 nM to about 10 μM, about 10 nM to about 5 μM, about 10 nM to about 4 μM, about 10 nM to about 2 μM, about 10 nM to about 1 μM, about 10 nM to about 900 nM, about 10 nM to about 800 nM, about 10 nM to about 700 nM, about 10 nM to about 600 nM, about 10 nM to about 500 nM, about 10 nM to about 400 nM, about 10 nM to about 300 nM, about 10 nM to about 200 nM, about 10 nM to about 100 nM, about 10 nM to about 90 nM, about 10 nM to about 80 nM, about 10 nM to about 70 nM, about 10 nM to about 60 nM, about 10 nM to about 50 nM, about 10 nM to about 40 nM, about 10 nM to about 30 nM, about 20 nM to about 1 mM, about 20 nM to about 900 μM, about 20 nM to about 800 μM, about 20 nM to about 700 μM, about 20 nM to about 600 μM, about 20 nM to about 500 μM, about 20 nM to about 400 μM, about 20 nM to about 300 μM, about 20 nM to about 200 μM, about 20 nM to about 100 μM, about 20 nM to about 90 μM, about 20 nM to about 80 μM, about 20 nM to about 70 μM, about 20 nM to about 60 μM, about 20 nM to about 50 μM, about 20 nM to about 40 μM, about 20 nM to about 30 μM, about 20 nM to about 20 μM, about 20 nM to about 10 μM, about 20 nM to about 5 μM, about 20 nM to about 4 μM, about 20 nM to about 2 μM, about 20 nM to about 1 pM, about 20 nM to about 900 nM, about 20 nM to about 800 nM, about 20 nM to about 700 nM, about 20 nM to about 600 nM, about 20 nM to about 500 nM, about 20 nM to about 400 nM, about 20 nM to about 300 nM, about 20 nM to about 200 nM, about 20 nM to about 100 nM, about 20 nM to about 90 nM, about 20 nM to about 80 nM, about 20 nM to about 70 nM, about 20 nM to about 60 nM, about 20 nM to about 50 nM, about 20 nM to about 40 nM, about 20 nM to about 30 nM; about 1 μM to about 1 mM, about 1 μM to about 900 μM, about 1 μM to about 800 μM, about 1 μM to about 700 μM, about 1 μM to about 600 μM, about 1 μM to about 500 μM, about 1 μM to about 400 μM, about 1 μM to about 300 μM, about 1 μM to about 200 pM, about 1 μM to about 100 μM, about 1 μM to about 90 μM, about 1 μM to about 80 μM, about 1 μM to about 70 μM, about 1 μM to about 60 μM, about 1 μM to about 50 μM, about 1 μM to about 40 μM, about 1 μM to about 30 μM, about 1 μM to about 20 μM, about 1 μM to about 10 μM, about 1 μM to about 5 μM, about 1 μM to about 4 μM, about 1 μM to about 3 μM, about 1 μM to about 2 μM, about 2 μM to about 1 mM, about 2 μM to about 900 μM, about 2 μM to about 800 μM, about 2 μM to about 700 μM, about 2 μM to about 600 μM, about 2 μM to about 500 μM, about 2 μM to about 400 μM, about 2 μM to about 300 μM, about 2 μM to about 200 μM, about 2 μM to about 100 μM, about 2 μM to about 90 μM, about 2 μM to about 80 μM, about 2 μM to about 70 μM, about 2 μM to about 60 μM, about 2 μM to about 50 μM, about 2 μM to about 40 μM, about 2 μM to about 30 μM, about 2 μM to about 20 μM, about 2 μM to about 10 μM, about 2 μM to about 5 μM, about 2 μM to about 4 μM, about 2 μM to about 3 μM, about 5 μM to about 1 mM, about 5 μM to about 900 μM, about 5 μM to about 800 μM, about 5 μM to about 700 μM, about 5 μM to about 600 μM, about 5 μM to about 500 μM, about 5 μM to about 400 μM, about 5 μM to about 300 μM, about 5 μM to about 200 μM, about 5 μM to about 100 μM, about 5 μM to about 90 μM, about 5 μM to about 80 μM, about 5 μM to about 70 μM, about 5 μM to about 60 μM, about 5 μM to about 50 μM, about 5 μM to about 40 μM, about 5 μM to about 30 μM, about 5 μM to about 20 μM, about 5 μM to about 10 μM, about 10 μM to about 1 mM, about 10 μM to about 900 μM, about 10 μM to about 800 μM, about 10 μM to about 700 μM, about 10 μM to about 600 μM, about 10 μM to about 500 μM, about 10 μM to about 400 μM, about 10 μM to about 300 μM, about 10 μM to about 200 μM, about 10 μM to about 100 μM, about 10 μM to about 90 μM, about 10 μM to about 80 μM, about 10 μM to about 70 μM, about 10 μM to about 60 μM, about 10 μM to about 50 μM, about 10 μM to about 40 pM, about 10 μM to about 30 μM, about 10 μM to about 20 μM, about 20 μM to about 1 mM, about 20 μM to about 900 μM, about 20 μM to about 800 μM, about 20 μM to about 700 μM, about 20 μM to about 600 μM, about 20 μM to about 500 μM, about 20 μM to about 400 μM, about 20 μM to about 300 μM, about 20 μM to about 200 μM, about 20 μM to about 100 μM, about 20 μM to about 90 μM, about 20 μM to about 80 μM, about 20 μM to about 70 μM, about 20 μM to about 60 μM, about 20 μM to about 50 μM, about 20 μM to about 40 μM, about 20 μM to about 30 μM, about 30 μM to about 1 mM, about 30 μM to about 900 μM, about 30 μM to about 800 μM, about 30 μM to about 700 μM, about 30 μM to about 600 μM, about 30 μM to about 500 μM, about 30 μM to about 400 μM, about 30 μM to about 300 μM, about 30 μM to about 200 μM, about 30 μM to about 100 μM, about 30 μM to about 90 μM, about 30 μM to about 80 μM, about 30 μM to about 70 μM, about 30 μM to about 60 μM, about 30 μM to about 50 μM, about 30 μM to about 40 μM, about 40 μM to about 1 mM, about 40 μM to about 900 pM, about 40 μM to about 800 μM, about 40 μM to about 700 μM, about 40 μM to about 600 pM, about 40 μM to about 500 μM, about 40 μM to about 400 μM, about 40 μM to about 300 pM, about 40 μM to about 200 μM, about 40 μM to about 100 μM, about 40 μM to about 90 μM, about 40 μM to about 80 μM, about 40 μM to about 70 μM, about 40 μM to about 60 μM, about 40 μM to about 50 μM, about 50 μM to about 1 mM, about 50 μM to about 900 μM, about 50 μM to about 800 μM, about 50 μM to about 700 μM, about 50 μM to about 600 μM, about 50 μM to about 500 μM, about 50 μM to about 400 μM, about 50 μM to about 300 μM, about 50 μM to about 200 μM, about 50 μM to about 100

μM, about 50 μM to about 90 μM, about 50 μM to about 80 μM, about 50 μM to about 70 μM, about 50 μM to about 60 μM, about 60 μM to about 1 mM, about 60 μM to about 900 μM, about 60 μM to about 800 μM, about 60 μM to about 700 μM, about 60 μM to about 600 μM, about 60 μM to about 500 μM, about 60 μM to about 400 μM, about 60 μM to about 300 μM, about 60 μM to about 200 μM, about 60 μM to about 100 μM, about 60 μM to about 90 μM, about 60 μM to about 80 μM, about 60 μM to about 70 μM, about 70 μM to about 1 mM, about 70 μM to about 900 μM, about 70 μM to about 800 μM, about 70 μM to about 700 μM, about 70 μM to about 600 μM, about 70 μM to about 500 μM, about 70 μM to about 400 μM, about 70 μM to about 300 μM, about 70 μM to about 200 μM, about 70 μM to about 100 μM, about 70 μM to about 90 μM, about 70 μM to about 80 μM, about 80 μM to about 1 mM, about 80 μM to about 900 μM, about 80 μM to about 800 μM, about 80 μM to about 700 μM, about 80 μM to about 600 μM, about 80 μM to about 500 μM, about 80 μM to about 400 μM, about 80 μM to about 300 μM, about 80 μM to about 200 μM, about 80 μM to about 100 μM, about 80 μM to about 90 μM, about 90 μM to about 1 mM, about 90 μM to about 900 μM, about 90 μM to about 800 μM, about 90 μM to about 700 μM, about 90 μM to about 600 μM, about 90 μM to about 500 μM, about 90 μM to about 400 μM, about 90 μM to about 300 μM, about 90 μM to about 200 μM, about 90 μM to about 100 μM, about 100 μM to about 1 mM, about 100 11M to about 900 μM, about 100 11M to about 800 μM, about 100 μM to about 700 μM, about 100 11M to about 600 μM, about 100 11M to about 500 μM, about 100 μM to about 400 μM, about 100 11M to about 300 μM, about 100 11M to about 200 μM, about 200 μM to about 1 mM, about 200 11M to about 900 μM, about 200 11M to about 800 μM, about 200 μM to about 700 μM, about 200 11M to about 600 μM, about 200 11M to about 500 μM, about 200 μM to about 400 μM, about 200 11M to about 300 μM, about 300 11M to about 1 mM, about 300 μM to about 900 μM, about 300 11M to about 800 μM, about 300 11M to about 700 μM, about 300 μM to about 600 μM, about 300 11M to about 500 μM, about 300 11M to about 400 μM, about 400 μM to about 1 mM, about 400 11M to about 900 μM, about 400 11M to about 800 μM, about 400 μM to about 700 μM, about 400 11M to about 600 μM, about 400 11M to about 500 μM, about 500 μM to about 1 mM, about 500 11M to about 900 μM, about 500 11M to about 800 μM, about 500 μM to about 700 μM, about 500 11M to about 600 μM, about 600 11M to about 1 mM, about 600 μM to about 900 μM, about 600 11M to about 800 μM, about 600 11M to about 700 μM, about 700 μM to about 1 mM, about 700 11M to about 900 μM, about 700 11M to about 800 μM, about 800 μM to about 1 mM, about 800 11M to about 900 μM, or about 900 μM to about 1 mM).

A variety of different methods known in the art can be used to determine the $K_D$ values of any of the antibodies described herein (e.g., an electrophoretic mobility shift assay, a filter binding assay, surface plasmon resonance, a biomolecular binding kinetics assay, in vitro binding assay on antigen-expressing cells, etc.).

In some embodiments, the half-life of any of the antibodies described herein, the half-life of the antibody in vivo is increased (e.g., a detectable increase) relatively to a control antibody (e.g., the same antibody but not including the amino acid substitutions or insertions in the CH1-CH2-CH3 of the heavy chain or any the amino acid substitutions in the $C_L$ domain). In some embodiments, one or more amino acid substitutions can increase the half-life of any of the antibodies described herein. Non-limiting examples of amino acid substitutions that can increase the half-life of the antibody in vivo include a methionine to leucine substitution at amino acid position 311 and an asparagine to serine substitution at amino acid position 317 of SEQ ID NO: 155 or SEQ ID NO: 189 and/or a methionine to tyrosine substitution at amino acid position 135, a serine to threonine substitution at amino acid position 137, and a threonine to glutamic acid substitution at amino acid position 139 of SEQ ID NO: 155 or SEQ ID NO: 189. In some embodiments, the half-life of the antibody in vivo is increased (e.g., a detectable increase) (e.g., at least a 1% decrease, at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease, or about a 1% decrease to about a 99% decrease, about a 1% decrease to about a 95% decrease, about a 1% decrease to about a 90% decrease, about a 1% decrease to about a 85% decrease, about a 1% decrease to about a 80% decrease, about a 1% decrease to about a 75% decrease, about a 1% decrease to about a 70% decrease, about a 1% decrease to about a 65% decrease, about a 1% decrease to about a 60% decrease, about a 1% decrease to about a 55% decrease, about a 1% decrease to about a 50% decrease, about a 1% decrease to about a 45% decrease, about a 1% decrease to about a 40% decrease, about a 1% decrease to about a 35% decrease, about a 1% decrease to about a 30% decrease, about a 1% decrease to about a 25% decrease, about a 1% decrease to about a 20% decrease, about a 1% decrease to about a 15% decrease, about a 1% decrease to about a 10% decrease, about a 1% decrease to about a 5% decrease, about a 5% decrease to about a 99% decrease, about a 5% decrease to about a 95% decrease, about a 5% decrease to about a 90% decrease, about a 5% decrease to about a 85% decrease, about a 5% decrease to about a 80% decrease, about a 5% decrease to about a 75% decrease, about a 5% decrease to about a 70% decrease, about a 5% decrease to about a 65% decrease, about a 5% decrease to about a 60% decrease, about a 5% decrease to about a 55% decrease, about a 5% decrease to about a 50% decrease, about a 5% decrease to about a 45% decrease, about a 5% decrease to about a 40% decrease, about a 5% decrease to about a 35% decrease, about a 5% decrease to about a 30% decrease, about a 5% decrease to about a 25% decrease, about a 5% decrease to about a 20% decrease, about a 5% decrease to about a 15% decrease, about a 5% decrease to about a 10% decrease, about a 10% decrease to about a 99% decrease, about a 10% decrease to about a 95% decrease, about a 10% decrease to about a 90% decrease, about a 10% decrease to about a 85% decrease, about a 10% decrease to about a 80% decrease, about a 10% decrease to about a 75% decrease, about a 10% decrease to about a 70% decrease, about a 10% decrease to about a 65% decrease, about a 10% decrease to about a 60% decrease, about a 10% decrease to about a 55% decrease, about a 10% decrease to about a 50% decrease, about a 10% decrease to about a 45% decrease, about a 10% decrease to about a 40% decrease, about a 10% decrease to about a 35% decrease, about a 10% decrease to about a 30% decrease, about a 10% decrease to about a 25% decrease, about a 10% decrease to about a 20% decrease, about a 10% decrease to about a 15% decrease, about a 15% decrease to about a 99% decrease, about a 15% decrease to about a 95% decrease, about a 15% decrease to about a 90% decrease, about a 15% decrease to about a 85% decrease, about a 15% decrease to about a 80% decrease, about a 15% decrease to about a 75% decrease, about a 15% decrease to about a 70% decrease, about a 15% decrease to about a 65% decrease, about a 15% decrease to about a 60% decrease, about a 15% decrease to about a 55% decrease, about a 15% decrease to about a 50% decrease, about a 15% decrease to about a 45% decrease, about a 15% decrease to about a 40% decrease, about a 15% decrease to about a 35% decrease, about a 15% decrease to about a 30% decrease, about a 15% decrease to about a 25% decrease, about a 15% decrease to about a 20% decrease, about a 20% decrease to about a 99% decrease, about a 20% decrease to about a 95% decrease, about a 20% decrease to about a 90% decrease, about a 20% decrease to about a 85% decrease, about a 20% decrease to about a 80% decrease, about a 20% decrease to about a 75% decrease, about a 20% decrease to about a 70% decrease, about a 20% decrease to about a 65% decrease, about a 20% decrease to about a 60% decrease, about a 20% decrease to about a 55% decrease, about a 20% decrease to about a 50% decrease, about a 20% decrease to about a 45% decrease, about a 20% decrease to about a 40% decrease, about a 20% decrease to about a 35% decrease, about a 20% decrease to about a 30% decrease, about a 20% decrease to about a 25% decrease, about a 25% decrease to about a 99% decrease, about a 25% decrease to about a 95% decrease, about a 25% decrease to about a 90% decrease, about a 25% decrease to about a 85% decrease, about a 25% decrease to about a 80% decrease, about a 25% decrease to about a 75% decrease, about a 25% decrease to about a 70% decrease, about a 25% decrease to about a 65% decrease, about a 25% decrease to about a 60% decrease, about a 25% decrease to about a 55% decrease, about a 25% decrease to about a 50% decrease, about a 25% decrease to about a 45% decrease, about a 25% decrease to about a 40% decrease, about a 25% decrease to about a 35% decrease, about a 25% decrease to about a 30% decrease, about a 30% decrease to about a 99% decrease, about a 30% decrease to about a 95% decrease, about a 30% decrease to about a 90% decrease, about a 30% decrease to about a 85% decrease, about a 30% decrease to about a 80% decrease, about a 30% decrease to about a 75% decrease, about a 30% decrease to about a 70% decrease, about a 30% decrease to about a 65% decrease, about a 30% decrease to about a 60% decrease, about a 30% decrease to about a 55% decrease, about a 30% decrease to about a 50% decrease, about a 30% decrease to about a 45% decrease, about a 30% decrease to about a 40% decrease, about a 30% decrease to about a 35% decrease, about a 35% decrease to about a 99% decrease, about a 35% decrease to about a 95% decrease, about a 35% decrease to about a 90% decrease, about a 35% decrease to about a 85% decrease, about a 35% decrease to about a 80% decrease, about a 35% decrease to about a 75% decrease, about a 35% decrease to about a 70% decrease, about a 35% decrease to about a 65% decrease, about a 35% decrease to about a 60% decrease, about a 35% decrease to about a 55% decrease, about a 35% decrease to about a 50% decrease, about a 35% decrease to about a 45% decrease, about a 35% decrease to about a 40% decrease, about a 40% decrease to about a 99% decrease, about a 40% decrease to about a 95% decrease, about a 40% decrease to about a 90% decrease, about a 40% decrease to about a 85% decrease, about a 40% decrease to about a 80% decrease, about a 40% decrease to about a 75% decrease, about a 40% decrease to about a 70% decrease, about a 40% decrease to about a 65% decrease, about a 40% decrease to about a 60% decrease, about a 40% decrease to about a 55% decrease, about a 40% decrease to about a 50% decrease, about a 40% decrease to about a 45% decrease, about a 45% decrease to about a 99% decrease, about a 45% decrease to about a 95% decrease, about a 45% decrease to about a 90% decrease, about a 45% decrease to about a 85% decrease, about a 45% decrease to about a 80% decrease, about a 45% decrease to about a 75% decrease, about a 45% decrease to about a 70% decrease, about a 45% decrease to about a 65% decrease, about a 45% decrease to about a 60% decrease, about a 45% decrease to about a 55% decrease, about a 45% decrease to about a 50% decrease, about a 50% decrease to about a 99% decrease, about a 50% decrease to about a 95% decrease, about a 50% decrease to about a 90% decrease, about a 50% decrease to about a 85% decrease, about a 50% decrease to about a 80% decrease, about a 50% decrease to about a 75% decrease, about a 50% decrease to about a 70% decrease, about a 50% decrease to about a 65% decrease, about a 50% decrease to about a 60% decrease, about a 50% decrease to about a 55% decrease, about a 55% decrease to about a 99% decrease, about a 55% decrease to about a 95% decrease, about a 55% decrease to about a 90% decrease, about a 55% decrease to about a 85% decrease, about a 55% decrease to about a 80% decrease, about a 55% decrease to about a 75% decrease, about a 55% decrease to about a 70% decrease, about a 55% decrease to about a 65% decrease, about a 55% decrease to about a 60% decrease, about a 60% decrease to about a 99% decrease, about a 60% decrease to about a 95% decrease, about a 60% decrease to about a 90% decrease, about a 60% decrease to about a 85% decrease, about a 60% decrease to about a 80% decrease, about a 60% decrease to about a 75% decrease, about a 60% decrease to about a 70% decrease, about a 60% decrease to about a 65% decrease, about a 65% decrease to about a 99% decrease, about a 65% decrease to about a 95% decrease, about a 65% decrease to about a 90% decrease, about a 65% decrease to about a 85% decrease, about a 65% decrease to about a 80% decrease, about a 65% decrease to about a 75% decrease, about a 65% decrease to about a 70% decrease, about a 70% decrease to about a 99% decrease, about a 70% decrease to about a 95% decrease, about a 70% decrease to about a 90% decrease, about a 70% decrease to about a 85% decrease, about a 70% decrease to about a 80% decrease, about a 70% decrease to about a 75% decrease, about a 75% decrease to about a 99% decrease, about a 75% decrease to about a 95% decrease, about a 75% decrease to about a 90% decrease, about a 75% decrease to about a 85% decrease, about a 75% decrease to about a 80% decrease, about a 80% decrease to about a 99% decrease, about a 80% decrease to about a 95% decrease, about a 80% decrease to about a 90% decrease, about a 80% decrease to about a 85% decrease, about a 85% decrease to about a 99% decrease, about a 85% decrease to about a 95% decrease, about a 85% decrease to about a 90% decrease, about a 90% decrease to about a 99% decrease, about a 90% decrease to about a 95% decrease, or about a 95% decrease to about a 99% decrease) as compared to the half-life of a control antibody (e.g., the same antibody but not including the amino acid substitutions or insertions in the CH1-CH2-CH3 of the heavy chain or any the amino acid substitutions in the $C_L$ domain).

In some examples of any of the antibodies described herein, the half-life of the antibody in vivo is decreased (e.g., a detectable decrease) (e.g., at least a 1% decrease, at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease, or about a 1% decrease to about a 99% decrease, about a 1% decrease to about a 95% decrease, about a 1% decrease to about a 90% decrease, about a 1% decrease to about a 85% decrease, about a 1% decrease to about a 80% decrease, about a 1% decrease to about a 75% decrease, about a 1% decrease to about a 70% decrease, about a 1% decrease to about a 65% decrease, about a 1% decrease to about a 60% decrease, about a 1% decrease to about a 55% decrease, about a 1% decrease to about a 50% decrease, about a 1% decrease to about a 45% decrease, about a 1% decrease to about a 40% decrease, about a 1% decrease to about a 35% decrease, about a 1% decrease to about a 30% decrease, about a 1% decrease to about a 25% decrease, about a 1% decrease to about a 20% decrease, about a 1% decrease to about a 15% decrease, about a 1% decrease to about a 10% decrease, about a 1% decrease to about a 5% decrease, about a 5% decrease to about a 99% decrease, about a 5% decrease to about a 95% decrease, about a 5% decrease to about a 90% decrease, about a 5% decrease to about a 85% decrease, about a 5% decrease to about a 80% decrease, about a 5% decrease to about a 75% decrease, about a 5% decrease to about a 70% decrease, about a 5% decrease to about a 65% decrease, about a 5% decrease to about a 60% decrease, about a 5% decrease to about a 55% decrease, about a 5% decrease to about a 50% decrease, about a 5% decrease to about a 45% decrease, about a 5% decrease to about a 40% decrease, about a 5% decrease to about a 35% decrease, about a 5% decrease to about a 30% decrease, about a 5% decrease to about a 25% decrease, about a 5% decrease to about a 20% decrease, about a 5% decrease to about a 15% decrease, about a 5% decrease to about a 10% decrease, about a 10% decrease to about a 99% decrease, about a 10% decrease to about a 95% decrease, about a 10% decrease to about a 90% decrease, about a 10% decrease to about a 85% decrease, about a 10% decrease to about a 80% decrease, about a 10% decrease to about a 75% decrease, about a 10% decrease to about a 70% decrease, about a 10% decrease to about a 65% decrease, about a 10% decrease to about a 60% decrease, about a 10% decrease to about a 55% decrease, about a 10% decrease to about a 50% decrease, about a 10% decrease to about a 45% decrease, about a 10% decrease to about a 40% decrease, about a 10% decrease to about a 35% decrease, about a 10% decrease to about a 30% decrease, about a 10% decrease to about a 25% decrease, about a 10% decrease to about a 20% decrease, about a 10% decrease to about a 15% decrease, about a 15% decrease to about a 99% decrease, about a 15% decrease to about a 95% decrease, about a 15% decrease to about a 90% decrease, about a 15% decrease to about a 85% decrease, about a 15% decrease to about a 80% decrease, about a 15% decrease to about a 75% decrease, about a 15% decrease to about a 70% decrease, about a 15% decrease to about a 65% decrease, about a 15% decrease to about a 60% decrease, about a 15% decrease to about a 55% decrease, about a 15% decrease to about a 50% decrease, about a 15% decrease to about a 45% decrease, about a 15% decrease to about a 40% decrease, about a 15% decrease to about a 35% decrease, about a 15% decrease to about a 30% decrease, about a 15% decrease to about a 25% decrease, about a 15% decrease to about a 20% decrease, about a 20% decrease to about a 99% decrease, about a 20% decrease to about a 95% decrease, about a 20% decrease to about a 90% decrease, about a 20% decrease to about a 85% decrease, about a 20% decrease to about a 80% decrease, about a 20% decrease to about a 75% decrease, about a 20% decrease to about a 70% decrease, about a 20% decrease to about a 65% decrease, about a 20% decrease to about a 60% decrease, about a 20% decrease to about a 55% decrease, about a 20% decrease to about a 50% decrease, about a 20% decrease to about a 45% decrease, about a 20% decrease to about a 40% decrease, about a 20% decrease to about a 35% decrease, about a 20% decrease to about a 30% decrease, about a 20% decrease to about a 25% decrease, about a 25% decrease to about a 99% decrease, about a 25% decrease to about a 95% decrease, about a 25% decrease to about a 90% decrease, about a 25% decrease to about a 85% decrease, about a 25% decrease to about a 80% decrease, about a 25% decrease to about a 75% decrease, about a 25% decrease to about a 70% decrease, about a 25% decrease to about a 65% decrease, about a 25% decrease to about a 60% decrease, about a 25% decrease to about a 55% decrease, about a 25% decrease to about a 50% decrease, about a 25% decrease to about a 45% decrease, about a 25% decrease to about a 40% decrease, about a 25% decrease to about a 35% decrease, about a 25% decrease to about a 30% decrease, about a 30% decrease to about a 99% decrease, about a 30% decrease to about a 95% decrease, about a 30% decrease to about a 90% decrease, about a 30% decrease to about a 85% decrease, about a 30% decrease to about a 80% decrease, about a 30% decrease to about a 75% decrease, about a 30% decrease to about a 70% decrease, about a 30% decrease to about a 65% decrease, about a 30% decrease to about a 60% decrease, about a 30% decrease to about a 55% decrease, about a 30% decrease to about a 50% decrease, about a 30% decrease to about a 45% decrease, about a 30% decrease to about a 40% decrease, about a 30% decrease to about a 35% decrease, about a 35% decrease to about a 99% decrease, about a 35% decrease to about a 95% decrease, about a 35% decrease to about a 90% decrease, about a 35% decrease to about a 85% decrease, about a 35% decrease to about a 80% decrease, about a 35% decrease to about a 75% decrease, about a 35% decrease to about a 70% decrease, about a 35% decrease to about a 65% decrease, about a 35% decrease to about a 60% decrease, about a 35% decrease to about a 55% decrease, about a 35% decrease to about a 50% decrease, about a 35% decrease to about a 45% decrease, about a 35% decrease to about a 40% decrease, about a 40% decrease to about a 99% decrease, about a 40% decrease to about a 95% decrease, about a 40% decrease to about a 90% decrease, about a 40% decrease to about a 85% decrease, about a 40% decrease to about a 80% decrease, about a 40% decrease to about a 75% decrease, about a 40% decrease to about a 70% decrease, about a 40% decrease to about a 65% decrease, about a 40% decrease to about a 60% decrease, about a 40% decrease to about a 55% decrease, about a 40% decrease to about a 50% decrease, about a 40% decrease to about a 45% decrease, about a 45% decrease to about a 99% decrease, about a 45% decrease to about a 95% decrease, about a 45% decrease to about a 90% decrease, about a 45% decrease to about a 85% decrease, about a 45% decrease to about a 80% decrease, about a 45% decrease to about a 75% decrease, about a 45% decrease to about a 70% decrease, about a 45% decrease to about a 65% decrease, about a 45% decrease to about a 60% decrease, about a 45% decrease to about a 55% decrease, about a 45% decrease to about a 50% decrease, about a 50% decrease to about a 99% decrease, about a 50% decrease to about a 95% decrease, about a 50% decrease to about a 90% decrease, about a 50% decrease to about a 85% decrease, about a 50% decrease to about a 80% decrease, about a 50% decrease to about a 75% decrease, about a 50% decrease to about a 70% decrease, about a 50% decrease to about a 65% decrease, about a 50% decrease to about a 60% decrease, about a 50% decrease to about a 55% decrease, about a 55% decrease to about a 99% decrease, about a 55% decrease to about a 95% decrease, about a 55% decrease to about a 90% decrease, about a 55% decrease to about a 85% decrease, about a 55% decrease to about a 80% decrease, about a 55% decrease to about a 75% decrease, about a 55% decrease to about a 70% decrease, about a 55% decrease to about a 65% decrease, about a 55% decrease to about a 60% decrease, about a 60% decrease to about a 99% decrease, about a 60% decrease to about a 95% decrease, about a 60% decrease to about a 90% decrease, about a 60% decrease to about a 85% decrease, about a 60% decrease to about a 80% decrease, about a 60% decrease to about a 75% decrease, about a 60% decrease to about a 70% decrease, about a 60% decrease to about a 65% decrease, about a 65% decrease to about a 99% decrease, about a 65% decrease to about a 95% decrease, about a 65% decrease to about a 90% decrease, about a 65% decrease to about a 85% decrease, about a 65% decrease to about a 80% decrease, about a 65% decrease to about a 75% decrease, about a 65% decrease to about a 70% decrease, about a 70% decrease to about a 99% decrease, about a 70% decrease to about a 95% decrease, about a 70% decrease to about a 90% decrease, about a 70% decrease to about a 85% decrease, about a 70% decrease to about a 80% decrease, about a 70% decrease to about a 75% decrease, about a 75% decrease to about a 99% decrease, about a 75% decrease to about a 95% decrease, about a 75% decrease to about a 90% decrease, about a 75% decrease to about a 85% decrease, about a 75% decrease to about a 80% decrease, about a 80% decrease to about a 99% decrease, about a 80% decrease to about a 95% decrease, about a 80% decrease to about a 90% decrease, about a 80% decrease to about a 85% decrease, about a 85% decrease to about a 99% decrease, about a 85% decrease to about a 95% decrease, about a 85% decrease to about a 90% decrease, about a 90% decrease to about a 99% decrease, about a 90% decrease to about a 95% decrease, or about a 95% decrease to about a 99% decrease) as compared to the half-life of a control antibody (e.g., the same antibody but not including the amino acid substitutions or insertions in the CH1-CH2-CH3 of the heavy chain or any the amino acid substitutions in the $C_L$ domain).

Conjugation

In some embodiments, the antibodies provided herein can be conjugated to a drug (e.g., a chemotherapeutic drug, a small molecule), a toxin, or a radioisotope. Non-limiting examples of drugs, toxins, and radioisotopes (e.g., known to be useful for the treatment of cancer) are known in the art.

In some embodiments, at least one polypeptide of any of the antibodies described herein is conjugated to the toxin, the radioisotope, or the drug via a cleavable linker. In some embodiments, the cleavable linker includes a protease cleavage site. In some embodiments, the cleavable linker is cleaved on the antibody once it is transported to the lysosome or late endosome by the target mammalian cell. In some embodiments, cleavage of the linker functionally activates the drug or toxin.

In some embodiments, at least one polypeptide of any of the antibodies described herein is conjugated to the toxin, the radioisotope, or the drug via a non-cleavable linker. In some embodiments, the conjugated toxin, radioisotope, or drug is released during lysosomal and/or late endosomal degradation of the antibody.

Non-limiting examples of cleavable linkers include: hydrazone linkers, peptide linkers, disulfide linkers, and thioether linkers. See, e.g., Carter et al., *Cancer J.* 14(3): 154-169, 2008; Sanderson et al., *Clin. Cancer Res.* 11(2 Pt1):843-852, 2005; Chari et al., *Acc. Chem. Res.* 41(1):98-107, 2008; Oflazoglu et al., *Clin. Cancer Res.* 14(19): 6171-6180, 2008; and Lu et al., *Int. J. Mol. Sci.* 17(4): 561, 2016.

Non-limiting examples of non-cleavable linkers include: maleimide alkane-linkers and meleimide cyclohexane linker (MMC) (see, e.g., those described in McCombs et al., *AAPS J.* 17(2):339-351, 2015).

In some embodiments, any of the antibodies described herein is cytotoxic or cytostatic to the target mammalian cell.

In some embodiments, the antibodies provided herein can comprise one or more amino acid substitutions to provide a conjugation site (e.g., conjugated to a drug, a toxin, a radioisotope). In some embodiments, the antibodies provided herein can have one conjugation site. In some embodiments, the antibodies described herein can have two conjugation sites. In some embodiments, the antibodies provided herein can have three or more conjugation sites. A non-limiting example of an amino acid substitution to produce a conjugation site (e.g., "a triple hinge" conjugation site) is described in U.S. Patent Application No. 2017/0348429, which is incorporated herein by reference in its entirety. For example, a lysine to cysteine substitution at amino acid position 105 and deletion of a threonine at amino acid positions 106 and 108 of SEQ ID NO: 155 or SEQ ID NO: 189 can provide a "triple hinge" conjugation site in any of the antibodies described herein. In some embodiments, an alanine to a cysteine substitution at amino acid position 1 of SEQ ID NO: 155 or SEQ ID NO: 189 can provide a conjugation site for any of the antibodies described herein. In some embodiments, a valine to cysteine substitution at amino acid position 98 of SEQ ID NO: 157 can provide a conjugation site for any of the antibodies described herein.

Naturally-occurring cysteine amino acids can also provide a conjugation (e.g., conjugated to a drug, a toxin, a radioisotope.). In some embodiments, the antibodies provided herein can have a drug, a toxin, or a radioisotope conjugated at one or more (e.g., one, two, three, or four) naturally-occurring conjugation sites. In some embodiments, the cysteine at amino acid position 103 of SEQ ID NO: 155 or 189 is a naturally occurring conjugation site. In some embodiments, the cysteine at amino acid position 109 of SEQ ID NO: 155 or 189 is a naturally occurring conjugation site. In some embodiments, the cysteine at amino acid position 112 of SEQ ID NO: 155 or SEQ 189 is a naturally-occurring conjugation site. In some embodiments, the cysteine at amino acid position 107 of SEQ ID NO: 157 is a naturally-occurring conjugation site.

In some embodiments, the antibodies provided herein can have a drug, a toxin, or a radioisotope conjugated at one or more (e.g., two, three, or four) naturally occurring conjugation sites, e.g., the cysteine at amino acid position 103, the cysteine at cysteine at amino acid position 109, and/or the cysteine at amino acid position 112 of SEQ ID NO: 155 or SEQ 189, and/or the cysteine at amino acid position 107 of SEQ ID NO: 157. In some embodiments, the antibodies provided herein can have a drug, a toxin, or a radioisotope conjugated at one or more (e.g., two, three, or four) naturally occurring conjugation sites and one or more (e.g., two, or three) engineered conjugation sites (e.g., engineered by amino acid substitutions, deletions, additions, etc.).

Conjugation through engineered cysteines is achieved by methods known in the art. Briefly, engineered cysteine-containing antibody is prepared for conjugation by treatment with a reducing agent, for example, tris (2-carboxyethyl) phosphine (TCEP), Dithiothreitol (DTT), or 2-Mercaptoethanol (BME). In the reduction reaction the reducing reagent with disulfide bonds in the antibody, breaking interchain disulfides and removing disulfide caps from the engineered cysteines. An optional reoxidation step, achieved by exposure of the solution to air, or an oxidizing agent such as dehydroascorbic acid, allows reformation of the interchain disulfide bonds, leaving the engineered cysteines with a thiolate reactive group. Conjugation with a maleimide functionality on the linker-payload, maleimide-vc-MMAE, is achieved by reaction with the payload in buffered solution, containing cosolvent such as ethanol, dimethylacetamide (DMA), or dimethyl sulfoxide (DMSO). The crude conjugated antibody solution is purified by size exclusion chromatography, or selective filtration methods, such as tangential flow filtration. In this step, residual unreacted payload, reducing agent and oxidizing agents are removed from the reaction mixture, and the conjugated ADC product may be transferred into a desirable formulation buffer.

Conjugation through hinge cysteines is achieved by similar methods, using antibodies with, or without, additional engineered cysteine conjugation sites. Briefly, the antibody is prepared for conjugation by treatment with a reducing agent, for example, tris (2-carboxyethyl) phosphine (TCEP) or Dithiothreitol (DTT). The reducing strength and concentration of the reducing agent are selected such that some or all of the interchain disulfide bonds are reduced leaving free cysteines for conjugation. The solution may be directly conjugated in the presence of excess reducing agent. Conjugation with a maleimide functionality on the linker-payload, maleimide-vc-MMAE, is achieved by reaction with the payload in buffered solution, containing cosolvent such as ethanol, dimethylacetamide (DMA), or dimethyl sulfoxide (DMSO). Unreacted linker-payload may be rendered non-reactive by addition of a sacrificial thiolate molecule such as acetyl-cysteine. The crude conjugated antibody solution may be further purified by methods known in the art, including hydrophobic interaction chromatography, ion-exchange chromatography, or mixed-mode chromatography such as ceramic hydroxyapatite chromatography. Isolation of chromatography fractions allows selection of the desired antibody to payload ratio and removal of unreacted antibody, protein aggregates and fragments, and payload-related reaction side products. The purified antibody drug conjugate may be further purified and by size exclusion chromatography, or selective filtration methods, such as tangential flow filtration. In this step the conjugated ADC product may also be transferred into a desirable formulation buffer.

In some examples, an antibody conjugate can be made comprising an antibody linked to monomethyl auristatin E (MMAE) via a valine-citrulline (vc) linker (hereafter, MET-IgG-DC). Conjugation of the antigen-binding protein construct with vcMMAE begins with a partial reduction of the MET-IgG followed by reaction with maleimidocaproyl-Val-Cit-PABC-MMAE (vcMMAE). The MET-IgG (10 mg/mL) is partially reduced by addition of TCEP (molar equivalents of TCEP:mAb is 2:1) followed by incubation at 4° C. overnight. The reduction reaction is then warmed to 25° C. To conjugate all of the thiols, vcMMAE is added to a final vcMMAE:reduced Cys molar ratio of 1:10. The conjugation reaction is carried out in the presence of 10% v/v of Dimethylacetamide (DMA) and allowed to proceed at 25° C. for 60 minutes.

In some examples, an antibody conjugate (ADC) is made comprising the MET-binding IgG (hereafter, MET-IgG) described herein linked to monomethyl auristatin E (MMAE) via a valine-citrulline (vc) linker (hereafter, MET-IgG-DC). Conjugation of the antigen-binding protein construct with vcMMAE begins with a partial reduction of the MET-IgG followed by reaction with maleimidocaproyl-Val-Cit-PABC-MMAE (vcMMAE). The MET-IgG (10 mg/mL) is reduced by addition of DTT (molar equivalents of DTT:mAb is 100:1) followed by incubation at 25° C. overnight. The reduced MET-IgG (10 mg/mL) is then re-oxidized by exposure to DHAA (molar equivalents of DHAA:mAb is 10:1) followed by incubation at 25° C. for 2 hours. To conjugate all of the thiols, vcMMAE is added to a final vcMMAE:mAb molar ratio of 4:1. The conjugation reaction is carried out in the presence of 10% v/v of DMA and allowed to proceed at 25° C. for 3 hours.

Expression of an Antibody in a Cell

Also provided herein are methods of generating a recombinant cell that expresses an antibody (e.g., any of the antibodies described herein) that include: introducing into a cell a nucleic acid encoding the antibody to produce a recombinant cell; and culturing the recombinant cell under conditions sufficient for the expression of the antibody. In some embodiments, the introducing step includes introducing into a cell an expression vector including a nucleic acid encoding the antibody to produce a recombinant cell.

Any of the antibodies described herein can be produced by any cell, e.g., a eukaryotic cell or a prokaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. As used herein, the term "prokaryotic cell" refers to a cell that does not have a distinct, membrane-bound nucleus. In some embodiments, the prokaryotic cell is a bacterial cell.

Methods of culturing cells are well known in the art. Cells can be maintained in vitro under conditions that favor proliferation, differentiation, and growth. Briefly, cells can be cultured by contacting a cell (e.g., any cell) with a cell culture medium that includes the necessary growth factors and supplements to support cell viability and growth.

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection.

Provided herein are methods that further include isolation of the antibodies from a cell (e.g., a eukaryotic cell) using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of Treatment

Provided herein are methods of treating a cancer characterized by having a population of cancer cells that have MET or an epitope of MET presented on their surface, that include: administering a therapeutically effective amount of any of the pharmaceutical compositions described herein or any of the antibodies described herein to a subject identified as having a cancer characterized by having the population of cancer cells.

Also provided herein are methods of reducing the volume of a tumor in a subject, wherein the tumor is characterized by having a population of cancer cells that have MET or an epitope of MET presented on their surface, that include: administering a therapeutically effective amount of any of the pharmaceutical compositions described herein or any of the antibodies described herein to a subject identified as having a cancer characterized by having the population of cancer cells. In some embodiments of any of the methods described herein, the volume of at least one (e.g., 1, 2, 3, 4, or 5) tumor (e.g., solid tumor) or tumor location (e.g., a site of metastasis) is reduced (e.g., a detectable reduction) by at least 1%, at least 2%, at least 3%, at least 4%, at least 5%, at least 6%, at least 8%, at least 10%, at least 12%, at least 14%, at least 16%, at least 18%, at least 20%, at least 22%, at least 24%, at least 26%, at least 28%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) reduced as compared to the size of the at least one tumor (e.g., solid tumor) before administration of the antibody.

Also provided herein are methods of inducing cell death in a cancer cell in a subject, wherein the cancer cell has MET or an epitope of MET presented on its surface, that include: administering a therapeutically effective amount of any of the pharmaceutical compositions of described herein or any of the antibodies described herein to a subject identified as having a cancer characterized as having the population of cancer cells. In some embodiments, the cell death that is induced is necrosis. In some embodiments, the cell death that is induced is apoptosis.

In some embodiments of any of the methods described herein, the cancer is a primary tumor.

In some embodiments of any of the methods described herein, the cancer is a metastasis.

In some embodiments of any of the methods described herein, the cancer is a non-T-cell-infiltrating tumor. In some embodiments of any of the methods described herein, the cancer is a T-cell-infiltrating tumor.

Provided herein are methods of decreasing the risk of developing a metastasis or decreasing the risk of developing an additional metastasis in a subject having a cancer, wherein the cancer is characterized by having a population of cancer cells that have MET or an epitope of MET presented on their surface, that include: administering a therapeutically effective amount of any of the pharmaceutical compositions of described herein or any of the antibodies described herein to a subject identified as having a cancer characterized as having the population of cancer cells. In some embodiments, the risk of developing a metastasis or the risk of developing an additional metastasis is decreased (e.g., a detectable decrease) by at least 1%, by at least 2%, at least 3%, at least 4%, at least 5%, at least 6%, at least 8%, at least 10%, at least 12%, at least 14%, at least 16%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% in the subject as compared to the risk of a subject having a similar cancer, but administered no treatment or a treatment that does not include the administration of any of the antibodies described herein.

In some embodiments of any of the methods described herein, the cancer is a non-T-cell-infiltrating tumor. In some embodiments of any of the methods described herein, the cancer is a T-cell-infiltrating tumor. In some embodiments of any of the methods described herein, the cellular compartment is part of the endosomal/lysosomal pathway. In some embodiments of any of the methods described herein, the cellular compartment is an endosome.

The term "subject" refers to any mammal. In some embodiments, the subject or "subject suitable for treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject suitable for treatment" may be a non-human mammal, especially mammals that are conventionally used as models for demonstrating therapeutic efficacy in humans (e.g., murine, lapine, porcine, canine or primate animals) may be employed.

As used herein, treating includes reducing the number, frequency, or severity of one or more (e.g., two, three, four, or five) signs or symptoms of a cancer in a patient having a cancer (e.g., any of the cancers described herein). For example, treatment can reducing cancer progression, reduce the severity of a cancer, or reduce the risk of re-occurrence of a cancer in a subject having the cancer.

Provided herein are methods of inhibiting the growth of a solid tumor in a subject (e.g., any of the subjects described herein) that include administering to the subject a therapeutically effective amount of any of the antibodies described herein or any of the pharmaceutical compositions described herein (e.g., as compared to the growth of the solid tumor in the subject prior to treatment or the growth of a similar solid tumor in a different subject receiving a different treatment or receiving no treatment).

In some embodiments of any of the methods described herein, the growth of a solid tumor is primary growth of a solid tumor. In some embodiments of any of the methods described herein, the growth of a solid tumor is recurrent growth of a solid tumor. In some embodiments of any of the methods described herein, the growth of a solid tumor is metastatic growth of a solid tumor. In some embodiments, treatment results in about a 1% decrease to about 99% decrease (or any of the subranges of this range described herein) in the growth of a solid tumor in the subject (e.g., as compared to the growth of the solid tumor in the subject prior to treatment or the growth of a similar solid tumor in a different subject receiving a different treatment or receiving no treatment). The growth of a solid tumor in a subject can be assessed by a variety of different imaging methods, e.g., positron emission tomograph, X-ray computed tomography, computed axial tomography, and magnetic resonance imaging.

Also provided herein are methods of decreasing the risk of developing a metastasis or developing an additional metastasis over a period of time in a subject identified as having a cancer (e.g., any of the exemplary cancers described herein) that include administering to the subject a therapeutically effective amount of any of the proteins described herein or any of the pharmaceutical compositions described herein (e.g., as compared to a subject having a similar cancer and receiving a different treatment or receiving no treatment). In some embodiments of any of the methods described herein, the metastasis or additional metastasis is one or more to a bone, lymph nodes, brain, lung, liver, skin, chest wall including bone, cartilage and soft tissue, abdominal cavity, contralateral breast, soft tissue, muscle, bone marrow, ovaries, adrenal glands, and pancreas.

In some embodiments of any of the methods described herein, the period of time is about 1 month to about 3 years (e.g., about 1 month to about 2.5 years, about 1 month to about 2 years, about 2 months to about 1.5 years, about 1 month to about 1 year, about 1 month to about 10 months, about 1 month to about 8 months, about 1 month to about 6 months, about 1 month to about 5 months, about 1 month to about 4 months, about 1 month to about 3 months, about 1 month to about 2 months, about 2 months to about 3 years, about 2 months to about 2.5 years, about 2 months to about 2 years, about 2 months to about 1.5 years, about 2 months to about 1 year, about 2 months to about 10 months, about 2 months to about 8 months, about 2 months to about 6 months, about 2 months to about 5 months, about 2 months to about 4 months, about 2 months to about 3 months, about 3 months to about 3 years, about 3 months to about 2.5 years, about 3 months to about 2 years, about 3 months to about 1.5 years, about 3 months to about 1 year, about 3 months to about 10 months, about 3 months to about 8 months, about 3 months to about 6 months, about 3 months to about 5 months, about 3 months to about 4 months, about 4 months to about 3 years, about 4 months to about 2.5 years, about 4 months to about 2 years, about 4 months to about 1.5 years, about 4 months to about 1 year, about 4 months to about 10 months, about 4 months to about 8 months, about 4 months to about 6 months, about 4 months to about 5 months, about 5 months to about 3 years, about 5 months to about 2.5 years, about 5 months to about 2 years, about 5 months to about 1.5 years, about 5 months to about 1 year, about 5 months to about 10 months, about 5 months to about 8 months, about 5 months to about 6 months, about 6 months to about 3 years, about 6 months to about 2.5 years, about 6 months to about 2 years, about 6 months to about 1.5 years, about 6 months to about 1 year, about 6 months to about 10 months, about 6 months to about 8 months, about 8 months to about 3 years, about 8 months to about 2.5 years, about 8 months to about 2 years, about 8 months to about 1.5 years, about 8 months to about 1 year, about 8 months to about 10 months, about 10 months to about 3 years, about 10 months to about 2.5 years, about 10 months to about 2 years, about 10 months to about 1.5 years, about 10 months to about 1 year, about 1 year to about 3 years, about 1 year to about 2.5 years, about 1 year to about 2 years, about 1 year to about 1.5 years, about 1.5 years to about 3 years, about 1.5 years to about 2.5 years, about 1.5 years to about 2 years, about 2 years to about 3 years, about 2 years to about 2.5 years, or about 2.5 years to about 3 years).

In some embodiments, the risk of developing a metastasis or developing an additional metastasis over a period of time in a subject identified as having a cancer is decreased by about 1% to about 99% (e.g., or any of the subranges of this range described herein), e.g., as compared to the risk in a subject having a similar cancer receiving a different treatment or receiving no treatment.

Non-limiting examples of cancer include: acute lymphoblastic leukemia (ALL acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer. Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and para-nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms' tumor. Additional examples of cancer are known in the art.

In some embodiments, the patient is further administered one or more additional therapeutic agents (e.g., one or more of a chemotherapeutic agent, a recombinant cytokine or interleukin protein, a kinase inhibitor, and a checkpoint inhibitor). In some embodiments, the one or more additional therapeutic agents is administered to the patient at approximately the same time as any of the antibodies described herein are administered to the patient. In some embodiments, the one or more additional therapeutic agents are administered to the patient after the administration of any of the antibodies described herein to the patient. In some embodiments, the one or more additional therapeutic agents are administered to the patient before the administration of any of the antibodies described herein to the patient.

In some embodiments of any of the methods described herein, the cancer is a solid cancer (e.g., breast cancer, prostate cancer, or non-small cell lung cancer).

Avidity

Antibodies and antigens binding fragment thereof are multivalent, and thus comprise more than one binding site. Generally, the measure of total binding strength of an antibody at its binding site is termed avidity. Generally, the terms "fold avidity" and "selectivity" can refer to the fold-difference between the affinity of an antibody and the avidity of an antibody, for example as seen when measuring the total binding strength of an antibody on a cell line with high target expression (avidity; e.g. a cancer cell, e.g. Detroit-562 cells) as compared to the total binding strength of an antibody on a cell line with low target expression (affinity, e.g. a non-cancer cell, e.g. HUVEC cells). Generally, avidity is determined by four factors: the binding affinity (e.g., the strength of the binding at an individual binding site); valency (e.g., the total number of binding sites); structural arrangement (e.g., the structure of the antigen and antibody); and antigen density (e.g., the number of antigens per cell).

Provided herein are methods of decreasing the risk of developing a metastasis or decreasing the risk of developing an additional metastasis in a subject having a cancer, where the cancer is characterized by having a population of cancer cells that have MET or an epitope of MET presented on their surface the method comprising, administering a therapeutically effective amount of any of the antibodies described herein or any of the pharmaceutical compositions described herein to a subject identified as having a cancer characterized by having the population of cancer cells. In some embodiments, the antibodies described herein can have at least new at least 5%, at least 10%, at least 15%, 20%, 25%, 30%, 35%, 40%, 45%, 50%, 55%, 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, or at least 200% at least 205%, at least 210%, at least 215%, at least 220%, at least 225%, at least 230%, at least 235%, at least 240%, at least 245%, at least 250%, at least 255%, at least 260%, at least 265%, at least 270%, at least 275%, at least 280%, at least 285%, at least 290%, at least 295%, at least 300%, at least 305%, at least 310%, at least 315%, at least 320%, at least 325%, at least 330%, at least 335%, at least 340%, at least 345%, at least 350%, at least 355%, at least 360%, at least 365%, at least 370%, at least 375%, at least 380%, at least 385%, at least 390%, at least 395%, or at least 400%, increase in selectivity for a cancer cell as compared to a non-cancer cell.

Compositions

Also provided herein are compositions (e.g., pharmaceutical compositions) that include at least one of any of the antibodies described herein. In some embodiments, the compositions (e.g., pharmaceutical compositions) can be disposed in a sterile vial or a pre-loaded syringe.

In some embodiments, the compositions (e.g., pharmaceutical compositions) are formulated for different routes of administration (e.g., intravenous, subcutaneous, intramuscular, or intratumoral). In some embodiments, the compositions (e.g., pharmaceutical compositions) can include a pharmaceutically acceptable carrier (e.g., phosphate buffered saline). Single or multiple administrations of any of the pharmaceutical compositions described herein can be given to a subject depending on, for example: the dosage and frequency as required and tolerated by the patient. A dosage of the pharmaceutical composition should provide a sufficient quantity of the antibody to effectively treat or ameliorate conditions, diseases, or symptoms. Also provided herein are methods of treating a subject having a cancer (e.g., any of the cancers described herein) that include administering a therapeutically effective amount of at least one of any of the compositions or pharmaceutical compositions provided herein.

Kits

Also provided herein are kits that include any of the antibodies described herein, any of the compositions described herein, or any of the pharmaceutical compositions described herein. In some embodiments, the kits can include instructions for performing any of the methods described herein. In some embodiments, the kits can include at least one dose of any of the compositions (e.g., pharmaceutical compositions) described herein. In some embodiments, the kits can provide a syringe for administering any of the pharmaceutical compositions described herein.

The invention is further described in the following examples, which do not limit the scope of the invention described in the claims.

EXAMPLES

Example 1. Generation of MET Binders and Engineering of pH Binding Dependence pH-engineered antibodies specific for MET are generated using two methods. In the first approach, published monoclonal antibodies against MET are used as a starting template for introduction of additional mutations that allow engineering of pH-dependent binding to MET and i) enhanced endolysosomal accumulation of a conjugated toxin, as well as ii) enhanced MET recycling to the cell surface. The second approach involves discovery of de novo antibodies specific for MET via antibody display methods from naive libraries or libraries with defined CDR compositions and screening under conditions designed for selection of pH-engineered antibodies specific for MET. In either case, histidine residues play an important role in engineering pH-dependent binding proteins.

Histidine residues are at least partially protonated at a pH below 6.5 owing to its pKa of 6.0. Therefore, if a histidine side chain in an antigen-binding domain participates in an electrostatic binding interaction with its antigen it will start to turn positively charged at a pH at or below 6.5. This could either weaken or enhance the binding affinity of the interaction at a pH below 6.5, based on the corresponding charge of and interactions with the antigen epitope. Thus, systematic introduction of histidines into antibody complementarity determining regions (CDRs) in an antibody or other binder library (e.g., an scFv library) can be used to identify substitutions that will affect an antigen-binding domain's interaction with an antigen at lower pH values. The first approach therefore involves histidine-scanning of variable region sequences of published monoclonal antibodies to identify pH-dependent variants.

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. Briefly, for a subset of the antibody sequences, CDRs in each chain are identified using the methods described by Kabat et al (Kabat et al. (1992) Sequences of Proteins of Immunological Interest (DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To engineer pH-dependent sequence variants, individual amino acid residues within the heavy chain and/or light chain CDRs are systematically substituted with a histidine, one at a time. In cases where the starting CDR residue is a histidine, it is mutated to an alanine. Antibody variants with only one histidine or alanine mutation in a heavy/light chain CDR are generated by co-transfection of Expi293 cells with a) one heavy chain or light chain sequence variant, and b) the corresponding starting antibodies (e.g., the starting MET-binding monoclonal antibody) light chain or heavy chain, respectively, using methods known to the art. After allowing for a period of protein expression, cell culture supernatants are collected, quantified, and the pH dependence of the variant is evaluated using biolayer interferometry (BLI) or other methods known to the art. Briefly, cell culture supernatants are normalized to an antibody expression level of 50 pg/mL, and captured on an anti-human Fc sensor (Forte Bio). A baseline is established using 1× kinetics buffer (Forte Bio), and the sensor is associated with 100 nM of MET in 1×PBS at pH 7.4 for 300 sec to generate an association curve. In the dissociation phase, the antibody-antigen complex on the sensor is exposed to 1×PBS at either pH 5.5 or pH 7.4 for 300-500 sec. Association and dissociation phase curves are examined for the starting antibody and each corresponding antibody variant at pH 5.5 and pH 7.4 to inform on two criteria: a) enhanced dissociation (i.e., higher koff values) at pH 5.5 due to histidine or alanine substitution compared to the starting antibody, and b) reduced dissociation at pH 7.4 (i.e., lower koff values) compared to pH 5.5 in the antibody variant itself and with the starting antibody. Variants that show either enhanced dissociation at pH 5.5 or reduced dissociation at pH 7.4 or both are selected for further analysis. It is also noted that while some histidine and alanine mutations obliterate MET binding, others are tolerated with little (e.g., less than 1-fold change in $K_D$ or dissociation rate) or no change in MET binding kinetics. Especially because histidine is a large, positively charged amino acid, these histidine variants and alanine variants with no change are noted as positions that may tolerate a wide range of mutations and lead to antibodies with different sequence but similar binding properties, a designation that is not otherwise apparent. The variants selected for further analysis are expressed at a larger scale and purified using protein A affinity chromatography. Binding kinetics (kon and koff) of the purified starting antibody and variant antibodies are measured at pH 5.5 and pH 7.4 using Biacore (GE Healthcare). The ratio of the antibody's rate of dissociation (koff at pH 7.4 divided by koff at pH 5.5) is also used as a quantitative assessment of pH-dependent binding; similarly, the dissociation constant KD is calculated at both pH 5.5 and pH 7.4 as koff divided by kon and the ratio of the antibody's dissociation constant (KD at pH 7.4 divided by KD at pH 5.5) is also used as a quantitative assessment of pH-dependent binding. Antibodies with a rate of dissociation ratio less than that of the starting antibody and/or a dissociation constant ratio less than that of the starting antibody are selected for further assessment of combinatorial substitutions. Favorable histidine and/or alanine amino acid positions can also be combined to enhance pH dependence; this can be done by, e.g., combinatorially or rationally combining histidine and/or alanine substitutions on a given heavy or light chain that individually improve pH dependence, by, e.g., combinatorially or rationally combining modified heavy and light chains such that histidine and/or alanine substitutions are present on both chains, or combinations thereof. Such combinatorial variants are generated and tested/analyzed for differential pH dependence using the methods and protocols described herein, or others known to the art. Antibody variants that have the lowest rate of dissociation ratios and/or dissociation constant ratios are selected as candidates for further analysis (hereafter referred to as "pH-engineered antibodies specific for MET").

The second method for selection of pH-engineered antibodies specific for MET involves either screening libraries to identify de novo pH-dependent antibodies specific for MET or antibodies that could serve as templates for engineering pH-dependent binding as described herein. Two types of libraries can be used for these selections: naive phage/yeast display antibody libraries (e.g., Fab, scFv, VHH, VL, or others known to the art) or phage/yeast display libraries where CDRs have been mutated to express a subset of amino acid residues. Libraries are screened against soluble recombinant MET extracellular domains using methods known to the art with positive selection for variants that bind weakly (e.g., are eluted from beads) at pH 5.0 and bind strongly (e.g., are bound to beads) at pH 7.4. Three rounds of selections are performed. The final round of binders are screened using ELISA for binding to human MET and cyno MET and mouse MET or via mean fluorescence intensity in flow cytometric analysis. If more binders with cyno or murine cross-reactivity are desired, the final selection round can instead be performed on cyno MET or murine MET. Selected binding proteins are subcloned into mammalian expression vectors and expressed as either full IgG proteins or Fc fusions in Expi293 cells. BLI analysis is performed as described herein for selection of pH-dependent binder variants and confirmed using Biacore.

Example 2. In Vitro Demonstration of pH-Dependent Binding to MET, pH-Dependent Release of MET, Enhanced Endolysosomal Delivery in MET+ Cells, and Increased MET Antigen Density in MET+ Cells after Exposure to pH-Engineered Antibodies Specific for MET as Compared to Control Antibodies Specific for MET As discussed herein, pH-engineered antibodies specific for MET exhibit the desirable property of decreased MET binding at acidic pH (e.g., pH 5.0, pH 5.5), but enhanced binding at higher pH (e.g., pH 7.4), which enhances their accumulation in endolysosomes under physiological conditions.

pH-Dependent Binding to MET on Cells

To demonstrate that pH-engineered antibodies specific for MET binds cell surface MET at neutral pH, a cell surface binding assay is performed. A panel of human cells that are MET+ is assembled (e.g., Hs 746T ATCC Cat #HTB-135, NCI-H441 ATCC Cat #HTB-174, NCI-H820 ATCC Cat #HTB-181). Methods of identifying and quantifying gene expression (e.g., MET) for a given cell line are known to the art, and include, e.g., consulting the Cancer Cell Line Encyclopedia (CCLE; https://portals.broadinstitute.org/ccle) to ascertain the expression level and/or mutation status of a given gene in a tumor cell line), rtPCR, microarray, or RNA-Seq analysis, or cell staining with antibodies known in the art (e.g. Telisotuzumab or Cell Signaling Technology Met (D1C2) XP Rabbit mAb Cat #8198, or R&D Systems Human HGFR/c-MET Antibody Clone #95106 Cat #MAB3582 for MET). Cells are seeded at approximately 5-10,000 per well in 150 μL of pH 7.4 culture medium and incubated at 37° C. for 5 minutes at several doses (e.g., a two-fold dilution series) from 1 pM to 1 μM with one of the following antibodies: a known, control antibody specific for MET (e.g., an antibody, Telisotuzumab, emibetuzumab, hucMET27Gv1.3, or P3D12), the pH-engineered antibody specific for MET, and an appropriate negative isotype control mAb (e.g., Biolegend Purified Human IgG1 Isotype Control Recombinant Antibody, Cat #403501). Prior to the onset of the experiment, the binding properties of all antibodies are validated using methods known to the art. Following the 5 minute incubation, cells are fixed with 4% formaldehyde (20 min at room temperature) and incubated with an appropriate fluorophore-labeled secondary antibody (e.g., ThermoFisher Mouse anti-Human IgG1 Fc Secondary Antibody, Alexa Fluor 488, Cat #A-10631) for 60 minutes.

Unbound reagents are washed with a series of PBS washes, and the cell panels are imaged using confocal microscopy. Upon analysis of the images, significant fluorescence can be observed on the surface of cells bound with the known, control antibody specific for MET as well as the pH-engineered antibody specific for MET, but little surface binding can be observed for the isotype negative control. To isolate the effect of pH on surface binding, the same experiment is repeated twice, with the primary antibody incubation taking place at sequentially lower pH (e.g., pH 6.5 and 5.5 and 5.0). Analysis of the resulting confocal microscopy images can show significant fluorescence on the surface of cells bound with all mAbs tested, excepting the isotype negative control, and that this fluorescence decreases for the pH-engineered antibody specific for MET as the pH decreases. Alternatively, cells are analyzed for mean fluorescent intensity by flow cytometry using methods known in the art. A dissociation constant KD on cells at neutral pH of the antibodies analyzed is determined by nonlinear regression methods known in the art (e.g., a Scatchard plot). Taken together, the results can show that the pH engineering process results in the creation of a pH-engineered antibody specific for MET that is pH-dependent in its binding properties and that it more effectively binds at neutral pH as compared to more acidic pH. Other methods of assessing the pH dependence of the pH-engineered antibodies specific for MET are known in the art and include, e.g., using flow cytometry to measure antibody surface binding.

pH-Dependent Release of MET on Cells

To demonstrate that pH-engineered antibodies specific for MET are capable of releasing MET at low pH after binding at a neutral pH, a variant of the cell surface binding assay described above is performed using methods known to the art (e.g., as generally described in Gera N. (2012) PLoS ONE 7(11): e48928). Briefly, an appropriate MET+ cell line (passage number less than 25) is harvested and 50,000 cells per well are plated in a U-Bottomed 96-well microplate. Three conditions are tested; binding and secondary staining at pH 7.4, binding and secondary staining at pH 5.0, and binding at pH 7.4 followed by release at pH 5.0 for 30 minutes and secondary staining at pH 7.4. Both pH-engineered antibodies specific for MET as well as a control antibody specific for MET are tested. The cells are washed two times with 200 µL of FACS buffer (1×PBS containing 3% Fetal Bovine Serum) at either pH 7.4 or 5.0 depending on the condition being tested. The purified protein samples are diluted into FACS buffer of the appropriate pH and added to the cells and allowed to bind for one hour on ice. After incubation with the primary antibodies the pH 7.4 and pH 5.0 conditions are washed twice as before, and then 100 µl of secondary rat anti-human Fc AF488 (BioLegend 410706) or other appropriate antibody, diluted 1:50, or anti Myc-Tag mouse mAb-AF488 (Cell Signaling Technologies 2279S) diluted 1:50 is added in FACS buffer of the appropriate pH, and incubated for 30 minutes on ice. The pH 5.0 release condition is washed twice with FACS buffer pH 7.4 and then resuspended in 100 µl of FACS buffer pH 5.0 and incubated on ice for 30 minutes, followed by secondary staining in FACS buffer pH 7.4 as described for the other conditions. The plates are washed twice as before and resuspended in 1% paraformaldehyde in the appropriate FACS buffer to fix them for flow cytometry analysis. All conditions are read on a flow cytometer (Accuri C6, BD Biosciences). Binding is observed as a shift in the FL1 signal (as a mean fluorescence intensity) versus secondary alone. Upon analysis of the data, it can be determined that both the pH-engineered antibody specific for MET as well as the control antibody specific for MET effectively bind the surface of MET+ cells at neutral pH, but the pH-engineered antibody specific for MET binds poorly at pH 5.0; similarly, it can be determined that the pH-engineered antibody specific for MET binds effectively at pH 7.4, but then releases/unbinds MET at pH 5.0.

Enhanced Endolysosomal Delivery in MET+ Cells of pH-Engineered Antibodies Specific for MET as Compared to Control Antibodies Specific for MET (pHrodo)

To verify and demonstrate that antibodies specific for MET achieve endolysosomal localization following cellular uptake, an internalization assay is performed using methods known to the art (e.g., Mahmutefendic et al., Int. J. Biochem. Cell Bio., 2011). Briefly, as described herein, a panel of human cells that express MET highly is assembled using methods known to the art. Cells are plated, washed three times with PBS, and incubated at 37 degrees C. for 60 minutes in media at neutral pH, with added concentrations of 2 micrograms per milliliter of a known, control antibody specific for MET (e.g., as described herein), the pH-engineered antibody specific for MET, and an appropriate negative isotype control mAb (e.g., as described herein). In a subset of cells, validation of antibody internalization and endosomal localization is performed using methods known to the art; e.g., cells are fixed in 4% formaldehyde as described herein, permeabilized using TWEEN 20 or other methods known to the art (Jamur M C et al (2010) Permeabilization of cell membranes, Methods Mol Biol. 588:63-6), additionally stained with an endosomal marker, e.g., a fluorescent RAB11 antibody (RAB11 Antibody, Alexa Fluor 488, 3H18L5, ABfinity™ Rabbit Monoclonal), stained with an appropriate fluorescently labeled anti-human secondary antibody (e.g., as described herein), and imaged using confocal fluorescence microscopy, as described herein. Analysis of the confocal images can be used to show that both the pH-engineered antibody specific for MET as well as the control antibody specific for MET are internalized and accumulate in the endolysosomes.

To demonstrate that pH-engineered antibodies specific for MET achieve enhanced endolysosomal accumulation relative to a control antibody specific for MET, a pHrodo-based internalization assay is performed using both a known, control antibody specific for MET (e.g., as described herein) as well as the pH-engineered antibody specific for MET. The assay makes use of pHrodo™ iFL (P36014, ThermoFisher), a dye whose fluorescence increases with decreasing pH, such that its level of fluorescence outside the cell at neutral pH is lower than its level of fluorescence inside the acidic pH environment of endolysosomes. Briefly, an appropriate MET+ cell line (less than passage 25) is suspended in its recommended media (e.g., by cell banks or cell bank databases ATCC, DSMZ, or ExPASy Cellosaurus) and plated in a 24-well plate at a density of 2,000,000 cells/mL, 1 mL per well. While keeping the cells on ice, 1 mL of 2× pHrodo iFL-labeled antibody (prepared in accordance with the manufacturer's instructions) is added to each well, the well is pipetted/mixed five times, and the plate is incubated in a light-protected environment for 45 minutes, on ice. An identical but separate plate is also incubated on ice that is meant as a no-internalization negative control. Following this incubation, the experimental plate is moved to a 37 degree C. incubator, the negative control plate is kept on ice to slow or block internalization, and samples are taken at designated time points to create an internalization time course. Samples are placed into a U-bottom 96-well plate, and internalization is quenched via addition of 200 µL/well of ice-cold FACS buffer. The plates are spun down at 2000×g for 2 minutes, resuspended in 200 µL ice-cold FACS buffer, spun down again, and resuspended in FACS buffer a second time. Finally, the samples are loaded into a flow cytometer for read-out of cellular pHrodo fluorescence using excitation and emission wavelengths consistent with the excitation and emission maxima of the pHrodo iFL Red dye (566 nm and 590 nm, respectively). Upon completion of the flow cytometry experiment and analysis of the data, it can be observed that cells treated with the pH-engineered antibody specific for MET have a higher pHrodo iFL signal relative to a known, control antibody specific for MET, indicating that pH-engineered antibodies specific for MET achieve enhanced endolysosomal accumulation relative to a control antibody specific for MET.

Alternatively, to demonstrate that pH-engineered antibodies specific for MET achieve enhanced endolysosomal accumulation relative to a control antibody specific for MET, a variation of the above-described experiment is performed. MET+ cells are plated, washed three times with PBS, and incubated at 37 degrees C. for 60 minutes in media at neutral pH with added concentrations of 2 µg/mL of either pH-engineered antibody specific for MET or control antibody specific for MET. Following incubation, cells are washed three times with PBS, fixed and permeabilized, and stained with a panel of appropriately selected antibodies that bind late endosomal markers as well as lysosomes (e.g., RAB7, and LAMP1; Cell Signaling Technology, Endosomal Marker Antibody Sampler Kit #12666; AbCam, Anti-LAMP2 antibody [GL2A7], ab13524). After primary antibody staining, cells are stained with an appropriate mixture of fluorescently labeled secondary antibodies (e.g., Goat Anti-Human IgG (H&L) Secondary Antibody (Alexa Fluor 647), Cat #A-21445, and Abcam Goat Anti-Rabbit IgG H&L (Alexa Fluor 488), Cat #ab150077), imaged using confocal fluorescence microscopy, and regions of co-localization of signal from MET-specific antibodies and endosomal markers are visualized and quantified. Upon analysis of the data, it can be revealed that there is increased co-localization of endolysosomal and MET-specific antibody signal in wells treated with the pH-engineered antibodies specific for MET as compared to wells treated with control antibody specific for MET, and can thereby demonstrate that pH-engineered antibodies specific for MET achieve enhanced endolysosomal accumulation relative to control antibody specific for MET.

Increased MET Antigen Density in MET+ Cells after Exposure to pH-Engineered Antibodies Specific for MET as Compared to Control Antibodies Specific for MET To demonstrate that treatment of cells with the pH-engineered antibodies specific for MET does not result in a detectable reduction of the level of MET on the surface of cells exposed to the pH-engineered antibodies specific for MET, or that said treatment results in less of a reduction of the level of MET on the surface of cells exposed to the pH-engineered antibody specific for MET versus a control antibody specific for MET, an antigen density study is performed using flow cytometry. Briefly, 4.0×10^5 cells that express MET are plated per well in a 96-well plate in 100 µL media. Cells are treated with a titration from 1 pM to 1 µM of i) pH-engineered antibodies specific for MET, ii) a first control antibody specific for MET, iii) an appropriate isotype control, and iv) an untreated control. Cells are incubated for 2 hours at 37° C., at which point all cells are incubated with 200 nM of a fluorophore-labeled second control antibody specific for MET (e.g., as described herein) which has a different epitope (as determined by, e.g., competitive binding studies on cells) than either the first control antibody specific for MET or the pH-engineered antibodies specific for MET for 30 minutes at 4° C. Following this 30-minute incubation, the mean fluorescence intensity (MFI) of all cells is read out using, e.g., flow cytometry, using methods known to one of ordinary skill in the art. In parallel, a quantitative standard curve that can be used to quantify the presence of MET on the surface of treated cells as a function of MFI is generated using a commercially available quantification kit (e.g., BD Biosciences PE Phycoerythrin Fluorescence Quantitation Kit, catalog #340495); the quantitative standard curve is created by following the manufacturer's instructions. Other methods of determining the absolute number of MET on the cell surface are known in the art and include, e.g., use of radioisotopically labeled reagents. Upon analysis of the data, it can be revealed that at least one antibody concentration, cells treated with a control antibody specific for MET experience a reduction of the level of MET on their surface, whereas cells treated with pH-engineered antibodies specific for MET experience a significantly smaller reduction or no reduction at all, both relative to the isotype and untreated controls.

Example 3. Conjugation of pH-Engineered and Control Antibodies Specific for MET to Cytotoxic Drugs An antibody conjugate (ADC) is made comprising the MET-binding IgG (hereafter, MET-IgG) described herein linked to monomethyl auristatin E (MMAE) via a valine-citrulline (vc) linker (hereafter, MET-IgG-DC). Conjugation of the antigen-binding protein construct with vcMMAE begins with a partial reduction of the MET-IgG followed by reaction with maleimidocaproyl-Val-Cit-PABC-MMAE (vcMMAE). The MET-IgG (20 mg/mL) is partially reduced by addition of TCEP (molar equivalents of TCEP:mAb is 2:1) followed by incubation at 0° C. overnight. The reduction reaction is then warmed to 20° C. To conjugate all of the thiols, vcMMAE is added to a final vcMMAE:reduced Cys molar ratio of 1:15. The conjugation reaction is carried out in the presence of 10% v/v of DMSO and allowed to proceed at 20° C. for 60 minutes.

After the conjugation reaction, excess free N(acetyl)-Cysteine (2 equivalents vs. vcMMAE charge) is added to quench unreacted vcMMAE to produce the Cys-Val-Cit-MMAE adduct. The Cys quenching reaction is allowed to proceed at 20° C. for approximately 30 minutes. The Cys-quenched reaction mixture is purified as per below. The above conjugation method can also be used to conjugate maleimidocaproyl monomethylauristatin F (mcMMAF) to an antigen-binding protein construct.

The MET-IgG-DC is purified using a batch purification method. The reaction mixture is treated with the appropriate amount of water washed Bu-HIC resin (ToyoPearl; Tosoh Biosciences), i.e., seven weights of resin is added to the mixture. The resin/reaction mixture is stirred for the appropriate time, and monitored by analytical hydrophobic interaction chromatography for removal of drug conjugate products, filtered through a coarse polypropylene filter, and washed by two bed volumes of a buffer (0.28 M sodium chloride, 7 mM potassium phosphate, pH 7). The combined filtrate and rinses are combined and analyzed for product profile by HIC HPLC. The combined filtrate and rinses are buffer exchanged by ultrafiltration/diafiltration (UF/DF) to 15 mM histidine, pH 6 with 10 diavolumes 15 nM histidine buffer.

A similar protocol can be used to conjugate DNA toxins such as SG3249 and SGD-1910 to MET-IgG (see Tiberghien A C et al (2016) Design and Synthesis of Tesirine, a Clinical Antibody-Drug Conjugate Pyrrolobenzodiazepine Dimer Payload, ACS Med Chem Lett 7:983-987). Briefly, for SG3249, MET-IgG (15 mg, 100 nanomoles) is diluted into 13.5 mL of a reduction buffer containing 10 mM sodium borate pH 8.4, 2.5 mM EDTA and a final antibody concentration of 1.11 mg/mL. A 10 mM solution of TCEP is added (1.5 molar equivalent/antibody, 150 nanomoles, 15 microliters) and the reduction mixture is heated at +37° C. for 1.5 hours in an incubator. After cooling down to room temperature, SG3249 is added as a DMSO solution (5 molar equivalent/antibody, 500 nanomoles, in 1.5 mL DMSO). The solution is mixed for 1.25 hours at room temperature, then the conjugation is quenched by addition of N-acetyl cysteine (1 micromole, 100 microliters at 10 mM), and injected into an AKTA™ Pure FPLC using a GE Healthcare HiLoad™ 26/600 column packed with Superdex 200 PG, and eluted with 2.6 mL/min of sterile-filtered phosphate-buffered saline (PBS). Fractions corresponding to the MET-IgG-DC monomer peak are pooled, concentrated using a 15 mL Amicon Ultracell 50 KDa MWCO spin filter, analysed and sterile-filtered. UHPLC analysis on a Shimadzu Prominence system using a Phenomenex Aeris 3.6u XB-C18 150×2.1 mm column eluting with a gradient of water and acetonitrile on a reduced sample of MET-IgG-DC at 280 nm and 330 nm (SG3249 specific) can show a mixture of light and heavy chains attached to several molecules of SG3249, consistent with a drug-per-antibody ratio (DAR) of 1 to 4 molecules of SG3249 per antibody. UHPLC analysis on a Shimadzu Prominence system using a Phenomenex Yarra 3u SEC-3000 300 mm×4.60 mm column eluting with sterile-filtered SEC buffer containing 200 mM potassium phosphate pH 6.95, 250 mM potassium chloride and 10% isopropanol (v/v) on a sample of MET-IgG-DC at 280 nm can show a monomer purity of over 90% with no impurity detected. UHPLC SEC analysis allows determination of final MET-IgG-DC yield of greater than 30%.

Alternatively, methods to conjugate toxins to antibodies via lysine residues are known in the art (e.g., see Catcott K C et al (2016) Microscale screening of antibody libraries as maytansinoid antibody-drug conjugates, MAbs 8:513-23). In addition, similar methods to the above can be used to conjugate drugs and toxins to non-IgG formats with disulfide bonds, such as Vh-Fcs.

Example 4. Demonstration of Enhanced Cytotoxicity of pH-Engineered ADCs Specific for MET in MET+ Cells as Compared to a Control ADC Specific for MET The cytotoxic activity of both pH-engineered ADCs specific for MET (e.g., a pH-engineered MET-IgG-DC) and control antibody ADCs specific for MET (e.g., a control antibody MET-IgG-DC) are separately evaluated on a panel of MET+ cell lines expressing a variety of antigen densities (e.g., as described herein) and a MET− cell line (e.g., T-47D ATCC Cat #HTB-133), selected using the methods described herein, and, optionally, cells expressing transgenic MET, e.g., HEK293 cells transfected with MET using methods known in the art (e.g., Expi293™ Expression System Kit ThermoFisher Catalog number: A14635). For purposes of validation, prior to use, all cell lines are tested for expression of MET using methods known to the art, e.g., qPCR, flow cytometry, mRNA RPKM, and antibody staining using anti-MET antibodies known to the art (e.g., as described herein) followed by visualization of the stain using fluorescence microscopy, immunohistochemistry, flow cytometry, ELISA, or other methods known to the art. To evaluate the cytotoxicity of compounds, cells are seeded at approximately 10-40,000 per well in 150 microliters of culture medium, then treated with graded doses of compounds from 1 pM to 1 µM in quadruplicates at the initiation of the assay. Cytotoxicity assays are carried out for 96 hours after addition of test compounds. Fifty microliters of resazurin dye are added to each well during the last 4 to 6 hours of the incubation to assess viable cells at the end of culture. Dye reduction is determined by fluorescence spectrometry using the excitation and emission wavelengths of 535 nm and 590 nm, respectively. For analysis, the extent of resazurin reduction by the treated cells is compared to that of untreated control cells, and percent cytotoxicity is determined. Alternatively, a WST-8 kit is used to measure cytotoxicity per the manufacturer's instructions (e.g., Dojindo Molecular Technologies Catalog #CCK-8). IC50, the concentration at which half-maximal killing is observed, is calculated using curve-fitting methods known in the art. Upon analysis of the data, it can be determined that pH-engineered and control antibody ADCs specific for MET are substantially cytotoxic to one or more MET+ cell line, but less toxic to MET− cells. It also can be determined that pH-engineered ADCs specific for MET are more cytotoxic to one or more MET+ cell lines than control antibody ADCs specific for MET because: a) they show greater depth of killing at one or more concentrations or, b) they show lower IC50 or, c) they show a greater ratio of their dissociation constant KD on cells at neutral pH (as described herein) divided by their IC50 on those same cells.

Additionally, the cytotoxic activity of antibodies specific for MET can be measured in a secondary ADC assay. Secondary ADC assays are known in the art (e.g., Moradec Cat #αHFc-NC-MMAF and Cat #αHFc-$C_L$-MMAE, and associated manufacturer's instructions). Briefly, the assay is carried out as in the previous paragraph, except the antibody specific for MET is substituted for the ADC specific for MET, and to evaluate the cytotoxicity of compounds, cells are seeded at approximately 10-40,000 per well in 150 microliters of culture medium, then treated with graded doses of antibody specific for MET from 1 pM to 1 µM (final concentration in culture medium, having been pre-mixed with 100 nM, final concentration in culture medium, of Moradec Cat #αHFc-NC-MMAF secondary ADC reagent and pre-incubated at 37° C. for 30 min before addition of the mixture to the culture medium) in quadruplicates at the initiation of the assay.

The cytotoxic activity of pH-engineered ADCs specific for MET and control antibody ADCs specific for MET conjugates, as well as antibodies specific for MET in a secondary ADC assay, are additionally measured by a cell proliferation assay employing the following protocol (Promega Corp. Technical Bulletin TB288; Mendoza et al., Cancer Res. 62:5485-5488, 2002):

1. An aliquot of 100 microliters of cell culture containing about 104 cells (e.g., MET+ cells as described herein) in medium is deposited in each well of a 96-well, opaque-walled plate.
2. Control wells are prepared containing medium and without cells.
3. ADC specific for MET is added to the experimental wells at a range of concentrations from 1 pM-1 µM and incubated for 1-5 days. Alternatively, in a secondary ADC assay, 100 nM secondary ADC reagent (final concentration in culture medium, Moradec Cat #αHFc-NC-MMAF) and antibody specific for MET at a range of concentrations from 1 pM-1 µM (final concentration in culture medium) are pre-mixed and pre-incubated at 37° C. for 30 min before addition of the mixture to the culture medium, and incubated for 1-5 days.
4. The plates are equilibrated to room temperature for approximately 30 minutes.
5. A volume of CellTiter-Glo Reagent equal to the volume of cell culture medium present in each well is added.
6. The contents are mixed for 2 minutes on an orbital shaker to induce cell lysis.
7. The plate is incubated at room temperature for 10 minutes to stabilize the luminescence signal.
8. Luminescence is recorded and reported in graphs as RLU=relative luminescence units.

Example 5. Demonstration of Enhanced Toxin Liberation of pH-Engineered ADCs Specific for MET in MET+ Cells as Compared to a Control ADC Specific for MET The pH-engineered ADCs specific for MET (e.g., a pH-engineered MET-IgG-DC) can also demonstrate increased toxin liberation in MET+ cells as compared to a control antibody ADC specific for MET (e.g., a control antibody MET-IgG-DC). After treatment of MET+ cells with pH-engineered and control antibody ADCs specific for MET as described herein, an LC-MS/MS method is used to quantify unconjugated (i.e., liberated) MMAE in treated MET+ cells (Singh, A. P. and Shah, D. K. Drug Metabolism and Disposition 45.11 (2017): 1120-1132.) An LC-MS/MS system with electrospray interphase and triple quadrupole mass spectrometer is used. For the detection of MMAE, a)(Bridge BEH Amide column (Waters, Milford, MA) is used with mobile phase A as water (with 5 mM ammonium formate and 0.1% formic acid) and mobile phase B as 95:5 acetonitrile/water (with 0.1% formic acid and 1 mM ammonium formate), using a gradient at a flow rate of 0.25 mL/min at 40° C. The total duration of the chromatographic run is 12 minutes, where two MRM scans (718.5/686.5 and 718.5/152.1 amu) are monitored. Deuterated (d8) MMAE (MCE MedChem Express, Monmouth Junction, NJ) is used as an internal standard. First, an equation for quantifying unconjugated MMAE in a biological sample is derived by dividing the peak area for each drug standard by the peak area obtained for the internal standard. The resultant peak area ratios are then plotted as a function of the standard concentrations, and data points are fitted to the curve using linear regression. Three QC samples are included in the low, middle, and upper ranges of the standard curve to assess the predictive capability of the developed standard curve. The standard curves obtained are then used to deduce the observed concentrations of MMAE in a biologic sample. For measurement of MMAE concentration, treated cell samples are pelleted and reconstituted in fresh media to a final concentration of 0.25 million cells/100 µL. Samples are spiked with d8-MMAE (1 ng/mL) before performing cell lysis by the addition of a 2-fold volume of ice-cold methanol followed by freeze-thaw cycle of 45 minutes at −20° C. The final cell lysate is obtained by centrifuging the samples at 13,000 rpm for 15 minutes at 4° C. followed by collection of supernatant. For the preparation of standards and QC samples, a fresh cell suspension (0.25 million/100 µl) is spiked with known concentrations of MMAE and internal standard (d8-MMAE) before a procedure similar to the cell lysis mentioned above. The resulting cell lysates are then evaporated and reconstituted in mobile phase B before injection into LC-MS/MS. The concentration of unconjugated MMAE in lysates of MET+ cells treated with pH-engineered ADCs specific for MET is observed to be greater than that in MET+ cells treated with control antibody ADC specific for MET.

For tubulin-inhibiting toxins, toxin liberation is also assessed by monitoring of cell viability and cell cycle phase. ~2.0×10^5 MET+ cells are plated in a 96-well flat bottom plate and treated with pH-engineered and control antibody ADCs specific for MET as described herein. After treatment, cells are transferred to a 96-round bottom plate, and the plate is centrifuged at 400 rcf for 2 min to decant supernatant. Decanted cells are stained with Live/Dead eFluor 660. Cells are then centrifuged and washed with FACS buffer (PBS with 2% FBS), after which cell cycle distribution is analyzed with a BD Cycletest™ Plus DNA Kit (cat #340242). Briefly, cells are re-suspended in 76 ul Solution A and incubated for 10 min at room temperature. 61 µL Solution B is then added, and cells are incubated for another 10 min at room temperature. Finally, 61 µL of cold Solution C is added, and cells are again incubated for 10 min at room temp. Immediately after the last incubation step, cells are analyzed by flow cytometry (without washing) at a flow rate of 10 µL/sec. Increased G2/M-phase arrest can be observed with exposure to pH-engineered ADCs specific for MET as compared to control antibody ADC specific for MET.

For DNA-damaging toxins (e.g., pyrrolobenzodiazepine or "PBD"), DNA damage is assessed by measuring the phosphorylated histone H2AX (γH2AX). H2AX is normally phosphorylated in response to double-strand breaks in DNA; however, increased levels γH2AX may also be observed as a result of treatment with DNA-cross-linking toxins such as PBD or cisplatin (Huang, X. et al. 2004, Cytometry Part A 58A, 99-110). MET+ cells are treated with pH-engineered and control antibody ADCs specific for MET as described herein. After treatment, cells are rinsed with PBS, and then fixed in suspension in 1% methanol-free formaldehyde (Polysciences, Warrington, PA) in PBS at 0° C. for 15 min. Cells are resuspended in 70% ethanol for at least 2 h at −20° C. Cells are then washed twice in PBS and suspended in 0.2% Triton X-100 (Sigma) in a 1% (w/v) solution of BSA (Sigma) in PBS for 30 min to suppress nonspecific Ab binding. Cells are centrifuged again (200 g, 5 min) and the cell pellet is suspended in 100 µL of 1% BSA containing 1:800 diluted anti-histone γH2AX polyclonal Ab (Trevigen, Gaithersburg, MD). The cells are then incubated overnight at 4° C., washed twice with PBS, and resuspended in 100 µL of 1:30 diluted FITC-conjugated F(ab')2 fragment of swine anti-rabbit immunoglobulin (DAKO, Carpinteria, CA) for 30 min at room temperature in the dark. The cells are then counterstained with 5 µg/mL of PI (Molecular Probes, Eugene, OR) dissolved in PBS containing 100 µg/mL of DNase-free RNase A (Sigma), for 20 min at room temperature. Cellular fluorescence of the FITC γH2AX signal and the PI counterstain are measured using flow cytometry using methods known in the art. When comparing cells within the same stage of the cell cycle (based on total DNA content), treated MET+ cells can be observed to have an increased FITC γH2AX signal relative to untreated MET+ cells (which serve as a baseline). Furthermore, MET+ cells treated with pH-engineered ADCs specific for MET can be observed to have a greater increase in levels of γH2AX over baseline than cells treated with a control antibodyADC specific for MET. In addition to the γH2AX assay, DNA cross-linking can be more directly assessed with a Comet assay (Chandna, S. (2004) Cytometry 61A, 127-133).

In addition, as disclosed herein, pH-engineered and control antibodies can be assayed using the methods in this example without direct conjugation by performing a secondary ADC assay instead of using primary conjugated ADCs.

Example 6. Demonstration of Decreased Half-Life of pH-Engineered Antibodies Specific for MET as Compared to a Control Antibody Specific for MET in Tumor-Bearing Animals One of the surprising aspects of the pH-engineered antibodies specific for MET described by the invention can be their ability to facilitate increased dissociation of antibodies from the MET within the endosome or lysosome resulting in a decreased serum half-life relative to control antibodies specific for MET or antibodies that are not specific for MET in tumor-bearing animals. This decreased serum half-life is due to the enhanced frequency with which pH-engineered antibodies specific for MET are cleared from circulation due to their enhanced cellular internalization by tumor cells once bound to MET, which over time can be observed through a decrease in serum concentration of unbound pH-engineered antibody specific for MET in tumor-bearing animals. To demonstrate these properties, a series of animal studies in tumor bearing mice is performed using pH-engineered antibody specific for MET and control antibody specific for MET using methods known to the art (e.g., Gupta, P., et al. (2016), mAbs, 8:5, 991-997). Briefly, to conduct mouse studies, a single intravenous bolus (e.g., 5 mg/kg) of either pH-engineered antibody specific for MET or control antibody specific for MET is administered via tail vein to two groups of NOD SCID mice (e.g. Jackson Labs NOD.CB17-Prkdcscid/J Stock No: 001303) xenografted with a MET+ cell line (e.g., as described herein). Xenografted mice are prepared by growing 1-5 million MET+ cells in vitro and inoculating subcutaneously into the right flank of the mouse. Tumors are size matched at 300 mm3. Measurements of the length (L) and width (W) of the tumors are taken via electronic caliper and the volume is calculated according to the following equation: $V=L \times W^2/2$. Blood samples are collected via retro-orbital bleeds from each group at each of the following time points: 15 m, 30 m, 1 h, 8 h, 24 h, and 3 d, 7 d, 10 d, 14 d, 17 d, 21 d, and 28 d. Samples are processed to collect serum, and antibody concentrations are quantified using ELISA or other methods known to the art (e.g., PAC assay or MAC assay; Fischer, S. K. et al. (2012), mAbs, 4:5, 623-631, utilizing, e.g., anti-human IgG antibody Jackson ImmunoResearch Labs, Cat #109-006-006). Antibody concentrations of pH-engineered antibody specific for MET and control antibody specific for MET are plotted as a function of time. Upon analysis of the data, it can be observed that the pH-engineered antibody specific for MET has a significantly shorter serum half-life relative to control antibody specific for MET, thereby demonstrating the ability of the pH-engineered antibody specific for MET's pH dependence to facilitate an enhanced dissociation within the endosome or lysosome relative to other, similar binders (e.g., control antibody specific for MET) that bind the same antigen but that differ in their pH dependence.

In addition, the half-life of pH-engineered and control antibody ADCs specific for MET can be assessed using the above methods by substituting pH-engineered and control antibody ADCs specific for MET for the pH-engineered and control antibodies specific for MET (i.e., studying the antibodies after conjugation to a drug or toxin, as described herein).

Example 7. Increased Potency of pH-Engineered ADCs Specific for MET Vs. A Control Antibody ADC Specific for MET in Mouse Xenograft Models The enhanced anti-tumor activity of the pH-engineered ADCs specific for MET against MET+ tumors can be demonstrated in a subcutaneous xenograft model of MET+ cells. For the experiments, 1-5 million MET+ cells are grown in vitro and inoculated subcutaneously per mouse into the right flank of female immunodeficient (e.g., SCID-Beige or NOD scid) mice. Tumors are size matched at 100-200 mm3, and dosed intraperitoneally (IP) (1 dose given every ~4-7 days for a total of ~2-6 doses). Measurements of the length (L) and width (W) of the tumors are taken via electronic caliper and the volume is calculated according to the following equation: $V=L \times W^2/2$. A bolus (e.g., 5 mg/kg) of either pH-engineered ADC specific for MET or control antibody ADC specific for MET is administered via tail vein. Tumor growth inhibition (TGI) and tumor growth delay (TGD) and survival are significantly improved with administration of pH-engineered ADC specific for MET compared to administration of control antibody ADC specific for MET at the same regimen.

Optionally, spread of tumor cells into the various tissues is determined in sacrificed animals. Metastasis is measured according to Schneider, T., et al., Clin. Exp. Metas. 19 (2002) 571-582. Briefly, tissues are harvested and human Alu sequences are quantified by real-time PCR. Higher human DNA levels, quantified by real-time PCR, correspond to higher levels of metastasis. Levels of human Alu sequences (correlating to invasion of tumor cells into secondary tissue) are significantly lower in animals treated with pH-engineered ADC specific for MET, corresponding to reduced metastasis, compared to mice treated with control antibody ADC specific for MET at the same regimen. Alternatively, the enhanced anti-tumor activity of the pH-engineered ADC specific for MET can be shown in MET+ patient-derived xenograft models (e.g., available from The Jackson Laboratory).

Example 8. Creation of a pH-Engineered Bispecific MET Bispecific Antibody and Demonstration of Exemplary Properties as Compared to a Control Bispecific Antibody To create a pH-engineered antibody specific for MET with modified toxicity and internalization properties, a bispecific antibody that binds two different epitopes on MET is constructed. It is known in the art that biparatopic antibodies can show increased antigen-dependent internalization, and are therefore useful for applications such as antibody-drug conjugates (e.g., see Li et al (2016) A Biparatopic HER2-Targeting Antibody-Drug Conjugate Induces Tumor Regression in Primary Models Refractory to or Ineligible for HER2-Targeted Therapy, Cancer Cell 29:117-29). Briefly, a pH-engineered MET×MET bispecific, biparatopic antibody specific for MET is assembled using light chain/heavy chain pairs from two different pH-engineered antibodies specific for MET, each of which binds a distinct epitope on MET that does not overlap with the other epitope. A set of pH-engineered antibodies specific for MET that bind non-overlapping epitopes are discovered, e.g., using the methods described herein, or others known to one of ordinary skill in the art. Briefly, two binders are selected on the basis that they bind substantially different epitopes on MET, as determined by, e.g., a binding competition assay as in Abdiche Y N et al (2009) Exploring blocking assays using Octet, ProteOn, and Biacore biosensors, Anal Biochem 386:172-80. Alternatively, briefly, as described in herein, cell culture supernatants of cells transfected with a first antibody specific for MET are normalized to an antibody expression level of 50 µg/mL, and captured on an anti-human Fc sensor (Forte Bio). A baseline is established using 1× kinetics buffer (Forte Bio), and the sensor is associated with 50 nM of MET in 1×PBS (that has been mixed and pre-incubated for 30 min at 37 degrees C. with a second antibody specific for MET transfection supernatant or the first antibody specific for MET transfection supernatant, both normalized to 50 ug/mL) at pH 7.4 for 300 sec to generate an association curve. If the association rate in the presence of the second antibody specific for MET is significantly faster (as calculated by the instrument software, or as seen by an elevated level of association over time) than the association rate in the presence of the first antibody specific for MET, then the second antibody specific for MET is deemed to bind a non-overlapping epitope of MET. Optionally, each antibody is screened for its internalization properties when bound to its epitope on a cell expressing MET, and well-internalizing antibodies are selected. Assays for determining the internalization rate of a molecule present on the surface of a cell are known to the art. See, e.g., Wiley et al. (1991) J. Biol. Chem. 266: 11083-11094; and Sorkin and Duex (2010) Curr. Protoc. Cell Biol. Chapter, Unit-15.14; Vainshtein et al. (2015) Pharm Res. 32: 286-299. Once selected, heavy and light chain constructs with engineered mutations for heavy and light chain pairing (Spiess et al., "Alternative molecular formats and therapeutic applications of bispecific antibodies," 2015) are synthesized for both arms. Bispecific antibodies specific for MET are produced by co-expression of corresponding heavy and light chain plasmids in, e.g., Expi293 cells. Cell culture supernatants are harvested and subjected to Protein A purification. Heterodimeric antibodies specific for MET are separated from homodimeric species via additional purification steps such as ion exchange chromatography, hydrophobic interaction chromatography, and mixed mode chromatography. The purified pH-engineered MET×MET bispecific, biparatopic antibodies specific for MET are characterized via mass spectrometry to confirm the purity and absence of homodimeric species and size exclusion chromatography to confirm the presence of monomeric antigen-binding protein construct species. For the product antibody, binding to the MET is confirmed via Biacore analysis. Other methods of bispecific antibody production are known to the art and could also be used to create a bispecific antibody, e.g., the MET×MET bispecific, biparatopic antibodies specific for MET described herein (e.g., Labrijn et al (2014) "Controlled Fab-arm exchange for the generation of stable bispecific IgG1" Nature Protcols 9:2450-2463, accessed at http://www.nature.com/nprot/journal/v9/n10/abs/nprot.2014.169.html), as would be apparent to one of ordinary skill in the art. Alternatively, instead of a MET×MET antibody specific for MET, a pH-engineered MET×BINDER antibody specific for MET can be constructed using similar methods apparent to one skilled in the art, where BINDER is any antibody that has been published in the art or discovered using methods like those herein or those known in the art (e.g., display-based or immunization-based methods).

Next, exemplary properties of pH-engineered MET×MET antibodies specific for MET can be demonstrated using the methods described herein, with the appropriate control being a control antibody monospecific or bispecific antibody specific for MET. Briefly, it can be shown that, as compared to a control, the pH-engineered MET×MET antibodies specific for MET: a) bind in a pH-dependent manner to cells, e.g., bind at a neutral pH but not an acidic pH and b) release from cells in a pH-dependent manner, e.g. bind at a neutral pH and release at an acidic pH and c) show enhanced endolysosomal accumulation in MET+ cells and d) show increased MET antigen density after exposure to MET+ cells and e) when conjugated to a toxin, show increased cytotoxicity to MET+ cells and f) when conjugated to a toxin, show increased toxin liberation when incubated with MET+ cells and g) show decreased half-life when exposed to MET antigen in a relevant animal model and h) when conjugated to a toxin, show increased efficacy in a mouse xenograft model of MET+ cells. Similarly, the exemplary properties of pH-engineered MET×BINDER antibodies specific for MET can be demonstrated using the methods described herein, with the appropriate control being a control antibody MET×BINDER bispecific antibody specific for MET.

Example 9. Construction and Screening of pH-Engineered MET Antibodies

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected Telisotuzumab (Heavy chain SEQ ID NO: 159, Light chain SEQ ID NO: 160) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time. In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 384 instrument. Briefly, 15 µL of cell culture supernatant was diluted into 185 µL of 1×PBST pH 7.4 for loading onto the sensor tips. This resulted in a high concentration of 41.1 µg/mL, a low concentration of 13.7 µg/mL and an average concentration of 26.5 µg/mL. This diluted supernatant was then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of MET (cMET, Sino Biological Cat. No. 10692-H08H, Lot No. LC11SE2008) in 1×PBST pH 7.4 for 120 sec to generate an association curve. In the dissociation phase, the antibody-antigen complex on the sensor was exposed to 1×PB ST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody, (with no substitutions), and b) reduced dissociation at pH 7.4 (i.e., lower koff values) compared to pH 5.4 in the antibody variant itself and with the starting antibody (with no substitutions). Heavy chain variants that showed either enhanced dissociation at pH 5.4 or reduced dissociation at pH 7.4 or both (as compared to the starting antibody), were selected for further analysis. It was also noted that while some histidine and alanine mutations obliterated MET binding, others were tolerated with little (e.g., less than 1-fold change in dissociation constant KD or dissociation rate) or no change in MET binding kinetics.

Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 10. Construction and Screening of pH-Engineered MET Antibodies

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected Telisotuzumab (Heavy chain SEQ ID NO: 159, Light chain SEQ ID NO: 160) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time. In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H) in 1×PB ST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody (with no substitutions), and b) reduced dissociation at pH 7.4 (i.e., lower koff values) compared to pH 5.4 in the antibody variant itself and with the starting antibody (with no substitutions). Light chain variants that showed either enhanced dissociation at pH 5.4 or reduced dissociation at pH 7.4 or both (as compared to the starting antibody), were selected for further analysis (e.g., MYT2040). It was also noted that some histidine and alanine mutations were tolerated with little (e.g., less than 1-fold change in dissociation constant $K_D$ or dissociation rate) or no change in MET binding kinetics. Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 11. Construction and Screening of pH-Engineered MET Antibodies

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected Telisotuzumab (Heavy chain SEQ ID NO: 159, Light chain SEQ ID NO: 160) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 9 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H)) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody (with no substitutions), and b) reduced dissociation at pH 7.4 (i.e., lower koff values) compared to pH 5.4 in the antibody variant itself and with the starting antibody (with no substitutions). Heavy chain combinations variants that showed either enhanced dissociation at pH 5.4 or reduced dissociation at pH 7.4 or both (as compared to the starting antibody), were selected for further analysis.

Example 12. Construction and Screening of pH-Engineered MET Antibodies

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected Telisotuzumab (Heavy chain SEQ ID NO: 159, Light chain SEQ ID NO: 160) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the light chain CDRs that had been previously selected for further analysis in Example 10 were systematically combined two or more at a time. In cases where the starting CDR residue was a histidine, it was mutated to an alanine. Antibody variants with two or more histidine or alanine mutations in the light chain CDRs were generated by co-transfection of Expi293 cells with a) one light chain combinations sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Light chain combinations variants that showed either enhanced dissociation at pH 5.4 or reduced dissociation at pH 7.4 or both (as compared to the starting antibody), were selected for further analysis.

Example 13. Construction and Screening of pH-Engineered MET Antibodies

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected Telisotuzumab (Heavy chain SEQ ID NO: 159, Light chain SEQ ID NO: 160) as a MET-binding monoclonal antibody for pH engineering via histidine scanning. Briefly, CDRs in the heavy and light chains were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy and light chain CDRs that had been previously selected for further analysis in Examples 9-12 were systematically combined two or more at a time. In cases where the starting CDR residue was a histidine, it was mutated to an alanine. Antibody variants with two or more histidine or alanine mutations were generated by co-transfection of Expi293 cells with a) one light chain sequence variant or light chain combinations sequence variant, and b) one heavy chain sequence variant or heavy chain combinations sequence variant using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument.

Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20), pH 7.4, and the sensor was associated with 50 nM of MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Paired heavy and light chain variants that showed either enhanced dissociation at pH 5.4 or reduced dissociation at pH 7.4 or both (as compared to the starting antibody), were selected for further analysis (MYT3463, MYT3477, MYT3491, MYT3603, MYT3604, MYT3606, MYT3607, MYT3608, MYT3609, MYT3610, MYT3611, MYT3612, MYT3614, MYT3615, MYT4211, MYT4212, MYT4214, MYT4217, and MYT4220).

Example 14. Construction and Screening of pH-Engineered MET Antibodies

Figure 1B:
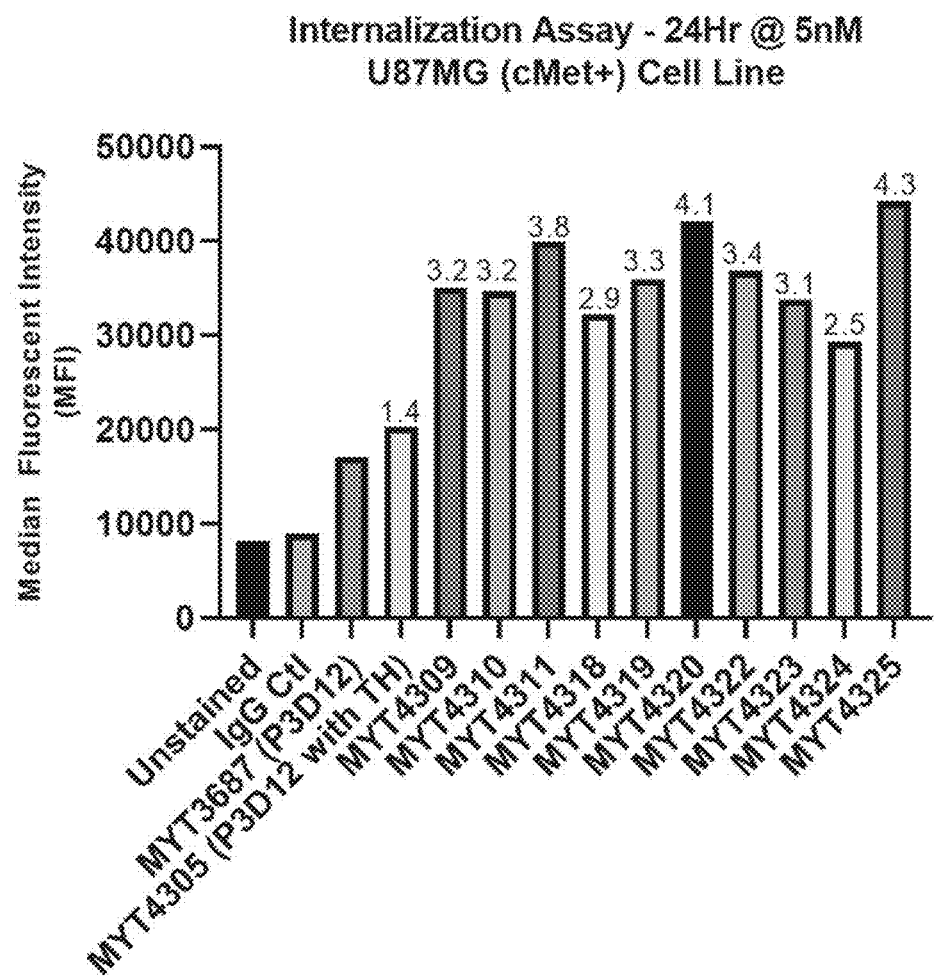
Figure 1C:
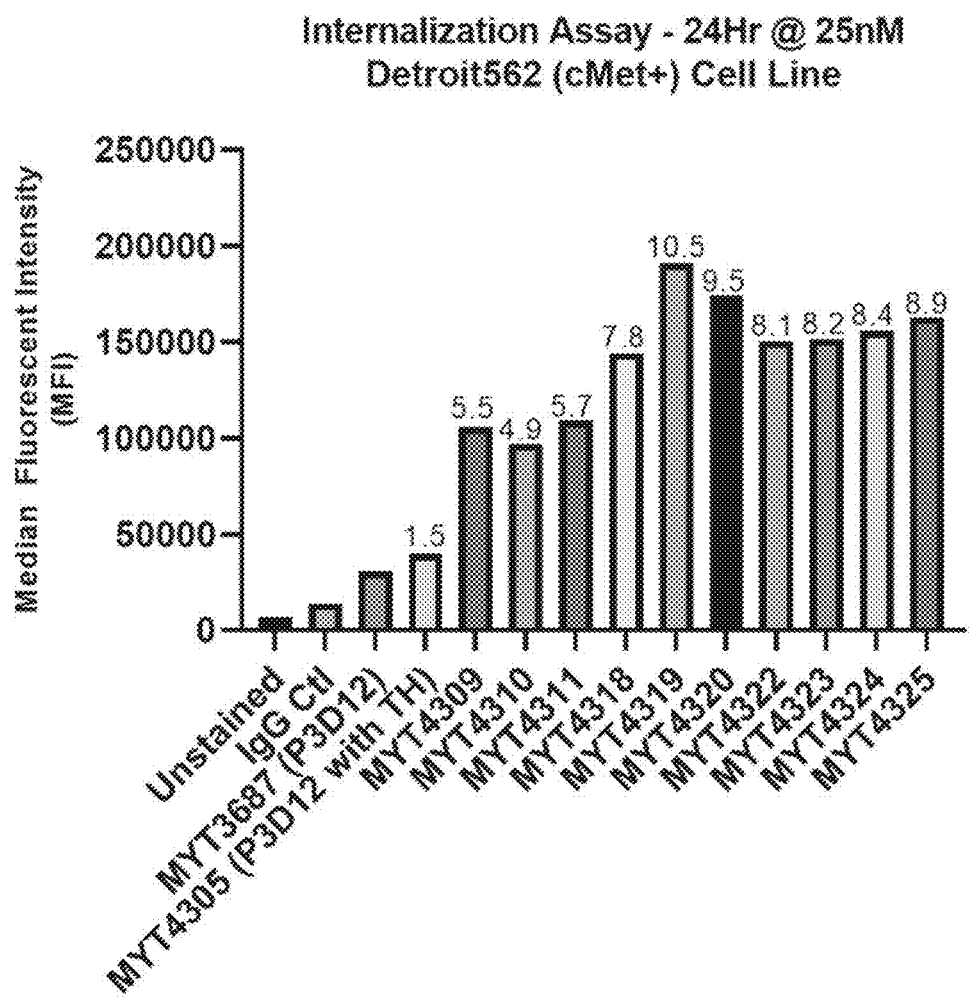
Figure 2:
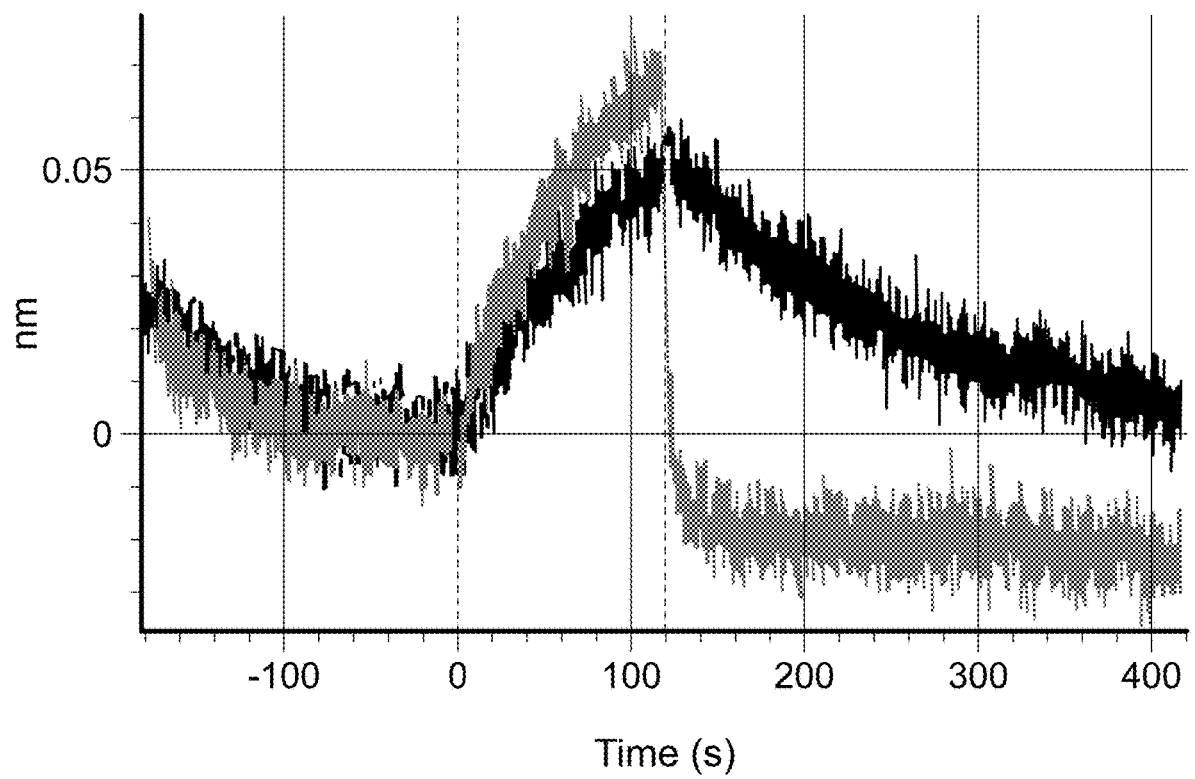
FIG. 2: Binding of histidine scanning and alanine scanning variants of TELISOTUZUMAB to MET by biolayer interferometry. MYT4953 heavy chain combination histidine scanning and alanine scanning variants, were captured on anti-human Fc biosensors and associated with MET at pH 7.4. Dissociation was at pH 7.4 (black trace) or pH 5.4 (grey trace). All variants include the TH and YTE substitution format.

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected Telisotuzumab (Heavy chain SEQ ID NO: 159, Light chain SEQ ID NO: 160) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 9 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant containing the triple hinge (TH) and YTE mutations described in (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000) and (Dall, W F et al "Increasing the Affinity of a Human IgG1 for the Neonatal Fc Receptor: Biological Consequences" The Journal of Immunology (2002); 169:5171-5180) respectively, and b) the corresponding starting antibody light chain using methods known to the art. After allowing for four days of protein expression, cell culture supernatants were collected, quantified by SDS-PAGE analysis, purified using protein A magnetic beads (Genscript L00273), and evaluated for endolysosomal delivery on Detroit 562 cells (ATCC CCL-138). Detroit 562 cells (ATCC; CCL-138) were collected and resuspended in EMEM medium (ATCC; 30-2003)+10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 100,000 cells/mL and 100 ul was seeded into 96-well flat bottom cell culture plates and allowed to attach overnight in 37 C 5% CO2. Primary antibodies were then diluted in native culture mediums to 20 nM and then mixed 1:1 with 60 nM Incucyte Human FabFluor-pH Red Antibody Labeling Reagent (Sartorius; 4722). The mixture was incubated for 20 minutes at room temperature, followed by addition to cells. Plates were then placed immediately into the Incucyte S3 Live-Cell Analysis System for image acquisition and analysis. Endolysosomal delivery was examined for the starting antibody (with no substitutions) and each corresponding antibody variant to inform on enhanced endolysosomal delivery due to histidine or alanine substitution compared to the starting antibody (with no substitutions). Heavy chain combinations variants that showed enhanced endolysosomal delivery (as compared to the starting antibody), e.g., as shown in FIG. 1, were selected for further analysis. The pH dependence of the selected variants were evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4 or pH 5.4, for 300-600 sec. Association and dissociation phase curves at pH 7.4 and pH 5.4 were examined for the starting antibody (with no substitutions) and each corresponding antibody variant to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Heavy chain combinations variants that showed either enhanced dissociation at pH 5.4 or reduced dissociation at pH 7.4 or both (as compared to the starting antibody), e.g., as shown in FIG. 2 were selected for further analysis.

Example 15. Construction and Screening of pH-Engineered MET Antibodies

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected Telisotuzumab (Heavy chain SEQ ID NO: 159, Light chain SEQ ID NO: 160) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the light chain CDRs that had been previously selected for further analysis in Example 10 were systematically combined two or more at a time. In cases where the starting CDR residue was a histidine, it was mutated to an alanine. Antibody variants with two or more histidine or alanine mutations in the light chain CDRs were generated by co-transfection of Expi293 cells with a) one light chain combinations sequence variant, and b) the corresponding starting antibody heavy chain containing the triple hinge (TH) and YTE mutations described in (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000) and (Dall, W F et al "Increasing the Affinity of a Human IgG1 for the Neonatal Fc Receptor: Biological Consequences" The Journal of Immunology (2002); 169:5171-5180) respectively using methods known to the art. After allowing for four days of protein expression, cell culture supernatants were collected, quantified by SDS-PAGE analysis, purified using protein A magnetic beads (Genscript L00273), and evaluated for endolysosomal delivery on Detroit 562 cells (ATCC CCL-138). Detroit 562 cells (ATCC; CCL-138) were collected and resuspended in EMEM medium (ATCC; 30-2003)+10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 100,000 cells/mL and 100 ul was seeded into 96-well flat bottom cell culture plates and allowed to attach overnight in 37 C 5% CO2. Primary antibodies were then diluted in native culture mediums to 20 nM and then mixed 1:1 with 60 nM Incucyte Human FabFluor-pH Red Antibody Labeling Reagent (Sartorius; 4722). The mixture was incubated for 20 minutes at room temperature, followed by addition to cells. Plates were then placed immediately into the Incucyte S3 Live-Cell Analysis System for image acquisition and analysis. Endolysosomal delivery was examined for the starting antibody (with no substitutions) and each corresponding antibody variant to inform on enhanced endolysosomal delivery due to histidine or alanine substitution compared to the starting antibody (with no substitutions).

Example 16. Construction and Screening of pH-Engineered MET Antibodies

Multiple MET-binding monoclonal antibodies have been described in the literature and can be used as a template for engineering pH-dependent binding (Feng Y et al. "MET Antibody Drug Conjugate" US Patent Application US 2020/0061204 A1 (2020)). We selected Emibetuzumab (Heavy chain SEQ ID NO: 161, Light chain SEQ ID NO: 162) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time. In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 of cell culture supernatant was diluted into 100 µL of 1×PBST, pH 7.4 for low expressors for loading onto the sensor tips. This diluted supernatant was then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody, (with no substitutions), and b) reduced dissociation at pH 7.4 (i.e., lower koff values) compared to pH 5.4 in the antibody variant itself and with the starting antibody (with no substitutions). Heavy chain variants that showed either enhanced dissociation at pH 5.4 or reduced dissociation at pH 7.4 or both (as compared to the starting antibody), were selected for further analysis (e.g., MYT2319). It was also noted that while some histidine and alanine mutations obliterated MET binding (e.g., MYT2341), others were tolerated with little (e.g., less than 1-fold change in dissociation constant KD or dissociation rate) or no change in MET binding kinetics.

Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 17. Construction and Screening of pH-Engineered MET Antibodies

Multiple MET-binding monoclonal antibodies have been described in the literature and can be used as a template for engineering pH-dependent binding (Feng Y et al. "MET Antibody Drug Conjugate" US Patent Application US 2020/0061204 A1 (2020)). We selected Emibetuzumab (Heavy chain SEQ ID NO: 161, Light chain SEQ ID NO: 162) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time. In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H) in 1×PB ST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting ABPC (with no substitutions), and b) reduced dissociation at pH 7.4 (i.e., lower koff values) compared to pH 5.4 in the antibody variant itself and with the starting antibody (with no substitutions). Light chain variants that showed either enhanced dissociation at pH 5.4 or reduced dissociation at pH 7.4 or both (as compared to the starting antibody), were selected for further analysis (e.g., MYT3978). It was also noted that some histidine and alanine mutations were tolerated with little (e.g., less than 1-fold change in dissociation constant KD or dissociation rate) or no change in MET binding kinetics. Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 18. Construction and Screening of pH-Engineered MET Antibodies

Multiple MET-binding monoclonal antibodies have been described in the literature and can be used as a template for engineering pH-dependent binding (Feng Y et al. "MET Antibody Drug Conjugate" US Patent Application US 2020/0061204 A1 (2020)). We selected Emibetuzumab (Heavy chain SEQ ID NO: 161, Light chain SEQ ID NO: 162) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 16 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H)) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody (with no substitutions), and b) reduced dissociation at pH 7.4 (i.e., lower koff values) compared to pH 5.4 in the antibody variant itself and with the starting antibody (with no substitutions). Heavy chain combinations variants that showed either enhanced dissociation at pH 5.4 or reduced dissociation at pH 7.4 or both (as compared to the starting antibody), were selected for further analysis (e.g., MYT2850, MYT2861).

Example 19. Construction and Screening of pH-Engineered MET Antibodies

Multiple MET-binding monoclonal antibodies have been described in the literature and can be used as a template for engineering pH-dependent binding (Feng Y et al. "MET Antibody Drug Conjugate" US Patent Application US 2020/0061204 A1 (2020)). We selected Emibetuzumab (Heavy chain SEQ ID NO: 161, Light chain SEQ ID NO: 162) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the light chain CDRs that had been previously selected for further analysis in Example 17 were systematically combined two or more at a time. In cases where the starting CDR residue was a histidine, it was mutated to an alanine. Antibody variants with two or more histidine or alanine mutations in the light chain CDRs were generated by co-transfection of Expi293 cells with a) one light chain combinations sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Light chain combinations variants that showed either enhanced dissociation at pH 5.4 or reduced dissociation at pH 7.4 or both (as compared to the starting antibody), were selected for further analysis (e.g., MYT4326).

Example 20. Construction and Screening of pH-Engineered MET Antibodies

Multiple MET-binding monoclonal antibodies have been described in the literature and can be used as a template for engineering pH-dependent binding (Feng Y et al. "MET Antibody Drug Conjugate" US Patent Application US 2020/0061204 A1 (2020)). We selected Emibetuzumab (Heavy chain SEQ ID NO: 161, Light chain SEQ ID NO: 162) as a MET-binding monoclonal antibody for pH engineering via histidine scanning. Briefly, CDRs in the heavy and light chains were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy and light chain CDRs that had been previously selected for further analysis in Examples 16-19 were systematically combined two or more at a time. In cases where the starting CDR residue was a histidine, it was mutated to an alanine. Antibody variants with two or more histidine or alanine mutations were generated by co-transfection of Expi293 cells with a) one light chain sequence variant or light chain combinations sequence variant, and b) one heavy chain sequence variant or heavy chain combinations sequence variant using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20), pH 7.4, and the sensor was associated with 50 nM of MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Paired heavy and light chain variants that showed either enhanced dissociation at pH 5.4 or reduced dissociation at pH 7.4 or both (as compared to the starting antibody), were selected for further analysis (e.g., MYT3999, MYT4001, MYT4007, MYT4010, MYT4011, MYT4012, MYT4013, MYT4014, MYT4015, MYT4016, MYT4017, MYT4018, MYT4019, MYT4023, MYT4032, MYT4034, MYT4040).

Example 21. Construction and Screening of pH-Engineered MET Antibodies

Multiple MET-binding monoclonal antibodies have been described in the literature and can be used as a template for engineering pH-dependent binding (Feng Y et al. "MET Antibody Drug Conjugate" US Patent Application US 2020/0061204 A1 (2020)). We selected Emibetuzumab (Heavy chain SEQ ID NO: 161, Light chain SEQ ID NO: 162) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 16 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant containing the triple hinge (TH) and YTE mutations described in (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000) and (Dall, W F et al "Increasing the Affinity of a Human IgG1 for the Neonatal Fc Receptor: Biological Consequences" The Journal of Immunology (2002); 169:5171-5180) respectively, and b) the corresponding starting antibody light chain using methods known to the art. After allowing for four days of protein expression, cell culture supernatants were collected, quantified by SDS-PAGE analysis, purified using protein A magnetic beads (Genscript L00273), and evaluated for endolysosomal delivery on Detroit 562 cells (ATCC CCL-138). Detroit 562 cells (ATCC; CCL-138) were collected and resuspended in EMEM medium (ATCC; 30-2003)+10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells are then diluted to 100,000 cells/mL and 100 ul was seeded into 96-well flat bottom cell culture plates and allowed to attach overnight in 37 C 5% CO2. Primary antibodies were then diluted in native culture mediums to 20 nM and then mixed 1:1 with 60 nM Incucyte Human FabFluor-pH Red Antibody Labeling Reagent (Sartorius; 4722). The mixture was incubated for 20 minutes at room temperature, followed by addition to cells. Plates were then placed immediately into the Incucyte S3 Live-Cell Analysis System for image acquisition and analysis. Endolysosomal delivery was examined for the starting antibody (with no substitutions) and each corresponding antibody variant to inform on enhanced endolysosomal delivery due to histidine or alanine substitution compared to the starting antibody (with no substitutions).

Example 22. Construction and Screening of pH-Engineered MET Antibodies

Multiple MET-binding monoclonal antibodies have been described in the literature and can be used as a template for engineering pH-dependent binding (Hicks, S W and Lai, K "MET Antibodies and Immunoconjugates and uses thereof" International Patent Application WO 2020/014306 A1 (2020)). We selected hucMET27Gv1.3 (Heavy chain SEQ ID NO: 225, Light chain SEQ ID NO: 235) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time. In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of MET (cMET, Sino Biological Cat. No. 10692-H08H) in 1×PBST pH 7.4 for 120 sec to generate an association curve. In the dissociation phase, the antibody-antigen complex on the sensor was exposed to 1×PB ST pH 7.4 for 300-600 sec. Baseline, association, and dissociation were repeated using 1×PBST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody, (with no substitutions), and b) reduced dissociation at pH 7.4 (i.e., lower koff values) compared to pH 5.4 in the antibody variant itself and with the starting antibody (with no substitutions). Heavy chain variants that showed either enhanced dissociation at pH 5.4 or reduced dissociation at pH 7.4 or both (as compared to the starting antibody), were selected for further analysis. It was also noted that while some histidine and alanine mutations obliterated MET binding, others were tolerated with little (e.g., less than 1-fold change in dissociation constant KD or dissociation rate) or no change in MET binding kinetics.

Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 23. Construction and Screening of pH-Engineered MET Antibodies

Multiple MET-binding monoclonal antibodies have been described in the literature and can be used as a template for engineering pH-dependent binding (Hicks, S W and Lai, K "MET Antibodies and Immunoconjugates and uses thereof" International Patent Application WO 2020/014306 A1 (2020)). We selected hucMET27Gv1.3 (Heavy chain SEQ ID NO: 225, Light chain SEQ ID NO: 235) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time. In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody (with no substitutions), and b) reduced dissociation at pH 7.4 (i.e., lower koff values) compared to pH 5.4 in the antibody variant itself and with the starting antibody (with no substitutions). Light chain variants that showed either enhanced dissociation at pH 5.4 or reduced dissociation at pH 7.4 or both (as compared to the starting antibody), were selected for further analysis. It was also noted that some histidine and alanine mutations were tolerated with little (e.g., less than 1-fold change in dissociation constant $K_D$ or dissociation rate) or no change in MET binding kinetics. Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 24. Construction and Screening of pH-Engineered MET Antibodies

Multiple MET-binding monoclonal antibodies have been described in the literature and can be used as a template for engineering pH-dependent binding (Hicks, S W and Lai, K "MET Antibodies and Immunoconjugates and uses thereof" International Patent Application WO 2020/014306 A1 (2020)). We selected hucMET27Gv1.3 (Heavy chain SEQ ID NO: 225, Light chain SEQ ID NO: 235) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 22 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H)) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody (with no substitutions), and b) reduced dissociation at pH 7.4 (i.e., lower koff values) compared to pH 5.4 in the antibody variant itself and with the starting antibody (with no substitutions). Heavy chain combinations variants that showed either enhanced dissociation at pH 5.4 or reduced dissociation at pH 7.4 or both (as compared to the starting antibody), were selected for further analysis.

Fc sensor (Forte Bio). A baseline was established using 1×PB ST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Light chain combinations variants that showed either enhanced dissociation at pH 5.4 or reduced dissociation at pH 7.4 or both (as compared to the starting antibody), were selected for further analysis (e.g., MYT4230).

Example 25. Construction and Screening of pH-Engineered MET Antibodies

Multiple MET-binding monoclonal antibodies have been described in the literature and can be used as a template for engineering pH-dependent binding (Hicks, S W and Lai, K "MET Antibodies and Immunoconjugates and uses thereof" International Patent Application WO 2020/014306 A1 (2020)). We selected hucMET27Gv1.3 (Heavy chain SEQ ID NO: 225, Light chain SEQ ID NO: 235) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the light chain CDRs that had been previously selected for further analysis in Example 23 were systematically combined two or more at a time. In cases where the starting CDR residue was a histidine, it was mutated to an alanine. Antibody variants with two or more histidine or alanine mutations in the light chain CDRs were generated by co-transfection of Expi293 cells with a) one light chain combinations sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Example 26. Construction and Screening of pH-Engineered MET Antibodies Multiple MET-binding monoclonal antibodies have been described in the literature and can be used as a template for engineering pH-dependent binding (Hicks, S W and Lai, K "MET Antibodies and Immunoconjugates and uses thereof" International Patent Application WO 2020/014306 A1 (2020)). We selected hucMET27Gv1.3 (Heavy chain SEQ ID NO: 225, Light chain SEQ ID NO: 235) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 22 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant containing the triple hinge (TH) and YTE mutations described in (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000) and (Dall, W F et al "Increasing the Affinity of a Human IgG1 for the Neonatal Fc Receptor: Biological Consequences" The Journal of Immunology (2002); 169:5171-5180) respectively, and b) the corresponding starting antibody light chain using methods known to the art. After allowing for four days of protein expression, cell culture supernatants were collected, quantified by SDS-PAGE analysis, purified using protein A magnetic beads (Genscript L00273), and evaluated for endolysosomal delivery on Detroit 562 cells (ATCC CCL-138). Detroit 562 cells (ATCC; CCL-138) were collected and resuspended in EMEM medium (ATCC; 30-2003)+10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 100,000 cells/mL and 100 ul was seeded into 96-well flat bottom cell culture plates and allowed to attach overnight in 37 C 5% CO2. Primary antibodies were then diluted in native culture mediums to 20 nM and then mixed 1:1 with 60 nM Incucyte Human FabFluor-pH Red Antibody Labeling Reagent (Sartorius; 4722). The mixture was incubated for 20 minutes at room temperature, followed by addition to cells. Plates were then placed immediately into the Incucyte S3 Live-Cell Analysis System for image acquisition and analysis. Endolysosomal delivery was examined for the starting antibody (with no substitutions) and each corresponding antibody variant to inform on enhanced endolysosomal delivery due to histidine or alanine substitution compared to the starting antibody (with no substitutions).

Example 27. Construction and Screening of pH-Engineered MET Antibodies

Multiple MET-binding monoclonal antibodies have been described in the literature and can be used as a template for engineering pH-dependent binding (Hicks, S W and Lai, K "MET Antibodies and Immunoconjugates and uses thereof" International Patent Application WO 2020/014306 A1 (2020)). We selected hucMET27Gv1.3 (Heavy chain SEQ ID NO: 225, Light chain SEQ ID NO: 235) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the light chain CDRs that had been previously selected for further analysis in Example 23 were systematically combined two or more at a time. In cases where the starting CDR residue was a histidine, it was mutated to an alanine. Antibody variants with two or more histidine or alanine mutations in the light chain CDRs were generated by co-transfection of Expi293 cells with a) one light chain combinations sequence variant, and b) the corresponding starting antibody heavy chain containing the triple hinge (TH) and YTE mutations described in (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000) and (Dall, W F et al "Increasing the Affinity of a Human IgG1 for the Neonatal Fc Receptor: Biological Consequences" The Journal of Immunology (2002); 169:5171-5180) respectively using methods known to the art. After allowing for four days of protein expression, cell culture supernatants were collected, quantified by SDS-PAGE analysis, purified using protein A magnetic beads (Genscript L00273), and evaluated for endolysosomal delivery on Detroit 562 cells (ATCC CCL-138). Detroit 562 cells (ATCC; CCL-138) were collected and resuspended in EMEM medium (ATCC; 30-2003)+10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 100,000 cells/mL and 100 ul was seeded into 96-well flat bottom cell culture plates and allowed to attach overnight in 37 C 5% CO2. Primary antibodies were then diluted in native culture mediums to 20 nM and then mixed 1:1 with 60 nM Incucyte Human FabFluor-pH Red Antibody Labeling Reagent (Sartorius; 4722). The mixture was incubated for 20 minutes at room temperature, followed by addition to cells. Plates were then placed immediately into the Incucyte S3 Live-Cell Analysis System for image acquisition and analysis. Endolysosomal delivery was examined for the starting antibody (with no substitutions) and each corresponding antibody variant to inform on enhanced endolysosomal delivery due to histidine or alanine substitution compared to the starting antibody (with no substitutions). Light chain combinations variants that showed enhanced endolysosomal delivery (as compared to the starting antibody), were selected for further analysis. The pH dependence of the selected variants were evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4 or pH 5.4, for 300-600 sec. Association and dissociation phase curves at pH 7.4 and pH 5.4 were examined for the starting antibody (with no substitutions) and each corresponding antibody variant to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Light chain combinations variants that showed either enhanced dissociation at pH 5.4 or reduced dissociation at pH 7.4 or both (as compared to the starting antibody), were selected for further analysis.

Example 28. Construction and Screening of pH-Engineered MET Antibodies

Multiple MET-binding monoclonal antibodies have been described in the literature and can be used as a template for engineering pH-dependent binding (Fujita, R et al (2020) A Novel Non-Agonist c-Met Antibody Drug Conjugate with Superior Potency Over a c-Met Tyrosine Kinase Inhibitor in c-Met Amplified and Non-Amplified Cancers, Cancer Biology and Therapy, 21(6):549-559). We selected P3D12 (Heavy chain SEQ ID NO: 163, Light chain SEQ ID NO: 164) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time. In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. This diluted supernatant was then captured on an anti-human Fc sensor (Forte Bio). A baseline was established using 1×PB ST (50 mM Potassium Phosphate Buffer+150 mM NaCl+ 0.05% Tween 20) pH 7.4, and the sensor was associated with 50 nM of MET (cMET, Sino Biological Cat. No. 10692-H08H) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody, (with no substitutions), and b) reduced dissociation at pH 7.4 (i.e., lower koff values) compared to pH 5.4 in the antibody variant itself and with the starting antibody (with no substitutions). Heavy chain variants that showed either enhanced dissociation at pH 5.4 or reduced dissociation at pH 7.4 or both (as compared to the starting antibody), were selected for further analysis (e.g., MYT3698 and MYT3701). It was also noted that some histidine and alanine mutations were tolerated with little (e.g., less than 1-fold change in dissociation constant KD or dissociation rate) or no change in MET binding kinetics.

Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 29. Construction and Screening of pH-Engineered MET Antibodies

Multiple MET-binding monoclonal antibodies have been described in the literature and can be used as a template for engineering pH-dependent binding (Fujita, R et al (2020) A Novel Non-Agonist c-Met Antibody Drug Conjugate with Superior Potency Over a c-Met Tyrosine Kinase Inhibitor in c-Met Amplified and Non-Amplified Cancers, Cancer Biology and Therapy, 21(6):549-559). We selected P3D12 (Heavy chain SEQ ID NO: 163, Light chain SEQ ID NO: 164) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time. In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H) in 1×PB ST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PB ST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody (with no substitutions), and b) reduced dissociation at pH 7.4 (i.e., lower koff values) compared to pH 5.4 in the antibody variant itself and with the starting antibody (with no substitutions). Light chain variants that showed either enhanced dissociation at pH 5.4 or reduced dissociation at pH 7.4 or both (as compared to the starting antibody), were selected for further analysis (e.g., MYT3735, and MYT3740). It was also noted that some histidine and alanine mutations were tolerated with little (e.g., less than 1-fold change in dissociation constant KD or dissociation rate) or no change in MET binding kinetics. Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 30. Construction and Screening of pH-Engineered MET Antibodies

Figure 3A:
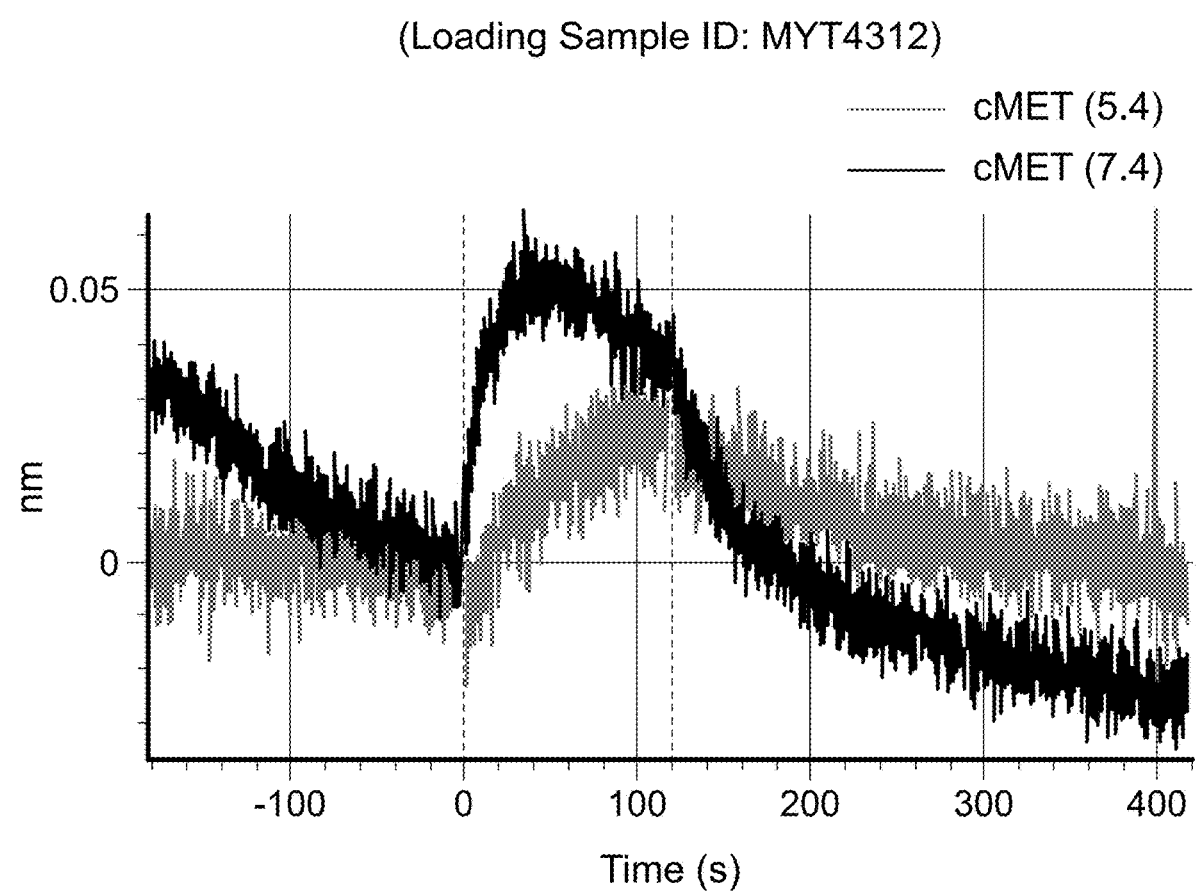
FIGS. 3A to 3C: Binding of histidine scanning and alanine scanning variants of P3D12 to MET by biolayer interferometry. MYT4312, MYT4313, and MYT4325, heavy chain combination histidine scanning and alanine scanning variants, were captured on anti-human Fc biosensors and associated with MET at low pH or high pH, as specified in the figures. All variants include the TH and YTE substitution format.
Figure 3B:
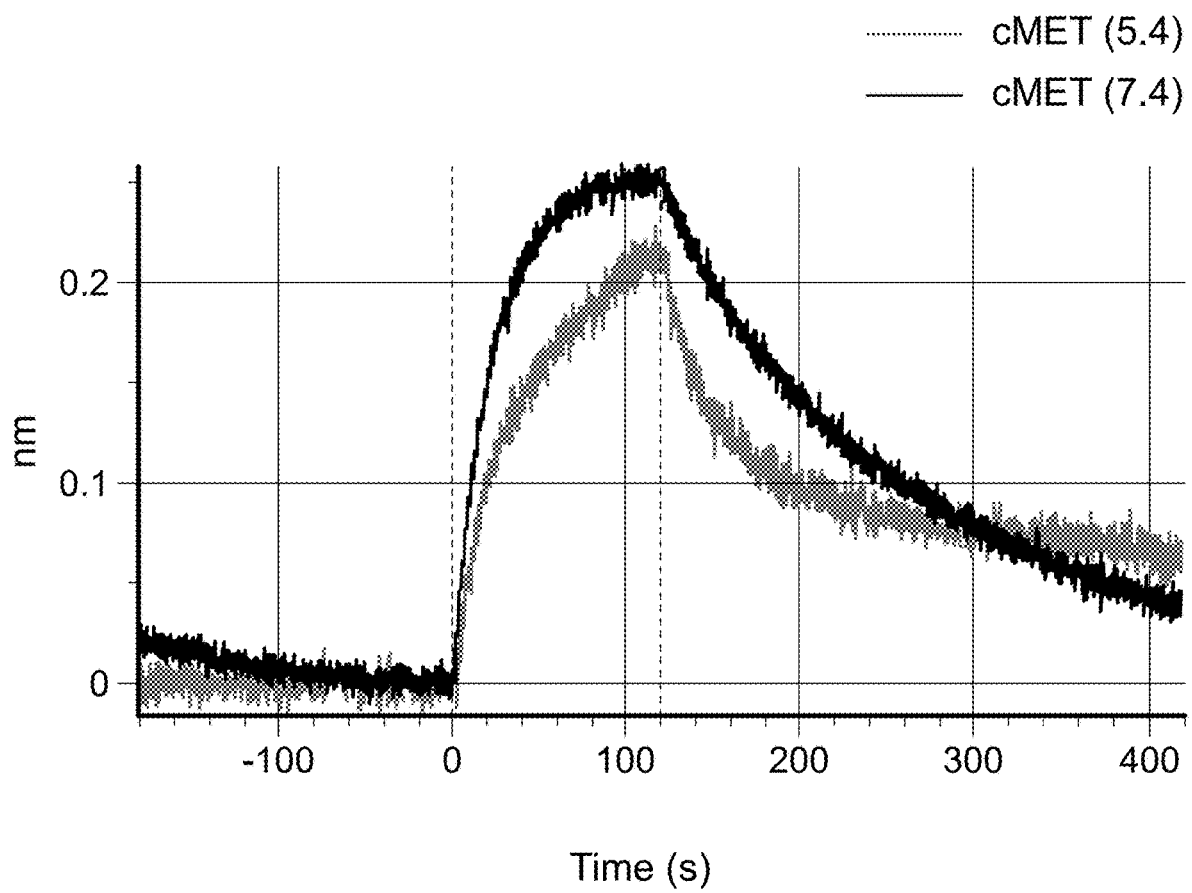
Figure 3C:
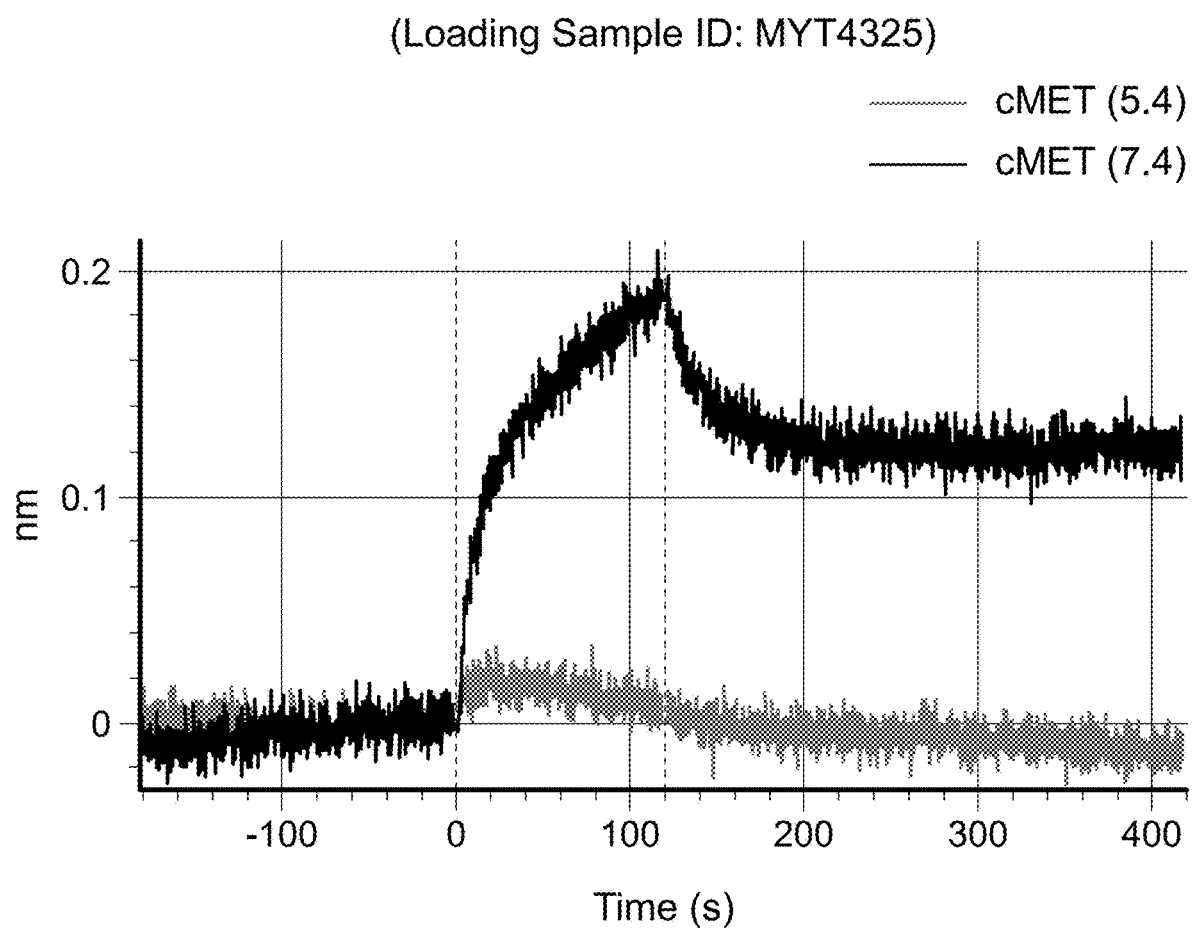
Figure 4A:
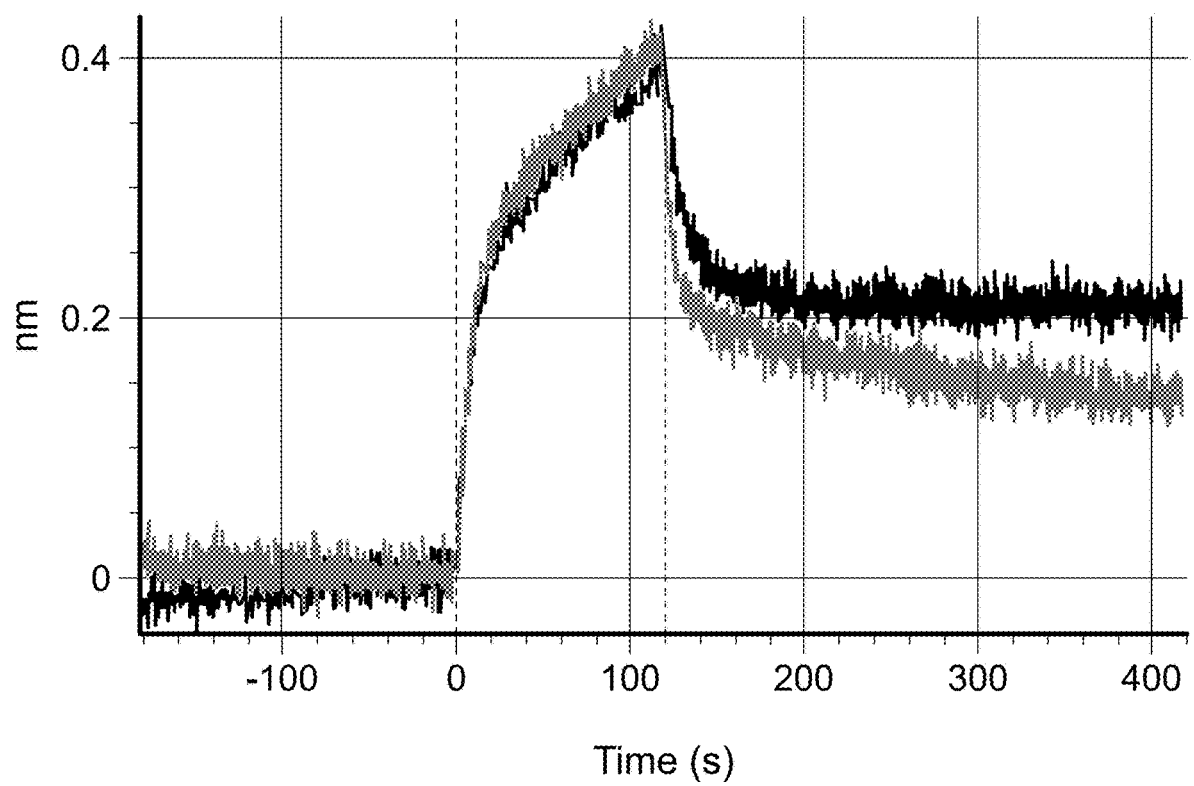
FIGS. 4A to 4D: Binding of histidine scanning and alanine scanning variants of P3D12 and Emibetuzumab to MET by biolayer interferometry. MYT5344, MYT5351, MYT5367, and MYT4826, paired heavy and light chain histidine scanning and alanine scanning variants, combining light chain histidine and alanine scanning variants or light chain combination histidine scanning and alanine scanning variants with heavy chain histidine and alanine scanning variants or heavy chain combination histidine scanning and alanine scanning variants, were captured on anti-human Fc biosensors and associated with MET at pH 7.4. Dissociation was at pH 7.4 (black trace) or pH 5.4 (grey trace). All variants include the TH and YTE substitution format.
Figure 4B:
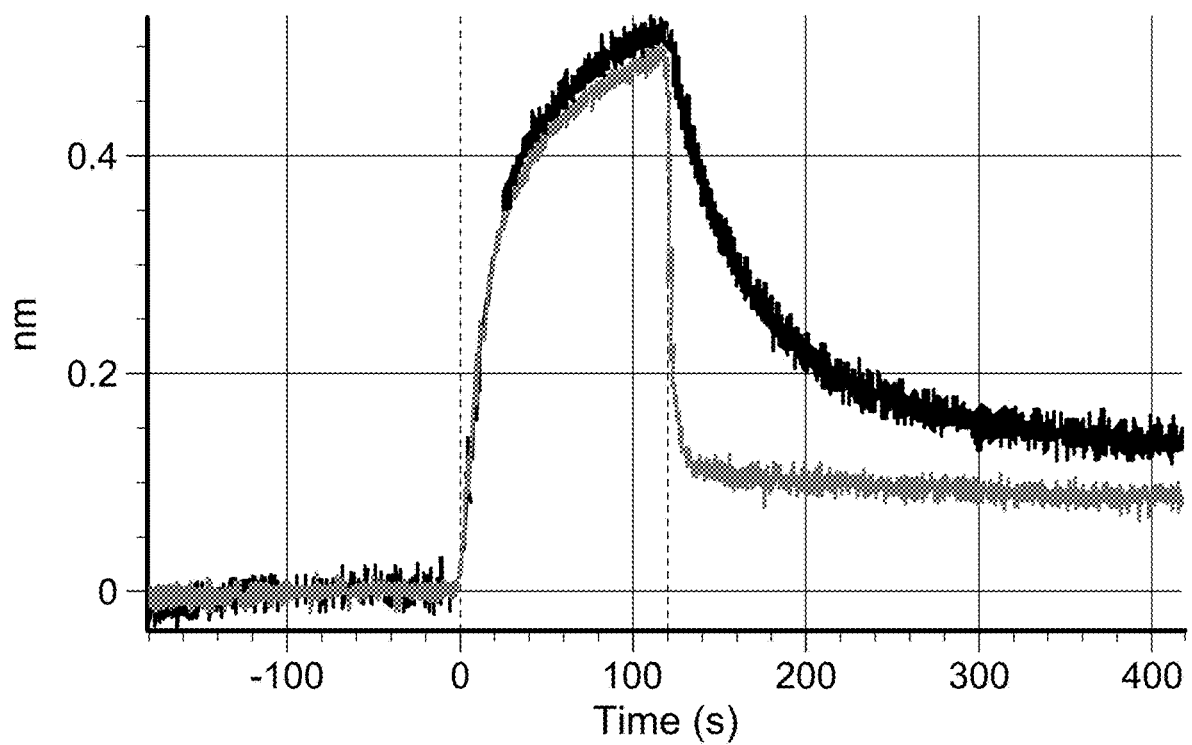
Figure 4C:
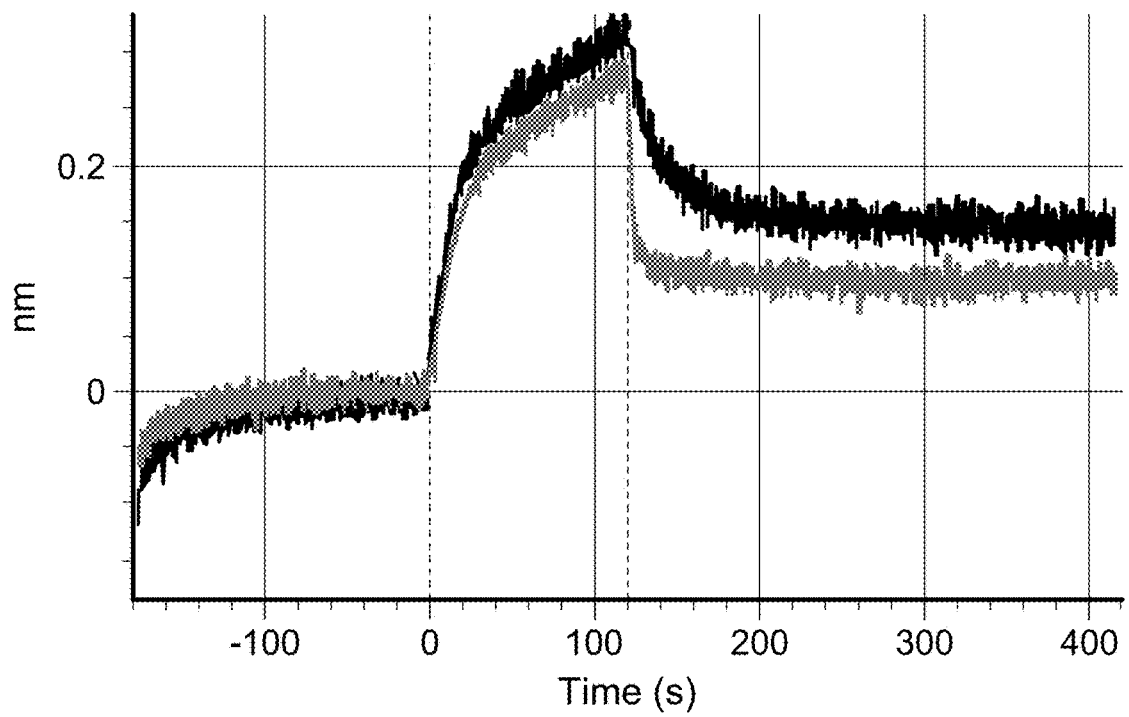
Figure 4D:
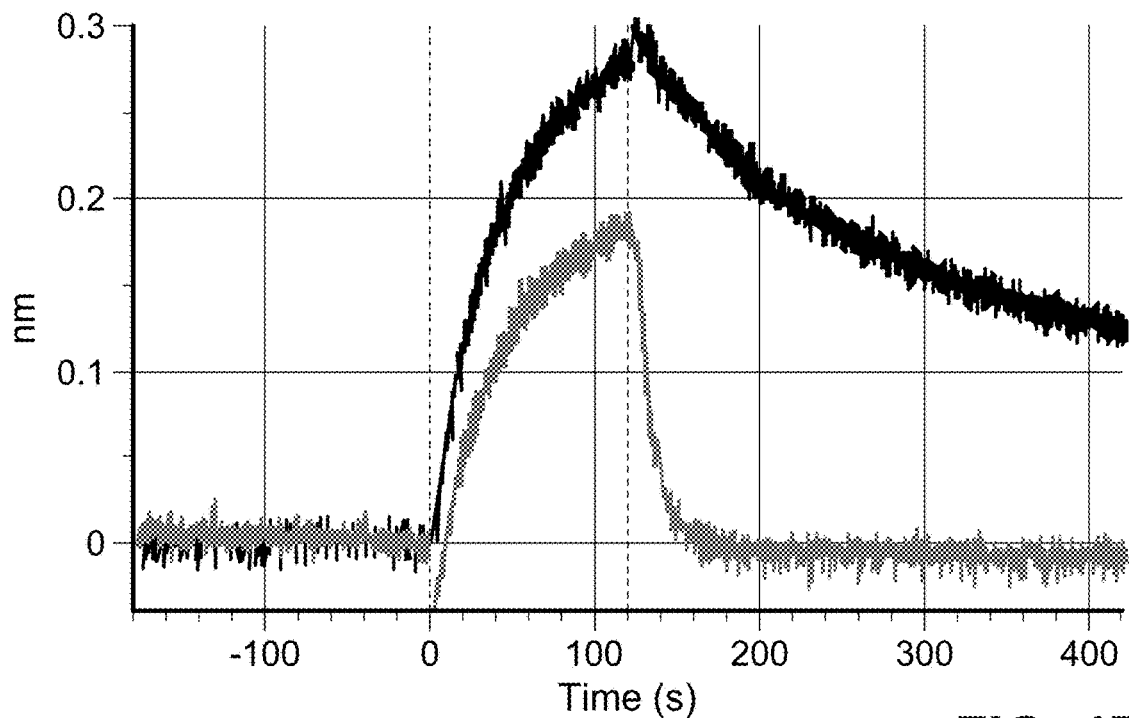
Figure 7A:
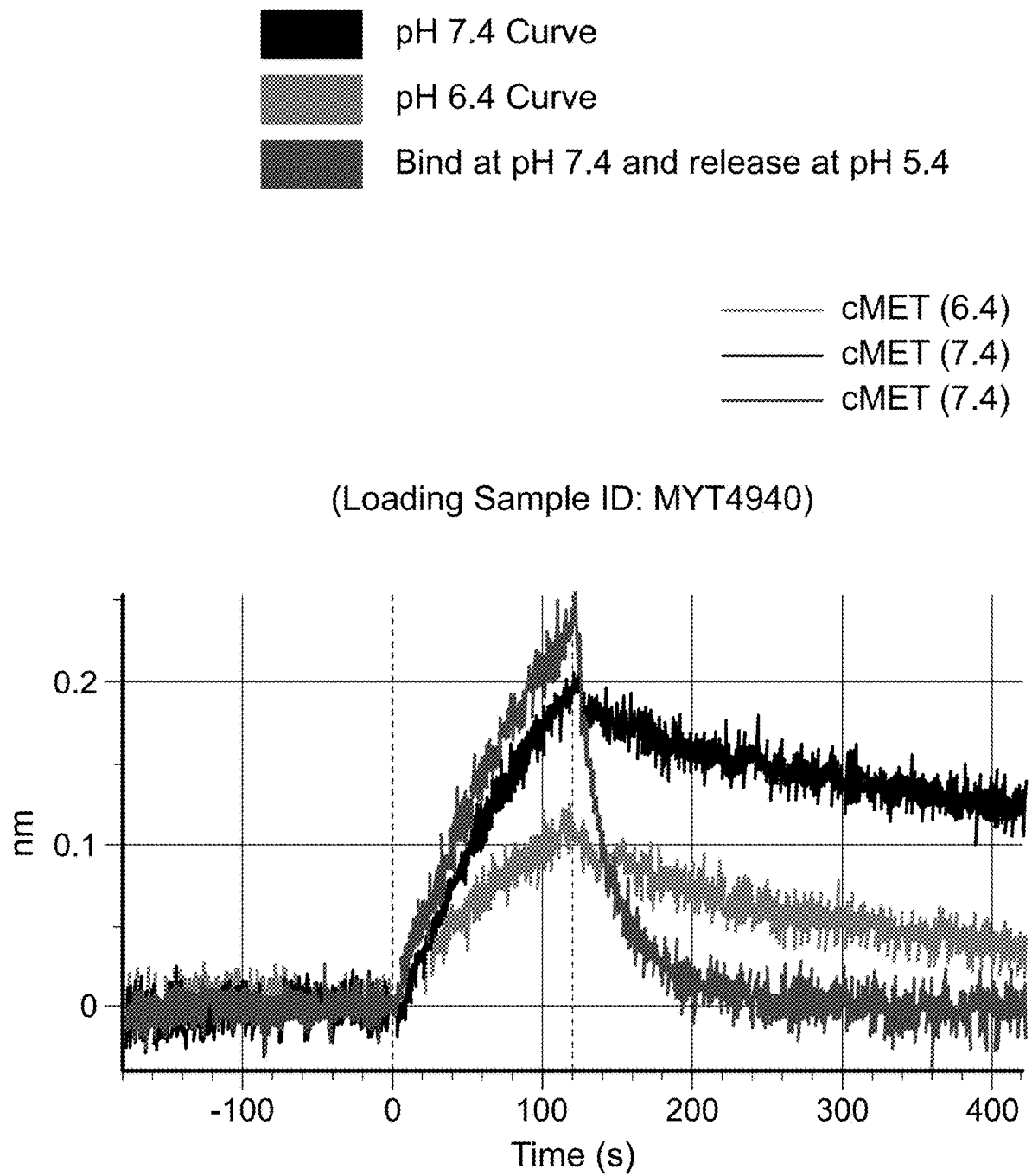
FIGS. 7A-G: Binding of histidine scanning and alanine scanning variants to MET by biolayer interferometry MYT4940, MYT4942, MYT4888, MYT4827, MYT4837, MYT4849, and MYT5309, paired heavy and light chain histidine scanning and alanine scanning variants, combining light chain histidine and alanine scanning variants or light chain combination histidine scanning and alanine scanning variants with heavy chain histidine and alanine scanning variants or heavy chain combination histidine scanning and alanine scanning variants, were captured on anti-human Fc biosensors and associated with MET at pH 7.4. The black trace represents pH 7.4, the red trace represents association at 7.4 and then dissociation at pH 6.4, and the orange trace represents pH 6.4 All variants include the TH and YTE substitution format.
Figure 7B:
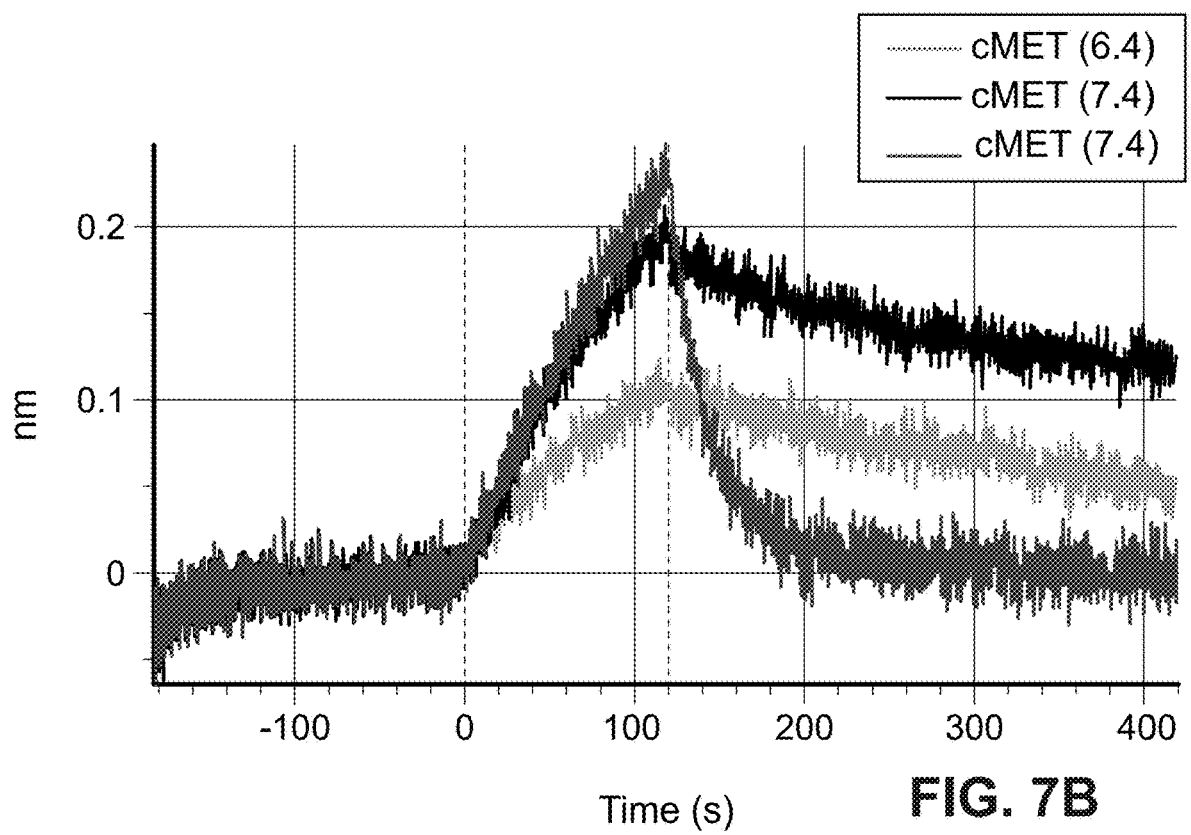
Figure 7C:
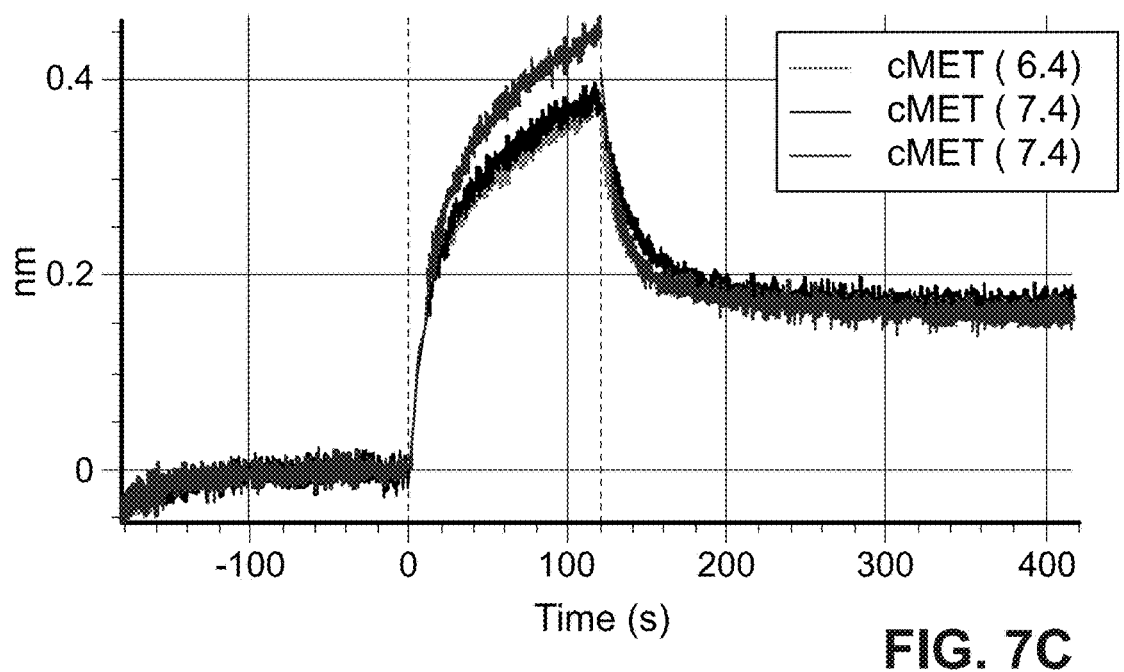
Figure 7D:
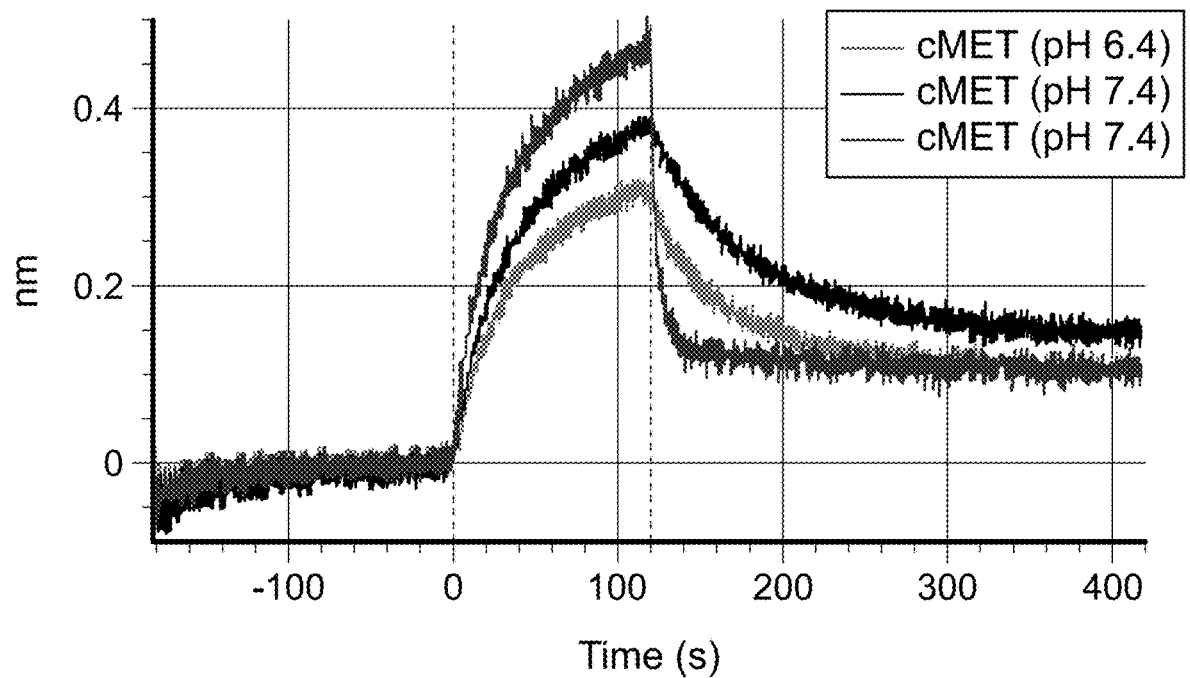
Figure 7E:
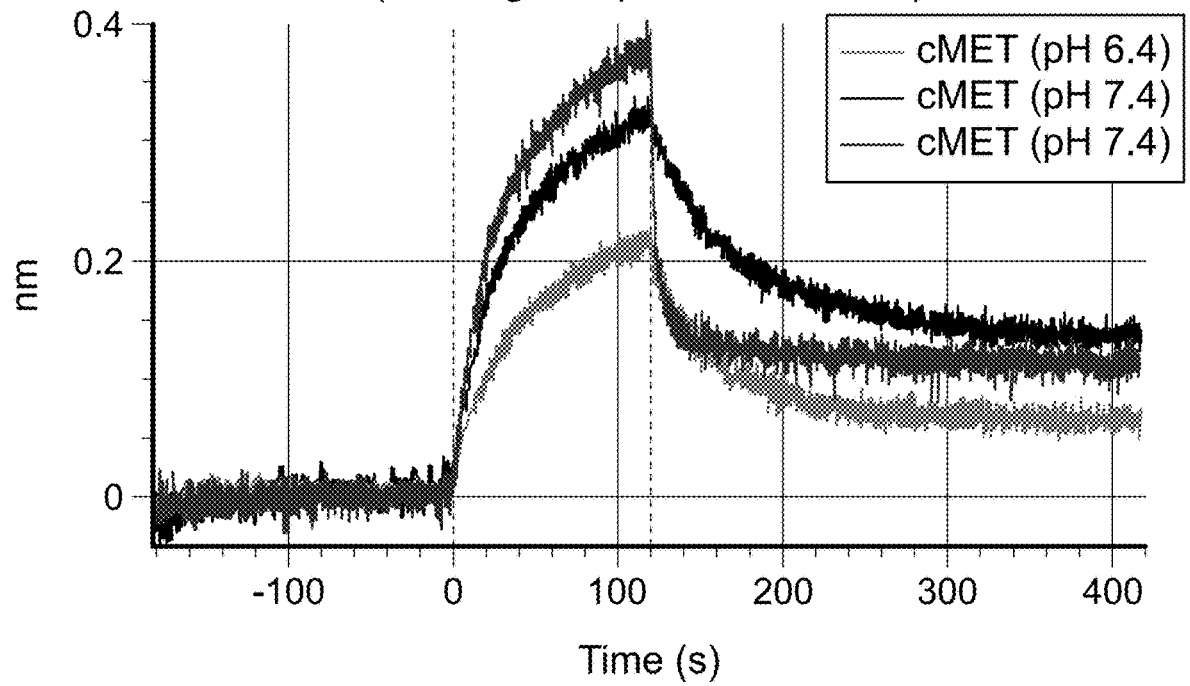
Figure 7F:
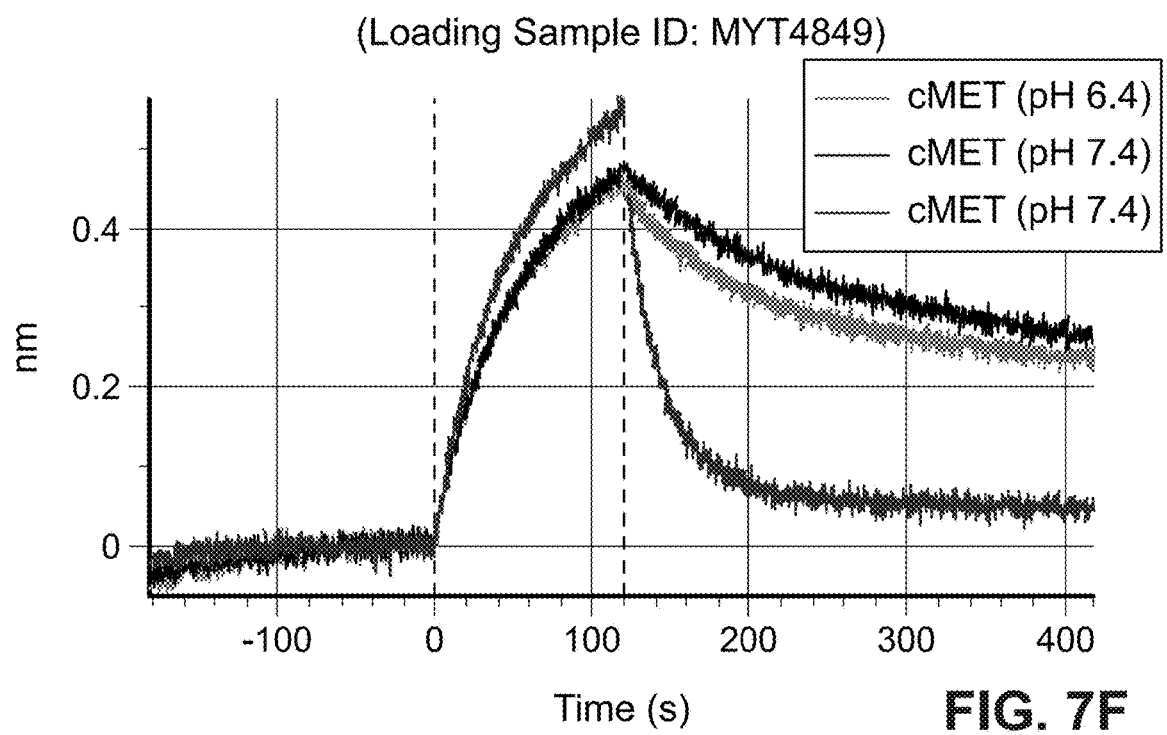
Figure 7G:
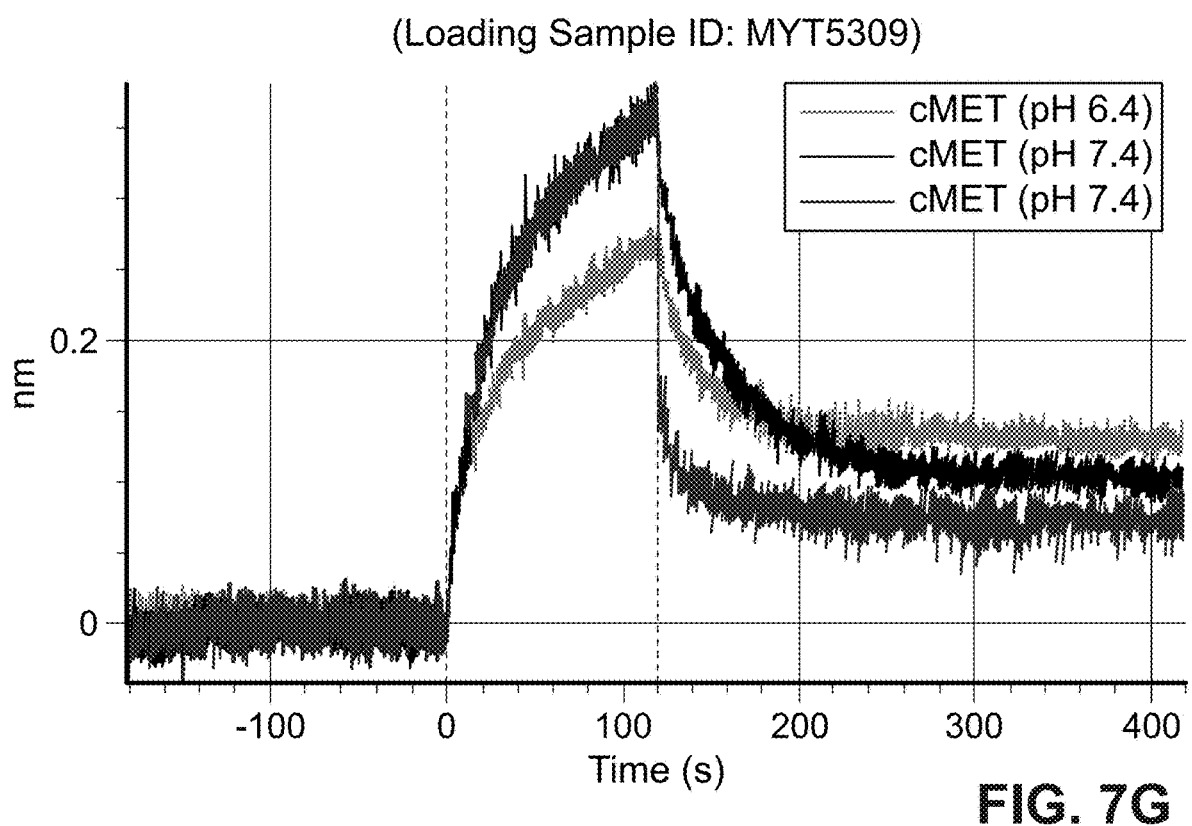

Multiple MET-binding monoclonal antibodies have been described in the literature and can be used as a template for engineering pH-dependent binding (Fujita, R et al (2020) A Novel Non-Agonist c-Met Antibody Drug Conjugate with Superior Potency Over a c-Met Tyrosine Kinase Inhibitor in c-Met Amplified and Non-Amplified Cancers, Cancer Biology and Therapy, 21(6):549-559). We selected P3D12 (Heavy chain SEQ ID NO: 163, Light chain SEQ ID NO: 164) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 28 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant, and b) the corresponding starting antibody light chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20) pH 7.4, and the sensor was associated with 50 nM of MET (cMET, Sino Biological Cat. No. 10692-H08H)) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting antibody (with no substitutions), and b) reduced dissociation at pH 7.4 (i.e., lower koff values) compared to pH 5.4 in the antibody variant itself and with the starting antibody (with no substitutions). Heavy chain combinations variants that showed either enhanced dissociation at pH 5.4 or reduced dissociation at pH 7.4 or both (as compared to the starting antibody), e.g., as shown in FIGS. 3A-3C were selected for further analysis (e.g., MYT4313).

Example 31. Construction and Screening of pH-Engineered MET Antibodies

Multiple MET-binding monoclonal antibodies have been described in the literature and can be used as a template for engineering pH-dependent binding (Fujita, R et al (2020) A Novel Non-Agonist c-Met Antibody Drug Conjugate with Superior Potency Over a c-Met Tyrosine Kinase Inhibitor in c-Met Amplified and Non-Amplified Cancers, Cancer Biology and Therapy, 21(6):549-559). We selected P3D12 (Heavy chain SEQ ID NO: 163, Light chain SEQ ID NO: 164) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the light chain CDRs that had been previously selected for further analysis in Example 29 were systematically combined two or more at a time. In cases where the starting CDR residue was a histidine, it was mutated to an alanine. Antibody variants with two or more histidine or alanine mutations in the light chain CDRs were generated by co-transfection of Expi293 cells with a) one light chain combinations sequence variant, and b) the corresponding starting antibody heavy chain using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Light chain combinations variants that showed either enhanced dissociation at pH 5.4 or reduced dissociation at pH 7.4 or both (as compared to the starting antibody), were selected for further analysis (e.g., MYT4247).

Example 32. Construction and Screening of pH-Engineered MET Antibodies

Multiple MET-binding monoclonal antibodies have been described in the literature and can be used as a template for engineering pH-dependent binding (Fujita, R et al (2020) A Novel Non-Agonist c-Met Antibody Drug Conjugate with Superior Potency Over a c-Met Tyrosine Kinase Inhibitor in c-Met Amplified and Non-Amplified Cancers, Cancer Biology and Therapy, 21(6):549-559). We selected P3D12 (Heavy chain SEQ ID NO: 163, Light chain SEQ ID NO: 164) as a MET-binding monoclonal antibody for pH engineering via histidine scanning. Briefly, CDRs in the heavy and light chains were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy and light chain CDRs that had been previously selected for further analysis in Examples 28-31 were systematically combined two or more at a time. In cases where the starting CDR residue was a histidine, it was mutated to an alanine. Antibody variants with two or more histidine or alanine mutations were generated by co-transfection of Expi293 cells with a) one light chain sequence variant or light chain combinations sequence variant, and b) one heavy chain sequence variant or heavy chain combinations sequence variant using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20), pH 7.4, and the sensor was associated with 50 nM of MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4 or pH 5.4, for 300-600 sec. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Paired heavy and light chain variants that showed either enhanced dissociation at pH 5.4 or reduced dissociation at pH 7.4 or both (as compared to the starting antibody), e.g., as shown in FIG. 4A-4D, were selected for further analysis (e.g., MYT5342, MYT5343, MYT5344, MYT5345, MYT5346, MYT5350, MYT5351, MYT5352, MYT5353, MYT5354, MYT5355, MYT5356, MYT5357, MYT5359, MYT5360, MYT5366, MYT5367, MYT5369, MYT5370, MYT5372, MYT5373, MYT5375, MYT5376, and MYT5381).

Example 33. Construction and Screening of pH-Engineered MET Antibodies

Multiple MET-binding monoclonal antibodies have been described in the literature and can be used as a template for engineering pH-dependent binding (Fujita, R et al (2020) A Novel Non-Agonist c-Met Antibody Drug Conjugate with Superior Potency Over a c-Met Tyrosine Kinase Inhibitor in c-Met Amplified and Non-Amplified Cancers, Cancer Biology and Therapy, 21(6):549-559). We selected P3D12 (Heavy chain SEQ ID NO: 163, Light chain SEQ ID NO: 164) as a MET-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 28 were systematically combined two or more at a time. In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant containing the triple hinge (TH) and YTE mutations described in (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000) and (Dall, W F et al "Increasing the Affinity of a Human IgG1 for the Neonatal Fc Receptor: Biological Consequences" The Journal of Immunology (2002); 169: 5171-5180) respectively, and b) the corresponding starting antibody light chain using methods known to the art. After allowing for four days of protein expression, cell culture supernatants were collected, quantified by SDS-PAGE analysis, purified using protein A magnetic beads (Genscript L00273), and evaluated for endolysosomal delivery on Detroit 562 cells (ATCC CCL-138). Briefly, Detroit 562 cells (ATCC; CCL-138) were collected and resuspended in EMEM medium (ATCC; 30-2003)+10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 100,000 cells/mL and 100 ul was seeded into 96-well flat bottom cell culture plates and allowed to attach overnight in 37 C 5% CO2. Primary antibodies were then diluted in native culture mediums to 20 nM and then mixed 1:1 with 60 nM Incucyte Human FabFluor-pH Red Antibody Labeling Reagent (Sartorius; 4722). The mixture was incubated for 20 minutes at room temperature, followed by addition to cells. Plates were then placed immediately into the Incucyte S3 Live-Cell Analysis System for image acquisition and analysis. Endolysosomal delivery was examined for the starting antibody (with no substitutions) and each corresponding antibody variant to inform on enhanced endolysosomal delivery due to histidine or alanine substitution compared to the starting antibody (with no substitutions). Heavy chain combinations variants that showed enhanced endolysosomal delivery (as compared to the starting antibody), were selected for further analysis. The pH dependence of the selected variants were evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4 or pH 5.4, for 300-600 sec. Association and dissociation phase curves at pH 7.4 and pH 5.4 were examined for the starting antibody (with no substitutions) and each corresponding antibody variant to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Heavy chain combinations variants that showed either enhanced dissociation at pH 5.4 or reduced dissociation at pH 7.4 or both (as compared to the starting antibody), were selected for further analysis.

Example 34. Construction and Screening of pH-Engineered MET Antibodies

Multiple MET-binding monoclonal antibodies have been described in the literature and can be used as a template for engineering pH-dependent binding (Fujita, R et al (2020) A Novel Non-Agonist c-Met Antibody Drug Conjugate with Superior Potency Over a c-Met Tyrosine Kinase Inhibitor in c-Met Amplified and Non-Amplified Cancers, Cancer Biology and Therapy, 21(6):549-559). We selected P3D12 (Heavy chain SEQ ID NO: 163, Light chain SEQ ID NO: 164) as a MET-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the light chain CDRs that had been previously selected for further analysis in Example 29 were systematically combined two or more at a time. In cases where the starting CDR residue was a histidine, it was mutated to an alanine. Antibody variants with two or more histidine or alanine mutations in the light chain CDRs were generated by co-transfection of Expi293 cells with a) one light chain combinations sequence variant, and b) the corresponding starting antibody heavy chain containing the triple hinge (TH) and YTE mutations described in (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000) and (Dall, W F et al "Increasing the Affinity of a Human IgG1 for the Neonatal Fc Receptor: Biological Consequences" The Journal of Immunology (2002); 169:5171-5180) respectively using methods known to the art. After allowing for four days of protein expression, cell culture supernatants were collected, quantified by SDS-PAGE analysis, purified using protein A magnetic beads (Genscript L00273), and evaluated for endolysosomal delivery on Detroit 562 cells (ATCC CCL-138). Briefly, Detroit 562 cells (ATCC; CCL-138) were collected and resuspended in EMEM medium (ATCC; 30-2003)+10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 100,000 cells/mL and 100 ul was seeded into 96-well flat bottom cell culture plates and allowed to attach overnight in 37 C 5% CO2. Primary antibodies were then diluted in native culture mediums to 20 nM and then mixed 1:1 with 60 nM Incucyte Human FabFluor-pH Red Antibody Labeling Reagent (Sartorius; 4722). The mixture was incubated for 20 minutes at room temperature, followed by addition to cells. Plates were then placed immediately into the Incucyte S3 Live-Cell Analysis System for image acquisition and analysis. Endolysosomal delivery was examined for the starting antibody (with no substitutions) and each corresponding antibody variant to inform on enhanced endolysosomal delivery due to histidine or alanine substitution compared to the starting antibody (with no substitutions). Light chain combinations variants that showed enhanced endolysosomal delivery (as compared to the starting antibody), were selected for further analysis. The pH dependence of the selected variants were evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20), pH 7.4, and the sensor was associated with MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4 or pH 5.4, for 300-600 sec. Association and dissociation phase curves at pH 7.4 and pH 5.4 were examined for the starting antibody (with no substitutions) and each corresponding antibody variant to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions). Light chain combinations variants that showed either enhanced dissociation at pH 5.4 or reduced dissociation at pH 7.4 or both (as compared to the starting antibody), were selected for further analysis.

Example 35. Reformatting of Anti-MET Antibodies

Select pH engineered anti-MET variants were generated as both wild-type IgG1 molecules (e.g., in Examples 9-13, 16-20, 22-25, and 28-32) and as IgG1 molecules containing the triple hinge (TH) mutations, as described by (Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000), and the YTE mutations, as described by (Dall, W F et al "Increasing the Affinity of a Human IgG1 for the Neonatal Fc Receptor: Biological Consequences" The Journal of Immunology (2002); 169: 5171-5180), by transfection of Expi293 cells with a plasmid encoding for the variable heavy region fused genetically to human IgG1 Fc with or without the TH and YTE mutations. Co-transfection of Expi293 cells with a) one heavy chain sequence consisting of a variable heavy chain region and constant regions corresponding to either wild-type human IgG1 isotype or the same sequence except with TH and YTE mutations, and b) one light chain sequence, using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fc sensor (Forte Bio). A baseline was established using 1×PB ST (50 mM Potassium Phosphate Buffer+150 mM NaCl+0.05% Tween 20), pH 7.4, and the sensor was associated with 50 nM of MET (cMET, Sino Biological Cat. No. 10692-H08H) in 1×PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for each corresponding antibody variant at pH 5.4 and pH 7.4 to inform on three criteria: a) enhanced dissociation (e.g., higher koff values) at pH 5.4 as compared to its corresponding starting antibody, b) reduced dissociation at pH 7.4 (e.g., lower koff values) compared to pH 5.4 in the antibody variant itself, and c) comparison of the wild-type human IgG1 antibodies and their TH and YTE containing variants. Wild-type human IgG1 and reformatted human IgG1 antibodies containing the TH and YTE mutations showed broadly similar association and dissociation curves. We conclude from this data that the desirable properties of our variant variable domain sequences, including but not limited to pH dependence and endolysosomal delivery, are retained whether in IgG1 format or in IgG1 format with the TH and YTE mutations.

Example 36. Characterization of Cellular Internalization and Endolysosomal Delivery of pH Engineered Anti-MET Antibodies Selected anti-MET pH engineered antibody variants from Examples 9-13, 16-20, 22-25, and 28-31 were analyzed for internalization and endolysosomal delivery in U-87 MG cells (MET+), SNU-5 cells (MET+), NCI-H1373 cells (MET+), NCI-H1573 cells (MET+) and/or Detroit 562 cells (MET+). U-87 MG cells (ATCC HTB-14), Detroit 562 cells (ATCC CCL-138), NCI-H1373 cells (ATCC CRL-5866), NCI-H1573 cells (ATCC CRL-5877) or SNU-5 cells (ATCC CRL-5973) were collected and resuspended in EMEM medium (U-87 MG and Detroit 562, ATCC; 30-2003), IMDM medium (SNU-5, ATCC; 30-2005), or RPMI medium (NCI-H1373 and NCI-H1573, ATCC 30-2001) plus 5% (NCI-H1573), 10% (U-87 MG, Detroit 562, NCI-H1373) or 20% (SNU-5) GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 2,000,000 cells/mL and 50 µl/well was seeded into 96-well flat bottom cell culture plates (Genesee Scientific; 25-109). Anti-MET pH engineered antibody variants, starting antibody antibodies, control IgG1 isotype control (BP0297, Bioxcell), and vehicle control were diluted in native culture media, and then mixed 1:1 with a 3× molar ratio Zenon pHrodo iFL Human IgG Labeling Reagent (ThermoFisher; Z25611). The mixture was incubated for 20 minutes at room temperature, followed by a 1:1 addition of cells for a final volume of 100 µL. The mixture of cells, anti-MET antibody variants, and Zenon pHrodo iFL Human IgG Labeling Reagent was incubated at 37° C., 5% CO2 for 1-24 hours. Following incubation, 100 µL of ice cold Flow Cytometry (FC) buffer (phosphate buffered saline (PBS), pH 7.4+2 mM ethylenediaminetetraacetic acid (EDTA)+2% (v/v) HI FBS is added to each well. Cells were then spun down at 4° C. for 2 min at 2000 rpm, washed with 200 µL ice cold FC buffer and resuspended in 100 µL ice cold FC buffer. Mean green fluorescence intensity was detected using a BD Accuri C6 flow cytometer. Data was analyzed using Flowjo analysis software. pHrodo green is a pH sensitive dye that fluoresces in the low pH environment of the endosomes and lysosomes and therefore can be used to quantify antibody internalization and endolysosomal delivery. Internalization and endolysosomal delivery of anti-MET starting antibodies and variants at concentrations, in U-87 MG (MET+), Detroit 562 (MET+), SNU-5 (MET+), NCI-H1573 (MET+), or NCI-H1373 (MET+) cells, was measured by pHrodo green mean fluorescence intensity. Several pH engineered anti-MET antibody variants showed increased mean fluorescence intensity relative to their corresponding starting antibodies demonstrating that increased dissociation at lower pH leads to enhanced internalization and endolysosomal delivery inside cells as shown by increased fluorescence or increased fluorescence as compared to IgG1 isotype control. Increased endolysosomal delivery is quantitated for each pH engineered anti-MET antibody variant on the top of each bar as a ratio of: the variant's mean fluorescence intensity minus the mean fluorescence intensity of the IgG control, then all divided by the variant's corresponding starting antibody's mean fluorescence intensity minus the mean fluorescence intensity of the IgG control. For example MYT2040, MYT3609, MYT3611, and MYT3615, antibody variants of telisotuzumab, show increased internalization and endolysosomal delivery relative to telisotuzumab (MYT0886). For example MYT2319, MYT2850, MYT2861, and MYT4326, antibody variants of emibetuzumab, show increased internalization and endolysosomal delivery relative to emibetuzumab. For example MYT3698, MYT3735, MYT3740, MYT4247, and MYT4325, an antibody variant of P3D12, shows increased internalization and endolysosomal delivery relative to P3D12. Such pH engineered anti-MET antibody variants with increased mean fluorescence intensity relative to their starting antibodies were selected for further analysis.

Example 37. Thermal Stability of Anti-MET mAbs

Protein melting temperature (Tm) was measured through the use of Differential Scanning Flourimetry (DSF). DSF visualizes protein unfolding by measuring the fluorescent signal from the molecule Sypro Orange (Thermo Scientific cat. no. 56650) as a protein unfolds due to heating. As a protein unfolds it exposes more hydrophilic regions to the Sypro Orange dye, which in turns binds to these hydrophilic regions resulting in increase in signal. The Tm for a protein is calculated as the half-maximal of the unfolding transition and can be visualized by plotting the first derivative of the Sypro Orange signal and finding a local maximum of this derivative plot. 20 µL of protein samples in 1×PBS, pH 7.4, was mixed with 5 µL of 25× Sypro Orange master mix, yielding a final concentration of 5× Sypro Orange. The samples were added to 96-well PCR plates (Thermo Scientific Cat. No. AB-2400/W) and sealed with optical covers (Thermo Scientific Cat. No. 4360954). The PCR plate was inserted into a real-time PCR machine (Thermo Scientific Quant Studio 3) and the plate temperature was stabilized for 3 minutes at 25° C. before ramping to 95° C. by 0.2° C. increments, stabilizing for 1 second before the Sypro Orange signal was measured. The melting temperature (Tm) values for anti-MET starting antibodies and variants were determined. Several variants show similar melting temperature values to their starting antibodies confirming that variants created through pH engineering can retain functionally appropriate thermal stabilities as compared to their corresponding starting antibodies (e.g., emibetuzumab, hucMET27Gv1.3 or P3D12). All variants tested had melting temperatures greater than or equal to the melting temperature of their corresponding starting antibody (e.g., mirvetuximab) minus 10° C. and so were selected for further analysis.

The discoveries herein are in contrast to similar engineering on other antigens such as CLEC12a and two other targets wherein multiple variants per target showed enhanced dissociation at low pH, however, despite the favorable pH-dependent binding properties of these variants (which specifically bound CLEC12a and the two other targets), they had less than 10% increase in cell internalization and endolysosomal delivery as compared to the corresponding starting antibody (e.g., the starting antibody). These variants (which specifically bound CLEC12a and the two other targets) also had similar biophysical characteristics (e.g., antibody expression, thermal stability, affinity at pH 7.4 etc.) to the corresponding starting antibody (e.g., the starting antibody) confirming that this was not specific to the biophysical properties of the tested variant (i.e. the biophysical properties unrelated to enhanced dissociation at pH 5.4).

Example 38. Characterization of MYT5351 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT5351 includes a variable heavy chain domain comprising SEQ ID NO: 5 and a variable light chain domain comprising SEQ ID NO: 6. Various modified constant regions (e.g., a modified heavy constant region, a modified light constant region) can be combined with variable chains described herein (e.g., SEQ ID NO: 5, SEQ ID NO: 6, respectively). The following represent the following heavy and light chain combinations as such: triple hinge conjugation only (heavy chain of SEQ ID NO: 35 and light chain of SEQ ID NO: 41); triple hinge conjugation and LS substitution (heavy chain: SEQ ID NO: 36 and a light chain: SEQ ID NO: 4)1; triple hinge substitution and YTE substitution (heavy chain of SEQ ID NO: 37 and a light chain of SEQ ID NO: 41); triple hinge conjugation and V205 substitution (heavy chain of SEQ ID NO: 35 and a light chain of SEQ ID NO: 42); a triple hinge substitution and LS substitution and V205 substitution (heavy chain of SEQ NO: 36 and a light chain of SEQ ID NO: 42); a triple hinge substitution and a YTE substitution and a V205C substitution (heavy chain of SEQ ID NO: 37 and a light chain of SEQ ID NO: 42); a triple hinge substitution and an A118C substitution (heavy chain of SEQ ID NO: 38 and a light chain of SEQ ID NO: 41); a triple hinge substitution and a LS substitution and a A118C substitution (a heavy chain of SEQ ID NO: 39 and a light chain of SEQ ID NO: 41); a triple hinge substitution and a YTE substitution and a A118C substitution (heavy chain of SEQ ID NO: 40 and a light chain of SEQ NO: 41).

The combinations above can be assessed by any of the assays described in the above examples.

Example 39. Characterization of MYT4313 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4313 includes a variable heavy chain domain comprising SEQ ID NO: 7 and a variable light chain domain comprising SEQ ID NO: 8. Various modified constant regions (e.g., a modified heavy constant region, a modified light constant region) can be combined with variable chains described herein (e.g., SEQ ID NO: 7, SEQ ID NO: 8, respectively). The following represent the following heavy and light chain combinations as such: triple hinge conjugation only (heavy chain of SEQ ID NO: 43 and light chain of SEQ ID NO: 49); triple hinge conjugation and LS substitution (heavy chain: SEQ ID NO: 44 and a light chain: SEQ ID NO: 49); triple hinge substitution and YTE substitution (heavy chain of SEQ ID NO: 45 and a light chain of SEQ ID NO: 49); triple hinge conjugation and V205 substitution (heavy chain of SEQ ID NO: 43 and a light chain of SEQ ID NO: 50); a triple hinge substitution and LS substitution and V205 substitution (heavy chain of SEQ NO: 44 and a light chain of SEQ ID NO: 50); a triple hinge substitution and a YTE substitution and a V205C substitution (heavy chain of SEQ ID NO: 45 and a light chain of SEQ ID NO: 50); a triple hinge substitution and an A118C substitution (heavy chain of SEQ ID NO: 46 and a light chain of SEQ ID NO: 49); a triple hinge substitution and a LS substitution and a A118C substitution (a heavy chain of SEQ ID NO: 47 and a light chain of SEQ ID NO: 49); a triple hinge substitution and a YTE substitution and a A118C substitution (heavy chain of SEQ ID NO: 48 and a light chain of SEQ NO: 49).

The combinations above can be assessed by any of the assays described in the above examples.

Example 40. Characterization of MYT4325 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4325 includes a variable heavy chain domain comprising SEQ ID NO: 9 and a variable light chain domain comprising SEQ ID NO: 10. Various modified constant regions (e.g., a modified heavy constant region, a modified light constant region) can be combined with variable chains described herein (e.g., SEQ ID NO: 9, SEQ ID NO: 10, respectively). The following represent the following heavy and light chain combinations as such: triple hinge conjugation only (heavy chain of SEQ ID NO: 51 and light chain of SEQ ID NO: 57); triple hinge conjugation and LS substitution (heavy chain: SEQ ID NO: 51 and a light chain: SEQ ID NO: 57); triple hinge substitution and YTE substitution (heavy chain of SEQ ID NO: 51 and a light chain of SEQ ID NO: 57); triple hinge conjugation and V205 substitution (heavy chain of SEQ ID NO: 51 and a light chain of SEQ ID NO: 58); a triple hinge substitution and LS substitution and V205 substitution (heavy chain of SEQ NO: 52 and a light chain of SEQ ID NO: 58); a triple hinge substitution and a YTE substitution and a V205C substitution (heavy chain of SEQ ID NO: 53 and a light chain of SEQ ID NO: 58); a triple hinge substitution and an A118C substitution (heavy chain of SEQ ID NO: 54 and a light chain of SEQ ID NO: 57); a triple hinge substitution and a LS substitution and a A118C substitution (a heavy chain of SEQ ID NO: 55 and a light chain of SEQ ID NO: 57); a triple hinge substitution and a YTE substitution and a A118C substitution (heavy chain of SEQ ID NO: 56 and a light chain of SEQ NO: 57).

The combinations above can be assessed by any of the assays described in the above examples.

Example 41. Characterization of MYT4826 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4826 includes a variable heavy chain domain comprising SEQ ID NO: 11 and a variable light chain domain comprising SEQ ID NO: 12. Various modified constant regions (e.g., a modified heavy constant region, a modified light constant region) can be combined with variable chains described herein (e.g., SEQ ID NO: 11, SEQ ID NO: 12, respectively). The following represent the following heavy and light chain combinations as such: triple hinge conjugation only (heavy chain of SEQ ID NO: 59 and light chain of SEQ ID NO: 65); triple hinge conjugation and LS substitution (heavy chain: SEQ ID NO: 60 and a light chain: SEQ ID NO: 65); triple hinge substitution and YTE substitution (heavy chain of SEQ ID NO: 61 and a light chain of SEQ ID NO: 65); triple hinge conjugation and V205 substitution (heavy chain of SEQ ID NO: 59 and a light chain of SEQ ID NO: 66); a triple hinge substitution and LS substitution and V205 substitution (heavy chain of SEQ NO: 60 and a light chain of SEQ ID NO: 66); a triple hinge substitution and a YTE substitution and a V205C substitution (heavy chain of SEQ ID NO: 61 and a light chain of SEQ ID NO: 66); a triple hinge substitution and an A118C substitution (heavy chain of SEQ ID NO: 62 and a light chain of SEQ ID NO: 65); a triple hinge substitution and a LS substitution and a A118C substitution (a heavy chain of SEQ ID NO: 63 and a light chain of SEQ ID NO: 65); a triple hinge substitution and a YTE substitution and a A118C substitution (heavy chain of SEQ ID NO: 64 and a light chain of SEQ NO: 65).

The combinations above can be assessed by any of the assays described in the above examples.

Example 42. Characterization of MYT4837 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4837 includes a variable heavy chain domain comprising SEQ ID NO: 13 and a variable light chain domain comprising SEQ ID NO: 14. Various modified constant regions (e.g., a modified heavy constant region, a modified light constant region) can be combined with variable chains described herein (e.g., SEQ ID NO: 13, SEQ ID NO: 14, respectively). The following represent the following heavy and light chain combinations as such: triple hinge conjugation only (heavy chain of SEQ ID NO: 67 and light chain of SEQ ID NO: 73); triple hinge conjugation and LS substitution (heavy chain: SEQ ID NO: 68 and a light chain: SEQ ID NO: 73); triple hinge substitution and YTE substitution (heavy chain of SEQ ID NO: 69 and a light chain of SEQ ID NO: 73); triple hinge conjugation and V205 substitution (heavy chain of SEQ ID NO: 67 and a light chain of SEQ ID NO: 74); a triple hinge substitution and LS substitution and V205 substitution (heavy chain of SEQ NO: 68 and a light chain of SEQ ID NO: 74); a triple hinge substitution and a YTE substitution and a V205C substitution (heavy chain of SEQ ID NO: 69 and a light chain of SEQ ID NO: 74); a triple hinge substitution and an A118C substitution (heavy chain of SEQ ID NO: 70 and a light chain of SEQ ID NO: 73); a triple hinge substitution and a LS substitution and a A118C substitution (a heavy chain of SEQ ID NO: 71 and a light chain of SEQ ID NO: 73); a triple hinge substitution and a YTE substitution and a A118C substitution (heavy chain of SEQ ID NO: 72 and a light chain of SEQ NO: 73).

The combinations above can be assessed by any of the assays described in the above examples.

Example 43. Characterization of MYT4849 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4849 includes a variable heavy chain domain comprising SEQ ID NO: 15 and a variable light chain domain comprising SEQ ID NO: 16. Various modified constant regions (e.g., a modified heavy constant region, a modified light constant region) can be combined with variable chains described herein (e.g., SEQ ID NO: 15, SEQ ID NO: 16, respectively). The following represent the following heavy and light chain combinations as such: triple hinge conjugation only (heavy chain of SEQ ID NO: 75 and light chain of SEQ ID NO: 81); triple hinge conjugation and LS substitution (heavy chain: SEQ ID NO: 76 and a light chain: SEQ ID NO: 81); triple hinge substitution and YTE substitution (heavy chain of SEQ ID NO: 77 and a light chain of SEQ ID NO: 81); triple hinge conjugation and V205 substitution (heavy chain of SEQ ID NO: 75 and a light chain of SEQ ID NO: 82); a triple hinge substitution and LS substitution and V205 substitution (heavy chain of SEQ NO: 76 and a light chain of SEQ ID NO: 82); a triple hinge substitution and a YTE substitution and a V205C substitution (heavy chain of SEQ ID NO: 77 and a light chain of SEQ ID NO: 82); a triple hinge substitution and an A118C substitution (heavy chain of SEQ ID NO: 78 and a light chain of SEQ ID NO: 11); a triple hinge substitution and a LS substitution and a A118C substitution (a heavy chain of SEQ ID NO: 79 and a light chain of SEQ ID NO: 81); a triple hinge substitution and a YTE substitution and a A118C substitution (heavy chain of SEQ ID NO: 80 and a light chain of SEQ NO: 81).

The combinations above can be assessed by any of the assays described in the above examples.

Example 44. Characterization of MYT4942 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4942 includes a variable heavy chain domain comprising SEQ ID NO: 17 and a variable light chain domain comprising SEQ ID NO: 18. Various modified constant regions (e.g., a modified heavy constant region, a modified light constant region) can be combined with variable chains described herein (e.g., SEQ ID NO: 17, SEQ ID NO: 18, respectively). The following represent the following heavy and light chain combinations as such: triple hinge conjugation only (heavy chain of SEQ ID NO: 83 and light chain of SEQ ID NO: 89); triple hinge conjugation and LS substitution (heavy chain: SEQ ID NO: 84 and a light chain: SEQ ID NO: 89); triple hinge substitution and YTE substitution (heavy chain of SEQ ID NO: 85 and a light chain of SEQ ID NO: 89); triple hinge conjugation and V205 substitution (heavy chain of SEQ ID NO: 83 and a light chain of SEQ ID NO: 90); a triple hinge substitution and LS substitution and V205 substitution (heavy chain of SEQ NO: 84 and a light chain of SEQ ID NO: 90); a triple hinge substitution and a YTE substitution and a V205C substitution (heavy chain of SEQ ID NO: 85 and a light chain of SEQ ID NO: 90); a triple hinge substitution and an A118C substitution (heavy chain of SEQ ID NO: 86 and a light chain of SEQ ID NO: 89); a triple hinge substitution and a LS substitution and a A118C substitution (a heavy chain of SEQ ID NO: 87 and a light chain of SEQ ID NO: 89); a triple hinge substitution and a YTE substitution and a A118C substitution (heavy chain of SEQ ID NO: 88 and a light chain of SEQ NO: 89).

The combinations above can be assessed by any of the assays described in the above examples.

Example 45. Characterization of MYT5309 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT5309 includes a variable heavy chain domain comprising SEQ ID NO: 19 and a variable light chain domain comprising SEQ ID NO: 20. Various modified constant regions (e.g., a modified heavy constant region, a modified light constant region) can be combined with variable chains described herein (e.g., SEQ ID NO: 19, SEQ ID NO: 20, respectively). The following represent the following heavy and light chain combinations as such: triple hinge conjugation only (heavy chain of SEQ ID NO: 91 and light chain of SEQ ID NO: 97); triple hinge conjugation and LS substitution (heavy chain: SEQ ID NO: 92 and a light chain: SEQ ID NO: 97); triple hinge substitution and YTE substitution (heavy chain of SEQ ID NO: 93 and a light chain of SEQ ID NO: 97); triple hinge conjugation and V205 substitution (heavy chain of SEQ ID NO: 91 and a light chain of SEQ ID NO: 98); a triple hinge substitution and LS substitution and V205 substitution (heavy chain of SEQ NO: 92 and a light chain of SEQ ID NO: 98); a triple hinge substitution and a YTE substitution and a V205C substitution (heavy chain of SEQ ID NO: 93 and a light chain of SEQ ID NO: 98); a triple hinge substitution and an A118C substitution (heavy chain of SEQ ID NO: 94 and a light chain of SEQ ID NO: 97); a triple hinge substitution and a LS substitution and a A118C substitution (a heavy chain of SEQ ID NO: 95 and a light chain of SEQ ID NO: 97); a triple hinge substitution and a YTE substitution and a A118C substitution (heavy chain of SEQ ID NO: 96 and a light chain of SEQ NO: 97).

The combinations above can be assessed by any of the assays described in the above examples.

Example 46. Characterization of MYT5344 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT5344 includes a variable heavy chain domain comprising SEQ ID NO: 21 and a variable light chain domain comprising SEQ ID NO: 22. Various modified constant regions (e.g., a modified heavy constant region, a modified light constant region) can be combined with variable chains described herein (e.g., SEQ ID NO: 21, SEQ ID NO: 22, respectively). The following represent the following heavy and light chain combinations as such: triple hinge conjugation only (heavy chain of SEQ ID NO: 99 and light chain of SEQ ID NO: 105); triple hinge conjugation and LS substitution (heavy chain: SEQ ID NO: 100 and a light chain: SEQ ID NO: 105); triple hinge substitution and YTE substitution (heavy chain of SEQ ID NO: 101 and a light chain of SEQ ID NO: 105); triple hinge conjugation and V205 substitution (heavy chain of SEQ ID NO: 99 and a light chain of SEQ ID NO: 106); a triple hinge substitution and LS substitution and V205 substitution (heavy chain of SEQ NO: 100 and a light chain of SEQ ID NO: 106); a triple hinge substitution and a YTE substitution and a V205C substitution (heavy chain of SEQ ID NO: 101 and a light chain of SEQ ID NO: 106); a triple hinge substitution and an A118C substitution (heavy chain of SEQ ID NO: 102 and a light chain of SEQ ID NO: 105); a triple hinge substitution and a LS substitution and a A118C substitution (a heavy chain of SEQ ID NO: 103 and a light chain of SEQ ID NO: 105); a triple hinge substitution and a YTE substitution and a A118C substitution (heavy chain of SEQ ID NO: 104 and a light chain of SEQ NO: 105).

The combinations above can be assessed by any of the assays described in the above examples.

Example 47. Characterization of MYT5367 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT5367 includes a variable heavy chain domain comprising SEQ ID NO: 23 and a variable light chain domain comprising SEQ ID NO: 24. Various modified constant regions (e.g., a modified heavy constant region, a modified light constant region) can be combined with variable chains described herein (e.g., SEQ ID NO: 23, SEQ ID NO: 24, respectively). The following represent the following heavy and light chain combinations as such: triple hinge conjugation only (heavy chain of SEQ ID NO: 107 and light chain of SEQ ID NO: 113); triple hinge conjugation and LS substitution (heavy chain: SEQ ID NO: 108 and a light chain: SEQ ID NO: 113); triple hinge substitution and YTE substitution (heavy chain of SEQ ID NO: 109 and a light chain of SEQ ID NO: 113); triple hinge conjugation and V205 substitution (heavy chain of SEQ ID NO: 107 and a light chain of SEQ ID NO: 114); a triple hinge substitution and LS substitution and V205 substitution (heavy chain of SEQ NO: 108 and a light chain of SEQ ID NO: 114); a triple hinge substitution and a YTE substitution and a V205C substitution (heavy chain of SEQ ID NO: 109 and a light chain of SEQ ID NO: 114); a triple hinge substitution and an A118C substitution (heavy chain of SEQ ID NO: 110 and a light chain of SEQ ID NO: 113); a triple hinge substitution and a LS substitution and a A118C substitution (a heavy chain of SEQ ID NO: 111 and a light chain of SEQ ID NO: 113); a triple hinge substitution and a YTE substitution and a A118C substitution (heavy chain of SEQ ID NO: 112 and a light chain of SEQ NO: 113).

The combinations above can be assessed by any of the assays described in the above examples.

Example 48. Characterization of MYT4827 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4827 includes a variable heavy chain domain comprising SEQ ID NO: 25 and a variable light chain domain comprising SEQ ID NO: 26. Various modified constant regions (e.g., a modified heavy constant region, a modified light constant region) can be combined with variable chains described herein (e.g., SEQ ID NO: 25, SEQ ID NO: 26, respectively). The following represent the following heavy and light chain combinations as such: triple hinge conjugation only (heavy chain of SEQ ID NO: 115 and light chain of SEQ ID NO: 121); triple hinge conjugation and LS substitution (heavy chain: SEQ ID NO: 116 and a light chain: SEQ ID NO: 121); triple hinge substitution and YTE substitution (heavy chain of SEQ ID NO: 117 and a light chain of SEQ ID NO: 121); triple hinge conjugation and V205 substitution (heavy chain of SEQ ID NO: 115 and a light chain of SEQ ID NO: 122); a triple hinge substitution and LS substitution and V205 substitution (heavy chain of SEQ NO: 116 and a light chain of SEQ ID NO: 122); a triple hinge substitution and a YTE substitution and a V205C substitution (heavy chain of SEQ ID NO: 117 and a light chain of SEQ ID NO: 122); a triple hinge substitution and an A118C substitution (heavy chain of SEQ ID NO: 118 and a light chain of SEQ ID NO: 121); a triple hinge substitution and a LS substitution and a A118C substitution (a heavy chain of SEQ ID NO: 119 and a light chain of SEQ ID NO: 121); a triple hinge substitution and a YTE substitution and a A118C substitution (heavy chain of SEQ ID NO: 120 and a light chain of SEQ NO: 121).

The combinations above can be assessed by any of the assays described in the above examples.

Example 49. Characterization of MYT4312 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4312 includes a variable heavy chain domain comprising SEQ ID NO: 27 and a variable light chain domain comprising SEQ ID NO: 28. Various modified constant regions (e.g., a modified heavy constant region, a modified light constant region) can be combined with variable chains described herein (e.g., SEQ ID NO: 27, SEQ ID NO: 28, respectively). The following represent the following heavy and light chain combinations as such: triple hinge conjugation only (heavy chain of SEQ ID NO: 123 and light chain of SEQ ID NO: 129); triple hinge conjugation and LS substitution (heavy chain: SEQ ID NO: 124 and a light chain: SEQ ID NO: 129); triple hinge substitution and YTE substitution (heavy chain of SEQ ID NO: 125 and a light chain of SEQ ID NO: 129); triple hinge conjugation and V205 substitution (heavy chain of SEQ ID NO: 123 and a light chain of SEQ ID NO: 130); a triple hinge substitution and LS substitution and V205 substitution (heavy chain of SEQ NO: 124 and a light chain of SEQ ID NO: 130); a triple hinge substitution and a YTE substitution and a V205C substitution (heavy chain of SEQ ID NO: 125 and a light chain of SEQ ID NO: 130); a triple hinge substitution and an A118C substitution (heavy chain of SEQ ID NO: 126 and a light chain of SEQ ID NO: 129); a triple hinge substitution and a LS substitution and a A118C substitution (a heavy chain of SEQ ID NO: 127 and a light chain of SEQ ID NO: 129); a triple hinge substitution and a YTE substitution and a A118C substitution (heavy chain of SEQ ID NO: 128 and a light chain of SEQ NO: 129).

The combinations above can be assessed by any of the assays described in the above examples.

Example 50. Characterization of MYT4953 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4953 includes a variable heavy chain domain comprising SEQ ID NO: 29 and a variable light chain domain comprising SEQ ID NO: 30. Various modified constant regions (e.g., a modified heavy constant region, a modified light constant region) can be combined with variable chains described herein (e.g., SEQ ID NO: 29, SEQ ID NO: 30, respectively). The following represent the following heavy and light chain combinations as such: triple hinge conjugation only (heavy chain of SEQ ID NO: 131 and light chain of SEQ ID NO: 137); triple hinge conjugation and LS substitution (heavy chain: SEQ ID NO: 132 and a light chain: SEQ ID NO: 137); triple hinge substitution and YTE substitution (heavy chain of SEQ ID NO: 133 and a light chain of SEQ ID NO: 137); triple hinge conjugation and V205 substitution (heavy chain of SEQ ID NO: 131 and a light chain of SEQ ID NO: 138); a triple hinge substitution and LS substitution and V205 substitution (heavy chain of SEQ NO: 132 and a light chain of SEQ ID NO: 138); a triple hinge substitution and a YTE substitution and a V205C substitution (heavy chain of SEQ ID NO: 133 and a light chain of SEQ ID NO: 138); a triple hinge substitution and an A118C substitution (heavy chain of SEQ ID NO: 134 and a light chain of SEQ ID NO: 137); a triple hinge substitution and a LS substitution and a A118C substitution (a heavy chain of SEQ ID NO: 135 and a light chain of SEQ ID NO: 137); a triple hinge substitution and a YTE substitution and a A118C substitution (heavy chain of SEQ ID NO: 136 and a light chain of SEQ NO: 137).

The combinations above can be assessed by any of the assays described in the above examples.

Example 51. Characterization of MYT4940 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4940 includes a variable heavy chain domain comprising SEQ ID NO: 31 and a variable light chain domain comprising SEQ ID NO: 32. Various modified constant regions (e.g., a modified heavy constant region, a modified light constant region) can be combined with variable chains described herein (e.g., SEQ ID NO: 31, SEQ ID NO: 32, respectively). The following represent the following heavy and light chain combinations as such: triple hinge conjugation only (heavy chain of SEQ ID NO: 139 and light chain of SEQ ID NO: 145); triple hinge conjugation and LS substitution (heavy chain: SEQ ID NO: 140 and a light chain: SEQ ID NO: 145); triple hinge substitution and YTE substitution (heavy chain of SEQ ID NO: 141 and a light chain of SEQ ID NO: 145); triple hinge conjugation and V205 substitution (heavy chain of SEQ ID NO: 139 and a light chain of SEQ ID NO: 146); a triple hinge substitution and LS substitution and V205 substitution (heavy chain of SEQ NO: 140 and a light chain of SEQ ID NO: 146); a triple hinge substitution and a YTE substitution and a V205C substitution (heavy chain of SEQ ID NO: 141 and a light chain of SEQ ID NO: 146); a triple hinge substitution and an A118C substitution (heavy chain of SEQ ID NO: 142 and a light chain of SEQ ID NO: 145); a triple hinge substitution and a LS substitution and a A118C substitution (a heavy chain of SEQ ID NO: 143 and a light chain of SEQ ID NO: 145); a triple hinge substitution and a YTE substitution and a A118C substitution (heavy chain of SEQ ID NO: 144 and a light chain of SEQ NO: 145).

The combinations above can be assessed by any of the assays described in the above examples.

Example 52. Characterization of MYT4888 Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Thus, MYT4888 includes a variable heavy chain domain comprising SEQ ID NO: 33 and a variable light chain domain comprising SEQ ID NO: 34. Various modified constant regions (e.g., a modified heavy constant region, a modified light constant region) can be combined with variable chains described herein (e.g., SEQ ID NO: 33, SEQ ID NO: 34, respectively). The following represent the following heavy and light chain combinations as such: triple hinge conjugation only (heavy chain of SEQ ID NO: 147 and light chain of SEQ ID NO: 153); triple hinge conjugation and LS substitution (heavy chain: SEQ ID NO: 148 and a light chain: SEQ ID NO: 153); triple hinge substitution and YTE substitution (heavy chain of SEQ ID NO: 149 and a light chain of SEQ ID NO: 153); triple hinge conjugation and V205 substitution (heavy chain of SEQ ID NO: 147 and a light chain of SEQ ID NO: 154); a triple hinge substitution and LS substitution and V205 substitution (heavy chain of SEQ NO: 148 and a light chain of SEQ ID NO: 154); a triple hinge substitution and a YTE substitution and a V205C substitution (heavy chain of SEQ ID NO: 149 and a light chain of SEQ ID NO: 154); a triple hinge substitution and an A118C substitution (heavy chain of SEQ ID NO: 150 and a light chain of SEQ ID NO: 153); a triple hinge substitution and a LS substitution and a A118C substitution (a heavy chain of SEQ ID NO: 151 and a light chain of SEQ ID NO: 153); a triple hinge substitution and a YTE substitution and a A118C substitution (heavy chain of SEQ ID NO: 152 and a light chain of SEQ NO: 153).

The combinations above can be assessed by any of the assays described in the above examples.

Example 53. Characterization of Telisotuzumab Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Telisotuzumab variations that include constant domain substitutions include a variable heavy chain domain comprising SEQ ID NO: 159 and a variable light chain domain comprising SEQ ID NO: 160. Various modified constant regions (e.g., a modified heavy constant region, a modified light constant region) can be combined with variable chains described herein (e.g., SEQ ID NO: 159, SEQ ID NO: 160, respectively). The following represent the following heavy and light chain combinations as such: triple hinge conjugation only (heavy chain of SEQ ID NO: 165 and light chain of SEQ ID NO: 171); triple hinge conjugation and LS substitution (heavy chain: SEQ ID NO: 166 and a light chain: SEQ ID NO: 171); triple hinge substitution and YTE substitution (heavy chain of SEQ ID NO: 167 and a light chain of SEQ ID NO: 171); triple hinge conjugation and V205 substitution (heavy chain of SEQ ID NO: 165 and a light chain of SEQ ID NO: 172); a triple hinge substitution and LS substitution and V205 substitution (heavy chain of SEQ NO: 166 and a light chain of SEQ ID NO: 172); a triple hinge substitution and a YTE substitution and a V205C substitution (heavy chain of SEQ ID NO: 167 and a light chain of SEQ ID NO: 172); a triple hinge substitution and an A118C substitution (heavy chain of SEQ ID NO: 168 and a light chain of SEQ ID NO: 171); a triple hinge substitution and a LS substitution and a A118C substitution (a heavy chain of SEQ ID NO: 169 and a light chain of SEQ ID NO: 171); a triple hinge substitution and a YTE substitution and a A118C substitution (heavy chain of SEQ ID NO: 170 and a light chain of SEQ NO: 171).

The combinations above can be assessed by any of the assays described in the above examples.

Example 54. Characterization of Emibetuzumab Constant Domain Substitutions

As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

Emibetuzumab variations that include constant domain substitutions include a variable heavy chain domain comprising SEQ ID NO: 161 and a variable light chain domain comprising SEQ ID NO: 162. Various modified constant regions (e.g., a modified heavy constant region, a modified light constant region) can be combined with variable chains described herein (e.g., SEQ ID NO: 161, SEQ ID NO: 162, respectively). The following represent the following heavy and light chain combinations as such: triple hinge conjugation only (heavy chain of SEQ ID NO: 173 and light chain of SEQ ID NO: 179); triple hinge conjugation and LS substitution (heavy chain: SEQ ID NO: 174 and a light chain: SEQ ID NO: 179); triple hinge substitution and YTE substitution (heavy chain of SEQ ID NO: 175 and a light chain of SEQ ID NO: 179); triple hinge conjugation and V205 substitution (heavy chain of SEQ ID NO: 173 and a light chain of SEQ ID NO: 180); a triple hinge substitution and LS substitution and V205 substitution (heavy chain of SEQ NO: 174 and a light chain of SEQ ID NO: 180); a triple hinge substitution and a YTE substitution and a V205C substitution (heavy chain of SEQ ID NO: 175 and a light chain of SEQ ID NO: 180); a triple hinge substitution and an A118C substitution (heavy chain of SEQ ID NO: 176 and a light chain of SEQ ID NO: 179); a triple hinge substitution and a LS substitution and a A118C substitution (a heavy chain of SEQ ID NO: 177 and a light chain of SEQ ID NO: 179); a triple hinge substitution and a YTE substitution and a A118C substitution (heavy chain of SEQ ID NO: 178 and a light chain of SEQ NO: 179).

The combinations above can be assessed by any of the assays described in the above examples.

Example 55. Characterization of P3D12 Anti-cMET Constant Domain Substitutions As discussed above histidine scanning was performed where CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. Certain heavy variable chain domain and light variable chain domains were selected for additional experimentation.

Additionally, various methods of conjugating a cytotoxic or cytostatic agent to an antibody are known. For example, conjugation is possible at either naturally occurring amino acid positions and/or at introduced (e.g., engineered amino acids). As discussed herein, various methods of introducing conjugation sites into an antibody are known.

Examples of engineered amino acid conjugation sites include, but are not limited to the following: a substitution to produce "a triple hinge" conjugation site (e.g., a lysine to cysteine substitution at amino acid position 105 and deletion of a threonine at amino acid positions 106 and 108 of SEQ ID NO: 155 or SEQ ID NO: 189 generates the triple hinge conjugation site, an alanine to a cysteine substitution at amino acid position 1 of SEQ ID NO: 155 or SEQ ID NO: 189, and/or a valine to cysteine substitution at amino acid position 98 of SEQ ID NO: 157.

Examples of naturally occurring amino acid conjugation sites include, but are not limited to the following: the cysteine at amino acid position 103, the cysteine of a lysine to cysteine substitution at amino acid position 105, (iii) the cysteine at amino acid position 109, and/or the cysteine at amino acid position 112 and/or the cysteine at amino acid position 107 of SEQ ID NO: 157.

The antibodies provided herein can also include modified constant regions. For example, one or more amino acid substitutions, insertion, and/or deletions can be introduced (e.g., engineered) into the constant domains (e.g., constant heavy and/or constant light) of any of the antibodies provided herein. Amino acid substitutions in the constant region can have varying effects on the antibody, including, for example extending the half-life of the antibody. Non-limiting examples of such substitutions include the following: a methionine to tyrosine substitution at amino acid position 135, a serine to threonine substitution at amino acid position 137, and a threonine to glutamic acid substitution at amino acid position 139 (e.g., "YTE" substitution) and a methionine to leucine substitution at amino acid position 311 and an asparagine to serine substitution at amino acid position 317 (e.g., "LS" substitution).

P3D12 anti-cMET variations that include constant domain substitutions include a variable heavy chain domain comprising SEQ ID NO: 163 and a variable light chain domain comprising SEQ ID NO: 164. Various modified constant regions (e.g., a modified heavy constant region, a modified light constant region) can be combined with variable chains described herein (e.g., SEQ ID NO: 163, SEQ ID NO: 164, respectively). The following represent the following heavy and light chain combinations as such: triple hinge conjugation only (heavy chain of SEQ ID NO: 181 and light chain of SEQ ID NO: 187); triple hinge conjugation and LS substitution (heavy chain: SEQ ID NO: 182 and a light chain: SEQ ID NO: 187); triple hinge substitution and YTE substitution (heavy chain of SEQ ID NO: 183 and a light chain of SEQ ID NO: 187); triple hinge conjugation and V205 substitution (heavy chain of SEQ ID NO: 181 and a light chain of SEQ ID NO: 188); a triple hinge substitution and LS substitution and V205 substitution (heavy chain of SEQ NO: 182 and a light chain of SEQ ID NO: 188); a triple hinge substitution and a YTE substitution and a V205C substitution (heavy chain of SEQ ID NO: 183 and a light chain of SEQ ID NO: 188); a triple hinge substitution and an A118C substitution (heavy chain of SEQ ID NO: 184 and a light chain of SEQ ID NO: 187); a triple hinge substitution and a LS substitution and a A118C substitution (a heavy chain of SEQ ID NO: 185 and a light chain of SEQ ID NO: 187); a triple hinge substitution and a YTE substitution and a A118C substitution (heavy chain of SEQ ID NO: 186 and a light chain of SEQ NO: 187).

The combinations above can be assessed by any of the assays described in the above examples.

Example 56. Improvement in Selective Binding Affinity of pH Engineered Antibodies Measurement of the affinity of pH-engineered antibodies specific for MET was performed by FACS analysis on cell lines with ranges of cMET expression; Detroit-562 cells (ATCC; CCL-138), NCI-H1975 (ATCC CRL-5908) and HUVEC (C2519A, Lonza). Cell lines selected for this study were obtained from commercial sources and cultured using manufacturer recommended conditions. All cell lines were cultured upon receipt, expanded and cryopreserved at a similar passage number for use in the affinity experiments. Briefly, $1.0 \times 10^5$ cells that express MET are plated per well in a 96-well plate in 100 µL media. The cells are washed two times with 200 µL of FACS buffer (1×PBS containing 3% Fetal Bovine Serum) at pH 7.4. The purified protein samples are diluted into FACS buffer at pH 7.4, for a titration from 100 nM to 1 pM, and added to the cells and allowed to bind for 2 hours on ice. After incubation with the primary antibodies, cells are washed twice as before, and then 100 µl of secondary goat anti-Human AF488 (IgG Cross-Adsorbed polyclonal secondary antibody), diluted 1:200, is added in FACS buffer pH 7.4, and incubated for 1 hour on ice. The plates are washed twice Binding is read on a flow cytometer (Accuri C6, BD Biosciences). Binding is observed as a shift in the FL1 signal (as a mean fluorescence intensity) versus secondary alone.

Parent antibodies binding to Detroit-562 cells, expressing high levels of MET, and HUVEC cells, expressing lower levels of MET, showed similar affinity. Unexpectedly, select pH-engineered antibodies specific for MET bind more strongly to target cells with higher MET expression levels, Detroit-562, than to target cells with lower MET expression, HUVEC cells. The affinity for the series of test articles against several cell lines is presented in Table 1. The pH engineered antibody constructs are therefore differentiated from the parent compounds in their avidity, which may be expected to translate to increased selectivity to high expressing target cells in the treatment of cMET overexpressing malignancies, with reduced binding to normal hepatocytes for the selected antibodies.

TABLE 1

| Mythic code # | Parent | Affinity at pH 7.4 (nM) | | | Fold Avidity |
|---|---|---|---|---|---|
| | | Detroit-562 (125K/cell) | HUVEC (8k/cell) | | |
| MYT4305 (P3D12) | n/a | 0.2925 | 0.2 | | 0.7 |
| MYT4813 (Emibetuzumab) | n/a | 0.5267 | 0.2 | | 0.4 |
| MYT4325 | P3D12 | 0.9031 | >200 | | >220 |
| MYT5351 | P3D12 | 0.4864 | >100 | | >200 |
| MYT5309 | Emibetuzumab | 1.343 | >200 | | >50 |
| MYT4837 | Emibetuzumab | 1.021 | >100 | | >100 |

Example 57. Demonstration of Increased Half-Life of pH-Engineered ADCs Specific for MET as Compared to a Control ADCs Specific for MET Another aspect of the pH-engineered ADCs specific for MET described by the invention can be their ability to facilitate increased serum half-life relative to control antibody ADCs specific for MET. To demonstrate these properties, a series of animal studies in cynomolgus monkeys is performed using pH-engineered ADC specific for MET and control antibody ADC specific for MET using methods known to the art (e.g., Gupta, P., et al. (2016), mAbs, 8:5, 991-997). Female monkeys (3 per test article) are administered a bolus of either pH-engineered ADC specific for MET or control antibody ADC specific for MET at a dose of 2.7 mg/kg via saphenous vein injection. Alternatively, several different doses of MET-binding protein are administered across a group of several monkeys. Blood samples are collected via the peripheral vein or femoral vein at the following time points: pre-dose, 15 minutes, 12 hours, 2 days, 3 days, 4 days, 7 days, 10 days, 14 days, 17 days, 21 days and 28 days post-dose. Blood samples are analyzed for the presence of either pH-engineered ADC specific for MET or control antibody ADC specific for MET using methods known to the art (e.g., ELISA).

Antibody concentrations of pH-engineered ADC specific for MET and control antibody ADC specific for MET are plotted as a function of time. Upon analysis of the data, it can be observed that the pH-engineered ADC specific for MET has a significantly longer serum half-life relative to control antibody ADC specific for MET, thereby demonstrating the improved serum stability and exposure profile.

Example 58. Increased Potency of pH-Engineered ADCs Specific for MET Vs. A Control Antibody ADC Specific for MET in Mouse Xenograft Models The enhanced anti-tumor activity of the pH-engineered ADCs specific for MET against MET+ tumors can be demonstrated in a subcutaneous xenograft model of MET+ cells. For the experiments, 5 million H1375 human lung adenocarcinoma cells (part ##), or H1975 human lung adenocarcinoma cells (part #) are grown in vitro and inoculated subcutaneously per mouse into the right flank of female immunodeficient (e.g., CB.17 SCID Jax vs Charles river part #) mice. Additionally, 10 million Detroit 562 human pharyngeal carcinoma cells (part ##) are grown in vitro and inoculated subcutaneously per mouse into the right flank of female athymic nude mice (NCr nu/nu, Jax/vs charles river part #). Tumors are size matched at 100-150 mm3 for H1375 and H1975 xenografts, and 125-175 mm3 for Detroit-562 xenografts. Measurements of the length (L) and width (W) of the tumors are taken via electronic caliper and the volume is calculated according to the following equation: $V=L \times W^2/2$. A bolus (4 mg/kg) of pH-engineered ADC specific for MET or 2 or 4 mg of control antibody ADC specific for MET is administered via tail vein. Tumor growth inhibition (TGI) and tumor growth delay (TGD) and survival are significantly improved with administration of pH-engineered ADC specific for MET compared to administration of control antibody ADC specific for MET at the same regimen.

Optionally, blood samples are collected via mandibular bleeds from each group at each of the following time points: 2 d, 7 d, 14 d. Samples are processed to collect serum, and antibody concentrations are quantified using ELISA or other methods known to the art (e.g., PAC assay or MAC assay; Fischer, S. K. et al. (2012), mAbs, 4:5, 623-631, utilizing, e.g., anti-human IgG antibody Jackson ImmunoResearch Labs, Cat #109-006-006). Antibody concentrations of pH-engineered antibody specific for MET and control antibody specific for MET are plotted as a function of time.

Optionally, spread of tumor cells into the various tissues is determined in sacrificed animals. Metastasis is measured according to Schneider, T., et al., Clin. Exp. Metas. 19 (2002) 571-582. Briefly, tissues are harvested and human Alu sequences are quantified by real-time PCR. Higher human DNA levels, quantified by real-time PCR, correspond to higher levels of metastasis. Levels of human Alu sequences (correlating to invasion of tumor cells into secondary tissue) are significantly lower in animals treated with pH-engineered ADC specific for MET, corresponding to reduced metastasis, compared to mice treated with control antibody ADC specific for MET at the same regimen. Alternatively, the enhanced anti-tumor activity of the pH-engineered ADC specific for MET can be shown in MET+ patient-derived xenograft models (e.g., available from The Jackson Laboratory).

Example 59. Characterization of Cellular Internalization and Endolysosomal Delivery of pH Engineered Anti-MET Antibodies Selected anti-MET pH engineered antibody variants were analyzed for internalization and endolysosomal delivery in U-87 MG cells (MET+), SNU-5 cells (MET+), NCI-H1373 cells (MET+), NCI-H1573 cells (MET+) and/or Detroit 562 cells (MET+). U-87 MG cells (ATCC HTB-14), Detroit 562 cells (ATCC CCL-138), NCI-H1373 cells (ATCC CRL-5866), NCI-H1573 cells (ATCC CRL-5877) or SNU-5 cells (ATCC CRL-5973) were collected and resuspended in EMEM medium (U-87 MG and Detroit 562, ATCC; 30-2003), IMDM medium (SNU-5, ATCC; 30-2005), or RPMI medium (NCI-H1373 and NCI-H1573, ATCC 30-2001) plus 5% (NCI-H1573), 10% (U-87 MG, Detroit 562, NCI-H1373) or 20% (SNU-5) GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 2,000,000 cells/mL and 50 µl/well was seeded into 96-well flat bottom cell culture plates (Genesee Scientific; 25-109).

Anti-MET pH engineered antibody variants, starting antibody antibodies, control IgG1 isotype control (BP0297, Bioxcell), and vehicle control were diluted in native culture media, and then mixed 1:1 with a 3x molar ratio Zenon pHrodo iFL Human IgG Labeling Reagent (ThermoFisher; Z25611). The mixture was incubated for 20 minutes at room temperature, followed by a 1:1 addition of cells for a final volume of 100 μL. The mixture of cells, anti-MET antibody variants, and Zenon pHrodo iFL Human IgG Labeling Reagent was incubated at 37° C., 5% CO2 for 1-24 hours. Following incubation, 100 μL of ice cold Flow Cytometry (FC) buffer (phosphate buffered saline (PBS), pH 7.4+2 mM ethylenediaminetetraacetic acid (EDTA)+2% (v/v) HI FBS is added to each well. Cells were then spun down at 4° C. for 2 min at 2000 rpm, washed with 200 μL ice cold FC buffer and resuspended in 100 μL ice cold FC buffer. Mean green fluorescence intensity was detected using a BD Accuri C6 flow cytometer. Data was analyzed using Flowjo analysis software. pHrodo green is a pH sensitive dye that fluoresces in the low pH environment of the endosomes and lysosomes and therefore can be used to quantify antibody internalization and endolysosomal delivery. Internalization and endolysosomal delivery of anti-MET starting antibodies and variants at concentrations, in U-87 MG (MET+), Detroit 562 (MET+), SNU-5 (MET+), NCI-H1573 (MET+), or NCI-H1373 (MET+) cells, was measured by pHrodo green mean fluorescence intensity. Several pH engineered anti-MET antibody variants showed increased mean fluorescence intensity relative to their corresponding starting antibodies demonstrating that increased dissociation at lower pH leads to enhanced internalization and endolysosomal delivery inside cells as shown by increased fluorescence or increased fluorescence as compared to IgG1 isotype control. Increased endolysosomal delivery is quantitated for each pH engineered anti-MET antibody variant on the top of each bar as a ratio of: the variant's mean fluorescence intensity minus the mean fluorescence intensity of the IgG control, then all divided by the variant's corresponding starting antibody's mean fluorescence intensity minus the mean fluorescence intensity of the IgG control.

MYT4826, MYT4827, MYT4837, MYT4325, MYT5351, MYT4312, MYT5309, MYT4849, MYTH4888, MYT5344, MYT4313, MYT5367, MYT4942, MYT4953, and MYT4940 show increased internalization and endolysosomal delivery relative to their respective control antibodies.

For example MYT2040, MYT3609, MYT3611, and MYT3615, antibody variants of telisotuzumab, show increased internalization and endolysosomal delivery relative to telisotuzumab (MYT0886). For example MYT2319, MYT2850, MYT2861, and MYT4326, antibody variants of emibetuzumab, show increased internalization and endolysosomal delivery relative to emibetuzumab. For example MYT3698, MYT3735, MYT3740, MYT4247, and MYT4325, an antibody variant of P3D12, shows increased internalization and endolysosomal delivery relative to P3D12. Such pH engineered anti-MET antibody variants with increased mean fluorescence intensity relative to their starting antibodies were selected for further analysis.

Example 60. Construction and Screening of pH-Engineered MET Antibodies

Multiple MET-binding monoclonal antibodies have been described in the literature and can be used as a template for engineering pH-dependent binding [Wang J et al (2017) ABBV-399, a c-Met Antibody-Drug Conjugate that Targets Both MET-Amplified and c-Met-Overexpressing Tumors, Irrespective of MET Pathway Dependence, Clin Cancer Res, 23:992-1000]. We selected MYT4940, MYT4942, MYT4888, MYT4827, MYT4837, MYT4849, and MYT5309 MET-binding monoclonal antibodies for pH engineering via histidine scanning. Briefly, CDRs in the heavy and light chains were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. In cases where the starting CDR residue was a histidine, it was mutated to an alanine. Antibody variants with two or more histidine or alanine mutations were generated by co-transfection of Expi293 cells with a) one light chain sequence variant or light chain combinations sequence variant, and b) one heavy chain sequence variant or heavy chain combinations sequence variant using methods known to the art. After allowing for four days of protein expression, cell culture supernatants were collected, quantified by SDS-PAGE analysis, and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1xPBST, pH 7.4 for high expressors, 25 μL of cell culture supernatant was diluted into 175 μL of 1xPBST, pH 7.4 for medium expressors and 100 μL of cell culture supernatant was diluted into 100 μL of 1xPBST, pH 7.4 for low expressors for loading onto the sensor tips. Diluted supernatants were then captured on an anti-human Fc sensor (Forte Bio). A baseline was established using 1xPB ST (50 mM Potassium Phosphate Buffer+150 mM NaCl+0.05% Tween 20), pH 7.4, and the sensor was associated with 50 nM of MET (cMET, Sino Biological Cat. No. 10692-H08H) in 1xPBST, pH 7.4, for 120 sec to generate an association curve. In the dissociation phase, the antibody-antigen complex on the sensor was exposed to 1xPBST, pH 7.4, for 300-600 sec. Baseline, association, and dissociation were repeated using 1xPBST, pH 5.4, throughout in a separate condition. An additional condition was run with baseline and association using 1xPBST, pH 7.4 and dissociation using 1xPBST, pH 5.4. Association and dissociation phase curves were examined for the starting antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting antibody (with no substitutions), and b) reduced dissociation at pH 7.4 (e.g., lower koff values) compared to pH 5.4 in the antibody variant itself and with the starting antibody (with no substitutions).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Sequence Appendix
Mature Human MET
(SEQ ID NO: 1)
ECKEALAKSEMNVNMKYQLPNFTAETPIQNVILHEHHIFLGATNY
IYVLNEEDLQKVAEYKTGPVLEHPDCFPCQDCSSKANLSGGVWKD
NINMALVVDTYYDDQLISCGSVNRGTCQRHVFPHNHTADIQSEVH
CIFSPQIEEPSQCPDCVVSALGAKVLSSVKDRFINFFVGNTINSS
YFPDHPLHSISVRRLKETKDGFMFLTDQSYIDVLPEFRDSYPIKY
VHAFESNNFIYFLTVQRETLDAQTFHTRIIRFCSINSGLHSYMEM
PLECILTEKRKKRSTKKEVFNILQAAYVSKPGAQLARQIGASLND
DILFGVFAQSKPDSAEPMDRSAMCAFPIKYVNDFFNKIVNKNNVR
CLQHFYGPNHEHCFNRTLLRNSSGCEARRDEYRTEFTTALQRVDL
FMGQFSEVLLTSISTFIKGDLTIANLGTSEGRFMQVVVSRSGPST
PHVNFLLDSHPVSPEVIVEHTLNQNGYTLVITGKKITKIPLNGLG
CRHFQSCSQCLSAPPFVQCGWCHDKCVRSEECLSGTWTQQICLPA
IYKVFPNSAPLEGGTRLTICGWDFGFRRNNKFDLKKTRVLLGNES
CTLTLSESTMNTLKCTVGPAMNKHFNMSIIISNGHGTTQYSTFSY
VDPVITSISPKYGPMAGGTLLTLTGNYLNSGNSRHISIGGKTCTL
KSVSNSILECYTPAQTISTEFAVKLKIDLANRETSIFSYREDPIV
YEIHPTKSFISGGSTITGVGKNLNSVSVPRMVINVHEAGRNFTVA
CQHRSNSEIICCTTPSLQQLNLQLPLKTKAFFMLDGILSKYFDLI
YVHNPVFKPFEKPVMISMGNENVLEIKGNDIDPEAVKGEVLKVGN
KSCENIHLHSEAVLCTVPNDLLKLNSELNIEWKQAISSTVLGKVI
VQPDQNFTGLIAGVVSISTALLLLLGFFLWLKKRKQIKDLGSELV
RYDARVHTPHLDRLVSARSVSPTTEMVSNESVDYRATFPEDQFPN
SSQNGSCRQVQYPLTDMSPILTSGDSDISSPLLQNTVHIDLSALN
PELVQAVQHVVIGPSSLIVHFNEVIGRGHFGCVYHGTLLDNGKK
IHCAVKSLNRITDIGEVSQFLTEGIIMKDFSHPNVLSLLGICLRS
EGSPLVVLPYMKHGDLRNFIRNETHNPTVKDLIGFGLQVAKGMKY
LASKKFVHRDLAARNCMLDEKFTVKVADFGLARDMYDKEYYSVHN
KTGAKLPVKWMALESLQTQKFTTKSDVWSFGVLLWELMTRGAPPY
PDVNTFDITVYLLQGRRLLQPEYCPDPLYEVMLKCWHPKAEMRPS
FSELVSRISAIFSTFIGEHYVHVNATYVNVKCVAPYPSLLSSEDN
ADDEVDTRPASFWETS cDNA Encoding Mature Human MET
(SEQ ID NO: 2)
GAGTGTAAAGAGGCACTAGCAAAGTCCGAGATGAATGTGAATATG
AAGTATCAGCTTCCCAACTTCACCGCGGAAACACCCATCCAGAAT
GTCATTCTACATGAGCATCACATTTTCCTTGGTGCCACTAACTAC
ATTTATGTTTTAAATGAGGAAGACCTTCAGAAGGTTGCTGAGTAC
AAGACTGGGCCTGTGCTGGAACACCCAGATTGTTTCCCATGTCAG
GACTGCAGCAGCAAAGCCAATTTATCAGGAGGTGTTTGGAAAGAT
AACATCAACATGGCTCTAGTTGTCGACACCTACTATGATGATCAA CTCATTAGCTGTGGCAGCGTCAACAGAGGGACCTGCCAGCGACAT
GTCTTTCCCCACAATCATACTGCTGACATACAGTCGGAGGTTCAC
TGCATATTCTCCCCACAGATAGAAGAGCCCAGCCAGTGTCCTGAC
TGTGTGGTGAGCGCCCTGGGAGCAAAAGTCCTTTCATCTGTAAAG
GACCGGTTCATCAACTTCTTTGTAGGCAATACCATAAATTCTTCT
TATTTCCCAGATCATCCATTGCATTCGATATCAGTGAGAAGGCTA
AAGGAAACGAAAGATGGTTTTATGTTTTTGACGGACCAGTCCTAC
ATTGATGTTTTACCTGAGTTCAGAGATTCTTACCCCATTAAGTAT
GTCCATGCCTTTGAAAGCAACAATTTTATTTACTTCTTGACGGTC
CAAAGGGAAACTCTAGATGCTCAGACTTTTCACACAAGAATAATC
AGGTTCTGTTCCATAAACTCTGGATTGCATTCCTACATGGAAATG
CCTCTGGAGTGTATTCTCACAGAAAAGAGAAAAAAGAGATCCACA
AAGAAGGAAGTGTTTAATATACTTCAGGCTGCGTATGTCAGCAAG
CCTGGGGCCCAGCTTGCTAGACAAATAGGAGCCAGCCTGAATGAT
GACATTCTTTTCGGGGTGTTCGCACAAAGCAAGCCAGATTCTGCC
GAACCAATGGATCGATCTGCCATGTGTGCATTCCCTATCAAATAT
GTCAACGACTTCTTCAACAAGATCGTCAACAAAAACAATGTGAGA
TGTCTCCAGCATTTTTACGGACCCAATCATGAGCACTGCTTTAAT
AGGACACTTCTGAGAAATTCATCAGGCTGTGAAGCGCGCCGTGAT
GAATATCGAACAGAGTTTACCACAGCTTTGCAGCGCGTTGACTTA
TTCATGGGTCAATTCAGCGAAGTCCTCTTAACATCTATATCCACC
TTCATTAAAGGAGACCTCACCATAGCTAATCTTGGGACATCAGAG
GGTCGCTTCATGCAGGTTGTGGTTTCTCGATCAGGACCATCAACC
CCTCATGTGAATTTTCTCCTGGACTCCCATCCAGTGTCTCCAGAA
GTGATTGTGGAGCATACATTAAACCAAAATGGCTACACACTGGTT
ATCACTGGGAAGAAGATCACGAAGATCCCATTGAATGGCTTGGGC
TGCAGACATTTCCAGTCCTGCAGTCAATGCCTCTCTGCCCCACCC
TTTGTTCAGTGTGGCTGGTGCCACGACAAATGTGTGCGATCGGAG
GAATGCCTGAGCGGGACATGGACTCAACAGATCTGTCTGCCTGCA
ATCTACAAGGTTTTCCCAAATAGTGCACCCCTTGAAGGAGGGACA
AGGCTGACCATATGGCTGGGACTTTGGATTTCGGAGGAATAAT
AAATTTGATTTAAAGAAAACTAGAGTTCTCCTTGGAAATGAGAGC
TGCACCTTGACTTTAAGTGAGAGCACGATGAATACATTGAAATGC
ACAGTTGGTCCTGCCATGAATAAGCATTTCAATATGTCCATAATT
ATTTCAAATGGCCACGGGACAACACAATACAGTACATTCTCCTAT
GTGGATCCTGTAATAACAAGTATTTCGCCGAAATACGGTCCTATG
GCTGGTGGCACTTTACTTACTTTAACTGGAAATTACCTAAACAGT
GGGAATTCTAGACACATTTCAATTGGTGGAAAAACATGTACTTTA
AAAAGTGTGTCAAACAGTATTCTTGAATGTTATACCCCAGCCCAA
ACCATTTCAACTGAGTTTGCTGTTAAATTGAAAATTGACTTAGCC
AACCGAGAGACAAGCATCTTCAGTTACCGTGAAGATCCCATTGTC

```
TATGAAATTCATCCAACCAAATCTTTTATTAGTGGTGGGAGCACA
ATAACAGGTGTTGGGAAAAACCTGAATTCAGTTAGTGTCCCGAGA
ATGGTCATAAATGTGCATGAAGCAGGAAGGAACTTTACAGTGGCA
TGTCAACATCGCTCTAATTCAGAGATAATCTGTTGTACCACTCCT
TCCCTGCAACAGCTGAATCTGCAACTCCCCCTGAAAACCAAAGCC
TTTTTCATGTTAGATGGGATCCTTTCCAAATACTTTGATCTCATT
TATGTACATAATCCTGTGTTTAAGCCTTTTGAAAAGCCAGTGATG
ATCTCAATGGGCAATGAAAATGTACTGGAAATTAAGGGAAATGAT
ATTGACCCTGAAGCAGTTAAAGGTGAAGTGTTAAAAGTTGGAAAT
AAGAGCTGTGAGAATATACACTTACATTCTGAAGCCGTTTTATGC
ACGGTCCCCAATGACCTGCTGAAATTGAACAGCGAGCTAAATATA
GAGTGGAAGCAAGCAATTTCTTCAACCGTCCTTGGAAAAGTAATA
GTTCAACCAGATCAGAATTTCACAGGATTGATTGCTGGTGTTGTC
TCAATATCAACAGCACTGTTATTACTACTTGGGTTTTTCCTGTGG
CTGAAAAAGAGAAAGCAAATTAAAGATCTGGGCAGTGAATTAGTT
CGCTACGATGCAAGAGTACACACTCCTCATTGGATAGGCTTGTA
AGTGCCCGAAGTGTAAGCCCAACTACAGAAATGGTTTCAAATGAA
TCTGTAGACTACCGAGCTACTTTCCAGAAGATCAGTTTCCTAAT
TCATCTCAGAACGGTTCATGCCGACAAGTGCAGTATCCTCTGACA
GACATGTCCCCATCCTAACTAGTGGGGACTCTGATATATCCAGT
CCATTACTGCAAAATACTGTCCACATTGACCTCAGTGCTCTAAAT
CCAGAGCTGGTCCAGGCAGTGCAGCATGTAGTGATTGGGCCCAGT
AGCCTGATTGTGCATTTCAATGAAGTCATAGGAAGAGGGCATTTT
GGTTGTGTATATCATGGGACTTTGTTGGACAATGATGGCAAGAAA
ATTCACTGTGCTGTGAAATCCTTGAACAGAATCACTGACATAGGA
GAAGTTTCCCAATTTCTGACCGAGGGAATCATCATGAAAGATTTT
AGTCATCCCAATGTCCTCTCGCTCCTGGGAATCTGCCTGCAAGT
GAAGGGTCTCCGCTGGTGGTCCTACCATACATGAAACATGGAGAT
CTTCGAAATTTCATTCGAAATGAGACTCATAATCCAACTGTAAAA
GATCTTATTGGCTTTGGTCTTCAAGTAGCCAAAGGCATGAAATAT
CTTGCAAGCAAAAAGTTTGTCCACAGAGACTTGGCTGCAAGAAAC
TGTATGCTGGATGAAAAATTCACAGTCAAGGTTGCTGATTTTGGT
CTTGCCAGAGACATGTATGATAAAGAATACTATAGTGTACACAAC
AAAACAGGTGCAAAGCTGCCAGTGAAGTGGATGGCTTTGGAAAGT
CTGCAAACTCAAAAGTTTACCACCAAGTCAGATGTGTGGTCCTTT
GGCGTGCTCCTCTGGGAGCTGATGACAAGAGGAGCCCCACCTTAT
CCTGACGTAAACACCTTTGATATAACTGTTTACTTGTTGCAAGGG
AGAAGACTCCTACAACCCGAATACTGCCCAGACCCCTTATATGAA
GTAATGCTAAAATGCTGGCACCCTAAAGCCGAAATGCGCCCATCC
TTTTCTGAACTGGTGTCCCGGATATCAGCGATCTTCTCTACTTTC
```

```
ATTGGGGAGCACTATGTCCATGTGAACGCTACTTATGTGAACGTA
AAATGTGTCGCTCCGTATCCTTCTCTGTTGTCATCAGAAGATAAC
GCTGATGATGAGGTGGACACACGACCAGCCTCCTTCTGGGAGACA
TCA
```

Extracellular Domain of MET
(SEQ ID NO: 3)
ECKEALAKSEMNVNMKYQLPNFTAETPIQNVILHEHHIFLGATNY
IYVLNEEDLQKVAEYKTGPVLEHPDCFPCQDCSSKANLSGGVWKD
NINMALVVDTYYDDQLISCGSVNRGTCQRHVFPHNHTADIQSEVH
CIFSPQIEEPSQCPDCVVSALGAKVLSSVKDRFINFFVGNTINSS
YFPDHPLHSISVRRLKETKDGFMFLTDQSYIDVLPEFRDSYPIKY
VHAFESNNFIYFLTVQRETLDAQTFHTRIIRFCSINSGLHSYMEM
PLECILTEKRKKRSTKKEVFNILQAAYVSKPGAQLARQIGASLND
DILFGVFAQSKPDSAEPMDRSAMCAFPIKYVNDFFNKIVNKNNVR
CLQHFYGPNHEHCFNRTLLRNSSGCEARRDEYRTEFTTALQRVDL
FMGQFSEVLLTSISTFIKGDLTIANLGTSEGRFMQVVVSRSGPST
PHVNFLLDSHPVSPEVIVEHTLNQNGYTLVITGKKITKIPLNGLG
CRHFQSCSQCLSAPPFVQCGWCHDKCVRSEECLSGTWTQQICLPA
IYKVFPNSAPLEGGTRLTICGWDFGFRRNNKFDLKKTRVLLGNES
CTLTLSESTMNTLKCTVGPAMNKHFNMSIIISNGHGTTQYSTFSY
VDPVITSISPKYGPMAGGTLLTLTGNYLNSGNSRHISIGGKTCTL
KSVSNSILECYTPAQTISTEFAVKLKIDLANRETSIFSYREDPIV
YEIHPTKSFISGGSTITGVGKNLNSVSVPRMVINVHEAGRNFTVA
CQHRSNSEIICCTTPSLQQLNLQLPLKTKAFFMLDGILSKYFDLI
YVHNPVFKPFEKPVMISMGNENVLEIKGNDIDPEAVKGEVLKVGN
KSCENIHLHSEAVLCTVPNDLLKLNSELNIEWKQAISSTVLGKVI
VQPDQNFT cDNA Encoding Extracellular Domain of MET
(SEQ ID NO: 4)
GAGTGTAAAGAGGCACTAGCAAAGTCCGAGATGAATGTGAATATG
AAGTATCAGCTTCCCAACTTCACCGCGGAAACACCCATCCAGAAT
GTCATTCTACATGAGCATCACATTTTCCTTGGTGCCACTAACTAC
ATTTATGTTTTAAATGAGGAAGACCTTCAGAAGGTTGCTGAGTAC
AAGACTGGGCCTGTGCTGGAACACCCAGATTGTTTCCCATGTCAG
GACTGCAGCAGCAAAGCCAATTTATCAGGAGGTGTTTGGAAAGAT
AACATCAACATGGCTCTAGTTGTCGACACCTACTATGATGATCAA
CTCATTAGCTGTGGCAGCGTCAACAGAGGGACCTGCCAGCGACAT
GTCTTTCCCCACAATCATACTGCTGACATACAGTCGGAGGTTCAC
TGCATATTCTCCCCACAGATAGAAGAGCCCAGCCAGTGTCCTGAC
TGTGTGGTGAGCGCCCTGGGAGCCAAAGTCCTTTCATCTGTAAAG
GACCGGTTCATCAACTTCTTTGTAGGCAATACCATAAATTCTTCT
TATTTCCCAGATCATCCATTGCATTCGATATCAGTGAGAAGGCTA
AAGGAAACGAAAGATGGTTTTATGTTTTTGACGGACCAGTCCTAC
```

```
ATTGATGTTTTACCTGAGTTCAGAGATTCTTACCCCATTAAGTAT

GTCCATGCCTTTGAAAGCAACAATTTTATTTACTTCTTGACGGTC

CAAAGGGAAACTCTAGATGCTCAGACTTTTCACACAAGAATAATC

AGGTTCTGTTCCATAAACTCTGGATTGCATTCCTACATGGAAATG

CCTCTGGAGTGTATTCTCACAGAAAAGAGAAAAAAGAGATCCACA

AAGAAGGAAGTGTTTAATATACTTCAGGCTGCGTATGTCAGCAAG

CCTGGGGCCCAGCTTGCTAGACAAATAGGAGCCAGCCTGAATGAT

GACATTCTTTTCGGGGTGTTCGCACAAAGCAAGCCAGATTCTGCC

GAACCAATGGATCGATCTGCCATGTGTGCATTCCCTATCAAATAT

GTCAACGACTTCTTCAACAAGATCGTCAACAAAAACAATGTGAGA

TGTCTCCAGCATTTTTACGGACCCAATCATGAGCACTGCTTTAAT

AGGACACTTCTGAGAAATTCATCAGGCTGTGAAGCGCGCCGTGAT

GAATATCGAACAGAGTTTACCACAGCTTTGCAGCGCGTTGACTTA

TTCATGGGTCAATTCAGCGAAGTCCTCTTAACATCTATATCCACC

TTCATTAAAGGAGACCTCACCATAGCTAATCTTGGGACATCAGAG

GGTCGCTTCATGCAGGTTGTGGTTTCTCGATCAGGACCATCAACC

CCTCATGTGAATTTTCTCCTGGACTCCCATCCAGTGTCTCCAGAA

GTGATTGTGGAGCATACATTAAACCAAAATGGCTACACACTGGTT

ATCACTGGGAAGAAGATCACGAAGATCCCATTGAATGGCTTGGGC

TGCAGACATTTCCAGTCCTGCAGTCAATGCCTCTCTGCCCCACCC

TTTGTTCAGTGTGGCTGGTGCCACGACAAATGTGTGCGATCGGAG

GAATGCCTGAGCGGGACATGGACTCAACAGATCTGTCTGCCTGCA

ATCTACAAGGTTTTCCCAAATAGTGCACCCCTTGAAGGAGGGACA

AGGCTGACCATATGTGGCTGGGACTTTGGATTTCGGAGGAATAAT

AAATTTGATTTAAAGAAAACTAGAGTTCTCCTTGGAAATGAGAGC

TGCACCTTGACTTTAAGTGAGAGCACGATGAATACATTGAAATGC

ACAGTTGGTCCTGCCATGAATAAGCATTTCAATATGTCCATAATT

ATTTCAAATGGCCACGGGACAACACAATACAGTACATTCTCCTAT

GTGGATCCTGTAATAACAAGTATTTCGCCGAAATACGGTCCTATG

GCTGGTGGCACTTTACTTACTTTAACTGGAAATTACCTAAACAGT

GGGAATTCTAGACACATTTCAATTGGTGGAAAACATGTACTTTA

AAAAGTGTGTCAAACAGTATTCTTGAATGTTATACCCCAGCCCAA

ACCATTTCAACTGAGTTTGCTGTTAAATTGAAAATTGACTTAGCC

AACCGAGAGACAAGCATCTTCAGTTACCGTGAAGATCCCATTGTC

TATGAAATTCATCCAACCAAATCTTTTATTAGTGGTGGGAGCACA

ATAACAGGTGTTGGGAAAAACCTGAATTCAGTTAGTGTCCCGAGA

ATGGTCATAAATGTGCATGAAGCAGGAAGGAACTTTACAGTGGCA

TGTCAACATCGCTCTAATTCAGAGATAATCTGTTGTACCACTCCT

TCCCTGCAACAGCTGAATCTGCAACTCCCCCTGAAAACCAAAGCC

TTTTTCATGTTAGATGGGATCCTTTCCAAATACTTTGATCTCATT

TATGTACATAATCCTGTGTTTAAGCCTTTTGAAAAGCCAGTGATG

ATCTCAATGGGCAATGAAAATGTACTGGAAATTAAGGGAAATGAT

ATTGACCCTGAAGCAGTTAAAGGTGAAGTGTTAAAAGTTGGAAAT

AAGAGCTGTGAGAATATACACTTACATTCTGAAGCCGTTTATGC

ACGGTCCCCAATGACCTGCTGAAATTGAACAGCGAGCTAAATATA

GAGTGGAAGCAAGCAATTTCTTCAACCGTCCTTGGAAAAGTAATA

GTTCAACCAGATCAGAATTTCACA

MYT5351 Heavy Chain Variable Region
                             (SEQ ID NO: 5)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGNYPLMDYWGQGTTVTVSS

MYT5351 Light Variable Region
                             (SEQ ID NO: 6)
QIVLTQSPAILSLSPGERATLSCSASSSVTSNYLYWYQQKPGSSP

KLLIYSHSNLASGVPARFSGSGSGTSYTLTISSLEAEDAASYFCH

QWSSYPPTFGSGTKLEIK

MYT4313 Heavy Chain Variable Region
                             (SEQ ID NO: 7)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMDYWGQGTTVTVSS

MYT4313 Light Chain Variable Region
                             (SEQ ID NO: 8)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIK

MYT4325 Heavy Chain Variable Region
                             (SEQ ID NO: 9)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMHYWGQGTTVTVSS

MYT4325 Light Chain Variable Region
                             (SEQ ID NO: 10)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIK

MYT4826 Heavy Chain Variable Region
                             (SEQ ID NO: 11)
QVQLVQSGAEVKKPGASVKVSCKASGYTFTHYYMHWVRQAPGQGL

EWMGRVNPNRRHTTYNQKFEGRVTMTTDTSTSTAYMELRSLRSDD

TAVYYCARANWLDYWGQGTTVTVSS

MYT4826 Light Chain Variable Region
                             (SEQ ID NO: 12)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VYSGYPLTFGGGTKVEIK
```

MYT4837 Heavy Chain Variable Region
(SEQ ID NO: 13)
QVQLVQSGAEVKKPGASVKVSCKASGYTFTHYYMHWVRQAPGQGL
EWMGRVNPHRRHTTYNQKFEGRVTMTTDTSTSTAYMELRSLRSDD
TAVYYCARANWLDYWGQGTTVTVSS MYT4837 Light Chain Variable Region
(SEQ ID NO: 14)
DIQMTQSPSSLSASVGDRVTITCSVSSSVSSIYLHWYQQKPGKAP
KLLIYSTSNLASGVPSRFSGSGSGTDFTLTISSLQPEDFATYYCQ
VYSGYPLTFGGGTKVEIK MYT4849 Heavy Chain Variable Region
(SEQ ID NO: 15)
QVQLVQSGAEVKKPGASVKVSCKASGYTFTDYYMHWVRQAPGQGL
EWMGRVNPNRRGTTYNQKFEGRVTMTTDTSTSTAYMELRSLRSDD
TAVYYCARANWLDYWGQGTTVTVSS MYT4849 Light Chain Variable Region
(SEQ ID NO: 16)
DIQMTQSPSSLSASVGDRVTITCSVSSSVSSIHLHWYQQKPGKAP
KLLIYHTSNLASGVPSRFSGSGSGTDFTLTISSLQPEDFATYYCQ
VYSGYPLTFGGGTKVEIK MYT4942 Heavy Chain Variable Region
(SEQ ID NO: 17)
QVQLVQSGAEVKKPGASVKVSCKASGHIFTAYTMHWVRQAPGQGL
EWMGWIKPNNGLANYAQKFQGRVTMTRDTSISTAYMELSRLRSDD
TAVYYCARSEITHEFDHWGQGTL VTVSS MYT4942 Light Chain Variable Region
(SEQ ID NO: 18)
DIVMTQSPDSLAVSLGERATINCKSSESVDSYANSHLHWYQQKPG
QPPKLLIYRASTRESGVPDRFSGSGSGTDFTLTISSLQAEDVAVY
YCQQSKEDPLTFGGGTKVEIK MYT5309 Heavy Chain Variable Region
(SEQ ID NO: 19)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARANWLDYWGQGTTVTVSS MYT5309 Light Chain Variable Region
(SEQ ID NO: 20)
DIQMTQSPSSLSASVGDRVTITCSVSSSVSSIYLHWYQQKPGKAP
KLLIYSTSNLASGVPSRFSGSGSGTDFTLTISSLQPEDFATYYCQ
HYSGYPLTFGGGTKVEIK MYT5344 Heavy Chain Variable Region
(SEQ ID NO: 21)
QVQLVQSGAEVKKPGASVKVSCKASGYTFTSYWMHWVKQAPGQGL
DWIGYIKHSTDNTEYNQKFKDKATLTADKSTSTAYMELSSLRSED
TAVYYCARSYGNYPLMDYWGQGTTVTVSS MYT5344 Light Chain Variable Region
(SEQ ID NO: 22)
QIVLTQSPAILSLSPGERATLSCSASSSVTSHYLYWYQQKPGSSP
KLLIYSTSNLASGVPARFSGSGSGTSYTLTISSLEAEDAASYFCH
QWSSYPPTFGSGTKLEIK MYT5367 Heavy Chain Variable Region
(SEQ ID NO: 23)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSS MYT5367 Light Chain Variable Region
(SEQ ID NO: 24)
QIVLTQSPAILSLSPGERATLSCSASSSVTSNYLYWYQQKPGSSP
KLLIYSTSNLASGVPARFSGSGSGTSYTLTISSLEAEDAASYFCH
QWSHYHPTFGSGTKLEIK MYT4827 Heavy Chain Variable Region
(SEQ ID NO: 25)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARAHWLDYWGQGTTVTVSS MYT4827 Light Chain Variable Region
(SEQ ID NO: 26)
DIQMTQSPSSLSASVGDRVTITCSVSSSVSSIYLHWYQQKPGKAP
KLLIYSTSNLASGVPSRFSGSGSGTDFTLTISSLQPEDFATYYCQ
VYSGYPLTFGGGTKVEIK MYT4312 Heavy Chain Variable Region
(SEQ ID NO: 27)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMHWGQGTTVTVSS MYT4312 Light Chain Variable Region
(SEQ ID NO: 28)
QIVLTQSPAILSLSPGERATLSCSASSSVTSNYLYWYQQKPGSSP
KLLIYSTSNLASGVPARFSGSGSGTSYTLTISSLEAEDAASYFCH
QWSSYPPTFGSGTKLEIK MYT4953 Heavy Chain Variable Region
(SEQ ID NO: 29)
QVQLVQSGAEVKKPGASVKVSCKASGYIFTAYTMHWVRQAPGQGL
EWMGWIKPNNGLANYAQKFQGRVTMTRDTSISTAYMELSRLRSDD
TAVYYCHRSEITHEFDYWGQGTLVTVSS MYT4953 Light Chain Variable Region
(SEQ ID NO: 30)
DIVMTQSPDSLAVSLGERATINCKSSESVDSYANSFLHWYQQKPG
QPPKLLIYRASTRESGVPDRFSGSGSGTDFTLTISSLQAEDVAVY
YCQQSKEDPLTFGGGTKVEIK MYT4940 Heavy Chain Variable Region
(SEQ ID NO: 31)
QVQLVQSGAEVKKPGASVKVSCKASGYIFTAYTMHWVRQAPGQGL
EWMGWIKPNNGLANYAQKFQGRVTMTRDTSISTAYMELSRLRSDD
TAVYYCARHEITTEFDHWGQGTLVTVSS MYT4940 Light Chain Variable Region
(SEQ ID NO: 32)
DIVMTQSPDSLAVSLGERATINCKSSESVDSYANSHLHWYQQKPG
QPPKLLIYRASTRESGVPDRFSGSGSGTDFTLTISSLQAEDVAVY
YCQQSKEDPLTFGGGTKVEIK -continued MYT4888 Heavy Chain Variable Region
(SEQ ID NO: 33)
QVQLVQSGAEVKKPGASVKVSCKASGYTFTSYWMHWVKQAPGQGL
DWIGYIKPSTDNTEYNQKFKDKATLTADKSTSTAYMELSSLRSED
TAVYYCARSYGNYPLHDYWGQGTTVTVSS MYT4888 Light Chain Variable Region
(SEQ ID NO: 34)
QIVLTQSPAILSLSPGERATLSCSASSSVTSNYLYWYQQKPGSSP
KLLIYSTSNLASGVPARFSGSGSGTSYTLTISSLEAEDAASYFCH
QWSSYPPTFGSGTKLEIK MYT5351 Heavy chain Triple hinge
(SEQ ID NO: 35)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG*

MYT5351 Heavy chain Triple hinge + LS mutation
(SEQ ID NO: 36)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG MYT5351 Heavy chain Triple hinge + YTE mutation
(SEQ ID NO: 37)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

MYT5351 Heavy chain Triple hinge and A118C
(SEQ ID NO: 38)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG*

MYT5351 Heavy chain Triple hinge + LS mutation and A118C
(SEQ ID NO: 39)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG**

MYT5351 Heavy chain Triple hinge + YTE mutation and A118C
(SEQ ID NO: 40)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

MYT5351 Light Chain
(SEQ ID NO: 41)
QIVLTQSPAILSLSPGERATLSCSASSSVTSNYLYWYQQKPGSSP
KLLIYSHSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC**

MYT5351 Light Chain
(V205C)
(SEQ ID NO: 42)
QIVLTQSPAILSLSPGERATLSCSASSSVTSNYLYWYQQKPGSSP

KLLIYSHSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPCTKSFNRGEC**

MYT4313 Heavy chain Triple hinge
(SEQ ID NO: 43)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMDYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG**

MYT4313 Heavy chain Triple hinge + LS
mutation
(SEQ ID NO: 44)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMDYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTK

NQVSLTCLVKGFYPSDIAVEWESNGQPENNYKTTPPVLDSDGSFF

LYSKLTVDKSRWQQGNVFSCSVLHEALHSHYTQKSLSLSPG*

MYT4313 Heavy chain Triple hinge + YTE
mutation
(SEQ ID NO: 45)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMDYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLYITREPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG**

MYT4313 Heavy chain Triple hinge and A118C
(SEQ ID NO: 46)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMDYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG**

MYT4313 Heavy chain Triple hinge + LS
mutation and A118C
(SEQ ID NO: 47)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMDYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTK

NQVSLTCLVKGFYPSDIAVEWESNGQPENNYKTTPPVLDSDGSFF

LYSKLTVDKSRWQQGNVFSCSVLHEALHSHYTQKSLSLSPG**

MYT4313 Heavy chain Triple hinge + YTE
mutation and A118C
(SEQ ID NO: 48)
QVQLVQSGAEVKKPGASVKVSCKASGYTFTSYWMHWVKQAPGQGL

DWIGYIKPSTDNTHYNQKFKDKATLTADKSTSTAYMELSSLRSED

TAVYYCARSYGHYPLMDYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLYITREPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG**

MYT4313 Light Chain
(SEQ ID NO: 49)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL
TLSKADYEKHKVYACEVTHQGLSSPVTKSFNRGEC**

MYT4313 Light Chain V205C
(SEQ ID NO: 50)
QIVLTQSPAILSLSPGERATLSCSASSSVTSNYLYWYQQKPGSSP
KLLIYSTSNLASGVPARFSGSGSGTSYTLTISSLEAEDAASYFCH
QWSSYPPTFGSGTKLEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPCTKSFNRGEC*

MYT4325 Heavy chain Triple hinge
(SEQ ID NO: 51)
QVQLVQSGAEVKKPGASVKVSCKASGYTFTSYWMHWVKQAPGQGL
DWIGYIKPSTDNTHYNQKFKDKATLTADKSTSTAYMELSSLRSED
TAVYYCARSYGHYPLMHYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

MYT4325 Heavy chain Triple hinge + LS mutation
(SEQ ID NO: 52)
QVQLVQSGAEVKKPGASVKVSCKASGYTFTSYWMHWVKQAPGQGL
DWIGYIKPSTDNTHYNQKFKDKATLTADKSTSTAYMELSSLRSED
TAVYYCARSYGHYPLMHYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG**

MYT4325 Heavy chain Triple hinge + YTE mutation
(SEQ ID NO: 53)
QVQLVQSGAEVKKPGASVKVSCKASGYTFTSYWMHWVKQAPGQGL
DWIGYIKPSTDNTHYNQKFKDKATLTADKSTSTAYMELSSLRSED
TAVYYCARSYGHYPLMHYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

MYT4325 Heavy chain Triple hinge and A118C
(SEQ ID NO: 54)
QVQLVQSGAEVKKPGASVKVSCKASGYTFTSYWMHWVKQAPGQGL
DWIGYIKPSTDNTHYNQKFKDKATLTADKSTSTAYMELSSLRSED
TAVYYCARSYGHYPLMHYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

MYT4325 Heavy chain
(triple hinge + LS mutation and A118C)
(SEQ ID NO: 55)
QVQLVQSGAEVKKPGASVKVSCKASGYTFTSYWMHWVKQAPGQGL
DWIGYIKPSTDNTHYNQKFKDKATLTADKSTSTAYMELSSLRSED
TAVYYCARSYGHYPLMHYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG**

MYT4325 Heavy chain
(triple hinge + YTE mutation and A118C)
(SEQ ID NO: 56)
QVQLVQSGAEVKKPGASVKVSCKASGYTFTSYWMHWVKQAPGQGL
DWIGYIKPSTDNTHYNQKFKDKATLTADKSTSTAYMELSSLRSED
TAVYYCARSYGHYPLMHYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG MYT4325 Light Chain
(SEQ ID NO: 57)
QIVLTQSPAILSLSPGERATLSCSASSSVTSNYLYWYQQKPGSSP
KLLIYSTSNLASGVPARFSGSGSGTSYTLTISSLEAEDAASYFCH
QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC*

MYT4325 Light Chain V205C
(SEQ ID NO: 58)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPCTKSFNRGEC**

MYT4826 Heavy chain Triple hinge
(SEQ ID NO: 59)
QVQLVQSGAEVKKPGASVKVSCKASGYTFTHYYMHWVRQAPGQGL

EWMGRVNPNRRHTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG*

MYT4826 Heavy chain
(triple hinge + LS
mutation)
(SEQ ID NO: 60)
QVQLVQSGAEVKKPGASVKVSCKASGYTFTHYYMHWVRQAPGQGL

EWMGRVNPNRRHTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSRDELTKNQVS

LTCLVKGFYPSDIAVEWESNGQPENNYKTTPPVLDSDGSFFLYSK

LTVDKSRWQQGNVFSCSVLHEALHSHYTQKSLSLSPG

MYT4826 Heavy chain Triple hinge + YTE
mutation
(SEQ ID NO: 61)
QVQLVQSGAEVKKPGASVKVSCKASGYTFTHYYMHWVRQAPGQGL

EWMGRVNPNRRHTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLYITREPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG**

MYT4826 Heavy chain Triple hinge only and A118
(SEQ ID NO: 62)
QVQLVQSGAEVKKPGASVKVSCKASGYTFTHYYMHWVRQAPGQGL

EWMGRVNPNRRHTTYNQKFEGRVTMTTDTSTSTAYMELRSLRSDD

TAVYYCARANWLDYWGQGTTVTVSSCSTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG*

MYT4826 Heavy chain Triple hinge + LS
mutation and A118C
(SEQ ID NO: 63)
QVQLVQSGAEVKKPGASVKVSCKASGYTFTHYYMHWVRQAPGQGL

EWMGRVNPNRRHTTYNQKFEGRVTMTTDTSTSTAYMELRSLRSDD

TAVYYCARANWLDYWGQGTTVTVSSCSTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSRDELTKNQVS

LTCLVKGFYPSDIAVEWESNGQPENNYKTTPPVLDSDGSFFLYSK

LTVDKSRWQQGNVFSCSVLHEALHSHYTQKSLSLSPG*

MYT4826 Heavy chain Triple hinge + YTE
mutation and A118C
(SEQ ID NO: 64)
QVQLVQSGAEVKKPGASVKVSCKASGYTFTHYYMHWVRQAPGQGL

EWMGRVNPNRRHTTYNQKFEGRVTMTTDTSTSTAYMELRSLRSDD

TAVYYCARANWLDYWGQGTTVTVSSCSTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLYITREPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG*

MYT4826 Light Chain
(SEQ ID NO: 65)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VYSGYPLTFGGGTKVEIKRTVAAPSVFIFPPSDEQLKSGTASVVC

```
LLNNFYPREAKVQWKVDNALQSGNSQESVTEQDSKDSTYSLSSTL
TLSKADYEKHKVYACEVTHQGLSSPVTKSFNRGEC**
```

MYT4826 Light Chain V205C
(SEQ ID NO: 66)
```
DIQMTQSPSSLSASVGDRVTITCSVSSSVSSIYLHWYQQKPGAP
KLLIYSTSNLASGVPSRFSGSGSGTDFTLTISSLQPEDFATYYCQ
VYSGYPLTFGGGTKVEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPCTKSFNRGEC'
```

MYT4837 Heavy chain Triple hinge
(SEQ ID NO: 67)
```
QVQLVQSGAEVKKPGASVKVSCKASGYTFTHYYMHWVRQAPGQGL
EWMGRVNPHRRHTTYNQKFEGRVTMTTDTSTSTAYMELRSLRSDD
TAVYYCARANWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*
```

MYT4837 Heavy chain Triple hinge + LS mutation
(SEQ ID NO: 68)
```
QVQLVQSGAEVKKPGASVKVSCKASGYTFTHYYMHWVRQAPGQGL
EWMGRVNPHRRHTTYNQKFEGRVTMTTDTSTSTAYMELRSLRSDD
TAVYYCARANWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG*
```

MYT4837 Heavy chain (Triple hinge + YTE mutation
(SEQ ID NO: 69)
```
QVQLVQSGAEVKKPGASVKVSCKASGYTFTHYYMHWVRQAPGQGL
EWMGRVNPHRRHTTYNQKFEGRVTMTTDTSTSTAYMELRSLRSDD
TAVYYCARANWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLYITREPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*
```

MYT4837 Heavy chain Triple hinge and A118C
(SEQ ID NO: 70)
```
QVQLVQSGAEVKKPGASVKVSCKASGYTFTHYYMHWVRQAPGQGL
EWMGRVNPHRRHTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*
```

MYT4837 Heavy chain Triple hinge + LS mutation and A118C
(SEQ ID NO: 71)
```
QVQLVQSGAEVKKPGASVKVSCKASGYTFTHYYMHWVRQAPGQGL
EWMGRVNPHRRHTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG*
```

MYT4837 Heavy chain (triple hinge + YTE mutation and A118C
(SEQ ID NO: 72)
```
QVQLVQSGAEVKKPGASVKVSCKASGYTFTHYYMHWVRQAPGQGL
EWMGRVNPHRRHTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLYITREPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG**
```

MYT4837 Light Chain
(SEQ ID NO: 73)
```
DIQMTQSPSSLSASVGDRVTITCSVSSSVSSIYLHWYQQKPGAP
KLLIYSTSNLASGVPSRFSGSGSGTDFTLTISSLQPEDFATYYCQ
VYSGYPLTFGGGTKVEIKRTVAAPSVFIFPPSDEQLKSGTASVVC
```

MYT4837 Light Chain V205C
(SEQ ID NO: 74)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VYSGYPLTFGGGTKVEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPCTKSFNRGEC**

MYT4849 Heavy chain Triple hinge
(SEQ ID NO: 75)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG**

MYT4849 Heavy chain Triple hinge + LS
mutation
(SEQ ID NO: 76)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSRDELTKNQVS

LTCLVKGFYPSDIAVEWESNGQPENNYKTTPPVLDSDGSFFLYSK

LTVDKSRWQQGNVFSCSVLHEALHSHYTQKSLSLSPG**

MYT4849 Heavy chain Triple hinge + YTE
mutation
(SEQ ID NO: 77)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLYITREPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG**

MYT4849 Heavy chain Triple hinge and A118C
(SEQ ID NO: 78)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSCSTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG**

MYT4849 Heavy chain Triple hinge + LS
mutation and A118C
(SEQ ID NO: 79)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSCSTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSRDELTKNQVS

LTCLVKGFYPSDIAVEWESNGQPENNYKTTPPVLDSDGSFFLYSK

LTVDKSRWQQGNVFSCSVLHEALHSHYTQKSLSLSPG**

MYT4849 Heavy chain Triple hinge + YTE
mutation and A118C
(SEQ ID NO: 80)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSCSTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLYITREPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG*

MYT4849 Light Chain
(SEQ ID NO: 81)
DIQMTQSPSSLSASVGDRVTITCSVSSSVSSIHLHWYQQKPGKAP

KLLIYHTSNLASGVPSRFSGSGSGTDFTLTISSLQPEDFATYYCQ

VYSGYPLTFGGGTKVEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC**

MYT4849 Light Chain V205C
(SEQ ID NO: 82)
DIQMTQSPSSLSASVGDRVTITCSVSSSVSSIHLHWYQQKPGKAP

KLLIYHTSNLASGVPSRFSGSGSGTDFTLTISSLQPEDFATYYCQ

VYSGYPLTFGGGTKVEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPCTKSFNRGEC**

MYT4942 Heavy chain Triple hinge
(SEQ ID NO: 83)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITHEFDHWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

MYT4942 Heavy chain Triple hinge + LS
mutation
(SEQ ID NO: 84)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITHEFDHWGQGTLVTVSSASTKGPSVFPLAPSSK

STSGGTAALGCLVKDYFPEPVTVS

WNSGALTSGVHTFPAVLQSSGLYSLSSVVTVPSSSLGTQTYICNV

NHKPSNTKVDKRVEPKSCDCHCPPCPAPELLGGPSVFLFPPKPKD

TLMISRTPEVTCVVVDVSHEDPEVKFNWYVDGVEVHNAKTKPREE

QYNSTYRVVSVLTVLHQDWLNGKEYKCKVSNKALPAPIEKTISKA

KGQPREPQVYTLPPSRDELTKNQVSLTCLVKGFYPSDIAVEWESN

GQPENNYKTTPPVLDSDGSFFLYSKLTVDKSRWQQGNVFSCSVLH

EALHSHYTQKSLSLSPG*

MYT4942 Heavy chain Triple hinge + YTE
mutation
(SEQ ID NO: 85)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITHEFDHWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLYITREPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

MYT4942 Heavy chain Triple hinge and A118C
(SEQ ID NO: 86)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITHEFDHWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

MYT4942 Heavy chain Triple hinge + LS
mutation and A118C
(SEQ ID NO: 87)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITHEFDHWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPG**

MYT4942 Heavy chain Triple hinge + YTE
mutation and A118C
(SEQ ID NO: 88)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITHEFDHWGQGTLVTVSSCSTKGPSVFPLAPSSKS

TSGGTAALGCLVKDYFPEPVTVS

WNSGALTSGVHTFPAVLQSSGLYSLSSVVTVPSSSLGTQTYICNV

NHKPSNTKVDKRVEPKSCDCHCPPCPAPELLGGPSVFLFPPKPKD

TLYITREPEVTCVVVDVSHEDPEVKFNWYVDGVEVHNAKTKPREE

QYNSTYRVVSVLTVLHQDWLNGKEYKCKVSNKALPAPIEKTISKA

KGQPREPQVYTLPPSREEMTKNQVSLTCLVKGFYPSDIAVEWESN

GQPENNYKTTPPVLDSDGSFFLYSKLTVDKSRWQQGNVFSCSVMH

EALHNHYTQKSLSLSPG

MYT4942 Light Chain
(SEQ ID NO: 89)
DIVMTQSPDSLAVSLGERATINCKSSESVDSYANSHLHWYQQKPG
QPPKLLIYRASTRESGVPDRFSGSGSGTDFTLTISSLQAEDVAVY
YCQQSKEDPLTFGGGTKVEIKRTVAAPSVFIFPPSDEQLKSGTAS
VVCLLNNFYPREAKVQWKVDNALQSGNSQESVTEQDSKDSTYSLS
STLTLSKADYEKHKVYACEVTHQGLSSPVTKSFNRGEC**

MYT4942 Light Chain V205C
(SEQ ID NO: 90)
DIVMTQSPDSLAVSLGERATINCKSSESVDSYANSHLHWYQQKPG
QPPKLLIYRASTRESGVPDRFSGSGSGTDFTLTISSLQAEDVAVY
YCQQSKEDPLTFGGGTKVEIKRTVAAPSVFIFPPSDEQLKSGTAS
VVCLLNNFYPREAKVQWKVDNALQSGNSQESVTEQDSKDSTYSLS
STLTLSKADYEKHKVYACEVTHQGLSSPCTKSFNRGEC*

MYT5309 Heavy chain Triple hinge
(SEQ ID NO: 91)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARANWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*

MYT5309 Heavy chain Triple hinge + LS
mutation
(SEQ ID NO: 92)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARANWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG*

MYT5309 Heavy chain Triple hinge + YTE
mutation
(SEQ ID NO: 93)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARANWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLYITREPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*

MYT5309 Heavy chain Triple hinge and A118C
(SEQ ID NO: 94)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG MYT5309 Heavy chain Triple hinge + LS
mutation and A118C
(SEQ ID NO: 95)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG MYT5309 Heavy chain Triple hinge + YTE
mutation and A118C
(SEQ ID NO: 96)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLYITREPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*

MYT5309 Light Chain
(SEQ ID NO: 97)
DIQMTQSPSSLSASVGDRVTITCSVSSSVSSIYLHWYQQKPGKAP
KLLIYSTSNLASGVPSRFSGSGSGTDFTLTISSLQPEDFATYYCQ
HYSGYPLTFGGGTKVEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPVTKSFNRGEC**

MYT5309 Light Chain V205C
(SEQ ID NO: 98)
DIQMTQSPSSLSASVGDRVTITCSVSSSVSSIYLHWYQQKPGKAP
KLLIYSTSNLASGVPSRFSGSGSGTDFTLTISSLQPEDFATYYCQ
HYSGYPLTFGGGTKVEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPCTKSFNRGEC**

MYT5344 Heavy chain Triple hinge
(SEQ ID NO: 99)
QVQLVQSGAEVKKPGASVKVSCKASGYTFTSYWMHWVKQAPGQGL
DWIGYIKHSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

MYT5344 Heavy chain Triple hinge + LS
mutation
(SEQ ID NO: 100)
QVQLVQSGAEVKKPGASVKVSCKASGYTFTSYWMHWVKQAPGQGL
DWIGYIKHSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG*

MYT5344 Heavy chain Triple hinge + YTE
mutation
(SEQ ID NO: 101)
QVQLVQSGAEVKKPGASVKVSCKASGYTFTSYWMHWVKQAPGQGL
DWIGYIKHSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG*

MYT5344 Heavy chain Triple hinge and A118C
(SEQ ID NO: 102)
QVQLVQSGAEVKKPGASVKVSCKASGYTFTSYWMHWVKQAPGQGL
DWIGYIKHSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

MYT5344 Heavy chain Triple hinge + LS
mutation and A118C
(SEQ ID NO: 103)
QVQLVQSGAEVKKPGASVKVSCKASGYTFTSYWMHWVKQAPGQGL
DWIGYIKHSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG**

MYT5344 Heavy chain Triple hinge + YTE
mutation and A118C
(SEQ ID NO: 104)
QVQLVQSGAEVKKPGASVKVSCKASGYTFTSYWMHWVKQAPGQGL
DWIGYIKHSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG>

MYT5344 Light Chain
(SEQ ID NO: 105)
QIVLTQSPAILSLSPGERATLSCSASSSVTSHYLYWYQQKPGSSP
KLLIYSTSNLASGVPARFSGSGSGTSYTLTISSLEAEDAASYFCH
QWSSYPPTFGSGTKLEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPVTKSFNRGEC**

MYT5344 Light Chain V205C
(SEQ ID NO: 106)
QIVLTQSPAILSLSPGERATLSCSASSSVTSHYLYWYQQKPGSSP
KLLIYSTSNLASGVPARFSGSGSGTSYTLTISSLEAEDAASYFCH
QWSSYPPTFGSGTKLEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPCTKSFNRGEC:

MYT5367 Heavy chain Triple hinge
(SEQ ID NO: 107)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG>

MYT5367 Heavy chain Triple hinge + LS
mutation
(SEQ ID NO: 108)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG**

MYT5367 Heavy chain Triple hinge + YTE
mutation
(SEQ ID NO: 109)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG>

MYT5367 Heavy chain Triple hinge and A118C
(SEQ ID NO: 110)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG*

MYT5367 Heavy chain Triple hinge + LS
mutation and A118C
(SEQ ID NO: 111)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG**

MYT5367 Heavy chain Triple hinge + YTE
mutation and A118C
(SEQ ID NO: 112)
QVQLVQSGAEVKKPGASVKVSCKASGYTFTSYWMHWVKQAPGQGL
DWIGHIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG*

MYT5367 Light Chain
(SEQ ID NO: 113)
QIVLTQSPAILSLSPGERATLSCSASSSVTSNYLYWYQQKPGSSP
KLLIYSTSNLASGVPARFSGSGSGTSYTLTISSLEAEDAASYFCH
QWSHYHPTFGSGTKLEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPVTKSFNRGEC MYT5367 Light Chain V205C
(SEQ ID NO: 114)
QIVLTQSPAILSLSPGERATLSCSASSSVTSNYLYWYQQKPGSSP
KLLIYSTSNLASGVPARFSGSGSGTSYTLTISSLEAEDAASYFCH
QWSHYHPTFGSGTKLEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPCTKSFNRGEC**

MYT4827 Heavy Chain Triple hinge
(SEQ ID NO: 115)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARAHWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*

MYT4827 Heavy Chain Triple hinge + LS
mutation
(SEQ ID NO: 116)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARAHWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG'*

MYT4827 Heavy Chain Triple hinge + YTE
mutation
(SEQ ID NO: 117)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARAHWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLYITREPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG**

MYT4827 Heavy Chain Triple hinge and A118C
(SEQ ID NO: 118)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARAHWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*

MYT4827 Heavy Chain Triple hinge + LS
mutation and A118C
(SEQ ID NO: 119)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARAHWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG**

MYT4827 Heavy Chain Triple hinge + YTE
mutation and A118C
(SEQ ID NO: 120)
QVQLVQSGAEVKKPGASVKVSCKASGYTFTHYYMHWVRQAPGQGL
EWMGRVNPNRRGTTYNQKFEGRVTMTTDTSTSTAYMELRSLRSDD
TAVYYCARAHWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPPC
PAPELLGGPSVFLFPPKPKDTLYITREPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG**

```
MYT4827 Light Chain
                        (SEQ ID NO: 121)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VYSGYPLTFGGGTKVEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC**

MYT4827 Light Chain V205C
                        (SEQ ID NO: 122)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VYSGYPLTFGGGTKVEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPCTKSFNRGEC**

MYT4312 Heavy Chain Triple hinge
                        (SEQ ID NO: 123)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGNYPLMHYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG*

MYT4312 Heavy Chain Triple hinge + LS
mutation
                        (SEQ ID NO: 124)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGNYPLMHYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTK

NQVSLTCLVKGFYPSDIAVEWESNGQPENNYKTTPPVLDSDGSFF

LYSKLTVDKSRWQQGNVFSCSVLHEALHSHYTQKSLSLSPG**

MYT4312 Heavy Chain Triple hinge + YTE
mutation
                        (SEQ ID NO: 125)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGNYPLMHYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLYITREPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG**

MYT4312 Heavy Chain Triple hinge and A118C
                        (SEQ ID NO: 126)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGNYPLMHYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG

MYT4312 Heavy Chain Triple hinge + LS
mutation and A118C
                        (SEQ ID NO: 127)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGNYPLMHYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTK

NQVSLTCLVKGFYPSDIAVEWESNGQPENNYKTTPPVLDSDGSFF

LYSKLTVDKSRWQQGNVFSCSVLHEALHSHYTQKSLSLSPG:**

MYT4312 Heavy Chain
(triple hinge + YTE
mutation and A118C
                        (SEQ ID NO: 128)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGNYPLMHYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLYITREPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK
```

-continued
NQVSLTCLVKGFYPSDIAVEWESNGQPENNYKTTPPVLDSDGSFF

LYSKLTVDKSRWQQGNVFSCSVMHEALHNHYTQKSLSLSPG**

MYT4312 Light Chain
(SEQ ID NO: 129)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC**

MYT4312 Light Chain V205C
(SEQ ID NO: 130)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPCTKSFNRGEC**

MYT4953 Heavy Chain Triple hinge
(SEQ ID NO: 131)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCHRSEITHEFDYWGQGTLVTVSSASTKGPSVFPLAPSSKS

TSGGTAALGCLVKDYFPEPVTVSWNSGALTSGVHTFPAVLQSSGL

YSLSSVVTVPSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

MYT4953 Heavy Chain Triple hinge + LS
mutation
(SEQ ID NO: 132)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCHRSEITHEFDYWGQGTLVTVSSASTKGPSVFPLAPSSKS

TSGGTAALGCLVKDYFPEPVTVSWNSGALTSGVHTFPAVLQSSGL

YSLSSVVTVPSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPG*

MYT4953 Heavy Chain Triple hinge + YTE
mutation
(SEQ ID NO: 133)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCHRSEITHEFDYWGQGTLVTVSSASTKGPSVFPLAPSSKS

TSGGTAALGCLVKDYFPEPVTVSWNSGALTSGVHTFPAVLQSSGL

YSLSSVVTVPSSLGTQTYICNVNHKPSNTKVDKRVEPKSCDCHC

PPCPAPELLGGPSVFLFPPKPKDTLYITREPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG

MYT4953 Heavy Chain Triple hinge and A118C
(SEQ ID NO: 134)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCHRSEITHEFDYWGQGTLVTVSSCSTKGPSVFPLAPSSKS

TSGGTAALGCLVKDYFPEPVTVSWNSGALTSGVHTFPAVLQSSGL

YSLSSVVTVPSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

MYT4953 Heavy Chain Triple hinge + LS
mutation and A118C
(SEQ ID NO: 135)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCHRSEITHEFDYWGQGTLVTVSSCSTKGPSVFPLAPSSKS

TSGGTAALGCLVKDYFPEPVTVSWNSGALTSGVHTFPAVLQSSGL

YSLSSVVTVPSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPG**

MYT4953 Heavy Chain Triple hinge + YTE
mutation and A118C
(SEQ ID NO: 136)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCHRSEITHEFDYWGQGTLVTVSSCSTKGPSVFPLAPSSKS

TSGGTAALGCLVKDYFPEPVTVSWNSGALTSGVHTFPAVLQSSGL

YSLSSVVTVPSSLGTQTYICNVNHKPSNTKVDKRVEPKSCDCHC

PPCPAPELLGGPSVFLFPPKPKDTLYITREPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

```
QVSLTCLVKGFYPSDIAVEWESNGQPENNYKTTPPVLDSDGSFFL

YSKLTVDKSRWQQGNVFSCSVMHEALHNHYTQKSLSLSPG**

MYT4953 Light Chain
                                    (SEQ ID NO: 137)
DIVMTQSPDSLAVSLGERATINCKSSESVDSYANSFLHWYQQKPG

QPPKLLIYRASTRESGVPDRFSGSGSGTDFTLTISSLQAEDVAVY

YCQQSKEDPLTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPVTKSFNRGEC*

MYT4953 Light Chain V205C
                                    (SEQ ID NO: 138)
DIVMTQSPDSLAVSLGERATINCKSSESVDSYANSFLHWYQQKPG

QPPKLLIYRASTRESGVPDRFSGSGSGTDFTLTISSLQAEDVAVY

YCQQSKEDPLTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPCTKSFNRGEC**

MYT4940 Heavy Chain Triple hinge
                                    (SEQ ID NO: 139)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITTEFDHWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

MYT4940 Heavy Chain
(Triple hinge + LS
mutation
                                    (SEQ ID NO: 140)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITTEFDHWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPG**

MYT4940 Heavy Chain Triple hinge + YTE
mutation
                                    (SEQ ID NO: 141)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITTEFDHWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLYITREPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG*

MYT4940 Heavy Chain Triple hinge and A118C
                                    (SEQ ID NO: 142)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITTEFDHWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG*

MYT4940 Heavy Chain Triple hinge + LS
mutation and A118C
                                    (SEQ ID NO: 143)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITTEFDHWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPG**

MYT4940 Heavy Chain Triple hinge + YTE
mutation and A118C
                                    (SEQ ID NO: 144)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITTEFDHWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLYITREPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN
```

-continued

QVSLTCLVKGFYPSDIAVEWESNGQPENNYKTTPPVLDSDGSFFL

YSKLTVDKSRWQQGNVFSCSVMHEALHNHYTQKSLSLSPG**

MYT4940 Light Chain
(SEQ ID NO: 145)
DIVMTQSPDSLAVSLGERATINCKSSESVDSYANSHLHWYQQKPG

QPPKLLIYRASTRESGVPDRFSGSGSGTDFTLTISSLQAEDVAVY

YCQQSKEDPLTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPVTKSFNRGEC**

MYT4940 Light Chain V205C
(SEQ ID NO: 146)
DIVMTQSPDSLAVSLGERATINCKSSESVDSYANSHLHWYQQKPG

QPPKLLIYRASTRESGVPDRFSGSGSGTDFTLTISSLQAEDVAVY

YCQQSKEDPLTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPCTKSFNRGEC

MYT4888 Heavy Chain Triple hinge
(SEQ ID NO: 147)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSYGNYPLHDYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG**

MYT4888 Heavy Chain Triple hinge + LS
mutation
(SEQ ID NO: 148)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSYGNYPLHDYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTK

NQVSLTCLVKGFYPSDIAVEWESNGQPENNYKTTPPVLDSDGSFF

LYSKLTVDKSRWQQGNVFSCSVLHEALHSHYTQKSLSLSPG**

MYT4888 Heavy Chain Triple hinge + YTE
mutation
(SEQ ID NO: 149)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSYGNYPLHDYWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLYITREPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG*

MYT4888 Heavy Chain Triple hinge and A118C
(SEQ ID NO: 150)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSYGNYPLHDYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPG:*

MYT4888 Heavy Chain Triple hinge + LS
mutation and A118C
(SEQ ID NO: 151)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSYGNYPLHDYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTK

NQVSLTCLVKGFYPSDIAVEWESNGQPENNYKTTPPVLDSDGSFF

LYSKLTVDKSRWQQGNVFSCSVLHEALHSHYTQKSLSLSPG**

MYT4888 Heavy Chain Triple hinge + YTE
mutation and A118C
(SEQ ID NO: 152)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSYGNYPLHDYWGQGTTVTVSSCSTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKRVEPKSCDCH

CPPCPAPELLGGPSVFLFPPKPKDTLYITREPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

-continued

NQVSLTCLVKGFYPSDIAVEWESNGQPENNYKTTPPVLDSDGSFF

LYSKLTVDKSRWQQGNVFSCSVMHEALHNHYTQKSLSLSPG

MYT4888 Light Chain
(SEQ ID NO: 153)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC**

MYT4888 Light Chain V205C
(SEQ ID NO: 154)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPCTKSFNRGEC*

Heavy Chain Constant Domain
(SEQ ID NO: 155)
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKRVEPKSCDKTHTCPPCPAPELLGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSREEMTKNQVSLTCLVKGFYPSDIAVEWESNGQP

ENNYKTTPPVLDSDGSFFLYSKLTVDKSRWQQGNVFSCSVMHEAL

HNHYTQKSLSLSPG*

Heavy Chain Constant Domain A118C
(SEQ ID NO: 156)
CSTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKRVEPKSCDCHCPPCPAPELLGGPSVFLFPPKPKDTLYIT

REPEVTCVVVDVSHEDPEVKFNWYVDGVEVHNAKTKPREEQYNST

YRVVSVLTVLHQDWLNGKEYKCKVSNKALPAPIEKTISKAKGQPR

EPQVYTLPPSREEMTKNQVSLTCLVKGFYPSDIAVEWESNGQPE

NNYKTTPPVLDSDGSFFLYSKLTVD

KSRWQQGNVFSCSVLHEALHSHYTQKSLSLSPG**

Light Chain Constant Domain
(SEQ ID NO: 157)
RTVAAPSVFIFPPSDEQLKSGTASVVCLLNNFYPREAKVQWKVDN

ALQSGNSQESVTEQDSKDSTYSLSSTLTLSKADYEKHKVYACEVT

HQGLSSPVTKSFNRGEC**

Light Chain Constant Domain V205C
(SEQ ID NO: 158)
RTVAAPSVFIFPPSDEQLKSGTASVVCLLNNFYPREAKVQWKVDN

ALQSGNSQESVTEQDSKDSTYSLSSTLTLSKADYEKHKVYACEVT

HQGLSSPCTKSFNRGEC

Telisotuzumab Heavy chain variable region
(SEQ ID NO: 159)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDYWGQGTLVTVSS

Telisotuzumab Light chain variable region
(SEQ ID NO: 160)
DIVMTQSPDSLAVSLGERATINCKSSESVDSYANSFLHWYQQKPG

QPPKLLIYRASTRESGVPDRFSGSGSGTDFTLTISSLQAEDVAVY

YCQQSKEDPLTFGGGTKVEIK

Emibetuzumab heavy chain variable region
(SEQ ID NO: 161)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSS

Emibetuzumab light chain variable region
(SEQ ID NO: 162)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VYSGYPLTFGGGTKVEIK

P3D12 anti-cMET heavy chain variable region
(SEQ ID NO: 163)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSYGNYPLMDYWGQGTTVTVSS

P3D12 anti-cMET light chain variable region
(SEQ ID NO: 164)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPPTFGSGTKLEIK

Telisotuzumab Heavy chain Triple Hinge
(SEQ ID NO: 165)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDYWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

Telisotuzumab Heavy chain Triple Hinge + LS
(SEQ ID NO: 166)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDYWGQGTLVTVSSASTKGPSVFPLAPSSKS

-continued

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPG**

Telisotuzumab Heavy chain Triple Hinge + YTE
(SEQ ID NO: 167)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDYWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLYITREPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG*

Telisotuzumab Heavy chain Triple Hinge and
A118C
(SEQ ID NO: 168)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDYWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG

Telisotuzumab Heavy chain Triple Hinge + LS
and A118C
(SEQ ID NO: 169)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDYWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPG**

Telisotuzumab Heavy chain Triple Hinge + YTE
and A118C
(SEQ ID NO: 170)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDYWGQGTLVTVSSCSTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKRVEPKSCDCHC

PPCPAPELLGGPSVFLFPPKPKDTLYITREPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG**

Telisotuzumab Light chain
(SEQ ID NO: 171)
DIVMTQSPDSLAVSLGERATINCKSSESVDSYANSFLHWYQQKPG

QPPKLLIYRASTRESGVPDRFSGSGSGTDFTLTISSLQAEDVAVY

YCQQSKEDPLTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPVTKSFNRGEC**

Telisotuzumab Light chain V205C
(SEQ ID NO: 172)
DIVMTQSPDSLAVSLGERATINCKSSESVDSYANSFLHWYQQKPG

QPPKLLIYRASTRESGVPDRFSGSGSGTDFTLTISSLQAEDVAVY

YCQQSKEDPLTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPCTKSFNRGEC**

Emibetuzumab heavy chain with Triple Hinge
(SEQ ID NO: 173)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDCHCPPC

PAPELLGGPSVFLFPPKPKDTLMISRTPEVTCVVVDVSHEDPEVK

FNWYVDGVEVHNAKTKPREEQYNSTYRVVSVLTVLHQDWLNGKEY

KCKVSNKALPAPIEKTISKAKGQPREPQVYTLPPSREEMTKNQVS

LTCLVKGFYPSDIAVEWESNGQPENNYKTTPPVLDSDGSFFLYSK

LTVDKSRWQQGNVFSCSVMHEALHNHYTQKSLSLSPG*

Emibetuzumab heavy chain with Triple Hinge
and LS
(SEQ ID NO: 174)
QVQLVQSGAEVKKPGASVKVSCKASGYTFTDYYMHWVRQAPGQGL

EWMGRVNPNRRGTTYNQKFEGRVTMTTDTSTSTAYMELRSLRSDD

TAVYYCARANWLDYWGQGTTVTVSSASTKGPSVFPLAPSSKSTSG

GTAALGCLVKDYFPEPVTVSWNSGALTSGVHTFPAVLQSSGLYSL

-continued

SSVVTVPSSSLGTQTYICNVNHKPSNTKVDKRVEPKSCDCHCPP<u>C</u>
<u>PAPELLGGPSVFLFPPKPKDTLMISRTPEVTCVVVDVSHEDPEVK</u>
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG*

Emibetuzumab heavy chain with Triple Hinge
and YTE
(SEQ ID NO: 175)
QVQLVQSGAEVKKPGASVKVSCKASGYTFTDYYMHWVRQAPGQGL
EWMGRVNPNRRGTTYNQKFEGRVTMTTDTSTSTAYMELRSLRSDD
TAVYYCARANWLDYWGQGTTVTVSSASTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPP<u>C</u>
<u>PAPELLGGPSVFLFPPKPKDTLYITREPEVTCVVVDVSHEDPEVK</u>
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG**

Emibetuzumab heavy chain with Triple Hinge
and A118C
(SEQ ID NO: 176)
QVQLVQSGAEVKKPGASVKVSCKASGYTFTDYYMHWVRQAPGQGL
EWMGRVNPNRRGTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPP<u>C</u>
<u>PAPELLGGPSVFLFPPKPKDTLMISRTPEVTCVVVDVSHEDPEVK</u>
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*

Emibetuzumab heavy chain with Triple Hinge
and LS and A118C
(SEQ ID NO: 177)
QVQLVQSGAEVKKPGASVKVSCKASGYTFTDYYMHWVRQAPGQGL
EWMGRVNPNRRGTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPP<u>C</u>
<u>PAPELLGGPSVFLFPPKPKDTLMISRTPEVTCVVVDVSHEDPEVK</u>
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFLYSK
LTVDKSRWQQGNVFSCSVLHEALHSHYTQKSLSLSPG**

Emibetuzumab heavy chain with Triple Hinge
and YTE and A118C
(SEQ ID NO: 178)
QVQLVQSGAEVKKPGASVKVSCKASGYTFTDYYMHWVRQAPGQGL
EWMGRVNPNRRGTTYNQKFEGRVTMTTDTSTSTAYMELRSLRSDD
TAVYYCARANWLDYWGQGTTVTVSSCSTKGPSVFPLAPSSKSTSG
GTAALGCLVKDYFPEPVTVSWNSGALTSGVHTFPAVLQSSGLYSL
SSVVTVPSSSLGTQTYICNVNHKPSNTKVDKRVEPKSCDCHCPP<u>C</u>
<u>PAPELLGGPSVFLFPPKPKDTLYITREPEVTCVVVDVSHEDPEVK</u>
FNWYVDGVEVHNAKTKPREEQYNSTYRVVSVLTVLHQDWLNGKEY
KCKVSNKALPAPIEKTISKAKGQPREPQVYTLPPSREEMTKNQVS
LTCLVKGFYPSDIAVEWESNGQPENNYKTTPPVLDSDGSFFLYSK
LTVDKSRWQQGNVFSCSVMHEALHNHYTQKSLSLSPG*

Emibetuzumab light chain
(SEQ ID NO: 179)
DIQMTQSPSSLSASVGDRVTITCSVSSSVSSIYLHWYQQKPGKAP
KLLIYSTSNLASGVPSRFSGSGSGTDFTLTISSLQPEDFATYYCQ
VYSGYPLTFGGGTKVEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPVTKSFNRGEC**

Emibetuzumab light chain V205C
(SEQ ID NO: 180)
DIQMTQSPSSLSASVGDRVTITCSVSSSVSSIYLHWYQQKPGKAP
KLLIYSTSNLASGVPSRFSGSGSGTDFTLTISSLQPEDFATYYCQ
VYSGYPLTFGGGTKVEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPCTKSFNRGEC P3D12 anti-cMET heavy chain with Triple Hinge
(SEQ ID NO: 181)
QVQLVQSGAEVKKPGASVKVSCKASGYTFTSYWMHWVKQAPGQGL
DWIGYIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
<u>CPPCPAPELLGGPSVFLFPPKPKDTLMISRTPEVTCVVVDVSHED</u>
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG*

P3D12 anti-cMET heavy chain with Triple
Hinge and LS
(SEQ ID NO: 182)
QVQLVQSGAEVKKPGASVKVSCKASGYTFTSYWMHWVKQAPGQGL
DWIGYIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG P3D12 anti-cMET heavy chain with Triple
Hinge and YTE
(SEQ ID NO: 183)
QVQLVQSGAEVKKPGASVKVSCKASGYTFTSYWMHWVKQAPGQGL
DWIGYIKPSTDNTEYNQKFKDKATLTADKSTSTAYMELSSLRSED
TAVYYCARSYGNYPLMDYWGQGTTVTVSSASTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG*

P3D12 anti-cMET heavy chain with Triple
Hinge and A118C
(SEQ ID NO: 184)
QVQLVQSGAEVKKPGASVKVSCKASGYTFTSYWMHWVKQAPGQGL
DWIGYIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

P3D12 anti-cMET heavy chain with Triple
Hinge and LS and A118C
(SEQ ID NO: 185)
QVQLVQSGAEVKKPGASVKVSCKASGYTFTSYWMHWVKQAPGQGL
DWIGYIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSRDELTK
NQVSLTCLVKGFYPSDIAVEWESNGQPENNYKTTPPVLDSDGSFF
LYSKLTVDKSRWQQGNVFSCSVLHEALHSHYTQKSLSLSPG P3D12 anti-cMET heavy chain with Triple
Hinge and YTE and A118C
(SEQ ID NO: 186)
QVQLVQSGAEVKKPGASVKVSCKASGYTFTSYWMHWVKQAPGQGL
DWIGYIKPSTDNTEYNQKFKDKATLTADKSTSTAYMELSSLRSED
TAVYYCARSYGNYPLMDYWGQGTTVTVSSCSTKGPSVFPLAPSSK
STSGGTAALGCLVKDYFPEPVTVSWNSGALTSGVHTFPAVLQSSG
LYSLSSVVTVPSSSLGTQTYICNVNHKPSNTKVDKRVEPKSCDCH
CPPCPAPELLGGPSVFLFPPKPKDTLYITREPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPSREEMTK
NQVSLTCLVKGFYPSDIAVEWESNGQPENNYKTTPPVLDSDGSFF
LYSKLTVDKSRWQQGNVFSCSVMHEALHNHYTQKSLSLSPG**

P3D12 anti-cMET light chain
(SEQ ID NO: 187)
QIVLTQSPAILSLSPGERATLSCSASSSVTSNYLYWYQQKPGSSP
KLLIYSTSNLASGVPARFSGSGSGTSYTLTISSLEAEDAASYFCH
QWSSYPPTFGSGTKLEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPVTKSFNRGEC**

P3D12 anti-cMET light chain V205C
(SEQ ID NO: 188)
QIVLTQSPAILSLSPGERATLSCSASSSVTSNYLYWYQQKPGSSP
KLLIYSTSNLASGVPARFSGSGSGTSYTLTISSLEAEDAASYFCH
QWSSYPPTFGSGTKLEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPCTKSFNRGEC**

Heavy Chain Constant Domain
(SEQ ID NO: 189)
ASTKGPSVFPLAPSSKSTSGGTAALGCLVKDYFPEPVTVSWNSGA
LTSGVHTFPAVLQSSGLYSLSSVVTVPSSSLGTQTYICNVNHKPS
NTKVDKRVEPKSCDKTHTCPPCPAPELLGGPSVFLFPPKPKDTLM
ISRTPEVTCVVVDVSHEDPEVKFNWYVDGVEVHNAKTKPREEQYN
STYRVVSVLTVLHQDWLNGKEYKCKVSNKALPAPIEKTISKAKGQ
PREPQVYTLPPSRDELTKNQVSLTCLVKGFYPSDIAVEWESNGQP
ENNYKTTPPVLDSDGSFFLYSKLTVDKSRWQQGNVFSCSVMHEAL
HNHYTQKSLSLSPG**

Light Chain of Telisotuzumab
IgG histidine scanning variant #1
(SEQ ID NO: 190)
DIVMTQSPDSLAVSLGERATINCKSSESVDSYANSFLHWYQQKPG
QPPKLLIYRASTREHGVPDRFSGSGSGTDFTLTISSLQAEDVAVY
YCQQSKEDPLTFGGGTKVEIK Light Chain of Telisotuzumab
IgG histidine scanning variant #2
(SEQ ID NO: 191)
DIVMTQSPDSLAVSLGERATINCKSSESVDSYAHSFLHWYQQKPG

QPPKLLIYRASTRESGVPDRFSGSGSGTDFTLTISSLQAEDVAVY

YCQQSKEDPLTFGGGTKVEIK

Light Chain of Telisotuzumab
IgG histidine scanning variant #3
(SEQ ID NO: 192)
DIVMTQSPDSLAVSLGERATINCKSSESVDSYANSFLHWYQQKPG

QPPKLLIYHASTRESGVPDRFSGSGSGTDFTLTISSLQAEDVAVY

YCQQSKEDPLTFGGGTKVEIK

Heavy Chain of Telisotuzumab
IgG histidine scanning variant #1
(SEQ ID NO: 193)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITTEFDYWGQGTLVTVSS

Heavy Chain of Telisotuzumab
IgG histidine scanning variant #2
(SEQ ID NO: 194)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITTEFDYWGQGTLVTVSS

Heavy Chain of Telisotuzumab
IgG histidine scanning variant #3
(SEQ ID NO: 195)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITHEFDYWGQGTLVTVSS

Heavy Chain of Telisotuzumab
IgG histidine scanning variant #4
(SEQ ID NO: 196)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITTEFDHWGQGTLVTVSS

Heavy Chain Combinations of Telisotuzumab
IgG histidine scanning variant #5
(SEQ ID NO: 197)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARHEITTEFDYWGQGTLVTVSS

Heavy Chain Combinations of Telisotuzumab
IgG histidine scanning variant #6
(SEQ ID NO: 198)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITHEFDYWGQGTLVTVSS

Heavy Chain Combinations of Telisotuzumab
IgG histidine scanning variant #7
(SEQ ID NO: 199)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARSEITTEFDHWGQGTLVTVSS

Heavy Chain Combinations of Telisotuzumab
IgG histidine scanning variant #8
(SEQ ID NO: 200)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITHEFDYWGQGTLVTVSS

Heavy Chain Combinations of Telisotuzumab
IgG histidine scanning variant #9
(SEQ ID NO: 201)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARSEITHEFDHWGQGTLVTVSS

Heavy Chain Combinations of Telisotuzumab
IgG histidine scanning variant #10
(SEQ ID NO: 202)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARHEITHEFDYWGQGTLVTVSS

Heavy Chain Combinations of Telisotuzumab
IgG histidine scanning variant #11
(SEQ ID NO: 203)
QVQLVQSGAEVKKPGASVKVSCKASGHIFTAYTMHWVRQAPGQGL

EWMGWIKPNNGLANYAQKFQGRVTMTRDTSISTAYMELSRLRSDD

TAVYYCARHEITTEFDHWGQGTLVTVSS

Heavy Chain Combinations of Telisotuzumab
IgG histidine scanning variant #12
(SEQ ID NO: 204)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCARHEITHEFDHWGQGTLVTVSS

Light Chain Combinations of Telisotuzumab
IgG histidine scanning variant #1
(SEQ ID NO: 205)
DIVMTQSPDSLAVSLGERATINCKSSESVDSYAHSHLHWYQQKPG

QPPKLLIYRASTRESGVPDRFSGSGSGTDFTLTISSLQAEDVAVY

YCQQSKEDPLTFGGGTKVEIK

Light Chain Combinations of Telisotuzumab
IgG histidine scanning variant #2
(SEQ ID NO: 206)
DIVMTQSPDSLAVSLGERATINCKSSESVDSYAHSFLHWYQQKPG

QPPKLLIYHASTRESGVPDRFSGSGSGTDFTLTISSLQAEDVAVY

YCQQSKEDPLTFGGGTKVEIK

Light Chain Combinations of Telisotuzumab
IgG histidine scanning variant #3
(SEQ ID NO: 207)
DIVMTQSPDSLAVSLGERATINCKSSESVDSYAHSFLHWYQQKPG

QPPKLLIYRASTREHGVPDRFSGSGSGTDFTLTISSLQAEDVAVY

YCQQSKEDPLTFGGGTKVEIK

Light Chain Combinations of Telisotuzumab
IgG histidine scanning variant #4
(SEQ ID NO: 208)
DIVMTQSPDSLAVSLGERATINCKSSESVDSYANSHLHWYQQKPG

QPPKLLIYHASTRESGVPDRFSGSGSGTDFTLTISSLQAEDVAVY

YCQQSKEDPLTFGGGTKVEIK

Light Chain Combinations of Telisotuzumab
IgG histidine scanning variant #5
(SEQ ID NO: 209)
DIVMTQSPDSLAVSLGERATINCKSSESVDSYANSHLHWYQQKPG

QPPKLLIYRASTREHGVPDRFSGSGSGTDFTLTISSLQAEDVAVY

YCQQSKEDPLTFGGGTKVEIK

Light Chain Combinations of Telisotuzumab
IgG histidine scanning variant #6
(SEQ ID NO: 210)
DIVMTQSPDSLAVSLGERATINCKSSESVDSYANSFLHWYQQKPG

QPPKLLIYHASTREHGVPDRFSGSGSGTDFTLTISSLQAEDVAVY

YCQQSKEDPLTFGGGTKVEIK

Light Chain Combinations of Telisotuzumab
IgG histidine scanning variant #7
(SEQ ID NO: 211)
DIVMTQSPDSLAVSLGERATINCKSSESVDSYAHSLHWYQQKPG

QPPKLLIYHASTRESGVPDRFSGSGSGTDFTLTISSLQAEDVAVY

YCQQSKEDPLTFGGGTKVEIK

Light Chain Combinations of Telisotuzumab
IgG histidine scanning variant #8
(SEQ ID NO: 212)
DIVMTQSPDSLAVSLGERATINCKSSESVDSYAHSHLHWYQQKPG

QPPKLLIYRASTREHGVPDRFSGSGSGTDFTLTISSLQAEDVAVY

YCQQSKEDPLTFGGGTKVEIK

Light Chain Combinations of Telisotuzumab
IgG histidine scanning variant #9
(SEQ ID NO: 213)
DIVMTQSPDSLAVSLGERATINCKSSESVDSYAHSFLHWYQQKPG

QPPKLLIYHASTREHGVPDRFSGSGSGTDFTLTISSLQAEDVAVY

YCQQSKEDPLTFGGGTKVEIK

Light Chain Combinations of Telisotuzumab
IgG histidine scanning variant #10
(SEQ ID NO: 214)
DIVMTQSPDSLAVSLGERATINCKSSESVDSYANSHLHWYQQKPG

QPPKLLIYHASTREHGVPDRFSGSGSGTDFTLTISSLQAEDVAVY

YCQQSKEDPLTFGGGTKVEIK

Light Chain of Emibetuzumab
IgG histidine scanning variant #1
(SEQ ID NO: 215)
DIQMTQSPSSLSASVGDRVTITCSVSSSVSSIHLHWYQQKPGKAP

KLLIYSTSNLASGVPSRFSGSGSGTDFTLTISSLQPEDFATYYCQ

VYSGYPLTFGGGTKVEIK

Heavy Chain of Emibetuzumab
IgG histidine scanning variant #1
(SEQ ID NO: 216)
QVQLVQSGAEVKKPGASVKVSCKASGYTFTDYYMHWVRQAPGQGL

EWMGRVHPNRRGTTYNQKFEGRVTMTTDTSTSTAYMELRSLRSDD

TAVYYCARANWLDYWGQGTTVTVSS

Heavy Chain Combinations of Emibetuzumab
IgG histidine scanning variant #2
(SEQ ID NO: 217)
QVQLVQSGAEVKKPGASVKVSCKASGYTFTDYYMHWVRQAPGQGL

EWMGRVHPHRRGTTYNQKFEGRVTMTTDTSTSTAYMELRSLRSDD

TAVYYCARANWLDYWGQGTTVTVSS

Heavy Chain Combinations of Emibetuzumab
IgG histidine scanning variant #3
(SEQ ID NO: 218)
QVQLVQSGAEVKKPGASVKVSCKASGYTFTDYYMHWVRQAPGQGL

EWMGRVHPNRRHTTYNQKFEGRVTMTTDTSTSTAYMELRSLRSDD

TAVYYCARANWLDYWGQGTTVTVSS

Heavy Chain Combinations of Emibetuzumab
IgG histidine scanning variant #4
(SEQ ID NO: 219)
QVQLVQSGAEVKKPGASVKVSCKASGYTFTDYYMHWVRQAPGQGL

EWMGRVNPHRRHTTYNQKFEGRVTMTTDTSTSTAYMELRSLRSDD

TAVYYCARANWLDYWGQGTTVTVSS

Heavy Chain Combinations of Emibetuzumab
IgG histidine scanning variant #5
(SEQ ID NO: 220)
QVQLVQSGAEVKKPGASVKVSCKASGYTFTDYYMHWVRQAPGQGL

EWMGRVNPHRRGTTYNQKFEGRVTMTTDTSTSTAYMELRSLRSDD

TAVYYCARAHWLDYWGQGTTVTVSS

Heavy Chain Combinations of Emibetuzumab
IgG histidine scanning variant #6
(SEQ ID NO: 221)
QVQLVQSGAEVKKPGASVKVSCKASGYTFTDYYMHWVRQAPGQGL

EWMGRVHPHRRHTTYNQKFEGRVTMTTDTSTSTAYMELRSLRSDD

TAVYYCARANWLDYWGQGTTVTVSS

Heavy Chain Combinations of Emibetuzumab
IgG histidine scanning variant #7
(SEQ ID NO: 222)
QVQLVQSGAEVKKPGASVKVSCKASGYTFTDYYMHWVRQAPGQGL

EWMGRVHPHRRGTTYNQKFEGRVTMTTDTSTSTAYMELRSLRSDD

TAVYYCARAHWLDYWGQGTTVTVSS

Light Chain of Emibetuzumab
IgG histidine scanning variant #1
(SEQ ID NO: 223)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VHSGYPLTFGGGTKVEIK

Light Chain of Emibetuzumab
IgG histidine scanning variant #2
(SEQ ID NO: 224)
DIQMTQSPSSLSASVGDRVTITCSVSSSVSSIYLHWYQQKPGKAP

KLLIYSTSNLASGVPSRFSGSGSGTDFTLTISSLQPEDFATYYCQ

VYSGHPLTFGGGTKVEIK

Heavy Chain of hucMET27Gv1.3
IgG
(SEQ ID NO: 225)
EVQLVESGGGLVQPGGSLRLSCAASGFTFSSYDMSWVRQAPGKGL

EWVATINSNGVSIYYPDSVKGRFTISRDNAKNSLYLQMNSLRAED

TAVYYCAREEITTEMDYWGQGTLVTVSS

Light Chain Combinations of hucMET27Gv1.3
IgG histidine scanning variant #1
(SEQ ID NO: 226)
EIVLTQSPATLSLSPGERATLSCRASESVDSYGNSHIHWYQQKPG

QAPRLLIYRASNLESGIPARFSGSGSGTDFTLTISSLEPEDFAVY

YCQQSNEEHLTFGQGTKVELK

Heavy Chain of P3D12
IgG histidine scanning variant #1
(SEQ ID NO: 227)
QVQLVQSGAEVKKPGASVKVSCKASGYTFTSYWMAWVKQAPGQGL

DWIGYIKPSTDNTEYNQKFKDKATLTADKSTSTAYMELSSLRSED

TAVYYCARSYGNYPLMDYWGQGTTVTVSS

Heavy Chain of P3D12
IgG histidine scanning variant #2
(SEQ ID NO: 228)
QVQLVQSGAEVKKPGASVKVSCKASGYTFTSYWMHWVKQAPGQGL

DWIGYIKPSTDNTEYNQKFKDKATLTADKSTSTAYMELSSLRSED

TAVYYCARSHGNYPLMDYWGQGTTVTVSS

Heavy Chain Combinations of P3D12
IgG histidine scanning variant #1
(SEQ ID NO: 229)
QVQLVQSGAEVKKPGASVKVSCKASGYTHTSYWMHWVKQAPGQGL

DWIGYIKPSTDNTHYNQKFKDKATLTADKSTSTAYMELSSLRSED

TAVYYCARSYGHYPLMDYWGQGTTVTVSS

Heavy Chain Combinations of P3D12
IgG histidine scanning variant #2
(SEQ ID NO: 230)
QVQLVQSGAEVKKPGASVKVSCKASGYTHTSYWMHWVKQAPGQGL

DWIGYIKPSTDNTHYNQKFKDKATLTADKSTSTAYMELSSLRSED

TAVYYCARSYGNYPLMHYWGQGTTVTVSS

Heavy Chain Combinations of P3D12
IgG histidine scanning variant #3
(SEQ ID NO: 231)
QVQLVQSGAEVKKPGASVKVSCKASGYTFTSYWMHWVKQAPGQGL

DWIGHIKPSTDNTEYNQKFKDKATLTADKSTSTAYMELSSLRSED

TAVYYCARSYGHYPLMHYWGQGTTVTVSS

Light Chain of P3D12
IgG histidine scanning variant #1
(SEQ ID NO: 232)
QIVLTQSPAILSLSPGERATLSCSASSSVTSNYLYWYQQKPGSSP

KLLIYSTSNLASGVPARFSGSGSGTSYTLTISSLEAEDAASYFCH

QWSSYPHTFGSGTKLEIK

Light Chain Combinations of P3D12
IgG histidine scanning variant #1
(SEQ ID NO: 233)
QIVLTQSPAILSLSPGERATLSCSASSSVTSNYLYWYQQKPGSSP

KLLIYSTSNLASGVPARFSGSGSGTSYTLTISSLEAEDAASYFCH

QWSHHHPTFGSGTKLEIK

Heavy Chain Combinations of Telisotuzumab
IgG histidine scanning variant #13
(SEQ ID NO: 234)
QVQLVQSGAEVKKPGASVKVSCKASGYIFTAYTMHWVRQAPGQGL

EWMGWIKPNNGLANYAQKFQGRVTMTRDTSISTAYMELSRLRSDD

TAVYYCAHSEITHEFDHWGQGTLVTVSS

Light Chain of hucMET27Gv1.3
IgG
(SEQ ID NO: 235)
EIVLTQSPATLSLSPGERATLSCRASESVDSYGNSFIHWYQQKPG

QAPRLLIYRASNLESGIPARFSGSGSGTDFTLTISSLEPEDFAVY

YCQQSNEEPLTFGQGTKVELK

---

SEQUENCE LISTING

```
Sequence total quantity: 235
SEQ ID NO: 1              moltype = AA   length = 1366
FEATURE                   Location/Qualifiers
source                    1..1366
                          mol_type = protein
                          organism = Homo sapiens
SEQUENCE: 1
ECKEALAKSE MNVNMKYQLP NFTAETPIQN VILHEHHIFL GATNYIYVLN EEDLQKVAEY   60
KTGPVLEHPD CFPCQDCSSK ANLSGGVWKD NINMALVVDT YYDDQLISCG SVNRGTCQRH  120
VFPHNHTADI QSEVHCIFSP QIEEPSQCPD CVVSALGAKV LSSVKDRFIN FFVGNTINSS  180
YFPDHPLHSI SVRRLKETKD GFMFLTDQSY IDVLPEFRDS YPIKYVHAFE SNNFIYFLTV  240
QRETLDAQTF HTRIIRFCSI NSGLHSYMEM PLECILTEKR KKRSTKKEVF NILQAAYVSK  300
PGAQLARQIG ASLNDDILFG VFAQSKPDSA EPMDRSAMCA FPIKYVNDFF NKIVNKNNVR  360
CLQHFYGPNH EHCFNRTLLR NSSGCEARRD EYRTEFTTAL QRVDLFMGQF SEVLLTSIST  420
FIKGDLTIAN LGTSEGRFMQ VVVSRSGPST PHVNFLLDSH PVSPEVIVEH TLNQNGYTLV  480
ITGKKITKIP LNGLGCRHFQ SCSQCLSAPP FVQCGWCHDK CVRSEECLSG TWTQQICLPA  540
IYKVPNSAP LEGGTRLTIC GWDPGFRRNN KFDLKKTRVL GNESCTLTL SESTMNTLKC  600
TVGPAMNKHF NMSIIISNGH GTTQYSTFSY VDPVITSISP KYGPMAGGTL LTLTGNYLNS  660
GNSRHISIGG KTCTLKSVSN SILECYTPAQ TISTEFAVKL KIDLANRETS IFSYREDPIV  720
YEIHPTKSFI SGGSTITGVG KNLNSVSVPR MVINVHEAGR NFTVACQHRS NSEIICCTTP  780
SLQQLNLQLP LKTKAFFMLD GILSKYFDLI YVHNPVFKPF EKPVMISMGN ENVLEIKGND  840
IDPEAVKGEV LKVGNKSCEN IHLHSEAVLC TVPNDLLKLN SELNIEWKQA ISSTVLGKVI  900
VQPDQNFTGL IAGVVSISTA LLLLLGFFLW LKKRKQIKDL GSELVRYDAR VHTPHLDRLV  960
SARSVSPTTE MVSNESVDYR ATFPEDQFPN SSQNGSCRQV QYPLMTSPI LTSGDSDISS 1020
PLLQNTVHID LSALNPELVQ AVQHVVIGPS SLIVHFNEVI GRGHFGCVYH GTLLDNDGKK 1080
IHCAVKSLNR ITDIGEVSQF LTEGIIMKDF SHPNVLSLLG ICLRSEGSPL VVLPYMKHGD 1140
LRNFIRNETH NPTVKDLIGF GLQVAKGMKY LASKKFVHRD LAARNCMLDE KFTVKVADFG 1200
LARDMYDKEY YSVHNKTGAK LPVKWMALES LQTQKFTTKS DVWSFGVLLW ELMTRGAPPY 1260
PDVNTFDITV YLLQGRRLLQ PEYCPDPLYE VMLKCWHPKA EMRPSFSELV SRISAIFSTF 1320
IGEHYVHVNA TYVNVKCVAP YPSLLSSEDN ADDEVDTRPA SFWETS                1366
```

```
SEQ ID NO: 2           moltype = DNA  length = 4098
FEATURE                Location/Qualifiers
source                 1..4098
                       mol_type = unassigned DNA
                       organism = Homo sapiens
SEQUENCE: 2
gagtgtaaag aggcactagc aaagtccgag atgaatgtga atatgaagta tcagcttccc   60
aacttcaccg cggaaacacc catccagaat gtcattctac atgagcatca cattttcctt  120
ggtgccacta actacattta tgttttaaat gaggaagacc ttcagaaggt tgctgagtac  180
aagactgggc ctgtgctgga acacccagat tgtttcccat gtcaggactg cagcagcaaa  240
gccaatttat caggaggtgt ttggaaagat aacatcaaca tggctctagt tgtcgacacc  300
tactatgatg atcaactcat tagctgtggc agcgtcaaca gagggacctg ccagcgacat  360
gtctttcccc acaatcatac tgctgacata cagtcggagg ttcactgcat attctcccca  420
cagatagaag agcccagcca gtgtcctgac tgtgtggtga gcgccctggg agccaaagtc  480
ctttcatctg taaaggaccg gttcatcaac ttctttgtag gcaataccat aaattcttct  540
tatttcccag atcatccatt gcattcgata tcagtgagaa ggctaaagga aacgaaagat  600
ggttttatgt ttttgacgga ccagtcctac attgatgttt tacctgagtt cagagattct  660
taccccatta agtatgtcca tgcctttgaa agcaacaatt ttatttactt cttgacggtc  720
caaagggaaa ctctagatgc tcagactttt cacacaagaa taatcaggtt ctgttccata  780
aactctggat tgcattccta catggaaatg cctctggagt gtattctcac agaaaagaga  840
aaaaagagat ccacaaagaa ggaagtgttt aatatacttc aggtgcgtca tgtcagcaag  900
cctgggggcc agcttgctag acaaatagga gccagcctga atgatgacat tctttcggg   960
gtgttcgcac aaagcaagcc agattctgcc gaaccaatgg atcgatctgc catgtgtgca 1020
ttccctatca aatatgtcaa cgacttcttc aacaagatct caacaaaaa caatgtgaga 1080
tgtctccagc attttacgg acccaatcat gagcactgct ttaataggac acttcgtgaga 1140
aattcatcag gctgtgaagc gcgccgtgat gaatatcgaa cagagtttac cacagctttg 1200
cagcgcgttg acttattcat gggtcaattc agcgaagtcc tcttaacatc tatatccacc 1260
ttcattaaag gagacctcac catagctaat cttgggacat cagagggtcg cttcatgcag 1320
gttgtggttt ctcgatcagg accatcaacc cctcatgtga atttctcct ggactcccat 1380
ccagtgtctc cagaagtgat tgtggagcat acattaaacc aaaatggcta cacactggtt 1440
atcactggga agaagatcac gaagatccca ttgaatgget tgggctgcag acatttccag 1500
tcctgcagtc aatgcctctc tgccccaccc tttgttcagt gtggctggtg ccacgacaaa 1560
tgtgtgcgat cggaggaatg cctgagcggg acatggactc aacagatctg tctgcctgca 1620
atctacaagg ttttcccaaa tagtgcaccc cttgaaggag ggacaaggct gaccatatgt 1680
ggctgggact ttggatttcg gaggaataat aaatttgatt taaagaaaac tagagttctc 1740
cttgaaatgg agagctgcac cttgacttta agtgagagca cgatgaatac attgaaatgc 1800
acagttggtc ctgccatgaa taagcattc aatatgtcca taattatttc aaatggccac 1860
gggacaacac aatacagtac attctcctat gtggatcctg taataacaag tatttcgccg 1920
aaatacggtc ctatgctgg tggcactttta cttactttaa ctggaaatta cctaaacagt 1980
gggaattcta gacacatttc aattggtgga aaaacatgta cttttaaaag tgtgtcaaac 2040
agtattcttg aatgttatac cccagcccaa accatttcaa ctgagtttgc tgttaaattg 2100
aaaattgact tagccaaccg agagacaagc atcttcagtt accgtgaaga tcccattgtc 2160
tatgaaattc atccaaccaa atcttttatt agtggtggga gcacaataac aggtgttggg 2220
aaaaacctga attcagttag tgtcccgaga atggtcataa atgtgcatga agcaggaagg 2280
aactttacag tggcatgtca acatcgctct aattcagaga taatctgttg taccactcct 2340
tccctgcaac agctgaatct gcaactcccc ctgaaaacca aagccttttt catgttagat 2400
gggatcctttt ccaaatactt tgatctcatt tatgtacata atcctgtgtt taagccttt 2460
gaaaagccag tgatgatctc aatgggcaat gaaaatgtac tggaaattaa gggaaatgat 2520
attgaccctg aagcagttaa aggtgaagtg ttaaagttg gaaataagag ctgtgagaat 2580
atacacttac attctgaagc cgttttatgc acggtcccca atgacctgct gaaattgaac 2640
agcgagctaa atatagagtg gaagcaagca atttcttcaa ccgtccttgg aaaagtaata 2700
gttcaaccag atcagaattt cacaggattg attgctggtg ttgtctcaat atcaacagca 2760
ctgttattac tacttgggtt tttcctgtgg ctgaaaaaga gaagcaaat taaagatctg 2820
ggcagtgaat tagttcgcta cgatgcaaga gtacacactc ctcattttga taggcttgta 2880
agtgccgaa gtgtaagccc aactacagaa atggtttcaa atgaatctgt agactaccga 2940
gctactttc cagaagatca gtttcctaat tcatctcaga acggttcatg ccgacaagtg 3000
cagtatcctc tgcagacat gtcccccatc ctaactagtg gggactctga tatatccagt 3060
ccattactgc aaaatactgt ccacattgac ctcagtgctc taaatccaga gctggtccag 3120
gcagtgcagc atgtagtgat tgggcccagt agcctgattg tgcatttcaa tgaagtcata 3180
ggaagagggc attttggttg tgtatatcat gggactttgt tggacaatga tggcaagaaa 3240
attcactgtg ctgtgaaatc cttgaacaga atcactgaca taggagaagt ttcccaattt 3300
ctgaccgagg gaatcatcat gaaagatttt agtcatccca atgtcctctc gctcctggga 3360
atctgcctgc gaagtgaagg gtctccgctg gtggtcctac catacatgaa acatggtgat 3420
cttcgaaatt tcattcgaaa tgagactcat aatccaactg taaaagatct tattggcttt 3480
ggtcttcaag tagccaaagg catgaaatat cttgcaagca aaagtttgt ccacagagac 3540
ttggctgcaa gaaactgtat gctggatgaa aaattcacag tcaaggttgc tgattttggt 3600
cttgccagag acatgtatga taaagaatac tatagtgtac acaacaaaac aggtgcaaag 3660
ctgccagtga agtggatggc tttggaaagt ctgcaaactc aaaagtttac caccaagtca 3720
gatgtgtggt cctttggcgt gctcctctgg gagctgatga agaggagc ccacccttat 3780
cctgacgtaa acacctttga tataactgtt tacttgttgc aagggagaag actcctacaa 3840
cccgaatact gcccagaccc cttatatgaa gtaatgctaa aatgctggca ccctaaagcc 3900
gaaatgcgcc catcctttttc tgaactggtg tcccggatat cagcgatctt ctctactttc 3960
attggggagc actatgtcca tgtaacgct acttatgtga acgtaaaatg tgtcgctccg 4020
tatccttctc tgttgtcatc agaagataac gctgatgatg aggtggacac acgaccagcc 4080
tccttctggg agacatca                                               4098

SEQ ID NO: 3           moltype = AA  length = 908
FEATURE                Location/Qualifiers
```

```
                        -continued source               1..908
                     mol_type = protein
                     organism = Homo sapiens
SEQUENCE: 3
ECKEALAKSE MNVNMKYQLP NFTAETPIQN VILHEHHIFL GATNYIYVLN EEDLQKVAEY    60
KTGPVLEHPD CFPCQDCSSK ANLSGGVWKD NINMALVVDT YYDDQLISCG SVNRGTCQRH   120
VFPHNHTADI QSEVHCIFSP QIEEPSQCPD CVVSALGAKV LSSVKDRFIN FFVGNTINSS   180
YFPDHPLHSI SVRRLKETKD GFMFLTDQSY IDVLPEFRDS YPIKYVHAFE SNNFIYFLTV   240
QRETLDAQTF HTRIIRFCSI NSGLHSYMEM PLECILTEKR KKRSTKKEVF NILQAAYVSK   300
PGAQLARQIG ASLNDDILFG VFAQSKPDSA EPMDRSAMCA FPIKYVNDFF NKIVNKNNVR   360
CLQHFYGPNH EHCFNRTLLR NSSGCEARRD EYRTEFTTAL QRVDLFMGQF SEVLLTSIST   420
FIKGDLTIAN LGTSEGRFMQ VVVSRSGPST PHVNFLLDSH PVSPEVIVEH TLNQNGYTLV   480
ITGKKITKIP LNGLGCRHFQ SCSQCLSAPP FVQCGWCHDK CVRSEECLSG TWTQQICLPA   540
IYKVFPNSAP LEGGTRLTIC GWDFGFRRNN KFDLKKTRVL LGNESCTLTL SESTMNTLKC   600
TVGPAMNKHF NMSIIISNGH GTTQYSTFSY VDPVITSISP KYGPMAGGTL LTLTGNYLNS   660
GNSRHISIGG KTCTLKSVSN SILECYTPAQ TISTEFAVKL KIDLANRETS IFSYREDPIV   720
YEIHPTKSFI SGGSTITGVG KNLNSVSVPR MVINVHEAGR NFTVACQHRS NSEIICCTTP   780
SLQQLNLQLP LKTKAFFMLD GILSKYFDLI YVHNPVFKPF EKPVMISMGN ENVLEIKGND   840
IDPEAVKGEV LKVGNKSCEN IHLHSEAVLC TVPNDLLKLN SELNIEWKQA ISSTVLGKVI   900
VQPDQNFT                                                           908

SEQ ID NO: 4         moltype = DNA  length = 2724
FEATURE              Location/Qualifiers
source               1..2724
                     mol_type = unassigned DNA
                     organism = Homo sapiens
SEQUENCE: 4
gagtgtaaag aggcactagc aaagtccgag atgaatgtga atatgaagta tcagcttccc    60
aacttcaccg cggaaacacc catccagaat gtcattctac atgagcatca cattttcctt   120
ggtgccacta actacattta tgttttaaat gaggaagacc ttcagaaggt tgctgagtac   180
aagactgggc ctgtgctgga acacccagat tgtttcccat gtcaggactg cagcagcaaa   240
gccaatttat caggaggtgt ttggaaagat aacatcaaca tggctctagt tgtcgacact   300
tactatgatg atcaactcat tagctgtggc agcgtcaaca gagggacctg ccagcgacat   360
gtctttcccc acaatcatac tgctgacata cagtcggagg ttcactgcat attctcccca   420
cagatagaag agcccagcca gtgtcctgac tgtgtggtga gcgcccctggg agccaaagtc   480
ctttcatctg taaaggaccg gttcatcaac ttctttgtag gcaataccat aaattcttct   540
tatttcccag atcatccatt gcattcgata tcagtgagaa ggctaaagga aacgaaagat   600
ggttttatgt ttttgacgga ccagtcctac attgatgttt tacctgagtt cagagattct   660
taccccatta agtatgtcca tgcctttgaa agcaacaatt ttatttactt cttgacggtc   720
caaagggaaa ctctagatgc tcagactttt cacacaagaa taatcaggtt ctgttccata   780
aactctggat tgcattccta catggaaatg cctctggagt gtattctcac agaaaagaga   840
aaaagagat ccacaaagaa ggaagtgttt aatatacttc aggctgcgta tgtcagcaag   900
cctgggggcc cagcttgctag acaaatagga gccagcctga atgatgacat tctttttcggg   960
gtgttcgcac aaagcaagcc agattctgcc gaaccaatgg atcgatctgc catgtgtgca  1020
ttccctatca aatatgtcaa cgacttcttc aacaagatcg tcaacaaaaa caatgtgaga  1080
tgtctccagc attttttacgg acccaatcat gagcactgct taataggac acttctgaga  1140
aattcatcag gctgtgaagc gcgccgtgat gaatatcgaa cagagtttac cacagctttg  1200
cagcgcgttg acttattcat gggtcaattc agcgaagtcc tcttaacatc tatatccacc  1260
ttcattaaag agacctcac catagctaat cttgggacat cagagggtcg cttcatgcag  1320
gttgtggttt ctcgatcagg accatcaacc cctcatgtga attttctcct ggactcccat  1380
ccagtgtctc cagaagtgat tgtggagcat acattaaaac aaaatggcta cactgtgtt  1440
atcactggga agaagatcac gaagatccca ttgaatggct tgggctgcag acatttccag  1500
tcctgcagtc aatgcctctc tgccccaccc tttgttcagt gtggctggtg ccacgacaaa  1560
tgtgtgcgat cggaggaatg cctgagcggg acatggactc aacagatctg tctgcctgca  1620
atctacaagg ttttcccaaa tagtgcaccc cttgaaggag ggacaaggct gaccatatgt  1680
ggctgggact ttggatttcg gaggaataat aaatttgatt taagaaaaac tagagttctc  1740
cttggaaatg agagctgcac cttgacttta agtgagagca cgatgaatac attgaaatgc  1800
acagttggtc ctgccatgaa taagcatttc aatatgtcca taattatttc aaatggccac  1860
gggacaacac aatacagtac attctcctat gtggatccctg taataacaag tatttcgccg  1920
aaatacggtc ctatggctgg tggcactta cttactttaa ctggaaatta cctaaacagt  1980
gggaattcta gacacatttc aattggtgga aaaacatgta ctttaaaaag tgtgtcaaac  2040
agtattcttg aatgttatac cccagcccaa accatttcaa ctgagtttgc tgttaaattg  2100
aaaattgact tagccaaccg agagacaagc atcttcagtt accgtgaaga tcccattgtc  2160
tatgaaattc atccaaccaa atcttttatt agtggtggga gcaacataac aggtgttggg  2220
aaaaacctga attcagttag tgtcccgaga atggtcataa atgtgcatga agcaggaagg  2280
aactttacag tggcatgtca acatgctctc aattcagaga taatctgttg taccactcct  2340
tccctgcaac agctgaatct gcaactcccc ctgaaaacca aagcctttt catgttagat  2400
gggatccttt ccaaatactt tgatctcatt tatgtacata atcctgtgtt taagcctttt  2460
gaaaagccag tgatgatctc aatgggcaat gaaaatgtac tggaaattaa gggaaatgat  2520
attgaccctg aagcagttaa aggtgaagtg ttaaaagttg gaaataagag ctgtgagaat  2580
atacacttac attctgaagc cgttttatgc acggtcccca tgaccctgct gaaattgaac  2640
agcgagctaa atatagagtg gaagcaagca atttcttcaa ccgtccttgg aaaagtaata  2700
gttcaaccag atcagaattt caca                                         2724

SEQ ID NO: 5         moltype = AA  length = 119
FEATURE              Location/Qualifiers
REGION               1..119
                     note = MYT5351 Heavy Chain Variable Region
source               1..119
```

```
                        mol_type = protein
                        organism = synthetic construct
SEQUENCE: 5
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSS    119

SEQ ID NO: 6            moltype = AA  length = 108
FEATURE                 Location/Qualifiers
REGION                  1..108
                        note = MYT5351 Light Variable Region
source                  1..108
                        mol_type = protein
                        organism = synthetic construct
SEQUENCE: 6
QIVLTQSPAI LSLSPGERAT LSCSASSSVT SNYLYWYQQK PGSSPKLLIY SHSNLASGVP    60
ARFSGSGSGT SYTLTISSLE AEDAASYFCH QWSSYPPTFG SGTKLEIK                108

SEQ ID NO: 7            moltype = AA  length = 119
FEATURE                 Location/Qualifiers
REGION                  1..119
                        note = MYT4313 Heavy Chain Variable Region
source                  1..119
                        mol_type = protein
                        organism = synthetic construct
SEQUENCE: 7
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMDYWG QGTTVTVSS    119

SEQ ID NO: 8            moltype = AA  length = 108
FEATURE                 Location/Qualifiers
REGION                  1..108
                        note = MYT4313 Light Chain Variable Region
source                  1..108
                        mol_type = protein
                        organism = synthetic construct
SEQUENCE: 8
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIK                108

SEQ ID NO: 9            moltype = AA  length = 119
FEATURE                 Location/Qualifiers
REGION                  1..119
                        note = MYT4325 Heavy Chain Variable Region
source                  1..119
                        mol_type = protein
                        organism = synthetic construct
SEQUENCE: 9
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMHYWG QGTTVTVSS    119

SEQ ID NO: 10           moltype = AA  length = 108
FEATURE                 Location/Qualifiers
REGION                  1..108
                        note = MYT4325 Light Chain Variable Region
source                  1..108
                        mol_type = protein
                        organism = synthetic construct
SEQUENCE: 10
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIK                108

SEQ ID NO: 11           moltype = AA  length = 115
FEATURE                 Location/Qualifiers
REGION                  1..115
                        note = MYT4826 Heavy Chain Variable Region
source                  1..115
                        mol_type = protein
                        organism = synthetic construct
SEQUENCE: 11
QVQLVQSGAE VKKPGASVKV SCKASGYTFT HYYMHWVRQA PGQGLEWMGR VNPNRRHTTY    60
NQKFEGRVTM TTDTSTSTAY MELRSLRSDD TAVYYCARAN WLDYWGQGTT VTVSS        115

SEQ ID NO: 12           moltype = AA  length = 108
FEATURE                 Location/Qualifiers
REGION                  1..108
                        note = MYT4826 Light Chain Variable Region
source                  1..108
                        mol_type = protein
                        organism = synthetic construct
```

```
SEQUENCE: 12
DIQMTQSPSS LSASVGDRVT ITCSVSSSVS SIYLHWYQQK PGKAPKLLIY STSNLASGVP          60
SRFSGSGSGT DFTLTISSLQ PEDFATYYCQ VYSGYPLTFG GGTKVEIK                      108

SEQ ID NO: 13              moltype = AA   length = 115
FEATURE                    Location/Qualifiers
REGION                     1..115
                           note = MYT4837 Heavy Chain Variable Region
source                     1..115
                           mol_type = protein
                           organism = synthetic construct
SEQUENCE: 13
QVQLVQSGAE VKKPGASVKV SCKASGYTFT HYYMHWVRQA PGQGLEWMGR VNPHRRHTTY          60
NQKFEGRVTM TTDTSTSTAY MELRSLRSDD TAVYYCARAN WLDYWGQGTT VTVSS               115

SEQ ID NO: 14              moltype = AA   length = 108
FEATURE                    Location/Qualifiers
REGION                     1..108
                           note = MYT4837 Light Chain Variable Region
source                     1..108
                           mol_type = protein
                           organism = synthetic construct
SEQUENCE: 14
DIQMTQSPSS LSASVGDRVT ITCSVSSSVS SIYLHWYQQK PGKAPKLLIY STSNLASGVP          60
SRFSGSGSGT DFTLTISSLQ PEDFATYYCQ VYSGYPLTFG GGTKVEIK                      108

SEQ ID NO: 15              moltype = AA   length = 115
FEATURE                    Location/Qualifiers
REGION                     1..115
                           note = MYT4849 Heavy Chain Variable Region
source                     1..115
                           mol_type = protein
                           organism = synthetic construct
SEQUENCE: 15
QVQLVQSGAE VKKPGASVKV SCKASGYTFT DYYMHWVRQA PGQGLEWMGR VNPNRRGTTY          60
NQKFEGRVTM TTDTSTSTAY MELRSLRSDD TAVYYCARAN WLDYWGQGTT VTVSS               115

SEQ ID NO: 16              moltype = AA   length = 108
FEATURE                    Location/Qualifiers
REGION                     1..108
                           note = MYT4849 Light Chain Variable Region
source                     1..108
                           mol_type = protein
                           organism = synthetic construct
SEQUENCE: 16
DIQMTQSPSS LSASVGDRVT ITCSVSSSVS SIHLHWYQQK PGKAPKLLIY HTSNLASGVP          60
SRFSGSGSGT DFTLTISSLQ PEDFATYYCQ VYSGYPLTFG GGTKVEIK                      108

SEQ ID NO: 17              moltype = AA   length = 118
FEATURE                    Location/Qualifiers
REGION                     1..118
                           note = MYT4942 Heavy Chain Variable Region
source                     1..118
                           mol_type = protein
                           organism = synthetic construct
SEQUENCE: 17
QVQLVQSGAE VKKPGASVKV SCKASGHIFT AYTMHWVRQA PGQGLEWMGW IKPNNGLANY          60
AQKFQGRVTM TRDTSISTAY MELSRLRSDD TAVYYCARSE ITHEFDHWGQ GTLVTVSS            118

SEQ ID NO: 18              moltype = AA   length = 111
FEATURE                    Location/Qualifiers
REGION                     1..111
                           note = MYT4942 Light Chain Variable Region
source                     1..111
                           mol_type = protein
                           organism = synthetic construct
SEQUENCE: 18
DIVMTQSPDS LAVSLGERAT INCKSSESVD SYANSHLHWY QQKPGQPPKL LIYRASTRES          60
GVPDRFSGSG SGTDFTLTIS SLQAEDVAVY YCQQSKEDPL TFGGGTKVEI K                   111

SEQ ID NO: 19              moltype = AA   length = 115
FEATURE                    Location/Qualifiers
REGION                     1..115
                           note = MYT5309 Heavy Chain Variable Region
source                     1..115
                           mol_type = protein
                           organism = synthetic construct
SEQUENCE: 19
QVQLVQSGAE VKKPGASVKV SCKASGYTFT HYYMHWVRQA PGQGLEWMGR VNPNRRGTTY          60
```

```
NQKFEGRVTM TTDTSTSTAY MELRSLRSDD TAVYYCARAN WLDYWGQGTT VTVSS          115

SEQ ID NO: 20           moltype = AA   length = 108
FEATURE                 Location/Qualifiers
REGION                  1..108
                        note = MYT5309 Light Chain Variable Region
source                  1..108
                        mol_type = protein
                        organism = synthetic construct
SEQUENCE: 20
DIQMTQSPSS LSASVGDRVT ITCSVSSSVS SIYLHWYQQK PGKAPKLLIY STSNLASGVP      60
SRFSGSGSGT DFTLTISSLQ PEDFATYYCQ HYSGYPLTFG GGTKVEIK                  108

SEQ ID NO: 21           moltype = AA   length = 119
FEATURE                 Location/Qualifiers
REGION                  1..119
                        note = MYT5344 Heavy Chain Variable Region
source                  1..119
                        mol_type = protein
                        organism = synthetic construct
SEQUENCE: 21
QVQLVQSGAE VKKPGASVKV SCKASGYTFT SYWMHWVKQA PGQGLDWIGY IKHSTDNTEY      60
NQKFKDKATL TADKSTSTAY MELSSLRSED TAVYYCARSY GNYPLMDYWG QGTTVTVSS      119

SEQ ID NO: 22           moltype = AA   length = 108
FEATURE                 Location/Qualifiers
REGION                  1..108
                        note = MYT5344 Light Chain Variable Region
source                  1..108
                        mol_type = protein
                        organism = synthetic construct
SEQUENCE: 22
QIVLTQSPAI LSLSPGERAT LSCSASSSVT SHYLYWYQQK PGSSPKLLIY STSNLASGVP      60
ARFSGSGSGT SYTLTISSLE AEDAASYFCH QWSSYPPTFG SGTKLEIK                  108

SEQ ID NO: 23           moltype = AA   length = 119
FEATURE                 Location/Qualifiers
REGION                  1..119
                        note = MYT5367 Heavy Chain Variable Region
source                  1..119
                        mol_type = protein
                        organism = synthetic construct
SEQUENCE: 23
QVQLVQSGAE VKKPGASVKV SCKASGYTFT SYWMHWVKQA PGQGLDWIGH IKPSTDNTEY      60
NQKFKDKATL TADKSTSTAY MELSSLRSED TAVYYCARSY GNYPLMDYWG QGTTVTVSS      119

SEQ ID NO: 24           moltype = AA   length = 108
FEATURE                 Location/Qualifiers
REGION                  1..108
                        note = MYT5367 Light Chain Variable Region
source                  1..108
                        mol_type = protein
                        organism = synthetic construct
SEQUENCE: 24
QIVLTQSPAI LSLSPGERAT LSCSASSSVT SNYLYWYQQK PGSSPKLLIY STSNLASGVP      60
ARFSGSGSGT SYTLTISSLE AEDAASYFCH QWSHYHPTFG SGTKLEIK                  108

SEQ ID NO: 25           moltype = AA   length = 115
FEATURE                 Location/Qualifiers
REGION                  1..115
                        note = MYT4827 Heavy Chain Variable Region
source                  1..115
                        mol_type = protein
                        organism = synthetic construct
SEQUENCE: 25
QVQLVQSGAE VKKPGASVKV SCKASGYTFT HYYMHWVRQA PGQGLEWMGR VNPNRRGTTY      60
NQKFEGRVTM TTDTSTSTAY MELRSLRSDD TAVYYCARAH WLDYWGQGTT VTVSS          115

SEQ ID NO: 26           moltype = AA   length = 108
FEATURE                 Location/Qualifiers
REGION                  1..108
                        note = MYT4827 Light Chain Variable Region
source                  1..108
                        mol_type = protein
                        organism = synthetic construct
SEQUENCE: 26
DIQMTQSPSS LSASVGDRVT ITCSVSSSVS SIYLHWYQQK PGKAPKLLIY STSNLASGVP      60
SRFSGSGSGT DFTLTISSLQ PEDFATYYCQ VYSGYPLTFG GGTKVEIK                  108
```

```
SEQ ID NO: 27              moltype = AA  length = 119
FEATURE                    Location/Qualifiers
REGION                     1..119
                           note = MYT4312 Heavy Chain Variable Region
source                     1..119
                           mol_type = protein
                           organism = synthetic construct
SEQUENCE: 27
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMHYWG QGTTVTVSS    119

SEQ ID NO: 28              moltype = AA  length = 108
FEATURE                    Location/Qualifiers
REGION                     1..108
                           note = MYT4312 Light Chain Variable Region
source                     1..108
                           mol_type = protein
                           organism = synthetic construct
SEQUENCE: 28
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIK                108

SEQ ID NO: 29              moltype = AA  length = 118
FEATURE                    Location/Qualifiers
REGION                     1..118
                           note = MYT4953 Heavy Chain Variable Region
source                     1..118
                           mol_type = protein
                           organism = synthetic construct
SEQUENCE: 29
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCHRSE ITHEFDYWGQ GTLVTVSS     118

SEQ ID NO: 30              moltype = AA  length = 111
FEATURE                    Location/Qualifiers
REGION                     1..111
                           note = MYT4953 Light Chain Variable Region
source                     1..111
                           mol_type = protein
                           organism = synthetic construct
SEQUENCE: 30
DIVMTQSPDS LAVSLGERAT INCKSSESVD SYANSFLHWY QQKPGQPPKL LIYRASTRES    60
GVPDRFSGSG SGTDFTLTIS SLQAEDVAVY YCQQSKEDPL TFGGGTKVEI K            111

SEQ ID NO: 31              moltype = AA  length = 118
FEATURE                    Location/Qualifiers
REGION                     1..118
                           note = MYT4940 Heavy Chain Variable Region
source                     1..118
                           mol_type = protein
                           organism = synthetic construct
SEQUENCE: 31
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARHE ITTEFDHWGQ GTLVTVSS     118

SEQ ID NO: 32              moltype = AA  length = 111
FEATURE                    Location/Qualifiers
REGION                     1..111
                           note = MYT4940 Light Chain Variable Region
source                     1..111
                           mol_type = protein
                           organism = synthetic construct
SEQUENCE: 32
DIVMTQSPDS LAVSLGERAT INCKSSESVD SYANSHLHWY QQKPGQPPKL LIYRASTRES    60
GVPDRFSGSG SGTDFTLTIS SLQAEDVAVY YCQQSKEDPL TFGGGTKVEI K            111

SEQ ID NO: 33              moltype = AA  length = 119
FEATURE                    Location/Qualifiers
REGION                     1..119
                           note = MYT4888 Heavy Chain Variable Region
source                     1..119
                           mol_type = protein
                           organism = synthetic construct
SEQUENCE: 33
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLHDYWG QGTTVTVSS    119

SEQ ID NO: 34              moltype = AA  length = 108
FEATURE                    Location/Qualifiers
```

```
REGION                      1..108
                            note = MYT4888 Light Chain Variable Region
source                      1..108
                            mol_type = protein
                            organism = synthetic construct
SEQUENCE: 34
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIK                108

SEQ ID NO: 35               moltype = AA   length = 446
FEATURE                     Location/Qualifiers
REGION                      1..446
                            note = MYT5351 Heavy chain Triple hinge
source                      1..446
                            mol_type = protein
                            organism = synthetic construct
SEQUENCE: 35
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 36               moltype = AA   length = 446
FEATURE                     Location/Qualifiers
REGION                      1..446
                            note = MYT5351 Heavy chain Triple hinge + LS mutation
source                      1..446
                            mol_type = protein
                            organism = synthetic construct
SEQUENCE: 36
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 37               moltype = AA   length = 446
FEATURE                     Location/Qualifiers
REGION                      1..446
                            note = MYT5351 Heavy chain Triple hinge + YTE mutation
source                      1..446
                            mol_type = protein
                            organism = synthetic construct
SEQUENCE: 37
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 38               moltype = AA   length = 446
FEATURE                     Location/Qualifiers
REGION                      1..446
                            note = MYT5351 Heavy chain Triple hinge and A118C
source                      1..446
                            mol_type = protein
                            organism = synthetic construct
SEQUENCE: 38
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 39               moltype = AA   length = 446
FEATURE                     Location/Qualifiers
```

```
REGION                  1..446
                        note = MYT5351 Heavy chain Triple hinge + LS mutation and
                        A118C
source                  1..446
                        mol_type = protein
                        organism = synthetic construct
SEQUENCE: 39
QVQLVQSGAE VKKPGASVKV SCKASGYTFT SYWMHWVKQA PGQGLDWIGH IKPSTDNTEY   60
NQKFKDKATL TADKSTSTAY MELSSLRSED TAVYYCARSY GNYPLMDYWG QGTTVTVSSC  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDCHCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVLHE ALHSHYTQKS LSLSPG                                       446

SEQ ID NO: 40           moltype = AA  length = 446
FEATURE                 Location/Qualifiers
REGION                  1..446
                        note = MYT5351 Heavy chain Triple hinge + YTE mutation and
                        A118C
source                  1..446
                        mol_type = protein
                        organism = synthetic construct
SEQUENCE: 40
QVQLVQSGAE VKKPGASVKV SCKASGYTFT SYWMHWVKQA PGQGLDWIGH IKPSTDNTEY   60
NQKFKDKATL TADKSTSTAY MELSSLRSED TAVYYCARSY GNYPLMDYWG QGTTVTVSSC  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDCHCPPCP APELLGGPSV  240
FLFPPKPKDT LYITREPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                       446

SEQ ID NO: 41           moltype = AA  length = 215
FEATURE                 Location/Qualifiers
REGION                  1..215
                        note = MYT5351 Light Chain
source                  1..215
                        mol_type = protein
                        organism = synthetic construct
SEQUENCE: 41
QIVLTQSPAI LSLSPGERAT LSCSASSSVT SNYLYWYQQK PGSSPKLLIY SHSNLASGVP   60
ARFSGSGSGT SYTLTISSLE AEDAASYFCH QWSSYPPTFG SGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 42           moltype = AA  length = 215
FEATURE                 Location/Qualifiers
REGION                  1..215
                        note = MYT5351 Light Chain (V205C)
source                  1..215
                        mol_type = protein
                        organism = synthetic construct
SEQUENCE: 42
QIVLTQSPAI LSLSPGERAT LSCSASSSVT SNYLYWYQQK PGSSPKLLIY SHSNLASGVP   60
ARFSGSGSGT SYTLTISSLE AEDAASYFCH QWSSYPPTFG SGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPCTKSF NRGEC                             215

SEQ ID NO: 43           moltype = AA  length = 446
FEATURE                 Location/Qualifiers
REGION                  1..446
                        note = MYT4313 Heavy chain Triple hinge
source                  1..446
                        mol_type = protein
                        organism = synthetic construct
SEQUENCE: 43
QVQLVQSGAE VKKPGASVKV SCKASGYTFT SYWMHWVKQA PGQGLDWIGY IKPSTDNTHY   60
NQKFKDKATL TADKSTSTAY MELSSLRSED TAVYYCARSY GHYPLMDYWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDCHCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                       446

SEQ ID NO: 44           moltype = AA  length = 446
FEATURE                 Location/Qualifiers
```

```
REGION                    1..446
                          note = MYT4313 Heavy chain Triple hinge + LS mutation
source                    1..446
                          mol_type = protein
                          organism = synthetic construct
SEQUENCE: 44
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 45             moltype = AA  length = 446
FEATURE                   Location/Qualifiers
REGION                    1..446
                          note = MYT4313 Heavy chain Triple hinge + YTE mutation
source                    1..446
                          mol_type = protein
                          organism = synthetic construct
SEQUENCE: 45
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 46             moltype = AA  length = 446
FEATURE                   Location/Qualifiers
REGION                    1..446
                          note = MYT4313 Heavy chain Triple hinge and A118C
source                    1..446
                          mol_type = protein
                          organism = synthetic construct
SEQUENCE: 46
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 47             moltype = AA  length = 446
FEATURE                   Location/Qualifiers
REGION                    1..446
                          note = MYT4313 Heavy chain Triple hinge + LS mutation and
                          A118C
source                    1..446
                          mol_type = protein
                          organism = synthetic construct
SEQUENCE: 47
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 48             moltype = AA  length = 446
FEATURE                   Location/Qualifiers
REGION                    1..446
                          note = MYT4313 Heavy chain Triple hinge + YTE mutation and
                          A118C
source                    1..446
                          mol_type = protein
                          organism = synthetic construct
SEQUENCE: 48
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMDYWG QGTTVTVSSC   120
STKGPSVFPL APSSKSTSGG TAALGCLVKD YFPEPVTVSW NSGALTSGVH TFPAVLQSSG   180
```

```
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 49              moltype = AA  length = 215
FEATURE                    Location/Qualifiers
REGION                     1..215
                           note = MYT4313 Light Chain
source                     1..215
                           mol_type = protein
                           organism = synthetic construct
SEQUENCE: 49
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 50              moltype = AA  length = 215
FEATURE                    Location/Qualifiers
REGION                     1..215
                           note = MYT4313 Light Chain V205C
source                     1..215
                           mol_type = protein
                           organism = synthetic construct
SEQUENCE: 50
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                              215

SEQ ID NO: 51              moltype = AA  length = 446
FEATURE                    Location/Qualifiers
REGION                     1..446
                           note = MYT4325 Heavy chain Triple hinge
source                     1..446
                           mol_type = protein
                           organism = synthetic construct
SEQUENCE: 51
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMHYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 52              moltype = AA  length = 446
FEATURE                    Location/Qualifiers
REGION                     1..446
                           note = MYT4325 Heavy chain Triple hinge + LS mutation
source                     1..446
                           mol_type = protein
                           organism = synthetic construct
SEQUENCE: 52
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMHYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 53              moltype = AA  length = 446
FEATURE                    Location/Qualifiers
REGION                     1..446
                           note = MYT4325 Heavy chain Triple hinge + YTE mutation
source                     1..446
                           mol_type = protein
                           organism = synthetic construct
SEQUENCE: 53
QVQLVQSGAE VKKPGASVKV SCKASGYTFT SYWMHWVKQA PGQGLDWIGY IKPSTDNTHY    60
NQKFKDKATL TADKSTSTAY MELSSLRSED TAVYYCARSY GHYPLMHYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
```

```
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 54           moltype = AA  length = 446
FEATURE                 Location/Qualifiers
REGION                  1..446
                        note = MYT4325 Heavy chain Triple hinge and A118C
source                  1..446
                        mol_type = protein
                        organism = synthetic construct
SEQUENCE: 54
QVQLVQSGAE VKKPGASVKV SCKASGYTFT SYWMHWVKQA PGQGLDWIGY IKPSTDNTHY   60
NQKFKDKATL TADKSTSTAY MELSSLRSED TAVYYCARSY GHYPLMHYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 55           moltype = AA  length = 446
FEATURE                 Location/Qualifiers
REGION                  1..446
                        note = MYT4325 Heavy chain (triple hinge + LS mutation and
                         A118C)
source                  1..446
                        mol_type = protein
                        organism = synthetic construct
SEQUENCE: 55
QVQLVQSGAE VKKPGASVKV SCKASGYTFT SYWMHWVKQA PGQGLDWIGY IKPSTDNTHY   60
NQKFKDKATL TADKSTSTAY MELSSLRSED TAVYYCARSY GHYPLMHYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 56           moltype = AA  length = 446
FEATURE                 Location/Qualifiers
REGION                  1..446
                        note = MYT4325 Heavy chain (triple hinge + YTE mutation and
                         A118C)
source                  1..446
                        mol_type = protein
                        organism = synthetic construct
SEQUENCE: 56
QVQLVQSGAE VKKPGASVKV SCKASGYTFT SYWMHWVKQA PGQGLDWIGY IKPSTDNTHY   60
NQKFKDKATL TADKSTSTAY MELSSLRSED TAVYYCARSY GHYPLMHYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 57           moltype = AA  length = 215
FEATURE                 Location/Qualifiers
REGION                  1..215
                        note = MYT4325 Light Chain
source                  1..215
                        mol_type = protein
                        organism = synthetic construct
SEQUENCE: 57
QIVLTQSPAI LSLSPGERAT LSCSASSSVT SNYLYWYQQK PGSSPKLLIY STSNLASGVP   60
ARFSGSGSGT SYTLTISSLE AEDAASYFCH QWSSYPPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 58           moltype = AA  length = 215
FEATURE                 Location/Qualifiers
REGION                  1..215
                        note = MYT4325 Light Chain V205C
source                  1..215
                        mol_type = protein
                        organism = synthetic construct
SEQUENCE: 58
QIVLTQSPAI LSLSPGERAT LSCSASSSVT SNYLYWYQQK PGSSPKLLIY STSNLASGVP   60
```

```
ARFSGSGSGT SYTLTISSLE AEDAASYFCH QWSSYPPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                              215

SEQ ID NO: 59              moltype = AA   length = 442
FEATURE                    Location/Qualifiers
REGION                     1..442
                           note = MYT4826 Heavy chain Triple hinge
source                     1..442
                           mol_type = protein
                           organism = synthetic construct
SEQUENCE: 59
QVQLVQSGAE VKKPGASVKV SCKASGYTFT HYYMHWVRQA PGQGLEWMGR VNPNRRHTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 60              moltype = AA   length = 442
FEATURE                    Location/Qualifiers
REGION                     1..442
                           note = MYT4826 Heavy chain (triple hinge + LS mutation)
source                     1..442
                           mol_type = protein
                           organism = synthetic construct
SEQUENCE: 60
QVQLVQSGAE VKKPGASVKV SCKASGYTFT HYYMHWVRQA PGQGLEWMGR VNPNRRHTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS RDELTKNQVS   360
LTCLVKGFYP SDIAVEWESN GQPENNYKTT PPVLDSDGSF FLYSKLTVDK SRWQQGNVFS   420
CSVLHEALHS HYTQKSLSLS PG                                            442

SEQ ID NO: 61              moltype = AA   length = 442
FEATURE                    Location/Qualifiers
REGION                     1..442
                           note = MYT4826 Heavy chain Triple hinge + YTE mutation
source                     1..442
                           mol_type = protein
                           organism = synthetic construct
SEQUENCE: 61
QVQLVQSGAE VKKPGASVKV SCKASGYTFT HYYMHWVRQA PGQGLEWMGR VNPNRRHTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLYIT REPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 62              moltype = AA   length = 442
FEATURE                    Location/Qualifiers
REGION                     1..442
                           note = MYT4826 Heavy chain Triple hinge only and A118
source                     1..442
                           mol_type = protein
                           organism = synthetic construct
SEQUENCE: 62
QVQLVQSGAE VKKPGASVKV SCKASGYTFT HYYMHWVRQA PGQGLEWMGR VNPNRRHTTY    60
NQKFEGRVTM TTDTSTSTAY MELRSLRSDD TAVYYCARAN WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 63              moltype = AA   length = 442
FEATURE                    Location/Qualifiers
REGION                     1..442
                           note = MYT4826 Heavy chain Triple hinge + LS mutation and
                            A118C
source                     1..442
                           mol_type = protein
```

```
                              organism = synthetic construct
SEQUENCE: 63
QVQLVQSGAE VKKPGASVKV SCKASGYTFT HYYMHWVRQA PGQGLEWMGR VNPNRRHTTY      60
NQKFEGRVTM TTDTSTSTAY MELRSLRSDD TAVYYCARAN WLDYWGQGTT VTVSSCSTKG     120
PSVFPLAPSS KSTSGGTAAL GCLVKDYFPE PVTVSWNSGA LTSGVHTFPA VLQSSGLYSL     180
SSVVTVPSSS LGTQTYICNV NHKPSNTKVD KRVEPKSCDC HCPPCPAPEL LGGPSVFLFP     240
PKPKDTLMIS RTPEVTCVVV DVSHEDPEVK FNWYVDGVEV HNAKTKPREE QYNSTYRVVS     300
VLTVLHQDWL NGKEYKCKVS NKALPAPIEK TISKAKGQPR EPQVYTLPPS RDELTKNQVS     360
LTCLVKGFYP SDIAVEWESN GQPENNYKTT PPVLDSDGSF FLYSKLTVDK SRWQQGNVFS     420
CSVLHEALHS HYTQKSLSLS PG                                              442

SEQ ID NO: 64            moltype = AA   length = 442
FEATURE                  Location/Qualifiers
REGION                   1..442
                         note = MYT4826 Heavy chain Triple hinge + YTE mutation and
                          A118C
source                   1..442
                         mol_type = protein
                         organism = synthetic construct
SEQUENCE: 64
QVQLVQSGAE VKKPGASVKV SCKASGYTFT HYYMHWVRQA PGQGLEWMGR VNPNRRHTTY      60
NQKFEGRVTM TTDTSTSTAY MELRSLRSDD TAVYYCARAN WLDYWGQGTT VTVSSCSTKG     120
PSVFPLAPSS KSTSGGTAAL GCLVKDYFPE PVTVSWNSGA LTSGVHTFPA VLQSSGLYSL     180
SSVVTVPSSS LGTQTYICNV NHKPSNTKVD KRVEPKSCDC HCPPCPAPEL LGGPSVFLFP     240
PKPKDTLYIT REPEVTCVVV DVSHEDPEVK FNWYVDGVEV HNAKTKPREE QYNSTYRVVS     300
VLTVLHQDWL NGKEYKCKVS NKALPAPIEK TISKAKGQPR EPQVYTLPPS REEMTKNQVS     360
LTCLVKGFYP SDIAVEWESN GQPENNYKTT PPVLDSDGSF FLYSKLTVDK SRWQQGNVFS     420
CSVMHEALHN HYTQKSLSLS PG                                              442

SEQ ID NO: 65            moltype = AA   length = 215
FEATURE                  Location/Qualifiers
REGION                   1..215
                         note = MYT4826 Light Chain
source                   1..215
                         mol_type = protein
                         organism = synthetic construct
SEQUENCE: 65
DIQMTQSPSS LSASVGDRVT ITCSVSSSVS SIYLHWYQQK PGKAPKLLIY STSNLASGVP      60
SRFSGSGSGT DFTLTISSLQ PEDFATYYCQ VYSGYPLTFG GGTKVEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 66            moltype = AA   length = 215
FEATURE                  Location/Qualifiers
REGION                   1..215
                         note = MYT4826 Light Chain V205C
source                   1..215
                         mol_type = protein
                         organism = synthetic construct
SEQUENCE: 66
DIQMTQSPSS LSASVGDRVT ITCSVSSSVS SIYLHWYQQK PGKAPKLLIY STSNLASGVP      60
SRFSGSGSGT DFTLTISSLQ PEDFATYYCQ VYSGYPLTFG GGTKVEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPCTKSF NRGEC                                215

SEQ ID NO: 67            moltype = AA   length = 442
FEATURE                  Location/Qualifiers
REGION                   1..442
                         note = MYT4837 Heavy chain Triple hinge
source                   1..442
                         mol_type = protein
                         organism = synthetic construct
SEQUENCE: 67
QVQLVQSGAE VKKPGASVKV SCKASGYTFT HYYMHWVRQA PGQGLEWMGR VNPHRRHTTY      60
NQKFEGRVTM TTDTSTSTAY MELRSLRSDD TAVYYCARAN WLDYWGQGTT VTVSSASTKG     120
PSVFPLAPSS KSTSGGTAAL GCLVKDYFPE PVTVSWNSGA LTSGVHTFPA VLQSSGLYSL     180
SSVVTVPSSS LGTQTYICNV NHKPSNTKVD KRVEPKSCDC HCPPCPAPEL LGGPSVFLFP     240
PKPKDTLMIS RTPEVTCVVV DVSHEDPEVK FNWYVDGVEV HNAKTKPREE QYNSTYRVVS     300
VLTVLHQDWL NGKEYKCKVS NKALPAPIEK TISKAKGQPR EPQVYTLPPS REEMTKNQVS     360
LTCLVKGFYP SDIAVEWESN GQPENNYKTT PPVLDSDGSF FLYSKLTVDK SRWQQGNVFS     420
CSVMHEALHN HYTQKSLSLS PG                                              442

SEQ ID NO: 68            moltype = AA   length = 442
FEATURE                  Location/Qualifiers
REGION                   1..442
                         note = MYT4837 Heavy chain Triple hinge + LS mutation
source                   1..442
                         mol_type = protein
                         organism = synthetic construct
```

```
SEQUENCE: 68
QVQLVQSGAE VKKPGASVKV SCKASGYTFT HYYMHWVRQA PGQGLEWMGR VNPHRRHTTY   60
NQKFEGRVTM TTDTSTSTAY MELRSLRSDD TAVYYCARAN WLDYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLMIS RTPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS RDELTKNQVS  360
LTCLVKGFYP SDIAVEWESN GQPENNYKTT PPVLDSDGSF FLYSKLTVDK SRWQQGNVFS  420
CSVLHEALHS HYTQKSLSLS PG                                          442

SEQ ID NO: 69          moltype = AA   length = 442
FEATURE                Location/Qualifiers
REGION                 1..442
                       note = MYT4837 Heavy chain (Triple hinge + YTE mutation
source                 1..442
                       mol_type = protein
                       organism = synthetic construct
SEQUENCE: 69
QVQLVQSGAE VKKPGASVKV SCKASGYTFT HYYMHWVRQA PGQGLEWMGR VNPHRRHTTY   60
NQKFEGRVTM TTDTSTSTAY MELRSLRSDD TAVYYCARAN WLDYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLYIT REPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS REEMTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PG                                          442

SEQ ID NO: 70          moltype = AA   length = 442
FEATURE                Location/Qualifiers
REGION                 1..442
                       note = MYT4837 Heavy chain Triple hinge and A118C
source                 1..442
                       mol_type = protein
                       organism = synthetic construct
SEQUENCE: 70
QVQLVQSGAE VKKPGASVKV SCKASGYTFT HYYMHWVRQA PGQGLEWMGR VNPHRRHTTY   60
NQKFEGRVTM TTDTSTSTAY MELRSLRSDD TAVYYCARAN WLDYWGQGTT VTVSSCSTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLMIS RTPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS REEMTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PG                                          442

SEQ ID NO: 71          moltype = AA   length = 442
FEATURE                Location/Qualifiers
REGION                 1..442
                       note = MYT4837 Heavy chain Triple hinge + LS mutation and
                        A118C
source                 1..442
                       mol_type = protein
                       organism = synthetic construct
SEQUENCE: 71
QVQLVQSGAE VKKPGASVKV SCKASGYTFT HYYMHWVRQA PGQGLEWMGR VNPHRRHTTY   60
NQKFEGRVTM TTDTSTSTAY MELRSLRSDD TAVYYCARAN WLDYWGQGTT VTVSSCSTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLMIS RTPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS RDELTKNQVS  360
LTCLVKGFYP SDIAVEWESN GQPENNYKTT PPVLDSDGSF FLYSKLTVDK SRWQQGNVFS  420
CSVLHEALHS HYTQKSLSLS PG                                          442

SEQ ID NO: 72          moltype = AA   length = 442
FEATURE                Location/Qualifiers
REGION                 1..442
                       note = MYT4837 Heavy chain (triple hinge + YTE mutation
                        and A118C)
source                 1..442
                       mol_type = protein
                       organism = synthetic construct
SEQUENCE: 72
QVQLVQSGAE VKKPGASVKV SCKASGYTFT HYYMHWVRQA PGQGLEWMGR VNPHRRHTTY   60
NQKFEGRVTM TTDTSTSTAY MELRSLRSDD TAVYYCARAN WLDYWGQGTT VTVSSCSTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLYIT REPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS REEMTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PG                                          442
```

```
SEQ ID NO: 73            moltype = AA   length = 215
FEATURE                  Location/Qualifiers
REGION                   1..215
                         note = MYT4837 Light Chain
source                   1..215
                         mol_type = protein
                         organism = synthetic construct
SEQUENCE: 73
DIQMTQSPSS LSASVGDRVT ITCSVSSSVS SIYLHWYQQK PGKAPKLLIY STSNLASGVP   60
SRFSGSGSGT DFTLTISSLQ PEDFATYYCQ VYSGYPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 74            moltype = AA   length = 215
FEATURE                  Location/Qualifiers
REGION                   1..215
                         note = MYT4837 Light Chain V205C
source                   1..215
                         mol_type = protein
                         organism = synthetic construct
SEQUENCE: 74
DIQMTQSPSS LSASVGDRVT ITCSVSSSVS SIYLHWYQQK PGKAPKLLIY STSNLASGVP   60
SRFSGSGSGT DFTLTISSLQ PEDFATYYCQ VYSGYPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPCTKSF NRGEC                             215

SEQ ID NO: 75            moltype = AA   length = 442
FEATURE                  Location/Qualifiers
REGION                   1..442
                         note = MYT4849 Heavy chain Triple hinge
source                   1..442
                         mol_type = protein
                         organism = synthetic construct
SEQUENCE: 75
QVQLVQSGAE VKKPGASVKV SCKASGYTFT DYYMHWVRQA PGQGLEWMGR VNPNRRGTTY   60
NQKFEGRVTM TTDTSTSTAY MELRSLRSDD TAVYYCARAN WLDYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLMIS RTPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS REEMTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PG                                           442

SEQ ID NO: 76            moltype = AA   length = 442
FEATURE                  Location/Qualifiers
REGION                   1..442
                         note = MYT4849 Heavy chain Triple hinge + LS mutation
source                   1..442
                         mol_type = protein
                         organism = synthetic construct
SEQUENCE: 76
QVQLVQSGAE VKKPGASVKV SCKASGYTFT DYYMHWVRQA PGQGLEWMGR VNPNRRGTTY   60
NQKFEGRVTM TTDTSTSTAY MELRSLRSDD TAVYYCARAN WLDYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLMIS RTPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS RDELTKNQVS  360
LTCLVKGFYP SDIAVEWESN GQPENNYKTT PPVLDSDGSF FLYSKLTVDK SRWQQGNVFS  420
CSVLHEALHS HYTQKSLSLS PG                                           442

SEQ ID NO: 77            moltype = AA   length = 442
FEATURE                  Location/Qualifiers
REGION                   1..442
                         note = MYT4849 Heavy chain Triple hinge + YTE mutation
source                   1..442
                         mol_type = protein
                         organism = synthetic construct
SEQUENCE: 77
QVQLVQSGAE VKKPGASVKV SCKASGYTFT DYYMHWVRQA PGQGLEWMGR VNPNRRGTTY   60
NQKFEGRVTM TTDTSTSTAY MELRSLRSDD TAVYYCARAN WLDYWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDC HCPPCPAPEL LGGPSVFLFP  240
PKPKDTLYIT REPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS REEMTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PG                                           442

SEQ ID NO: 78            moltype = AA   length = 442
```

```
FEATURE                 Location/Qualifiers
REGION                  1..442
                        note = MYT4849 Heavy chain Triple hinge and A118C
source                  1..442
                        mol_type = protein
                        organism = synthetic construct
SEQUENCE: 78
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 79           moltype = AA  length = 442
FEATURE                 Location/Qualifiers
REGION                  1..442
                        note = MYT4849 Heavy chain Triple hinge + LS mutation and
                         A118C
source                  1..442
                        mol_type = protein
                        organism = synthetic construct
SEQUENCE: 79
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS RDELTKNQVS   360
LTCLVKGFYP SDIAVEWESN GQPENNYKTT PPVLDSDGSF FLYSKLTVDK SRWQQGNVFS   420
CSVLHEALHS HYTQKSLSLS PG                                            442

SEQ ID NO: 80           moltype = AA  length = 442
FEATURE                 Location/Qualifiers
REGION                  1..442
                        note = MYT4849 Heavy chain Triple hinge + YTE mutation and
                         A118C
source                  1..442
                        mol_type = protein
                        organism = synthetic construct
SEQUENCE: 80
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLYIT REPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 81           moltype = AA  length = 215
FEATURE                 Location/Qualifiers
REGION                  1..215
                        note = MYT4849 Light Chain
source                  1..215
                        mol_type = protein
                        organism = synthetic construct
SEQUENCE: 81
DIQMTQSPSS LSASVGDRVT ITCSVSSSVS SIHLHWYQQK PGKAPKLLIY HTSNLASGVP    60
SRFSGSGSGT DFTLTISSLQ PEDFATYYCQ VYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 82           moltype = AA  length = 215
FEATURE                 Location/Qualifiers
REGION                  1..215
                        note = MYT4849 Light Chain V205C
source                  1..215
                        mol_type = protein
                        organism = synthetic construct
SEQUENCE: 82
DIQMTQSPSS LSASVGDRVT ITCSVSSSVS SIHLHWYQQK PGKAPKLLIY HTSNLASGVP    60
SRFSGSGSGT DFTLTISSLQ PEDFATYYCQ VYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                              215

SEQ ID NO: 83           moltype = AA  length = 445
```

```
FEATURE                 Location/Qualifiers
REGION                  1..445
                        note = MYT4942 Heavy chain Triple hinge
source                  1..445
                        mol_type = protein
                        organism = synthetic construct
SEQUENCE: 83
QVQLVQSGAE VKKPGASVKV SCKASGHIFT AYTMHWVRQA PGQGLEWMGW IKPNNGLANY   60
AQKFQGRVTM TRDTSISTAY MELSRLRSDD TAVYYCARSE ITHEFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDCHCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 84           moltype = AA   length = 445
FEATURE                 Location/Qualifiers
REGION                  1..445
                        note = MYT4942 Heavy chain Triple hinge + LS mutation
source                  1..445
                        mol_type = protein
                        organism = synthetic construct
SEQUENCE: 84
QVQLVQSGAE VKKPGASVKV SCKASGHIFT AYTMHWVRQA PGQGLEWMGW IKPNNGLANY   60
AQKFQGRVTM TRDTSISTAY MELSRLRSDD TAVYYCARSE ITHEFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDCHCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVLHEA LHSHYTQKSL SLSPG                                        445

SEQ ID NO: 85           moltype = AA   length = 445
FEATURE                 Location/Qualifiers
REGION                  1..445
                        note = MYT4942 Heavy chain Triple hinge + YTE mutation
source                  1..445
                        mol_type = protein
                        organism = synthetic construct
SEQUENCE: 85
QVQLVQSGAE VKKPGASVKV SCKASGHIFT AYTMHWVRQA PGQGLEWMGW IKPNNGLANY   60
AQKFQGRVTM TRDTSISTAY MELSRLRSDD TAVYYCARSE ITHEFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDCHCPPCPA PELLGGPSVF  240
LFPPKPKDTL YITREPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 86           moltype = AA   length = 445
FEATURE                 Location/Qualifiers
REGION                  1..445
                        note = MYT4942 Heavy chain Triple hinge and A118C
source                  1..445
                        mol_type = protein
                        organism = synthetic construct
SEQUENCE: 86
QVQLVQSGAE VKKPGASVKV SCKASGHIFT AYTMHWVRQA PGQGLEWMGW IKPNNGLANY   60
AQKFQGRVTM TRDTSISTAY MELSRLRSDD TAVYYCARSE ITHEFDHWGQ GTLVTVSSCS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDCHCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 87           moltype = AA   length = 445
FEATURE                 Location/Qualifiers
REGION                  1..445
                        note = MYT4942 Heavy chain Triple hinge + LS mutation and
                        A118C
source                  1..445
                        mol_type = protein
                        organism = synthetic construct
SEQUENCE: 87
QVQLVQSGAE VKKPGASVKV SCKASGHIFT AYTMHWVRQA PGQGLEWMGW IKPNNGLANY   60
AQKFQGRVTM TRDTSISTAY MELSRLRSDD TAVYYCARSE ITHEFDHWGQ GTLVTVSSCS  120
TKGPSVFPLA PSSKSTSGGT AALGCLVKDY FPEPVTVSWN SGALTSGVHT FPAVLQSSGL  180
```

```
YSLSSVVTVP SSSLGTQTYI CNVNHKPSNT KVDKRVEPKS CDCHCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVLHEA LHSHYTQKSL SLSPG                                       445

SEQ ID NO: 88           moltype = AA  length = 445
FEATURE                 Location/Qualifiers
REGION                  1..445
                        note = MYT4942 Heavy chain Triple hinge + YTE mutation and
                         A118C
source                  1..445
                        mol_type = protein
                        organism = synthetic construct
SEQUENCE: 88
QVQLVQSGAE VKKPGASVKV SCKASGHIFT AYTMHWVRQA PGQGLEWMGW IKPNNGLANY    60
AQKFQGRVTM TRDTSISTAY MELSRLRSDD TAVYYCARSE ITHEFDHWGQ GTLVTVSSCS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL YITREPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                       445

SEQ ID NO: 89           moltype = AA  length = 218
FEATURE                 Location/Qualifiers
REGION                  1..218
                        note = MYT4942 Light Chain
source                  1..218
                        mol_type = protein
                        organism = synthetic construct
SEQUENCE: 89
DIVMTQSPDS LAVSLGERAT INCKSSESVD SYANSHLHWY QQKPGQPPKL LIYRASTRES    60
GVPDRFSGSG SGTDFTLTIS SLQAEDVAVY YCQQSKEDPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 90           moltype = AA  length = 218
FEATURE                 Location/Qualifiers
REGION                  1..218
                        note = MYT4942 Light Chain V205C
source                  1..218
                        mol_type = protein
                        organism = synthetic construct
SEQUENCE: 90
DIVMTQSPDS LAVSLGERAT INCKSSESVD SYANSHLHWY QQKPGQPPKL LIYRASTRES    60
GVPDRFSGSG SGTDFTLTIS SLQAEDVAVY YCQQSKEDPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPCT KSFNRGEC                          218

SEQ ID NO: 91           moltype = AA  length = 442
FEATURE                 Location/Qualifiers
REGION                  1..442
                        note = MYT5309 Heavy chain Triple hinge
source                  1..442
                        mol_type = protein
                        organism = synthetic construct
SEQUENCE: 91
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                           442

SEQ ID NO: 92           moltype = AA  length = 442
FEATURE                 Location/Qualifiers
REGION                  1..442
                        note = MYT5309 Heavy chain Triple hinge + LS mutation
source                  1..442
                        mol_type = protein
                        organism = synthetic construct
SEQUENCE: 92
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
```

```
PKPKDTLMIS RTPEVTCVVV DVSHEDPEVK FNWYVDGVEV HNAKTKPREE QYNSTYRVVS    300
VLTVLHQDWL NGKEYKCKVS NKALPAPIEK TISKAKGQPR EPQVYTLPPS RDELTKNQVS    360
LTCLVKGFYP SDIAVEWESN GQPENNYKTT PPVLDSDGSF FLYSKLTVDK SRWQQGNVFS    420
CSVLHEALHS HYTQKSLSLS PG                                             442

SEQ ID NO: 93           moltype = AA   length = 442
FEATURE                 Location/Qualifiers
REGION                  1..442
                        note = MYT5309 Heavy chain Triple hinge + YTE mutation
source                  1..442
                        mol_type = protein
                        organism = synthetic construct
SEQUENCE: 93
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAN WLDYWGQGTT VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDC HCPPCPAPEL LGGPSVFLFP    240
PKPKDTLYIT REPEVTCVVV DVSHEDPEVK FNWYVDGVEV HNAKTKPREE QYNSTYRVVS    300
VLTVLHQDWL NGKEYKCKVS NKALPAPIEK TISKAKGQPR EPQVYTLPPS REEMTKNQVS    360
LTCLVKGFYP SDIAVEWESN GQPENNYKTT PPVLDSDGSF FLYSKLTVDK SRWQQGNVFS    420
CSVMHEALHN HYTQKSLSLS PG                                             442

SEQ ID NO: 94           moltype = AA   length = 442
FEATURE                 Location/Qualifiers
REGION                  1..442
                        note = MYT5309 Heavy chain Triple hinge and A118C
source                  1..442
                        mol_type = protein
                        organism = synthetic construct
SEQUENCE: 94
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDC HCPPCPAPEL LGGPSVFLFP    240
PKPKDTLMIS RTPEVTCVVV DVSHEDPEVK FNWYVDGVEV HNAKTKPREE QYNSTYRVVS    300
VLTVLHQDWL NGKEYKCKVS NKALPAPIEK TISKAKGQPR EPQVYTLPPS REEMTKNQVS    360
LTCLVKGFYP SDIAVEWESN GQPENNYKTT PPVLDSDGSF FLYSKLTVDK SRWQQGNVFS    420
CSVMHEALHN HYTQKSLSLS PG                                             442

SEQ ID NO: 95           moltype = AA   length = 442
FEATURE                 Location/Qualifiers
REGION                  1..442
                        note = MYT5309 Heavy chain Triple hinge + LS mutation and
                         A118C
source                  1..442
                        mol_type = protein
                        organism = synthetic construct
SEQUENCE: 95
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDC HCPPCPAPEL LGGPSVFLFP    240
PKPKDTLMIS RTPEVTCVVV DVSHEDPEVK FNWYVDGVEV HNAKTKPREE QYNSTYRVVS    300
VLTVLHQDWL NGKEYKCKVS NKALPAPIEK TISKAKGQPR EPQVYTLPPS RDELTKNQVS    360
LTCLVKGFYP SDIAVEWESN GQPENNYKTT PPVLDSDGSF FLYSKLTVDK SRWQQGNVFS    420
CSVLHEALHS HYTQKSLSLS PG                                             442

SEQ ID NO: 96           moltype = AA   length = 442
FEATURE                 Location/Qualifiers
REGION                  1..442
                        note = MYT5309 Heavy chain Triple hinge + YTE mutation and
                         A118C
source                  1..442
                        mol_type = protein
                        organism = synthetic construct
SEQUENCE: 96
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDC HCPPCPAPEL LGGPSVFLFP    240
PKPKDTLYIT REPEVTCVVV DVSHEDPEVK FNWYVDGVEV HNAKTKPREE QYNSTYRVVS    300
VLTVLHQDWL NGKEYKCKVS NKALPAPIEK TISKAKGQPR EPQVYTLPPS REEMTKNQVS    360
LTCLVKGFYP SDIAVEWESN GQPENNYKTT PPVLDSDGSF FLYSKLTVDK SRWQQGNVFS    420
CSVMHEALHN HYTQKSLSLS PG                                             442

SEQ ID NO: 97           moltype = AA   length = 215
FEATURE                 Location/Qualifiers
REGION                  1..215
                        note = MYT5309 Light Chain
```

```
                        source          1..215
                                        mol_type = protein
                                        organism = synthetic construct
SEQUENCE: 97
DIQMTQSPSS LSASVGDRVT ITCSVSSSVS SIYLHWYQQK PGKAPKLLIY STSNLASGVP    60
SRFSGSGSGT DFTLTISSLQ PEDFATYYCQ HYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 98           moltype = AA   length = 215
FEATURE                 Location/Qualifiers
REGION                  1..215
                        note = MYT5309 Light Chain V205C
source                  1..215
                        mol_type = protein
                        organism = synthetic construct
SEQUENCE: 98
DIQMTQSPSS LSASVGDRVT ITCSVSSSVS SIYLHWYQQK PGKAPKLLIY STSNLASGVP    60
SRFSGSGSGT DFTLTISSLQ PEDFATYYCQ HYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                              215

SEQ ID NO: 99           moltype = AA   length = 446
FEATURE                 Location/Qualifiers
REGION                  1..446
                        note = MYT5344 Heavy chain Triple hinge
source                  1..446
                        mol_type = protein
                        organism = synthetic construct
SEQUENCE: 99
QVQLVQSGAE VKKPGASVKV SCKASGYTFT SYWMHWVKQA PGQGLDWIGY IKHSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                        446

SEQ ID NO: 100          moltype = AA   length = 446
FEATURE                 Location/Qualifiers
REGION                  1..446
                        note = MYT5344 Heavy chain Triple hinge + LS mutation
source                  1..446
                        mol_type = protein
                        organism = synthetic construct
SEQUENCE: 100
QVQLVQSGAE VKKPGASVKV SCKASGYTFT SYWMHWVKQA PGQGLDWIGY IKHSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                        446

SEQ ID NO: 101          moltype = AA   length = 446
FEATURE                 Location/Qualifiers
REGION                  1..446
                        note = MYT5344 Heavy chain Triple hinge + YTE mutation
source                  1..446
                        mol_type = protein
                        organism = synthetic construct
SEQUENCE: 101
QVQLVQSGAE VKKPGASVKV SCKASGYTFT SYWMHWVKQA PGQGLDWIGY IKHSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                        446

SEQ ID NO: 102          moltype = AA   length = 446
FEATURE                 Location/Qualifiers
REGION                  1..446
                        note = MYT5344 Heavy chain Triple hinge and A118C
source                  1..446
                        mol_type = protein
```

```
                          organism = synthetic construct
SEQUENCE: 102
QVQLVQSGAE VKKPGASVKV SCKASGYTFT SYWMHWVKQA PGQGLDWIGY IKHSTDNTEY      60
NQKFKDKATL TADKSTSTAY MELSSLRSED TAVYYCARSY GNYPLMDYWG QGTTVTVSSC     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKRVEPK SCDCHCPPCP APELLGGPSV     240
FLFPPKPKDT LMISRTPEVT CVVVDVSHED PEVKFNWYVD GVEVHNAKTK PREEQYNSTY     300
RVVSVLTVLH QDWLNGKEYK CKVSNKALPA PIEKTISKAK GQPREPQVYT LPPSREEMTK     360
NQVSLTCLVK GFYPSDIAVE WESNGQPENN YKTTPPVLDS DGSFFLYSKL TVDKSRWQQG     420
NVFSCSVMHE ALHNHYTQKS LSLSPG                                         446

SEQ ID NO: 103            moltype = AA   length = 446
FEATURE                   Location/Qualifiers
REGION                    1..446
                          note = MYT5344 Heavy chain Triple hinge + LS mutation and
                          A118C
source                    1..446
                          mol_type = protein
                          organism = synthetic construct
SEQUENCE: 103
QVQLVQSGAE VKKPGASVKV SCKASGYTFT SYWMHWVKQA PGQGLDWIGY IKHSTDNTEY      60
NQKFKDKATL TADKSTSTAY MELSSLRSED TAVYYCARSY GNYPLMDYWG QGTTVTVSSC     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKRVEPK SCDCHCPPCP APELLGGPSV     240
FLFPPKPKDT LMISRTPEVT CVVVDVSHED PEVKFNWYVD GVEVHNAKTK PREEQYNSTY     300
RVVSVLTVLH QDWLNGKEYK CKVSNKALPA PIEKTISKAK GQPREPQVYT LPPSRDELTK     360
NQVSLTCLVK GFYPSDIAVE WESNGQPENN YKTTPPVLDS DGSFFLYSKL TVDKSRWQQG     420
NVFSCSVLHE ALHSHYTQKS LSLSPG                                         446

SEQ ID NO: 104            moltype = AA   length = 446
FEATURE                   Location/Qualifiers
REGION                    1..446
                          note = MYT5344 Heavy chain Triple hinge + YTE mutation and
                          A118C
source                    1..446
                          mol_type = protein
                          organism = synthetic construct
SEQUENCE: 104
QVQLVQSGAE VKKPGASVKV SCKASGYTFT SYWMHWVKQA PGQGLDWIGY IKHSTDNTEY      60
NQKFKDKATL TADKSTSTAY MELSSLRSED TAVYYCARSY GNYPLMDYWG QGTTVTVSSC     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKRVEPK SCDCHCPPCP APELLGGPSV     240
FLFPPKPKDT LYITREPEVT CVVVDVSHED PEVKFNWYVD GVEVHNAKTK PREEQYNSTY     300
RVVSVLTVLH QDWLNGKEYK CKVSNKALPA PIEKTISKAK GQPREPQVYT LPPSREEMTK     360
NQVSLTCLVK GFYPSDIAVE WESNGQPENN YKTTPPVLDS DGSFFLYSKL TVDKSRWQQG     420
NVFSCSVMHE ALHNHYTQKS LSLSPG                                         446

SEQ ID NO: 105            moltype = AA   length = 215
FEATURE                   Location/Qualifiers
REGION                    1..215
                          note = MYT5344 Light Chain
source                    1..215
                          mol_type = protein
                          organism = synthetic construct
SEQUENCE: 105
QIVLTQSPAI LSLSPGERAT LSCSASSSVT SHYLYWYQQK PGSSPKLLIY STSNLASGVP      60
ARFSGSGSGT SYTLTISSLE AEDAASYFCH QWSSYPPTFG SGTKLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 106            moltype = AA   length = 215
FEATURE                   Location/Qualifiers
REGION                    1..215
                          note = MYT5344 Light Chain V205C
source                    1..215
                          mol_type = protein
                          organism = synthetic construct
SEQUENCE: 106
QIVLTQSPAI LSLSPGERAT LSCSASSSVT SHYLYWYQQK PGSSPKLLIY STSNLASGVP      60
ARFSGSGSGT SYTLTISSLE AEDAASYFCH QWSSYPPTFG SGTKLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPCTKSF NRGEC                                215

SEQ ID NO: 107            moltype = AA   length = 446
FEATURE                   Location/Qualifiers
REGION                    1..446
                          note = MYT5367 Heavy chain Triple hinge
source                    1..446
                          mol_type = protein
```

```
                        organism = synthetic construct
SEQUENCE: 107
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 108          moltype = AA  length = 446
FEATURE                 Location/Qualifiers
REGION                  1..446
                        note = MYT5367 Heavy chain Triple hinge + LS mutation
source                  1..446
                        mol_type = protein
                        organism = synthetic construct
SEQUENCE: 108
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 109          moltype = AA  length = 446
FEATURE                 Location/Qualifiers
REGION                  1..446
                        note = MYT5367 Heavy chain Triple hinge + YTE mutation
source                  1..446
                        mol_type = protein
                        organism = synthetic construct
SEQUENCE: 109
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 110          moltype = AA  length = 446
FEATURE                 Location/Qualifiers
REGION                  1..446
                        note = MYT5367 Heavy chain Triple hinge and A118C
source                  1..446
                        mol_type = protein
                        organism = synthetic construct
SEQUENCE: 110
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 111          moltype = AA  length = 446
FEATURE                 Location/Qualifiers
REGION                  1..446
                        note = MYT5367 Heavy chain Triple hinge + LS mutation and
                         A118C
source                  1..446
                        mol_type = protein
                        organism = synthetic construct
SEQUENCE: 111
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446
```

```
SEQ ID NO: 112            moltype = AA   length = 446
FEATURE                   Location/Qualifiers
REGION                    1..446
                          note = MYT5367 Heavy chain Triple hinge + YTE mutation and
                           A118C
source                    1..446
                          mol_type = protein
                          organism = synthetic construct
SEQUENCE: 112
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 113            moltype = AA   length = 215
FEATURE                   Location/Qualifiers
REGION                    1..215
                          note = MYT5367 Light Chain
source                    1..215
                          mol_type = protein
                          organism = synthetic construct
SEQUENCE: 113
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSHYHPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 114            moltype = AA   length = 215
FEATURE                   Location/Qualifiers
REGION                    1..215
                          note = MYT5367 Light Chain V205C
source                    1..215
                          mol_type = protein
                          organism = synthetic construct
SEQUENCE: 114
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSHYHPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                             215

SEQ ID NO: 115            moltype = AA   length = 442
FEATURE                   Location/Qualifiers
REGION                    1..442
                          note = MYT4827 Heavy Chain Triple hinge
source                    1..442
                          mol_type = protein
                          organism = synthetic construct
SEQUENCE: 115
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAH WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                           442

SEQ ID NO: 116            moltype = AA   length = 442
FEATURE                   Location/Qualifiers
REGION                    1..442
                          note = MYT4827 Heavy Chain Triple hinge + LS mutation
source                    1..442
                          mol_type = protein
                          organism = synthetic construct
SEQUENCE: 116
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAH WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS RDELTKNQVS   360
LTCLVKGFYP SDIAVEWESN GQPENNYKTT PPVLDSDGSF FLYSKLTVDK SRWQQGNVFS   420
CSVLHEALHS HYTQKSLSLS PG                                           442
```

-continued

```
SEQ ID NO: 117          moltype = AA  length = 442
FEATURE                 Location/Qualifiers
REGION                  1..442
                        note = MYT4827 Heavy Chain Triple hinge + YTE mutation
source                  1..442
                        mol_type = protein
                        organism = synthetic construct
SEQUENCE: 117
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAH WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLYIT REPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 118          moltype = AA  length = 442
FEATURE                 Location/Qualifiers
REGION                  1..442
                        note = MYT4827 Heavy Chain Triple hinge and A118C
source                  1..442
                        mol_type = protein
                        organism = synthetic construct
SEQUENCE: 118
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAH WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 119          moltype = AA  length = 442
FEATURE                 Location/Qualifiers
REGION                  1..442
                        note = MYT4827 Heavy Chain Triple hinge + LS mutation and
                         A118C
source                  1..442
                        mol_type = protein
                        organism = synthetic construct
SEQUENCE: 119
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAH WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS RDELTKNQVS   360
LTCLVKGFYP SDIAVEWESN GQPENNYKTT PPVLDSDGSF FLYSKLTVDK SRWQQGNVFS   420
CSVLHEALHS HYTQKSLSLS PG                                            442

SEQ ID NO: 120          moltype = AA  length = 442
FEATURE                 Location/Qualifiers
REGION                  1..442
                        note = MYT4827 Heavy Chain Triple hinge + YTE mutation and
                         A118C
source                  1..442
                        mol_type = protein
                        organism = synthetic construct
SEQUENCE: 120
QVQLVQSGAE VKKPGASVKV SCKASGYTFT HYYMHWVRQA PGQGLEWMGR VNPNRRGTTY    60
NQKFEGRVTM TTDTSTSTAY MELRSLRSDD TAVYYCARAH WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLYIT REPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                            442

SEQ ID NO: 121          moltype = AA  length = 215
FEATURE                 Location/Qualifiers
REGION                  1..215
                        note = MYT4827 Light Chain
source                  1..215
                        mol_type = protein
                        organism = synthetic construct
SEQUENCE: 121
DIQMTQSPSS LSASVGDRVT ITCSVSSSVS SIYLHWYQQK PGKAPKLLIY STSNLASGVP    60
```

```
SRFSGSGSGT DFTLTISSLQ PEDFATYYCQ VYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 122          moltype = AA   length = 215
FEATURE                 Location/Qualifiers
REGION                  1..215
                        note = MYT4827 Light Chain V205C
source                  1..215
                        mol_type = protein
                        organism = synthetic construct
SEQUENCE: 122
DIQMTQSPSS LSASVGDRVT ITCSVSSSVS SIYLHWYQQK PGKAPKLLIY STSNLASGVP    60
SRFSGSGSGT DFTLTISSLQ PEDFATYYCQ VYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                              215

SEQ ID NO: 123          moltype = AA   length = 446
FEATURE                 Location/Qualifiers
REGION                  1..446
                        note = MYT4312 Heavy Chain Triple hinge
source                  1..446
                        mol_type = protein
                        organism = synthetic construct
SEQUENCE: 123
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMHYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 124          moltype = AA   length = 446
FEATURE                 Location/Qualifiers
REGION                  1..446
                        note = MYT4312 Heavy Chain Triple hinge + LS mutation
source                  1..446
                        mol_type = protein
                        organism = synthetic construct
SEQUENCE: 124
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMHYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 125          moltype = AA   length = 446
FEATURE                 Location/Qualifiers
REGION                  1..446
                        note = MYT4312 Heavy Chain Triple hinge + YTE mutation
source                  1..446
                        mol_type = protein
                        organism = synthetic construct
SEQUENCE: 125
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMHYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 126          moltype = AA   length = 446
FEATURE                 Location/Qualifiers
REGION                  1..446
                        note = MYT4312 Heavy Chain Triple hinge and A118C
source                  1..446
                        mol_type = protein
                        organism = synthetic construct
SEQUENCE: 126
QVQLVQSGAE VKKPGASVKV SCKASGYTFT SYWMHWVKQA PGQGLDWIGH IKPSTDNTEY    60
NQKFKDKATL TADKSTSTAY MELSSLRSED TAVYYCARSY GNYPLMHYWG QGTTVTVSSC   120
STKGPSVFPL APSSKSTSGG TAALGCLVKD YFPEPVTVSW NSGALTSGVH TFPAVLQSSG   180
```

```
LYSLSSVVTV PSSSLGTQTY ICNVNHKPSN TKVDKRVEPK SCDCHCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPG                                        446

SEQ ID NO: 127          moltype = AA  length = 446
FEATURE                 Location/Qualifiers
REGION                  1..446
                        note = MYT4312 Heavy Chain Triple hinge + LS mutation and
                        A118C
source                  1..446
                        mol_type = protein
                        organism = synthetic construct
SEQUENCE: 127
QVQLVQSGAE VKKPGASVKV SCKASGYTFT SYWMHWVKQA PGQGLDWIGH IKPSTDNTEY     60
NQKFKDKATL TADKSTSTAY MELSSLRSED TAVYYCARSY GNYPLMHYWG QGTTVTVSSC    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDCHCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVLHE ALHSHYTQKS LSLSPG                                        446

SEQ ID NO: 128          moltype = AA  length = 446
FEATURE                 Location/Qualifiers
REGION                  1..446
                        note = MYT4312 Heavy Chain (triple hinge + YTE mutation and
                        A118C)
source                  1..446
                        mol_type = protein
                        organism = synthetic construct
SEQUENCE: 128
QVQLVQSGAE VKKPGASVKV SCKASGYTFT SYWMHWVKQA PGQGLDWIGH IKPSTDNTEY     60
NQKFKDKATL TADKSTSTAY MELSSLRSED TAVYYCARSY GNYPLMHYWG QGTTVTVSSC    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDCHCPPCP APELLGGPSV    240
FLFPPKPKDT LYITREPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPG                                        446

SEQ ID NO: 129          moltype = AA  length = 215
FEATURE                 Location/Qualifiers
REGION                  1..215
                        note = MYT4312 Light Chain
source                  1..215
                        mol_type = protein
                        organism = synthetic construct
SEQUENCE: 129
QIVLTQSPAI LSLSPGERAT LSCSASSSVT SNYLYWYQQK PGSSPKLLIY STSNLASGVP     60
ARFSGSGSGT SYTLTISSLE AEDAASYFCH QWSSYPPTFG SGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 130          moltype = AA  length = 215
FEATURE                 Location/Qualifiers
REGION                  1..215
                        note = MYT4312 Light Chain V205C
source                  1..215
                        mol_type = protein
                        organism = synthetic construct
SEQUENCE: 130
QIVLTQSPAI LSLSPGERAT LSCSASSSVT SNYLYWYQQK PGSSPKLLIY STSNLASGVP     60
ARFSGSGSGT SYTLTISSLE AEDAASYFCH QWSSYPPTFG SGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPCTKSF NRGEC                              215

SEQ ID NO: 131          moltype = AA  length = 445
FEATURE                 Location/Qualifiers
REGION                  1..445
                        note = MYT4953 Heavy Chain Triple hinge
source                  1..445
                        mol_type = protein
                        organism = synthetic construct
SEQUENCE: 131
QVQLVQSGAE VKKPGASVKV SCKASGYIFT AYTMHWVRQA PGQGLEWMGW IKPNNGLANY     60
AQKFQGRVTM TRDTSISTAY MELSRLRSDD TAVYYCHRSE ITHEFDYWGQ GTLVTVSSAS    120
TKGPSVFPLA PSSKSTSGGT AALGCLVKDY FPEPVTVSWN SGALTSGVHT FPAVLQSSGL    180
```

```
YSLSSVVTVP SSSLGTQTYI CNVNHKPSNT KVDKRVEPKS CDCHCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 132          moltype = AA   length = 445
FEATURE                 Location/Qualifiers
REGION                  1..445
                        note = MYT4953 Heavy Chain Triple hinge + LS mutation
source                  1..445
                        mol_type = protein
                        organism = synthetic construct
SEQUENCE: 132
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCHRSE ITHEFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CDCHCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVLHEA LHSHYTQKSL SLSPG                                         445

SEQ ID NO: 133          moltype = AA   length = 445
FEATURE                 Location/Qualifiers
REGION                  1..445
                        note = MYT4953 Heavy Chain Triple hinge + YTE mutation
source                  1..445
                        mol_type = protein
                        organism = synthetic construct
SEQUENCE: 133
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCHRSE ITHEFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CDCHCPPCPA PELLGGPSVF    240
LFPPKPKDTL YITREPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 134          moltype = AA   length = 445
FEATURE                 Location/Qualifiers
REGION                  1..445
                        note = MYT4953 Heavy Chain Triple hinge and A118C
source                  1..445
                        mol_type = protein
                        organism = synthetic construct
SEQUENCE: 134
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCHRSE ITHEFDYWGQ GTLVTVSSCS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CDCHCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 135          moltype = AA   length = 445
FEATURE                 Location/Qualifiers
REGION                  1..445
                        note = MYT4953 Heavy Chain Triple hinge + LS mutation and
                         A118C
source                  1..445
                        mol_type = protein
                        organism = synthetic construct
SEQUENCE: 135
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCHRSE ITHEFDYWGQ GTLVTVSSCS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CDCHCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVLHEA LHSHYTQKSL SLSPG                                         445

SEQ ID NO: 136          moltype = AA   length = 445
FEATURE                 Location/Qualifiers
REGION                  1..445
                        note = MYT4953 Heavy Chain Triple hinge + YTE mutation and
```

```
                              A118C
source                        1..445
                              mol_type = protein
                              organism = synthetic construct
SEQUENCE: 136
QVQLVQSGAE VKKPGASVKV SCKASGYIFT AYTMHWVRQA PGQGLEWMGW IKPNNGLANY   60
AQKFQGRVTM TRDTSISTAY MELSRLRSDD TAVYYCHRSE ITHEFDYWGQ GTLVTVSSCS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDCHCPPCPA PELLGGPSVF  240
LFPPKPKDTL YITREPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 137          moltype = AA  length = 218
FEATURE                 Location/Qualifiers
REGION                  1..218
                        note = MYT4953 Light Chain
source                  1..218
                        mol_type = protein
                        organism = synthetic construct
SEQUENCE: 137
DIVMTQSPDS LAVSLGERAT INCKSSESVD SYANSFLHWY QQKPGQPPKL LIYRASTRES   60
GVPDRFSGSG SGTDFTLTIS SLQAEDVAVY YCQQSKEDPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 138          moltype = AA  length = 218
FEATURE                 Location/Qualifiers
REGION                  1..218
                        note = MYT4953 Light Chain V205C
source                  1..218
                        mol_type = protein
                        organism = synthetic construct
SEQUENCE: 138
DIVMTQSPDS LAVSLGERAT INCKSSESVD SYANSFLHWY QQKPGQPPKL LIYRASTRES   60
GVPDRFSGSG SGTDFTLTIS SLQAEDVAVY YCQQSKEDPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPCT KSFNRGEC                         218

SEQ ID NO: 139          moltype = AA  length = 445
FEATURE                 Location/Qualifiers
REGION                  1..445
                        note = MYT4940 Heavy Chain Triple hinge
source                  1..445
                        mol_type = protein
                        organism = synthetic construct
SEQUENCE: 139
QVQLVQSGAE VKKPGASVKV SCKASGYIFT AYTMHWVRQA PGQGLEWMGW IKPNNGLANY   60
AQKFQGRVTM TRDTSISTAY MELSRLRSDD TAVYYCARHE ITTEFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDCHCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 140          moltype = AA  length = 445
FEATURE                 Location/Qualifiers
REGION                  1..445
                        note = MYT4940 Heavy Chain (Triple hinge + LS mutation)
source                  1..445
                        mol_type = protein
                        organism = synthetic construct
SEQUENCE: 140
QVQLVQSGAE VKKPGASVKV SCKASGYIFT AYTMHWVRQA PGQGLEWMGW IKPNNGLANY   60
AQKFQGRVTM TRDTSISTAY MELSRLRSDD TAVYYCARHE ITTEFDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDCHCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHSHYTQKSL SLSPG                                       445

SEQ ID NO: 141          moltype = AA  length = 445
FEATURE                 Location/Qualifiers
REGION                  1..445
                        note = MYT4940 Heavy Chain Triple hinge + YTE mutation
source                  1..445
```

```
                        mol_type = protein
                        organism = synthetic construct
SEQUENCE: 141
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARHE ITTEFDHWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL YITREPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 142          moltype = AA  length = 445
FEATURE                 Location/Qualifiers
REGION                  1..445
                        note = MYT4940 Heavy Chain Triple hinge and A118C
source                  1..445
                        mol_type = protein
                        organism = synthetic construct
SEQUENCE: 142
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARHE ITTEFDHWGQ GTLVTVSSCS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 143          moltype = AA  length = 445
FEATURE                 Location/Qualifiers
REGION                  1..445
                        note = MYT4940 Heavy Chain Triple hinge + LS mutation and
                         A118C
source                  1..445
                        mol_type = protein
                        organism = synthetic construct
SEQUENCE: 143
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARHE ITTEFDHWGQ GTLVTVSSCS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVLHEA LHSHYTQKSL SLSPG                                        445

SEQ ID NO: 144          moltype = AA  length = 445
FEATURE                 Location/Qualifiers
REGION                  1..445
                        note = MYT4940 Heavy Chain Triple hinge + YTE mutation and
                         A118C
source                  1..445
                        mol_type = protein
                        organism = synthetic construct
SEQUENCE: 144
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARHE ITTEFDHWGQ GTLVTVSSCS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL YITREPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 145          moltype = AA  length = 218
FEATURE                 Location/Qualifiers
REGION                  1..218
                        note = MYT4940 Light Chain
source                  1..218
                        mol_type = protein
                        organism = synthetic construct
SEQUENCE: 145
DIVMTQSPDS LAVSLGERAT INCKSSESVD SYANSHLHWY QQKPGQPPKL LIYRASTRES    60
GVPDRFSGSG SGTDFTLTIS SLQAEDVAVY YCQQSKEDPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 146          moltype = AA  length = 218
```

| FEATURE | Location/Qualifiers |
|---|---|
| REGION | 1..218 |
| | note = MYT4940 Light Chain V205C |
| source | 1..218 |
| | mol_type = protein |
| | organism = synthetic construct |

SEQUENCE: 146
```
DIVMTQSPDS LAVSLGERAT INCKSSESVD SYANSHLHWY QQKPGQPPKL LIYRASTRES    60
GVPDRFSGSG SGTDFTLTIS SLQAEDVAVY YCQQSKEDPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPCT KSFNRGEC                           218
```

| SEQ ID NO: 147 | moltype = AA  length = 446 |
|---|---|
| FEATURE | Location/Qualifiers |
| REGION | 1..446 |
| | note = MYT4888 Heavy Chain Triple hinge |
| source | 1..446 |
| | mol_type = protein |
| | organism = synthetic construct |

SEQUENCE: 147
```
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLHDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                        446
```

| SEQ ID NO: 148 | moltype = AA  length = 446 |
|---|---|
| FEATURE | Location/Qualifiers |
| REGION | 1..446 |
| | note = MYT4888 Heavy Chain Triple hinge + LS mutation |
| source | 1..446 |
| | mol_type = protein |
| | organism = synthetic construct |

SEQUENCE: 148
```
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLHDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                        446
```

| SEQ ID NO: 149 | moltype = AA  length = 446 |
|---|---|
| FEATURE | Location/Qualifiers |
| REGION | 1..446 |
| | note = MYT4888 Heavy Chain Triple hinge + YTE mutation |
| source | 1..446 |
| | mol_type = protein |
| | organism = synthetic construct |

SEQUENCE: 149
```
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLHDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                        446
```

| SEQ ID NO: 150 | moltype = AA  length = 446 |
|---|---|
| FEATURE | Location/Qualifiers |
| REGION | 1..446 |
| | note = MYT4888 Heavy Chain Triple hinge and A118C |
| source | 1..446 |
| | mol_type = protein |
| | organism = synthetic construct |

SEQUENCE: 150
```
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLHDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                        446
```

```
SEQ ID NO: 151          moltype = AA   length = 446
FEATURE                 Location/Qualifiers
REGION                  1..446
                        note = MYT4888 Heavy Chain Triple hinge + LS mutation and
                        A118C
source                  1..446
                        mol_type = protein
                        organism = synthetic construct
SEQUENCE: 151
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLHDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 152          moltype = AA   length = 446
FEATURE                 Location/Qualifiers
REGION                  1..446
                        note = MYT4888 Heavy Chain Triple hinge + YTE mutation and
                        A118C
source                  1..446
                        mol_type = protein
                        organism = synthetic construct
SEQUENCE: 152
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLHDYWG QGTTVTVSSC   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 153          moltype = AA   length = 215
FEATURE                 Location/Qualifiers
REGION                  1..215
                        note = MYT4888 Light Chain
source                  1..215
                        mol_type = protein
                        organism = synthetic construct
SEQUENCE: 153
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 154          moltype = AA   length = 215
FEATURE                 Location/Qualifiers
REGION                  1..215
                        note = MYT4888 Light Chain V205C
source                  1..215
                        mol_type = protein
                        organism = synthetic construct
SEQUENCE: 154
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                             215

SEQ ID NO: 155          moltype = AA   length = 329
FEATURE                 Location/Qualifiers
source                  1..329
                        mol_type = protein
                        organism = Homo sapiens
SEQUENCE: 155
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 156          moltype = AA   length = 327
FEATURE                 Location/Qualifiers
REGION                  1..327
```

```
                          note = Heavy Chain Constant Domain A118C
source                    1..327
                          mol_type = protein
                          organism = synthetic construct
SEQUENCE: 156
CSTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDCHCPPC PAPELLGGPS   120
VFLFPPKPKD TLYITREPEV TCVVVDVSHE DPEVKFNWYV DGVEVHNAKT KPREEQYNST   180
YRVVSVLTVL HQDWLNGKEY KCKVSNKALP APIEKTISKA KGQPREPQVY TLPPSREEMT   240
KNQVSLTCLV KGFYPSDIAV EWESNGQPEN NYKTTPPVLD SDGSFFLYSK LTVDKSRWQQ   300
GNVFSCSVLH EALHSHYTQK SLSLSPG                                      327

SEQ ID NO: 157            moltype = AA   length = 107
FEATURE                   Location/Qualifiers
REGION                    1..107
                          note = Derived from Homo sapiens
source                    1..107
                          mol_type = protein
                          organism = synthetic construct
SEQUENCE: 157
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 158            moltype = AA   length = 107
FEATURE                   Location/Qualifiers
REGION                    1..107
                          note = Light Chain Constant Domain V205C
source                    1..107
                          mol_type = protein
                          organism = synthetic construct
SEQUENCE: 158
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPCTK SFNRGEC                107

SEQ ID NO: 159            moltype = AA   length = 118
FEATURE                   Location/Qualifiers
REGION                    1..118
                          note = Telisotuzumab Heavy chain variable region
source                    1..118
                          mol_type = protein
                          organism = synthetic construct
SEQUENCE: 159
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARSE ITTEFDYWGQ GTLVTVSS    118

SEQ ID NO: 160            moltype = AA   length = 111
FEATURE                   Location/Qualifiers
REGION                    1..111
                          note = Telisotuzumab Light chain variable region
source                    1..111
                          mol_type = protein
                          organism = synthetic construct
SEQUENCE: 160
DIVMTQSPDS LAVSLGERAT INCKSSESVD SYANSFLHWY QQKPGQPPKL LIYRASTRES    60
GVPDRFSGSG SGTDFTLTIS SLQAEDVAVY YCQQSKEDPL TFGGGTKVEI K            111

SEQ ID NO: 161            moltype = AA   length = 115
FEATURE                   Location/Qualifiers
REGION                    1..115
                          note = Emibetuzumab heavy chain variable region
source                    1..115
                          mol_type = protein
                          organism = synthetic construct
SEQUENCE: 161
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSS        115

SEQ ID NO: 162            moltype = AA   length = 108
FEATURE                   Location/Qualifiers
REGION                    1..108
                          note = Emibetuzumab light chain variable region
source                    1..108
                          mol_type = protein
                          organism = synthetic construct
SEQUENCE: 162
DIQMTQSPSS LSASVGDRVT ITCSVSSSVS SIYLHWYQQK PGKAPKLLIY STSNLASGVP    60
SRFSGSGSGT DFTLTISSLQ PEDFATYYCQ VYSGYPLTFG GGTKVEIK                108

SEQ ID NO: 163            moltype = AA   length = 119
```

```
FEATURE                 Location/Qualifiers
REGION                  1..119
                        note = P3D12 anti-cMET heavy chain variable region
source                  1..119
                        mol_type = protein
                        organism = synthetic construct
SEQUENCE: 163
QVQLVQSGAE VKKPGASVKV SCKASGYTFT SYWMHWVKQA PGQGLDWIGY IKPSTDNTEY      60
NQKFKDKATL TADKSTSTAY MELSSLRSED TAVYYCARSY GNYPLMDYWG QGTTVTVSS       119

SEQ ID NO: 164          moltype = AA  length = 108
FEATURE                 Location/Qualifiers
REGION                  1..108
                        note = 3D12 anti-cMET light chain variable region
source                  1..108
                        mol_type = protein
                        organism = synthetic construct
SEQUENCE: 164
QIVLTQSPAI LSLSPGERAT LSCSASSSVT SNYLYWYQQK PGSSPKLLIY STSNLASGVP      60
ARFSGSGSGT SYTLTISSLE AEDAASYFCH QWSSYPPTFG SGTKLEIK                   108

SEQ ID NO: 165          moltype = AA  length = 445
FEATURE                 Location/Qualifiers
REGION                  1..445
                        note = Telisotuzumab Heavy chain Triple Hinge
source                  1..445
                        mol_type = protein
                        organism = synthetic construct
SEQUENCE: 165
QVQLVQSGAE VKKPGASVKV SCKASGYIFT AYTMHWVRQA PGQGLEWMGW IKPNNGLANY      60
AQKFQGRVTM TRDTSISTAY MELSRLRSDD TAVYYCARSE ITTEFDYWGQ GTLVTVSSAS      120
TKGPSVFPLA PSSKSTSGGT AALGCLVKDY FPEPVTVSWN SGALTSGVHT FPAVLQSSGL      180
YSLSSVVTVP SSSLGTQTYI CNVNHKPSNT KVDKRVEPKS CDCHCPPCPA PELLGGPSVF      240
LFPPKPKDTL MISRTPEVTC VVVDVSHEDP EVKFNWYVDG VEVHNAKTKP REEQYNSTYR      300
VVSVLTVLHQ DWLNGKEYKC KVSNKALPAP IEKTISKAKG QPREPQVYTL PPSREEMTKN      360
QVSLTCLVKG FYPSDIAVEW ESNGQPENNY KTTPPVLDSD GSFFLYSKLT VDKSRWQQGN      420
VFSCSVMHEA LHNHYTQKSL SLSPG                                            445

SEQ ID NO: 166          moltype = AA  length = 445
FEATURE                 Location/Qualifiers
REGION                  1..445
                        note = Telisotuzumab Heavy chain Triple Hinge + LS
source                  1..445
                        mol_type = protein
                        organism = synthetic construct
SEQUENCE: 166
QVQLVQSGAE VKKPGASVKV SCKASGYIFT AYTMHWVRQA PGQGLEWMGW IKPNNGLANY      60
AQKFQGRVTM TRDTSISTAY MELSRLRSDD TAVYYCARSE ITTEFDYWGQ GTLVTVSSAS      120
TKGPSVFPLA PSSKSTSGGT AALGCLVKDY FPEPVTVSWN SGALTSGVHT FPAVLQSSGL      180
YSLSSVVTVP SSSLGTQTYI CNVNHKPSNT KVDKRVEPKS CDCHCPPCPA PELLGGPSVF      240
LFPPKPKDTL MISRTPEVTC VVVDVSHEDP EVKFNWYVDG VEVHNAKTKP REEQYNSTYR      300
VVSVLTVLHQ DWLNGKEYKC KVSNKALPAP IEKTISKAKG QPREPQVYTL PPSRDELTKN      360
QVSLTCLVKG FYPSDIAVEW ESNGQPENNY KTTPPVLDSD GSFFLYSKLT VDKSRWQQGN      420
VFSCSVLHEA LHSHYTQKSL SLSPG                                            445

SEQ ID NO: 167          moltype = AA  length = 445
FEATURE                 Location/Qualifiers
REGION                  1..445
                        note = Telisotuzumab Heavy chain Triple Hinge + YTE
source                  1..445
                        mol_type = protein
                        organism = synthetic construct
SEQUENCE: 167
QVQLVQSGAE VKKPGASVKV SCKASGYIFT AYTMHWVRQA PGQGLEWMGW IKPNNGLANY      60
AQKFQGRVTM TRDTSISTAY MELSRLRSDD TAVYYCARSE ITTEFDYWGQ GTLVTVSSAS      120
TKGPSVFPLA PSSKSTSGGT AALGCLVKDY FPEPVTVSWN SGALTSGVHT FPAVLQSSGL      180
YSLSSVVTVP SSSLGTQTYI CNVNHKPSNT KVDKRVEPKS CDCHCPPCPA PELLGGPSVF      240
LFPPKPKDTL YITREPEVTC VVVDVSHEDP EVKFNWYVDG VEVHNAKTKP REEQYNSTYR      300
VVSVLTVLHQ DWLNGKEYKC KVSNKALPAP IEKTISKAKG QPREPQVYTL PPSREEMTKN      360
QVSLTCLVKG FYPSDIAVEW ESNGQPENNY KTTPPVLDSD GSFFLYSKLT VDKSRWQQGN      420
VFSCSVMHEA LHNHYTQKSL SLSPG                                            445

SEQ ID NO: 168          moltype = AA  length = 445
FEATURE                 Location/Qualifiers
REGION                  1..445
                        note = Telisotuzumab Heavy chain Triple Hinge and A118C
source                  1..445
                        mol_type = protein
                        organism = synthetic construct
```

-continued

```
SEQUENCE: 168
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARSE ITTEFDYWGQ GTLVTVSSCS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 169          moltype = AA  length = 445
FEATURE                 Location/Qualifiers
REGION                  1..445
                        note = Telisotuzumab Heavy chain Triple Hinge + LS and A118C
source                  1..445
                        mol_type = protein
                        organism = synthetic construct
SEQUENCE: 169
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARSE ITTEFDYWGQ GTLVTVSSCS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVLHEA LHSHYTQKSL SLSPG                                        445

SEQ ID NO: 170          moltype = AA  length = 445
FEATURE                 Location/Qualifiers
REGION                  1..445
                        note = Telisotuzumab Heavy chain Triple Hinge + YTE and
                         A118C
source                  1..445
                        mol_type = protein
                        organism = synthetic construct
SEQUENCE: 170
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCARSE ITTEFDYWGQ GTLVTVSSCS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDCHCPPCPA PELLGGPSVF   240
LFPPKPKDTL YITREPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 171          moltype = AA  length = 218
FEATURE                 Location/Qualifiers
REGION                  1..218
                        note = Telisotuzumab Light chain
source                  1..218
                        mol_type = protein
                        organism = synthetic construct
SEQUENCE: 171
DIVMTQSPDS LAVSLGERAT INCKSSESVD SYANSFLHWY QQKPGQPPKL LIYRASTRES    60
GVPDRFSGSG SGTDFTLTIS SLQAEDVAVY YCQQSKEDPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 172          moltype = AA  length = 218
FEATURE                 Location/Qualifiers
REGION                  1..218
                        note = Telisotuzumab Light chain V205C
source                  1..218
                        mol_type = protein
                        organism = synthetic construct
SEQUENCE: 172
DIVMTQSPDS LAVSLGERAT INCKSSESVD SYANSFLHWY QQKPGQPPKL LIYRASTRES    60
GVPDRFSGSG SGTDFTLTIS SLQAEDVAVY YCQQSKEDPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPCT KSFNRGEC                           218

SEQ ID NO: 173          moltype = AA  length = 442
FEATURE                 Location/Qualifiers
REGION                  1..442
                        note = Emibetuzumab heavy chain with Triple Hinge
source                  1..442
                        mol_type = protein
                        organism = synthetic construct
SEQUENCE: 173
```

```
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                           442

SEQ ID NO: 174          moltype = AA  length = 442
FEATURE                 Location/Qualifiers
REGION                  1..442
                        note = Emibetuzumab heavy chain with Triple Hinge and LS
source                  1..442
                        mol_type = protein
                        organism = synthetic construct
SEQUENCE: 174
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS RDELTKNQVS   360
LTCLVKGFYP SDIAVEWESN GQPENNYKTT PPVLDSDGSF FLYSKLTVDK SRWQQGNVFS   420
CSVLHEALHS HYTQKSLSLS PG                                           442

SEQ ID NO: 175          moltype = AA  length = 442
FEATURE                 Location/Qualifiers
REGION                  1..442
                        note = Emibetuzumab heavy chain with Triple Hinge and YTE
source                  1..442
                        mol_type = protein
                        organism = synthetic construct
SEQUENCE: 175
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLYIT REPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                           442

SEQ ID NO: 176          moltype = AA  length = 442
FEATURE                 Location/Qualifiers
REGION                  1..442
                        note = Emibetuzumab heavy chain with Triple Hinge and A118C
source                  1..442
                        mol_type = protein
                        organism = synthetic construct
SEQUENCE: 176
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                           442

SEQ ID NO: 177          moltype = AA  length = 442
FEATURE                 Location/Qualifiers
REGION                  1..442
                        note = Emibetuzumab heavy chain with Triple Hinge and LS
                         and A118C
source                  1..442
                        mol_type = protein
                        organism = synthetic construct
SEQUENCE: 177
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS RDELTKNQVS   360
LTCLVKGFYP SDIAVEWESN GQPENNYKTT PPVLDSDGSF FLYSKLTVDK SRWQQGNVFS   420
CSVLHEALHS HYTQKSLSLS PG                                           442

SEQ ID NO: 178          moltype = AA  length = 442
```

```
FEATURE                 Location/Qualifiers
REGION                  1..442
                        note = Emibetuzumab heavy chain with Triple Hinge and YTE
                         and A118C
source                  1..442
                        mol_type = protein
                        organism = synthetic construct
SEQUENCE: 178
QVQLVQSGAE VKKPGASVKV SCKASGYTFT DYYMHWVRQA PGQGLEWMGR VNPNRRGTTY    60
NQKFEGRVTM TTDTSTSTAY MELRSLRSDD TAVYYCARAN WLDYWGQGTT VTVSSCSTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDC HCPPCPAPEL LGGPSVFLFP   240
PKPKDTLYIT REPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPS REEMTKNQVS   360
LTCLVKGFYP SDIAVEWESN GQPENNYKTT PPVLDSDGSF FLYSKLTVDK SRWQQGNVFS   420
CSVMHEALHN HYTQKSLSLS PG                                           442

SEQ ID NO: 179         moltype = AA  length = 215
FEATURE                Location/Qualifiers
REGION                 1..215
                       note = Emibetuzumab light chain
source                 1..215
                       mol_type = protein
                       organism = synthetic construct
SEQUENCE: 179
DIQMTQSPSS LSASVGDRVT ITCSVSSSVS SIYLHWYQQK PGKAPKLLIY STSNLASGVP    60
SRFSGSGSGT DFTLTISSLQ PEDFATYYCQ VYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 180         moltype = AA  length = 215
FEATURE                Location/Qualifiers
REGION                 1..215
                       note = Emibetuzumab light chain V205C
source                 1..215
                       mol_type = protein
                       organism = synthetic construct
SEQUENCE: 180
DIQMTQSPSS LSASVGDRVT ITCSVSSSVS SIYLHWYQQK PGKAPKLLIY STSNLASGVP    60
SRFSGSGSGT DFTLTISSLQ PEDFATYYCQ VYSGYPLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPCTKSF NRGEC                              215

SEQ ID NO: 181         moltype = AA  length = 446
FEATURE                Location/Qualifiers
REGION                 1..446
                       note = P3D12 anti-cMET heavy chain with Triple Hinge
source                 1..446
                       mol_type = protein
                       organism = synthetic construct
SEQUENCE: 181
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 182         moltype = AA  length = 446
FEATURE                Location/Qualifiers
REGION                 1..446
                       note = P3D12 anti-cMET heavy chain with Triple Hinge and LS
source                 1..446
                       mol_type = protein
                       organism = synthetic construct
SEQUENCE: 182
QVQLVQSGAE VKKPGASVKV SCKASGYTFT SYWMHWVKQA PGQGLDWIGY IKPSTDNTEY    60
NQKFKDKATL TADKSTSTAY MELSSLRSED TAVYYCARSY GNYPLMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDCHCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVLHE ALHSHYTQKS LSLSPG                                       446

SEQ ID NO: 183         moltype = AA  length = 446
FEATURE                Location/Qualifiers
```

```
REGION                      1..446
                            note = P3D12 anti-cMET heavy chain with Triple Hinge and YTE
source                      1..446
                            mol_type = protein
                            organism = synthetic construct
SEQUENCE: 183
QVQLVQSGAE VKKPGASVKV SCKASGYTFT SYWMHWVKQA PGQGLDWIGY IKPSTDNTEY   60
NQKFKDKATL TADKSTSTAY MELSSLRSED TAVYYCARSY GNYPLMDYWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDCHCPPCP APELLGGPSV  240
FLFPPKPKDT LYITREPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                      446

SEQ ID NO: 184              moltype = AA  length = 446
FEATURE                     Location/Qualifiers
REGION                      1..446
                            note = P3D12 anti-cMET heavy chain with Triple Hinge and
                            A118C
source                      1..446
                            mol_type = protein
                            organism = synthetic construct
SEQUENCE: 184
QVQLVQSGAE VKKPGASVKV SCKASGYTFT SYWMHWVKQA PGQGLDWIGY IKPSTDNTEY   60
NQKFKDKATL TADKSTSTAY MELSSLRSED TAVYYCARSY GNYPLMDYWG QGTTVTVSSC  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDCHCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                      446

SEQ ID NO: 185              moltype = AA  length = 446
FEATURE                     Location/Qualifiers
REGION                      1..446
                            note = P3D12 anti-cMET heavy chain with Triple Hinge and LS
                            and A118C
source                      1..446
                            mol_type = protein
                            organism = synthetic construct
SEQUENCE: 185
QVQLVQSGAE VKKPGASVKV SCKASGYTFT SYWMHWVKQA PGQGLDWIGY IKPSTDNTEY   60
NQKFKDKATL TADKSTSTAY MELSSLRSED TAVYYCARSY GNYPLMDYWG QGTTVTVSSC  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDCHCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVLHE ALHSHYTQKS LSLSPG                                      446

SEQ ID NO: 186              moltype = AA  length = 446
FEATURE                     Location/Qualifiers
REGION                      1..446
                            note = P3D12 anti-cMET heavy chain with Triple Hinge and
                            YTE and A118C
source                      1..446
                            mol_type = protein
                            organism = synthetic construct
SEQUENCE: 186
QVQLVQSGAE VKKPGASVKV SCKASGYTFT SYWMHWVKQA PGQGLDWIGY IKPSTDNTEY   60
NQKFKDKATL TADKSTSTAY MELSSLRSED TAVYYCARSY GNYPLMDYWG QGTTVTVSSC  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDCHCPPCP APELLGGPSV  240
FLFPPKPKDT LYITREPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                      446

SEQ ID NO: 187              moltype = AA  length = 215
FEATURE                     Location/Qualifiers
REGION                      1..215
                            note = P3D12 anti-cMET light chain
source                      1..215
                            mol_type = protein
                            organism = synthetic construct
SEQUENCE: 187
QIVLTQSPAI LSLSPGERAT LSCSASSSVT SNYLYWYQQK PGSSPKLLIY STSNLASGVP   60
ARFSGSGSGT SYTLTISSLE AEDAASYFCH QWSSYPPTFG SGTKLEIKRT VAAPSVFIFP  120
```

```
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 188           moltype = AA  length = 215
FEATURE                  Location/Qualifiers
REGION                   1..215
                         note = P3D12 anti-cMET light chain V205C
source                   1..215
                         mol_type = protein
                         organism = synthetic construct
SEQUENCE: 188
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSSYPPTFG SGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPCTKSF NRGEC                              215

SEQ ID NO: 189           moltype = AA  length = 329
FEATURE                  Location/Qualifiers
source                   1..329
                         mol_type = protein
                         organism = Homo sapiens
SEQUENCE: 189
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 190           moltype = AA  length = 111
FEATURE                  Location/Qualifiers
REGION                   1..111
                         note = Light Chain of Telisotuzumab IgG histidine scanning
                          variant #1
source                   1..111
                         mol_type = protein
                         organism = synthetic construct
SEQUENCE: 190
DIVMTQSPDS LAVSLGERAT INCKSSESVD SYAHSFLHWY QQKPGQPPKL LIYRASTREH    60
GVPDRFSGSG SGTDFTLTIS SLQAEDVAVY YCQQSKEDPL TFGGGTKVEI K             111

SEQ ID NO: 191           moltype = AA  length = 111
FEATURE                  Location/Qualifiers
REGION                   1..111
                         note = Light Chain of Telisotuzumab IgG histidine scanning
                          variant #2
source                   1..111
                         mol_type = protein
                         organism = synthetic construct
SEQUENCE: 191
DIVMTQSPDS LAVSLGERAT INCKSSESVD SYAHSFLHWY QQKPGQPPKL LIYRASTRES    60
GVPDRFSGSG SGTDFTLTIS SLQAEDVAVY YCQQSKEDPL TFGGGTKVEI K             111

SEQ ID NO: 192           moltype = AA  length = 111
FEATURE                  Location/Qualifiers
REGION                   1..111
                         note = Light Chain of Telisotuzumab IgG histidine scanning
                          variant #3
source                   1..111
                         mol_type = protein
                         organism = synthetic construct
SEQUENCE: 192
DIVMTQSPDS LAVSLGERAT INCKSSESVD SYANSFLHWY QQKPGQPPKL LIYHASTRES    60
GVPDRFSGSG SGTDFTLTIS SLQAEDVAVY YCQQSKEDPL TFGGGTKVEI K             111

SEQ ID NO: 193           moltype = AA  length = 118
FEATURE                  Location/Qualifiers
REGION                   1..118
                         note = Heavy Chain of Telisotuzumab IgG histidine scanning
                          variant #1
source                   1..118
                         mol_type = protein
                         organism = synthetic construct
SEQUENCE: 193
QVQLVQSGAE VKKPGASVKV SCKASGHIFT AYTMHWVRQA PGQGLEWMGW IKPNNGLANY    60
AQKFQGRVTM TRDTSISTAY MELSRLRSDD TAVYYCARSE ITTEFDYWGQ GTLVTVSS      118

SEQ ID NO: 194           moltype = AA  length = 118
FEATURE                  Location/Qualifiers
```

```
REGION                    1..118
                          note = Heavy Chain of Telisotuzumab IgG histidine scanning
                           variant #2
source                    1..118
                          mol_type = protein
                          organism = synthetic construct
SEQUENCE: 194
QVQLVQSGAE VKKPGASVKV SCKASGYIFT AYTMHWVRQA PGQGLEWMGW IKPNNGLANY     60
AQKFQGRVTM TRDTSISTAY MELSRLRSDD TAVYYCARHE ITTEFDYWGQ GTLVTVSS     118

SEQ ID NO: 195            moltype = AA   length = 118
FEATURE                   Location/Qualifiers
REGION                    1..118
                          note = Heavy Chain of Telisotuzumab IgG histidine scanning
                           variant #3
source                    1..118
                          mol_type = protein
                          organism = synthetic construct
SEQUENCE: 195
QVQLVQSGAE VKKPGASVKV SCKASGYIFT AYTMHWVRQA PGQGLEWMGW IKPNNGLANY     60
AQKFQGRVTM TRDTSISTAY MELSRLRSDD TAVYYCARSE ITHEFDYWGQ GTLVTVSS     118

SEQ ID NO: 196            moltype = AA   length = 118
FEATURE                   Location/Qualifiers
REGION                    1..118
                          note = Heavy Chain of Telisotuzumab IgG histidine scanning
                           variant #4
source                    1..118
                          mol_type = protein
                          organism = synthetic construct
SEQUENCE: 196
QVQLVQSGAE VKKPGASVKV SCKASGYIFT AYTMHWVRQA PGQGLEWMGW IKPNNGLANY     60
AQKFQGRVTM TRDTSISTAY MELSRLRSDD TAVYYCARSE ITTEFDHWGQ GTLVTVSS     118

SEQ ID NO: 197            moltype = AA   length = 118
FEATURE                   Location/Qualifiers
REGION                    1..118
                          note = Heavy Chain Combinations of Telisotuzumab IgG
                           histidine scanning variant #5
source                    1..118
                          mol_type = protein
                          organism = synthetic construct
SEQUENCE: 197
QVQLVQSGAE VKKPGASVKV SCKASGHIFT AYTMHWVRQA PGQGLEWMGW IKPNNGLANY     60
AQKFQGRVTM TRDTSISTAY MELSRLRSDD TAVYYCARHE ITTEFDYWGQ GTLVTVSS     118

SEQ ID NO: 198            moltype = AA   length = 118
FEATURE                   Location/Qualifiers
REGION                    1..118
                          note = Heavy Chain Combinations of Telisotuzumab IgG
                           histidine scanning variant #6
source                    1..118
                          mol_type = protein
                          organism = synthetic construct
SEQUENCE: 198
QVQLVQSGAE VKKPGASVKV SCKASGHIFT AYTMHWVRQA PGQGLEWMGW IKPNNGLANY     60
AQKFQGRVTM TRDTSISTAY MELSRLRSDD TAVYYCARSE ITHEFDYWGQ GTLVTVSS     118

SEQ ID NO: 199            moltype = AA   length = 118
FEATURE                   Location/Qualifiers
REGION                    1..118
                          note = Heavy Chain Combinations of Telisotuzumab IgG
                           histidine scanning variant #7
source                    1..118
                          mol_type = protein
                          organism = synthetic construct
SEQUENCE: 199
QVQLVQSGAE VKKPGASVKV SCKASGHIFT AYTMHWVRQA PGQGLEWMGW IKPNNGLANY     60
AQKFQGRVTM TRDTSISTAY MELSRLRSDD TAVYYCARSE ITTEFDHWGQ GTLVTVSS     118

SEQ ID NO: 200            moltype = AA   length = 118
FEATURE                   Location/Qualifiers
REGION                    1..118
                          note = Heavy Chain Combinations of Telisotuzumab IgG
                           histidine scanning variant #8
source                    1..118
                          mol_type = protein
                          organism = synthetic construct
SEQUENCE: 200
```

```
QVQLVQSGAE VKKPGASVKV SCKASGYIFT AYTMHWVRQA PGQGLEWMGW IKPNNGLANY   60
AQKFQGRVTM TRDTSISTAY MELSRLRSDD TAVYYCARHE ITHEFDYWGQ GTLVTVSS    118

SEQ ID NO: 201          moltype = AA  length = 118
FEATURE                 Location/Qualifiers
REGION                  1..118
                        note = Heavy Chain Combinations of Telisotuzumab IgG
                         histidine scanning variant #9
source                  1..118
                        mol_type = protein
                        organism = synthetic construct
SEQUENCE: 201
QVQLVQSGAE VKKPGASVKV SCKASGYIFT AYTMHWVRQA PGQGLEWMGW IKPNNGLANY   60
AQKFQGRVTM TRDTSISTAY MELSRLRSDD TAVYYCARSE ITHEFDHWGQ GTLVTVSS    118

SEQ ID NO: 202          moltype = AA  length = 118
FEATURE                 Location/Qualifiers
REGION                  1..118
                        note = Heavy Chain Combinations of Telisotuzumab IgG
                         histidine scanning variant #10
source                  1..118
                        mol_type = protein
                        organism = synthetic construct
SEQUENCE: 202
QVQLVQSGAE VKKPGASVKV SCKASGHIFT AYTMHWVRQA PGQGLEWMGW IKPNNGLANY   60
AQKFQGRVTM TRDTSISTAY MELSRLRSDD TAVYYCARHE ITHEFDYWGQ GTLVTVSS    118

SEQ ID NO: 203          moltype = AA  length = 118
FEATURE                 Location/Qualifiers
REGION                  1..118
                        note = Heavy Chain Combinations of Telisotuzumab IgG
                         histidine scanning variant #11
source                  1..118
                        mol_type = protein
                        organism = synthetic construct
SEQUENCE: 203
QVQLVQSGAE VKKPGASVKV SCKASGHIFT AYTMHWVRQA PGQGLEWMGW IKPNNGLANY   60
AQKFQGRVTM TRDTSISTAY MELSRLRSDD TAVYYCARHE ITTEFDHWGQ GTLVTVSS    118

SEQ ID NO: 204          moltype = AA  length = 118
FEATURE                 Location/Qualifiers
REGION                  1..118
                        note = Heavy Chain Combinations of Telisotuzumab IgG
                         histidine scanning variant #12
source                  1..118
                        mol_type = protein
                        organism = synthetic construct
SEQUENCE: 204
QVQLVQSGAE VKKPGASVKV SCKASGYIFT AYTMHWVRQA PGQGLEWMGW IKPNNGLANY   60
AQKFQGRVTM TRDTSISTAY MELSRLRSDD TAVYYCARHE ITHEFDHWGQ GTLVTVSS    118

SEQ ID NO: 205          moltype = AA  length = 111
FEATURE                 Location/Qualifiers
REGION                  1..111
                        note = Light Chain Combinations of Telisotuzumab IgG
                         histidine scanning variant #1
source                  1..111
                        mol_type = protein
                        organism = synthetic construct
SEQUENCE: 205
DIVMTQSPDS LAVSLGERAT INCKSSESVD SYAHSHLHWY QQKPGQPPKL LIYRASTRES   60
GVPDRFSGSG SGTDFTLTIS SLQAEDVAVY YCQQSKEDPL TFGGGTKVEI K           111

SEQ ID NO: 206          moltype = AA  length = 111
FEATURE                 Location/Qualifiers
REGION                  1..111
                        note = Light Chain Combinations of Telisotuzumab IgG
                         histidine scanning variant #2
source                  1..111
                        mol_type = protein
                        organism = synthetic construct
SEQUENCE: 206
DIVMTQSPDS LAVSLGERAT INCKSSESVD SYAHSFLHWY QQKPGQPPKL LIYHASTRES   60
GVPDRFSGSG SGTDFTLTIS SLQAEDVAVY YCQQSKEDPL TFGGGTKVEI K           111

SEQ ID NO: 207          moltype = AA  length = 111
FEATURE                 Location/Qualifiers
REGION                  1..111
                        note = Light Chain Combinations of Telisotuzumab IgG
```

```
                        histidine scanning variant #3
source                  1..111
                        mol_type = protein
                        organism = synthetic construct
SEQUENCE: 207
DIVMTQSPDS LAVSLGERAT INCKSSESVD SYAHSFLHWY QQKPGQPPKL LIYRASTREH   60
GVPDRFSGSG SGTDFTLTIS SLQAEDVAVY YCQQSKEDPL TFGGGTKVEI K           111

SEQ ID NO: 208          moltype = AA   length = 111
FEATURE                 Location/Qualifiers
REGION                  1..111
                        note = Light Chain Combinations of Telisotuzumab IgG
                        histidine scanning variant #4
source                  1..111
                        mol_type = protein
                        organism = synthetic construct
SEQUENCE: 208
DIVMTQSPDS LAVSLGERAT INCKSSESVD SYANSHLHWY QQKPGQPPKL LIYHASTRES   60
GVPDRFSGSG SGTDFTLTIS SLQAEDVAVY YCQQSKEDPL TFGGGTKVEI K           111

SEQ ID NO: 209          moltype = AA   length = 111
FEATURE                 Location/Qualifiers
REGION                  1..111
                        note = Light Chain Combinations of Telisotuzumab IgG
                        histidine scanning variant #5
source                  1..111
                        mol_type = protein
                        organism = synthetic construct
SEQUENCE: 209
DIVMTQSPDS LAVSLGERAT INCKSSESVD SYANSHLHWY QQKPGQPPKL LIYRASTREH   60
GVPDRFSGSG SGTDFTLTIS SLQAEDVAVY YCQQSKEDPL TFGGGTKVEI K           111

SEQ ID NO: 210          moltype = AA   length = 111
FEATURE                 Location/Qualifiers
REGION                  1..111
                        note = Light Chain Combinations of Telisotuzumab IgG
                        histidine scanning variant #6
source                  1..111
                        mol_type = protein
                        organism = synthetic construct
SEQUENCE: 210
DIVMTQSPDS LAVSLGERAT INCKSSESVD SYANSFLHWY QQKPGQPPKL LIYHASTREH   60
GVPDRFSGSG SGTDFTLTIS SLQAEDVAVY YCQQSKEDPL TFGGGTKVEI K           111

SEQ ID NO: 211          moltype = AA   length = 111
FEATURE                 Location/Qualifiers
REGION                  1..111
                        note = Light Chain Combinations of Telisotuzumab IgG
                        histidine scanning variant #7
source                  1..111
                        mol_type = protein
                        organism = synthetic construct
SEQUENCE: 211
DIVMTQSPDS LAVSLGERAT INCKSSESVD SYAHSHLHWY QQKPGQPPKL LIYHASTRES   60
GVPDRFSGSG SGTDFTLTIS SLQAEDVAVY YCQQSKEDPL TFGGGTKVEI K           111

SEQ ID NO: 212          moltype = AA   length = 111
FEATURE                 Location/Qualifiers
REGION                  1..111
                        note = Light Chain Combinations of Telisotuzumab IgG
                        histidine scanning variant #8
source                  1..111
                        mol_type = protein
                        organism = synthetic construct
SEQUENCE: 212
DIVMTQSPDS LAVSLGERAT INCKSSESVD SYAHSHLHWY QQKPGQPPKL LIYRASTREH   60
GVPDRFSGSG SGTDFTLTIS SLQAEDVAVY YCQQSKEDPL TFGGGTKVEI K           111

SEQ ID NO: 213          moltype = AA   length = 111
FEATURE                 Location/Qualifiers
REGION                  1..111
                        note = Light Chain Combinations of Telisotuzumab IgG
                        histidine scanning variant #9
source                  1..111
                        mol_type = protein
                        organism = synthetic construct
SEQUENCE: 213
DIVMTQSPDS LAVSLGERAT INCKSSESVD SYAHSFLHWY QQKPGQPPKL LIYHASTREH   60
GVPDRFSGSG SGTDFTLTIS SLQAEDVAVY YCQQSKEDPL TFGGGTKVEI K           111
```

```
SEQ ID NO: 214            moltype = AA  length = 111
FEATURE                   Location/Qualifiers
REGION                    1..111
                          note = Light Chain Combinations of Telisotuzumab IgG
                           histidine scanning variant #10
source                    1..111
                          mol_type = protein
                          organism = synthetic construct
SEQUENCE: 214
DIVMTQSPDS LAVSLGERAT INCKSSESVD SYANSHLHWY QQKPGQPPKL LIYHASTREH   60
GVPDRFSGSG SGTDFTLTIS SLQAEDVAVY YCQQSKEDPL TFGGGTKVEI K           111

SEQ ID NO: 215            moltype = AA  length = 108
FEATURE                   Location/Qualifiers
REGION                    1..108
                          note = Light Chain of Emibetuzumab IgG histidine scanning
                           variant #1
source                    1..108
                          mol_type = protein
                          organism = synthetic construct
SEQUENCE: 215
DIQMTQSPSS LSASVGDRVT ITCSVSSSVS SIHLHWYQQK PGKAPKLLIY STSNLASGVP   60
SRFSGSGSGT DFTLTISSLQ PEDFATYYCQ VYSGYPLTFG GGTKVEIK               108

SEQ ID NO: 216            moltype = AA  length = 115
FEATURE                   Location/Qualifiers
REGION                    1..115
                          note = Heavy Chain of Emibetuzumab IgG histidine scanning
                           variant #1
source                    1..115
                          mol_type = protein
                          organism = synthetic construct
SEQUENCE: 216
QVQLVQSGAE VKKPGASVKV SCKASGYTFT DYYMHWVRQA PGQGLEWMGR VHPNRRGTTY   60
NQKFEGRVTM TTDTSTSTAY MELRSLRSDD TAVYYCARAN WLDYWGQGTT VTVSS       115

SEQ ID NO: 217            moltype = AA  length = 115
FEATURE                   Location/Qualifiers
REGION                    1..115
                          note = Heavy Chain Combinations of Emibetuzumab IgG
                           histidine scanning variant #2
source                    1..115
                          mol_type = protein
                          organism = synthetic construct
SEQUENCE: 217
QVQLVQSGAE VKKPGASVKV SCKASGYTFT DYYMHWVRQA PGQGLEWMGR VHPHRRGTTY   60
NQKFEGRVTM TTDTSTSTAY MELRSLRSDD TAVYYCARAN WLDYWGQGTT VTVSS       115

SEQ ID NO: 218            moltype = AA  length = 115
FEATURE                   Location/Qualifiers
REGION                    1..115
                          note = Heavy Chain Combinations of Emibetuzumab IgG
                           histidine scanning variant #3
source                    1..115
                          mol_type = protein
                          organism = synthetic construct
SEQUENCE: 218
QVQLVQSGAE VKKPGASVKV SCKASGYTFT DYYMHWVRQA PGQGLEWMGR VHPNRRHTTY   60
NQKFEGRVTM TTDTSTSTAY MELRSLRSDD TAVYYCARAN WLDYWGQGTT VTVSS       115

SEQ ID NO: 219            moltype = AA  length = 115
FEATURE                   Location/Qualifiers
REGION                    1..115
                          note = Heavy Chain Combinations of Emibetuzumab IgG
                           histidine scanning variant #4
source                    1..115
                          mol_type = protein
                          organism = synthetic construct
SEQUENCE: 219
QVQLVQSGAE VKKPGASVKV SCKASGYTFT DYYMHWVRQA PGQGLEWMGR VNPHRRHTTY   60
NQKFEGRVTM TTDTSTSTAY MELRSLRSDD TAVYYCARAN WLDYWGQGTT VTVSS       115

SEQ ID NO: 220            moltype = AA  length = 115
FEATURE                   Location/Qualifiers
REGION                    1..115
                          note = Heavy Chain Combinations of Emibetuzumab IgG
                           histidine scanning variant #5
source                    1..115
```

```
                              mol_type = protein
                              organism = synthetic construct
SEQUENCE: 220
QVQLVQSGAE VKKPGASVKV SCKASGYTFT DYYMHWVRQA PGQGLEWMGR VNPHRRGTTY        60
NQKFEGRVTM TTDTSTSTAY MELRSLRSDD TAVYYCARAH WLDYWGQGTT VTVSS             115

SEQ ID NO: 221            moltype = AA  length = 115
FEATURE                   Location/Qualifiers
REGION                    1..115
                          note = Heavy Chain Combinations of Emibetuzumab IgG
                           histidine scanning variant #6
source                    1..115
                          mol_type = protein
                          organism = synthetic construct
SEQUENCE: 221
QVQLVQSGAE VKKPGASVKV SCKASGYTFT DYYMHWVRQA PGQGLEWMGR VHPHRRHTTY        60
NQKFEGRVTM TTDTSTSTAY MELRSLRSDD TAVYYCARAN WLDYWGQGTT VTVSS             115

SEQ ID NO: 222            moltype = AA  length = 115
FEATURE                   Location/Qualifiers
REGION                    1..115
                          note = Heavy Chain Combinations of Emibetuzumab IgG
                           histidine scanning variant #7
source                    1..115
                          mol_type = protein
                          organism = synthetic construct
SEQUENCE: 222
QVQLVQSGAE VKKPGASVKV SCKASGYTFT DYYMHWVRQA PGQGLEWMGR VHPHRRGTTY        60
NQKFEGRVTM TTDTSTSTAY MELRSLRSDD TAVYYCARAH WLDYWGQGTT VTVSS             115

SEQ ID NO: 223            moltype = AA  length = 108
FEATURE                   Location/Qualifiers
REGION                    1..108
                          note = Light Chain of Emibetuzumab IgG histidine scanning
                           variant #1
source                    1..108
                          mol_type = protein
                          organism = synthetic construct
SEQUENCE: 223
DIQMTQSPSS LSASVGDRVT ITCSVSSSVS SIYLHWYQQK PGKAPKLLIY STSNLASGVP        60
SRFSGSGSGT DFTLTISSLQ PEDFATYYCQ VHSGYPLTFG GGTKVEIK                     108

SEQ ID NO: 224            moltype = AA  length = 108
FEATURE                   Location/Qualifiers
REGION                    1..108
                          note = Light Chain of Emibetuzumab IgG histidine scanning
                           variant #2
source                    1..108
                          mol_type = protein
                          organism = synthetic construct
SEQUENCE: 224
DIQMTQSPSS LSASVGDRVT ITCSVSSSVS SIYLHWYQQK PGKAPKLLIY STSNLASGVP        60
SRFSGSGSGT DFTLTISSLQ PEDFATYYCQ VYSGHPLTFG GGTKVEIK                     108

SEQ ID NO: 225            moltype = AA  length = 118
FEATURE                   Location/Qualifiers
REGION                    1..118
                          note = Heavy Chain of hucMET27Gv1.3 IgG
source                    1..118
                          mol_type = protein
                          organism = synthetic construct
SEQUENCE: 225
EVQLVESGGG LVQPGGSLRL SCAASGFTFS SYDMSWVRQA PGKGLEWVAT INSNGVSIYY        60
PDSVKGRFTI SRDNAKNSLY LQMNSLRAED TAVYYCAREE ITTEMDYWGQ GTLVTVSS          118

SEQ ID NO: 226            moltype = AA  length = 111
FEATURE                   Location/Qualifiers
REGION                    1..111
                          note = Light Chain Combinations of hucMET27Gv1.3 IgG
                           histidine scanning variant #1
source                    1..111
                          mol_type = protein
                          organism = synthetic construct
SEQUENCE: 226
EIVLTQSPAT LSLSPGERAT LSCRASESVD SYGNSHIHWY QQKPGQAPRL LIYRASNLES        60
GIPARFSGSG SGTDFTLTIS SLEPEDFAVY YCQQSNEEHL TFGQGTKVEL K                 111

SEQ ID NO: 227            moltype = AA  length = 119
FEATURE                   Location/Qualifiers
```

| | | |
|---|---|---|
| REGION | 1..119 | |
| | note = Heavy Chain of P3D12 IgG histidine scanning variant #1 | |
| source | 1..119 | |
| | mol_type = protein | |
| | organism = synthetic construct | |

SEQUENCE: 227
QVQLVQSGAE VKKPGASVKV SCKASGYTFT SYWMAWVKQA PGQGLDWIGY IKPSTDNTEY 60
NQKFKDKATL TADKSTSTAY MELSSLRSED TAVYYCARSY GNYPLMDYWG QGTTVTVSS 119

| | | |
|---|---|---|
| SEQ ID NO: 228 | moltype = AA length = 119 | |
| FEATURE | Location/Qualifiers | |
| REGION | 1..119 | |
| | note = Heavy Chain of P3D12 IgG histidine scanning variant #2 | |
| source | 1..119 | |
| | mol_type = protein | |
| | organism = synthetic construct | |

SEQUENCE: 228
QVQLVQSGAE VKKPGASVKV SCKASGYTFT SYWMHWVKQA PGQGLDWIGY IKPSTDNTEY 60
NQKFKDKATL TADKSTSTAY MELSSLRSED TAVYYCARSH GNYPLMDYWG QGTTVTVSS 119

| | | |
|---|---|---|
| SEQ ID NO: 229 | moltype = AA length = 119 | |
| FEATURE | Location/Qualifiers | |
| REGION | 1..119 | |
| | note = Heavy Chain Combinations of P3D12 IgG histidine scanning variant #1 | |
| source | 1..119 | |
| | mol_type = protein | |
| | organism = synthetic construct | |

SEQUENCE: 229
QVQLVQSGAE VKKPGASVKV SCKASGYTHT SYWMHWVKQA PGQGLDWIGY IKPSTDNTHY 60
NQKFKDKATL TADKSTSTAY MELSSLRSED TAVYYCARSY GHYPLMDYWG QGTTVTVSS 119

| | | |
|---|---|---|
| SEQ ID NO: 230 | moltype = AA length = 119 | |
| FEATURE | Location/Qualifiers | |
| REGION | 1..119 | |
| | note = Heavy Chain Combinations of P3D12 IgG histidine scanning variant #2 | |
| source | 1..119 | |
| | mol_type = protein | |
| | organism = synthetic construct | |

SEQUENCE: 230
QVQLVQSGAE VKKPGASVKV SCKASGYTHT SYWMHWVKQA PGQGLDWIGY IKPSTDNTHY 60
NQKFKDKATL TADKSTSTAY MELSSLRSED TAVYYCARSY GNYPLMHYWG QGTTVTVSS 119

| | | |
|---|---|---|
| SEQ ID NO: 231 | moltype = AA length = 119 | |
| FEATURE | Location/Qualifiers | |
| REGION | 1..119 | |
| | note = Heavy Chain Combinations of P3D12 IgG histidine scanning variant #3 | |
| source | 1..119 | |
| | mol_type = protein | |
| | organism = synthetic construct | |

SEQUENCE: 231
QVQLVQSGAE VKKPGASVKV SCKASGYTFT SYWMHWVKQA PGQGLDWIGH IKPSTDNTEY 60
NQKFKDKATL TADKSTSTAY MELSSLRSED TAVYYCARSY GHYPLMHYWG QGTTVTVSS 119

| | | |
|---|---|---|
| SEQ ID NO: 232 | moltype = AA length = 108 | |
| FEATURE | Location/Qualifiers | |
| REGION | 1..108 | |
| | note = Light Chain of P3D12 IgG histidine scanning variant #1 | |
| source | 1..108 | |
| | mol_type = protein | |
| | organism = synthetic construct | |

SEQUENCE: 232
QIVLTQSPAI LSLSPGERAT LSCSASSSVT SNYLYWYQQK PGSSPKLLIY STSNLASGVP 60
ARFSGSGSGT SYTLTISSLE AEDAASYFCH QWSSYPHTFG SGTKLEIK 108

| | | |
|---|---|---|
| SEQ ID NO: 233 | moltype = AA length = 108 | |
| FEATURE | Location/Qualifiers | |
| REGION | 1..108 | |
| | note = Light Chain Combinations of P3D12 IgG histidine scanning variant #1 | |
| source | 1..108 | |
| | mol_type = protein | |
| | organism = synthetic construct | |

SEQUENCE: 233

```
QIVLTQSPAI LSLSPGERAT LSCSASSSVT SNYLYWYQQK PGSSPKLLIY STSNLASGVP    60
ARFSGSGSGT SYTLTISSLE AEDAASYFCH QWSHHHPTFG SGTKLEIK               108

SEQ ID NO: 234         moltype = AA  length = 118
FEATURE                Location/Qualifiers
REGION                 1..118
                       note = Heavy Chain Combinations of Telisotuzumab IgG
                        histidine scanning variant #13
source                 1..118
                       mol_type = protein
                       organism = synthetic construct
SEQUENCE: 234
QVQLVQSGAE VKKPGASVKV SCKASGYIFT AYTMHWVRQA PGQGLEWMGW IKPNNGLANY    60
AQKFQGRVTM TRDTSISTAY MELSRLRSDD TAVYYCAHSE ITHEFDHWGQ GTLVTVSS    118

SEQ ID NO: 235         moltype = AA  length = 111
FEATURE                Location/Qualifiers
REGION                 1..111
                       note = Light Chain of hucMET27Gv1.3 IgG
source                 1..111
                       mol_type = protein
                       organism = synthetic construct
SEQUENCE: 235
EIVLTQSPAT LSLSPGERAT LSCRASESVD SYGNSFIHWY QQKPGQAPRL LIYRASNLES    60
GIPARFSGSG SGTDFTLTIS SLEPEDFAVY YCQQSNEEPL TFGQGTKVEL K           111
```

What is claimed is:

1. An antibody-drug conjugate, wherein the antibody-drug conjugate comprises:
   (a) a heavy chain variable domain and a light chain variable domain selected from the group of:
      (i) SEQ ID NO: 5 and SEQ ID NO: 6, respectively;
      (ii) SEQ ID NO: 11 and SEQ ID NO: 12, respectively;
      (iii) SEQ ID NO: 13 and SEQ ID NO: 14, respectively;
      (iv) SEQ ID NO: 15 and SEQ ID NO: 16, respectively;
      (v) SEQ ID NO: 17 and SEQ ID NO: 18, respectively; and
      (vi) SEQ ID NO: 21 and SEQ ID NO: 22, respectively;
   (b) a light chain constant region sequence of SEQ ID NO: 157 comprising a valine to cysteine substitution at amino acid position 98, wherein the drug is monomethyl auristatin E (MMAE) and the MMAE is conjugated to the cysteine at amino acid position 98 via a valine-citrulline (vc) linker; and
   (c) a heavy chain CH1-CH2-CH3 sequence of SEQ ID NO: 155 or SEQ ID NO: 189 optionally comprising one or more of (A) through (C):
      (A) a lysine to cysteine substitution at amino acid position 105 and deletion of a threonine at amino acid positions 106 and 108;
      (B) a methionine to tyrosine substitution at amino acid position 135, a serine to threonine substitution at amino acid position 137, and a threonine to glutamic acid substitution at amino acid position 139; and
      (C) a methionine to leucine substitution at amino acid position 311 and an asparagine to serine substitution at amino acid position 317.

2. The antibody-drug conjugate of claim 1, comprising a heavy chain CH1-CH2-CH3 sequence of SEQ ID NO: 155 or SEQ ID NO: 189 further comprising a lysine to cysteine substitution at amino acid position 105 and deletion of a threonine at amino acid positions 106 and 108.

3. The antibody-drug conjugate of claim 2, comprising heavy chain and light chain sequences selected from the group of:
   (i) SEQ ID NO: 35 and SEQ ID NO: 42, respectively;
   (ii) SEQ ID NO: 59 and SEQ ID NO: 66, respectively;
   (iii) SEQ ID NO: 67 and SEQ ID NO: 74, respectively;
   (iv) SEQ ID NO: 75 and SEQ ID NO: 82, respectively;
   (v) SEQ ID NO: 83 and SEQ ID NO: 90, respectively; and
   (vi) SEQ ID NO: 99 and SEQ ID NO: 106, respectively.

4. The antibody-drug conjugate of claim 3, wherein the heavy and light chain sequences comprise SEQ ID NO: 75 and SEQ ID NO: 82, respectively.

5. The antibody-drug conjugate of claim 1, comprising a heavy chain CH1-CH2-CH3 sequence of SEQ ID NO: 155 or SEQ ID NO: 189 comprising a lysine to cysteine substitution at amino acid position 105 and deletion of a threonine at amino acid positions 106 and 108; and a methionine to leucine substitution at amino acid position 311 and an asparagine to serine substitution at amino acid position 317.

6. The antibody-drug conjugate of claim 5, wherein the antibody comprises heavy chain and light chain sequences selected from the group of:
   (i) SEQ ID NO: 36 and SEQ ID NO: 42, respectively;
   (ii) SEQ ID NO: 60 and SEQ ID NO: 66, respectively;
   (iii) SEQ ID NO: 68 and SEQ ID NO: 74, respectively;
   (iv) SEQ ID NO: 76 and SEQ ID NO: 82, respectively;
   (v) SEQ ID NO: 84 and SEQ ID NO: 90, respectively; and
   (vi) SEQ ID NO: 100 and SEQ ID NO: 106, respectively.

7. The antibody-drug conjugate of claim 1, wherein the heavy chain CH1-CH2-CH3 sequence of SEQ ID NO: 155 or SEQ ID NO: 189 comprises:
   a lysine to cysteine substitution at amino acid position 105 and deletion of a threonine at amino acid positions 106 and 108; and
   a methionine to tyrosine substitution at amino acid position 135, a serine to threonine substitution at amino acid position 137, and a threonine to glutamic acid substitution at amino acid position 139.

8. The antibody-drug conjugate of claim 7, wherein the antibody comprises heavy chain and light chain sequences selected from the group of:
   (i) SEQ ID NO: 37 and SEQ ID NO: 42, respectively;
   (ii) SEQ ID NO: 61 and SEQ ID NO: 66, respectively;
   (iii) SEQ ID NO: 69 and SEQ ID NO: 74, respectively;
   (iv) SEQ ID NO: 77 and SEQ ID NO: 82, respectively;
   (v) SEQ ID NO: 85 and SEQ ID NO: 90, respectively; and
   (vi) SEQ ID NO: 101 and SEQ ID NO: 106, respectively.

9. A pharmaceutical composition comprising an effective amount of the antibody-drug conjugate of claim 1.

10. A method of treating cancer, reducing the volume of a tumor, or inducing cell death in a cancer cell, wherein the cancer or tumor is characterized by having a population of cancer cells that have cMet presented on their surface, comprising administering an effective amount of the antibody-drug conjugate of claim 1 to the subject.

* * * * *